US011220675B2

(12) United States Patent
Leonard et al.

(10) Patent No.: US 11,220,675 B2
(45) Date of Patent: Jan. 11, 2022

(54) MULTI-SUBSTRATE METABOLISM FOR IMPROVING BIOMASS AND LIPID PRODUCTION

(71) Applicant: Provivi, Inc., Santa Monica, CA (US)

(72) Inventors: Effendi Leonard, Anaheim, CA (US); Micah Sheppard, Los Angeles, CA (US); Thomas Heel, Los Angeles, CA (US); Kathryn Christina Wu, Los Angeles, CA (US)

(73) Assignee: Provivi, Inc., Santa Monica, CA (US)

( * ) Notice: Subject to any disclaimer, the term of this patent is extended or adjusted under 35 U.S.C. 154(b) by 0 days.

(21) Appl. No.: 16/401,690

(22) Filed: May 2, 2019

(65) Prior Publication Data

US 2019/0338295 A1 Nov. 7, 2019

Related U.S. Application Data

(60) Provisional application No. 62/665,809, filed on May 2, 2018.

(51) Int. Cl.

| | |
|---|---|
| ***C12N 9/04*** | (2006.01) |
| ***C12P 7/64*** | (2006.01) |
| ***C12N 15/00*** | (2006.01) |
| ***C12N 1/20*** | (2006.01) |
| ***C12N 1/14*** | (2006.01) |
| ***C12N 9/02*** | (2006.01) |
| ***C12N 9/18*** | (2006.01) |
| ***C12N 15/52*** | (2006.01) |
| ***C12N 15/81*** | (2006.01) |

(52) U.S. Cl.
CPC ......... *C12N 9/0006* (2013.01); *C12N 9/0071* (2013.01); *C12N 9/18* (2013.01); *C12N 15/52* (2013.01); *C12N 15/815* (2013.01); *C12P 7/6409* (2013.01); *C12Y 101/0104* (2013.01); *C12Y 101/01042* (2013.01); *C12Y 101/01044* (2013.01); *C12Y 101/01049* (2013.01); *C12Y 114/19005* (2013.01); *C12Y 301/01031* (2013.01)

(58) Field of Classification Search
CPC ..... C12P 7/6409; C12P 7/6436; C12N 9/0006
See application file for complete search history.

(56) References Cited

U.S. PATENT DOCUMENTS 6,150,144 A * 11/2000 Akimoto ............... C12P 7/6427 435/134

FOREIGN PATENT DOCUMENTS

WO WO 2016/207339 A1 12/2016
WO WO 2017/087846 A1 5/2017

OTHER PUBLICATIONS

Studer. Residue mutations and their impact on protein structure and function: detecting beneficial and pathogenic changes. Biochem. J. (2013) 449, 581-594.*
Chuang (Co-expression of heterologous desaturase genes in Yarrowia lipolytica. New Biotechnology. vol. 27, Issue 4, Sep. 30, 2010, pp. 277-282.*
Zhu. Metabolic engineering of Yarrowia lipolytica for industrial applications. Current Opinion in Biotechnology 2015, 36:65-72.*
Wasylenko. The oxidative pentose phosphate pathway is the primary source of NADPH for lipid over production from glucose in Yarrowia lipolytica. Metabolic Engineering30(2015)27-39.*
Lin. (Homologous Binding Sites in Yeast Isocitrate Dehydrogenase for Cofactor (NAD+) and Allosteric Activator (AMP). The Journal of Biological Chemistry vol. 278, No. 15, Issue of Apr. 11, pp. 12864-12872, 2003.*
Dujon. Q6C6Z1_YARLI. UniProtKB Database. 2017.*
Q8GAX0_ACITH. UniProtKB/TrEMBL Database. Mar. 15, 2017.*
Dulermo, et al., "Analysis of ATP-citrate lyase and malic enzyme mutants of Yarrowia lipolytica points out the importance of mannitol metabolism in fatty acid synthesis." Biochim Biophys Acta. (Sep. 2015); 1851(9): 1107-1117. Epub May 8, 2015.
Emanuelsson, et al., "Predicting Subcellular Localization of Proteins Based on their N-terminal Amino Acid Sequence." Journal of Molecular Biology (Jul. 21, 2000); 300(4): 1005-1016.
Halperin, et al., "Effects of Palmitoyl CoA on Citrate and Malate Transport by Rat Liver Mitochondria." Proc Natl Acad Sci U S A. (Apr. 1972); 69(4): 1003-1007.
Il'ichev, et al., "Sprayable Microencapsulated Sex Pheromone Formulation for Mating Disruption of Oriental Fruit Moth (*Lepidoptera*: Tortricidae) in Australian Peach and Pear Orchards." Journal of Economic Entomology (Dec. 2006); 99(6): 2048-2054.
Kavšček, et al., "Optimization of lipid production with a genome-scale model of Yarrowia lipolytica." BMC Systems Biology (2015); 9: 72; pp. 1-13.
Maniatis, et al., "Regulation of inducible and tissue-specific gene expression" Science (1987); 236 (4806): 1237-1245.
Mauersberger, et al., "Insertional Mutagenesis in the n-Alkane-Assimilating Yeast Yarrowia lipolytica: Generation of Tagged Mutations in Genes Involved in Hydrophobic Substrate Utilization." Journal of Bacteriology (2001); 183 (17): 5102-5109.
Morin, et al., "Transcriptomic Analyses during the Transition from Biomass Production to Lipid Accumulation in the Oleaginous Yeast Yarrowia lipolytica." PLoS ONE (Nov. 2011); (11): e27966, pp. 1-13. Epub Nov. 22, 2011.

(Continued)

*Primary Examiner* — Yong D Pak
(74) *Attorney, Agent, or Firm* — Cooley LLP

(57) ABSTRACT

The present application relates to methods to improve biomass or lipid production in a microorganism from one or more fatty acid and one or more simple carbon co-substrates. Produced lipids may include unsaturated $C_6$-$C_{24}$ fatty acids, alcohols, aldehydes, and acetates which may be useful as final products or precursors to insect pheromones, fragrances, flavors, and polymer intermediates. The application further relates to recombinant microorganisms modified for improved production of biomass or lipid, or improved lipid selectivity. Also provided are methods of producing one or more lipid using the recombinant microorganisms, as well as compositions comprising the recombinant microorganisms and/or optionally one or more of the product lipid.

11 Claims, 15 Drawing Sheets

Specification includes a Sequence Listing.

(56) References Cited

OTHER PUBLICATIONS

Stelinski, et al., "Sprayable microencapsulated sex pheromone formulations for mating disruption of four tortricid species: effects of application height, rate, frequency, and sticker adjuvant" J Econ. Entomol. (2007); 100(4): 1360-1369.
Zhang, et al., "Enhanced lipid accumulation in the yeast Yarrowia lipolytica by over-expression of ATP:citrate lyase from Mus musculus." Journal of Biotechnology (Dec. 20, 2014); 192 Pt A: 78-84. Epub Oct. 16, 2014.
Aoshima and Igarashi, "Nondecarboxylating and Decarboxylating Isocitrate Dehydrogenases: Oxalosuccinate Reductase as an Ancestral Form of Isocitrate Dehydrogenase". Journal of Bacteriology (Mar. 2008); 190(6): 2050-2055. Epub Jan. 18, 2008.
Extended European Search Report in European Application No. 19172410.3, dated Jul. 25, 2019, 10 pages.
Fernandez-Moya and Da Silva, "Engineering *Saccharomyces cerevisiae* for high-level synthesis of fatty acids and derived products", FEMS Yeast Research (Nov. 1, 2017); 17(7): 1-15.
Hagström, et al., "A moth pheromone brewery: production of (Z)-11-hexadecenol by heterologous co-expression of two biosynthetic genes from a noctuid moth in a yeast cell factory" Microbial Cell Factories (Dec. 13, 2013); 12(1): 125, 11 pages.
Rutter and Rao, "Production of 1-decanol by metabolically engineered Yarrowia lipolytica", Metabolic Engineering (Nov. 2016); 38: 139-147. Epub Jul. 26, 2016.
Tang, et al., "Metabolic engineering for enhanced fatty acids synthesis in *Saccharomyces cerevisiae*", Metabolic Engineering (Mar. 2012); 16: 95-102. Epub Jan. 23, 2013.

* cited by examiner

FIG. 11

```
     (SEQ ID NO: 50)ACACA_RAT       MDEPSPLAKTLELNQHSRFIIGSVSEDNSEDEISNLVKLD-LEEKEGSLSPASVSSDTLS
   (SEQ ID NO: 51)|ACACA_MOUSE     MDEPSPLAKTLELNQHSRFIIGSVSEDNSEDEISNLVKLD-LEEKEGSLSPASVSSDTLS
    (SEQ ID NO: 52)|ACAC_YEAST     -----------------------------------------------------------M
   (SEQ ID NO: 53)|ACACA_HUMAN     ------------------------------------------------------------
   (SEQ ID NO: 54)|ACACA_HUMAN     MDEPSPLAQPLELNQHSRFIIGSVSEDNSEDEISNLVKLDLLEEKEGSLSPASVGSDTLS
(SEQ ID NO: 55)|A0A0H3VB41_LIPST   ------------------------------------------------------------
    (SEQ ID NO: 56)|F2QLC7_KOMPC   ------------------------------------------------------------
    (SEQ ID NO: 57)|Q6CC91_YARLI   ---------------------------------------------------MRLQLRTLT

     (SEQ ID NO: 50)ACACA_RAT       DLGISALQDGLAFHMRSSMSGLHLVKQGRDRKKIDSQRDFTVASPAEFVTRFGGNKVIEK
   (SEQ ID NO: 51)|ACACA_MOUSE     DLGISGLQDGLAFHMRSSMSGLHLVKQGRDRKKIDSQRDFTVASPAEFVTRFGGNKVIEK
    (SEQ ID NO: 52)|ACAC_YEAST     SEESLFESSPQKMEYEITNYSERHTELPGHFIGLNTVDKLEESPLRDFVKSHGGHTVISK
   (SEQ ID NO: 53)|ACACA_HUMAN     ------------------MSGLHLVKQGRDRKKIDSQRDFTVASPAEFVTRFGGNKVIEK
   (SEQ ID NO: 54)|ACACA_HUMAN     DLGISSLQDGLALHIRSSMSGLHLVKQGRDRKKIDSQRDFTVASPAEFVTRFGGNKVIEK
(SEQ ID NO: 55)|A0A0H3VB41_LIPST   -------------------MSAAASSLPSHFIGLNTVDVAANSPVKDFVQNHGGHTVITS
    (SEQ ID NO: 56)|F2QLC7_KOMPC   --------------MSSVNHSLRHSKLPPHFLGLNSVEVAAPSKVRDFVRDHGGHSVITR
    (SEQ ID NO: 57)|Q6CC91_YARLI   RRFFSMASGSSTPDVAPLVDPNIHKGLASHFFGLNSVHTAKPSKVKEFVASHGGHTVINK

     (SEQ ID NO: 50)ACACA_RAT      VLIANNGIAAVKCMRSIRRWSYEMFRNERAIRFVVMVTPEDLKANAEYIKMADHYVPVPG
   (SEQ ID NO: 51)|ACACA_MOUSE    VLIANNGIAAVKCMRSIRRWSYEMFRNERAIRFVVMVTPEDLKANAEYIKMADHYVPVPG
    (SEQ ID NO: 52)|ACAC_YEAST    ILIANNGIAAVKEIRSVRKWAYETFGDDRTVQFVAMATPEDLEANAEYIRMADQYIEVPG
   (SEQ ID NO: 53)|ACACA_HUMAN    VLIANNGIAAVKCMRSIRRWSYEMFRNERAIRFVVMVTPEDLKANAEYIKMADHYVPVPG
   (SEQ ID NO: 54)|ACACA_HUMAN    VLIANNGIAAVKCMRSIRRWSYEMFRNERAIRFVVMVTPEDLKANAEYIKMADHYVPVPG
(SEQ ID NO: 55)|A0A0H3VB41_LIPST  VLIANNGIAAVKEIRSVRKWAYETFGDERAISFTVMATPEDLKANADYIRMADQYVEVPG
    (SEQ ID NO: 56)|F2QLC7_KOMPC  VLIANNGIAAVKEIRSVRKWAYETFGNDRAIQFIVMATPEDLEANAEYIRMADQYVMVPG
    (SEQ ID NO: 57)|Q6CC91_YARLI  VLIANNGIAAVKEIRSVRKWAYETFGDERAISFTVMATPEDLAANADYIRMADQYVEVPG

     (SEQ ID NO: 50)ACACA_RAT      GANNNNYANVELILDIAKRIPVQAVWAGWGHASENPKLPELLLKN--GIAFMGPPSQAMW
   (SEQ ID NO: 51)|ACACA_MOUSE    GPNNNNYANVELILDIAKRIPVQAVWAGWGHASENPKLPELLLKN--GIAFMGPPSQAMW
    (SEQ ID NO: 52)|ACAC_YEAST    GTNNNNYANVDLIVDIAERADVDAVWAGWGHASENPLLPEKLSQSKRKVIFIGPPGNAMR
   (SEQ ID NO: 53)|ACACA_HUMAN    GPNNNNYANVELILDIAKRIPVQAVWAGWGHASENPKLPELLLKN--GIAFMGPPSQAMW
   (SEQ ID NO: 54)|ACACA_HUMAN    GPNNNNYANVELILDIAKRIPVQAVWAGWGHASENPKLPELLLKN--GIAFMGPPSQAMW
(SEQ ID NO: 55)|A0A0H3VB41_LIPST  GTNNNNFANVELIVDIAERMNVHAVWAGWGHASENPKLPESLAQSPKKIVFIGPPGSAMR
    (SEQ ID NO: 56)|F2QLC7_KOMPC  GTANNNYANVDLIVEIAESTDAHAVWAGWGFASENPHLPEQLAASPKKIIFIGPPGSAMR
    (SEQ ID NO: 57)|Q6CC91_YARLI  GTNNNNYANVELIVDVAERFGVDAVWAGWGHASENPLLPESLAASPRKIVFIGPPGAAMR

     (SEQ ID NO: 50)ACACA_RAT      ALGDKIASSIVAQTAGIPTLPWSGSGLRVDWQENDFSKRILNVPQDLYEKGYVKDVDDGL
   (SEQ ID NO: 51)|ACACA_MOUSE    ALGDKIASSIVAQTAGIPTLPWSGSGLRVDWQENDFSKRILNVPQDLYEKGYVKDVDDGL
    (SEQ ID NO: 52)|ACAC_YEAST    SLGDKISSTIVAQSAKVPCIPWSGTG--VDTVHVDEKTGLVSVDDDIYQKGCCTSPEDGL
   (SEQ ID NO: 53)|ACACA_HUMAN    ALGDKIASSIVAQTAGIPTLPWSGSGLRVDWQENDFSKRILNVPQELYEKGYVKDVDDGL
   (SEQ ID NO: 54)|ACACA_HUMAN    ALGDKIASSIVAQTAGIPTLPWSGSGLRVDWQENDFSKRILNVPQELYEKGYVKDVDDGL
(SEQ ID NO: 55)|A0A0H3VB41_LIPST  SLGDKISSTIVAQHAKVPCIPWSGTG--VDEVQIDSVSGLVTVSDEIYAKGCTSTAEEAL
    (SEQ ID NO: 56)|F2QLC7_KOMPC  SLGDKISSTIVAQHAKVPCIPWSGTG--VDQVIIDPVSNLVSVDEETYAKGCCSDPQDGL
    (SEQ ID NO: 57)|Q6CC91_YARLI  SLGDKISSTIVAQHAKVPCIPWSGTG--VDEVVVDKSTNLVSVSEEVYTKGCTTGPKQGL

     (SEQ ID NO: 50)ACACA_RAT      KAAEEVGYPVMIKASEGGGGKGIRKVNNADDFPNLFRQVQAEVPGSPIFVMRLAKQSRHL
   (SEQ ID NO: 51)|ACACA_MOUSE    KAAEEVGYPVMIKASEGGGGKGIRKVNNADDFPNLFRQVQAEVPGSPIFVMRLAKQSRHL
    (SEQ ID NO: 52)|ACAC_YEAST    QKAKRIGFPVMIKASEGGGGKGIRQVEREEDFIALYHQAANEIPGSPIFIMKLAGRARHL
   (SEQ ID NO: 53)|ACACA_HUMAN    QAAEEVGYPVMIKASEGGGGKGIRKVNNADDFPNLFRQVQAEVPGSPIFVMRLAKQSRHL
   (SEQ ID NO: 54)|ACACA_HUMAN    QAAEEVGYPVMIKASEGGGGKGIRKVNNADDFPNLFRQVQAEVPGSPIFVMRLAKQSRHL
(SEQ ID NO: 55)|A0A0H3VB41_LIPST  EKARIIGFPVMIKASEGGGGKGIRKVESEDNFHSLYSQVANEVPGSPIFVMKLAGNARHL
    (SEQ ID NO: 56)|F2QLC7_KOMPC  AKAKAIGFPVMIKASEGGGGKGIRKVDREEDFLSLYDQAANEIPGSPIFIMKLAGDARHL
    (SEQ ID NO: 57)|Q6CC91_YARLI  EKAKQIGFPVMIKASEGGGGKGIRKVEREEDFEAAYHQVEGEIPGSPIFIMQLAGNARHL

     (SEQ ID NO: 50)ACACA_RAT      EVQILADQYGNAISLFGRDCSVQRRHQKIIEEAPAAIATPAVFEHMEQCAVKLAKMVGYV
   (SEQ ID NO: 51)|ACACA_MOUSE    EVQILADQYGNAISLFGRDCSVQRRHQKIIEEAPAAIATPAVFEHMEQCAVKLAKMVGYV
    (SEQ ID NO: 52)|ACAC_YEAST    EVQLLADQYGTNISLFGRDCSVQRRHQKIIEEAPVTIAKAETFHEMEKAAVRLGKLVGYV
   (SEQ ID NO: 53)|ACACA_HUMAN    EVQILADQYGNAISLFGRDCSVQRRHQKIIEEAPATIATPAVFEHMEQCAVKLAKMVGYV
   (SEQ ID NO: 54)|ACACA_HUMAN    EVQILADQYGNAISLFGRDCSVQRRHQKIIEEAPATIATPAVFEHMEQCAVKLAKMVGYV
(SEQ ID NO: 55)|A0A0H3VB41_LIPST  EVQLLADQYGNNISLFGRDCSVQRRHQKIIEEAPVTVANPATFSAMEHAAVRLGQLVGYV
    (SEQ ID NO: 56)|F2QLC7_KOMPC  EVQLLADQYGTNISLFGRDCSVQRRHQKIIEEAPVTIAKQDTFRQMEQAAVRLGQLVGYV
    (SEQ ID NO: 57)|Q6CC91_YARLI  EVQLLADQYGNNISLFGRDCSVQRRHQKIIEEAPVTVAGQQTFTAMEKAAVRLGKLVGYV

     (SEQ ID NO: 50)ACACA_RAT      SAGTVEYLYSQ-DGSFYFLELNPRLQVEHPCTEMVADVNLPAAQLQIAMGIPLFRIKDIR
   (SEQ ID NO: 51)|ACACA_MOUSE    SAGTVEYLYSQ-DGSFYFLELNPRLQVEHPCTEMVADVNLPAAQLQIAMGIPLFRIKDIR
    (SEQ ID NO: 52)|ACAC_YEAST    SAGTVEYLYSHDDGKFYFLELNPRLQVEHPTTEMVSGVNLPAAQLQIAMGIPMHRISDIR
   (SEQ ID NO: 53)|ACACA_HUMAN    SAGTVEYLYSQ-DGSFYFLELNPRLQVEHPCTEMVADVNLPAAQLQIAMGIPLYRIKDIR
   (SEQ ID NO: 54)|ACACA_HUMAN    SAGTVEYLYSQ-DGSFYFLELNPRLQVEHPCTEMVADVNLPAAQLQIAMGIPLYRIKDIR
(SEQ ID NO: 55)|A0A0H3VB41_LIPST  SAGTVEYLYSHDDDKFYFLELNPRLQVEHPTTEMVTGVNLPAAQLQIAMGVSLHRIRDIR
    (SEQ ID NO: 56)|F2QLC7_KOMPC  SAGTVEYLYSHAEDKFYFLELNPRLQVEHPTTEMATGVNLPVAQLLIAMGIPLNRIRDIR
    (SEQ ID NO: 57)|Q6CC91_YARLI  SAGTVEYLYSHEDDKFYFLELNPRLQVEHPTTEMVTGVNLPAAQLQIAMGIPLDRIKDIR
```

FIG. 11 (continued)

```
 SEQ ID NO: 50)ACACA_RAT          MMYGVSPWGDAPIDFE-------NSAHVPCPRGHVIAARITSENPDEGFKPSSGTVQELN
(SEQ ID NO: 51)|ACACA_MOUSE       MMYGVSPWGDAPIDFE-------NSAHVPCPRGHVIAARITSENPDEGFKPSSGTVQELN
(SEQ ID NO: 52)|ACAC_YEAST        TLYGMNPHSASEIDFEFKTQDATKKQRRPIPKGHCTACRITSEDPNDGFKPSGGTLHELN
(SEQ ID NO: 53)|ACACA_HUMAN       MMYGVSPWGDSPIDFE-------DSAHVPCPRGHVIAARITSENPDEGFKPSSGTVQELN
(SEQ ID NO: 54)|ACACA_HUMAN       MMYGVSPWGDSPIDFED-------SAHVPCPRGHVIAARITSENPDEGFKPSSGTVQELN
(SEQ ID NO: 55)|A0A0H3VB41_LIPST  LFYGVDPHTSTEIDFDFSKEGSLQTQRRPVPKGHTTACRITSEDPGEGFKPSSGVMHELN
(SEQ ID NO: 56)|F2QLC7_KOMPC      VLYGLEPNGATEIDFEFKTEESLKSQRKPIPKGHTIACRITSEDPGEGFKPSGGALYELN
(SEQ ID NO: 57)|Q6CC91_YARLI      LFYGVNPHTTTPIDFDFSGEDADKTQRRPVPRGHTTACRITSEDPGEGFKPSGGTMHELN

(SEQ ID NO: 50)ACACA_RAT          FRSNKNVWGYFSVAAAGGLHEFADSQFGHCFSWGENREEAISNMVVALKELSIRGDFRTT
(SEQ ID NO: 51)|ACACA_MOUSE       FRSNKNVWGYFSVAAAGGLHEFADSQFGHCFSWGENREEAISNMVVALKELSIRGDFRTT
(SEQ ID NO: 52)|ACAC_YEAST        FRSSSNVWGYFSVGNNGNIHSFSDSQFGHIFAFGENRQASRKHMVVALKELSIRGDFRTT
(SEQ ID NO: 53)|ACACA_HUMAN       FRSNKNVWGYFSVAAAGGLHEFADSQFGHCFSWGENREEAISNMVVALKELSIRGDFRTT
(SEQ ID NO: 54)|ACACA_HUMAN       FRSNKNVWGYFSVAAAGGLHEFADSQFGHCFSWGENREEAISNMVVALKELSIRGDFRTT
(SEQ ID NO: 55)|A0A0H3VB41_LIPST  FRSSSNVWGYFSVGNQGGIHSFSDSQFGHIFAFGENRSASRKHMVVALKELSIRGDFRTT
(SEQ ID NO: 56)|F2QLC7_KOMPC      FRSSSSVWGYFSVGNKSSIHSFSDSQFGHIFSFGENRQIARKNMVVALKELSIRGDFRTT
(SEQ ID NO: 57)|Q6CC91_YARLI      FRSSSNVWGYFSVGNQGGIHSFSDSQFGHIFAFGENRSASRKHMVVALKELSIRGDFRTT

(SEQ ID NO: 50)ACACA_RAT          VEYLIKLLETESFQLNRIDTGWLDRLIAEKVQAERPDTMLGVVCGALHVADVNLRNSISN
(SEQ ID NO: 51)|ACACA_MOUSE       VEYLIKLLETESFQLNRIDTGWLDRLIAEKVQAERPDTMLGVVCGALHVADVSLRNSISN
(SEQ ID NO: 52)|ACAC_YEAST        VEYLIKLLETEDFEDNTITTGWLDDLITHKMTAEKPDPTLAVICGAATKAFLASEEARHK
(SEQ ID NO: 53)|ACACA_HUMAN       VEYLIKLLETESFQMNRIDTGWLDRLIAEKVQAERPDTMLGVVCGALHVADVSLRNSVSN
(SEQ ID NO: 54)|ACACA_HUMAN       VEYLIKLLETESFQMNRIDTGWLDRLIAEKVQAERPDTMLGVVCGALHVADVSLRNSVSN
(SEQ ID NO: 55)|A0A0H3VB41_LIPST  VEYLIKLLETPDFESNKITTGWLDELISKKLTAERPDPVVAVVCGAVTKAHLASEACFQE
(SEQ ID NO: 56)|F2QLC7_KOMPC      IEYLIKLLETADFENNTITTGWLDELISKKLTAERPDETTAILCGAVTKAYIQWDLCRKE
(SEQ ID NO: 57)|Q6CC91_YARLI      VEYLIKLLETPDFEDNTITTGWLDELISNKLTAERPDSFLAVVCGAATKAHRASEDSIAT

(SEQ ID NO: 50)ACACA_RAT          FLHSLERGQVLPAHTLLNTVDVELIYEGIKYVLKVTRQSPNSYVVIMNGSCVEVDVHRLS
(SEQ ID NO: 51)|ACACA_MOUSE       FLHSLERGQVLPAHTLLNTVDVELIYEGIKYVLKVTRQSPNSYVVIMNGSCVEVDVHRLS
(SEQ ID NO: 52)|ACAC_YEAST        YIESLQKGQVLSKDLLQTMFPVDFIHEGKRYKFTVAKSGNDRYTLFINGSKCDIILRQLS
(SEQ ID NO: 53)|ACACA_HUMAN       FLHSLERGQVLPAHTLLNTVDVELIYEGVKYVLKVTRQSPNSYVVIMNGSCVEVDVHRLS
(SEQ ID NO: 54)|ACACA_HUMAN       FLHSLERGQVLPAHTLLNTVDVELIYEGVKYVLKVTRQSPNSYVVIMNGSCVEVDVHRLS
(SEQ ID NO: 55)|A0A0H3VB41_LIPST  YKNSLEKGQVPSKDILKTLFPVDFIYEGSRYKFTVTRSSMDLYQIFINGSKCLVGVKSLS
(SEQ ID NO: 56)|F2QLC7_KOMPC      YVASLEKGQIPGKELLRTIFPIEFIYEGKKYKFTVVQAAFDKYNVFVNGCMITVSVTHLK
(SEQ ID NO: 57)|Q6CC91_YARLI      YMASLEKGQVPARDILKTLFPVDFIYEGQRYKFTATRSSEDSYTLFINGSRCDIGVRPLS

(SEQ ID NO: 50)ACACA_RAT          DGGLLLSYDGSSYTTY-MKEEVDRYRITIGNKTCVFEKENDPSVMRSPSAGKLIQYIVED
(SEQ ID NO: 51)|ACACA_MOUSE       DGGLLLSYDGSSYTTY-MKEEVDRYRITIGNKTCVFEKENDPSVMRSPSAGKLIQYIVED
(SEQ ID NO: 52)|ACAC_YEAST        DGGLLIAIGGKSHTIY-WKEEVAATRLSVDSMTTLLEVENDPTQLRTPSPGKLVKFLVEN
(SEQ ID NO: 53)|ACACA_HUMAN       DGGLLLSYDGSSYTTY-MKEEVDRYRITIGNKTCVFEKENDPSVMRSPSAGKLIQYIVED
(SEQ ID NO: 54)|ACACA_HUMAN       DGGLLLSYDGSSYTTY-MKEEVDRYRITIGNKTCVFEKENDPSVMRSPSAGKLIQYIVED
(SEQ ID NO: 55)|A0A0H3VB41_LIPST  DGGLLVLLGGKSHNVY-WKDEVGTTRLSVDSKTCLLEQENDPTQLRTPSPGKLVKFLVEN
(SEQ ID NO: 56)|F2QLC7_KOMPC      DGSLLVALDGKSHSVYYLQEEVGNTRLSVDGKSCILEVEHEPTELRTPSPGKLIKYLVEH
(SEQ ID NO: 57)|Q6CC91_YARLI      DGGILCLVGGRSHNVY-WKEEVGATRLSVDSKTCLLEVENDPTQLRSPSPGKLVKFLVEN

(SEQ ID NO: 50)ACACA_RAT          GGHVFAGQCYAEIEVMKMVMTLTAVESGCIHYVKRPGAALDPGCVIAKMQLDNPSKVQQA
(SEQ ID NO: 51)|ACACA_MOUSE       GGHVFAGQCYAEIEVMKMVMTLTAVESGCIHYVKRPGAALDPGCVIAKMQLDNPSKVQQA
(SEQ ID NO: 52)|ACAC_YEAST        GEHIIKGQPYAEIEVMKMQMPLVSQENGIVQLLKQPGSTIVAGDIMAIMTLDDPSKVKHA
(SEQ ID NO: 53)|ACACA_HUMAN       GGHVFAGQCYAEIEVMKMVMTLTAVESGCIHYVKRPGAALDPGCVLAKMQLDNPSKVQQA
(SEQ ID NO: 54)|ACACA_HUMAN       GGHVFAGQCYAEIEVMKMVMTLTAVESGCIHYVKRPGAALDPGCVLAKMQLDNPSKVQQA
(SEQ ID NO: 55)|A0A0H3VB41_LIPST  GEHVKTGQPFAEVEVMKMYMPLIAQEDGIVQLIKQPGATLEAGDILGILALDDPSRVKHA
(SEQ ID NO: 56)|F2QLC7_KOMPC      GDHVKIGQPYAEVEVMKMCMPLVSQENGTIRLLKQPGSSVAAGDILAILALDDPSKVKHA
(SEQ ID NO: 57)|Q6CC91_YARLI      GDHVRANQPYAEIEVMKMYMTLTAQEDGIVQLMKQPGSTIEAGDILGILALDDPSKVKHA

(SEQ ID NO: 50)ACACA_RAT          ELHTGSLPQIQSTALRGEKLHRVFHYVLDNLVNVMNGYCLPDPFFSSKVKDWVERLMKTL
(SEQ ID NO: 51)|ACACA_MOUSE       ELHTGSLPQIQSTALRGEKLHRVFHYVLDNLVNVMNGYCLPDPFFSSRVKDWVERLMKTL
(SEQ ID NO: 52)|ACAC_YEAST        LPFEGMLPDFGSPVIEGTKPAYKFKSLVSTLENILKGY---DN--QVIMNASLQQLIEVL
(SEQ ID NO: 53)|ACACA_HUMAN       ELHTGSLPRIQSTALRGEKLHRVFHYVLDNLVNVMNGYCLPDPFFSSKVKDWVERLMKTL
(SEQ ID NO: 54)|ACACA_HUMAN       ELHTGSLPRIQSTALRGEKLHRVFHYVLDNLVNVMNGYCLPDPFFSSKVKDWVERLMKTL
(SEQ ID NO: 55)|A0A0H3VB41_LIPST  KPFEGQLPDFGSPLVLGSKPSQRFNLLLSTLRNILAGF---DN--QVLLASTLKDLSQVL
(SEQ ID NO: 56)|F2QLC7_KOMPC      LPFDGTIPDMKQPFIHSNKPVYKFISLLSVLKNILAGY---DN--QVVMNDTLQSLLDVL
(SEQ ID NO: 57)|Q6CC91_YARLI      KPFEGQLPELGPPTLSGNKPHQRYEHCQNVLHNILLGF---DN—QVVMKSTLQEMVGLL

(SEQ ID NO: 50)ACACA_RAT          RDPSLPLLELQDIMTSVSGRIPLNVEKSIKKEMAQYASNITSVLCQFPSQQIANILDSHA
(SEQ ID NO: 51)|ACACA_MOUSE       RDPSLPLLELQDIMTSVSGRIPLNVEKSIKKEMAQYASNITSVLCQFPSQQIANILDSHA
(SEQ ID NO: 52)|ACAC_YEAST        RNPKLPYSEWKLHISALHSRLPAKLDEQMEELVARSLRRG----AVFPARQLSKLIDM-A
(SEQ ID NO: 53)|ACACA_HUMAN       RDPSLPLLELQDIMTSVSGRIPPNVEKSIKKEMAQYASNITSVLCQFPSQQIANILDSHA
(SEQ ID NO: 54)|ACACA_HUMAN       RDPSLPLLELQDIMTSVSGRIPPNVEKSIKKEMAQYASNITSVLCQFPSQQIANILDSHA
(SEQ ID NO: 55)|A0A0H3VB41_LIPST  KDDALPYSEWNAQFSALHSRIPQKLDATLSSLIERSKSKD----AEFPAKLLLRAIERFA
(SEQ ID NO: 56)|F2QLC7_KOMPC      KNPELPYSEWNHSISALHSRLPIHLDEQLTSLIERSHQRG----ADFPAKHLLKLLDKEQ
(SEQ ID NO: 57)|Q6CC91_YARLI      RNPELPYLQWAHQVSSLHTRMSAKLDATLAGLIDKAKQRGG----EFPAKQLLRALEKEA
```

FIG. 11 (continued)

```
     (SEQ ID NO: 50)ACACA_RAT      ATLNRKSEREVFFMNTQSIVQLVQRYRSGIRGHMKAVVMDLLRQYLRVETQF--QNGHYD
   (SEQ ID NO: 51)|ACACA_MOUSE     ATLNRKSEREVFFMNTQSIVQLVQRYRSGIRGHMKAVVMDLLRQYLRVETQF--QNGHYD
    (SEQ ID NO: 52)|ACAC_YEAST     VKNPEYNPDKLLGAVVEPLADIAHKYSNGLEAHEHSIFVHFLEEYYEVEKLFNGPNVREE
   (SEQ ID NO: 53)|ACACA_HUMAN     ATLNRKSEREVFFMNTQSIVQLVQRYRSGIRGHMKAVVMDLLRQYLRVETQF--QNGHYD
   (SEQ ID NO: 54)|ACACA_HUMAN     ATLNRKSEREVFFMNTQSIVQLVQRYRSGIRGHMKAVVMDLLRQYLRVETQF--QNGHYD
(SEQ ID NO: 55)|A0A0H3VB41_LIPST   EEFIQPQDLFVFKQQVEPLVTIATRYQAGLKAHEYGVIAELLEQYLAVEKLFSGANIRDE
    (SEQ ID NO: 56)|F2QLC7_KOMPC   AV----NPDPLFSQVIAPLTAVAKSYEHGLEVHEHNVFADLITQYYDIESLF--ADKREE
    (SEQ ID NO: 57)|Q6CC91_YARLI   SS---GEVDALFQQTLAPLFDLAREYQDGLAIHELQVAAGLLQAYYDSEARFCGPNVRDE

     (SEQ ID NO: 50)ACACA_RAT      KCVFALREENKSDMNTVLNYIFSHAQVTKKNLLVTMLIDQL--C---GRDPT-----LTD
   (SEQ ID NO: 51)|ACACA_MOUSE     KCVFALREENKSDMNTVLNYIFSHAQVTKKNLLVTMLIDQL--C---GRDPT-----LTD
    (SEQ ID NO: 52)|ACAC_YEAST     NIILKLRDENPKDLDKVALTVLSHSKVSAKNNLILAILKHY--QPLCKLSSK-----VSA
   (SEQ ID NO: 53)|ACACA_HUMAN     KCVFALREENKSDMNTVLNYIFSHAQVTKKNLLVTMLIDQL--C---GRDPT-----LTD
   (SEQ ID NO: 54)|ACACA_HUMAN     KCVFALREENKSDMNTVLNYIFSHAQVTKKNLLVTMLIDQL--C---GRDPT-----LTD
(SEQ ID NO: 55)|A0A0H3VB41_LIPST   DVFLRLRDENKDDIFKVVMTVFSHGRVGAKNNLILAILAAL--RSDRSEVSE-----VAK
    (SEQ ID NO: 56)|F2QLC7_KOMPC   DVILQLRDENKSSLDKVIDVVLSHSRVGAKNHLIRAILEIY--QTICQNDLQ-----AAT
    (SEQ ID NO: 57)|Q6CC91_YARLI   DVILKLREENRDSLRKVVMAQLSHSRVGAKNNLVLALLDEYKVADQAGTDSPASNVHVAK

     (SEQ ID NO: 50)ACACA_RAT      ELLNILTELTQLSKTTNAKVALRARQVLIASHLPSYDVRHNQVESIFLSAI--DMYGHQF
   (SEQ ID NO: 51)|ACACA_MOUSE     ELLNILTELTQLSKTTNAKVALRARQVLIASHLPSYELRHNQVESIFLSAI--DMYGHQF
    (SEQ ID NO: 52)|ACAC_YEAST     IFSTPLQHIVELESKATAKVALQAREILIQGALPSVKERTEQIEHILKSSVVKVAYGSS-
   (SEQ ID NO: 53)|ACACA_HUMAN     ELLNILTELTQLSKTTNAKVALRARQVLIASHLPSYELRHNQVESIFLSAI--DMYGHQF
   (SEQ ID NO: 54)|ACACA_HUMAN     ELLNILTELTQLSKTTNAKVALRARQVLIASHLPSYELRHNQVESIFLSAI--DMYGHQF
(SEQ ID NO: 55)|A0A0H3VB41_LIPST   YLRPALKTLTELDSGVTAPVALKARELLIQCALPSLEERTAQLEHILRSSVVESRYGEV-
    (SEQ ID NO: 56)|F2QLC7_KOMPC   ILKKPLKKIVELDSRFTAKVSLKAREILIQCSLPSIKERSDQLEHILRSSVVQTQYGESF
    (SEQ ID NO: 57)|Q6CC91_YARLI   YLRPVLRKIVELESRASAKVSLKAREILIQCALPSLKERTDQLEHILRSSVVESRYGEV-

     (SEQ ID NO: 50)ACACA_RAT      CIEN--------LQKLILSETSIFDVLPNFFYHSNQVVRMAALEVYVRRAYIAYELNSVQH
   (SEQ ID NO: 51)|ACACA_MOUSE     CIEN--------LQKLILSETSIFDVLPNFFYHSNQVVRMAALEVYVRRAYIAYELNSVQH
    (SEQ ID NO: 52)|ACAC_YEAST     NPKRSEPDLNILKDLIDSNYVVFDVLLQFLTHQDPVVTAAAAQVYIRRAYRAYTIGDIRV
   (SEQ ID NO: 53)|ACACA_HUMAN     CIEN--------LQKLILSETSIFDVLPNFFYHSNQVVRMAALEVYVRRAYIAYELNSVQH
   (SEQ ID NO: 54)|ACACA_HUMAN     CIEN--------LQKLILSETSIFDVLPNFFYHSNQVVRMAALEVYVRRAYIAYELNSVQH
(SEQ ID NO: 55)|A0A0H3VB41_LIPST   GFEHSAPRIDVLKEVIDSQYIVFDVLPKFFAHSDRYVTLAALELYVRRAYRAYNVMSMEY
    (SEQ ID NO: 56)|F2QLC7_KOMPC   NGNYKLPNLDVIQDVIDSKYIVFDVLTQFVVSPNKYIFAAAAEVYLRRAYRAYSVREVKH
    (SEQ ID NO: 57)|Q6CC91_YARLI   GLEHRTPRADILKEVVDSKYIVFDVLAQFFAHDDPWIVLAALELYIRRACKAYSILDINY

     (SEQ ID NO: 50)ACACA_RAT      RQLKDNTC-VVEFQFMLPTSHPNRGNIPTLNRMSFASNLNHYGMTHVASVSDV-LLDNAF
   (SEQ ID NO: 51)|ACACA_MOUSE     RQLKDNTC-VVEFQFMLPTSHPNRGNIPTLNRMSFASNLNHYGMTHVASVSDV-LLDNAF
    (SEQ ID NO: 52)|ACAC_YEAST     HE--GVTVPIVEWKFQLPSAAFS-----------TFPTVKSKMGMNRAVSVSDLSYVANSQ
   (SEQ ID NO: 53)|ACACA_HUMAN     RQLKDNTC-VVEFQFMLPTSHPNRGNIPTLNRMSFSSNLNHYGMTHVASVSDV-LLDNSF
   (SEQ ID NO: 54)|ACACA_HUMAN     RQLKDNTC-VVEFQFMLPTSHPNRGNIPTLNRMSFSSNLNHYGMTHVASVSDV-LLDNSF
(SEQ ID NO: 55)|A0A0H3VB41_LIPST   HNEGDLV-PVVTFKFLLAAIGNPAYNIVG---QGAPSGDSRIDFQRAASVSDLTFMMSKS
    (SEQ ID NO: 56)|F2QLC7_KOMPC   HFVGDSALPIVEWKFQLPLLSTAAYNSVPEAMRNSSSNRSSISMDRAVSVSDLTFMINKN
    (SEQ ID NO: 57)|Q6CC91_YARLI   HQDSDLP-PVISWRFRLPTMSSALYNSVV---SSGSKTPTSPSVSRADSVSDFSYTVERD
     (SEQ ID NO: 50)ACACA_RAT      TPPCQRMGGMVSFRTFEDFVRIFDEVMGCFCDSPPQ-SPTFPESGHT---SLYDEDKVPR
   (SEQ ID NO: 51)|ACACA_MOUSE     TPPCQRMGGMVSFRTFEDFVRIFDEIMGCFCDSPPQ-SPTFPESGHT---SLYDEDKVPR
    (SEQ ID NO: 52)|ACAC_YEAST     SSP-LREGILMAVDHLDDVDEILSQSLEVIPRHQ---------SSSNG---PAPDRSGSSA
   (SEQ ID NO: 53)|ACACA_HUMAN     TPPCQRMGGMVSFRTFEDFVRIFDEVMGCFSDSPPQ-SPTFPEAGHT---SLYDEDKVPR
   (SEQ ID NO: 54)|ACACA_HUMAN     TPPCQRMGGMVSFRTFEDFVRIFDEVMGCFSDSPPQ-SPTFPEAGHT---SLYDEDKVPR
(SEQ ID NO: 55)|A0A0H3VB41_LIPST   DSESLRSGVIVPVADIADIDEVLPRALDYLPQRAGAGSGGFSFSAKS---DL-DSKRRPA
    (SEQ ID NO: 56)|F2QLC7_KOMPC   DSQPLRTGIIIPTNHLDDIEESLSSAIDVFPKRP----------RNNG---PAPDRTNVAP
    (SEQ ID NO: 57)|Q6CC91_YARLI   SAPA-RTGAIVAVPHLDDLEDALTRVLENLPKRGAGLAISVGASNKSAAASARDAAAAAA

     (SEQ ID NO: 50)ACACA_RAT      DE----PIHILNVAI-KTDGDIEDDRLAAMFREFTQQNKATLVEHGIRRLTFLVAQKDFR
   (SEQ ID NO: 51)|ACACA_MOUSE     DE----PIHILNVAI-KTDGDIEDDRLAAMFREFTQQNKATLVEHGIRRLTFLVAQKDFR
    (SEQ ID NO: 52)|ACAC_YEAST     S-----LSNVANVCVASTEGFESEEEILVRLREILDLNKQELINASIRRITFMFGFKD--
   (SEQ ID NO: 53)|ACACA_HUMAN     DE----PIHILNVAI-KTDCDIEDDRLAAMFREFTQQNKATLVDHGIRRLTFLVAQKDFR
   (SEQ ID NO: 54)|ACACA_HUMAN     DE----PIHILNVAI-KTDCDIEDDRLAAMFREFTQQNKATLVDHGIRRLTFLVAQKDFR
(SEQ ID NO: 55)|A0A0H3VB41_LIPST   PPKPESLSNICNVLIRKT-AKTDDAALVSDIKFIVDEYKEEFLLRSIRRVTFVCGRED--
    (SEQ ID NO: 56)|F2QLC7_KOMPC   EQ----PTNVCNVFIANVSGYNSEAEIVDKISSVLSELKDDLRASGVRRVTFVLGDKV--
    (SEQ ID NO: 57)|Q6CC91_YARLI   SSVDTGLSNICNVMIGRVDESDDDDTLIARISQVIEDFKEDFEACSLRRITFSFGNSR--

     (SEQ ID NO: 50)ACACA_RAT      KQVNCEVDQRFHREFPKFFTFRARDKFEEDRIYRHLEPALAFQLELNRMRNFDLTAIPCA
   (SEQ ID NO: 51)|ACACA_MOUSE     KQVNCEVDQRFHREFPKFFTFRARDKFEEDRIYRHLEPALAFQLELNRMRNFDLTAIPCA
    (SEQ ID NO: 52)|ACAC_YEAST     -------------GSYPKYYTFNGPN-YNENETIRHIEPALAFQLELGRLSNFNIKPIFTD
   (SEQ ID NO: 53)|ACACA_HUMAN     KQVNYEVDRRFHREFPKFFTFRARDKFEEDRIYRHLEPALAFQLELNRMRNFDLTAIPCA
   (SEQ ID NO: 54)|ACACA_HUMAN     KQVNYEVDRRFHREFPKFFTFRARDKFEEDRIYRHLEPALAFQLELNRMRNFDLTAIPCA
(SEQ ID NO: 55)|A0A0H3VB41_LIPST   -------------GSYPGYFTFRGPD-YVEDESIRHIEPALAYQLELGRLSNFNYKPIFTD
    (SEQ ID NO: 56)|F2QLC7_KOMPC   -------------GTYPKYYTFKFPD-YFEDETIRHIEPALAFQLELRRLSNFNIKPVPTE
    (SEQ ID NO: 57)|Q6CC91_YARLI   -------------GTYPKYFTFRGPA-YEEDPTIRHIEPALAFQLELARLSNFDIKPVHTD
```

FIG. 11 (continued)

```
    (SEQ ID NO: 50)ACACA_RAT     NHKMHLYLGAAKVEVGTEVTDYRFFVRAIIRHSDLVTKEASFEYLQNEGERLLLEAMDEL
   (SEQ ID NO: 51)|ACACA_MOUSE   NHKMHLYLGAAKVEVGTEVTDYRFFVRAIIRHSDLVTKEASFEYLQNEGERLLLEAMDEL
    (SEQ ID NO: 52)|ACAC_YEAST   NRNIHVYEAVSK----TSPLDKRFFTRGIIRTGHIRDDISIQEYLTSEANRLMSDILDNL
   (SEQ ID NO: 53)|ACACA_HUMAN   NHKMHLYLGAAKVEVGTEVTDYRFFVRAIIRHSDLVTKEASFEYLQNEGERLLLEAMDEL
   (SEQ ID NO: 54)|ACACA_HUMAN   NHKMHLYLGAAKVEVGTEVTDYRFFVRAIIRHSDLVTKEASFEYLQNEGERLLLEAMDEL
(SEQ ID NO: 55)|A0A0H3VB41_LIPST NRNIHVYQAIGK----DVPSDKRFFVRGIVRPGRLRDEIPTSEYLISETDRLMSDILDAL
  (SEQ ID NO: 56)|F2QLC7_KOMPC   NRNIHVYEAVAK---NTSCIDRRFFTRGIIRTSRIREDVTISEYLISEANRLMSDILDAL
  (SEQ ID NO: 57)|Q6CC91_YARLI   NRNIHVYEATGK----NAASDKRFFTRGIVRPGRLRENIPTSEYLISEADRLMSDILDAL

    (SEQ ID NO: 50)ACACA_RAT     EVAFNNTNVRTDCNHIFLNFVPTVIMDPSKIEESVRSMVMRYGSRLWKLRVLQAELKINI
   (SEQ ID NO: 51)|ACACA_MOUSE   EVAFNNTNVRTDCNHIFLNFVPTVIMDPSKIEESVRSMVMRYGSRLWKLRVLQAELKINI
    (SEQ ID NO: 52)|ACAC_YEAST   EV-TDTSN--SDLNHIFINFIAVFDISPEDVEAAFGGFLERFGKRLLRLRVSSAEIRIII
   (SEQ ID NO: 53)|ACACA_HUMAN   EVAFNNTNVRTDCNHIFLNFVPTVIMDPSKIEESVRSMVMRYGSRLWKLRVLQAELKINI
   (SEQ ID NO: 54)|ACACA_HUMAN   EVAFNNTNVRTDCNHIFLNFVPTVIMDPSKIEESVRSMVMRYGSRLWKLRVLQAELKINI
(SEQ ID NO: 55)|A0A0H3VB41_LIPST EV-IGPNN--TDMNHIFINFSPIFHLVPEEVEAAFGQFLERFGRRLWRLRVTGAEIRIMC
  (SEQ ID NO: 56)|F2QLC7_KOMPC   EI-IDTSN--TDLNHIFINFSAVFNVTPDDVEAAFGGFLERFGRRLWRLRVSAAEIRIMC
  (SEQ ID NO: 57)|Q6CC91_YARLI   EV-IGTTN—SDLNHIFINFSAVFALKPEEVEAAFGGFLERFGRRLWRLRVTGAEIRMMV

    (SEQ ID NO: 50)ACACA_RAT     RLTTTGKAIPIRLFLTNESGYYLDISLYKEVTDSRTAQIMFQAYGDKQGPLHGMLINTPY
   (SEQ ID NO: 51)|ACACA_MOUSE   RLTTTGKAIPIRLFLTNESGYYLDISLYKEVTDSRTAQIMFQAYGDKQGPLHGMLINTPY
    (SEQ ID NO: 52)|ACAC_YEAST   KDPQTGAPVPLRALINNVSGYVIKTEMYTEVKNAK-GEWVFKSLGK-PGSMHLRPIATPY
   (SEQ ID NO: 53)|ACACA_HUMAN   RLTPTGKAIPIRLFLTNESGYYLDISLYKEVTDSRTAQIMFQAYGDKQGPLHGMLINTPY
   (SEQ ID NO: 54)|ACACA_HUMAN   RLTPTGKAIPIRLFLTNESGYYLDISLYKEVTDSRTAQIMFQAYGDKQGPLHGMLINTPY
(SEQ ID NO: 55)|A0A0H3VB41_LIPST TDPETNVPYPLRAIITNVSGYVVQSELYTEVKNDK-GQWVFKSLGK-PGNMHLRSITTPY
  (SEQ ID NO: 56)|F2QLC7_KOMPC   TDPETGIPFPLRALINNVSGYVVKSEMYQEVKNDH-GEWVFKSLGPTPGSMHLRPISTPY
  (SEQ ID NO: 57)|Q6CC91_YARLI   SDPETGSAFPLRAMINNVSGYVVQSELYAEAKNDK-GQWIFKSLGK-PGSMHMRSINTPY

    (SEQ ID NO: 50)ACACA_RAT     VTKDLLQSKRFQAQSLGTTYIYDIPEMFRQSLIKLWESMSTQAFLPSPPLPSDILTYTEL
   (SEQ ID NO: 51)|ACACA_MOUSE   VTKDLLQSKRFQAQSLGTTYIYDIPEMFRQSLIKLWESMSTQAFLPSPPLPSDILTYTEL
    (SEQ ID NO: 52)|ACAC_YEAST   PVKEWLQPKRYKAHLMGTTYVYDFPELFRQASSSQWKNFSADV-----KLTDDFFISNEL
   (SEQ ID NO: 53)|ACACA_HUMAN   VTKDLLQSKRFQAQSLGTTYIYDIPEMFRQSLIKLWESMSTQAFLPSPPLPSDMLTYTEL
   (SEQ ID NO: 54)|ACACA_HUMAN   VTKDLLQSKRFQAQSLGTTYIYDIPEMFRQSLIKLWESMSTQAFLPSPPLPSDMLTYTEL
(SEQ ID NO: 55)|A0A0H3VB41_LIPST ATKEWLQPKRYKAHLMGTTFVYDFPELFNQAIRASWRAAQQQS-------PENVLTYKEL
  (SEQ ID NO: 56)|F2QLC7_KOMPC   PTKEWLQPKRYKAHLMGTTYVYDFPELFRQATLSQWKKYSPTA-----RVPSDVFVANEL
  (SEQ ID NO: 57)|Q6CC91_YARLI   PTKEWLQPKRYKAHLMGTTYCYDFPELFRQSIESDWKKYDGKA-------PDDLMTCNEL

    (SEQ ID NO: 50)ACACA_RAT     VLD-DQGQLVHMNRLPGGNEIGMVAWKMSLKSPEYPDGRDVIVIGNDITYRIGSFGPQED
   (SEQ ID NO: 51)|ACACA_MOUSE   VLD-DQGQLVHMNRLPGGNEIGMVAWKMSLKSPEYPDGRDIIVIGNDITYRIGSFGPQED
    (SEQ ID NO: 52)|ACAC_YEAST   IED-ENGELTEVEREPGANAIGMVAFKITVKTPEYPRGRQFVVVANDITFKIGSFGPQED
   (SEQ ID NO: 53)|ACACA_HUMAN   VLD-DQGQLVHMNRLPGGNEIGMVAWKMTFKSPEYPEGRDIIVIGNDITYRIGSFGPQED
   (SEQ ID NO: 54)|ACACA_HUMAN   VLD-DQGQLVHMNRLPGGNEIGMVAWKMTFKSPEYPEGRDIIVIGNDITYRIGSFGPQED
(SEQ ID NO: 55)|A0A0H3VB41_LIPST IMD-DSGELSEVSREPGANTCGMVAWLFTALTPEYPTGRQFIVVANDITYKIGSFGPQED
  (SEQ ID NO: 56)|F2QLC7_KOMPC   IVD-DSGELTEVSREPGANVVGMVAFKVTAKTPEYPRGRHFIIIANDITFKIGSFGPQED
  (SEQ ID NO: 57)|Q6CC91_YARLI   ILDEDSGELQEVNREPGANNVGMVAWKFEAKTPEYPRGRSFIVVANDITFQIGSFGPAED

    (SEQ ID NO: 50)ACACA_RAT     LLFLRASELARAEGIPRIYVAANSGARIGLAEEIRHMFHVAWVDSEDPYKGYKYLYLTPQ
   (SEQ ID NO: 51)|ACACA_MOUSE   LLFLRASELARAEGIPRIYVAANSGARIGLAEEIRHMFHVAWVDPEDPYKGYKYLYLTPQ
    (SEQ ID NO: 52)|ACAC_YEAST   EFFNKVTEYARKRGIPRIYLAANSGARIGMAEEIVPLFQVAWNDAANPDKGFQYLYLTSE
   (SEQ ID NO: 53)|ACACA_HUMAN   LLFLRASELARAEGIPRIYVSANSGARIGLAEEIRHMFHVAWVDPEDPYKGYRYLYLTPQ
   (SEQ ID NO: 54)|ACACA_HUMAN   LLFLRASELARAEGIPRIYVSANSGARIGLAEEIRHMFHVAWVDPEDPYKGYRYLYLTPQ
(SEQ ID NO: 55)|A0A0H3VB41_LIPST KYFHTVTQLAVKLGIPRIYLSANSGARIGVADEFVSLFSVAWNDSSNPEKGFKYLYLTPA
  (SEQ ID NO: 56)|F2QLC7_KOMPC   EYFNKATQLARKLGIPRIYLSANSGARIGVAEELLPLFKVAWKEEGKPSKGFEYLYLTSE
  (SEQ ID NO: 57)|Q6CC91_YARLI   QFFFKVTELARKLGIPRIYLSANSGARIGIADELVGKYKVAWNDETDPSKGFKYLYFTPE

    (SEQ ID NO: 50)ACACA_RAT     DYKRVS---ALNSVHCEHVEDEGESRYKITDIIGKEEGLGAENLRGSGMIAGESSLAYDE
   (SEQ ID NO: 51)|ACACA_MOUSE   DYKRVS---ALNSVHCEHVEDEGESRYKITDIIGKEEGLGAENLRGSGMIAGESSLAYDE
    (SEQ ID NO: 52)|ACAC_YEAST   GMETLKKFDKENSVLTERTVINGEERFVIKTIIGSEDGLGVECLRGSGLIAGATSRAYHD
   (SEQ ID NO: 53)|ACACA_HUMAN   DYKRVS---ALNSVHCEHVEDEGESRYKITDIIGKEEGIGPENLRGSGMIAGESSLAYNE
   (SEQ ID NO: 54)|ACACA_HUMAN   DYKRVS---ALNSVHCEHVEDEGESRYKITDIIGKEEGIGPENLRGSGMIAGESSLAYNE
(SEQ ID NO: 55)|A0A0H3VB41_LIPST IYNGLSD-AAKKTVLTERIVEEGEERYVITTIIGAEDGLGVECLRGSGLIAGATSKAYKD
  (SEQ ID NO: 56)|F2QLC7_KOMPC   DLTLLEKSGKSNSVTTQRIVEEGEERHVITAIIGASDGLGVECLRGSGLIAGATSRAYKD
  (SEQ ID NO: 57)|Q6CC91_YARLI   SLATLKPDTVVTTEIEEEGPNGVEKRHVIDYIVGEKDGLGVECLRGSGLIAGATSRAYKD

    (SEQ ID NO: 50)ACACA_RAT     IITISLVTCRAIGIGAYLVRLGQRTIQVENSHLILTGAGALNKVLGREVYTSNNQLGGIQ
   (SEQ ID NO: 51)|ACACA_MOUSE   VITISLVTCRAIGIGAYLVRLGQRTIQVENSHLILTGAGALNKVLGREVYTSNNQLGGIQ
    (SEQ ID NO: 52)|ACAC_YEAST   IFTITLVTCRSVGIGAYLVRLGQRAIQVEGQPIILTGAPAINKMLGREVYTSNLQLGGTQ
   (SEQ ID NO: 53)|ACACA_HUMAN   IITISLVTCRAIGIGAYLVRLGQRTIQVENSHLILTGAGALNKVLGREVYTSNNQLGGIQ
   (SEQ ID NO: 54)|ACACA_HUMAN   IITISLVTCRAIGIGAYLVRLGQRTIQVENSHLILTGAGALNKVLGREVYTSNNQLGGIQ
(SEQ ID NO: 55)|A0A0H3VB41_LIPST IFTITLVTCRSVGIGAYLVRLGQRAIQIEGQPIILTGAPAINKLLGREVYSSNLQLGGTQ
  (SEQ ID NO: 56)|F2QLC7_KOMPC   IFTITLVTCRSVGIGAYLVRLGQRAIQIEGQPIILTGAPAINKLLGREVYSSNLQLGGTQ
  (SEQ ID NO: 57)|Q6CC91_YARLI   IFTLTLVTCRSVGIGAYLVRLGQRAIQIEGQPIILTGAPAINKLLGREVYSSNLQLGGTQ
```

FIG. 11 (continued)

```
     (SEQ ID NO: 50)ACACA_RAT     IMHNNGVTHCTVCDDFEGVFTVLHWLSYMPKNVHSSVPLLNS-KDPIDRIIEFVPTK-AP
   (SEQ ID NO: 51)|ACACA_MOUSE    IMHNNGVTHSTVCDDFEGVFTVLHWLSYMPKSVHSSVPLLNS-KDPIDRIIEFVPTK-AP
    (SEQ ID NO: 52)|ACAC_YEAST    IMYNNGVSHLTAVDDLAGVEKIVEWMSYVPAKRNMPVPILET-KDTWDRPVDFTPTNDET
   (SEQ ID NO: 53)|ACACA_HUMAN    IMHNNGVTHCTVCDDFEGVFTVLHWLSYMPKSVHSSVPLLNS-KDPIDRIIEFVPTK-TP
   (SEQ ID NO: 54)|ACACA_HUMAN    IMHNNGVTHCTVCDDFEGVFTVLHWLSYMPKSVHSSVPLLNS-KDPIDRIIEFVPTK-TP
(SEQ ID NO: 55)|A0A0H3VB41_LIPST  IMYKNGVSHLTANDDLAGVMKIIEWMSYVPYKKGGQLPIYPS-SDTWDRDVTYTPPKQVP
  (SEQ ID NO: 56)|F2QLC7_KOMPC    IMYKNGVSHLTANDDLAGVEKIMDWLAYVPAKRNMPVPILESLHDKWDRDVDYKPTRNEP
  (SEQ ID NO: 57)|Q6CC91_YARLI    IMYNNGVSHLTARDDLNGVHKIMQWLSYIPASRGLPVPVLPHKTDVWDRDVTFQPVRGEQ

     (SEQ ID NO: 50)ACACA_RAT     YDPRWMLAGRPHPTQKGQWLSGFFDYGSFSEIMQPWAQTVVVGRARLGGIPVGVVAVETR
   (SEQ ID NO: 51)|ACACA_MOUSE    YDPRWMLAGRPHPTQKGQWLSGFFDYGSFSEIMQPWAQTVVVGRARLGGIPVGVVAVETR
    (SEQ ID NO: 52)|ACAC_YEAST    YDVRWMIEGRE--TESG-FEYGLFDKGSFFETLSGWAKGVVVGRARLGGIPLGVIGVETR
   (SEQ ID NO: 53)|ACACA_HUMAN    YDPRWMLAGRPHPTQKGQWLSGFFDYGSFSEIMQPWAQTVVVGRARLGGIPVGVVAVETR
   (SEQ ID NO: 54)|ACACA_HUMAN    YDPRWMLAGRPHPTQKGQWLSGFFDYGSFSEIMQPWAQTVVVGRARLGGIPVGVVAVETR
(SEQ ID NO: 55)|A0A0H3VB41_LIPST  YDVRWLIAGRE--DEEGGFEYGLFDKDSFQETLSGWARTVVVGRARLGGIPVGVIGVEVR
  (SEQ ID NO: 56)|F2QLC7_KOMPC    YDVRWMISGRE--TPDGEFESGLFDSGSFTETLSGWAKGVVVGRARLGGIPMGVIGVETR
  (SEQ ID NO: 57)|Q6CC91_YARLI    YDVRWLISGRT-LEDGAFESGLFDKDSFQETLSGWAKGVVVGRARLGGIPFGVIGVETA

     (SEQ ID NO: 50)ACACA_RAT     TVELSVPADPANLDSEAKIIQQAGQVWFPDSAFKTYQAIKDFNR-EGLPLMVFANWRGFS
   (SEQ ID NO: 51)|ACACA_MOUSE    TVELSIPADPANLDSEAKIIQQAGQVWFPDSAFKTYQAIKDFNR-EGLPLMVFANWRGFS
    (SEQ ID NO: 52)|ACAC_YEAST    TVENLIPADPANPNSAETLIQEPGQVWHPNSAFKTAQAINDFNNGEQLPMMILANWRGFS
   (SEQ ID NO: 53)|ACACA_HUMAN    TVELSIPADPANLDSEAKIIQQAGQVWFPDSAFKTYQAIKDFNR-EGLPLMVFANWRGFS
   (SEQ ID NO: 54)|ACACA_HUMAN    TVELSIPADPANLDSEAKIIQQAGQVWFPDSAFKTYQAIKDFNR-EGLPLMVFANWRGFS
(SEQ ID NO: 55)|A0A0H3VB41_LIPST  SVENIFPADPANPDSTEMVVQEAGQVWYPNSAFKTAQAINDFNHGEELPLVILANWRGFS
  (SEQ ID NO: 56)|F2QLC7_KOMPC    VTENLIPADPANPDSTEMMIQEAGQVWYPNSAFKTAQAINDFNNGEQLPLMILANWRGFS
  (SEQ ID NO: 57)|Q6CC91_YARLI    TVDNTTPADPANPDSIEMSTSEAGQVWYPNSAFKTSQAINDFNHGEALPLMILANWRGFS

     (SEQ ID NO: 50)ACACA_RAT     GGMKDMYDQVLKFGAYIVDGLRECSQPVMVYIPPQAELRGGSWVVIDPTINPRHMEMYAD
   (SEQ ID NO: 51)|ACACA_MOUSE    GGMKDMYDQVLKFGAYIVDGLRECSQPVMVYIPPQAELRGGSWVVIDPTINPRHMEMYAD
    (SEQ ID NO: 52)|ACAC_YEAST    GGQRDMFNEVLKYGSFIVDALVDYKQPIIIYIPPTGELRGGSWVVVDPTINADQMEMYAD
   (SEQ ID NO: 53)|ACACA_HUMAN    GGMKDMYDQVLKFGAYIVDGLRECCQPVLVYIPPQAELRGGSWVVIDSSINPRHMEMYAD
   (SEQ ID NO: 54)|ACACA_HUMAN    GGMKDMYDQVLKFGAYIVDGLRECCQPVLVYIPPQAELRGGSWVVIDSSINPRHMEMYAD
(SEQ ID NO: 55)|A0A0H3VB41_LIPST  GGQRDMYNEVLKYGSFIVDALVGYKQPIFVYIPPHAELRGGSWVVIDPTINSDQMEMYAD
  (SEQ ID NO: 56)|F2QLC7_KOMPC    GGQRDMYNEVLKYGSFIVDALVDFKQPIFTYIPPTAELRGGSWVVVDPTINEDMMEMYAD
  (SEQ ID NO: 57)|Q6CC91_YARLI    GGQRDMYNEVLKYGSFIVDALVDYKQPIMVYIPPTGELRGGSWVVVDPTINSDMMEMYAD

     (SEQ ID NO: 50)ACACA_RAT     RESRGSVLEPEGTVEIKFRKKDLVKTMRRVDPVYIRLAERLGTPELSPTERKELESKLKE
   (SEQ ID NO: 51)|ACACA_MOUSE    RESRGSVLEPEGTVEIKFRKKDLVKTMRRVDPVYIRLAERLGTPELSPTERKELESKLKE
    (SEQ ID NO: 52)|ACAC_YEAST    VNARAGVLEPQGMVGIKFRREKLLDTMNRLDDKYRELRSQLSNKSLAPEVHQQISKQLAD
   (SEQ ID NO: 53)|ACACA_HUMAN    RESRGSVLEPEGTVEIKFRRKDLVKTMRRVDPVYIHLAERLGTPELSTAERKELENKLKE
   (SEQ ID NO: 54)|ACACA_HUMAN    RESRGSVLEPEGTVEIKFRRKDLVKTMRRVDPVYIHLAERLGTPELSTAERKELENKLKE
(SEQ ID NO: 55)|A0A0H3VB41_LIPST  DEARAGVLEPEGMVGIKYRRDRLLETMTRLDPVYASLKRQADKKDLAPAIAQDLKVKLSE
  (SEQ ID NO: 56)|F2QLC7_KOMPC    VESRAGVLEPEGMVGIKYRKDKLLATMERLDAKYAELKSKVSDTSLSEKDVSEIKKQIEQ
  (SEQ ID NO: 57)|Q6CC91_YARLI    VESRGGVLEPEGMVGIKYRRDKLLDTMARLDPEYSSLKKQL---EESP-DSEELKVKLSV

     (SEQ ID NO: 50)ACACA_RAT     REEFLIPIYHQVAVQFADLHDTPGRMQEKGVINDILDWKTSRTFFYWRLRRLLLEDLVKK
   (SEQ ID NO: 51)|ACACA_MOUSE    REEFLIPIYHQVAVQFADLHDTPGRMQEKGVINDILDWKTSRTFFYWRLRRLLLEDLVKK
    (SEQ ID NO: 52)|ACAC_YEAST    RERELLPIYGQISLQFADLHDRSSRMVAKGVISKELEWTEARRFFFWRLRRRLNEEYLIK
   (SEQ ID NO: 53)|ACACA_HUMAN    REEFLIPIYHQVAVQFADLHDTPGRMQEKGVISDILDWKTSRTFFYWRLRRLLLEDLVKK
   (SEQ ID NO: 54)|ACACA_HUMAN    REEFLIPIYHQVAVQFADLHDTPGRMQEKGVISDILDWKTSRTFFYWRLRRLLLEDLVKK
(SEQ ID NO: 55)|A0A0H3VB41_LIPST  RESTLMPIYRQISLQFADLHDRAGRMKAKGTIREVLHWREARRFFYWRVRRRVGESYILR
  (SEQ ID NO: 56)|F2QLC7_KOMPC    REKQLLPIYAQISIQFADLHDRSGRMLAKGVIKKELEWVNSRRFFFWRVRRRLNEEYLIK
  (SEQ ID NO: 57)|Q6CC91_YARLI    REKSLMPIYQQISVQFADLHDRAGRMEAKGVIREALVWKDARRFFFWRIRRRLVEEYLIT

     (SEQ ID NO: 50)ACACA_RAT     KIHS-ANPELTDGQIQAMLRRWFVEVEGTVKAYVWDNNKDLVEWLEKQLTEEDGVRSVIE
   (SEQ ID NO: 51)|ACACA_MOUSE    KIHN-ANPELTDGQIQAMLRRWFVEVEGTVKAYVWDNNKDLVEWLEKQLTEEDGVRSVIE
    (SEQ ID NO: 52)|ACAC_YEAST    RLSHQVG-EASRLEKIARIRSWYPA------SVDHEDDRQVATWIEEN-------YKTLD
   (SEQ ID NO: 53)|ACACA_HUMAN    KIHN-ANPELTDGQIQAMLRRWFVEVEGTVKAYVWDNNKDLAEWLEKQLTEEDGVHSVIE
   (SEQ ID NO: 54)|ACACA_HUMAN    KIHN-ANPELTDGQIQAMLRRWFVEVEGTVKAYVWDNNKDLAEWLEKQLTEEDGVHSVIE
(SEQ ID NO: 55)|A0A0H3VB41_LIPST  DLEA-ANPKSTRLERVARLKSWYAEA-----GINESSDADVASWIEKS-------GAAIT
  (SEQ ID NO: 56)|F2QLC7_KOMPC    RITEFLSASATRLDKISRINSWLPT------SIDLEDDQKVAIWLEEN-------RKALD
  (SEQ ID NO: 57)|Q6CC91_YARLI    KINSIL-PSCTRLECLARIKSWKPA------TLDQGSDRGVAEWFDEN-------SDAVS

     (SEQ ID NO: 50)ACACA_RAT     ENIKYISRDYVLKQIRSLVQANPEVAMDSIVHMTQHISPTQRAEVVRILSTMDSPST
   (SEQ ID NO: 51)|ACACA_MOUSE    ENIKYISRDYVLKQIRSLVQANPEVAMDSIVHMTQHISPTQRAEVVRILSTMDSPST
    (SEQ ID NO: 52)|ACAC_YEAST    DKLKGLKLESFAQDLAKKIRSDHDNAIDGLSEVIKMLSTDDKEKLLKTLK-------
   (SEQ ID NO: 53)|ACACA_HUMAN    ENIKCISRDYVLKQIRSLVQANPEVAMDSIIHMTQHISPTQRAEVIRILSTMDSPST
   (SEQ ID NO: 54)|ACACA_HUMAN    ENIKCISRDYVLKQIRSLVQANPEVAMDSIIHMTQHISPTQRAEVIRILSTMDSPST
(SEQ ID NO: 55)|A0A0H3VB41_LIPST  SKVKQVRKDAKIQDLLALVRADKDVALQGLVESLKALSTEERDAIFKQASN------
  (SEQ ID NO: 56)|F2QLC7_KOMPC    ANIKELRAEHVRRTLATLVRTDMDTTSKSLAELINLLPETEKESILSKIKS------
  (SEQ ID NO: 57)|Q6CC91_YARLI    ARLSELKKDASAQSFASQLRKDRQGTLQGMKQALASLSEAERAELLKGL--------
```

MULTI-SUBSTRATE METABOLISM FOR IMPROVING BIOMASS AND LIPID PRODUCTION

CROSS REFERENCE TO RELATED APPLICATIONS

The current application claims the benefit of priority to U.S. Provisional Application Ser. No. 62/665,809, filed on May 2, 2018, which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVI_019_02_SeqList_ST25.txt, date recorded: May 2, 2019, file size 326 kilobytes).

TECHNICAL FIELD

This application relates to recombinant microorganisms useful in the biosynthesis of biomass or one or more lipid from one or more fatty acid and one or more simple carbon co-substrate. The one or more lipid can be unsaturated C6-C24 fatty acids, fatty alcohols, aldehydes, and acetates which may be useful as final products or precursors to insect pheromones, fragrances, flavors, and polymer intermediates. The application further relates to methods to improve biomass or lipid production in a microorganism from one or more fatty acid and one or more simple carbon co-substrate. The application also relates to methods of producing one or more lipid using the recombinant microorganisms, as well as compositions comprising the recombinant microorganisms and/or optionally one or more of the product lipid.

BACKGROUND

Derivatives of microbial lipids can be harnessed as precursors of fuels, and as chemicals used in detergent formulation, fragrances, and insect control agents. By applying metabolic engineering strategies to increase lipid content in some microbes, several microbial oleochemicals have been produced at commercial scale. A pathway to produce lipids from simple carbon sources such as glucose, fructose, and glycerol is referred to as a de novo pathway.

De novo lipid biosynthetic pathways rely on several key enzymes, such as fatty acid synthase. De novo pathways yield a broad range of fatty acid moieties with differing chain lengths and unsaturation. Engineering microbial de novo pathways for the purpose of enriching certain lipid species is challenging. De novo lipid pathways also require reducing equivalents. Biosynthetic pathways, such as an insect fatty alcohol pathway to generate pheromone precursors, require NADPH and NADH. Therefore, an improvement in reducing equivalent pool is needed to achieve high level lipid production.

Furthermore, in the presence of multiple substrates, metabolic regulations prevent the full utilization of biosynthetic pathways for the formation of lipids and biomass. The present disclosure addresses these challenges with the development of microorganisms modified to improve production of valuable products such as lipids from multiple substrates while maintaining or increasing biomass of the microorganism. Products produced by these modified microorganisms can include a wide-range of unsaturated $C_6$-$C_{24}$ fatty acids, fatty alcohols, aldehydes, and acetates including insect pheromones.

SUMMARY OF THE DISCLOSURE

The present application relates to microorganisms modified to improve production of valuable products such as lipids from one or more fatty acids and one or more simple carbon co-substrates while maintaining or increasing biomass of the microorganism. The recombinant microorganisms described herein may be used for the production of at least one compound, such as an insect pheromone, a fragrance, or a flavoring agent. In some embodiments, at least one compound comprise unsaturated $C_6$-$C_{24}$ fatty acids, fatty alcohols, aldehydes, and acetates.

In one aspect, the application relates to a recombinant microorganism having improved production of biomass or improved production of one or more lipid from one or more fatty acids and one or more simple carbon co-substrates, wherein the recombinant microorganism comprises one or more modifications associated with: tricarboxylic acid cycle; lipid synthesis; reducing equivalent availability; metabolic intermediates availability; and/or increased product purity, wherein the recombinant microorganism has improved production of biomass or improved production of one or more lipids compared to a microorganism without the same modifications.

In some embodiments, the one or more modifications associated with comprising tricarboxylic acid cycle comprises the overexpression of at least one endogenous and/or exogenous nucleic acid molecule encoding an AMP-insensitive isocitrate dehydrogenase (IDH) variant in the recombinant microorganism. In certain embodiments, the at least one nucleic acid molecule encodes for a protein that has at least 70% sequence identity, at least 80% sequence identity, or at least 90% sequence identity to IDH from *Escherichia coli, Mycobacterium smegmatis, Acidithiobacillus thiooxidans*, or *Yarrowia lipolytica*. In further embodiments, the at least one nucleic acid molecule is from *Yarrowia lipolytica* and comprises isoleucine to alanine substitutions at amino acid positions 279 and 280 of XP_503571.2 (SEQ ID NO: 30). In some embodiments, the one or more modifications associated with tricarboxylic acid cycle results in extended activation of the tricarboxylic acid cycle.

In some embodiments, the one or more modifications associated with tricarboxylic acid cycle or one or more metabolic intermediates availability comprises the overexpression of at least one endogenous and/or exogenous nucleic acid molecule encoding a pyruvate transporter in the recombinant microorganism. In other embodiments, the one or more metabolic intermediates availability comprises mitochondrial pyruvate availability. In certain embodiments, the at least one nucleic acid molecule encodes for a protein that has at least 70% sequence identity, at least 80% sequence identity, or at least 90% sequence identity to pyruvate transporter from *Saccharomyces cerevisiae, Hanseniaspora osmophila, Yarrowia lipolytica*, or *Talaromyces marneffei* PM1. In further embodiments, the pyruvate transporter is selected from *Saccharomyces cerevisiae* mpc1, *Saccharomyces cerevisiae* mpc3 (NP 011759.1-SEQ ID NO: 31), *Hanseniaspora osmophila* mpc3 (0EJ86292.1), *Yarrowia lipolytica* mpc, and *Talaromyces marneffei* PM1 mpc3 (KFX48982.1), or homolog thereof. In yet a further embodiment, the recombinant microorganism is *Saccharomyces cerevisiae* comprising a deletion, disruption, or loss of function mutation in a gene encoding an mpc2 pyruvate transporter. In some embodiments, the recombinant microorganism is *Yarrowia* lipolytica.

In some embodiments, the one or more modifications associated with lipid synthesis comprises alleviation of acetyl-CoA carboxylase (ACC) inhibition. In certain embodiments, alleviation of ACC inhibition comprises the replacement of the endogenous ACC, or overexpression of at least one endogenous and/or exogenous nucleic acid molecule encoding a feedback-insensitive ACC variant in the recombinant microorganism. In further embodiments, the at least one nucleic acid molecule encodes for a protein that has at least 70% sequence identity, at least 80% sequence identity, or at least 90% sequence identity to ACC from *Mus musculus, Rattus norvegicus*, or *Homo sapiens.*

In some embodiments, the one or more modifications associated with reducing equivalent availability comprises the overexpression of at least one endogenous and/or exogenous nucleic acid molecule encoding an NADP/NAD-dependent isocitrate dehydrogenase (IDH) in the cytosol of the recombinant microorganism. In certain embodiments, the at least one nucleic acid molecule encodes for a protein that has at least 70% sequence identity, at least 80% sequence identity, or at least 90% sequence identity to IDH from *Escherichia coli, Mycobacterium smegmatis, Acidithiobacillus thiooxidans*, or *Yarrowia lipolytica*. In further embodiments, the IDH is selected from *Escherichia coli* Idh (WP_000444484.1-SEQ ID NO: 21), *Mycobacterium smegmatis* Icd2 (WP_011727802.1-SEQ ID NO: 23), *Acidithiobacillus thiooxidans* Idh (PDB: 2D4V_A-SEQ ID NO: 22), and *Yarrowia lipolytica* Idh1 (XP_503571.2-SEQ ID NO: 20 for mutant, or SEQ ID NO: 30 for wild type), or homolog thereof.

In some embodiments, the one or more modifications associated with reducing equivalent availability further comprises the overexpression of at least one endogenous and/or exogenous nucleic acid encoding an aconitase in the cytosol of the recombinant microorganism. In certain embodiments, the at least one endogenous and/or exogenous nucleic acid molecule encoding the IDH and the at least one endogenous and/or exogenous nucleic acid molecule encoding the aconitase lack a sequence encoding a mitochondrial-targeting peptide.

In some embodiments, the one or more modifications associated with reducing equivalent availability or one or more metabolic intermediates availability comprises the overexpression of at least one endogenous or exogenous nucleic acid encoding a citrate transporter in the recombinant microorganism. In certain embodiments, the one or more intermediate comprises cytosolic citrate/isocitrate. In further embodiments, the at least one nucleic acid molecule encodes for a protein that has at least 70% sequence identity, at least 80% sequence identity, or at least 90% sequence identity to a citrate transporter from *Yarrowia lipolytica, Saccharomyces cerevisiae, Rattus norvegicus, Caenorhabditis elegans*, or *Caliqus clemensi*. In yet further embodiments, the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

In some embodiments, the one or more modifications associated with reducing equivalent availability comprises the overexpression of at least one exogenous nucleic acid molecule encoding a decarboxylating malic enzyme in the recombinant microorganism. In certain embodiments, the at least one nucleic acid molecule encodes for a protein that has at least 70% sequence identity, at least 80% sequence identity, or at least 90% sequence identity to a decarboxylating malic enzyme from *Arabidopsis thaliana, Amaranthus hypochondriacus, Rhizobium meliloti, Solanum tuberosum, Homo sapiens*, or *Escherichia coli*. In further embodiments, the decarboxylating malic enzyme is selected from *Arabidopsis thaliana* Q9SIU0, *Amaranthus hypochondriacus* P37224, *Rhizobium meliloti* 030807, *Solanum tuberosum* P37221, *Homo sapiens* Q16798, and *Escherichia coli* P26616, or homolog thereof. In yet a further embodiment, the decarboxylating malic enzyme lacks a sequence encoding a mitochondrial-targeting peptide.

In some embodiments, the one or more modifications associated with one or more metabolic intermediates availability comprises the overexpression of at least one endogenous and/or exogenous nucleic acid encoding an ATP-citrate lyase in the recombinant microorganism. In certain embodiments, the one or more intermediates availability comprises cytosolic oxaloacetate availability. In further embodiments, the at least one nucleic acid molecule encodes for a protein that has at least 70% sequence identity, at least 80% sequence identity, or at least 90% sequence identity to an ATP-citrate lyase from *Saccharomyces cerevisiae, Yarrowia lipolytica, Mus musculus*, and *Aspergillus niger*. In a yet further embodiment, the ATP-citrate lyase is selected from *Mus musculus* NP 001186225.1, *Mus musculus* NP 598798.1, *Aspergillus niger* XP_001394055.1, and *Aspergillus niger* XP_001394057.1, or homolog thereof.

In some embodiments, the one or more modifications associated with comprising reducing equivalent availability comprises one or more modifications in the pentose phosphate pathway (PPP) in the recombinant microorganism. In certain embodiments, the one or more modifications in the PPP comprises one or more of: downregulation of hexose kinase activity; upregulation of one or more oxidative PPP enzyme activity; downregulation of fructose-6-phosphate kinase activity; and/or expression of one or more oxidative PPP enzyme variant. In further embodiments, the upregulation of one or more oxidative PPP enzyme activity comprises the overexpression of one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1). In yet a further embodiment, the downregulation of hexose kinase activity and/or fructose-6-phosphate kinase activity comprises deletion, disruption, and/or mutation of one or more endogenous gene encoding one or more hexose kinase enzyme and/or fructose-6-phosphate kinase enzyme. In some embodiments, the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1). In certain embodiments, the one or more nucleic acid molecule encodes for a protein that has at least 70% sequence identity, at least 80% sequence identity, or at least 90% sequence identity to an NAD-dependent glucose-6-phosphate dehydrogenase (ZWF1) from *Leuconostoc*. In further embodiments, the NAD-dependent glucose-6-phosphate dehydrogenase (ZWF1) is selected from *Leuconostoc* AAA25265.1 and *Leuconostoc* P11411, or homolog thereof. In certain embodiments, the one or more nucleic acid molecule encodes for a protein that has at least 70% sequence identity, at least 80% sequence identity, or at least 90% sequence identity to an NAD-dependent 6-phosphogluconate dehydrogenase (GND1) from *Bradyrhizobium* or *Methylobacillus*. In further embodiments, the NAD-dependent 6-phosphogluconate dehydrogenase (GND1) is selected from *Bradyrhizobium* WP_012029377.1, *Bradyrhizobium* A4YZZ8, *Methylobacillus* AAF34407.1, and *Methylobacillus* Q9L9P8, or homolog thereof.

In some embodiments, the one or more modifications associated with reducing equivalent availability comprises downregulation of mannitol synthesis pathway in the recombinant microorganism. In certain embodiments, downregulation of mannitol synthesis pathway comprises deletion, disruption, and/or mutation of one or more gene encoding an NADPH-dependent mannitol dehydrogenase and/or an aldo-keto reductase. In further embodiments, the one or more gene encoding an NADPH-dependent mannitol dehydrogenase is selected from YALI0B16192g, YALI0D18964g, and YALI0E12463g, or homolog thereof. In further embodiments, the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0C09119g, YALI0D04092g, YALI0B15268g, YALI0C00319g, and YALI0A19910g, or homolog thereof.

In some embodiments, the one or more modifications associated with reducing equivalent availability comprises decoupling and increasing glucose uptake in the recombinant microorganism. In certain embodiments, decoupling and increasing glucose uptake comprises: upregulation of hexose transporter activity; and/or downregulation of hexose kinase activity. In further embodiments, the upregulation of one or more hexose transporter activity comprises the overexpression of one or more endogenous and/or exogenous nucleic acid molecule encoding a hexose transporter operably linked to one or more heterologous promoters. In some embodiments, the one or more endogenous and/or exogenous nucleic acid molecule encodes for a protein that has at least 70% sequence identity, at least 80% sequence identity, or at least 90% sequence identity to a hexose transporter from *Yarrowia lipolytica*. In certain embodiments, the one or more endogenous and/or exogenous nucleic acid molecule encoding a hexose transporter is selected from YALI0A14212g, YALI0D01111g, YALI0D00363g, YALI0C16522g, and YALI0F25553g, or homolog thereof. In some embodiments, the downregulation of hexose kinase activity comprises deletion, disruption, and/or mutation of one or more endogenous gene encoding one or more hexose kinase enzyme.

In some embodiments, the one or more modifications associated with reducing equivalent availability, one or more metabolic intermediates availability, or increased product purity comprises downregulation or inhibition of acetyl-CoA carboxylase (ACC) activity in the recombinant microorganism. In certain embodiments, the downregulation or inhibition of ACC activity comprises deletion, disruption, and/or mutation of one or more endogenous gene encoding one or more ACC enzyme.

In some embodiments of a recombinant microorganism having improved production of biomass or improved production of one or more lipid from one or more fatty acid and one or more simple carbon co-substrates, the one or more fatty acid co-substrate is a saturated fatty acid. In some embodiments of a recombinant microorganism having improved production of biomass or improved production of one or more lipid from one or more fatty acid and one or more simple carbon co-substrates, the one or more simple carbon co-substrate is selected from glucose, fructose, and glycerol.

In some embodiments of a recombinant microorganism having improved production of biomass or improved production of one or more lipid from one or more fatty acid and one or more simple carbon co-substrates, the improved production of one or more lipid comprises improved production of one or more mono- or poly-unsaturated $C_6$-$C_{24}$ fatty acid, fatty alcohol, aldehyde, or acetate. In certain embodiments, the one or more mono- or poly-unsaturated $C_6$-$C_{24}$ fatty acid, fatty alcohol, aldehyde, or acetate is an insect pheromone. In further embodiments, the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

In some embodiments of a recombinant microorganism having improved production of biomass or improved production of one or more lipid from one or more fatty acid and one or more simple carbon co-substrates, the recombinant microorganism is a eukaryotic microorganism. In certain embodiments, the eukaryotic microorganism is a yeast. In further embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*. In yet a further embodiment, the yeast is an oleaginous yeast. In some embodiments, the oleaginous yeast is a member of a genus selected from the group consisting of *Yarrowia, Candida, Rhodotorula, Rhodosporidium, Cryptococcus, Trichosporon*, and *Lipomyces*. In certain embodiments, the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T cutaneum, Cryptococcus curvatus, R. glutinis*, and *R. graminis*.

In another aspect, the present application provides methods of producing one or more lipid using a recombinant microorganism as described herein. In one embodiment, the method includes cultivating the recombinant microorganism in a culture medium containing a feedstock providing one or more simple carbon and one or more fatty acid co-substrates until the one or more lipid is produced.

In another aspect, the present application provides methods of producing a recombinant microorganism having improved production of biomass or improved production of one or more lipid from one or more fatty acid and one or more simple carbon co-substrates, comprising introducing into a microorganism one or more modifications associated with: tricarboxylic acid cycle; lipid synthesis; reducing equivalent availability; one or more metabolic intermediates availability; and/or increased product purity, wherein the introducing one or more modifications yields a recombinant microorganism having improved production of biomass or improved production of one or more lipid compared to a microorganism not comprising the same modifications.

In yet another aspect, the present application provides compositions comprising one or more of the recombinant microorganisms described herein. In certain embodiments, the composition may further comprise one or more lipid produced by the recombinant microorganism. In some embodiments, the composition may further comprise one or more mono- or poly-unsaturated $C_6$-$C_{24}$ fatty acid, fatty alcohol, aldehyde, or acetate produced by the recombinant microorganism. In some embodiments, the composition may further comprise one or more insect pheromone produced by the recombinant microorganism.

BRIEF DESCRIPTION OF DRAWINGS

Illustrative embodiments of the disclosure are illustrated in the drawings, in which:

FIG. 11—Alignment of feedback insensitive acetyl-CoA carboxylase (ACC) enzymes of the present disclosure.

DETAILED DESCRIPTION

Definitions

Figure 1:
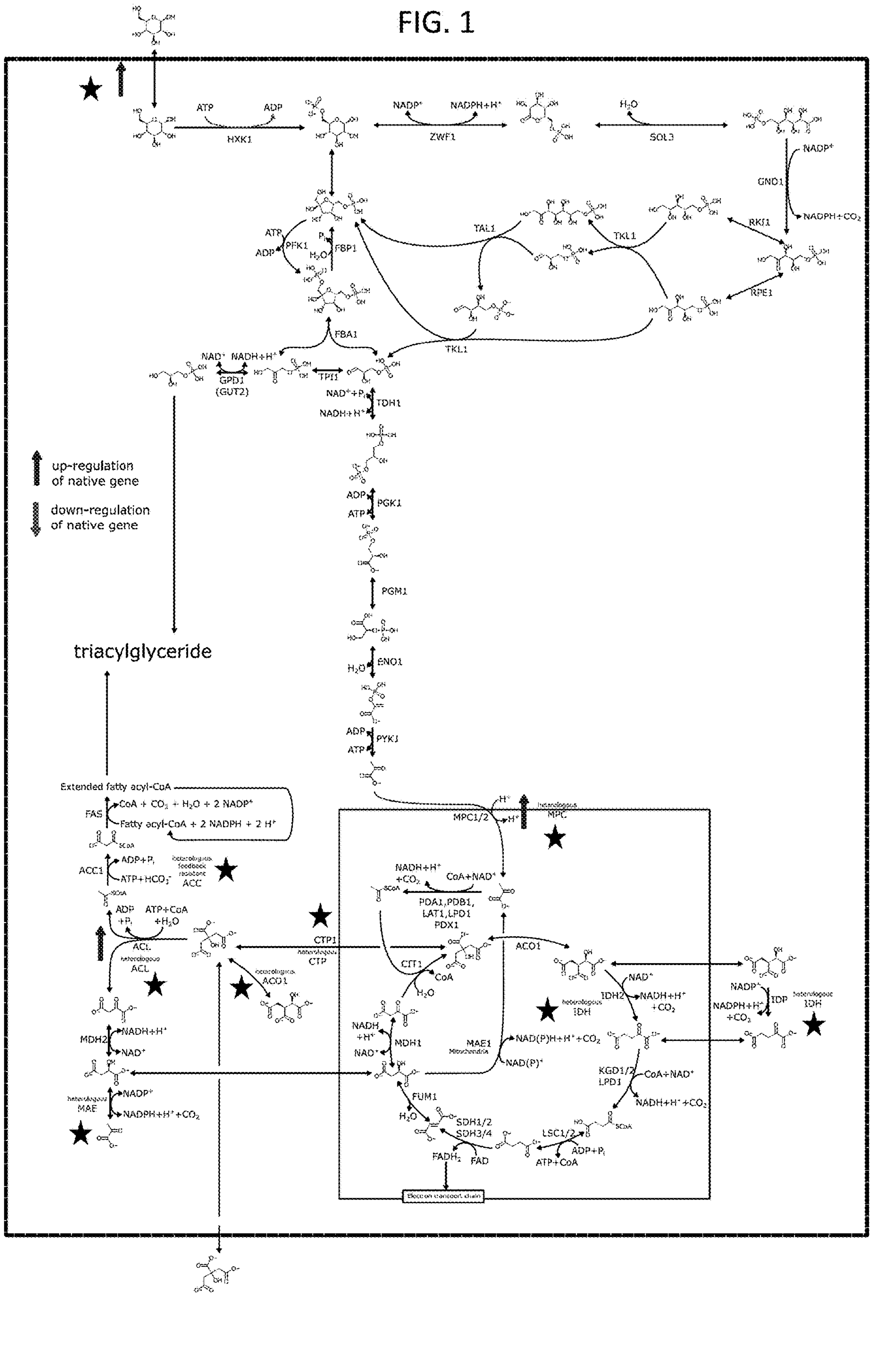
FIG. 1—Lipid biosynthetic pathway showing genetic modifications of the present disclosure. Enzymes with stars are identified as candidates for increasing de novo lipid synthesis or lipid synthesis from fatty acid precursors.
Figure 2:
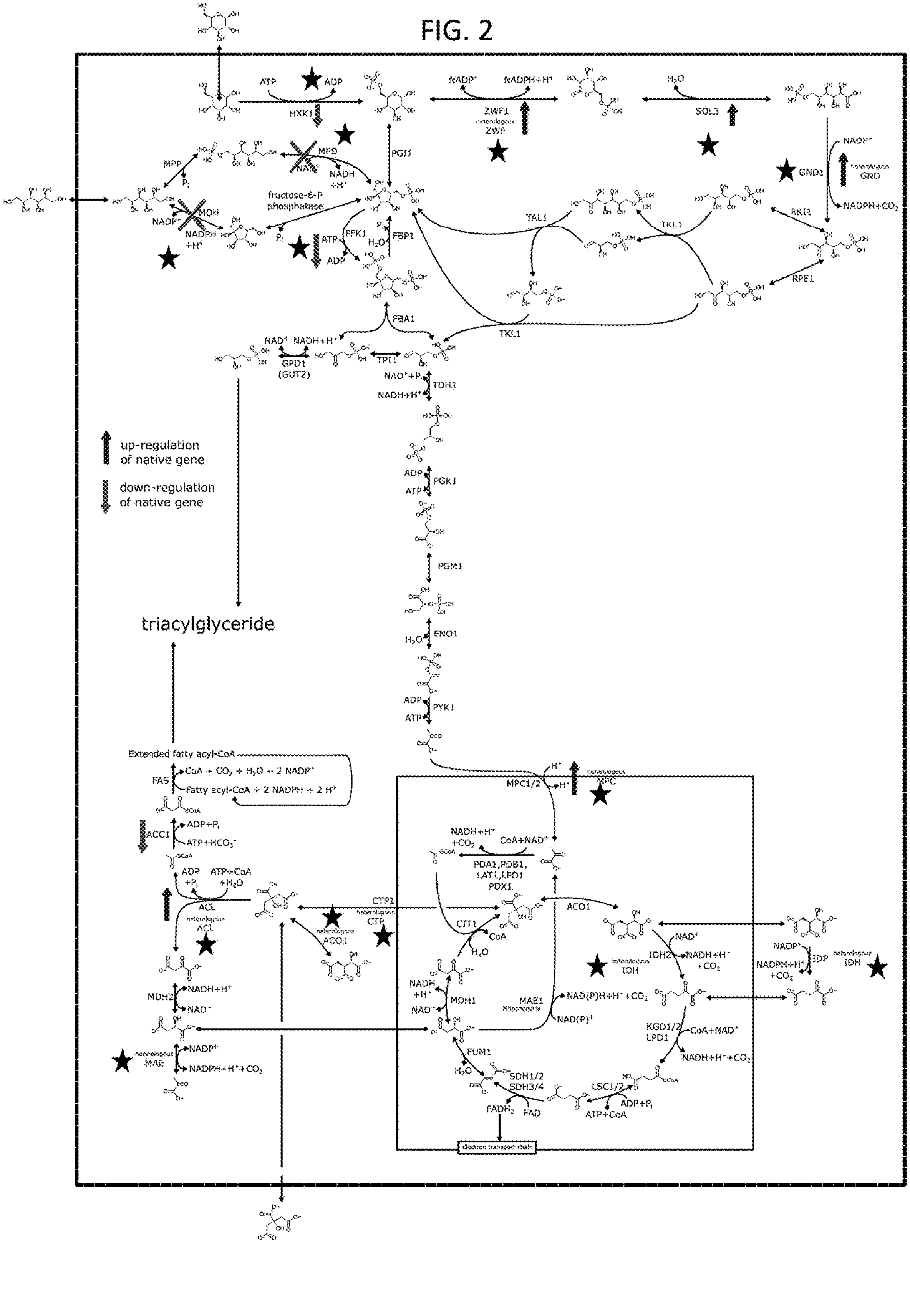
FIG. 2—Lipid biosynthetic pathway showing genetic modifications of the present disclosure. Enzymes with stars are identified as candidates for increasing cofactors important for lipid synthesis.

The following definitions and abbreviations are to be used for the interpretation of the disclosure.

As used herein and in the appended claims, the singular forms “a,” “an,” and “the” include plural referents unless the context clearly dictates otherwise. Thus, for example, reference to “a pheromone” includes a plurality of such pheromones and reference to “the microorganism” includes reference to one or more microorganisms, and so forth.

As used herein, the terms “comprises,” “comprising,” “includes,” “including,” “has,” “having, “contains,” “containing,” or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, “or” refers to an inclusive “or” and not to an exclusive “or.”

The terms “about” and “around,” as used herein to modify a numerical value, indicate a close range surrounding that explicit value. If “X” were the value, “about X” or “around X” would indicate a value from 0.9X to 1.1X, or, in some embodiments, a value from 0.95X to 1.05X. Any reference to “about X” or “around X” specifically indicates at least the values X, 0.95X, 0.96X, 0.97X, 0.98X, 0.99X, 1.01X, 1.02X, 1.03X, 1.04X, and 1.05X. Thus, “about X” and “around X” are intended to teach and provide written description support for a claim limitation of, e.g., “0.98X.”

As used herein, the terms “microbial,” “microbial organism,” and “microorganism” include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganism. In some embodiments, the prokaryotic microorganisms are bacteria. “Bacteria”, or “eubacteria”, refers to a domain of prokaryotic organisms. Bacteria include at least eleven distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho* thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides.

As used herein, the term "non-naturally occurring," when used in reference to a microorganism organism or enzyme activity of the disclosure, is intended to mean that the microorganism organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s).

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution.

The term "fatty acid" as used herein refers to a compound of structure R—COOH, wherein R is a $C_6$ to $C_{24}$ saturated, unsaturated, linear, branched or cyclic hydrocarbon and the carboxyl group is at position 1. In a particular embodiment, R is a $C_6$ to $C_{24}$ saturated or unsaturated linear hydrocarbon and the carboxyl group is at position 1.

The term "fatty alcohol" as used herein refers to an aliphatic alcohol having the formula R—OH, wherein R is a $C_6$ to $C_{24}$ saturated, unsaturated, linear, branched or cyclic hydrocarbon. In a particular embodiment, R is a $C_6$ to $C_{24}$ saturated or unsaturated linear hydrocarbon.

The term "fatty acyl-CoA" refers to a compound having the structure R—(CO)—S—$R_1$, wherein $R_1$ is Coenzyme A, and the term "fatty acyl-ACP" refers to a compound having the structure R—(CO)—S—$R_1$, wherein $R_1$ is an acyl carrier protein ACP.

The term "one or more modifications associated with . . . " refer to one or more modifications in, for example: a biochemical pathway; biological process; growth; cell division; tricarboxylic acid cycle; lipid synthesis; the availability of cofactors, reducing equivalents or metabolic intermediates; and/or product purity in a microorganism or microbial host. The one or more modifications can include, but is not limited to: expression or overexpression of genes or gene variants; deletion, disruption or downregulation of genes; increasing or decreasing activities of gene products; altered localization of a protein within the microorganism, for example, from mitochondria to cytosol or vice versa; alleviation of enzyme feedback inhibition; uptake or secretion of compounds, nutrients, or molecules.

The term "Z11-16 acid selectivity" refers to the degree to which the recombinant microorganism produces Z11-16 acid from palmitate substrate over other lipid variants. Microorganisms that produce higher relative levels of Z11-16 acid over other C6-C24 carbon chain lipids are considered to have higher Z11-16 acid selectivity. Z11-16 acid selectivity can be calculated as done in Example 2, by the formula=[Z11-16Acid]/([Z9-16Acid]+[Z11-16Acid]+[18Acid]+[Z9-18Acid]+[Z11-18Acid]+[Z13-18Acid]+[Z9Z12-18Acid].

The term reduced or eliminated activity refers to enzymes which are either expressed at lower rates than their wild type counterparts, or have been somehow modified to exhibit less enzymatic activity when compared to similarly expressed wild type versions of the enzyme. The reduction in the activity of proteins can be achieved by various methods known to the person skilled in the art such as, for example: (i) through the inhibition or reduction in the expression of the gene coding for the target enzyme; (ii) by partial or complete deletion of the genes coding for the target enzyme, (iii) by expression of non-functional genes that compete against the functional native target enzyme; and/or by inhibition or reduction in the activity of the expressed genes. The inhibition or reduction of the expression of a gene coding for a protein can, for example, be accomplished by inhibition or reduction of the transcription of the coding gene or the translation of the mRNA formed. The deletion of the coding genes can be performed, for example, by a removal of the genes by means of deletion cassettes. The expression of a dysfunctional or activity-reduced gene product can be accomplished, for example, by insertion, substitution or point mutation in the gene coding for the protein. In some embodiments, the deletion of a coding gene is a reduction in activity.

The term "control microorganism" refers to a microorganism that is substantially identical to the referenced recombinant microorganism except for the referenced genetic alteration. References to improvements of the recombinant microorganisms, such as improved lipid production, improved Z11-16 acid selectivity, or improved biomass, should be understood as improvements over a control microorganism lacking the referenced genetic change.

As used herein, the term "bypass pathway culture" refers to a dual substrate culture comprising growth media with a fatty acid precursor substrate and a simple carbon co-substrate. Bypass pathway cultures are designed to bypass de novo lipid synthesis by providing a fatty acid precursor that a microorganism can convert to the final desired desaturated lipid. The simple carbon co-substrate provides the energy input required to maintain the culture, allowing the fatty acid precursor to be used in the final steps of the desired lipid biosynthesis.

INTRODUCTION

The present disclosure addresses the need for novel technologies for improved production of biomass or one or more lipid from multiple substrates. The present disclosure solves the problem of carbon utilization to unwanted metabolites in an engineered microbial system. The present disclosure solves the problem of insufficient reducing equivalent pool for high lipid production. Specifically, the present inventors have addressed these problems with the development of recombinant microorganisms having one or more modifications associated with: tricarboxylic acid cycle; lipid synthesis; reducing equivalent availability; one or more metabolic intermediates availability; and/or increased product purity.

In one embodiment, the one or more lipid can be unsaturated $C_6$-$C_{24}$ fatty acids, alcohols, aldehydes, and acetates including final products or fatty acid precursors of insect pheromones, fragrances, flavors, and polymer intermediates produced from one or more fatty acid and one or more simple carbon co-substrates. Thus, aspects of the disclosure are based on the inventors' discovery that recombinant microorganisms can be engineered to improve production of valuable products such as lipids from one or more fatty acid and one or more simple carbon co-substrates while maintaining or increasing biomass of the recombinant microorganism.

Derivatives of microbial lipids can be harnessed as precursors of fuels, and as chemicals used in detergent formulation, fragrances, and insect control agents. By applying metabolic engineering strategies to increase lipid content in some microbes, several microbial oleochemicals have been produced at commercial scale. Lipid biosynthetic pathways from simple carbon sources such as glucose, fructose, and glycerol (de novo pathway) generate a mixture of fatty acids with different chain lengths and degrees of unsaturation. For certain commercial applications, however, increasing biosynthetic selectivity towards one or a group of some fatty acid species is desirable.

De novo lipid biosynthetic pathways rely on several key enzymes. Fatty acid synthase is a cytosolic enzyme ensemble which catalyzes the polymerization of acyl-CoA with malonyl-CoA. At a certain length, elongation of fatty acyl-ACP polymers is terminated by transacylase activity to produce fatty acyl-CoAs, the precursors of lipids used in diverse functions (e.g. membrane building blocks such as phospholipid, and sphingolipid, or energy storage in the form of mono-, di-, triglycerides, and sterol esters). Prior to conversion into membrane lipid bilayers and storage lipids, fatty acyl-CoAs are processed in the endoplasmic reticulum to undergo desaturations or further elongation. De novo pathways yield a broad range of fatty acid moieties with differing chain lengths and unsaturation. Engineering microbial de novo pathways for the purpose of enriching certain lipid species is challenging, and may compromise host viability because of the interconnectivity of fatty acid enzyme complexes (especially in eukaryotic cells such as yeasts) and the importance of certain fatty acid species on cellular function. De novo lipid pathways are also NADPH intensive. Biosynthetic pathways, such as an insect fatty alcohol pathway to generate pheromone precursors, require NADPH and NADH. Therefore, an improvement in reducing equivalent pool is needed to achieve high level lipid production.

To bypass the limitations in de novo pathway engineering, a strategy was developed to utilize inexpensive plant derived saturated fatty acids in addition to sugar as bioconversion co-substrates to enrich the synthesis of select unsaturated lipid species (bypass pathway). In the presence of multiple substrates, however, metabolic regulations prevent the full utilization of both de novo and bypass pathways for the formation of lipids and biomass. Under a nitrogen-starved and glucose-rich environment, low levels of intracellular AMP reduce the activity of isocitrate dehydrogenase (IDH), a key allosteric enzyme in the TCA cycle in yeast mitochondria. The reduction of IDH activity slows the TCA cycle used for synthesis of biomass and reducing equivalents, and accumulates citrate (the equilibrium form of isocitrate). Build-up of isocitrate in mitochondria creates citrate overflow to the cytosolic compartment. This cytosolic citrate is cleaved into oxaloacetate and acetyl-CoA, the committed precursor of fatty acid synthesis, eliciting lipogenesis and reducing growth. High citrate accumulation has been observed in oleagenic yeast cultivation under nitrogen-limited conditions. Therefore, it is desirable to engineer an oleochemical production host to repurpose citrate for improvement in biomass generation. This can be achieved by an extended activation of the TCA cycle during lipogenesis, while increasing the malonyl-CoA pool, the lipid precursor. Additionally, the number of malonyl-CoA generated for every molecule of glucose consumed can be reduced by the existence of the mannitol synthesis pathway. The NADPH required for 18-carbon triacylglyceride synthesis is balanced if 0.35 moles of mannitol is generated for every mole of glucose consumed resulting in 0.92 moles of malonyl-CoA, 0.04 moles glycerol, and 1.65 moles of NADPH. Alternative sources of NADPH may reduce the required flux through the mannitol pathway and balance NADPH generation. Therefore, in some embodiments, the deletion of the mannitol synthesis pathway can be used to enhance generation of reducing equivalents and improve glucose yields to support production of fatty acid derived products.

Another aspect of the invention relates to increasing the availability of reducing equivalents in the cytosolic compartment. Many heterologous proteins are expressed in the cytosol, or with an active site that is exposed to the cytosol. Of interest is a system which expresses insect desaturases and alcohol forming reductases to generate insect pheromone fatty alcohol precursors. These desaturases and reductases are bound to the endoplasmic reticulum membrane with active sites facing the cytosol. They require cytosolic NADH and NADPH as cofactors to transform a fatty acid precursor into an unsaturated fatty acid, and subsequently into a fatty alcohol. Glycolysis and the pentose phosphate pathway can provide the necessary reducing equivalents. The majority of NADPH required for de novo or bypass fatty acid synthesis in *Y. lipolytica* comes from the oxidative branch of the pentose phosphate pathway. Under growth conditions which elicit fatty acid synthesis and lipid storage, the majority of glucose flux can be funneled through the pentose phosphate pathway in order to supply the NADPH required for fatty acid synthesis. Depending on various factors such as feeding strategy and cultivation conditions, however, the pool of reducing equivalents in the cytosol may not be sufficient to support heterologous high fatty alcohol production. Therefore, it is desirable to engineer an oleochemical production host with high cytosolic pool of reducing equivalents to allow high level synthesis of lipid products.

Overall, the disclosure describes methods to engineer oleagenic microbes to maximize the conversion efficiency of carbons derived from simple carbons in conjunction with fatty acids for improved microbial production of chemicals such as lipids and fatty acid derivatives by re-directing biosynthetic pathways for reducing overflow metabolites, rebalancing and increasing reducing equivalent, and increasing lipid precursor metabolite.

In one aspect, methods for increasing biomass and precursors of lipid synthesis and microorganisms capable of improved production of biomass and one or more lipid are disclosed.

In some embodiments, microorganisms are modified to alleviate inhibition of isocitrate dehydrogenase (IDH) in the TCA cycle. Specifically, in some embodiments, the locus which corresponds to IDH is replaced with a sequence of an AMP-insensitive IDH variant. Examples of AMP-insensitive IDH variants can be sourced from multiple organisms (Table 1). AMP-insensitive IDH variant can also be engineered in *Y. lipolytica* IDH1 by mutations of I279A and I280A (Table 1). An AMP-insensitive IDH variant can also be introduced in addition to the native IDH variant to achieve a similar phenotype.

TABLE 1

Exemplary isocitrate dehydrogenase (IDH) enzymes

| Species | Enzyme | Gene ID/ Protein ID | co-factor | Inhibition |
|---|---|---|---|---|
| *Escherichia coli* | Idh | WP_000444484.1 (SEQ ID NO: 21) | NADP | phosphorylation (inhibiting via AceK) |
| *Mycobacterium smegmatis* | Icd2 | WP_011727802.1 (SEQ ID NO: 23) | NADP | feedback via glyoxylate (activating) |
| *Acidithiobacillus thiooxidans* | Idh | PDB: 2D4V_A (SEQ ID NO: 22) | NAD | likely phosphorylation |
| *Yarrowia lipolytica* | Idh1 | XP_503571.2 (SEQ ID NO: 30) AMP-insensitive variant in (SEQ ID NO: 20) | NAD | AMP |

In some embodiments, microorganisms are modified to increase mitochondrial pyruvate pool. Pyruvate is a precursor of multiple enzymes involved in the TCA cycle used for biomass and reducing equivalent generation. To increase pyruvate pool in mitochondria, pyruvate flux from cytosol is enhanced by overexpressing select pyruvate transporter proteins. In *Saccharomyces cerevisiae*, this is achieved via deletion or truncation of mpc2 gene locus, and overexpression of mpc1, and mpc3 loci. In *Y. lipolytica*, overexpression of the endogenous mpc genes, co-expression or replacement with heterologous mpc genes can achieve a similar phenotype. Heterologous mpc genes can be sourced from multiple organisms (Table 2).

TABLE 2

Exemplary pyruvate transporters (MPC)

| Species | Enzyme | Gene ID/Protein ID |
|---|---|---|
| *Saccharomyces cerevisiae* | mpc | NP_011759.1 |
| *Hanseniaspora osmophila* | mpc3 | OEJ86292.1 |
| *Talaromyces marneffei* PM1 | mpc3 | KFX48982.1 |

In some embodiments, microorganisms are modified to alleviate inhibition of lipid synthesis by removing acetyl-CoA carboxylase (ACC) regulation. Inclusion of a fatty acid as a co-substrate in addition to simple carbon sources (glucose, fructose, etc.) may inhibit de novo lipid biosynthesis due to excess fatty acyl-CoA. A key enzyme in de novo lipid pathway is ACC, an allosterically regulated enzyme to convert acetyl-CoA into malonyl-CoA (lipid precursor). To relieve ACC inhibition, the native gene locus in *Y. lipolytica* which encodes for ACC is replaced by or co-expressed with a non-native gene fragment that encodes for a feedback-insensitive ACC variant. Heterologous feedback-insensitive ACC genes can be sourced from multiple organisms (Table 3).

TABLE 3

Exemplary acetyl-CoA carboxylases (ACC)

| Species | Enzyme | Gene ID/Protein ID |
|---|---|---|
| *Mus musculus* | ACC1 | Q5SWU9 |
| *Mus musculus* | ACC2 | E9Q4Z2 |
| *Rattus norvegicus* | ACC1 | P11497 |
| *Rattus norvegicus* | ACC2 | P11497 |
| *Homo sapiens* | ACC | Q13085 |
| *Homo sapiens* | ACC2 | O00763 |

In another aspect, methods for increasing and balancing reducing equivalents and microorganisms capable of increasing and balancing reducing equivalents are disclosed.

In some embodiments, microorganisms are engineered to assimilate cytosolic citrate or isocitrate into alpha-ketoglutarate, and generation of reducing equivalents. In certain embodiments, an NADP/NAD-dependent IDH is functionally expressed in the cytosol alone or together with an aconitase. To functionally express aconitase and NADP/NAD-linked IDH, a variety of yeast promoter sequences can be used. To redirect expression into the cytosolic compartment, the mitochondrial-targeting peptide of respective enzymes are removed. In the case of NAD/NADP-specific IDHs, cytosolic bacterial proteins can be utilized (Table 1).

In some embodiments, the citrate/isocitrate pool in the cytosol is increased by overexpression of citrate transporter protein in a microorganism to increase and/or rebalance reducing equivalent. In certain embodiments, one or more copies of citrate transporter genes are introduced into a microorganism. Citrate transporter sequences include, but are not limited to, *Yarrowia lipolytica* YALI0F26323p, *Saccharomyces cerevisiae* AAC48984.1, *Rattus norvegicus* AAA18899.1, *Caenorhabditis elegans* P34519.1, and *Caligus clemensi* ACO14982.1.

In some embodiments, microorganisms are engineered to express a decarboxylating malic enzyme to generate reducing equivalent in the cytosol from citrate. An ATP-dependent citrate lyase cleaves cytosolic citrate into acetyl-CoA and oxaloacetate. Subsequently, an NADPH-dependent malate dehydrogenase converts oxaloacetate into malate, a metabolite which is transported back into the mitochondria to enter the TCA cycle. A heterologous decarboxylating malic enzyme is expressed to convert malate into pyruvate and $CO_2$ while generating a reducing equivalent either in the form of NADH or NADPH. To redirect expression into the cytosolic compartment, the mitochondrial-targeting peptide of the malate dehydrogenase is removed. Examples of gene sequences which encode decarboxylating malic enzymes include *Arabidopsis thaliana* Q9SIU0 (SEQ ID NO: 34), *Amaranthus hypochondriacus* P37224 (SEQ ID NO: 35), *Rhizobium meliloti* 030807 (SEQ ID NO: 36), *Solanum tuberosum* P37221 (SEQ ID NO: 37), *Homo sapiens* Q16798 (SEQ ID NO: 38), and *Escherichia coli* P26616 (SEQ ID NO: 29).

In some embodiments, the oxaloacetate pool in the cytosol is increased by upregulation of ATP-citrate lyase to increase and/or rebalance reducing equivalent. Further improvement of reducing equivalent by expressing a malic enzyme is gained by improving oxaloacetate (malic enzyme precursor) via upregulation of ATP-citrate lyase. In some embodiments, upregulation of ATP-citrate lyase in a microorganism comprises replacing the native promoter sequence of the endogenous ATP-citrate lyase with a strong promoter sequence such as one derived from a transaldolase gene. In other embodiments, the activity of ATP-citrate lyase is increased by introducing additional sequences which encode the enzyme. Native or heterologous ATP-citrate lyase sequences such as *Mus musculus* NP_001186225.1, *Mus musculus* NP_598798.1, *Aspergillus niger* XP_001394055.1, and *Aspergillus niger* XP_001394057.1 can be used for this purpose.

In some embodiments, flux through the pentose phosphate pathway (PPP) is increased upon entering lipogenesis and lipid storage phase after biomass synthesis to increase and/or rebalance reducing equivalent. Several strategies are utilized to funnel carbon into PPP. In some embodiments, hexose kinase activity is downregulated to limit flux of glucose to glucose-6-phosphate. In other embodiments, independent from or in concert with hexose kinase downregulation, the activity of glucose-6-phosphate dehydrogenase (ZWF1), 6-phosphogluconolactonase (SOL3), and 6-phosphogluconate dehydrogenase (GND1) is increased to draw down the pool of glucose-6-phosphate and pull additional fructose-6-phosphate to enter the oxidative pentose phosphate pathway. In certain embodiments, fructose-6-phsophate kinase is downregulated to reduce flux through upper glycolysis. In another aspect, native glucose-6-phosphate dehydrogenase (ZWF1) or 6-phosphogluconate dehydrogenase (GND1) is replaced with recombinant or engineered variants which use NAD+ in place of NADP+ producing NADH instead of NADPH to match cofactor requirements of recombinant pathways. Examples of suitable NAD-dependent variants of GND include *Bradyrhizobium* WP_012029377.1, *Bradyrhizobium* A4YZZ8, *Methylobacillus* AAF34407.1, and *Methylobacillus* Q9L9P8. Examples of suitable NAD-dependent ZWF include *Leuconostoc* AAA25265.1 and *Leuconostoc* P11411.

In some embodiments, deletion or downregulation of mannitol synthesis pathway can increase and/or rebalance reducing equivalent. In certain embodiments, downregulation of mannitol synthesis pathway comprises deletion, disruption, and/or mutation of one or more gene encoding an NADPH-dependent mannitol dehydrogenase and/or an aldo-keto reductase. In some embodiments, the NADPH-dependent mannitol dehydrogenase is selected from YALI0B16192g, YALI0D18964g, and YALI0E12463g. In other embodiments, the aldo-keto reductase is selected from YALI0D07634g, YALI0F18590g, YALI0C13508g, YALI0F06974g, YALI0A15906g, YALI0B21780g, YALI0E18348g, YALI0B07117g, YALI0009119g, YALI0D04092g, YALI0B15268g, YALI0000319g, and YALI0A19910g.

In some embodiments, reducing equivalent can be increased and/or rebalanced by decoupling and increasing glucose uptake via amplifying the activity of both high and low affinity hexose transporters. Yeasts possess several variants of hexose transporters that are distinguished based on their specificity and mode of activation. It is desirable to optimize biomass and lipid synthesis regardless of glucose concentration and media composition throughout the fermentation period. It was shown that under distinct fermentation conditions such as nitrogen limitation, glucose uptake rates drop significantly. Thus, glucose depletion might diminish the pool of reducing equivalents necessary for lipid synthesis, desaturation of fatty acids and reduction of fatty acids to fatty alcohols. In some embodiments, hexokinase deletion or downregulation increases both high and low affinity hexose transporters in yeasts such as *Saccharomyces cerevisiae* and *Yarrowia lipolytica*. The deletion of a hexokinase variant leads to an increase in pyruvate, a precursor of the TCA cycle used for biomass and reducing equivalent generation. An alternative strategy involves the expression of specific glucose transporters using heterologous promoters. The use of heterologous promoters achieves a decoupling of hexose transporter expression from cellular regulation. In some embodiments, a microorganism can be modified to overexpress *Yarrowia lipolytica* hexose transporter genes selected from YALI0A14212g, YALI0D01111g, YALI0D00363g, YALI0C16522g and YALI0F25553g.

In another aspect, methods of increasing product purity, reducing equivalents, and pathway intermediates and microorganisms capable of increasing product purity, reducing equivalents, and pathway intermediates are disclosed.

In some embodiments, downregulation or inhibition of ACC activity during conversion phase to reduce flux to 18 carbon fatty acids increases product purity, available NADPH, and acetyl-CoA units as potential building blocks for fatty esters or for NADH generation via respiration.

In some embodiments, the recombinant microorganisms of the disclosure can be used to synthesize mono- or poly-unsaturated $C_6$-$C_{24}$ fatty acids. In other embodiments, the recombinant microorganisms of the disclosure can be used to synthesize mono- or poly-unsaturated $C_6$-$C_{24}$ fatty alcohols. Mono- or poly-unsaturated $C_6$-$C_{24}$ fatty alcohols can be further converted into the corresponding aldehydes or acetates. Thus, various embodiments of the present disclosure can be used to synthesize a variety of insect pheromones selected from fatty alcohols, aldehydes, and acetates. Additionally, embodiments described herein can also be used for the synthesis of fragrances, flavors, and polymer intermediates.

Pheromones

As described above, embodiments of the disclosure provide for the production of one or more insect pheromones using a recombinant microorganism of the disclosure. A pheromone is a volatile chemical compound that is secreted by a particular insect for the function of chemical communication within the species. That is, a pheromone is secreted or excreted chemical factor that triggers a social response in members of the same species. There are, inter alia, alarm pheromones, food trail pheromones, sex pheromones, aggregation pheromones, epideictic pheromones, releaser pheromones, primer pheromones, and territorial pheromones, that affect behavior or physiology.

Non-limiting examples of insect pheromones which can be produced using the recombinant microorganisms and methods disclosed herein include linear alcohols, aldehydes, and acetates listed in Table 4.

TABLE 4

$C_6$-$C_{20}$ Linear Pheromones

| Name | Name |
|---|---|
| (E)-2-Decen-1-ol | (E,E)-10,12-Tetradecadien-1-ol |
| (E)-2-Decenyl acetate | (E,E)-10,12-Tetradecadienyl acetate |
| (E)-2-Decenal | (E,E)-10,12-Tetradecadienal |
| (Z)-2-Decen-1-ol | (E,Z)-10,12-Tetradecadienyl acetate |

TABLE 4-continued

| $C_6$-$C_{20}$ Linear Pheromones | |
|---|---|
| Name | Name |
| (Z)-2-Decenyl acetate | (Z,E)-10,12-Tetradecadienyl acetate |
| (Z)-2-Decenal | (Z,Z)-10,12-Tetradecadien-1-ol |
| (E)-3-Decen-1-ol | (Z,Z)-10,12-Tetradecadienyl acetate |
| (Z)-3-Decenyl acetate | (E,Z,Z)-3,8,11-Tetradecatrienyl acetate |
| (Z)-3-Decen-1-ol | (E)-8-Pentadecen-1-ol |
| (Z)-4-Decen-1-ol | (E)-8-Pentadecenyl acetate |
| (E)-4-Decenyl acetate | (Z)-8-Pentadecen-1-ol |
| (Z)-4-Decenyl acetate | (Z)-8-Pentadecenyl acetate |
| (Z)-4-Decenal | (Z)-9-Pentadecenyl acetate |
| (E)-5-Decen-1-ol | (E)-9-Pentadecenyl acetate |
| (E)-5-Decenyl acetate | (Z)-10-Pentadecenyl acetate |
| (Z)-5-Decen-1-ol | (Z)-10-Pentadecenal |
| (Z)-5-Decenyl acetate | (E)-12-Pentadecenyl acetate |
| (Z)-5-Decenal | (Z)-12-Pentadecenyl acetate |
| (E)-7-Decenyl acetate | (Z,Z)-6,9-Pentadecadien-1-ol |
| (Z)-7-Decenyl acetate | (Z,Z)-6,9-Pentadecadienyl acetate |
| (E)-8-Decen-1-ol | (Z,Z)-6,9-Pentadecadienal |
| (E,E)-2,4-Decadienal | (E,E)-8,10-Pentadecadienyl acetate |
| (E,Z)-2,4-Decadienal | (E,Z)-8,10-Pentadecadien-1-ol |
| (Z,Z)-2,4-Decadienal | (E,Z)-8,10-Pentadecadienyl acetate |
| (E,E)-3,5-Decadienyl acetate | (Z,E)-8,10-Pentadecadienyl acetate |
| (Z,E)-3,5-Decadienyl acetate | (Z,Z)-8,10-Pentadecadienyl acetate |
| (Z,Z)-4,7-Decadien-1-ol | (E,Z)-9,11-Pentadecadienal |
| (Z,Z)-4,7-Decadienyl acetate | (Z,Z)-9,11-Pentadecadienal |
| (E)-2-Undecenyl acetate | (Z)-3-Hexadecenyl acetate |
| (E)-2-Undecenal | (E)-5-Hexadecen-1-ol |
| (Z)-5-Undecenyl acetate | (E)-5-Hexadecenyl acetate |
| (Z)-7-Undecenyl acetate | (Z)-5-Hexadecen-1-ol |
| (Z)-8-Undecenyl acetate | (Z)-5-Hexadecenyl acetate |
| (Z)-9-Undecenyl acetate | (E)-6-Hexadecenyl acetate |
| (E)-2-Dodecenal | (E)-7-Hexadecen-1-ol |
| (Z)-3-Dodecen-1-ol | (E)-7-Hexadecenyl acetate |
| (E)-3-Dodecenyl acetate | (E)-7-Hexadecenal |
| (Z)-3-Dodecenyl acetate | (Z)-7-Hexadecen-1-ol |
| (E)-4-Dodecenyl acetate | (Z)-7-Hexadecenyl acetate |
| (E)-5-Dodecen-1-ol | (Z)-7-Hexadecenal |
| (E)-5-Dodecenyl acetate | (E)-8-Hexadecenyl acetate |
| (Z)-5-Dodecen-1-ol | (E)-9-Hexadecen-1-ol |
| (Z)-5-Dodecenyl acetate | (E)-9-Hexadecenyl acetate |
| (Z)-5-Dodecenal | (E)-9-Hexadecenal |
| (E)-6-Dodecen-1-ol | (Z)-9-Hexadecen-1-ol |
| (Z)-6-Dodecenyl acetate | (Z)-9-Hexadecenyl acetate |
| (E)-6-Dodecenal | (Z)-9-Hexadecenal |
| (E)-7-Dodecen-1-ol | (E)-10-Hexadecen-1-ol |
| (E)-7-Dodecenyl acetate | (E)-10-Hexadecenal |
| (E)-7-Dodecenal | (Z)-10-Hexadecenyl acetate |
| (Z)-7-Dodecen-1-ol | (Z)-10-Hexadecenal |
| (Z)-7-Dodecenyl acetate | (E)-11-Hexadecen-1-ol |
| (Z)-7-Dodecenal | (E)-11-Hexadecenyl acetate |
| (E)-8-Dodecen-1-ol | (E)-11-Hexadecenal |
| (E)-8-Dodecenyl acetate | (Z)-11-Hexadecen-1-ol |
| (E)-8-Dodecenal | (Z)-11-Hexadecenyl acetate |
| (Z)-8-Dodecen-1-ol | (Z)-11-Hexadecenal |
| (Z)-8-Dodecenyl acetate | (Z)-12-Hexadecenyl acetate |
| (E)-9-Dodecen-1-ol | (Z)-12-Hexadecenal |
| (E)-9-Dodecenyl acetate | (E)-14-Hexadecenal |
| (E)-9-Dodecenal | (Z)-14-Hexadecenyl acetate |
| (Z)-9-Dodecen-1-ol | (E,E)-1,3-Hexadecadien-1-ol |
| (Z)-9-Dodecenyl acetate | (E,Z)-4,6-Hexadecadien-1-ol |
| (Z)-9-Dodecenal | (E,Z)-4,6-Hexadecadienyl acetate |
| (E)-10-Dodecen-1-ol | (E,Z)-4,6-Hexadecadienal |
| (E)-10-Dodecenyl acetate | (E,Z)-6,11-Hexadecadienyl acetate |
| (E)-10-Dodecenal | (E,Z)-6,11-Hexadecadienal |
| (Z)-10-Dodecen-1-ol | (Z,Z)-7,10-Hexadecadien-1-ol |
| (Z)-10-Dodecenyl acetate | (Z,Z)-7,10-Hexadecadienyl acetate |
| (E,Z)-3,5-Dodecadienyl acetate | (Z,E)-7,11-Hexadecadien-1-ol |
| (Z,E)-3,5-Dodecadienyl acetate | (Z,E)-7,11-Hexadecadienyl acetate |
| (Z,Z)-3,6-Dodecadien-1-ol | (Z,E)-7,11-Hexadecadienal |
| (E,E)-4,10-Dodecadienyl acetate | (Z,Z)-7,11-Hexadecadien-1-ol |
| (E,E)-5,7-Dodecadien-1-ol | (Z,Z)-7,11-Hexadecadienyl acetate |
| (E,E)-5,7-Dodecadienyl acetate | (Z,Z)-7,11-Hexadecadienal |
| (E,Z)-5,7-Dodecadien-1-ol | (Z,Z)-8,10-Hexadecadienyl acetate |
| (E,Z)-5,7-Dodecadienyl acetate | (E,Z)-8,11-Hexadecadienal |
| (E,Z)-5,7-Dodecadienal | (E,E)-9,11-Hexadecadienal |
| (Z,E)-5,7-Dodecadien-1-ol | (E,Z)-9,11-Hexadecadienyl acetate |
| (Z,E)-5,7-Dodecadienyl acetate | (E,Z)-9,11-Hexadecadienal |

TABLE 4-continued

| $C_6$-$C_{20}$ Linear Pheromones | |
|---|---|
| Name | Name |
| (Z,E)-5,7-Dodecadienal | (Z,E)-9,11-Hexadecadienal |
| (Z,Z)-5,7-Dodecadienyl acetate | (Z,Z)-9,11-Hexadecadienal |
| (Z,Z)-5,7-Dodecadienal | (E,E)-10,12-Hexadecadien-1-ol |
| (E,E)-7,9-Dodecadienyl acetate | (E,E)-10,12-Hexadecadienyl acetate |
| (E,Z)-7,9-Dodecadien-1-ol | (E,E)-10,12-Hexadecadienal |
| (E,Z)-7,9-Dodecadienyl acetate | (E,Z)-10,12-Hexadecadien-1-ol |
| (E,Z)-7,9-Dodecadienal | (E,Z)-10,12-Hexadecadienyl acetate |
| (Z,E)-7,9-Dodecadien-1-ol | (E,Z)-10,12-Hexadecadienal |
| (Z,E)-7,9-Dodecadienyl acetate | (Z,E)-10,12-Hexadecadienyl acetate |
| (Z,Z)-7,9-Dodecadien-1-ol | (Z,E)-10,12-Hexadecadienal |
| (Z,Z)-7,9-Dodecadienyl acetate | (Z,Z)-10,12-Hexadecadienal |
| (E,E)-8,10-Dodecadien-1-ol | (E,E)-11,13-Hexadecadien-1-ol |
| (E,E)-8,10-Dodecadienyl acetate | (E,E)-11,13-Hexadecadienyl acetate |
| (E,E)-8,10-Dodecadienal | (E,E)-11,13-Hexadecadienal |
| (E,Z)-8,10-Dodecadien-1-ol | (E,Z)-11,13-Hexadecadien-1-ol |
| (E,Z)-8,10-Dodecadienyl acetate | (E,Z)-11,13-Hexadecadienyl acetate |
| (E,Z)-8,10-Dodecadienal | (E,Z)-11,13-Hexadecadienal |
| (Z,E)-8,10-Dodecadien-1-ol | (Z,E)-11,13-Hexadecadien-1-ol |
| (Z,E)-8,10-Dodecadienyl acetate | (Z,E)-11,13-Hexadecadienyl acetate |
| (Z,E)-8,10-Dodecadienal | (Z,E)-11,13-Hexadecadienal |
| (Z,Z)-8,10-Dodecadien-1-ol | (Z,Z)-11,13-Hexadecadien-1-ol |
| (Z,Z)-8,10-Dodecadienyl acetate | (Z,Z)-11,13-Hexadecadienyl acetate |
| (Z,E,E)-3,6,8-Dodecatrien-1-ol | (Z,Z)-11,13-Hexadecadienal |
| (Z,Z,E)-3,6,8-Dodecatrien-1-ol | (E,E)-10,14-Hexadecadienal |
| (E)-2-Tridecenyl acetate | (Z,E)-11,14-Hexadecadienyl acetate |
| (Z)-2-Tridecenyl acetate | (E,E,Z)-4,6,10-Hexadecatrien-1-ol |
| (E)-3-Tridecenyl acetate | (E,E,Z)-4,6,10-Hexadecatrienyl acetate |
| (E)-4-Tridecenyl acetate | (E,Z,Z)-4,6,10-Hexadecatrien-1-ol |
| (Z)-4-Tridecenyl acetate | (E,Z,Z)-4,6,10-Hexadecatrienyl acetate |
| (Z)-4-Tridecenal | (E,E,Z)-4,6,11-Hexadecatrienyl acetate |
| (E)-6-Tridecenyl acetate | (E,E,Z)-4,6,11-Hexadecatrienal |
| (Z)-7-Tridecenyl acetate | (Z,Z,E)-7,11,13-Hexadecatrienal |
| (E)-8-Tridecenyl acetate | (E,E,E)-10,12,14-Hexadecatrienyl acetate |
| (Z)-8-Tridecenyl acetate | (E,E,E)-10,12,14-Hexadecatrienal |
| (E)-9-Tridecenyl acetate | (E,E,Z)-10,12,14-Hexadecatrienyl acetate |
| (Z)-9-Tridecenyl acetate | (E,E,Z)-10,12,14-Hexadecatrienal |
| (Z)-10-Tridecenyl acetate | (E,E,Z,Z)-4,6,11,13-Hexadecatetraenal |
| (E)-11-Tridecenyl acetate | (E)-2-Heptadecenal |
| (Z)-11-Tridecenyl acetate | (Z)-2-Heptadecenal |
| (E,Z)-4,7-Tridecadienyl acetate | (E)-8-Heptadecen-1-ol |
| (Z,Z)-4,7-Tridecadien-1-ol | (E)-8-Heptadecenyl acetate |
| (Z,Z)-4,7-Tridecadienyl acetate | (Z)-8-Heptadecen-1-ol |
| (E,Z)-5,9-Tridecadienyl acetate | (Z)-9-Heptadecenal |
| (Z,E)-5,9-Tridecadienyl acetate | (E)-10-Heptadecenyl acetate |
| (Z,Z)-5,9-Tridecadienyl acetate | (Z)-11-Heptadecen-1-ol |
| (Z,Z)-7,11-Tridecadienyl acetate | (Z)-11-Heptadecenyl acetate |
| (E,Z,Z)-4,7,10-Tridecatrienyl acetate | (E,E)-4,8-Heptadecadienyl acetate |
| (E)-3-Tetradecen-1-ol | (Z,Z)-8,10-Heptadecadien-1-ol |
| (E)-3-Tetradecenyl acetate | (Z,Z)-8,11-Heptadecadienyl acetate |
| (Z)-3-Tetradecen-1-ol | (E)-2-Octadecenyl acetate |
| (Z)-3-Tetradecenyl acetate | (E)-2-Octadecenal |
| (E)-5-Tetradecen-1-ol | (Z)-2-Octadecenyl acetate |
| (E)-5-Tetradecenyl acetate | (Z)-2-Octadecenal |
| (E)-5-Tetradecenal | (E)-9-Octadecen-1-ol |
| (Z)-5-Tetradecen-1-ol | (E)-9-Octadecenyl acetate |
| (Z)-5-Tetradecenyl acetate | (E)-9-Octadecenal |
| (Z)-5-Tetradecenal | (Z)-9-Octadecen-1-ol |
| (E)-6-Tetradecenyl acetate | (Z)-9-Octadecenyl acetate |
| (Z)-6-Tetradecenyl acetate | (Z)-9-Octadecenal |
| (E)-7-Tetradecen-1-ol | (E)-11-Octadecen-1-ol |
| (E)-7-Tetradecenyl acetate | (E)-11-Octadecenal |
| (Z)-7-Tetradecen-1-ol | (Z)-11-Octadecen-1-ol |
| (Z)-7-Tetradecenyl acetate | (Z)-11-Octadecenyl acetate |
| (Z)-7-Tetradecenal | (Z)-11-Octadecenal |
| (E)-8-Tetradecenyl acetate | (E)-13-Octadecenyl acetate |
| (Z)-8-Tetradecen-1-ol | (E)-13-Octadecenal |
| (Z)-8-Tetradecenyl acetate | (Z)-13-Octadecen-1-ol |
| (Z)-8-Tetradecenal | (Z)-13-Octadecenyl acetate |
| (E)-9-Tetradecen-1-ol | (Z)-13-Octadecenal |
| (E)-9-Tetradecenyl acetate | (E)-14-Octadecenal |
| (Z)-9-Tetradecen-1-ol | (E,Z)-2,13-Octadecadien-1-ol |
| (Z)-9-Tetradecenyl acetate | (E,Z)-2,13-Octadecadienyl acetate |
| (Z)-9-Tetradecenal | (E,Z)-2,13-Octadecadienal |
| (E)-10-Tetradecenyl acetate | (Z,E)-2,13-Octadecadienyl acetate |
| (Z)-10-Tetradecenyl acetate | (Z,Z)-2,13-Octadecadien-1-ol |
| (E)-11-Tetradecen-1-ol | (Z,Z)-2,13-Octadecadienyl acetate |

TABLE 4-continued

| $C_6$-$C_{20}$ Linear Pheromones | |
|---|---|
| Name | Name |
| (E)-11-Tetradecenyl acetate | (E,E)-3,13-Octadecadienyl acetate |
| (E)-11-Tetradecenal | (E,Z)-3,13-Octadecadienyl acetate |
| (Z)-11-Tetradecen-1-ol | (E,Z)-3,13-Octadecadienal |
| (Z)-11-Tetradecenyl acetate | (Z,E)-3,13-Octadecadienyl acetate |
| (Z)-11-Tetradecenal | (Z,Z)-3,13-Octadecadienyl acetate |
| (E)-12-Tetradecenyl acetate | (Z,Z)-3,13-Octadecadienal |
| (Z)-12-Tetradecenyl acetate | (E,E)-5,9-Octadecadien-1-ol |
| (E,E)-2,4-Tetradecadienal | (E,E)-5,9-Octadecadienyl acetate |
| (E,E)-3,5-Tetradecadienyl acetate | (E,E)-9,12-Octadecadien-1-ol |
| (E,Z)-3,5-Tetradecadienyl acetate | (Z,Z)-9,12-Octadecadienyl acetate |
| (Z,E)-3,5-Tetradecadienyl acetate | (Z,Z)-9,12-Octadecadienal |
| (E,Z)-3,7-Tetradecadienyl acetate | (Z,Z)-11,13-Octadecadienal |
| (E,Z)-3,8-Tetradecadienyl acetate | (E,E)-11,14-Octadecadienal |
| (E,Z)-4,9-Tetradecadienyl acetate | (Z,Z)-13,15-Octadecadienal |
| (E,Z)-4,9-Tetradecadienal | (Z,Z,Z)-3,6,9-Octadecatrienyl acetate |
| (E,Z)-4,10-Tetradecadienyl acetate | (E,E,E)-9,12,15-Octadecatrien-1-ol |
| (E,E)-5,8-Tetradecadienal | (Z,Z,Z)-9,12,15-Octadecatrienyl acetate |
| (Z,Z)-5,8-Tetradecadien-1-ol | (Z,Z,Z)-9,12,15-Octadecatrienal |
| (Z,Z)-5,8-Tetradecadienyl acetate | (Z,E)-9,11-Tetradecadien-1-ol |
| (Z,Z)-5,8-Tetradecadienal | (Z,E)-9,11-Tetradecadienyl acetate |
| (E,E)-8,10-Tetradecadien-1-ol | (Z,E)-9,11-Tetradecadienal |
| (E,E)-8,10-Tetradecadienyl acetate | (Z,Z)-9,11-Tetradecadien-1-ol |
| (E,E)-8,10-Tetradecadienal | (Z,Z)-9,11-Tetradecadienyl acetate |
| (E,Z)-8,10-Tetradecadienyl acetate | (Z,Z)-9,11-Tetradecadienal |
| (E,Z)-8,10-Tetradecadienal | (E,E)-9,12-Tetradecadienyl acetate |
| (Z,E)-8,10-Tetradecadien-1-ol | (Z,E)-9,12-Tetradecadien-1-ol |
| (Z,E)-8,10-Tetradecadienyl acetate | (Z,E)-9,12-Tetradecadienyl acetate |
| (Z,Z)-8,10-Tetradecadienal | (Z,E)-9,12-Tetradecadienal |
| (E,E)-9,11-Tetradecadienyl acetate | (Z,Z)-9,12-Tetradecadien-1-ol |
| (E,Z)-9,11-Tetradecadienyl acetate | (Z,Z)-9,12-Tetradecadienyl acetate |

In some aspects, one or more pheromones that can be produced using a recombinant microorganism of the disclosure include at least one pheromone listed in Table 5 to modulate the behavior of an insect listed in Table 5. In other aspects, non-limiting examples of insect pheromones which can be produced using the recombinant microorganisms and methods disclosed herein include alcohols, aldehydes, and acetates listed in Table 5. However, the microorganisms described herein are not limited to the production of $C_6$-$C_{20}$ pheromones listed in Table 4 and Table 5. Rather, the disclosed microorganisms can also be utilized in the synthesis of various $C_6$-$C_{24}$ mono- or poly-unsaturated fatty acids, alcohols, aldehydes, and acetates, including fragrances, flavors, and polymer intermediates.

TABLE 5

| Exemplary pheromones that can be produced using recombinant microorganisms and methods of the present disclosure. | | |
|---|---|---|
| Name | Structure | Example of Biological importance |
| (Z)-3-hexen-1-ol | 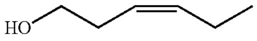 | See, Sugimoto et al. (2014) |
| (Z)-3-nonen-1-ol | 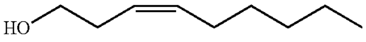 | West Indian Fruity Fly male sex pheromone |
| (Z)-5-decen-1-ol | 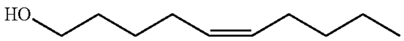 | |
| (Z)-5-decenyl acetate | 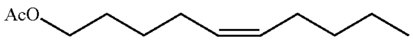 | *Agrotis segetum* sex pheromone component |
| (E)-5-decen-1-ol | 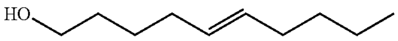 | *Anarsia lineatella* sex pheromone component |
| (E)-5-decenyl acetate | 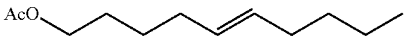 | *Anarsia lineatella* sex pheromone component |
| (Z)-7-dodecen-1-ol | 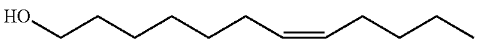 | |
| (Z)-7-dodecenyl acetate | 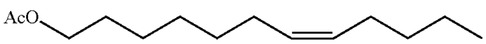 [SMILES: CCCC/C=C\CCCCCCOC(C)=O] | *Pseudoplusia includens* sex pheromone<br>*Agrotis segetum* sex pheromone component |

TABLE 5-continued

Exemplary pheromones that can be produced using recombinant microorganisms and methods of the present disclosure.

| Name | Structure | Example of Biological importance |
|---|---|---|
| (E)-8-dodecen-1-ol | 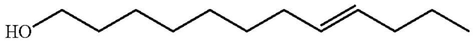 | Citrus Fruit Moth sex pheromone |
| (E)-8-dodecenyl acetate | 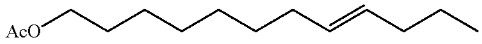 [SMILES: CCC/C=C/CCCCCCCOC(C)=O] | *Grapholitha molesta*, *Ecdytolopha aurantiana* sex pheromone component |
| (Z)-8-dodecen-1-ol | 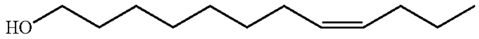 | *Grapholitha molesta*, *Ecdytolopha aurantiana* sex pheromone component |
| (Z)-8-dodecenyl acetate | 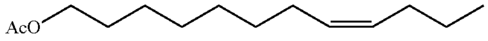 [SMILES: CCC/C=C\CCCCCCCOC(C)=O] | *Grapholitha molesta* sex pheromone component |
| (Z)-9-dodecen-1-ol | 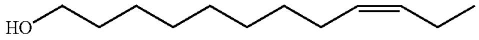 | |
| (Z)-9-dodecenyl acetate | 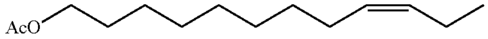 | *Eupoecilia ambiguella* sex pheromone |
| (E,E)-8,10-dodecadien-1-ol | 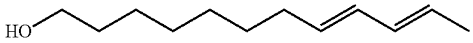 | *Cydia pomonella* |
| (7E,9Z)-dodecadienyl acetate | 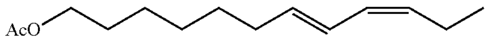 [SMILES: CC/C=C\C=C\CCCCCCOC(C)=O] | *Lobesia botrana* |
| (Z)-9-tetradecen-1-ol | 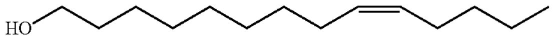 | |
| (Z)-9-tetradecenyl acetate | 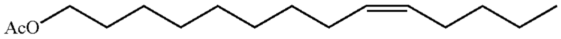 [SMILES: CCCC/C=C\CCCCCCCCOC(C)=O] | *Pandemis pyrusana*, *Naranga aenescens*, *Agrotis segetum* sex pheromone component |
| (Z)-11-tetradecen-1-ol | 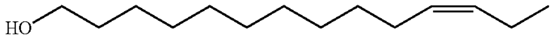 | |
| (Z)-11-tetradecenyl acetate | 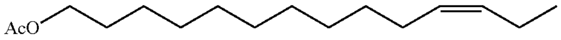 | *Pandemis pyrusana*, *Choristoneura roseceana* sex pheromone component |
| (E)-11-tetradecen-1-ol | 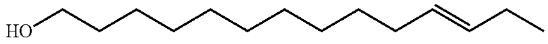 | |
| (E)-11-tetradecenyl acetate | 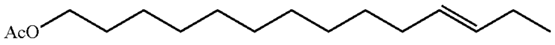 [SMILES: CC/C=C/CCCCCCCCCCOC(C)=O] | *Choristoneura roseceana*, *Crocidolomia pavonana* sex pheromone component |
| (Z)-7-hexadecen-1-ol | 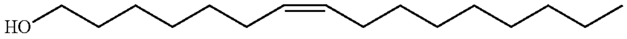 | |
| (Z)-7-hexadecenal | 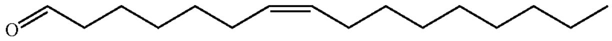 [SMILES: CCCCCCCC/C=C\CCCCCC=O] | *Diatraea considerata* sex pheromone component |
| (Z)-9-hexadecen-1-ol | 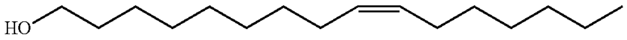 [SMILES: CCCCCC/C=C\CCCCCCCCO] | |
| (Z)-9-hexadecenal | 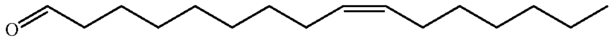 [SMILES: CCCCCC/C=C\CCCCCCCC=O] | *Helicoverpa zea*, *Helicoverpa armigera*, *Heliothis virescens* sex pheromone component |
| (Z)-9-hexadecenyl acetate | 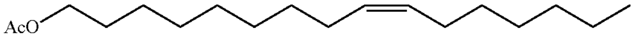 [SMILES: CCCCCC/C=C\CCCCCCCCOC(C)=O] | *Naranga aenescens* sex pheromone component |
| (Z)-11-hexadecen-1-ol | 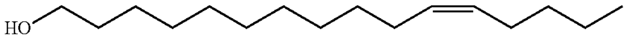 [SMILES: CCCC/C=C\CCCCCCCCCCO] | |
| (Z)-11-hexadecenal | 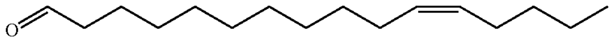 [SMILES: CCCC/C=C\CCCCCCCCCC=O] | *Platyptila carduidactyla*, *Heliothis virescens* sex pheromone *Helicoverpa zea*, *Helicoverpa armigera*, *Plutella xylostella*, *Diatraea considerate*, *Diatraea grandiosella*, *Diatraea saccharalis*, *Acrolepiopsis assectella* sex pheromone component |

TABLE 5-continued

| Exemplary pheromones that can be produced using recombinant microorganisms and methods of the present disclosure. | | |
|---|---|---|
| Name | Structure | Example of Biological importance |
| (Z)-11-hexadecenyl acetate | 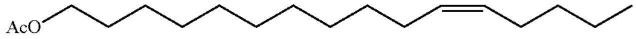 | *Discestra trifolii* sex pheromone *Heliothis virescens*, *Plutella xylostella*, *Acrolepiopsis assectella*, *Crocidolomia pavonana*, *Naranga aenescens* sex pheromone component |
| (Z,Z)-11,13-hexadecadienal | 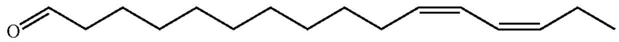 | *Amyelosis transitella* |
| (Z,Z)-11,13-hexadecadien-1-ol | 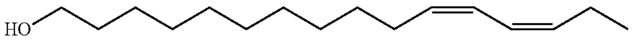 | *Amyelosis transitella* |
| (11Z,13E)-hexadecadien-1-ol | 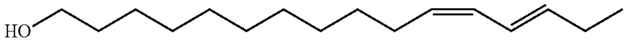 [SMILES: CC/C=C/C=C\CCCCCCCCCCO] | *Amyelosis transitella* |
| (9Z,11E)-hexadecadienal | 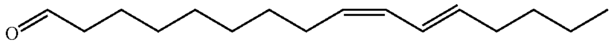 | |
| (Z)-13-octadecen-1-ol | 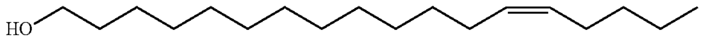 | |
| (Z)-13-octadecenal | 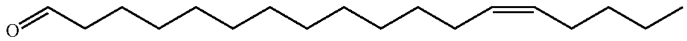 [SMILES: CCCC/C=C\CCCCCCCCCCCC=O] | *Diatraea considerata*, *Diatraea grandiosella* sex pheromone component |
| (Z,Z,Z,Z,Z)-3,6,9,12,15-tricosapentaene | 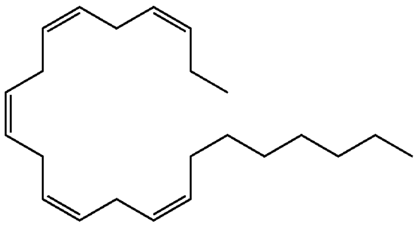 [SMILES: CC/C=C\C/C=C\C/C=C\C/C=C\C/C=C\CCCCCCC] | *Amyelosis transitella* |

Most pheromones comprise a hydrocarbon skeleton with the terminal hydrogen substituted by a functional group (Ryan M F (2002). Insect Chemoreception. Fundamental and Applied. Kluwer Academic Publishers). Table 6 shows some common functional groups, along with their formulas, prefixes and suffixes. The presence of one or more double bonds, generated by the loss of hydrogens from adjacent carbons, determines the degree of unsaturation of the molecule and alters the designation of a hydrocarbon from -ane (no multiple bonds) to -ene. The presence of two and three double bonds is indicated by ending the name with -diene and -triene, respectively. The position of each double bond is represented by a numeral corresponding to that of the carbon from which it begins, with each carbon numbered from that attached to the functional group. The carbon to which the functional group is attached is designated -1-. Pheromones may have, but are not limited to, hydrocarbon chain lengths numbering 10 (deca-), 12 (dodeca-), 14 (tetradeca-), 16 (hexadeca-), or 18 (octadeca-) carbons long. The presence of a double bond has another effect. It precludes rotation of the molecule by fixing it in one of two possible configurations, each representing geometric isomers that are different molecules. These are designated either E (from the German word Entgegen, opposite) or Z (Zusammen, together), when the carbon chains are connected on the opposite (trans) or same (cis) side, respectively, of the double bond.

TABLE 6

| Prefixes and suffixes for common functional groups | | | |
|---|---|---|---|
| Functional group | Formula | Prefix | Suffix |
| Alcohol | —OH | Hydroxy- | -ol |
| Aldehyde | —CH═O | Formyl- | -al |
| Amine | $—NH_2$ | Amino- | -amine |
| Carboxylic acid | —COOH | Carboxy- | -oic acid |
| Ester | —COOR | R-oxycarbonyl- | -R-oate |
| Ketone | 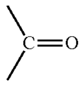 | Oxo- | -one |

From Howse, PE, Stevens, IDR and Jones, OT (1998). Insect pheromones and their use in pest management. London: Chapman and Hall.

Pheromones described herein can be referred to using IUPAC nomenclature or various abbreviations or variations known to one skilled in the art. For example, (11Z)-hexadecen-1-al, can also be written as Z-11-hexadecen-1-al, Z-11-hexadecenal, or Z-x-y:Ald, wherein x represents the position of the double bond and y represents the number of carbons in the hydrocarbon skeleton. Abbreviations used herein and known to those skilled in the art to identify functional groups on the hydrocarbon skeleton include "Ald," indicating an aldehyde, "OH," indicating an alcohol, and "Ac," indicating an acetyl. Also, the number of carbons in the chain can be indicated using numerals rather than using the written name. Thus, as used herein, an unsaturated carbon chain comprised of sixteen carbons can be written as hexadecene or 16.

Similar abbreviation and derivations are used herein to describe pheromone precursors. For example, the fatty acyl-CoA precursors of (11Z)-hexadecen-1-al can be identified as (11Z)-hexadecenyl-CoA or Z-11-16:Acyl-CoA.

The present disclosure relates to recombinant microorganisms expressing one or more enzyme or transporter that contributes to improved production of biomass or one or more lipid. The present disclosure also relates to recombinant microorganisms comprising downregulation of one or more enzyme in one or more pathways that contributes to improved production of biomass or one or more lipid.

Isocitrate Dehydrogenase

In some embodiments, the present disclosure teaches microorganisms comprising an AMP-deficient isocitrate dehydrogenase (IDH). IDH catalyzes the oxidation of isocitrate to oxalosuccinate in the TCA pathway. In many microorganisms, including *Y. lipolytica*, IDH is an allosteric enzyme, sensitive to AMP levels. Under non-optimal growTH conditions, such as nitrogen deprivation, AMP levels are reduced by AMP deaminase (AMD1), thus reducing IDH activity. IDH enzymes produce NADPH/NADH, which are important for native fatty acid synthesis and for methyl palmitate desaturation. Thus in some embodiments, the recombinant microorganisms of the present disclosure exhibit improved lipid production from fatty acid precursors, in part, because they comprise a nucleic acid encoding for an AMP-deficient IDH enzyme.

The present disclosure describes enzymes that catalyze the oxidative decarboxylation of isocitrate, producing alpha-ketoglutarate (α-ketoglutarate) and $CO_2$. This is a two-step process, which involves oxidation of isocitrate (a secondary alcohol) to oxalosuccinate (a ketone), followed by the decarboxylation of the carboxyl group beta to the ketone, forming alpha-ketoglutarate.

Isocitrate dehydrogenase can catalyze the following reactions:

$$\text{Isocitrate}+\text{NAD}^+\leftrightarrow\text{2-oxoglutarate}+CO_2+\text{NADH}+H^+$$

$$\text{Isocitrate}+\text{NADP}^+\leftrightarrow\text{2-oxoglutarate}+CO_2+\text{NADPH}+H^+$$

$$\text{Isocitrate}+\text{NADP}^+\text{Mg}^{2+}\text{(metal ion)}\leftrightarrow\text{alpha-ketoglutarate}+\text{NADPH}+H^++CO_2$$

The isocitrate dehydrogenase (IDH) enzyme structure in *Escherichia coli* was the first structure to be elucidated and understood. Most isocitrate dehydrogenases are dimers, to be specific, homodimers (two identical monomer subunits forming one dimeric unit).

Isocitrate dehydrogenase is the first bacterial enzyme shown to be regulated by phosphorylation/dephosphorylation. The modulation of this key enzyme activity enables *E. coli* to make rapid shifts between TCA and glyoxalate bypass pathways. Fluxes and intercellular concentrations for this junction have been determined. The state of phosphorylation of isocitrate dehydrogenase determines its activity.

There are marked differences in the properties of enzymes from different sources. The *E. coli* enzyme is not an allosteric protein as isocitrate dehydrogenases from other sources are, and it is cold sensitive. IcdA is observed to have several distinct isoforms. Phosphorylation of the enzyme on a serine residue by isocitrate dehydrogenase kinase/phosphatase inactivates it, and dephosphorylation by the phosphatase reactivates it. Phosphorylation affects the binding of NADP. The enzyme shows allosteric inhibition by phosphoenolpyruvate.

In some embodiments, the one or more modifications associated with tricarboxylic acid cycle comprises the overexpression of at least one endogenous and/or exogenous nucleic acid molecule encoding an AMP-insensitive isocitrate dehydrogenase (IDH) variant in the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to IDH from *Escherichia coli, Mycobacterium smegmatis, Acidithiobacillus thiooxidans*, or *Yarrowia lipolytica*. In further embodiments, the at least one nucleic acid molecule is from *Yarrowia lipolytica* and comprises isoleucine to alanine substitutions at amino acid positions 279 and 280 of XP_503571.2. In some embodiments, the one or more modifications associated with tricarboxylic acid cycle results in extended activation of the tricarboxylic acid cycle.

In some embodiments, the one or more modifications associated with reducing equivalent availability comprises the overexpression of at least one endogenous and/or exogenous nucleic acid molecule encoding an NADP/NAD-dependent isocitrate dehydrogenase (IDH) in the cytosol of the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to IDH from *Escherichia coli, Mycobacterium smegmatis, Acidithiobacillus thiooxidans*, or *Yarrowia lipolytica*. In further embodiments, the IDH is selected from *Escherichia coli* Idh (WP_000444484.1), *Mycobacterium smegmatis* Icd2 (WP_011727802.1), *Acidithiobacillus thiooxidans* Idh (PDB: 2D4V_A), and *Yarrowia lipolytica* Idh1 (XP_503571.2), or homolog thereof.

Pyruvate Transporter

Pyruvate is the end-product of glycolysis, a major substrate for oxidative metabolism, and a branching point for glucose, lactate, fatty acid and amino acid synthesis. The mitochondrial enzymes that metabolize pyruvate are physically separated from cytosolic pyruvate pools and rely on a membrane transport system to shuttle pyruvate across the impermeable inner mitochondrial membrane (IMM). Two proteins, mitochondrial pyruvate carriers MPC1 and MPC2, form a hetero-oligomeric complex in the IMM to facilitate pyruvate transport.

In some embodiments, the one or more modifications associated with comprising tricarboxylic acid cycle or one or more metabolic intermediates availability comprises the overexpression of at least one endogenous and/or exogenous nucleic acid molecule encoding a pyruvate transporter in the recombinant microorganism. In other embodiments, the one or more metabolic intermediates availability comprises mitochondrial pyruvate availability. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to pyruvate transporter from *Saccharomyces cerevisiae, Hanseniaspora osmophila, Yarrowia lipolytica*, or *Talaromyces marneffei* PM1. In further embodiments, the pyruvate transporter is selected from *Saccharomyces cerevisiae* mpc1, *Saccharomyces cerevisiae* mpc3 (NP_011759.1), *Hanseniaspora osmophila* mpc3 (0EJ86292.1), *Yarrowia lipolytica* mpc, and *Talaromyces marneffei* PM1 mpc3 (KFX48982.1), or homolog thereof. In yet a further embodiment, the recombinant microorganism is *Saccharomyces cerevisiae* comprising a deletion, disruption, or loss of function mutation in a gene encoding an mpc2 pyruvate transporter. In some embodiments, the recombinant microorganism is *Yarrowia lipolytica*.

Aconitase

Aconitase (aconitate hydratase) is an enzyme that catalyzes the stereo-specific isomerization of citrate to isocitrate via cis-aconitate in the tricarboxylic acid cycle, a non-redox-active process.

Aconitase has two slightly different structures, depending on whether it is activated or inactivated. In the inactive form, its structure is divided into four domains. Counting from the N-terminus, only the first three of these domains are involved in close interactions with the [3Fe-4S] cluster, but the active site consists of residues from all four domains, including the larger C-terminal domain. The Fe—S cluster and a $SO_4$2-anion also reside in the active site. When the enzyme is activated, it gains an additional iron atom, creating a [4Fe-4S] cluster. However, the structure of the rest of the enzyme is nearly unchanged.

In contrast with the majority of iron-sulfur proteins that function as electron carriers, the iron-sulfur cluster of aconitase reacts directly with an enzyme substrate. Aconitase has an active [Fe4S4]2+ cluster, which may convert to an inactive [Fe3S4]+ form. Three cysteine (Cys) residues have been shown to be ligands of the [Fe4S4] center. In the active state, the labile iron ion of the [Fe4S4] cluster is not coordinated by Cys but by water molecules.

The iron-responsive element-binding protein (IRE-BP) and 3-isopropylmalate dehydratase (α-isopropylmalate isomerase), an enzyme catalyzing the second step in the biosynthesis of leucine, are known aconitase homologues. Iron regulatory elements (IREs) constitute a family of 28-nucleotide, non-coding, stem-loop structures that regulate iron storage, heme synthesis and iron uptake. They also participate in ribosome binding and control the mRNA turnover (degradation). The specific regulator protein, the IRE-BP, binds to IREs in both 5' and 3' regions, but only to RNA in the apo form, without the Fe—S cluster. Expression of IRE-BP in cultured cells has revealed that the protein functions either as an active aconitase, when cells are iron-replete, or as an active RNA-binding protein, when cells are iron-depleted. Mutant IRE-BPs, in which any or all of the three Cys residues involved in Fe—S formation are replaced by serine, have no aconitase activity, but retain RNA-binding properties.

Aconitase is inhibited by fluoroacetate, therefore fluoroacetate is poisonous. Fluoroacetate, in the citric acid cycle, can innocently enter as fluorocitrate. However, aconitase cannot bind this substrate and thus the citric acid cycle is halted. The iron sulfur cluster is highly sensitive to oxidation by superoxide.

In some embodiments, the one or more modifications associated with reducing equivalent availability further comprises the overexpression of at least one endogenous and/or exogenous nucleic acid encoding an aconitase in the cytosol of the recombinant microorganism. In certain embodiments, the at least one endogenous and/or exogenous nucleic acid molecule encoding the aconitase lack a sequence encoding a mitochondrial-targeting peptide.

Citrate Transporter

Citrate is a key intermediate in both catabolism and anabolism and thus occupies a prominent position in eukaryotic energy metabolism. When the cell has excess energy, citrate is transported out of the mitochondrial matrix across the inner membrane via the mitochondrial citrate transport protein (CTP). Citrate can then passively diffuse through an anion selective channel across the outer mitochondrial membrane into the cytoplasm. Once in the cytoplasm, citrate is broken down to acetyl CoA and oxaloacetate, the former providing the immediate carbon source to fuel fatty acid, triacylglycerol, and cholesterol biosyntheses.

The mitochondrial CTP catalyzes an obligatory exchange of tricarboxylates (i.e., citrate, isocitrate) either for each other or for the dicarboxylate malate or for phosphoenolpyruvate. In higher eukaryotes the transporter catalyzes citrate/malate exchange with citrate moving outwardly across the inner membrane. In yeast, the CTP is thought to catalyze a citrate/isocitrate exchange. In both cases, the CTP catalyzes a facilitated-diffusion with dianions being the transported species. The CTP is a member of the mitochondrial transporter family. Most members of this family display several common characteristics including: a size of approximately 300 amino acids and a basic isoelectric point, the presence of 3 homologous sequence domains, and a signature sequence motif of Px(D,E)x(V,I,A,M)(K,R)x(R,K,Q,A)(L,M,F,I) which repeats two-three times.

In some embodiments, the one or more modifications associated with reducing equivalent availability or one or more metabolic intermediates availability comprises the overexpression of at least one endogenous and/or exogenous nucleic acid encoding a citrate transporter in the recombinant microorganism. In certain embodiments, the one or more metabolic intermediates availability comprises cytosolic citrate/isocitrate. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a citrate transporter from *Yarrowia lipolytica, Saccharomyces cerevisiae, Rattus norvegicus, Caenorhabditis elegans*, or *Caliqus clemensi*. In yet further embodiments, the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

Decarboxylating Malic Enzyme

In some embodiments, the present disclosure teaches recombinant microorganisms comprising a nucleic acid encoding for a heterologous malic enzyme. In some embodiments, the recombinant microorganisms of the present disclosure exhibit improved production of lipids from fatty acid substrates. In some embodiments, the recombinant microorganisms of the present disclosure exhibit improved Z11-16 acid selectivity.

Figure 4:
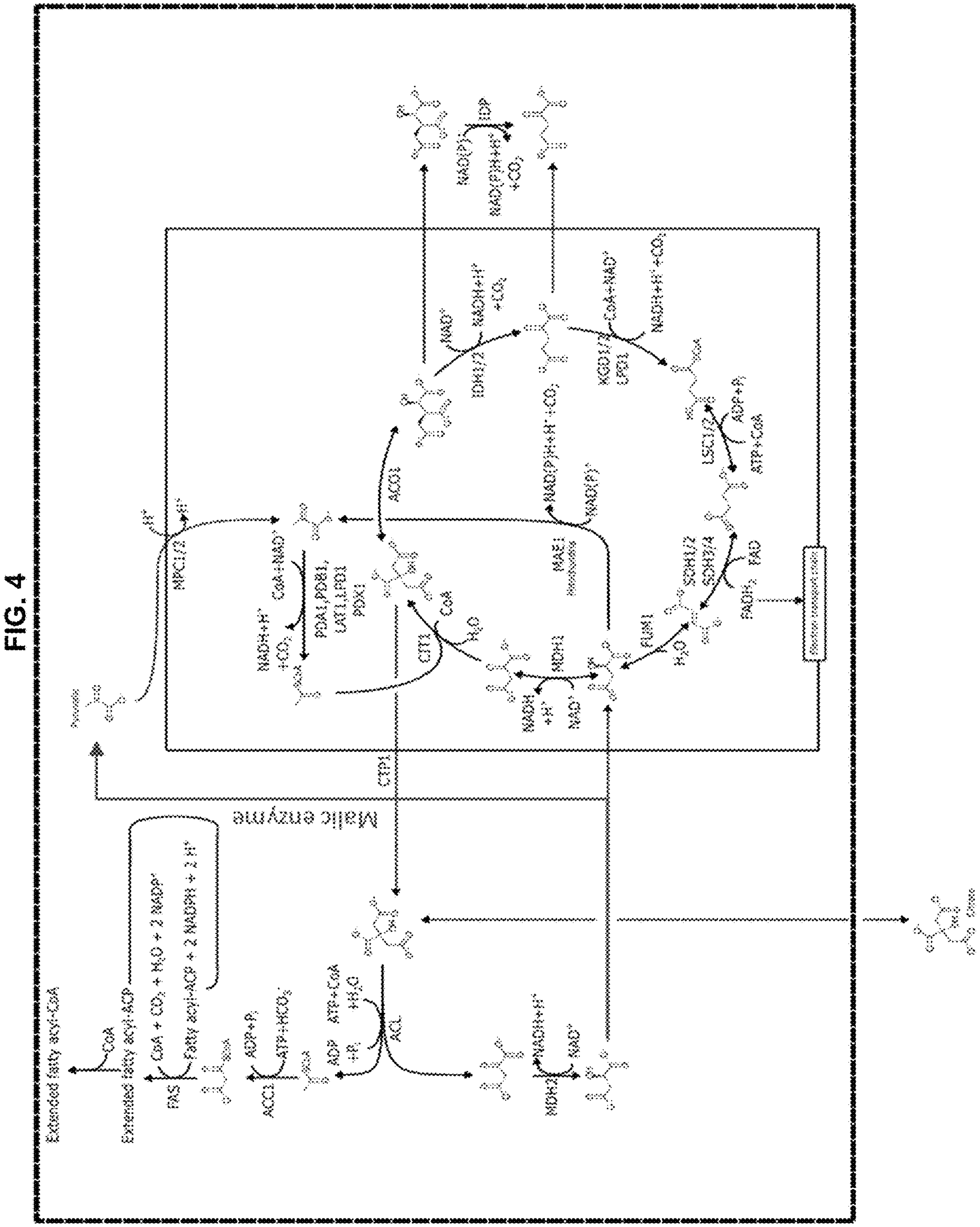
FIG. 4—TCA cycle, citrate shuttle, and FAS pathway diagram. Citrate overflow from the TCA cycle is transported into the cytoplasm and ultimately from the cell. Overexpression of cytosolic decarboxylating malic enzyme can harness citrate derived s-malate to produce pyruvate while supplying cofactor for lipogenesis ($NADP^+$ dependent malic enzyme) or desaturation ($NAD^+$ dependent malic enzyme).

Microorganisms of the present disclosure produce citrate as co-product under nitrogen-limited conditions. This is because during nitrogen starvation many organisms, including *Y. lipolytica* down-regulate respiration to divert carbon/energy storage via lipid synthesis. Citrate is first exported from mitochondria into the cytosol and subsequently from the cell. Exported citrate can be re-assimilated, especially when alternative carbon sources are scarce. Alternatively, the combination of the enzymes ATP citrate lyase (ACL), malate dehydrogenase (e.g., MDH2) and cytosolic malic enzyme can turn cytosolic citrate into pyruvate, to feed back into the TCA cycle to feed further lipid synthesis (FIG. 4).

Many organisms, including *Y. lipolytica* however, do not express a cytosolic malic enzyme.

The inventors further hypothesized that expression of a heterologous $NADP^+$ dependent cytosolic malic enzyme may increase fatty acid production if the primary rate limitation is cofactor supply. Surprisingly, the inventors also discovered that expression of a heterologous malic enzyme improved the Z11-16 acid selectivity of the recombinant microorganisms.

Malate dehydrogenase (decarboxylating) or NAD-malic enzyme (NAD-ME) is an enzyme that catalyzes the chemical reaction:

$$\text{(S)-malate+NAD+} \leftrightarrows \text{pyruvate+}CO_2\text{+NADH}$$

Thus, the two substrates of this enzyme are (S)-malate and NAD+, whereas its three products are pyruvate, $CO_2$, and NADH. Malate is oxidized to pyruvate and $CO_2$, and NAD+ is reduced to NADH.

This enzyme belongs to the family of oxidoreductases, to be specific, those acting on the CH—OH group of donor with NAD+ or NADP+ as acceptor. The systematic name of this enzyme class is (S)-malate:NAD+ oxidoreductase (decarboxylating). This enzyme participates in pyruvate metabolism and carbon fixation. NAD-malic enzyme is one of three decarboxylation enzymes used in the inorganic carbon concentrating mechanisms of C4 and CAM plants. The others are NADP-malic enzyme and PEP carboxykinase.

In some embodiments, the one or more modifications associated with reducing equivalent availability comprises the overexpression of at least one exogenous nucleic acid molecule encoding a decarboxylating malic enzyme in the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a decarboxylating malic enzyme from *Arabidopsis thaliana, Amaranthus hypochondriacus, Rhizobium meliloti, Solanum tuberosum, Homo sapiens*, or *Escherichia coli*. In further embodiments, the decarboxylating malic enzyme is selected from *Arabidopsis thaliana* Q9SIU0, *Amaranthus hypochondriacus* P37224, *Rhizobium meliloti* 030807, *Solanum tuberosum* P37221, *Homo sapiens* Q16798, and *Escherichia coli* P26616, or homolog thereof. In yet a further embodiment, the decarboxylating malic enzyme lacks a sequence encoding a mitochondrial-targeting peptide.

ATP-Citrate Lyase

ATP citrate lyase is an enzyme that represents an important step in fatty acid biosynthesis. ATP citrate lyase is important in that, by converting citrate to acetyl CoA, it links the metabolism of carbohydrates, which yields citrate as an intermediate, and the production of fatty acids, which requires acetyl CoA. ATP-citrate lyase is responsible for catalyzing the conversion of citrate and CoA into acetyl-CoA and oxaloacetate, along with the hydrolysis of ATP.

ATP citrate lyase is the primary enzyme responsible for the synthesis of cytosolic acetyl-CoA in many tissues. The enzyme is a tetramer of apparently identical subunits. The product, acetyl-CoA, serves several important biosynthetic pathways, including lipogenesis and cholesterogenesis. It is activated by insulin.

In some embodiments, the one or more modifications associated with one or more metabolic intermediates availability comprises the overexpression of at least one endogenous and/or exogenous nucleic acid encoding an ATP-citrate lyase in the recombinant microorganism. In certain embodiments, the one or more metabolic intermediates availability comprises cytosolic oxaloacetate availability. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an ATP-citrate lyase from *Saccharomyces cerevisiae, Yarrowia lipolytica, Mus musculus*, and *Aspergillus niger*. In a yet further embodiment, the ATP-citrate lyase is selected from *Mus musculus* NP_001186225.1, *Mus musculus* NP_598798.1, *Aspergillus niger* XP_001394055.1, and *Aspergillus niger* XP_001394057.1, or homolog thereof.

Hexose Transporter

The hexose transporters belong to a transporter superfamily termed the major facilitator superfamily. The members of this superfamily include a variety of sugar transporters and transporters of other carbon compounds in eukaryotes as well as prokaryotes. The yeast hexose transporters form a subfamily. Twenty hexose transporter proteins are found in *S. cerevisiae.*

Glucose-dependent modulation of the affinity of glucose transport in wild-type cells can depend upon a number of factors, including the regulation of expression of various sets of Hxtp proteins with significantly different affinities to the sugar, the removal and inactivation of transporter proteins under certain conditions, the modulation of the affinity of specific transporters and, possibly, interactions between the different transporter proteins.

In some embodiments, the one or more modifications associated with reducing equivalent availability comprises decoupling and increasing glucose uptake in the recombinant microorganism. In certain embodiments, decoupling and increasing glucose uptake comprises: upregulation of hexose transporter activity. In further embodiments, the upregulation of one or more hexose transporter activity comprises the overexpression of one or more endogenous and/or exogenous nucleic acid molecule encoding a hexose transporter operably linked to one or more heterologous promoters. In some embodiments, the one or more endogenous and/or exogenous nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a hexose transporter from *Yarrowia lipolytica*. In certain embodiments, the one or more endogenous and/or exogenous nucleic acid molecule encoding a hexose transporter is selected from YALI0A14212g, YALI0D01111g, YALI0D00363g, YALI0C16522g, and YALI0F25553g, or homolog thereof.

Acetyl-CoA Carboxylase

Acetyl-CoA carboxylase 1 catalyzes the carboxylation of acetyl-CoA to malonyl-CoA, the first committed and rate-limiting step in de novo fatty acid biosynthesis. Malonyl-CoA is used as a building block to extend the chain length of fatty acids by fatty acid synthase.

Two isoforms exist in mammals, acetyl-CoA carboxylase 1 and acetyl-CoA carboxylase 2. Both are dimeric, multifunctional enzymes composed of four distinct domains; a biotin carboxylase (BC) domain, a biotin carboxyl carrier protein (BCCP) domain, the ACC central region, and a carboxyltransferase (CT) domain.

The function of ACC is to regulate the metabolism of fatty acids. When the enzyme is active, the product, malonyl-CoA, is produced which is a building block for new fatty acids and can inhibit the transfer of the fatty acyl group from acyl CoA to carnitine with carnitine acyltransferase, which inhibits the beta-oxidation of fatty acids in the mitochondria.

The regulation of mammalian ACC is complex, in order to control two distinct pools of malonyl CoA that direct either the inhibition of beta oxidation or the activation of lipid biosynthesis.

Mammalian ACC1 and ACC2 are regulated transcriptionally by multiple promoters which mediate ACC abundance in response to the cells nutritional status. Activation of gene expression through different promoters results in alternative splicing. The sensitivity to nutritional status results from the control of these promoters by transcription factors such as SREBP1c, controlled by insulin at the transcriptional level, and ChREBP, which increases in expression with high carbohydrates diets.

Through a feedforward loop, citrate allosterically activates ACC. Citrate may increase ACC polymerization to increase enzymatic activity. Other allosteric activators include glutamate and other dicarboxylic acids. Long and short chain fatty acyl CoAs are negative feedback inhibitors of ACC.

Phosphorylation can result when the hormones glucagon or epinephrine bind to cell surface receptors, but the main cause of phosphorylation is due to a rise in AMP levels when the energy status of the cell is low, leading to the activation of the AMP-activated protein kinase (AMPK). AMPK is the main kinase regulator of ACC, able to phosphorylate a number of serine residues on both isoforms of ACC. On ACC1, AMPK phosphorylates Ser79, Ser1200, and Ser1215. Protein kinase A also has the ability to phosphorylate ACC, with a much greater ability to phosphorylate ACC2 than ACC1. Researchers hypothesize there are other ACC kinases important to its regulation as there are many other possible phosphorylation sites on ACC.

When insulin binds to its receptors on the cellular membrane, it activates a phosphatase enzyme called protein phosphatase 2A (PP2A) to dephosphorylate the enzyme, thereby removing the inhibitory effect. Furthermore, insulin induces a phosphodiesterase that lowers the level of cAMP in the cell, thus inhibiting PKA, and also inhibits AMPK directly.

In some embodiments, the one or more modifications associated with lipid synthesis comprises alleviation of acetyl-CoA carboxylase (ACC) inhibition. In certain embodiments, alleviation of ACC inhibition comprises the replacement of the endogenous ACC, or overexpression of at least one endogenous and/or exogenous nucleic acid molecule encoding a feedback-insensitive ACC variant in the recombinant microorganism. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to ACC from *Mus musculus, Rattus norvegicus*, or *Homo sapiens*.

In some embodiments, the one or more modifications associated with reducing equivalent availability, one or more metabolic intermediates availability, or increased product purity comprises downregulation or inhibition of acetyl-CoA carboxylase (ACC) activity in the recombinant microorganism. In certain embodiments, the downregulation or inhibition of ACC activity comprises deletion, disruption, and/or mutation of one or more endogenous gene encoding one or more ACC enzyme.

Hexose Kinase

A hexose kinase is an enzyme that phosphorylates hexoses (six-carbon sugars), forming hexose phosphate. In most organisms, glucose is the most important substrate of hexose kinases, and glucose-6-phosphate is the most important product. Hexose kinase also possesses the ability of transferring an inorganic phosphate group from ATP to a substrate.

They are categorized as actin fold proteins, sharing a common ATP binding site core that is surrounded by more variable sequences which determine substrate affinities and other properties.

Most bacterial hexose kinases are approximately 50 kD in size. Multicellular organisms such as plants and animals often have more than one hexose kinase isoform. Most are about 100 kD in size and consist of two halves (N and C terminal), which share much sequence homology.

By catalyzing the phosphorylation of glucose to yield glucose 6-phosphate, hexose kinases maintain the downhill concentration gradient that favors the facilitated transport of glucose into cells. This reaction also initiates all physiologically relevant pathways of glucose utilization, including glycolysis and the pentose phosphate pathway. The addition of a charged phosphate group at the 6-position of hexoses also ensures 'trapping' of glucose and 2-deoxyhexose glucose analogs (e.g. 2-deoxyglucose, and 2-fluoro-2-deoxyglucose) within cells, as charged hexose phosphates cannot easily cross the cell membrane.

In some embodiments, the one or more modifications associated with reducing equivalent availability comprises one or more modifications in the pentose phosphate pathway (PPP) in the recombinant microorganism. In certain embodiments, one or more modifications in the PPP comprises downregulation of hexose kinase activity. In yet a further embodiment, the downregulation of hexose kinase activity comprises deletion, disruption, and/or mutation of one or more endogenous gene encoding one or more hexose kinase enzyme.

In some embodiments, the one or more modifications associated with reducing equivalent availability comprises decoupling and increasing glucose uptake in the recombinant microorganism. In certain embodiments, decoupling and increasing glucose uptake comprises downregulation of hexose kinase activity. In some embodiments, the downregulation of hexose kinase activity comprises deletion, disruption, and/or mutation of one or more endogenous gene encoding one or more hexose kinase enzyme.

Fructose-6-Phosphate Kinase

Fructose-6-phosphate kinase (phosphofructokinase) is a kinase enzyme that phosphorylates fructose 6-phosphate in glycolysis.

The enzyme-catalyzed transfer of a phosphoryl group from ATP is an important reaction in a wide variety of biological processes. Fructose-6-phosphate kinase (PFK) catalyzes the phosphorylation of fructose-6-phosphate to fructose-1,6-bisphosphate, a key regulatory step in the glycolytic pathway. It is allosterically inhibited by ATP and allosterically activated by AMP, thus indicating the cell's energetic needs when it undergoes the glycolytic pathway. PFK exists as a homotetramer in bacteria and mammals (where each monomer possesses 2 similar domains) and as an octamer in yeast (where there are 4 alpha-(PFK1) and 4 beta-chains (PFK2), the latter, like the mammalian monomers, possessing 2 similar domains). This protein may use the morpheein model of allosteric regulation.

PFK is about 300 amino acids in length, and structural studies of the bacterial enzyme have shown it comprises two similar (alpha/beta) lobes: one involved in ATP binding and the other housing both the substrate-binding site and the allosteric site.

In some embodiments, the one or more modifications associated with reducing equivalent availability comprises one or more modifications in the pentose phosphate pathway (PPP) in the recombinant microorganism. In certain embodiments, the one or more modifications in the PPP comprises downregulation of fructose-6-phosphate kinase activity. In yet a further embodiment, the downregulation of fructose-6-phosphate kinase activity comprises deletion, disruption, and/or mutation of one or more endogenous gene encoding one or more fructose-6-phosphate kinase enzyme.

NADPH-Dependent Mannitol Dehydrogenase

Mannitol 2-dehydrogenase (NADP+) is an enzyme that catalyzes the chemical reaction:

D-mannitol+NADP+⇆D-fructose+NADPH+H+

Thus, the two substrates of this enzyme are D-mannitol and NADP+, whereas its 3 products are D-fructose, NADPH, and H+.

This enzyme belongs to the family of oxidoreductases, specifically those acting on the CH—OH group of donor with NAD+ or NADP+ as acceptor. The systematic name of this enzyme class is D-mannitol:NADP+2-oxidoreductase. This enzyme is also called mannitol 2-dehydrogenase (NADP+). This enzyme participates in fructose and mannose metabolism.

In some embodiments, the one or more modifications associated with reducing equivalent availability comprises downregulation of mannitol synthesis pathway in the recombinant microorganism. In certain embodiments, downregulation of mannitol synthesis pathway comprises deletion, disruption, and/or mutation of one or more gene encoding an NADPH-dependent mannitol dehydrogenase. In further embodiments, the one or more gene encoding an NADPH-dependent mannitol dehydrogenase is selected from YALI0B16192g, YALI0D18964g, and YALI0E12463g, or homolog thereof Aldo-Keto Reductase Aldo-keto reductases (AKR) comprise a superfamily of structurally-similar proteins that catalyze the NADPH-dependent conversion of various carbonyl compounds into their corresponding alcohol products.

The mannitol synthesis pathway comprises three unique enzymatic steps: (a) isomerization of fructose-6-phosphate to mannose-6-phosphate by mannose-6-phosphate isomerase; (b) reduction of mannose-6-phosphate to mannitol-1-phosphate by mannose-6-phosphate reductase; and (c) dephosphorylation of mannitol-1-phosphate to mannitol by mannitol-1-phosphate phosphatase. Radiotracer studies and kinetic analyses suggest that mannose-6-phosphate reductase, an aldo-keto reductase, plays a regulatory role in this pathway. In *Yarrowia*, a fructose-6-phosphate phosphatase produces fructose which is reduced by mannitol dehydrogenase into mannitol, and NADP.

In some embodiments, the one or more modifications associated with reducing equivalent availability comprises downregulation of mannitol synthesis pathway in the recombinant microorganism. In certain embodiments, downregulation of mannitol synthesis pathway comprises deletion, disruption, and/or mutation of one or more gene encoding an aldo-keto reductase. In further embodiments, the one or more gene encoding an NADPH-dependent mannitol dehydrogenase is selected from YALI0B16192g, YALI0D18964g, and YALI0E12463g, or homolog thereof. In further embodiments, the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0009119g, YALI0D04092g, YALI0B15268g, YALI0000319g, and YALI0A19910g, or homolog thereof.

Pentose Phosphate Pathway

The pentose phosphate pathway (PPP) is a central and widely conserved metabolic pathway of carbohydrate metabolism located in the cytoplasm in eukaryotic cells. This pathway serves two major functions: production of precursors for biosynthesis of macromolecules and production of reducing equivalents in the form of NADPH. Accordingly, these two roles are reflected in the two major phases of the PPP: in the "oxidative phase," glucose 6-phosphate (G6P) is converted into ribulose 5-phosphate (Ru5P) through the sequential action of: glucose-6-phosphate dehydrogenase (ZWF1) which converts G6P to 6-phospho D-glucono-1,5-lactone with generation of NADPH; 6-phosphogluconolactonase (SOL3, SOL4) which converts 6-phospho D-glucono-1,5-lactone to D-gluconate 6-phosphate; 6-phosphogluconate dehydrogenase (GND1, GND2) which converts D-gluconate 6-phosphate to Ru5P with generation of NADPH. The "non-oxidative phase" carries out the isomerization of Ru5P to ribose 5-phosphate (R5P), the epimerization of Ru5P to xylulose 5-phosphate (X5P) and, through the actions of transketolase (TKL1, TKL2) and transaldolase (TAL1, NQM1), a series of carbon skeleton transfers that can interconvert pentose phosphate into fructose 6-phosphate (F6P) and glyceraldehyde 3-phosphate (GAP)—both glycolytic intermediates—and erythrose 4-phosphate (E4P). The net effect of the non-oxidative phase is to produce an equilibrium between the pentoses needed for biosynthesis of macromolecules and the hexoses needed for energy management, allowing the two pools of sugars easily to interconvert.

The oxidative branch is considered to be largely irreversible under normal cellular conditions, whilst the non-oxidative branch is reversible. The PPP is not a simple linear pathway since several carbon atoms are recycled back into glycolysis. Furthermore, the enzyme transketolase catalyses two different reactions in the pathway, resulting in the substrates of these reactions being competitive inhibitors of one another. The PPP has three main products: reduced equivalents in the form of NADPH, produced in the oxidative phase, needed in biosynthetic pathways and for maintenance of the oxidative level of cells; R5P, for the biosynthesis of all nucleic acids; and E4P, for biosynthesis of the three aromatic amino acids. Different physiological states require operation of this biochemical network in different modes: in actively growing cells, such as during culture growth in reactors, the pathway must produce a sufficient amount of all three products, since all are required in the construction of new cells. Under stress conditions growth slows and the only product in considerable demand is NADPH.

The inventors hypothesized that the recombinant microorganism's lipid production could further be increased by overexpressing the genes of the upper (oxidative) pentose phosphate pathway (ZWF1, SOL3, and GND1), to increase NADPH supply for fatty acid biosynthesis. Surprisingly, the inventors discovered that upregulation of ZWF1, SOL3, and/or GND1 resulted in improved Z11-16 selectivity in recombinant microorganisms.

Enzymes to Express to Increase Levels of One or More Coenzymes

Nicotinamide adenine dinucleotide (NAD, including NAD+ and NADH) and nicotinamide adenine dinucleotide phosphate (NADP, including NADP+ and NADPH) belong to the fundamental common mediators of various biological processes, including energy metabolism, mitochondrial functions, calcium homeostasis, antioxidation/generation of oxidative stress, gene expression, immunological functions, aging, and cell death: NAD mediates energy metabolism and mitochondrial functions; NADPH is a key component in cellular antioxidation systems; NADH-dependent reactive oxygen species (ROS) generation from mitochondria and NADPH oxidase-dependent ROS generation are two critical mechanisms of ROS generation; cyclic ADP-ribose and several other molecules that are generated from NAD and NADP could mediate calcium homeostasis; NAD and NADP modulate multiple key factors in cell death, such as mitochondrial permeability transition, energy state, poly (ADP-ribose) polymerase-1, and apoptosis-inducing factor; and NAD and NADP profoundly affect aging-influencing factors such as oxidative stress and mitochondrial activities, and NAD-dependent sirtuins also mediate the aging process. Additionally, the in situ regeneration of reduced nicotinamide cofactors (NAD(P)H) is necessary for practical synthesis of many important chemicals in recombinant microorganisms.

In some embodiments, the one or more modifications associated with reducing equivalent availability comprises one or more modifications in the pentose phosphate pathway (PPP) in the recombinant microorganism. In certain embodiments, the one or more modifications in the PPP comprises upregulation of one or more oxidative PPP enzyme activity. In certain embodiments, the one or more modifications in the PPP comprises expression of one or more oxidative PPP enzyme variant. In further embodiments, the upregulation of one or more oxidative PPP enzyme activity comprises the overexpression of one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1).

In some embodiments, the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1). In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent glucose-6-phosphate dehydrogenase (ZWF1) from *Leuconostoc*. In further embodiments, the NAD-dependent glucose-6-phosphate dehydrogenase (ZWF1) is selected from *Leuconostoc* AAA25265.1 and *Leuconostoc* P11411, or homolog thereof. In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent 6-phosphogluconate dehydrogenase (GND1) from *Bradyrhizobium* or *Methylobacillus*. In further embodiments, the NAD-dependent 6-phosphogluconate dehydrogenase (GND1) is selected from *Bradyrhizobium* WP_012029377.1, *Bradyrhizobium* A4YZZ8, *Methylobacillus* AAF34407.1, and *Methylobacillus* Q9L9P8, or homolog thereof.

Dehydrogenase

In some embodiments, the recombinant microorganisms of the present disclosure are engineered to reduce or eliminate expression of one or more endogenous fatty alcohol dehydrogenases (i.e. FADH, ADH1, ADH2, ADH3, ADH4, ADH5, ADH6, and ADH7). In some embodiments, the recombinant microorganisms of the present disclosure are engineered comprise deletions of one or more endogenous fatty alcohol dehydrogenases (i.e. FADH, ADH1, ADH2, ADH3, ADH4, ADH5, ADH6, and ADH7). For example, in some embodiments, the recombinant microorganism is a *Y. lipolytica* strain, wherein the recombinant microorganism comprises reduced or eliminated activities of relevant (fatty) alcohol dehydrogenases selected from FADH: YALI0F09603g, ADH1: YALI0D25630g, ADH2: YALI0E17787g, ADH3: YALI0A16379g, ADH4: YALI0E15818g, ADH5: YALI0D02167g, ADH6: YALI0A15147g and/or ADH7: YALI0E07766g.

The present disclosure describes enzymes that catalyze the conversion of a fatty aldehyde to a fatty alcohol in various organisms. In some embodiments, an alcohol dehydrogenase (ADH, Table 6.1) is used to catalyze the conversion of a fatty aldehyde to a fatty alcohol. A number of ADHs identified from alkanotrophic organisms, *Pseudomonas fluorescens* NRRL B-1244 (Hou et al. 1983), *Pseudomonas butanovora* ATCC 43655 (Vangnai and Arp 2001), and *Acinetobacter* sp. strain M-1 (Tani et al. 2000), have shown to be active on short to medium-chain alkyl alcohols ($C_2$ to $C_{14}$). Additionally, commercially available ADHs from Sigma, Horse liver ADH and Baker's yeast ADH have detectable activity for substrates with length $C_{10}$ and greater. The reported activities for the longer fatty alcohols may be impacted by the difficulties in solubilizing the substrates. For the yeast ADH from Sigma, little to no activity is observed for $C_{12}$ to $C_{14}$ aldehydes by (Tani et al. 2000), however, activity for $C_{12}$ and $C_{16}$ hydroxy-w-fatty acids has been observed (Lu et al. 2010). Recently, two ADHs were characterized from *Geobacillus* thermodenitrificans NG80-2, an organism that degrades $C_{15}$ to $C_{36}$ alkanes using the LadA hydroxylase. Activity was detected from methanol to 1-triacontanol ($C_{30}$) for both ADHs, with 1-octanol being the preferred substrate for ADH2 and ethanol for ADH1 (Liu et al. 2009).

The use of ADHs in whole-cell bioconversions has been mostly focused on the production of chiral alcohols from ketones (Ernst et al. 2005) (Schroer et al. 2007). Using the ADH from *Lactobacillus brevis* and coupled cofactor regeneration with isopropanol, Schroer et al. reported the production of 797 g of (R)-methyl-3 hydroxybutanoate from methyl acetoacetate, with a space time yield of 29 g/L/h (Schroer et al. 2007). Examples of aliphatic alcohol oxidation in whole-cell transformations have been reported with commercially obtained *S. cerevisiae* for the conversion of hexanol to hexanal (Presecki et al. 2012) and 2-heptanol to 2-heptanone (Cappaert and Larroche 2004).

TABLE 6.1

Exemplary alcohol dehydrogenase enzymes.

| Organism | Gene Name | Accession No. |
|---|---|---|
| *Bactrocera oleae* (Olive fruit fly) (*Dacus oleae*) | ADH | Q9NAR7 |
| *Cupriavidus necator* (*Alcaligenes eutrophus*) (*Ralstonia eutropha*) | adh | P14940 |
| *Drosophila adiastola* (Fruit fly) (*Idiomyia adiastola*) | Adh | Q00669 |
| *Drosophila affinidisjuncta* (Fruit fly) (*Idiomyia affinidisjuncta*) | Adh | P21518 |
| *Drosophila ambigua* (Fruit fly) | Adh | P25139 |
| *Drosophila borealis* (Fruit fly) | Adh | P48584 |
| *Drosophila differens* (Fruit fly) | Adh | P22245 |
| *Drosophila equinoxialis* (Fruit fly) | Adh | Q9NG42 |
| *Drosophila flavomontana* (Fruit fly) | Adh | P48585 |
| *Drosophila guanche* (Fruit fly) | Adh | Q09009 |
| *Drosophila hawaiiensis* (Fruit fly) | Adh | P51549 |
| *Drosophila heteroneura* (Fruit fly) | Adh | P21898 |
| *Drosophila immigrans* (Fruit fly) | Adh | Q07588 |
| *Drosophila insularis* (Fruit fly) | Adh | Q9NG40 |
| *Drosophila lebanonensis* (Fruit fly) (*Scaptodrosophila lebanonensis*) | Adh | P10807 |
| *Drosophila mauritiana* (Fruit fly) | Adh | P07162 |
| *Drosophila madeirensis* (Fruit fly) | Adh | Q09010 |
| *Drosophila mimica* (Fruit fly) (*Idiomyia mimica*) | Adh | Q00671 |
| *Drosophila nigra* (Fruit fly) (*Idiomyia nigra*) | Adh | Q00672 |
| *Drosophila orena* (Fruit fly) | Adh | P07159 |
| *Drosophila pseudoobscura bogotana* (Fruit fly) | Adh | P84328 |
| *Drosophila picticornis* (Fruit fly) (*Idiomyia picticornis*) | Adh | P23361 |
| *Drosophila planitibia* (Fruit fly) | Adh | P23277 |
| *Drosophila paulistorum* (Fruit fly) | Adh | Q9U8S9 |
| *Drosophila silvestris* (Fruit fly) | Adh | P23278 |
| *Drosophila subobscura* (Fruit fly) | Adh | Q03384 |
| *Drosophila teissieri* (Fruit fly) | Adh | P28484 |
| *Drosophila tsacasi* (Fruit fly) | Adh | P51550 |
| *Fragaria ananassa* (Strawberry) | ADH | P17648 |
| *Malus domestica* (Apple) (*Pyrus malus*) | ADH | P48977 |
| *Scaptomyza albovittata* (Fruit fly) | Adh | P25988 |
| *Scaptomyza crassifemur* (Fruit fly) (*Drosophila crassifemur*) | Adh | Q00670 |
| *Sulfolobus* sp. (strain RC3) | adh | P50381 |
| *Zaprionus tuberculatus* (Vinegar fly) | Adh | P51552 |
| *Geobacillus stearothermophilus* (*Bacillus stearothermophilus*) | adh | P42327 |
| *Drosophila mayaguana* (Fruit fly) | Adh, Adh2 | P25721 |
| *Drosophila melanogaster* (Fruit fly) | Adh, CG3481 | P00334 |
| *Drosophila pseudoobscura pseudoobscura* (Fruit fly) | Adh, GA17214 | Q6LCE4 |
| *Drosophila simulans* (Fruit fly) | Adh, GD23968 | Q24641 |
| *Drosophila yakuba* (Fruit fly) | Adh, GE19037 | P26719 |
| *Drosophila ananassae* (Fruit fly) | Adh, GF14888 | Q50L96 |
| *Drosophila erecta* (Fruit fly) | Adh, GG25120 | P28483 |
| *Drosophila grimshawi* (Fruit fly) (*Idiomyia grimshawi*) | Adh, GH13025 | P51551 |
| *Drosophila willistoni* (Fruit fly) | Adh, GK18290 | Q05114 |
| *Drosophila persimilis* (Fruit fly) | Adh, GL25993 | P37473 |
| *Drosophila sechellia* (Fruit fly) | Adh, GM15656 | Q9GN94 |
| *Cupriavidus necator* (strain ATCC 17699/H16/DSM 428/Stanier 337) (*Ralstonia eutropha*) | adh, H16_A0757 | Q0KDL6 |
| *Mycobacterium tuberculosis* (strain CDC 1551/Oshkosh) | adh, MT1581 | P9WQC2 |
| *Staphylococcus aureus* (strain MW2) | adh, MW0568 | Q8NXU1 |
| *Mycobacterium tuberculosis* (strain ATCC 25618/H37Rv) | adh, Rv1530 | P9WQC3 |
| *Staphylococcus aureus* (strain N315) | adh, SA0562 | Q7A742 |
| *Staphylococcus aureus* (strain bovine RF122 ET3-1) | adh, SAB0557 | Q2YSX0 |
| *Sulfolobus acidocaldarius* (strain ATCC 33909/DSM 639/JCM 8929/NBRC 15157/NCIMB 11770) | adh, Saci_2057 | Q4J781 |
| *Staphylococcus aureus* (strain COL) | adh, SACOL0660 | Q5HI63 |
| *Staphylococcus aureus* (strain NCTC 8325) | adh, SAOUHSC_00608 | Q2G0G1 |
| *Staphylococcus aureus* (strain MRSA252) | adh, SAR0613 | Q6GJ63 |
| *Staphylococcus aureus* (strain MSSA476) | adh, SAS0573 | Q6GBM4 |
| *Staphylococcus aureus* (strain USA300) | adh, SAUSA300_0594 | Q2FJ31 |
| *Staphylococcus aureus* (strain Mu50/ATCC 700699) | adh, SAV0605 | Q99W07 |
| *Staphylococcus epidermidis* (strain ATCC 12228) | adh, SE_0375 | Q8CQ56 |
| *Staphylococcus epidermidis* (strain ATCC 35984/RP62A) | adh, SERP0257 | Q5HRD6 |

TABLE 6.1-continued

Exemplary alcohol dehydrogenase enzymes.

| Organism | Gene Name | Accession No. |
|---|---|---|
| *Sulfolobus solfataricus* (strain ATCC 35092/DSM 1617/JCM 11322/P2) | adh, SSO2536 | P39462 |
| *Sulfolobus tokodaii* (strain DSM 16993/JCM 10545/NBRC 100140/7) | adh, STK_25770 | Q96XE0 |
| *Anas platyrhynchos* (Domestic duck) (*Anas boschas*) | ADH1 | P30350 |
| *Apteryx australis* (Brown kiwi) | ADH1 | P49645 |
| *Ceratitis capitata* (Mediterranean fruit fly) (*Tephritis capitata*) | ADH1 | P48814 |
| *Ceratitis cosyra* (Mango fruit fly) (*Trypeta cosyra*) | ADH1 | Q70UN9 |
| *Gallus gallus* (Chicken) | ADH1 | P23991 |
| *Columba livia* (Domestic pigeon) | ADH1 | P86883 |
| *Coturnix coturnix japonica* (Japanese quail) (*Coturnix japonica*) | ADH1 | P19631 |
| *Drosophila hydei* (Fruit fly) | Adh1 | P23236 |
| *Drosophila montana* (Fruit fly) | Adh1 | P48586 |
| *Drosophila mettleri* (Fruit fly) | Adh1 | P22246 |
| *Drosophila mulleri* (Fruit fly) | Adh1 | P07161 |
| *Drosophila navojoa* (Fruit fly) | Adh1 | P12854 |
| *Geomys attwateri* (Attwater's pocket gopher) (*Geomys bursarius attwateri*) | ADH1 | Q9Z2M2 |
| *Geomys bursarius* (Plains pocket gopher) | ADH1 | Q64413 |
| *Geomys knoxjonesi* (Knox Jones's pocket gopher) | ADH1 | Q64415 |
| *Hordeum vulgare* (Barley) | ADH1 | P05336 |
| *Kluyveromyces marxianus* (Yeast) (*Candida kefyr*) | ADH1 | Q07288 |
| *Zea mays* (Maize) | ADH1 | P00333 |
| *Mesocricetus auratus* (Golden hamster) | ADH1 | P86885 |
| *Pennisetum americanum* (Pearl millet) (*Pennisetum glaucum*) | ADH1 | P14219 |
| *Petunia hybrida* (*Petunia*) | ADH1 | P25141 |
| *Oryctolagus cuniculus* (Rabbit) | ADH1 | Q03505 |
| *Solanum tuberosum* (Potato) | ADH1 | P14673 |
| *Struthio camelus* (Ostrich) | ADH1 | P80338 |
| *Trifolium repens* (Creeping white clover) | ADH1 | P13603 |
| *Zea luxurians* (Guatemalan teosinte) (*Euchlaena luxurians*) | ADH1 | Q07264 |
| *Saccharomyces cerevisiae* (strain ATCC 204508/S288c) (Baker's yeast) | ADH1, ADC1, YOL086C, O0947 | P00330 |
| *Arabidopsis thaliana* (Mouse-ear cress) | ADH1, ADH, At1g77120, F22K20.19 | P06525 |
| *Schizosaccharomyces pombe* (strain 972/ATCC 24843) (Fission yeast) | adh1, adh, SPCC13B11.01 | P00332 |
| *Drosophila lacicola* (Fruit fly) | Adh1, Adh-1 | Q27404 |
| *Mus musculus* (Mouse) | Adh1, Adh-1 | P00329 |
| *Peromyscus maniculatus* (North American deer mouse) | ADH1, ADH-1 | P41680 |
| *Rattus norvegicus* (Rat) | Adh1, Adh-1 | P06757 |
| *Drosophila virilis* (Fruit fly) | Adh1, Adh-1, GJ18208 | B4M8Y0 |
| *Scheffersomyces stipitis* (strain ATCC 58785/CBS 6054/NBRC 10063/NRRL Y-11545) (Yeast) (*Pichia stipitis*) | ADH1, ADH2, PICST_68558 | O00097 |
| *Aspergillus flavus* (strain ATCC 200026/FGSC A1120/NRRL 3357/JCM 12722/SRRC 167) | adh1, AFLA_048690 | P41747 |
| *Neurospora crassa* (strain ATCC 24698/74-OR23-1A/CBS 708.71/DSM 1257/FGSC 987) | adh-1, B17C10.210, NCU01754 | Q9P6C8 |
| *Candida albicans* (Yeast) | ADH1, CAD | P43067 |
| *Oryza sativa* subsp. *japonica* (Rice) | ADH1, DUPR11.3, Os11g0210300, LOC_Os11g10480, OsJ_032001 | Q2R8Z5 |
| *Drosophila mojavensis* (Fruit fly) | Adh1, GI17644 | P09370 |
| *Kluyveromyces lactis* (strain ATCC 8585/CBS 2359/DSM 70799/NBRC 1267/NRRL Y-1140/WM37) (Yeast) (*Candida sphaerica*) | ADH1, KLLA0F21010g | P20369 |
| *Oryza sativa* subsp. *indica* (Rice) | ADH1, OsI_034290 | Q75ZX4 |
| *Pongo abelii* (Sumatran orangutan) (*Pongo pygmaeus abelii*) | ADH1A | Q5RBP7 |
| *Homo sapiens* (Human) | ADH1A, ADH1 | P07327 |
| *Macaca mulatta* (Rhesus macaque) | ADH1A, ADH1 | P28469 |
| *Pan troglodytes* (Chimpanzee) | ADH1B | Q5R1W2 |
| *Papio hamadryas* (*Hamadryas* baboon) | ADH1B | P14139 |
| *Homo sapiens* (Human) | ADH1B, ADH2 | P00325 |
| *Homo sapiens* (Human) | ADH1C, ADH3 | P00326 |

TABLE 6.1-continued

Exemplary alcohol dehydrogenase enzymes.

| Organism | Gene Name | Accession No. |
|---|---|---|
| *Papio hamadryas* (*Hamadryas* baboon) | ADH1C, ADH3 | O97959 |
| *Ceratitis capitata* (Mediterranean fruit fly) (*Tephritis capitata*) | ADH2 | P48815 |
| *Ceratitis cosyra* (Mango fruit fly) (*Trypeta cosyra*) | ADH2 | Q70UP5 |
| *Ceratitis rosa* (Natal fruit fly) (*Pterandrus rosa*) | ADH2 | Q70UP6 |
| *Drosophila arizonae* (Fruit fly) | Adh2 | P27581 |
| *Drosophila buzzatii* (Fruit fly) | Adh2 | P25720 |
| *Drosophila hydei* (Fruit fly) | Adh2 | P23237 |
| *Drosophila montana* (Fruit fly) | Adh2 | P48587 |
| *Drosophila mulleri* (Fruit fly) | Adh2 | P07160 |
| *Drosophila wheeleri* (Fruit fly) | Adh2 | P24267 |
| *Entamoeba histolytica* | ADH2 | Q24803 |
| *Hordeum vulgare* (Barley) | ADH2 | P10847 |
| *Kluyveromyces marxianus* (Yeast) (*Candida kefyr*) | ADH2 | Q9P4C2 |
| *Zea mays* (Maize) | ADH2 | P04707 |
| *Oryza sativa* subsp. *indica* (Rice) | ADH2 | Q4R1E8 |
| *Solanum lycopersicum* (Tomato) (*Lycopersicon esculentum*) | ADH2 | P28032 |
| *Solanum tuberosum* (Potato) | ADH2 | P14674 |
| *Scheffersomyces stipitis* (strain ATCC 58785/CBS 6054/NBRC 10063/NRRL Y-11545) (Yeast) (*Pichia stipitis*) | ADH2, ADH1, PICST_27980 | O13309 |
| *Arabidopsis thaliana* (Mouse-ear cress) | ADH2, ADHIII, FDH1, At5g43940, MRH10.4 | Q96533 |
| *Saccharomyces cerevisiae* (strain ATCC 204508/S288c) (Baker's yeast) | ADH2, ADR2, YMR303C, YM9952.05C | P00331 |
| *Candida albicans* (strain SC5314/ATCC MYA-2876) (Yeast) | ADH2, Ca41C10.04, CaO19.12579, CaO19.5113 | O94038 |
| *Oryza sativa* subsp. *japonica* (Rice) | ADH2, DUPR11.1, Os11g0210500, LOC_Os11g10510 | Q0ITW7 |
| *Drosophila mojavensis* (Fruit fly) | Adh2, GI17643 | P09369 |
| *Kluyveromyces lactis* (strain ATCC 8585/CBS 2359/DSM 70799/NBRC 1267/NRRL Y-1140/WM37) (Yeast) (*Candida sphaerica*) | ADH2, KLLA0F18260g | P49383 |
| *Oryctolagus cuniculus* (Rabbit) | ADH2-1 | O46649 |
| *Oryctolagus cuniculus* (Rabbit) | ADH2-2 | O46650 |
| *Hordeum vulgare* (Barley) | ADH3 | P10848 |
| *Solanum tuberosum* (Potato) | ADH3 | P14675 |
| *Kluyveromyces lactis* (strain ATCC 8585/CBS 2359/DSM 70799/NBRC 1267/NRRL Y-1140/WM37) (Yeast) (*Candida sphaerica*) | ADH3, KLLA0B09064g | P49384 |
| *Saccharomyces cerevisiae* (strain ATCC 204508/S288c) (Baker's yeast) | ADH3, YMR083W, YM9582.08 | P07246 |
| *Homo sapiens* (Human) | ADH4 | P08319 |
| *Mus musculus* (Mouse) | Adh4 | Q9QYY9 |
| *Rattus norvegicus* (Rat) | Adh4 | Q64563 |
| *Struthio camelus* (Ostrich) | ADH4 | P80468 |
| *Kluyveromyces lactis* (strain ATCC 8585/CBS 2359/DSM 70799/NBRC 1267/NRRL Y-1140/WM37) (Yeast) (*Candida sphaerica*) | ADH4, KLLA0F13530g | P49385 |
| *Schizosaccharomyces pombe* (strain 972/ATCC 24843) (Fission yeast) | adh4, SPAC5H10.06c | Q09669 |
| *Saccharomyces cerevisiae* (strain YJM789) (Baker's yeast) | ADH4, ZRG5, SCY_1818 | A6ZTT5 |
| *Saccharomyces cerevisiae* (strain ATCC 204508/S288c) (Baker's yeast) | ADH4, ZRG5, YGL256W, NRC465 | P10127 |
| *Saccharomyces pastorianus* (Lager yeast) (*Saccharomyces cerevisiae* × *Saccharomyces eubayanus*) | ADH5 | Q6XQ67 |
| *Bos taurus* (Bovine) | ADH5 | Q3ZC42 |
| *Equus caballus* (Horse) | ADH5 | P19854 |
| *Mus musculus* (Mouse) | Adh5, Adh-2, Adh2 | P28474 |
| *Rattus norvegicus* (Rat) | Adh5, Adh-2, Adh2 | P12711 |
| *Oryctolagus cuniculus* (Rabbit) | ADH5, ADH3 | O19053 |
| *Homo sapiens* (Human) | ADH5, ADHX, FDH | P11766 |

TABLE 6.1-continued

Exemplary alcohol dehydrogenase enzymes.

| Organism | Gene Name | Accession No. |
|---|---|---|
| *Dictyostelium discoideum* (Slime mold) | adh5, DDB_G0281865 | Q54TC2 |
| *Saccharomyces cerevisiae* (strain ATCC 204508/S288c) (Baker's yeast) | ADH5, YBR145W, YBR1122 | P38113 |
| *Homo sapiens* (Human) | ADH6 | P28332 |
| *Peromyscus maniculatus* (North American deer mouse) | ADH6 | P41681 |
| *Pongo abelii* (Sumatran orangutan) (*Pongo pygmaeus abelii*) | ADH6 | Q5R7Z8 |
| *Rattus norvegicus* (Rat) | Adh6 | Q5XI95 |
| *Homo sapiens* (Human) | ADH7 | P40394 |
| *Rattus norvegicus* (Rat) | Adh7 | P41682 |
| *Mus musculus* (Mouse) | Adh7, Adh-3, Adh3 | Q64437 |
| *Mycobacterium tuberculosis* (strain CDC 1551/Oshkosh) | adhA, MT1911 | P9WQC0 |
| *Rhizobium meliloti* (strain 1021) (*Ensifer meliloti*) (*Sinorhizobium meliloti*) | adhA, RA0704, SMa1296 | O31186 |
| *Mycobacterium tuberculosis* (strain ATCC 25618/H37Rv) | adhA, Rv1862 | P9WQC1 |
| *Zymomonas mobilis* subsp. *mobilis* (strain ATCC 31821/ZM4/CP4) | adhA, ZMO1236 | P20368 |
| *Mycobacterium bovis* (strain ATCC BAA-935/AF2122/97) | adhB, Mb0784c | Q7U1B9 |
| *Mycobacterium tuberculosis* (strain CDC 1551/Oshkosh) | adhB, MT0786 | P9WQC6 |
| *Mycobacterium tuberculosis* (strain ATCC 25618/H37Rv) | adhB, Rv0761c, MTCY369.06c | P9WQC7 |
| *Zymomonas mobilis* subsp. *mobilis* (strain ATCC 31821/ZM4/CP4) | adhB, ZMO1596 | P0DJA2 |
| *Zymomonas mobilis* subsp. *mobilis* (strain ATCC 10988/DSM 424/LMG 404/NCIMB 8938/NRRL B-806/ZM1) | adhB, Zmob_1541 | F8DVL8 |
| *Mycobacterium tuberculosis* (strain CDC 1551/Oshkosh) | adhD, MT3171 | P9WQB8 |
| *Mycobacterium tuberculosis* (strain ATCC 25618/H37Rv) | adhD, Rv3086 | P9WQB9 |
| *Clostridium acetobutylicum* (strain ATCC 824/DSM 792/JCM 1419/LMG 5710/VKM B-1787) | adhE, aad, CA_P0162 | P33744 |
| *Escherichia coli* (strain K12) | adhE, ana, b1241, JW1228 | P0A9Q7 |
| *Escherichia coli* O157:H7 | adhE, Z2016, ECs1741 | P0A9Q8 |
| *Rhodobacter sphaeroides* (strain ATCC 17023/2.4.1/NCIB 8253/DSM 158) | adhI, RHOS4_11650, RSP_2576 | P72324 |
| *Oryza sativa* subsp. *indica* (Rice) | ADHIII, OsI_009236 | A2XAZ3 |
| *Escherichia coli* (strain K12) | adhP, yddN, b1478, JW1474 | P39451 |
| *Geobacillus stearothermophilus* (Bacillus stearothermophilus) | adhT | P12311 |
| *Emericella nidulans* (strain FGSC A4/ATCC 38163/CBS 112.46/NRRL 194/M139) (*Aspergillus nidulans*) | alcA, AN8979 | P08843 |
| *Emericella nidulans* (strain FGSC A4/ATCC 38163/CBS 112.46/NRRL 194/M139) (*Aspergillus nidulans*) | ale, AN3741 | P54202 |
| *Emericella nidulans* (strain FGSC A4/ATCC 38163/CBS 112.46/NRRL 194/M139) (*Aspergillus nidulans*) | alcC, adh3, AN2286 | P07754 |
| *Arabidopsis thaliana* (Mouse-ear cress) | At1g22430, F12K8.22 | Q9SK86 |
| *Arabidopsis thaliana* (Mouse-ear cress) | At1g22440, F12K8.21 | Q9SK87 |
| *Arabidopsis thaliana* (Mouse-ear cress) | At1g32780, F6N18.16 | A1L4Y2 |
| *Arabidopsis thaliana* (Mouse-ear cress) | At1g64710, F13O11.3 | Q8VZ49 |
| *Arabidopsis thaliana* (Mouse-ear cress) | At4g22110, F1N20.210 | Q0V7W6 |
| *Arabidopsis thaliana* (Mouse-ear cress) | At5g24760, T4C12_30 | Q8LEB2 |
| *Arabidopsis thaliana* (Mouse-ear cress) | At5g42250, K5J14.5 | Q9FH04 |

TABLE 6.1-continued

Exemplary alcohol dehydrogenase enzymes.

| Organism | Gene Name | Accession No. |
|---|---|---|
| *Zea mays* (Maize) | FDH | P93629 |
| *Drosophila melanogaster* (Fruit fly) | Fdh, gfd, ODH, CG6598 | P46415 |
| *Bacillus subtilis* (strain 168) | gbsB, BSU31050 | P71017 |
| *Caenorhabditis elegans* | H24K24.3 | Q17335 |
| *Oryza sativa* subsp. *japonica* (Rice) | Os02g0815500, LOC_Os02g57040, OsJ_008550, P0643F09.4 | Q0DWH1 |
| *Mycobacterium tuberculosis* (strain ATCC 25618/H37Rv) | Rv1895 | O07737 |
| *Caenorhabditis elegans* | sodh-1, K12G11.3 | Q17334 |
| *Caenorhabditis elegans* | sodh-2, K12G11.4 | O45687 |
| *Pseudomonas* sp. | terPD | P33010 |
| *Escherichia coli* (strain KI2) | yiaY, b3589, JW5648 | P37686 |
| *Moraxella* sp. (strain TAE123) | | P81786 |
| *Alligator mississippiensis* (American alligator) | | P80222 |
| *Catharanthus roseus* (Madagascar periwinkle) (*Vinca rosea*) | | P85440 |
| *Gadus morhua* subsp. *callarias* (Baltic cod) (*Gadus callarias*) | | P26325 |
| *Naja naja* (Indian cobra) | | P80512 |
| *Pisum sativum* (Garden pea) | | P12886 |
| *Pelophylax perezi* (Perez's frog) (*Rana perezi*) | | P22797 |
| *Saara hardwickii* (Indian spiny-tailed lizard) (*Uromastyx hardwickii*) | | P25405 |
| *Saara hardwickii* (Indian spiny-tailed lizard) (*Uromastyx hardwickii*) | | P25406 |
| *Equus caballus* (Horse) | | P00327 |
| *Equus caballus* (Horse) | | P00328 |
| *Geobacillus stearothermophilus* (*Bacillus stearothermophilus*) | | P42328 |
| *Gadus morhua* (Atlantic cod) | | P81600 |
| *Gadus morhua* (Atlantic cod) | | P81601 |
| *Myxine glutinosa* (Atlantic hagfish) | | P80360 |
| *Octopus vulgaris* (Common octopus) | | P81431 |
| *Pisum sativum* (Garden pea) | | P80572 |
| *Saara hardwickii* (Indian spiny-tailed lizard) (*Uromastyx hardwickii*) | | P80467 |
| *Scyliorhinus canicula* (Small-spotted catshark) (*Squalus canicula*) | | P86884 |
| *Sparus aurata* (Gilthead sea bream) | | P79896 |

Acyl-CoA Oxidases

In some embodiments, the present disclosure teaches recombinant microorganisms that are engineered to reduce or eliminate the expression or activity of one or more of the endogenous acyl-CoA oxidases (i.e. POX1, POX2, POX3, POX4, POX5, and POX6). In some embodiments, recombinant microorganisms of the present disclosure are engineered to comprise deletions of endogenous acyl-CoA oxidases (i.e. POX1, POX2, POX3, POX4, POX5, and POX6). For example, in some embodiments, the recombinant microorganism is a *Y. lipolytica* strain exhibiting a reduction in the activities of acyl-CoA oxidases (namely POX1: YALI0E32835g, POX2: YALI0F10857g, POX3: YALI0D24750g, POX4: YALI0E27654g, POX5: YALI0C23859g, POX6: YALI0E06567g).

Alcohol Oxidase

In some embodiments, the present disclosure teaches recombinant microorganisms that are engineered to reduce or eliminate the expression or activity of endogenous fatty alcohol oxidase (FAO1). In some embodiments, recombinant microorganisms of the present disclosure are engineered to comprise deletions of of endogenous fatty alcohol oxidase (FAO1). For example, in some embodiments, the recombinant microorganism is *Y. lipolytica*, and the microorganism comprises reduced activity of relevant (fatty) alcohol oxidases, namely FAO1: YALI0B14014g).

In some embodiments, an alcohol oxidase (AOX) is used to catalyze the conversion of a fatty alcohol to a fatty aldehyde. Alcohol oxidases catalyze the conversion of alcohols into corresponding aldehydes (or ketones) with electron transfer via the use of molecular oxygen to form hydrogen peroxide as a by-product. AOX enzymes utilize flavin adenine dinucleotide (FAD) as an essential cofactor and regenerate with the help of oxygen in the reaction medium. Catalase enzymes may be coupled with the AOX to avoid accumulation of the hydrogen peroxide via catalytic conversion into water and oxygen.

Based on the substrate specificities, AOXs may be categorized into four groups: (a) short chain alcohol oxidase, (b) long chain alcohol oxidase, (c) aromatic alcohol oxidase, and (d) secondary alcohol oxidase (Goswami et al. 2013). Depending on the chain length of the desired substrate, some members of these four groups are better suited than others as candidates for evaluation.

Short chain alcohol oxidases (including but not limited to those currently classified as EC 1.1.3.13, Table 6.2) catalyze the oxidation of lower chain length alcohol substrates in the range of $C_1$-$C_8$ carbons (van der Klei et al. 1991) (Ozimek et al. 2005). Aliphatic alcohol oxidases from methylotrophic yeasts such as *Candida boidinii* and *Komagataella pastoris* (formerly *Pichia pastoris*) catalyze the oxidation of primary alkanols to the corresponding aldehydes with a preference for unbranched short-chain aliphatic alcohols. The most broad substrate specificity is found for alcohol oxidase from the *Pichia pastoris* including propargyl alcohol, 2-chloroethanol, 2-cyanoethanol (Dienys et al. 2003). The major challenge encountered in alcohol oxidation is the high reactivity of the aldehyde product. Utilization of a two liquid phase system (water/solvent) can provide in-situ removal of the aldehyde product from the reaction phase before it is further converted to the acid. For example, hexanal production from hexanol using *Pichia pastoris* alcohol oxidase coupled with bovine liver catalase was achieved in a biphasic system by taking advantage of the presence of a stable alcohol oxidase in aqueous phase (Karra-Chaabouni et al. 2003). For example, alcohol oxidase from *Pichia pastoris* was able to oxidize aliphatic alcohols of $C_6$ to $C_{11}$ when used biphasic organic reaction system (Murray and Duff 1990). Methods for using alcohol oxidases in a biphasic system according to (Karra-Chaabouni et al. 2003) and (Murray and Duff 1990) are incorporated by reference in their entirety.

Long chain alcohol oxidases (including but not limited to those currently classified as EC 1.1.3.20; Table 6.3) include fatty alcohol oxidases, long chain fatty acid oxidases, and long chain fatty alcohol oxidases that oxidize alcohol substrates with carbon chain length of greater than six (Goswami et al. 2013). Banthorpe et al. reported a long chain alcohol oxidase purified from the leaves of *Tanacetum vulgare* that was able to oxidize saturated and unsaturated long chain alcohol substrates including hex-trans-2-en-1-ol and octan-1-ol (Banthorpe 1976) (Cardemil 1978). Other plant species, including *Simmondsia chinensis* (Moreau, R. A., Huang 1979), *Arabidopsis thaliana* (Cheng et al. 2004), and *Lotus japonicas* (Zhao et al. 2008) have also been reported as sources of long chain alcohol oxidases. Fatty alcohol oxidases are mostly reported from yeast species (Hommel and Ratledge 1990) (Vanhanen et al. 2000) (Hommel et al. 1994) (Kemp et al. 1990) and these enzymes play an important role in long chain fatty acid metabolism (Cheng et al. 2005). Fatty alcohol oxidases from yeast species that degrade and grow on long chain alkanes and fatty acid catalyze the oxidation of fatty alcohols. Fatty alcohol oxidase from *Candida tropicalis* has been isolated as microsomal cell fractions and characterized for a range of substrates (Eirich et al. 2004) (Kemp et al. 1988) (Kemp et al. 1991) (Mauersberger et al. 1992). Significant activity is observed for primary alcohols of length $C_8$ to $C_{16}$ with reported $K_M$ in the 10-50 μM range (Eirich et al. 2004). Alcohol oxidases described may be used for the conversion of medium chain aliphatic alcohols to aldehydes as described, for example, for whole-cells *Candida boidinii* (Gabelman and Luzio 1997), and *Pichia pastoris* (Duff and Murray 1988) (Murray and Duff 1990). Long chain alcohol oxidases from filamentous fungi were produced during growth on hydrocarbon substrates (Kumar and Goswami 2006) (Savitha and Ratledge 1991). The long chain fatty alcohol oxidase (LjFAO1) from *Lotus japonicas* has been heterologously expressed in *E. coli* and exhibited broad substrate specificity for alcohol oxidation including 1-dodecanol and 1-hexadecanol (Zhao et al. 2008).

TABLE 6.2

Alcohol oxidase enzymes capable of oxidizing short chain alcohols (EC 1.1.3.13)

| Organism | Gene names | Accession No. |
|---|---|---|
| *Komagataella pastoris* (strain ATCC 76273/CBS 7435/CECT 11047/NRRL Y-11430/Wegner 21-1) (Yeast) (*Pichia pastoris*) | AOX1 PP7435_Chr4-0130 | F2QY27 |
| *Komagataella pastoris* (strain GS115/ATCC 20864) (Yeast) (*Pichia pastoris*) | AOX1 PAS_chr4_0821 | P04842 |
| *Komagataella pastoris* (strain ATCC 76273/CBS 7435/CECT 11047/NRRL Y-11430/Wegner 21-1) (Yeast) (*Pichia pastoris*) | AOX2 PP7435_Chr4-0863 | F2R038 |
| *Komagataella pastoris* (strain GS115/ATCC 20864) (Yeast) (*Pichia pastoris*) | AOX2 PAS_chr4_0152 | C4R702 |
| *Candida boidinii* (Yeast) | AOD1 | Q00922 |
| *Pichia angusta* (Yeast) (*Hansenula polymorpha*) | MOX | P04841 |
| *Thanatephorus cucumeris* (strain AG1-IB/isolate 7/3/14) (Lettuce bottom rot fungus) (*Rhizoctonia solani*) | AOD1 BN14_10802 | M5CC52 |
| *Thanatephorus cucumeris* (strain AG1-IB/isolate 7/3/14) (Lettuce bottom rot fungus) (*Rhizoctonia solani*) | MOX BN14_12214 | M5CF32 |
| *Thanatephorus cucumeris* (strain AG1-IB/isolate 7/3/14) (Lettuce bottom rot fungus) (*Rhizoctonia solani*) | AOD1 BN14_10691 | M5CAV1 |
| *Thanatephorus cucumeris* (strain AG1-IB/isolate 7/3/14) (Lettuce bottom rot fungus) (*Rhizoctonia solani*) | AOD1 BN14_09479 | M5C7F4 |
| *Thanatephorus cucumeris* (strain AG1-IB/isolate 7/3/14) (Lettuce bottom rot fungus) (*Rhizoctonia solani*) | AOD1 BN14_10803 | M5CB66 |
| *Thanatephorus cucumeris* (strain AG1-IB/isolate 7/3/14) (Lettuce bottom rot fungus) (*Rhizoctonia solani*) | AOD1 BN14_09900 | M5C9N9 |
| *Thanatephorus cucumeris* (strain AG1-IB/isolate 7/3/14) (Lettuce bottom rot fungus) (*Rhizoctonia solani*) | AOD1 BN14_08302 | M5C2L8 |
| *Thanatephorus cucumeris* (strain AG1-IB/isolate 7/3/14) (Lettuce bottom rot fungus) (*Rhizoctonia solani*) | MOX BN14_09408 | M5C784 |
| *Thanatephorus cucumeris* (strain AG1-IB/isolate 7/3/14) (Lettuce bottom rot fungus) (*Rhizoctonia solani*) | MOX BN14_09478 | M5C8F8 |
| *Thanatephorus cucumeris* (strain AG1-IB/isolate 7/3/14) (Lettuce bottom rot fungus) (*Rhizoctonia solani*) | AOD1 BN14_11356 | M5CH40 |
| *Ogataea henricii* | AOD1 | A5LGF0 |
| *Candida methanosorbosa* | AOD1 | A5LGE5 |
| *Candida methanolovescens* | AOD1 | A5LGE4 |
| *Candida succiphila* | AOD1 | A5LGE6 |
| *Aspergillus niger* (strain CBS 513.88/FGSC A1513) | An15g02200 | A2R501 |
| *Aspergillus niger* (strain CBS 513.88/FGSC A1513) | An18g05480 | A2RB46 |

TABLE 6.2-continued

Alcohol oxidase enzymes capable of oxidizing short chain alcohols (EC 1.1.3.13)

| Organism | Gene names | Accession No. |
|---|---|---|
| *Moniliophthora perniciosa* (Witches'-broom disease fungus) (*Marasmius perniciosus*) | | I7CMK2 |
| *Candida cariosilignicola* | AOD1 | A5LGE3 |
| *Candida pignaliae* | AOD1 | A5LGE1 |
| *Candida pignaliae* | AOD2 | A5LGE2 |
| *Candida sonorensis* | AOD1 | A5LGD9 |
| *Candida sonorensis* | AOD2 | A5LGE0 |
| *Pichia naganishii* | AOD1 | A5LGF2 |
| *Ogataea minuta* | AOD1 | A5LGF1 |
| *Ogataea philodendra* | AOD1 | A5LGF3 |
| *Ogataea wickerhamii* | AOD1 | A5LGE8 |
| *Kuraishia capsulate* | AOD1 | A5LGE7 |
| *Talaromyces stipitatus* (strain ATCC 10500/CBS 375.48/ QM 6759/NRRL 1006) (*Penicillium stipitatum*) | TSTA_021940 | B8MHF8 |
| *Talaromyces stipitatus* (strain ATCC 10500/CBS 375.48/ QM 6759/NRRL 1006) (*Penicillium stipitatum*) | TSTA_065150 | B8LTH7 |
| *Talaromyces stipitatus* (strain ATCC 10500/CBS 375.48/ QM 6759/NRRL 1006) (*Penicillium stipitatum*) | TSTA_065150 | B8LTH8 |
| *Talaromyces stipitatus* (strain ATCC 10500/CBS 375.48/ QM 6759/NRRL 1006) (*Penicillium stipitatum*) | TSTA_000410 | B8MSB1 |
| *Ogataea glucozyma* | AOD1 | A5LGE9 |
| *Ogataea parapolymorpha* (strain DL-1/ATCC 26012/ NRRL Y-7560) (Yeast) (*Hansenula polymorpha*) | HPODL_03886 | W1QCJ3 |
| *Gloeophyllum trabeum* (Brown rot fungus) | AOX | A8DPS4 |
| *Pichia angusta* (Yeast) (*Hansenula polymorpha*) | mox1 | A6PZG8 |
| *Pichia trehalophila* | AOD1 | A5LGF4 |
| *Pichia angusta* (Yeast) (*Hansenula polymorpha*) | mox1 | A6PZG9 |
| *Pichia angusta* (Yeast) (*Hansenula polymorpha*) | mox1 | A6PZG7 |
| *Ixodes scapularis* (Black-legged tick) (Deer tick) | IscW_ISCW017898 | B7PIZ7 |

TABLE 6.3

Alcohol oxidase enzymes capable of oxidizing long chain alcohols including fatty alcohols (EC 1.1.3.20)

| Organism | Gene names | Accession No. |
|---|---|---|
| *Lotus japonicus* (*Lotus corniculatus* var. *japonicus*) | FAO1 | B5WWZ8 |
| *Arabidopsis thaliana* (Mouse-ear cress) | FAO1 At1g03990 F21M11.7 | Q9ZWB9 |
| *Lotus japonicus* (*Lotus corniculatus* var. *japonicus*) | FAO2 | B5WWZ9 |
| *Arabidopsis thaliana* (Mouse-ear cress) | FAO3 At3g23410 MLM24.14 MLM24.23 | Q9LW56 |
| *Arabidopsis thaliana* (Mouse-ear cress) | FAO4A At4g19380 T5K18.160 | O65709 |
| *Arabidopsis thaliana* (Mouse-ear cress) | FAO4B At4g28570 T5F17.20 | Q94BP3 |
| *Microbotryum violaceum* (strain p1A1 Lamole) (Anther smut fungus) (*Ustilago violacea*) | MVLG_06864 | U5HIL4 |
| *Ajellomyces dermatitidis* ATCC 26199 | BDFG_03507 | T5BNQ0 |
| *Gibberella zeae* (strain PH-1/ATCC MYA-4620/ FGSC 9075/NRRL 31084) (Wheat head blight fungus) (*Fusarium graminearum*) | FG06918.1 FGSG_06918 | I1RS14 |
| *Pichia sorbitophila* (strain ATCC MYA-4447/ BCRC 22081/CBS 7064/NBRC 10061/NRRL Y-12695) (Hybrid yeast) | Piso0_004410 GNLVRS01_PISO0K16268g GNLVRS01_PISO0L16269g | G8Y5E1 |
| *Emericella nidulans* (strain FGSC A4/ATCC 38163/CBS 112.46/NRRL 194/M139) (*Aspergillus nidulans*) | AN0623.2 ANIA_00623 | Q5BFQ7 |
| *Pyrenophora tritici-repentis* (strain Pt-1C-BFP) (Wheat tan spot fungus) (*Drechslera tritici-repentis*) | PTRG_10154 | B2WJW5 |
| *Paracoccidioides lutzii* (strain ATCC MYA-826/ Pb01) (*Paracoccidioides brasiliensis*) | PAAG_09117 | C1HEC6 |
| *Candida parapsilosis* (strain CDC 317/ATCC MYA-4646) (Yeast) (*Monilia parapsilosis*) | CPAR2_204420 | G8BG15 |
| *Pseudozyma brasiliensis* (strain GHG001) (Yeast) | PSEUBRA_SCAF2g03010 | V5GPS6 |
| *Candida parapsilosis* (strain CDC 317/ATCC MYA-4646) (Yeast) (*Monilia parapsilosis*) | CPAR2_204430 | G8BG16 |
| *Sclerotinia borealis* F-4157 | SBOR_5750 | W9CDE2 |
| *Sordaria macrospora* (strain ATCC MYA-333/ DSM 997/K(L3346)/K-hell) | SMAC_06361 | F7W6K4 |
| *Sordaria macrospora* (strain ATCC MYA-333/ DSM 997/K(L3346)/K-hell) | SMAC_01933 | F7VSA1 |

TABLE 6.3-continued

| Alcohol oxidase enzymes capable of oxidizing long chain alcohols including fatty alcohols (EC 1.1.3.20) | | |
|---|---|---|
| Organism | Gene names | Accession No. |
| *Meyerozyma guilliermondii* (strain ATCC 6260/CBS 566/DSM 6381/JCM 1539/NBRC 10279/NRRL Y-324) (Yeast) (*Candida guilliermondii*) | PGUG_03467 | A5DJL6 |
| *Trichophyton rubrum* CBS 202.88 | H107_00669 | A0A023ATC5 |
| *Arthrobotrys oligospora* (strain ATCC 24927/CBS 115.81/DSM 1491) (Nematode-trapping fungus) (*Didymozoophaga oligospora*) | AOL_s00097g516 | G1XJI9 |
| *Scheffersomyces stipitis* (strain ATCC 58785/CBS 6054/NBRC 10063/NRRL Y-11545) (Yeast) (*Pichia stipitis*) | FAO1 PICST_90828 | A3LYX9 |
| *Scheffersomyces stipitis* (strain ATCC 58785/CBS 6054/NBRC 10063/NRRL Y-11545) (Yeast) (*Pichia stipitis*) | FAO2 PICST_32359 | A3LW61 |
| *Aspergillus oryzae* (strain 3.042) (Yellow koji mold) | Ao3042_09114 | I8TL25 |
| *Fusarium oxysporum* (strain Fo5176) (*Fusarium* vascular wilt) | FOXB_17532 | F9GFU8 |
| *Rhizopus delemar* (strain RA 99-880/ATCC MYA-4621/FGSC 9543/NRRL 43880) (Mucormycosis agent) (*Rhizopus arrhizus* var. *delemar*) | RO3G_08271 | I1C536 |
| *Rhizopus delemar* (strain RA 99-880/ATCC MYA-4621/FGSC 9543/NRRL 43880) (Mucormycosis agent) (*Rhizopus arrhizus* var. *delemar*) | RO3G_00154 | I1BGX0 |
| *Fusarium oxysporum* (strain Fo5176) (*Fusarium* vascular wilt) | FOXB_07532 | F9FMA2 |
| *Penicillium roqueforti* | PROQFM164_S02g001772 | W6QPY1 |
| *Aspergillus clavatus* (strain ATCC 1007/CBS 513.65/DSM 816/NCTC 3887/NRRL 1) | ACLA_018400 | A1CNB5 |
| *Arthroderma otae* (strain ATCC MYA-4605/CBS 113480) (*Microsporum canis*) | MCYG_08732 | C5G1B0 |
| *Trichophyton tonsurans* (strain CBS 112818) (Scalp ringworm fungus) | TESG_07214 | F2S8I2 |
| *Colletotrichum higginsianum* (strain IMI 349063) (Crucifer anthracnose fungus) | CH063_13441 | H1VUE7 |
| *Ajellomyces capsulatus* (strain H143) (Darling's disease fungus) (*Histoplasma capsulatum*) | HCDG_07658 | C6HN77 |
| *Trichophyton rubrum* (strain ATCC MYA-4607/CBS 118892) (Athlete's foot fungus) | TERG_08235 | F2T096 |
| *Cochliobolus heterostrophus* (strain C5/ATCC 48332/race O) (Southern corn leaf blight fungus) (*Bipolaris maydis*) | COCHEDRAFT_1201414 | M2UMT9 |
| *Candida orthopsilosis* (strain 90-125) (Yeast) | CORT_0D04510 | H8X643 |
| *Candida orthopsilosis* (strain 90-125) (Yeast) | CORT_0D04520 | H8X644 |
| *Candida orthopsilosis* (strain 90-125) (Yeast) | CORT_0D04530 | H8X645 |
| *Pseudozyma aphidis* DSM 70725 | PaG_03027 | W3VP49 |
| *Coccidioides posadasii* (strain C735) (Valley fever fungus) | CPC735_000380 | C5P005 |
| *Magnaporthe oryzae* (strain P131) (Rice blast fungus) (*Pyricularia oryzae*) | OOW_P131scaffold01214g15 | L7IZ92 |
| *Neurospora tetrasperma* (strain FGSC 2508/ATCC MYA-4615/P0657) | NEUTE1DRAFT_82541 | F8MKD1 |
| *Hypocrea virens* (strain Gv29-8/FGSC 10586) (*Gliocladium virens*) (*Trichoderma virens*) | TRIVIDRAFT_54537 | G9MMY7 |
| *Hypocrea virens* (strain Gv29-8/FGSC 10586) (*Gliocladium virens*) (*Trichoderma virens*) | TRIVIDRAFT_53801 | G9MT89 |
| *Aspergillus niger* (strain CBS 513.88/FGSC A1513) | An01g09620 | A2Q9Z3 |
| *Verticillium dahliae* (strain VdLs.17/ATCC MYA-4575/FGSC 10137) (*Verticillium* wilt) | VDAG_05780 | G2X6J8 |
| *Ustilago maydis* (strain 521/FGSC 9021) (Corn smut fungus) | UM02023.1 | Q4PCZ0 |
| *Fusarium oxysporum f.* sp. *lycopersici* MN25 | FOWG_13006 | W9LNI9 |
| *Fusarium oxysporum f.* sp. *lycopersici* MN25 | FOWG_02542 | W9N9Z1 |
| *Candida tropicalis* (Yeast) | FAO1 | Q6QIR6 |
| *Magnaporthe oryzae* (strain 70-15/ATCC MYA-4617/FGSC 8958) (Rice blast fungus) (*Pyricularia oryzae*) | MGG_11317 | G4MVK1 |
| *Candida tropicalis* (Yeast) | faot | Q9P8D9 |
| *Candida tropicalis* (Yeast) | FAO2a | Q6QIR5 |
| *Phaeosphaeria nodorum* (strain SN15/ATCC MYA-4574/FGSC 10173) (Glume blotch fungus) (*Septoria nodorum*) | SNOG_02371 | Q0V0U3 |
| *Candida tropicalis* (Yeast) | FAO2b | Q6QIR4 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| *Pestalotiopsis* fici W106-1 | PFICI_11209 | W3WU04 |
| *Magnaporthe oryzae* (strain Y34) (Rice blast fungus) (*Pyricularia oryzae*) | OOU_Y34scaffold00240g57 | L7IFT5 |
| *Pseudogymnoascus destructans* (strain ATCC MYA-4855/20631-21) (Bat white-nose syndrome fungus) (*Geomyces destructans*) | GMDG_01756 | L8G0G6 |
| *Pseudogymnoascus destructans* (strain ATCC MYA-4855/20631-21) (Bat white-nose syndrome fungus) (*Geomyces destructans*) | GMDG_04950 | L8GCY2 |
| *Mycosphaerella fijiensis* (strain CIRAD86) (Black leaf streak disease fungus) (*Pseudocercospora fijiensis*) | MYCFIDRAFT_52380 | M2Z831 |
| *Bipolaris oryzae* ATCC 44560 | COCMIDRAFT_84580 | W7A0I8 |
| *Cladophialophora psammophila* CBS 110553 | A1O5_08147 | W9WTM9 |
| *Fusarium oxysporum f.* sp. *melonis* 26406 | FOMG_05173 | X0AEE6 |
| *Fusarium oxysporum f.* sp. *melonis* 26406 | FOMG_17829 | W9ZBB7 |
| *Cyphellophora europaea* CBS 101466 | HMPREF1541_02174 | W2S2S5 |
| *Aspergillus kawachii* (strain NBRC 4308) (White koji mold) (*Aspergillus awamori* var. kawachi) | AKAW_00147 | G7X626 |
| *Aspergillus terreus* (strain NIH 2624/FGSC A1156) | ATEG_05086 | Q0CMJ8 |
| *Coccidioides immitis* (strain RS) (Valley fever fungus) | CIMG_02987 | J3KAI8 |
| *Ajellomyces dermatitidis* (strain ER-3/ATCC MYA-2586) (*Blastomyces dermatitidis*) | BDCG_04701 | C5GLS5 |
| *Fusarium oxysporum f.* sp. *cubense* (strain race 1) (Panama disease fungus) | FOC1_g10013865 | N4U732 |
| *Rhodotorula glutinis* (strain ATCC 204091/IIP 30/MTCC 1151) (Yeast) | RTG_00643 | G0SVU8 |
| *Aspergillus niger* (strain ATCC 1015/CBS 113.46/FGSC A1144/LSHB Ac4/NCTC 3858a/NRRL 328/USDA 3528.7) | ASPNIDRAFT_35778 | G3XTM6 |
| *Candida cloacae* | fao1 | Q9P8D8 |
| *Candida cloacae* | fao2 | Q9P8D7 |
| *Fusarium oxysporum f.* sp. *cubense* (strain race 1) (Panama disease fungus) | FOC1_g10006358 | N4TUH3 |
| *Candida albicans* (strain SC5314/ATCC MYA-2876) (Yeast) | FAO1 CaO19.13562 orf19.13562 | Q59RS8 |
| *Candida albicans* (strain SC5314/ATCC MYA-2876) (Yeast) | FAO1 CaO19.6143 orf19.6143 | Q59RP0 |
| *Chaetomium thermophilum* (strain DSM 1495/CBS 144.50/IMI 039719) | CTHT_0018560 | G0S2U9 |
| *Mucor circinelloides f. circinelloides* (strain 1006PhL) (Mucormycosis agent) (*Calyptromyces circinelloides*) | HMPREF1544_05296 | S2JDN0 |
| *Mucor circinelloides f. circinelloides* (strain 1006PhL) (Mucormycosis agent) (*Calyptromyces circinelloides*) | HMPREF1544_05295 | S2JYP5 |
| *Mucor circinelloides f. circinelloides* (strain 1006PhL) (Mucormycosis agent) (*Calyptromyces circinelloides*) | HMPREF1544_06348 | S2JVK9 |
| *Botryotinia fuckeliana* (strain BcDW1) (Noble rot fungus) (*Botrytis cinerea*) | BcDW1_6807 | M7UD26 |
| *Podospora anserina* (strain S/ATCC MYA-4624/DSM 980/FGSC 10383) (*Pleurage anserina*) | PODANS_5_13040 | B2AFD8 |
| *Neosartorya fumigata* (strain ATCC MYA-4609/Af293/CBS 101355/FGSC A1100) (*Aspergillus fumigatus*) | AFUA_1G17110 | Q4WR91 |
| *Fusarium oxysporum f.* sp. *vasinfectum* 25433 | FOTG_00686 | X0MEE6 |
| *Fusarium oxysporum f.* sp. *vasinfectum* 25433 | FOTG_12485 | X0LE98 |
| *Trichophyton interdigitale* H6 | H101_06625 | A0A022U717 |
| *Beauveria bassiana* (strain ARSEF 2860) (White muscardine disease fungus) (*Tritirachium shiotae*) | BBA_04100 | J4UNY3 |
| *Fusarium oxysporum f.* sp. *radicis-lycopersici* 26381 | FOCG_00843 | X0GQ62 |
| *Fusarium oxysporum f.* sp. *radicis-lycopersici* 26381 | FOCG_15170 | X0F4T1 |
| *Neurospora tetrasperma* (strain FGSC 2509/P0656) | NEUTE2DRAFT_88670 | G4UNN6 |
| *Pseudozyma hubeiensis* (strain SY62) (Yeast) | PHSY_000086 | R9NVU1 |
| *Lodderomyces elongisporus* (strain ATCC 11503/CBS 2605/JCM 1781/NBRC 1676/NRRL YB-4239) (Yeast) (*Saccharomyces elongisporus*) | LELG_03289 | A5E102 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| *Malassezia globosa* (strain ATCC MYA-4612/CBS 7966) (Dandruff-associated fungus) | MGL_3855 | A8QAY8 |
| *Byssochlamys spectabilis* (strain No. 5/NBRC 109023) (*Paecilomyces variotii*) | PVAR5_7014 | V5GBL6 |
| *Ajellomyces capsulatus* (strain H88) (Darling's disease fungus) (*Histoplasma capsulatum*) | HCEG_03274 | F0UF47 |
| *Trichosporon asahii* var. *asahii* (strain ATCC 90039/CBS 2479/JCM 2466/KCTC 7840/NCYC 2677/UAMH 7654) (Yeast) | A1Q1_03669 | J6FBP4 |
| *Penicillium oxalicum* (strain 114-2/CGMCC 5302) (*Penicillium decumbens*) | PDE_00027 | S7Z8U8 |
| *Fusarium oxysporum f.* sp. *conglutinans* race 2 54008 | FOPG_02304 | X0IBE3 |
| *Fusarium oxysporum f.* sp. *conglutinans* race 2 54008 | FOPG_13066 | X0H540 |
| *Fusarium oxysporum f.* sp. *raphani* 54005 | FOQG_00704 | X0D1G8 |
| *Fusarium oxysporum f.* sp. *raphani* 54005 | FOQG_10402 | X0C482 |
| *Metarhizium acridum* (strain CQMa 102) | MAC_03115 | E9DZR7 |
| *Arthroderma benhamiae* (strain ATCC MYA-4681/CBS 112371) (*Trichophyton mentagrophytes*) | ARB_02250 | D4B1C1 |
| *Fusarium oxysporum f.* sp. *cubense* tropical race 4 54006 | FOIG_12161 | X0JFI6 |
| *Fusarium oxysporum f.* sp. *cubense* tropical race 4 54006 | FOIG_12751 | X0JDU5 |
| *Cochliobolus heterostrophus* (strain C4/ATCC 48331/race T) (Southern corn leaf blight fungus) (*Bipolaris maydis*) | COCC4DRAFT_52836 | N4WZZ0 |
| *Trichosporon asahii* var. *asahii* (strain CBS 8904) (Yeast) | A1Q2_00631 | K1VZW1 |
| *Mycosphaerella graminicola* (strain CBS 115943/IPO323) (Speckled leaf blotch fungus) (*Septoria tritici*) | MYCGRDRAFT_37086 | F9X375 |
| *Botryotinia fuckeliana* (strain T4) (Noble rot fungus) (*Botrytis cinerea*) | BofuT4_P072020.1 | G2XQ18 |
| *Metarhizium anisopliae* (strain ARSEF 23/ATCC MYA-3075) | MAA_05783 | E9F0I4 |
| *Cladophialophora carrionii* CBS 160.54 | G647_05801 | V9DAR1 |
| *Coccidioides posadasii* (strain RMSCC 757/Silveira) (Valley fever fungus) | CPSG_09174 | E9DH75 |
| *Rhodosporidium toruloides* (strain NP11) (Yeast) (*Rhodotorula gracilis*) | RHTO_06879 | M7X159 |
| Puccinia graminis *f.* sp. *tritici* (strain CRL 75-36-700-3/race SCCL) (Black stem rust fungus) | PGTG_10521 | E3KIL8 |
| *Trichophyton rubrum* CBS 288.86 | H103_00624 | A0A022WG28 |
| *Colletotrichum fioriniae* PJ7 | CFIO01_08202 | A0A010RKZ4 |
| *Trichophyton rubrum* CBS 289.86 | H104_00611 | A0A022XB46 |
| *Cladophialophora yegresii* CBS 114405 | A1O7_02579 | W9WC55 |
| *Colletotrichum orbiculare* (strain 104-T/ATCC 96160/CBS 514.97/LARS 414/MAFF 240422) (Cucumber anthracnose fungus) (*Colletotrichum lagenarium*) | Cob_10151 | N4VFP3 |
| *Drechslerella stenobrocha* 248 | DRE_03459 | W7IDL6 |
| *Neosartorya fumigata* (strain CEA10/CBS 144.89/FGSC A1163) (*Aspergillus fumigatus*) | AFUB_016500 | B0XP90 |
| *Thielavia terrestris* (strain ATCC 38088/NRRL 8126) (*Acremonium alabamense*) | THITE_2117674 | G2R8H9 |
| *Gibberella fujikuroi* (strain CBS 195.34/IMI 58289/NRRL A-6831) (Bakanae and foot rot disease fungus) (*Fusarium fujikuroi*) | FFUJ_02948 | S0DZP7 |
| *Gibberella fujikuroi* (strain CBS 195.34/IMI 58289/NRRL A-6831) (Bakanae and foot rot disease fungus) (*Fusarium fujikuroi*) | FFUJ_12030 | S0EMC6 |
| *Aspergillus flavus* (strain ATCC 200026/FGSC A1120/NRRL 3357/JCM 12722/SRRC 167) | AFLA_109870 | B8N941 |
| *Togninia minima* (strain UCR-PA7) (Esca disease fungus) (*Phaeoacremonium aleophilum*) | UCRPA7_1719 | R8BTZ6 |
| *Ajellomyces dermatitidis* (strain ATCC 18188/CBS 674.68) (*Blastomyces dermatitidis*) | BDDG_09783 | F2TUC0 |
| *Macrophomina phaseolina* (strain MS6) (Charcoal rot fungus) | MPH_10582 | K2RHA5 |
| *Neurospora crassa* (strain ATCC 24698/74-OR23-1A/CBS 708.71/DSM 1257/FGSC 987) | NCU08977 | Q7S2Z2 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| *Neosartorya fischeri* (strain ATCC 1020/DSM 3700/FGSC A1164/NRRL 181) (*Aspergillus fischerianus*) | NFIA_008260 | A1D156 |
| *Fusarium pseudograminearum* (strain CS3096) (Wheat and barley crown-rot fungus) | FPSE_11742 | K3U9J5 |
| *Spathaspora passalidarum* (strain NRRL Y-27907/11-Y1) | SPAPADRAFT_54193 | G3AJP0 |
| *Spathaspora passalidarum* (strain NRRL Y-27907/11-Y1) | SPAPADRAFT_67198 | G3ANX7 |
| *Trichophyton verrucosum* (strain HKI 0517) | TRV_07960 | D4DL86 |
| *Arthroderma gypseum* (strain ATCC MYA-4604/CBS 118893) (*Microsporum gypseum*) | MGYG_07264 | E4V2J0 |
| *Hypocrea jecorina* (strain QM6a) (*Trichoderma reesei*) | TRIREDRAFT_43893 | G0R7P8 |
| *Trichophyton rubrum* MR1448 | H110_00629 | A0A022Z1G4 |
| *Aspergillus ruber* CBS 135680 | EURHEDRAFT_512125 | A0A017SPR0 |
| *Glarea lozoyensis* (strain ATCC 20868/MF5171) | GLAREA_04397 | S3D6C1 |
| *Setosphaeria turcica* (strain 28A) (Northern leaf blight fungus) (*Exserohilum turcicum*) | SETTUDRAFT_20639 | R0K6H8 |
| *Paracoccidioides brasiliensis* (strain Pb18) | PADG_06552 | C1GH16 |
| *Fusarium oxysporum* Fo47 | FOZG_13577 | W9JPG9 |
| *Fusarium oxysporum* Fo47 | FOZG_05344 | W9KPH3 |
| *Trichophyton rubrum* MR1459 | H113_00628 | A0A022ZY09 |
| *Penicillium marneffei* (strain ATCC 18224/CBS 334.59/QM 7333) | PMAA_075740 | B6QBY3 |
| *Sphaerulina musiva* (strain SO2202) (Poplar stem canker fungus) (*Septoria musiva*) | SEPMUDRAFT_154026 | M3DAK6 |
| *Gibberella moniliformis* (strain M3125/FGSC 7600) (Maize ear and stalk rot fungus) (*Fusarium verticillioides*) | FVEG_10526 | W7N4P8 |
| *Gibberella moniliformis* (strain M3125/FGSC 7600) (Maize ear and stalk rot fungus) (*Fusarium verticillioides*) | FVEG_08281 | W7MVR9 |
| *Pseudozyma antarctica* (strain T-34) (Yeast) (*Candida antarctica*) | PANT_22d00298 | M9MGF2 |
| *Paracoccidioides brasiliensis* (strain Pb03) | PABG_07795 | C0SJD4 |
| *Rhizophagus irregularis* (strain DAOM 181602/DAOM 197198/MUCL 43194) (Arbuscular mycorrhizal fungus) (*Glomus intraradices*) | GLOINDRAFT_82554 | U9TF61 |
| *Penicillium chrysogenum* (strain ATCC 28089/DSM 1075/Wisconsin 54-1255) (*Penicillium notatum*) | Pc21g23700 PCH_Pc21g23700 | B6HJ58 |
| *Baudoinia compniacensis* (strain UAMH 10762) (Angels' share fungus) | BAUCODRAFT_274597 | M2M6Z5 |
| *Hypocrea atroviridis* (strain ATCC 20476/IMI 206040) (*Trichoderma atroviride*) | TRIATDRAFT_280929 | G9NJ32 |
| *Colletotrichum gloeosporioides* (strain Cg-14) (Anthracnose fungus) (*Glomerella cingulata*) | CGLO_06642 | T0LPH0 |
| *Cordyceps militaris* (strain CM01) (Caterpillar fungus) | CCM_02665 | G3JB34 |
| *Pyronema omphalodes* (strain CBS 100304) (*Pyronema confluens*) | PCON_13062 | U4LKE9 |
| *Colletotrichum graminicola* (strain Ml.001/M2/FGSC 10212) (Maize anthracnose fungus) (*Glomerella graminicola*) | GLRG_08499 | E3QR67 |
| *Glarea lozoyensis* (strain ATCC 74030/MF5533) | M7I_2117 | H0EHX4 |
| *Fusarium oxysporum f.* sp. *cubense* (strain race 4) (Panama disease fungus) | FOC4_g10002493 | N1S969 |
| *Fusarium oxysporum f.* sp. *cubense* (strain race 4) (Panama disease fungus) | FOC4_g10011461 | N1RT80 |
| *Cochliobolus sativus* (strain ND90Pr/ATCC 201652) (Common root rot and spot blotch fungus) (*Bipolaris sorokiniana*) | COCSADRAFT_295770 | M2TBE4 |
| *Mixia osmundae* (strain CBS 9802/IAM 14324/JCM 22182/KY 12970) | Mo05571 E5Q_05571 | G7E7S3 |
| *Mycosphaerella pini* (strain NZE10/CBS 128990) (Red band needle blight fungus) (*Dothistroma septosporum*) | DOTSEDRAFT_69651 | N1PXR0 |
| *Grosmannia clavigera* (strain kw1407/UAMH 11150) (Blue stain fungus) (*Graphiocladiella clavigera*) | CMQ_1113 | F0XC64 |
| *Fusarium oxysporum* FOSC 3-a | FOYG_03004 | W9IUE5 |
| *Fusarium oxysporum* FOSC 3-a | FOYG_16040 | W9HNP0 |
| *Fusarium oxysporum* FOSC 3-a | FOYG_17058 | W9HB31 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| *Nectria haematococca* (strain 77-13-4/ATCC MYA-4622/FGSC 9596/MPVI) (*Fusarium solani* subsp. *pisi*) | NECHADRAFT_37686 | C7YQL1 |
| *Nectria haematococca* (strain 77-13-4/ATCC MYA-4622/FGSC 9596/MPVI) (*Fusarium solani* subsp. *pisi*) | NECHADRAFT_77262 | C7ZJI0 |
| *Tuber melanosporum* (strain Mel28) (Perigord black truffle) | GSTUM_00010376001 | D5GLS0 |
| *Ajellomyces dermatitidis* (strain SLH14081) (*Blastomyces dermatitidis*) | BDBG_07633 | C5JYI9 |
| *Chaetomium globosum* (strain ATCC 6205/CBS 148.51/DSM 1962/NBRC 6347/NRRL 1970) (Soil fungus) | CHGG_9885 | Q2GQ69 |
| *Candida tenuis* (strain ATCC 10573/BCRC 21748/CBS 615/JCM 9827/NBRC 10315/ NRRL Y-1498/VKM Y-70) (Yeast) | CANTEDRAFT_108652 | G3B9Z1 |
| *Trichophyton rubrum* CBS 100081 | H102_00622 | A0A022VKY4 |
| *Pyrenophora teres f. teres* (strain 0-1) (Barley net blotch fungus) (*Drechslera teres f. teres*) | PTT_09421 | E3RLZ3 |
| *Colletotrichum gloeosporioides* (strain Nara gc5) (Anthracnose fungus) (*Glomerella cingulata*) | CGGC5_4608 | L2GB29 |
| *Gibberella zeae* (Wheat head blight fungus) (*Fusarium graminearum*) | FG05_06918 | A0A016PCS4 |
| *Trichophyton soudanense* CBS 452.61 | H105_00612 | A0A022Y6A6 |
| *Sclerotinia sclerotiorum* (strain ATCC 18683/ 1980/Ss-1) (White mold) (*Whetzelinia sclerotiorum*) | SS1G_07437 | A7EQ37 |
| *Fusarium oxysporum f.* sp. *pisi* HDV247 | FOVG_14401 | W9NWU8 |
| *Fusarium oxysporum f.* sp. *pisi* HDV247 | FOVG_02874 | W9Q5V3 |
| *Ustilago hordei* (strain Uh4875-4) (Barley covered smut fungus) | UHOR_03009 | I2G1Z4 |
| *Sporisorium reilianum* (strain SRZ2) (Maize head smut fungus) | sr12985 | E6ZYF7 |
| *Bipolaris zeicola* 26-R-13 | COCCADRAFT_81154 | W6YIP8 |
| *Melampsora larici-populina* (strain 98AG31/ pathotype 3-4-7) (Poplar leaf rust fungus) | MELLADRAFT_78490 | F4RUZ8 |
| *Fusarium oxysporum f.* sp. *lycopersici* (strain 4287/CBS 123668/FGSC 9935/NRRL 34936) (*Fusarium* vascular wilt of tomato) | FOXG_01901 | J9MG95 |
| *Fusarium oxysporum f.* sp. *lycopersici* (strain 4287/CBS 123668/FGSC 9935/NRRL 34936) (*Fusarium* vascular wilt of tomato) | FOXG_11941 | J9N9S4 |
| *Bipolaris victoriae* FI3 | COCVIDRAFT_39053 | W7EMJ8 |
| *Debaryomyces hansenii* (strain ATCC 36239/ CBS 767/JCM 1990/NBRC 0083/IGC 2968) (Yeast) (*Torulaspora hansenii*) | DEHA2E04268g | Q6BQL4 |
| *Clavispora lusitaniae* (strain ATCC 42720) (Yeast) (*Candida lusitaniae*) | CLUG_01505 | C4XZX3 |
| *Candida albicans* (strain WO-1) (Yeast) | CAWG_02023 | C4YME4 |
| *Trichophyton rubrum* MR850 | H100_00625 | A0A022U0Q2 |
| *Candida dubliniensis* (strain CD36/ATCC MYA-646/CBS 7987/NCPF 3949/NRRL Y-17841) (Yeast) | CD36_32890 | B9WMC7 |
| *Starmerella bombicola* | AOX1 | A0A024FB95 |
| *Thielavia heterothallica* (strain ATCC 42464/ BCRC 31852/DSM 1799) (*Myceliophthora thermophila*) | MYCTH_103590 | G2QJL7 |
| *Claviceps purpurea* (strain 20.1) (Ergot fungus) (*Sphacelia segetum*) | CPUR_07614 | M1WFI4 |
| *Aspergillus oryzae* (strain ATCC 42149/RIB 40) (Yellow koji mold) | AO090023000571 | Q2UH61 |
| *Dictyostelium discoideum* (Slime mold) | DDB_0184181 DDB_G0292042 | Q54DT6 |
| *Triticum urartu* (Red wild einkorn) (*Crithodium urartu*) | TRIUR3_22733 | M7YME5 |
| *Solanum tuberosum* (Potato) | PGSC0003DMG400017211 | M1BG07 |
| *Oryza sativa* subsp. *japonica* (Rice) | OSJNBb0044B19.5 LOC_Os10g33540 | Q8W5P8 |
| *Oryza sativa* subsp. *japonica* (Rice) | OJ1234_B11.20 Os02g0621800 | Q6K9N5 |
| *Oryza sativa* subsp. *japonica* (Rice) | OSJNBa0001K12.5 LOC_Os10g33520 | Q8W5P3 |
| *Zea mays* (Maize) | ZEAMMB73_809149 | C0P3J6 |
| *Citrus clementina* | CICLE_v10011111mg | V4S9P4 |
| *Citrus clementina* | CICLE_v10018992mg | V4U4C9 |

TABLE 6.3-continued

| Alcohol oxidase enzymes capable of oxidizing long chain alcohols including fatty alcohols (EC 1.1.3.20) | | |
|---|---|---|
| Organism | Gene names | Accession No. |
| *Citrus clementina* | CICLE_v10004405mg | V4S9D3 |
| *Citrus clementina* | CICLE_v10004403mg | V4RZZ6 |
| *Morus notabilis* | L484_011703 | W9RIK0 |
| *Morus notabilis* | L484_005930 | W9RET7 |
| *Medicago truncatula* (Barrel medic) (*Medicago tribuloides*) | MTR_1g075650 | G7I4U3 |
| *Arabidopsis thaliana* (Mouse-ear cress) | | Q8LDP0 |
| *Medicago truncatula* (Barrel medic) (*Medicago tribuloides*) | MTR_4g081080 | G7JF07 |
| *Simmondsia chinensis* (Jojoba) (*Buxus chinensis*) | | L7VFV2 |
| *Prunus persica* (Peach) (*Amygdalus persica*) | PRUPE_ppa018458mg | M5VXL1 |
| *Aphanomyces astaci* | H257_07411 | W4GI89 |
| *Aphanomyces astaci* | H257_07412 | W4GI44 |
| *Aphanomyces astaci* | H257_07411 | W4GKE3 |
| *Aphanomyces astaci* | H257_07411 | W4GK29 |
| *Aphanomyces astaci* | H257_07411 | W4GJ79 |
| *Aphanomyces astaci* | H257_07411 | W4GI38 |
| *Phaeodactylum tricomutum* (strain CCAP 1055/1) | PHATRDRAFT_48204 | B7G6C1 |
| *Hordeum vulgare* var. *distichum* (Two-rowed barley) | | F2E4R4 |
| *Hordeum vulgare* var. *distichum* (Two-rowed barley) | | F2DZG1 |
| *Hordeum vulgare* var. *distichum* (Two-rowed barley) | | M0YPG7 |
| *Hordeum vulgare* var. *distichum* (Two-rowed barley) | | M0YPG6 |
| *Hordeum vulgare* var. *distichum* (Two-rowed barley) | | F2CUY4 |
| *Ricinus communis* (Castor bean) | RCOM_0867830 | B9S1S3 |
| *Brassica rapa* subsp. *pekinensis* (Chinese cabbage) (*Brassica pekinensis*) | BRA014947 | M4DEM5 |
| *Ricinus communis* (Castor bean) | RCOM_0258730 | B9SV13 |
| *Brassica rapa* subsp. *pekinensis* (Chinese cabbage) (*Brassica pekinensis*) | BRA001912 | M4CCI2 |
| *Brassica rapa* subsp. *pekinensis* (Chinese cabbage) (*Brassica pekinensis*) | BRA012548 | M4D7T8 |
| *Brassica rapa* subsp. *pekinensis* (Chinese cabbage) (*Brassica pekinensis*) | BRA024190 | M4E5Y6 |
| *Brassica rapa* subsp. *pekinensis* (Chinese cabbage) (*Brassica pekinensis*) | BRA015283 | M4DFL0 |
| *Ricinus communis* (Castor bean) | RCOM_1168730 | B9SS54 |
| *Zea mays* (Maize) | | C4J691 |
| *Oryza glaberrima* (African rice) | | I1P2B7 |
| *Zea mays* (Maize) | | B6SXM3 |
| *Zea mays* (Maize) | | C0HFU4 |
| *Aegilops tauschii* (Tausch's goatgrass) (*Aegilops squarrosa*) | F775_19577 | R7W4J3 |
| *Solanum habrochaites* (Wild tomato) (*Lycopersicon hirsutum*) | | R9R6T0 |
| *Physcomitrella patens* subsp. *patens* (Moss) | PHYPADRAFT_124285 | A9S535 |
| *Physcomitrella patens* subsp. *patens* (Moss) | PHYPADRAFT_113581 | A9RG13 |
| *Physcomitrella patens* subsp. *patens* (Moss) | PHYPADRAFT_182504 | A9S9A5 |
| *Solanum pennellii* (Tomato) (*Lycopersicon pennellii*) | | R9R6Q1 |
| *Vitis vinifera* (Grape) | VIT_02s0087g00630 | F6HJ27 |
| *Vitis vinifera* (Grape) | VIT_07s0005g03780 | F6HZM3 |
| *Vitis vinifera* (Grape) | VIT_05s0049g01400 | F6H8T4 |
| *Vitis vinifera* (Grape) | VITISV_019349 | A5AH38 |
| *Capsella rubella* | CARUB_v10013046mg | R0HIT3 |
| *Capsella rubella* | CARUB_v10004212mg | R0GUX4 |
| *Capsella rubella* | CARUB_v10004208mg | R0F3X6 |
| *Capsella rubella* | CARUB_v10012453mg | R0ILD0 |
| *Capsella rubella* | CARUB_v10004208mg | R0GUX1 |
| *Eutrema salsugineum* (Saltwater cress) (*Sisymbrium salsugineum*) | EUTSA_v10024496mg | V4MD54 |
| *Eutrema salsugineum* (Saltwater cress) (*Sisymbrium salsugineum*) | EUTSA_v10020141mg | V4NM59 |
| *Eutrema salsugineum* (Saltwater cress) (*Sisymbrium salsugineum*) | EUTSA_v10024496mg | V4LUR9 |
| *Eutrema salsugineum* (Saltwater cress) (*Sisymbrium salsugineum*) | EUTSA_v10024528mg | V4P767 |
| *Eutrema salsugineum* (Saltwater cress) (*Sisymbrium salsugineum*) | EUTSA_v10006882mg | V4L2P6 |

TABLE 6.3-continued

Alcohol oxidase enzymes capable of oxidizing long chain alcohols including fatty alcohols (EC 1.1.3.20)

| Organism | Gene names | Accession No. |
|---|---|---|
| *Selaginella moellendorffii* (Spikemoss) | SELMODRAFT_87684 | D8R6Z6 |
| *Selaginella moellendorffii* (Spikemoss) | SELMODRAFT_87621 | D8R6Z5 |
| *Selaginella moellendorffii* (Spikemoss) | SELMODRAFT_74601 | D8QN81 |
| *Selaginella moellendorffii* (Spikemoss) | SELMODRAFT_73531 | D8QN82 |
| *Sorghum bicolor* (*Sorghum*) (*Sorghum vulgare*) | Sb04g026390 SORBIDRAFT_04g026390 | C5XXS4 |
| *Sorghum bicolor* (*Sorghum*) (*Sorghum vulgare*) | Sb04g026370 SORBIDRAFT_04g026370 | C5XXS1 |
| *Sorghum bicolor* (*Sorghum*) (*Sorghum vulgare*) | Sb01g019470 SORBIDRAFT_01g019470 | C5WYH6 |
| *Sorghum bicolor* (*Sorghum*) (*Sorghum vulgare*) | Sb01g019480 SORBIDRAFT_01g019480 | C5WYH7 |
| *Sorghum bicolor* (*Sorghum*) (*Sorghum vulgare*) | Sb01g019460 SORBIDRAFT_01g019460 | C5WYH5 |
| *Solanum pimpinellifolium* (Currant tomato) (*Lycopersicon pimpinellifolium*) | | R9R6J2 |
| *Phaseolus vulgaris* (Kidney bean) (French bean) | PHAVU_007G124200g | V7BGM7 |
| *Phaseolus vulgaris* (Kidney bean) (French bean) | PHAVU_011G136600g | V7AI35 |
| *Phaseolus vulgaris* (Kidney bean) (French bean) | PHAVU_001G162800g | V7D063 |
| *Solanum tuberosum* (Potato) | PGSC0003DMG400024294 | M1C923 |
| *Solanum tuberosum* (Potato) | PGSC0003DMG400018458 | M1BKV4 |
| *Solanum tuberosum* (Potato) | PGSC0003DMG400018458 | M1BKV3 |
| *Glycine max* (Soybean) (*Glycine hispida*) | | K7LK61 |
| *Glycine max* (Soybean) (*Glycine hispida*) | | K7KXQ9 |
| *Populus trichocarpa* (Western balsam poplar) (*Populus balsamifera* subsp. *trichocarpa*) | POPTR_0008s16920g | B9HKS3 |
| *Picea sitchensis* (Sitka spruce) (*Pinus sitchensis*) | | B8LQ84 |
| *Populus trichocarpa* (Western balsam poplar) (*Populus balsamifera* subsp. *trichocarpa*) | POPTR_0004s24310g | U5GKQ5 |
| *Populus trichocarpa* (Western balsam poplar) (*Populus balsamifera* subsp. *trichocarpa*) | POPTR_0010s07980g | B9HSG9 |
| *Glycine max* (Soybean) (*Glycine hispida*) | | I1N9S7 |
| *Glycine max* (Soybean) (*Glycine hispida*) | | I1LSK5 |
| *Setaria italica* (Foxtail millet) (*Panicum italicum*) | Si034362m.g | K4A658 |
| *Solanum lycopersicum* (Tomato) (*Lycopersicon esculentum*) | Solyc09g072610.2 | K4CUT7 |
| *Setaria italica* (Foxtail millet) (*Panicum italicum*) | Si016380m.g | K3YQ38 |
| *Solanum lycopersicum* (Tomato) (*Lycopersicon esculentum*) | | R9R6I9 |
| *Solanum lycopersicum* (Tomato) (*Lycopersicon esculentum*) | Solyc09g090350.2 | K4CW61 |
| *Solanum lycopersicum* (Tomato) (*Lycopersicon esculentum*) | Solyc08g005630.2 | K4CI54 |
| *Solanum lycopersicum* (Tomato) (*Lycopersicon esculentum*) | Solyc08g075240.2 | K4CMP1 |
| *Setaria italica* (Foxtail millet) (*Panicum italicum*) | Si034359m.g | K4A655 |
| *Setaria italica* (Foxtail millet) (*Panicum italicum*) | Si034354m.g | K4A650 |
| *Mimulus guttatus* (Spotted monkey flower) (Yellow monkey flower) | MIMGU_mgv1a001896mg | A0A022PU07 |
| *Mimulus guttatus* (Spotted monkey flower) (Yellow monkey flower) | MIMGU_mgv1a022390mg | A0A022RAV4 |
| *Mimulus guttatus* (Spotted monkey flower) (Yellow monkey flower) | MIMGU_mgv1a001868mg | A0A022S2E6 |
| *Mimulus guttatus* (Spotted monkey flower) (Yellow monkey flower) | MIMGU_mgv1a001883mg | A0A022S275 |
| *Mimulus guttatus* (Spotted monkey flower) (Yellow monkey flower) | MIMGU_mgv1a001761mg | A0A022QNF0 |
| *Musa acuminata* subsp. *malaccensis* (Wild banana) (*Musa malaccensis*) | | M0SNA8 |
| *Musa acuminata* subsp. *malaccensis* (Wild banana) (*Musa malaccensis*) | | M0RUT7 |
| *Musa acuminata* subsp. *malaccensis* (Wild banana) (*Musa malaccensis*) | | M0RUK3 |
| *Saprolegnia diclina* VS20 | SDRG_10901 | T0RG89 |
| *Brachypodium distachyon* (Purple false brome) (*Trachynia distachya*) | BRADI3G49085 | I1IBP7 |
| *Brachypodium distachyon* (Purple false brome) (*Trachynia distachya*) | BRADI3G28677 | I1I4N2 |
| *Brachypodium distachyon* (Purple false brome) (*Trachynia distachya*) | BRADI3G28657 | I1I4N0 |
| *Oryza sativa* subsp. *indica* (Rice) | OsI_34012 | B8BHG0 |
| *Oryza sativa* subsp. *indica* (Rice) | OsI_08118 | B8AFT8 |
| *Oryza sativa* subsp. *indica* (Rice) | OsI_34008 | A2Z8H1 |
| *Oryza sativa* subsp. *indica* (Rice) | OsI_34014 | B8BHG1 |
| *Oryza sativa* subsp. *japonica* (Rice) | LOC_Os10g33460 | Q7XDG3 |

TABLE 6.3-continued

| Alcohol oxidase enzymes capable of oxidizing long chain alcohols including fatty alcohols (EC 1.1.3.20) | | |
|---|---|---|
| Organism | Gene names | Accession No. |
| *Oryza sativa* subsp. *japonica* (Rice) | Os10g0474800 | Q0IX12 |
| *Oryza sativa* subsp. *japonica* (Rice) | Os10g0474966 | C7J7R1 |
| *Oryza sativa* subsp. *japonica* (Rice) | OSJNBa0001K12.13 | Q8W5N7 |
| *Oryza sativa* subsp. *japonica* (Rice) | OsJ_31873 | B9G683 |
| *Oryza sativa* subsp. *japonica* (Rice) | OsJ_31875 | B9G684 |
| *Oryza sativa* subsp. *japonica* (Rice) | OSJNBa0001K12.3 | Q8W5P5 |
| *Arabidopsis lyrata* subsp. *lyrata* (Lyre-leaved rock-cress) | ARALYDRAFT_470376 | D7KDA3 |
| *Arabidopsis lyrata* subsp. *lyrata* (Lyre-leaved rock-cress) | ARALYDRAFT_479855 | D7L3B6 |
| *Arabidopsis lyrata* subsp. *lyrata* (Lyre-leaved rock-cress) | ARALYDRAFT_491906 | D7MDA9 |
| *Arabidopsis lyrata* subsp. *lyrata* (Lyre-leaved rock-cress) | ARALYDRAFT_914728 | D7MGS9 |

Desaturase

The present disclosure describes enzymes that desaturate fatty acyl substrates to corresponding unsaturated fatty acyl substrates.

In some embodiments, a desaturase is used to catalyze the conversion of a fatty acyl-CoA or acyl-ACP to a corresponding unsaturated fatty acyl-CoA or acyl-ACP. A desaturase is an enzyme that catalyzes the formation of a carbon-carbon double bond in a saturated fatty acid or fatty acid derivative, e.g., fatty acyl-CoA or fatty acyl-ACP (collectively referred to herein as "fatty acyl"), by removing at least two hydrogen atoms to produce a corresponding unsaturated fatty acid/acyl. Desaturases are classified with respect to the ability of the enzyme to selectively catalyze double bond formation at a subterminal carbon relative to the methyl end of the fatty acid/acyl or a subterminal carbon relative to the carbonyl end of the fatty acid/acyl. Omega (ω) desaturases catalyze the formation of a carbon-carbon double bond at a fixed subterminal carbon relative to the methyl end of a fatty acid/acyl. For example, an $\omega^3$ desaturase catalyzes the formation of a double bond between the third and fourth carbon relative the methyl end of a fatty acid/acyl. Delta (Δ) desaturases catalyze the formation of a carbon-carbon double bond at a specific position relative to the carboxyl group of a fatty acid or the carbonyl group of a fatty acyl CoA. For example, a $\Delta^9$ desaturase catalyzes the formation of a double bond between the $C_9$ and $C_{10}$ carbons with respect to the carboxyl end of the fatty acid or the carbonyl group of a fatty acyl CoA.

As used herein, a desaturase can be described with reference to the location in which the desaturase catalyzes the formation of a double bond and the resultant geometric configuration (i.e., E/Z) of the unsaturated hydrocarbon. Accordingly, as used herein, a Z9 desaturase refers to a Δ desaturase that catalyzes the formation of a double bond between the $C_9$ and $C_{10}$ carbons with respect to the carbonyl end of a fatty acid/acyl, thereby orienting two hydrocarbons on opposing sides of the carbon-carbon double bonds in the cis or Z configuration. Similarly, as used herein, a Z11 desaturase refers to a Δ desaturase that catalyzes the formation of a double bond between the $C_{11}$ and $C_{12}$ carbons with respect to the carbonyl end of a fatty acid/acyl.

Desaturases have a conserved structural motif. This sequence motif of transmembrane desaturases is characterized by [HX3-4HX7-41(3 non-His)HX2-3(1 nonHis) HHX61-189(40 non-His)HX2-3(1 non-His)HH]. The sequence motif of soluble desaturases is characterized by two occurrences of [D/EEXXH].

In some embodiments, the desaturase is a fatty acyl-CoA desaturase that catalyzes the formation of a double bond in a fatty acyl-CoA. In some such embodiments, the fatty acyl-CoA desaturase described herein is capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms. Thus, the desaturase used in the recombinant microorganism can be selected based on the chain length of the substrate.

In some embodiments, the fatty acyl desaturase described herein is capable of catalyzing the formation of a double bond at a desired carbon relative to the terminal CoA on the unsaturated fatty acyl-CoA. Thus, in some embodiments, a desaturase can be selected for use in the recombinant microorganism which catalyzes double bond insertion at the 3, 4, 5, 6, 7, 8, 9, 10, 11, 12, or 13 position with respect to the carbonyl group on a fatty acyl-CoA.

In some embodiments, the fatty acyl desaturase described herein is capable of catalyzing the formation of a double bond in a saturated fatty acyl-CoA such that the resultant unsaturated fatty acyl-CoA has a cis or trans (i.e., Z or E) geometric configuration.

In some embodiments, the desaturase is a fatty acyl-ACP desaturase that catalyzes the formation of a double bond in a fatty acyl-ACP. In some embodiments, the fatty acyl-ACP desaturase described herein is capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms. Thus, the desaturase used in the recombinant microorganism can be selected based on the chain length of the substrate.

In some embodiments, the fatty acyl-ACP desaturase described herein is capable of catalyzing the formation of a double bond at a desired carbon relative to the terminal carbonyl on the unsaturated fatty acyl-ACP. Thus, in some embodiments, a desaturase can be selected for use in the recombinant microorganism which catalyzes double bond insertion at the 3, 4, 5, 6, 7, 8, 9, 10, 11, 12, or 13 position with respect to the carbonyl group on a fatty acyl-ACP.

In some embodiments, the fatty acyl desaturase described herein is capable of catalyzing the formation of a double bond in a saturated fatty acyl-CoA such that the resultant unsaturated fatty acyl-ACP has a cis or trans (i.e., Z or E) geometric configuration.

In one embodiment, the fatty acyl desaturase is a Z11 desaturase. In some embodiments, a nucleic acid sequence encoding a Z11 desaturase from organisms of the species *Agrotis segetum, Amyelois transitella, Argyrotaenia velutiana, Choristoneura rosaceana, Lampronia capitella, Trichoplusia ni, Helicoverpa zea*, or *Thalassiosira pseudonana* is codon optimized. In some embodiments, the Z11 desaturase comprises a sequence set forth in SEQ ID NO: 32 or 33 from *Helicoverpa zea.*

Fatty Acyl Reductase

The present disclosure describes enzymes that reduce fatty acyl substrates to corresponding fatty alcohols or aldehydes.

In some embodiments, a fatty alcohol forming fatty acyl-reductase is used to catalyze the conversion of a fatty acyl-CoA to a corresponding fatty alcohol. In some embodiments, a fatty aldehyde forming fatty acyl-reductase is used to catalyze the conversion of a fatty acyl-ACP to a corresponding fatty aldehyde. A fatty acyl reductase is an enzyme that catalyzes the reduction of a fatty acyl-CoA to a corresponding fatty alcohol or the reduction of a fatty acyl-ACP to a corresponding fatty aldehyde. A fatty acyl-CoA and fatty acyl-ACP has a structure of R—(CO)—S—$R_1$, wherein R is a $C_6$ to $C_{24}$ saturated, unsaturated, linear, branched or cyclic hydrocarbon, and $R_1$ represents CoA or ACP. In a particular embodiment, R is a $C_6$ to $C_{24}$ saturated or unsaturated linear hydrocarbon. "CoA" is a non-protein acyl carrier group involved in the synthesis and oxidation of fatty acids. "ACP" is an acyl carrier protein, i.e., a polypeptide or protein subunit, of fatty acid synthase used in the synthesis of fatty acids.

Thus, in some embodiments, the disclosure provides for a fatty alcohol forming fatty acyl-reductase which catalyzes the reduction of a fatty acyl-CoA to the corresponding fatty alcohol. For example, R—(CO)—S-CoA is converted to R—$CH_2OH$ and CoA-SH when two molecules of NAD(P)H are oxidized to $NAD(P)^+$. Accordingly, in some such embodiments, a recombinant microorganism described herein can include a heterologous fatty alcohol forming fatty acyl-reductase, which catalyzes the reduction a fatty acyl-CoA to the corresponding fatty alcohol. In an exemplary embodiment, a recombinant microorganism disclosed herein includes at least one exogenous nucleic acid molecule encoding a fatty alcohol forming fatty-acyl reductase which catalyzes the conversion of a mono- or poly-unsaturated $C_6$-$C_{24}$ fatty acyl-CoA into the corresponding mono- or poly-unsaturated $C_6$-$C_{24}$ fatty alcohol.

In other embodiments, the disclosure provides for a fatty aldehyde forming fatty acyl-reductase which catalyzes the reduction of a fatty acyl-ACP to the corresponding fatty aldehyde. For example, R—(CO)—S-ACP is converted to R—(CO)—H and ACP-SH when one molecule of NAD(P)H is oxidized to $NAD(P)^+$. In some such embodiments, a recombinant microorganism described herein can include a heterologous fatty aldehyde forming fatty acyl-reductase, which catalyzes the reduction a fatty acyl-ACP to the corresponding fatty aldehyde. In an exemplary embodiment, a recombinant microorganism disclosed herein includes at least one exogenous nucleic acid molecule encoding a fatty aldehyde forming fatty-acyl reductase which catalyzes the conversion of a mono- or poly-unsaturated $C_6$-$C_{24}$ fatty acyl-ACP into the corresponding mono- or poly-unsaturated $C_6$-$C_{24}$ fatty aldehyde.

In some embodiments, a nucleic acid sequence encoding a fatty-acyl reductase from organisms of the species *Agrotis segetum, Spodoptera littoralis*, or *Helicoverpa amigera* is codon optimized.

Acyl-ACP Synthetase

The present disclosure describes enzymes that ligate a fatty acid to the corresponding fatty acyl-ACP.

In some embodiments, an acyl-ACP synthetase is used to catalyze the conversion of a fatty acid to a corresponding fatty acyl-ACP. An acyl-ACP synthetase is an enzyme capable of ligating a fatty acid to ACP to produce a fatty acid acyl-ACP. In some embodiments, an acyl-ACP synthetase can be used to catalyze the conversion of a fatty acid to a corresponding fatty acyl-ACP. In some embodiments, the acyl-ACP synthetase is a synthetase capable of utilizing a fatty acid as a substrate that has a chain length of 6, 7, 8, 9, 10, 11, 12, 13, 14, 15, 16, 17, 18, 19, 20, 21, 22, 23, or 24 carbon atoms. In one such embodiment, a recombinant microorganism described herein can include a heterologous acyl-ACP synthetase, which catalyzes the conversion of a fatty acid to a corresponding fatty acyl-ACP. In an exemplary embodiment, a recombinant microorganism disclosed herein includes at least one exogenous nucleic acid molecule which encodes an acyl-ACP synthetase that catalyzes the conversion of a saturated $C_6$-$C_{24}$ fatty acid to a corresponding saturated $C_6$-$C_{24}$ fatty acyl-ACP.

Improved Production of Biomass and One or More Lipid Using a Recombinant Microorganism As discussed above, in a first aspect, the present disclosure relates to a recombinant microorganism having improved production of biomass or improved production of one or more lipid from one or more fatty acid and one or more simple carbon co-substrates, wherein the recombinant microorganism comprises one or more modifications associated with: tricarboxylic acid cycle; lipid synthesis; reducing equivalent availability; one or more metabolic intermediates availability; and/or increased product purity, wherein the recombinant microorganism has improved production of biomass or improved production of one or more lipid compared to a microorganism without the same modifications.

In some embodiments, the one or more modifications associated with tricarboxylic acid cycle comprises the overexpression of at least one endogenous and/or exogenous nucleic acid molecule encoding an AMP-insensitive isocitrate dehydrogenase (IDH) variant in the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to AMP-insensitive IDH from *Escherichia coli, Mycobacterium smegmatis, Acidithiobacillus thiooxidans*, or *Yarrowia lipolytica*. In further embodiments, the at least one nucleic acid molecule is from *Yarrowia lipolytica* and comprises isoleucine to alanine substitutions at amino acid positions 279 and 280 of XP_503571.2. In some embodiments, the one or more modifications associated with tricarboxylic acid cycle results in extended activation of the tricarboxylic acid cycle.

In some embodiments, the one or more modifications associated with tricarboxylic acid cycle or one or more metabolic intermediates availability comprises the overexpression of at least one endogenous and/or exogenous nucleic acid molecule encoding a pyruvate transporter in the recombinant microorganism. In other embodiments, the one or more metabolic intermediates availability comprises mitochondrial pyruvate availability. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to pyruvate transporter from *Saccharomyces cerevisiae, Hanseniaspora osmophila, Yarrowia lipolytica*, or *Talaromyces marneffei* PM1. In further embodiments, the pyruvate transporter is selected from *Saccharomyces cerevisiae* mpcl, *Saccharomyces cerevisiae* mpc3 (NP_011759.1), *Hanseniaspora osmophila* mpc3 (0EJ86292.1), *Yarrowia lipolytica* mpc, and *Talaromyces marneffei* PM1 mpc3 (KFX48982.1), or homolog thereof. In yet a further embodiment, the recombinant microorganism is *Saccharomyces cerevisiae* comprising a deletion, disruption, or loss of function mutation in a gene encoding an mpc2 pyruvate transporter. In some embodiments, the recombinant microorganism is *Yarrowia lipolytica.*

In some embodiments, the one or more modifications associated with lipid synthesis comprises alleviation of acetyl-CoA carboxylase (ACC) inhibition. In certain embodiments, alleviation of ACC inhibition comprises the replacement of the endogenous ACC, or overexpression of at least one endogenous and/or exogenous nucleic acid molecule encoding a feedback-insensitive ACC variant in the recombinant microorganism. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to ACC from *Mus musculus, Rattus norvegicus*, or *Homo sapiens.*

In some embodiments, the one or more modifications associated with reducing equivalent availability comprises the overexpression of at least one endogenous and/or exogenous nucleic acid molecule encoding an NADP/NAD-dependent isocitrate dehydrogenase (IDH) in the cytosol of the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to IDH from *Escherichia coli, Mycobacterium smegmatis, Acidithiobacillus thiooxidans*, or *Yarrowia lipolytica*. In further embodiments, the IDH is selected from *Escherichia coli* Idh (WP_000444484.1), *Mycobacterium smegmatis* Icd2 (WP_011727802.1), *Acidithiobacillus thiooxidans* Idh (PDB: 2D4V_A), and *Yarrowia lipolytica* Idh1 (XP_503571.2), or homolog thereof.

In some embodiments, the one or more modifications associated with reducing equivalent availability further comprises the overexpression of at least one endogenous and/or exogenous nucleic acid encoding an aconitase in the cytosol of the recombinant microorganism. In certain embodiments, the at least one endogenous and/or exogenous nucleic acid molecule encoding the IDH and the at least one endogenous and/or exogenous nucleic acid molecule encoding the aconitase lack a sequence encoding a mitochondrial-targeting peptide.

In some embodiments, the one or more modifications associated with reducing equivalent availability or one or more metabolic intermediates availability comprises the overexpression of at least one endogenous or exogenous nucleic acid encoding a citrate transporter in the recombinant microorganism. In certain embodiments, the one or more intermediate comprises cytosolic citrate/isocitrate. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a citrate transporter from *Yarrowia lipolytica, Saccharomyces cerevisiae, Rattus norvegicus, Caenorhabditis elegans*, or *Caliqus clemensi*. In yet further embodiments, the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

In some embodiments, the one or more modifications associated with reducing equivalent availability comprises the overexpression of at least one exogenous nucleic acid molecule encoding a decarboxylating malic enzyme in the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a decarboxylating malic enzyme from *Arabidopsis thaliana, Amaranthus hypochondriacus, Rhizobium meliloti, Solanum tuberosum, Homo sapiens*, or *Escherichia coli*. In further embodiments, the decarboxylating malic enzyme is selected from *Arabidopsis thaliana* Q9SIU0 (SEQ ID NO: 34), *Amaranthus hypochondriacus* P37224 (SEQ ID NO: 35), *Rhizobium meliloti* 030807 (SEQ ID NO: 36), *Solanum tuberosum* P37221 (SEQ ID NO: 37), *Homo sapiens* Q16798 (SEQ ID NO: 38), and *Escherichia coli* P26616 (SEQ ID NO: 29), or homolog thereof. In yet a further embodiment, the decarboxylating malic enzyme lacks a sequence encoding a mitochondrial-targeting peptide.

In some embodiments, the one or more modifications associated with one or more metabolic intermediates availability comprises the overexpression of at least one endogenous and/or exogenous nucleic acid encoding an ATP-citrate lyase in the recombinant microorganism. In certain embodiments, the one or more intermediates availability comprises cytosolic oxaloacetate availability. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an ATP-citrate lyase from *Saccharomyces cerevisiae, Yarrowia lipolytica, Mus musculus*, and *Aspergillus niger*. In a yet further embodiment, the ATP-citrate lyase is selected from *Mus musculus* NP_001186225.1, *Mus musculus* NP_598798.1, *Aspergillus niger* XP_001394055.1, and *Aspergillus niger* XP_001394057.1, or homolog thereof.

In some embodiments, the one or more modifications associated with reducing equivalent availability comprises one or more modifications in the pentose phosphate pathway (PPP) in the recombinant microorganism. In certain embodiments, the one or more modifications in the PPP comprises one or more of: downregulation of hexose kinase activity; upregulation of one or more oxidative PPP enzyme activity; downregulation of fructose-6-phosphate kinase activity; and/or expression of one or more oxidative PPP enzyme variant. In further embodiments, the upregulation of one or more oxidative PPP enzyme activity comprises the overexpression of one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1). In yet a further embodiment, the downregulation of hexose kinase activity and/or fructose-6-phosphate kinase activity comprises deletion, disruption, and/or mutation of one or more endogenous gene encoding one or more hexose kinase enzyme and/or fructose-6-phosphate kinase enzyme. In some embodiments, the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1). In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent glucose-6-phosphate dehydrogenase (ZWF1) from *Leuconostoc*. In further embodiments, the NAD-dependent glucose-6-phosphate dehydrogenase (ZWF1) is selected from *Leuconostoc* AAA25265.1 and *Leuconostoc* P11411, or homolog thereof. In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent 6-phosphogluconate dehydrogenase (GND1) from *Bradyrhizobium* or *Methylobacillus*. In further embodiments, the NAD-dependent 6-phosphogluconate dehydrogenase (GND1) is selected from *Bradyrhizobium* WP_012029377.1, *Bradyrhizobium* A4YZZ8, *Methylobacillus* AAF34407.1, and *Methylobacillus* Q9L9P8, or homolog thereof.

In some embodiments, the one or more modifications associated with reducing equivalent availability comprises downregulation of mannitol synthesis pathway in the recombinant microorganism. In certain embodiments, downregulation of mannitol synthesis pathway comprises deletion, disruption, and/or mutation of one or more gene encoding an NADPH-dependent mannitol dehydrogenase and/or an aldo-keto reductase. In further embodiments, the one or more gene encoding an NADPH-dependent mannitol dehydrogenase is selected from YALI0B16192g, YALI0D18964g, and YALI0E12463g, or homolog thereof. In further embodiments, the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0C09119g, YALI0D04092g, YALI0B15268g, YALI0C00319g, and YALI0A19910g, or homolog thereof.

In some embodiments, the one or more modifications associated with reducing equivalent availability comprises decoupling and increasing glucose uptake in the recombinant microorganism. In certain embodiments, decoupling and increasing glucose uptake comprises: upregulation of hexose transporter activity; and/or downregulation of hexose kinase activity. In further embodiments, the upregulation of one or more hexose transporter activity comprises the overexpression of one or more endogenous and/or exogenous nucleic acid molecule encoding a hexose transporter operably linked to one or more heterologous promoters. In some embodiments, the one or more endogenous and/or exogenous nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a hexose transporter from *Yarrowia lipolytica*. In certain embodiments, the one or more endogenous and/or exogenous nucleic acid molecule encoding a hexose transporter is selected from YALI0A14212g, YALI0D01111g, YALI0D00363g, YALI0C16522g, and YALI0F25553g, or homolog thereof. In some embodiments, the downregulation of hexose kinase activity comprises deletion, disruption, and/or mutation of one or more endogenous gene encoding one or more hexose kinase enzyme.

In some embodiments, the one or more modifications associated with reducing equivalent availability, one or more metabolic intermediates availability, or increased product purity comprises downregulation or inhibition of acetyl-CoA carboxylase (ACC) activity in the recombinant microorganism. In certain embodiments, the downregulation or inhibition of ACC activity comprises deletion, disruption, and/or mutation of one or more endogenous gene encoding one or more ACC enzyme.

In some embodiments of a recombinant microorganism having improved production of biomass or improved production of one or more lipid from one or more fatty acid and one or more simple carbon co-substrates, the one or more fatty acid co-substrate is a saturated fatty acid. In some embodiments of a recombinant microorganism having improved production of biomass or improved production one or more lipid from one or more fatty acid and one or more simple carbon co-substrates, the one or more simple carbon co-substrate is selected from glucose, fructose, and glycerol.

In some embodiments of a recombinant microorganism having improved production of biomass or improved production of one or more lipid from one or more fatty acid and one or more simple carbon co-substrates, the improved production of one or more lipid comprises improved production of one or more mono- or poly-unsaturated $C_6$-$C_{24}$ fatty acid, fatty alcohol, aldehyde, or acetate. In certain embodiments, the one or more mono- or poly-unsaturated $C_6$-$C_{24}$ fatty acid, fatty alcohol, aldehyde, or acetate is an insect pheromone. In further embodiments, the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

In some embodiments of a recombinant microorganism having improved production of biomass or improved production of one or more lipid from one or more fatty acid and one or more simple carbon co-substrates, the recombinant microorganism is a eukaryotic microorganism. In certain embodiments, the eukaryotic microorganism is a yeast. In further embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*. In yet a further embodiment, the yeast is an oleaginous yeast. In some embodiments, the oleaginous yeast is a member of a genus selected from the group consisting of *Yarrowia, Candida, Rhodotorula, Rho-*

*dosporidium, Cryptococcus, Trichosporon*, and *Lipomyces*. In certain embodiments, the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T cutaneum, Cryptococcus curvatus, R. glutinis*, and *R. graminis*.

Recombinant Microorganism

The disclosure provides microorganisms modified to have improved production of biomass or valuable products, such as one or more lipids or metabolic intermediates. In one embodiment, the valuable product is one or more lipids. In some embodiments, the valuable product is fatty acid, fatty alcohol, fatty aldehyde, and/or fatty acetate. In some embodiments, the valuable product is one or more pheromones. In some embodiments, the valuable product is one or more fatty acid precursors of one or more pheromones.

In various embodiments described herein, the recombinant microorganism is a eukaryotic microorganism. In some embodiments, the eukaryotic microorganism is a yeast. In exemplary embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*.

The present inventors have discovered that oleaginous yeast, such as *Candida* and *Yarrowia*, have a surprisingly high tolerance to the $C_6$-$C_{24}$ fatty alcohol substrates and products. Accordingly, in one such exemplary embodiment, the recombinant microorganism of the invention is an oleaginous yeast. In further embodiments, the oleaginous yeast is a member of a genus selected from the group consisting of *Yarrowia, Candida, Rhodotorula, Rhodosporidium, Cryptococcus, Trichosporon*, and *Lipomyces*. In even further embodiments, the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T cutaneum, Cryptococcus curvatus, R. glutinis*, and *R. graminis*.

In some embodiments, the recombinant microorganism is a prokaryotic microorganism. In exemplary embodiments, the prokaryotic microorganism is a member of a genus selected from the group consisting of *Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium*, and *Brevibacterium*.

In some embodiments, the recombinant microorganism is used to produce a mono- or poly-unsaturated $C_6$-$C_{24}$ fatty acid, alcohol, aldehyde, or acetate disclosed herein.

Accordingly, in another aspect, the present disclosure provides a method of producing one or more lipid using a recombinant microorganism described herein. In one embodiment, the method comprises cultivating the recombinant microorganism in a culture medium containing a feedstock providing one or more carbon source until the one or more lipid is produced. In some embodiments, the one or more lipid comprises one or more mono- or poly-unsaturated $C_6$-$C_{24}$ fatty acid, alcohol, aldehyde, or acetate. In further embodiments, the one or more mono- or poly-unsaturated $C_6$-$C_{24}$ fatty acid, alcohol, aldehyde, or acetate is one or more insect pheromone. In further embodiments, the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal. In a further embodiment, the one or more lipid is recovered. Recovery can be by methods known in the art, such as distillation, membrane-based separation gas stripping, solvent extraction, and expanded bed adsorption.

In some embodiments, the feedstock comprises a carbon source. In various embodiments described herein, the carbon source may be selected from sugars, glycerol, alcohols, organic acids, alkanes, fatty acids, lignocellulose, proteins, carbon dioxide, and carbon monoxide. In a further embodiment, the sugar is selected from the group consisting of glucose, fructose, and sucrose. In some embodiments, the one or more carbon source comprises one or more simple carbon and one or more fatty acid. In certain embodiments, the one or more simple carbon is selected from glucose, fructose and glycerol.

In some embodiments, the recombinant microorganism is a microalgae. Non-limiting examples of microalgae that can be used with the methods and compositions of the disclosure are members of the following divisions: cyanobacteria (Cyanophyceae), green algae (Chlorophyceae), diatoms (Bacillariophyceae), yellow green algae (Xanthophyceae), golden algae (Chrysophyceae), red algae (Rhodophyceae), brown algae (Phaeophyceae), dinoflagellates (Dinophyceae), and "pico-plankton" (Prasinophyceae and Eustigmatophyceae). In some embodiments, the preferred algae for use in connection with the production of Fas are green algae (fresh water), Cyanobacteria, and Diotoms (Marine). In certain embodiments, the microalgae used with the methods of the disclosure are members of one of the following classes: Bacillariophyceae, Eustigmatophyceae, and Chrysophyceae. In certain embodiments, the microalgae used with the methods of the disclosure are members of one of the following genera: *Nannochloropsis, Chlorella, Dunaliella, Scenedesmus*, Selenastrum, Oscillatoria, Phormidium, *Spirulina*, Amphora, and Ochromonas.

Non-limiting examples of microalgae species that can be used in connection with the present disclosure include: *Achnanthes orientalis*, Agmenellum spp., Amphiprora hyaline, Amphora coffeiformis, Amphora coffeiformis var. linea, Amphora coffeiformis var. *punctata*, Amphora coffeiformis var. taylori, Amphora coffeiformis var. *tenuis*, Amphora delicatissima, Amphora delicatissima var. *capitata*, Amphora sp., *Anabaena*, Ankistrodesmus, Ankistrodesmus *falcatus*, Boekelovia hooglandii, Borodinella sp., *Botryococcus braunii, Botryococcus* sudeticus, Bracteococcus minor, Bracteococcus medionucleatus, Carteria, *Chaetoceros* gracilis, *Chaetoceros muelleri, Chaetoceros muelleri* var. subsalsum, *Chaetoceros* sp., Chlamydomas perigranulata, *Chlorella* anitrata, *Chlorella antarctica, Chlorella aureoviridis, Chlorella Candida, Chlorella* capsulate, Chlorelladesiccate, *Chlorella* ellipsoidea, *Chlorella emersonii, Chlorella fusca, Chlorella fusca* var. vacuolate, *Chlorella* glucotropha, *Chlorella* infusionum, *Chlorella* infusionum var. actophila, *Chlorella* infusionum var. auxenophila, *Chlorella* kessleri, *Chlorella* lobophora, *Chlorella* luteoviridis, Chlorellaluteoviridis var. aureoviridis, *Chlorella* luteoviridis var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella* protothecoides var. acidicola, *Chlorella* regularis, *Chlorella* regularis var. minima, *Chlorella* regularis var. umbricata, *Chlorella* reisiglii, *Chlorella saccharophila*, Chlorellasaccharophila var. ellipsoidea, *Chlorella salina, Chlorella simplex, Chlorella sorokiniana, Chlorella* sp., *Chlorella sphaerica*, Chlorellastigmatophora, *Chlorella* vanniellii, *Chlorella vulgaris, Chlorella vulgaris* fo. tertia, *Chlorella vulgaris* var. *autotrophica, Chlorella vulgaris* var. *viridis, Chlorella vulgaris* var. vulgaris, *Chlorella vulgaris* var. vulgaris fo. tertia, *Chlorella vulgaris* var. vulgaris fo. *viridis, Chlorella xanthella, Chlorella zofingiensis, Chlorella trebouxioides, Chlorella vulgaris*, Chlorococcum infusionum, Chlorococcum sp., Chlorogonium, Chroomonas sp., *Chrysosphaera* sp., Cricosphaera sp., *Crypthecodinium cohnii*, Cryptomonas sp., Cyclotella cryptica, Cyclotella meneghiniana, Cyclotella sp., *Dunaliella* sp., *Dunaliella* bardawil, *Dunaliella* bioculata, *Dunaliella* granulate, *Dunaliella* maritime, *Dunaliella* minuta, *Dunaliella parva*, Dunaliellapeircei, *Dunaliella* primolecta, *Dunaliella salina, Dunaliella terricola, Dunaliella tertiolecta, Dunaliella viridis, Dunaliella tertiolecta, Eremosphaera viridis, Eremosphaera* sp., Ellipsoidon sp., *Euglena* spp., Franceia sp., Fragilaria crotonensis, Fragilaria sp., Gleocapsa sp., Gloeothamnion sp., Haematococcus pluvialis, Hymenomonas sp., *Isochrysis* off *galbana, Isochrysis galbana*, Lepocinclis, Micractinium, Micractinium, Monoraphidium *minutum*, Monoraphidium sp., Nannochloris sp., *Nannochloropsis salina, Nannochloropsis* sp., Navicula acceptata, Navicula biskanterae, Navicula pseudotenelloides, Navicula *pelliculosa*, Navicula saprophila, Navicula sp., Nephrochloris sp., Nephroselmis sp., Nitschia *communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., Ochromonas sp., *Oocystis parva, Oocystis pusilla, Oocystis* sp., Oscillatoria *limnetica*, Oscillatoria sp., Oscillatoria subbrevis, Parachlorella kessleri, Pascheria acidophila, Pavlova sp., *Phaeodactylum* tricomutum, Phagus, Phormidium, Platymonas sp., *Pleurochrysis* carter ae, *Pleurochrysis* dentate, *Pleurochrysis* sp., Prototheca *wickerhamii*, Prototheca stagnora, Prototheca *portoricensis*, Prototheca moriformis, Prototheca *zopfii, Pseudochlorella aquatica*, Pyramimonas sp., Pyrobotrys, *Rhodococcus opacus, Sarcinoid chrysophyte, Scenedesmus* armatus, Schizochytrium, Spirogyra, *Spirulina platensis*, Stichococcus sp., Synechococcus sp., Synechocystisf, *Tagetes erecta, Tagetes patula*, Tetraedron, *Tetraselmis* sp., *Tetraselmis suecica, Thalassiosira* weissflogii, and Viridiella fridericiana.

Methods of Producing a Recombinant Microorganism Having Improved Production of Biomass and One or More Lipid As discussed above, in another aspect, the present disclosure relates to a method of producing a recombinant microorganism having improved production of biomass or improved production of one or more lipid from one or more fatty acid and one or more simple carbon co-substrates, comprising introducing into a microorganism one or more modifications associated with: tricarboxylic acid cycle; lipid synthesis; reducing equivalent availability; one or more metabolic intermediates availability; and/or increased product purity, wherein the introducing one or more modifications yields a recombinant microorganism having improved production of biomass or improved production of one or more lipid compared to a microorganism not comprising the same modifications.

In some embodiments, the introducing one or more modifications associated with tricarboxylic acid cycle comprises introducing into and/or overexpressing in the recombinant microorganism at least one endogenous and/or exogenous nucleic acid molecule encoding an AMP-insensitive isocitrate dehydrogenase (IDH) variant. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to IDH from *Escherichia coli, Mycobacterium smegmatis, Acidithiobacillus thiooxidans*, or *Yarrowia lipolytica*. In further embodiments, the at least one nucleic acid molecule is from *Yarrowia lipolytica* and comprises isoleucine to alanine substitutions at amino acid positions 279 and 280 of XP_503571.2. In some embodiments, the one or more modifications associated with tricarboxylic acid cycle results in extended activation of the tricarboxylic acid cycle.

In some embodiments, the introducing one or more modifications associated with tricarboxylic acid cycle or one or more metabolic intermediates availability comprises introducing into and/or overexpressing in the recombinant microorganism at least one endogenous and/or exogenous nucleic acid molecule encoding a pyruvate transporter. In other embodiments, the one or more metabolic intermediates availability comprises mitochondrial pyruvate availability. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to pyruvate transporter from *Saccharomyces cerevisiae, Hanseniaspora osmophila, Yarrowia lipolytica*, or *Talaromyces marneffei* PM1. In further embodiments, the pyruvate transporter is selected from *Saccharomyces cerevisiae* mpc1, *Saccharomyces cerevisiae* mpc3 (NP_011759.1), *Hanseniaspora osmophila* mpc3 (0EJ86292.1), *Yarrowia lipolytica* mpc, and *Talaromyces marneffei* PM1 mpc3 (KFX48982.1), or homolog thereof. In yet a further embodiment, the recombinant microorganism is *Saccharomyces cerevisiae* comprising a deletion, disruption, or loss of function mutation in a gene encoding an mpc2 pyruvate transporter. In some embodiments, the recombinant microorganism is *Yarrowia lipolytica.*

In some embodiments, the introducing one or more modifications associated with lipid synthesis comprises alleviation of acetyl-CoA carboxylase (ACC) inhibition. In certain embodiments, alleviation of ACC inhibition comprises introducing into and/or overexpressing in the recombinant microorganism at least one endogenous and/or exogenous nucleic acid molecule encoding a feedback-insensitive ACC variant in the recombinant microorganism. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to ACC from *Mus musculus, Rattus norvegicus*, or *Homo sapiens.*

In some embodiments, the introducing one or more modifications associated with reducing equivalent availability comprises introducing into and/or overexpressing in the recombinant microorganism at least one endogenous and/or exogenous nucleic acid molecule encoding an NADP/NAD-dependent isocitrate dehydrogenase (IDH) in the cytosol of the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to IDH from *Escherichia coli, Mycobacterium smegmatis, Acidithiobacillus thiooxidans*, or *Yarrowia lipolytica*. In further embodiments, the IDH is selected from *Escherichia coli* Idh (WP_000444484.1), *Mycobacterium smegmatis* Icd2 (WP_011727802.1), *Acidithiobacillus thiooxidans* Idh (PDB: 2D4V_A), and *Yarrowia lipolytica* Idh1 (XP_503571.2), or homolog thereof.

In some embodiments, the introducing one or more modifications associated with reducing equivalent availability further comprises introducing into and/or overexpressing in the recombinant microorganism at least one endogenous and/or exogenous nucleic acid encoding an aconitase in the cytosol of the recombinant microorganism. In certain embodiments, the at least one endogenous and/or exogenous nucleic acid molecule encoding the IDH and the at least one endogenous and/or exogenous nucleic acid molecule encoding the aconitase lack a sequence encoding a mitochondrial-targeting peptide.

In some embodiments, the introducing one or more modifications associated with reducing equivalent availability or one or more metabolic intermediates availability comprises introducing into and/or overexpressing in the recombinant microorganism at least one endogenous and/or exogenous nucleic acid encoding a citrate transporter in the recombinant microorganism. In certain embodiments, the one or more intermediate comprises cytosolic citrate/isocitrate. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a citrate transporter from *Yarrowia lipolytica Saccharomyces cerevisiae, Rattus norvegicus, Caenorhabditis elegans*, or *Caliqus* clemensi. In yet further embodiments, the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

In some embodiments, the introducing one or more modifications associated with reducing equivalent availability comprises introducing into and/or overexpressing in the recombinant microorganism at least one exogenous nucleic acid molecule encoding a decarboxylating malic enzyme in the recombinant microorganism. In certain embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a decarboxylating malic enzyme from *Arabidopsis thaliana, Amaranthus hypochondriacus, Rhizobium meliloti, Solanum tuberosum, Homo sapiens*, or *Escherichia coli*. In further embodiments, the decarboxylating malic enzyme is selected from *Arabidopsis thaliana* Q9SIU0, *Amaranthus hypochondriacus* P37224, *Rhizobium meliloti* 030807, *Solanum tuberosum* P37221, *Homo sapiens* Q16798, and *Escherichia coli* P26616, or homolog thereof. In yet a further embodiment, the decarboxylating malic enzyme lacks a sequence encoding a mitochondrial-targeting peptide.

In some embodiments, the introducing one or more modifications associated with one or more metabolic intermediates availability comprises introducing into and/or overexpressing in the recombinant microorganism at least one endogenous and/or exogenous nucleic acid encoding an ATP-citrate lyase in the recombinant microorganism. In certain embodiments, the one or more metabolic intermediates availability comprises cytosolic oxaloacetate availability. In further embodiments, the at least one nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an ATP-citrate lyase from *Saccharomyces cerevisiae, Yarrowia lipolytica, Mus musculus*, and *Aspergillus niger*. In a yet further embodiment, the ATP-citrate lyase is selected from *Mus musculus* NP_001186225.1, *Mus musculus* NP_598798.1, *Aspergillus niger* XP_001394055.1, and *Aspergillus niger* XP_001394057.1, or homolog thereof.

In some embodiments, the introducing one or more modifications associated with reducing equivalent availability comprises one or more modifications in the pentose phosphate pathway (PPP) in the recombinant microorganism. In certain embodiments, the one or more modifications in the PPP comprises one or more of: downregulation of hexose kinase activity; upregulation of one or more oxidative PPP enzyme activity; downregulation of fructose-6-phosphate kinase activity; and/or expression of one or more oxidative PPP enzyme variant. In further embodiments, the upregulation of one or more oxidative PPP enzyme activity comprises introducing into and/or overexpressing in the recombinant microorganism one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1). In yet a further embodiment, the downregulation of hexose kinase activity and/or fructose-6-phosphate kinase activity comprises introducing into the recombinant microorganism a deletion, disruption, and/or mutation of one or more endogenous gene encoding one or more hexose kinase enzyme and/or fructose-6-phosphate kinase enzyme. In some embodiments, the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1). In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent glucose-6-phosphate dehydrogenase (ZWF1) from *Leuconostoc*. In further embodiments, the NAD-dependent glucose-6-phosphate dehydrogenase (ZWF1) is selected from *Leuconostoc* AAA25265.1 and *Leuconostoc* P11411, or homolog thereof. In certain embodiments, the one or more nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to an NAD-dependent 6-phosphogluconate dehydrogenase (GND1) from *Bradyrhizobium* or *Methylobacillus*. In further embodiments, the NAD-dependent 6-phosphogluconate dehydrogenase (GND1) is selected from *Bradyrhizobium* WP_012029377.1, *Bradyrhizobium* A4YZZ8, *Methylobacillus* AAF34407.1, and *Methylobacillus* Q9L9P8, or homolog thereof.

In some embodiments, the introducing one or more modifications associated with reducing equivalent availability comprises downregulation of mannitol synthesis pathway in the recombinant microorganism. In certain embodiments, downregulation of mannitol synthesis pathway comprises introducing into the recombinant microorganism a deletion, disruption, and/or mutation of one or more gene encoding an NADPH-dependent mannitol dehydrogenase and/or an aldo-keto reductase. In further embodiments, the one or more gene encoding an NADPH-dependent mannitol dehydrogenase is selected from YALI0B16192g, YALI0D18964g, and YALI0E12463g, or homolog thereof. In further embodiments, the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0C09119g, YALI0D04092g, YALI0B15268g, YALI0000319g, and YALI0A19910g, or homolog thereof.

In some embodiments, the introducing one or more modifications associated with reducing equivalent availability comprises decoupling and increasing glucose uptake in the recombinant microorganism. In certain embodiments, decoupling and increasing glucose uptake comprises: upregulation of hexose transporter activity; and/or downregulation of hexose kinase activity. In further embodiments, the upregulation of one or more hexose transporter activity comprises introducing into and/or overexpressing in the recombinant microorganism one or more endogenous and/or exogenous nucleic acid molecule encoding a hexose transporter operably linked to one or more heterologous promoters. In some embodiments, the one or more endogenous and/or exogenous nucleic acid molecule encodes for a protein that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a hexose transporter from *Yarrowia lipolytica*. In certain embodiments, the one or more endogenous and/or exogenous nucleic acid molecule encoding a hexose transporter is selected from YALI0A14212g, YALI0D01111g, YALI0D00363g, YALI0C16522g, and YALI0F25553g, or homolog thereof. In some embodiments, the downregulation of hexose kinase activity comprises introducing into the recombinant microorganism a deletion, disruption, and/or mutation of one or more endogenous gene encoding one or more hexose kinase enzyme.

In some embodiments, the introducing one or more modifications associated with reducing equivalent availability, one or more metabolic intermediates availability, and/or increased product purity comprises downregulation or inhibition of acetyl-CoA carboxylase (ACC) activity in the recombinant microorganism. In certain embodiments, the downregulation or inhibition of ACC activity comprises introducing into the recombinant microorganism a deletion, disruption, and/or mutation of one or more endogenous gene encoding one or more ACC enzyme.

In some embodiments of a method of producing a recombinant microorganism having improved production of biomass or improved production of one or more lipid from one or more fatty acid and one or more simple carbon co-substrates, the one or more fatty acid co-substrate is a saturated fatty acid. In some embodiments of a method of producing a recombinant microorganism having improved production of biomass or improved production of one or more lipid from one or more fatty acid and one or more simple carbon co-substrates, the one or more simple carbon co-substrate is selected from glucose, fructose, and glycerol.

In some embodiments of a method of producing a recombinant microorganism having improved production of biomass or improved production of one or more lipid from one or more fatty acid and one or more simple carbon co-substrates, the improved production of one or more lipid comprises improved production of one or more mono- or poly-unsaturated $C_6$-$C_{24}$ fatty acid, alcohol, aldehyde, or acetate. In certain embodiments, the one or more mono- or poly-unsaturated $C_6$-$C_{24}$ fatty acid, alcohol, aldehyde, or acetate is an insect pheromone. In further embodiments, the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

In some embodiments of a method of producing a recombinant microorganism having improved production of biomass or improved production of one or more lipid from one or more fatty acid and one or more simple carbon co-substrates, the recombinant microorganism is a eukaryotic microorganism. In certain embodiments, the eukaryotic microorganism is a yeast. In further embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma*. In yet a further embodiment, the yeast is an oleaginous yeast. In some embodiments, the oleaginous yeast is a member of a genus selected from the group consisting of *Yarrowia, Candida, Rhodotorula, Rhodosporidium, Cryptococcus, Trichosporon*, and *Lipomyces*. In certain embodiments, the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T cutaneum, Cryptococcus curvatus, R. glutinis*, and *R. graminis*.

Enzyme Engineering

The enzymes in the recombinant microorganism can be engineered to improve one or more aspects of the substrate to product conversion. Non-limiting examples of enzymes that can be further engineered for use in methods of the disclosure include an isocitrate dehydrogenase, a pyruvate transporter, an acetyl-CoA carboxylase, an aconitase, a citrate transporter, a decarboxylating malic enzyme, an ATP-citrate lyase, a glucose-6-phosphate dehydrogenase, a 6-phosphogluconolactonase, a 6-phosphogluconate dehydrogenase, a hexose transporter and combinations thereof. These enzymes can be engineered for improved catalytic activity, improved selectivity, improved stability, improved tolerance to various fermentations conditions (temperature, pH, etc.), altered selectivity of one or more substrate, altered selectivity of one or more co-factor, altered cellular localization, or improved tolerance to various metabolic substrates, products, by-products, intermediates, etc.

In some embodiments, an isocitrate dehydrogenase (IDH) enzyme can be engineered for insensitivity to AMP. Under a nitrogen-starved and glucose-rich environment, low levels of intracellular AMP reduce the activity of isocitrate dehydrogenase (IDH), a key allosteric enzyme in the TCA cycle in yeast mitochondria. The reduction of IDH activity slows the TCA cycle used for synthesis of biomass and reducing equivalents, and accumulates citrate (the equilibrium form of isocitrate). Therefore, in some embodiments, it is desirable to engineer an oleochemical production host to repurpose citrate for improvement in biomass generation. In certain embodiments, the AMP-insensitive IDH is from *Yarrowia lipolytica* and comprises isoleucine to alanine substitutions at amino acid positions 279 and 280 of XP_503571.2. In further non-limiting examples, an IDH can be engineered to lack a sequence encoding a mitochondrial-targeting peptide. In some embodiments, the IDH lacking a mitochondrial-targeting peptide localizes to the cytosol of a cell. In a further example, an aconitase can be engineered to lack a sequence encoding a mitochondrial-targeting peptide. In some embodiments, the aconitase lacking a mitochondrial-targeting peptide localizes to the cytosol of a cell. In a further example, a malate dehydrogenase can be engineered to lack a sequence encoding a mitochondrial-targeting peptide. In some embodiments, the malate dehydrogenase lacking a mitochondrial-targeting peptide localizes to the cytosol of a cell. In a further example, an acetyl-CoA carboxylase (ACC) enzyme can be engineered to be feedback-insensitive. In some embodiments, the feedback-insensitive ACC leads to increased lipid biosynthesis. In a further example, glucose-6-phosphate dehydrogenase (ZWF1) can be engineered to use NAD+ in place of NADP+ producing NADH instead of NADPH to match cofactor requirements of recombinant biosynthesis pathways. In a further example, 6-phosphogluconate dehydrogenase (GND1) can be engineered to use NAD+ in place of NADP+ producing NADH instead of NADPH to match cofactor requirements of recombinant biosynthesis pathways.

The term "improved catalytic activity" as used herein with respect to a particular enzymatic activity refers to a higher level of enzymatic activity than that measured relative to a comparable non-engineered enzyme, such as a non-engineered isocitrate dehydrogenase, an acetyl-CoA carboxylase, an aconitase, a decarboxylating malic enzyme, an ATP-citrate lyase, a glucose-6-phosphate dehydrogenase, a 6-phosphogluconolactonase, or a 6-phosphogluconate dehydrogenase. For example, overexpression of a specific enzyme can lead to an increased level of activity in the cells for that enzyme. Mutations can be introduced into an isocitrate dehydrogenase, an acetyl-CoA carboxylase, an aconitase, a decarboxylating malic enzyme, an ATP-citrate lyase, a glucose-6-phosphate dehydrogenase, a 6-phosphogluconolactonase, or a 6-phosphogluconate dehydrogenase enzyme resulting in engineered enzymes with improved catalytic activity. Methods to increase enzymatic activity are known to those skilled in the art. Such techniques can include increasing the expression of the enzyme by increasing plasmid copy number and/or use of a stronger promoter and/or use of activating riboswitches, introduction of mutations to relieve negative regulation of the enzyme, introduction of specific mutations to increase specific activity and/or decrease the $K_M$ for the substrate, or by directed evolution. See, e.g., Methods in Molecular Biology (vol. 231), ed. Arnold and Georgiou, Humana Press (2003).

Metabolic Engineering—Enzyme Overexpression and Gene Deletion/Downregulation for Increased Pathway Flux In various embodiments described herein, the exogenous and endogenous enzymes in the recombinant microorganism participating in the pathways described herein may be overexpressed.

The terms "overexpressed" or "overexpression" refers to an elevated level (e.g., aberrant level) of mRNAs encoding for a protein(s), and/or to elevated levels of protein(s) in cells as compared to similar corresponding unmodified cells expressing basal levels of mRNAs or having basal levels of proteins. In particular embodiments, mRNA(s) or protein(s) may be overexpressed by at least 25%, 35%, 45%, 55%, 65%, 75%, 85%, 95%, 2-fold, 3-fold, 4-fold, 5-fold, 6-fold, 8-fold, 10-fold, 12-fold, 15-fold or more in microorganisms engineered to exhibit increased gene mRNA, protein, and/or activity.

In some embodiments, it may be useful to increase the expression of endogenous or exogenous isocitrate dehydrogenase enzymes to extend activation of the tricarboxylic acid (TCA) cycle and increase flux from citrate, thereby resulting in increased biomass generation. In some embodiments, extended activation of the tricarboxylic acid cycle comprises the overexpression of at least one endogenous and/or exogenous nucleic acid molecule encoding an AMP-insensitive isocitrate dehydrogenase (IDH) variant in the recombinant microorganism. In some embodiments, the overexpression of an NADP/NAD-dependent isocitrate dehydrogenase (IDH) in the cytosol of the recombinant microorganism increases the availability or amount of reducing equivalents.

In some embodiments, it may be useful to increase the expression of endogenous or exogenous pyruvate transporters to enhance pyruvate flux from the cytosol to the mitochondria. In some embodiments, it may be useful to increase the expression of endogenous or exogenous pyruvate transporters to increase the mitochondrial pyruvate pool. In some embodiments, one or more modifications associated with tricarboxylic acid cycle and/or one or more metabolic intermediates availability comprises the overexpression of a pyruvate transporter in the recombinant microorganism. In other embodiments, the one or more metabolic intermediates availability comprises mitochondrial pyruvate availability.

In some embodiments, it may be useful to increase the expression of endogenous or exogenous acetyl-CoA carboxylase enzymes to increase lipid synthesis. In some embodiments, it may be useful to increase the expression of endogenous or exogenous acetyl-CoA carboxylase feedback-insensitive variant enzymes to alleviate inhibition of lipid synthesis.

In some embodiments, it may be useful to increase the expression of endogenous or exogenous aconitase enzymes to increase and/or rebalance reducing equivalents. In further embodiments, the overexpression of an aconitase in the cytosol of the recombinant microorganism increases and/or rebalances reducing equivalents.

In some embodiments, it may be useful to increase the expression of endogenous or exogenous citrate transporters to increase and/or rebalance reducing equivalents. In some embodiments, it may be useful to increase the expression of endogenous or exogenous citrate transporters to increase the amount of one or more metabolic intermediate. In certain embodiments, the one or more intermediate comprises cytosolic citrate/isocitrate.

In some embodiments, it may be useful to increase the expression of endogenous or exogenous decarboxylating malic enzymes to increase and/or rebalance reducing equivalents. In one embodiment, the malic enzyme is NAD+ dependent. In another embodiment, the malic enzyme is NADP+ dependent. In yet a further embodiment, it may be useful to increase the expression of endogenous or exogenous malate dehydrogenases in the cytosol of a recombinant microorganism.

In some embodiments, it may be useful to increase the expression of endogenous or exogenous ATP-citrate lyase to increase the amount of one or more metabolic intermediate. In certain embodiments, the one or more intermediate comprises cytosolic oxaloacetate.

In some embodiments, it may be useful to increase the expression of endogenous or exogenous oxidative pentose phosphate pathway (PPP) enzymes to increase flux through the PPP. In some embodiments, increasing the expression of oxidative PPP enzymes draws down the pool of glucose-6-phosphate and pulls additional fructose-6-phosphate to enter the oxidative PPP. In certain embodiments, increasing the flux through the PPP increases and/or rebalances reducing equivalents. In further embodiments, the upregulation of one or more oxidative PPP enzyme activity comprises the overexpression of a glucose-6-phosphate dehydrogenase (ZWF1), a 6-phosphogluconolactonase (SOL3), or a 6-phosphogluconate dehydrogenase (GND1). In some embodiments, it may be useful to increase the expression of endogenous or exogenous PPP enzyme variants which use NAD+ in place of NADP+ producing NADH instead of NADPH to match cofactor requirements of recombinant pathways. In some embodiments, the one or more oxidative PPP enzyme variant comprises an NAD-dependent glucose-6-phosphate dehydrogenase (ZWF1) and/or an NAD-dependent 6-phosphogluconate dehydrogenase (GND1).

In some embodiments, it may be useful to increase the expression of endogenous or exogenous hexose transporters to increase and/or rebalance reducing equivalents. In certain embodiments, the hexose transporter is high affinity. In some embodiments, the hexose transporter is low affinity.

Improved biomass or lipid production can be accomplished by, for example, overexpression of nucleic acids encoding one or more of the above-described enzymes or transporters. Overexpression of the above-described enzymes or proteins can occur, for example, through increased expression of an endogenous gene or genes, or through the expression, or increased expression, of an exogenous gene or genes. Therefore, naturally occurring organisms can be readily modified to generate non-natural microorganisms having improved biomass and lipid production through overexpression of one or more nucleic acid molecules encoding, for example, an isocitrate dehydrogenase, a pyruvate transporter, an acetyl-CoA carboxylase, an aconitase, a citrate transporter, a decarboxylating malic enzyme, an ATP-citrate lyase, a glucose-6-phosphate dehydrogenase, a 6-phosphogluconolactonase, a 6-phosphogluconate dehydrogenase, a hexose transporter, or combination thereof.

In addition, a non-naturally occurring organism can be generated by mutagenesis of an endogenous gene that results in an increase in activity of an enzyme or transporter as described herein.

Equipped with the present disclosure, the skilled artisan will be able to readily construct the recombinant microorganisms described herein, as the recombinant microorganisms of the disclosure can be constructed using methods well known in the art as exemplified above to exogenously express at least one nucleic acid encoding an enzyme or transporter described herein in sufficient amounts to produce lipid and generate biomass.

Methods for constructing and testing the expression levels of a non-naturally occurring lipid and biomass-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); Ausubo et al., *Current Protocols in Molecular Biology*, John Wiley and Sons, Baltimore, Md. (1999).

A variety of mechanisms known in the art can be used to express, or overexpress, exogenous or endogenous genes. For example, an expression vector or vectors can be constructed to harbor one or more enzyme or transporter encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art.

Expression control sequences are known in the art and include, for example, promoters, enhancers, polyadenylation signals, transcription terminators, internal ribosome entry sites (IVES), and the like, that provide for the expression of the polynucleotide sequence in a host cell. Expression control sequences interact specifically with cellular proteins involved in transcription (Maniatis et al., Science, 236:1237-1245 (1987)). Exemplary expression control sequences are described in, for example, Goeddel, *Gene Expression Technology: Methods in Enzymology*, Vol. 185, Academic Press, San Diego, Calif. (1990).

In various embodiments, an expression control sequence may be operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

In some embodiments, the recombinant microorganism is manipulated to delete, disrupt, mutate, and/or reduce the activity of one or more endogenous enzymes to increase and/or rebalance reducing equivalents. In some embodiments, the recombinant microorganism is manipulated to delete, disrupt, mutate, and/or reduce the activity of one or more endogenous enzymes to increase product purity. In some embodiments, the recombinant microorganism is manipulated to delete, disrupt, mutate, and/or reduce the activity of one or more endogenous enzymes to modify availability of metabolic intermediates.

In some embodiments, the recombinant microorganism is manipulated to delete, disrupt, mutate, and/or reduce the activity of one or more endogenous enzymes that catalyzes the conversion of glucose to glucose-6-phosphate. In some such embodiments, the enzymes that catalyze the conversion of glucose to glucose-6-phosphate are hexose kinases. In some embodiments, the deletion, disruption, mutation, and/or reduction in activity of one or more hexose kinase decouples and increases glucose uptake. In some embodiments, the deletion, disruption, mutation, and/or reduction in activity of one or more hexose kinase increases and/or rebalances reducing equivalents.

In other embodiments, the recombinant microorganism is manipulated to delete, disrupt, mutate, and/or reduce the activity of one or more endogenous enzymes that catalyzes the conversion of fructose-6-phosphate to fructose-1,6-bisphosphate to reduce flux through upper glycolysis. In some such embodiments, the enzymes that catalyze the conversion of fructose-6-phosphate to fructose-1,6-bisphosphate are fructose-6-phosphate kinases. In some embodiments, the deletion, disruption, mutation, and/or reduction in activity of one or more fructose-6-phosphate kinase increases and/or rebalances reducing equivalents.

In some embodiments, the recombinant microorganism is manipulated to delete, disrupt, mutate, and/or reduce the activity of one or more enzymes involved in the mannitol synthesis pathway. In some embodiments, disruption of the mannitol synthesis pathway can be used to enhance generation of reducing equivalents and improve glucose yields to support production of fatty acid derived products. In certain embodiments, the one or more enzyme involved in the mannitol synthesis pathway is an NADPH-dependent mannitol dehydrogenase. In certain embodiments, the NADPH-dependent mannitol dehydrogenase is selected from the group consisting of YALI0B16192g, YALI0D18964g, and YALI0E12463g, or homologs thereof. In certain embodiments, the one or more enzyme involved in the mannitol synthesis pathway is an aldo-keto reductase. In certain embodiments, the aldo-keto reductase is selected from the group consisting of YALI0D07634g, YALI0F18590g, YALI0C13508g, YALI0F06974g, YALI0A15906g, YALI0B21780g, YALI0E18348g, YALI0B07117g, YALI0009119g, YALI0D04092g, YALI0B15268g, YALI0000319g, YALI0A19910g, or homologs thereof.

In some embodiments, the recombinant microorganism is manipulated to delete, disrupt, mutate, and/or reduce the activity of one or more endogenous enzymes that catalyzes carboxylation of acetyl-CoA to malonyl-CoA. In one embodiment, the one or more endogenous enzymes comprise one or more acetyl-CoA carboxylase. In some embodiments, the deletion, disruption, mutation, and/or reduction in activity of one or more acetyl-CoA carboxylase increases availability or amount of reducing equivalents, increases amount of one or more metabolic intermediate, and/or increases product purity.

Pheromone Compositions and Uses Thereof

As described above, products made via the methods described herein may be pheromones. Pheromones prepared according to the methods of the invention can be formulated for use as insect control compositions. The pheromone compositions can include a carrier, and/or be contained in a dispenser. The carrier can be, but is not limited to, an inert liquid or solid. In some embodiments, the pheromone composition is combined with an active chemical agent such that a synergistic effect results. In some embodiments, the pheromone composition can include one or more insecticides, one or more solubilizing agents, one or more fillers, one or more solvents, one or more solubilizing agents, one or more binders, one or more surface-active agents, one or more wetting agents, one or more dispersing agents, one or more polymeric surfactants, one or more emulsifying agents, one or more gelling agents, one or more anti-foam agents, and/or one or more preservative. According to another embodiment of the disclosure, the pheromone composition may include one or more insect feeding stimulants. According to another embodiment of the disclosure, the pheromone composition may include one or more insect growth regulators ("IGRs"). According to another embodiment of the disclosure, the attractant-composition may include one or more insect sterilants that sterilize the trapped insects or otherwise block their reproductive capacity, thereby reducing the population in the following generation.

In some embodiments, the pheromone compositions disclosed herein can be formulated as a sprayable composition (i.e., a sprayable pheromone composition). In some embodiments, the pheromone compositions disclosed herein can be formulated as a microencapsulated pheromone, such as disclosed in Ill'Ichev, A L et al., *J. Econ. Entomol.* 2006; 99(6):2048-54; and Stelinki, L L et al., *J. Econ. Entomol.* 2007; 100(4):1360-9. Pheromone compositions can be formulated so as to provide slow release into the atmosphere, and/or so as to be protected from degradation following release. The pheromone compositions of the disclosure may be used in traps or lures. Pheromone compositions of the present disclosure can be used in conjunction with a dispenser for release of the composition in a particular environment.

Pheromone compositions prepared according to the methods disclosed herein can be used to control or modulate the behavior of insects. Thus, in some embodiments, the pheromones can be used to attract insects away from vulnerable crop areas. Pheromones prepared according to the methods of the disclosure can also be used to disrupt mating. Mating disruption is a pest management technique designed to control insect pests by introducing artificial stimuli (e.g., a pheromone composition as disclosed herein) that confuses the insects and disrupts mating localization and/or courtship, thereby preventing mating and blocking the reproductive cycle. In some embodiments, the pheromone compositions may be used in attract and kill. The attract and kill method utilizes an attractant, such as a sex pheromone, to lure insects of the target species to an insecticidal chemical, surface, device, etc., for mass-killing and ultimate population suppression.

Thus, in some embodiments, the present disclosure teaches edibles produced from the Specialty *Cannabis* and/or cannabinoid compositions disclosed herein.

This invention is further illustrated by the following examples, which should not be construed as limiting. The contents of all references, patents and published patent applications cited throughout this application, as well as the Figures and the Sequence Listing, are incorporated herein by reference.

EXAMPLES

Example 1. Improving Lipid Production by Alleviating AMP Allosteric Inhibition Background and Rationale Many microorganisms down-regulate respiration under non-optimal growth conditions to encourage carbon/energy storage via citrate and lipid synthesis. Under nitrogen limited conditions, intracellular AMP levels are depleted by an AMP deaminase (AMD1). Reduced AMP levels in these microorganisms, inactivate the mitochondrial isocitrate dehydrogenase complex (IDH1/2) through allosteric regulation, which results in accumulation of isocitrate, and reduced TCA cycle throughput.

Both native fatty acid synthesis, and the bypass methyl palmitate based synthesis of Z11-16 acid, require reducing equivalents in the form of NADPH and NADH. The inventors hypothesized that increasing the oxidation rate of citrate (through IDH activation) could increase the available reduced cofactor pool leading to increased production of unsaturated fatty acids.

Experimental Design

Figure 3:
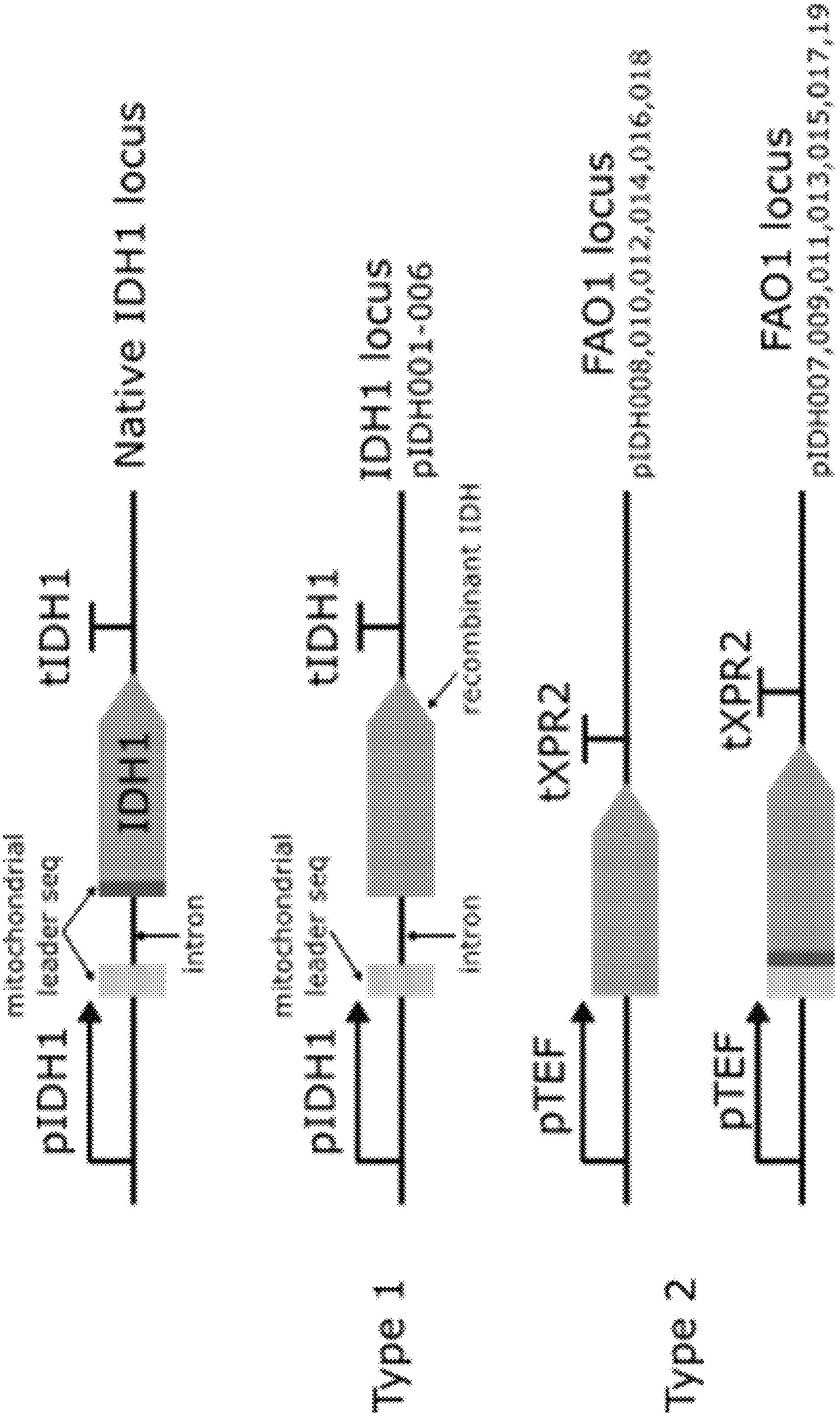
FIG. 3—IDH expression cassette architectures. The native IDH1 coding sequence is split by a single intron near the 5' end (Top). A mitochondrial targeting sequence at the 5' end of the coding sequence continues briefly after the intron. Three different expression cassettes were used for recombinant IDH expression. Each IDH was cloned into an IDH1 targeting vector which utilized the native promoter sequence (2nd from the top). Constructs were also cloned in a FAO1 targeting cassette either with or without the *Y. lipolytica* IDH1 mitochondrial targeting sequence (3rd and 4th from the top).

Two different loci were targeted to test the impact of individual IDHs on glucose consumption, growth, citrate, and fatty acid production. One cassette was designed to target the *Y. lipolytica* IDH1 locus replacing the native IDH1 variant with recombinant AMP-insensitive IDH enzymes (FIG. 3). This cassette takes advantage of the native intron promoter to drive expression of the alterative IDH genes (FIG. 3). Both native and codon optimized sequences were tested for the *Y. lipolytica* IDH1 D279A, 1280A double mutant, but only codon optimized bacterial IDHs were used in this Example. In addition, one construct replaced the native IDH with a GFP gene to serve as a negative control and to evaluate the IDH promoter.

A second cassette was designed to add a recombinant copy of IDH while retaining the wild type *Y. lipolytica* IDH1 copy. This cassette targets the FAO1 locus and uses the constitutive TEF promoter to drive expression (FIG. 3). The native sequence of the *Y. lipolytica* IDH1 D279A, 1280A mutant and four variants of each bacterial IDH were integrated using the FAO1 cassette. Both native source sequences and codon optimized sequences of bacterial IDHs were cloned either with or without the *Y. lipolytica* IDH1 mitochondrial targeting sequence. These designs tested the effects of compartmental targeting and codon optimization. Table 7 compiles the 19 constructs that were tested.

The 19 constructs described above were transformed into SPV739, a marker rescued descendent of SPV458. SPV458 was created by integrating a single copy of the *H. zea* Z11 desaturase into the XPR2 locus of SPV300 (H222 Δpox1 Δpox2 Δpox3 Δpox4 Δpox5 Δpox6 Δadh1 Δadh2 Δadh3 Δadh4 Δadh5 Δadh6 Δadh7 Δfao1 Δura3, herein also referred to as "H222 ΔP ΔA ΔF ura3"). H222 corresponds *Y. lipolytica* H222 (Mauersberger, S., H. J. Wang, et al. (2001), J Bacteriol 183(17): 5102-5109), according to Barth and Gaillardin (Barth G & Gaillardin C (1996) *Yarrowia lipolytica*. Springer-Verlag, Berlin, Heidelberg, New York).

TABLE 7

Constructs used in Example 1

| Source organism | Cassette type | Promoter | Localization | Codon optimization | IDH plasmid ID | IDH1 KO |
|---|---|---|---|---|---|---|
| *Y. Lipolytica* IDH1 (D279A, I280A) (SEQ ID NO: 20) | Type 1 | *Y. lipolytica* IDH1 | mitochondria | none | pIDH001 (SEQ ID NO: 1) Full Plasmid | Yes |
| | | | | *H. sapiens* | pIDH002 (SEQ ID NO: 2) Insert | Yes |
| | Type 2 | *Y. lipolytica* pTEF | mitochondria | none | pIDH007 (SEQ ID NO: 7) Insert | No |
| *E. Coli* IDH (NADPH) (SEQ ID NO: 21) | Type 1 | *Y. lipolytica* IDH1 | unknown | *H. sapiens* | pIDH003 (SEQ ID NO: 3) Insert | Yes |
| | Type 2 | *Y. lipolytica* pTEF | cytosol | *H. sapiens* | pIDH008 (SEQ ID NO: 8) Insert | No |
| | | | mitochondria | *H. sapiens* | pIDH009 (SEQ ID NO: 9) Insert | No |
| | | | cytosol | none | pIDH014 (SEQ ID NO: 14) Insert | No |
| | | | mitochondria | none | pIDH015 (SEQ ID NO: 15) Insert | No |
| *A. Thiooxidans* IDH (NADH) (SEQ ID NO: 22) | Type 1 | *Y. lipolytica* IDH1 | unknown | *H. sapiens* | pIDH004 (SEQ ID NO: 4) Insert | Yes |
| | Type 2 | *Y. lipolytica* pTEF | cytosol | *H. sapiens* | pIDH010 (SEQ ID NO: 10) Insert | No |
| | | | mitochondria | *H. sapiens* | pIDH011 (SEQ ID NO: 11) Insert | No |

TABLE 7-continued

| Constructs used in Example 1 | | | | | | |
|---|---|---|---|---|---|---|
| Source organism | Cassette type | Promoter | Localization | Codon optimization | IDH plasmid ID | IDH1 KO |
| | | | cytosol | none | pIDH016 (SEQ ID NO: 16) Insert | No |
| | | | mitochondria | none | pIDH017 (SEQ ID NO: 17) Insert | No |
| *M. smegmatis* IDH (NADPH) (SEQ ID NO: 23) | Type 1 | *Y. lipolytica* IDH1 | unknown | *H. sapiens* | pIDH005 (SEQ ID NO: 5) Insert | Yes |
| | Type 2 | *Y. lipolytica* pTEF | cytosol | *H. sapiens* | pIDH012 (SEQ ID NO: 12) Insert | No |
| | | | mitochondria | *H. sapiens* | pIDH013 (SEQ ID NO: 13) Insert | No |
| | | | cytosol | none | pIDH018 (SEQ ID NO: 18) Insert | No |
| | | | mitochondria | none | pIDH019 (SEQ ID NO: 19) Insert | No |
| *R. reniformis* GFP | Type 1 | *Y. lipolytica* IDH1 | unknown | *H. sapiens* | pIDH006 (SEQ ID NO: 6) Insert | Yes |

Four clonal isolates of each construct were selected for screening in a 24-deepwell plate assay (76 strains total) (See Materials and Methods for full description of protocol). Initial seeds were grown in YPD medium before transfer to a nitrogen limited medium supplemented with methyl palmitate as a saturated fatty acid substrate. To evaluate the impact of each IDH, extracellular glucose and citrate and fatty acid content were quantified (See Materials and Methods for sampling procedures).

Experimental Results

Analysis of Strains with Type 1 Cassettes (Single IDH Copy, Replaced Native IDH1)

Fatty Acid Analysis

Strain IDH002 (*Y. lipolytica* IDH1 D279A, I280A codon optimized), displayed increased OD-normalized Z11-16Acid titer at both 48 hours (~40%) and 72 hours (~20%). In addition, IDH002 produced increased titers of other native *Y. lipolytica* fatty acids including the major native fatty acid Z9-18Acid. Two other constructs, IDH001 (*Y. lipolytica* IDH1 D279A, I280A native sequence) and IDH004 (*A. thiooxidans* IDH) produced increased titers of other native *Y. lipolytica* fatty acids. As expected, the idh1::GFP knockout strains (IDH006) produced less fatty acids generally and −50% less Z11-16Acid.

Glucose Analysis

In agreement with increased TCA cycle flux, IDH001 and IDH002 also demonstrated increased glucose consumption over the 72-hour assay. IDH004 consumed an equivalent quantity of glucose to the SPV458 control. Two constructs which displayed the largest increase in fatty acid production also showed increased glucose consumption at 48 and 72 hours (IDH002, IDH011). The idh1::GFP knockout (IDH006) displayed reduced glucose consumption at both 48 and 72 hours. Initial concentration of 60 g/L glucose.

Citrate Analysis

Citrate titers followed multiple trends depending on the IDH variant. *Y. lipolytica* IDH1 D279A, I280A constructs (IDH001, IDH002) did not display reduced citrate titer (g/L-OD). The *A. thiooxidans* IDH construct, IDH004 however, displayed lower normalized citrate titer at 72.

Analysis of Strains with Type 2 Cassettes (Native+Recombinant IDH at FAO1 Locus)

Fatty Acid Analysis

Two FAO1 cassette constructs, IDH011 (*A. thiooxidans* IDH, mitochondria targeted, codon optimized) and IDH012 (*M. smegmatis* IDH, cytosol targeted, codon optimized), produced increased Z11-16 acid titer and OD-normalized titer at 48 hours. Increases were 20% for IDH011 and 10% for IDH012. Both these constructs also produced higher titers of native fatty acid species.

Increased native fatty acid titers were also observed for three other FAO1 cassette constructs: native coded *E. coli* constructs which were targeted to either the cytosol (IDH014) or mitochondria (IDH015) and codon optimized *M. smegmatis* IDH targeted to the mitochondria (IDH013). Of the two *E. coli* constructs, IDH014 (cytosol) sustained the increase in fatty acid production at the 72-hour time point while titers were stagnant for IDH015 (mitochondria).

Glucose Analysis

IDH009 (*E. coli* IDH, mitochondria targeted, codon optimized), IDH010 (*A. thiooxidans* IDH, cytosol targeted, codon optimized), IDH0011 (*A. thiooxidans* IDH, mitochondria targeted, codon optimized) and IDH019 (*M. smegmatis* IDH, mitochondria targeted, native sequence) displayed increased glucose consumption.

Citrate Analysis

As with IDH1 cassettes, citrate titers followed multiple trends depending on the IDH variant. Of the *E. coli* IDH constructs, only IDH009 produced less citrate than the SPV458. Both *A. thiooxidans* IDH constructs which consumed additional glucose, IDH010, and IDH011, also produced less citrate. *M. smegmatis* constructs which either showed increased fatty acid production (IDH012, IDH013) or increased glucose consumption (IDH019) also produced less citrate. Of the *M. smegmatis* constructs, the most significant reduction in citrate was observed for IDH019.

Summary of the 24 Well Assay

An additional trend emerges when citrate titers are examined as a function of expression cassette design for each of the recombinant IDHs. IDH1 targeted cassettes with the IDH1 promoters produced the highest citrate titers while FAO1 cassettes with the TEF promoter and the *Y. lipolytica* IDH1 mitochondrial targeting sequence produced the lowest citrate titers. This dependence on cassette design is consistent with high mitochondrial expression of IDH leading to increased TCA cycle flux. Finally, as expected, the IDH006 strains (idh1::GFP) grew slowly and produced the highest normalized citrate titers (g/L-OD). The increase was especially noticeable at 48 hours. This increase in citrate titer confirms the negative control hypothesis that reduced TCA cycle flux in the mitochondria leads to further accumulation of citrate.

Strains expressing codon optimized *A. thiooxidans* IDH using the TEF promoter and targeted to the mitochondria showed reduced citrate titer (g/L) and specific citrate production (g/L-OD) at 72 hours in the 24-deepwell plate assay. Cell density, as measured by OD600, increased by ~35% at 72 hours. Fatty acid titers were increased over the SPV458 control as follows:

Z11-16Acid: ~20% at 48 hours and 0% at 72 hours.
Z9-16Acid: ~130% at 48 hours and ~100% at 72 hours.
Z9-18Acid: ~80% at 48 hours and ~60% at 72 hours.
Z9Z12-18Acid: ~20% at 48 hours and ~50% at 72 hours Strains expressing a copy of the *Y. lipolytica* IDH1 mutant D279, I280A under the TEF promoter did not display reduced citrate titer or increased cell density in the 24-deepwell plate assay, but did produce increased fatty acid titers as follows:

Z11-16Acid: ~15% at 48 hours and ~20% at 72 hours
Z9-16Acid: 0% at 48 and 72 hours
Z9-18Acid: ~30% at 48 hours and ~40% at 72 hours
Z9Z12-18Acid ~30 at 48 hours and ~50% at 72 hours Materials & Methods HSD035 24-Deepwell Assay For each construct 4 clonal isolates were inoculated in 1 ml of YPD seed culture in 24-deepwell plates for 24 hours at 28° C. and 1000 rpm (Infors plate incubator). Seed cultures were pelleted and supernatant removed before resuspension in 2 ml of S2 medium. After cell pellets were resuspended, 24 μl of 37° C. methyl palmitate was added to each well (~10 g/L final concentration). The plates were then incubated for 48 hours at 28° C. and 1000 rpm (Infors plate incubator) before 250 μl samples were transferred to glass, crimp-top GC vials. Plates were incubated an additional 24 hours and a second set of 250 μl samples were taken at 72 hours. Vials were frozen at −80° C. before further processing. Cell density was measured with a Tecan M200 Pro plate reader at each sampling.

GC Sample Processing-Lyophilized Samples 250 uL of culture were lyophilized in open glass crimp top vials for at least 3 hours. 500 uL of TMSH were added to the vials and sealed with a crimp cap. These vials were arrayed in racks, which were placed in a 28° C. plate shaker for 2 hours at 250 rpm. After mixing these dried cells with the derivatizing agent, the vials were incubated in a heat block for 1 hour at 85° C. to lyse the cell membranes. Finally, the liquid portion of the methylated sample was transferred to a clean GC vial with glass insert to prevent solid debris from clogging the column during GC analysis. Samples were run on GC-FID.

Example 2. Improving Lipid Production and Z11-16 Selectivity Through Expression of Decarboxylating Malic Enzyme and/or Oxidative Pentose Phosphate Pathway Enzymes (PPP)

Background and Rationale

Microorganisms of the present disclosure produce citrate as co-product under nitrogen-limited conditions. This is because during nitrogen starvation many organisms, including *Y. lipolytica* down-regulate respiration to divert carbon/energy storage via lipid synthesis. Citrate is first exported from mitochondria into the cytosol and subsequently from the cell. Exported citrate can be re-assimilated, especially when alternative carbon sources are scarce. Alternatively, the combination of the enzymes ATP citrate lyase (ACL), malate dehydrogenase (e.g., MDH2) and cytosolic malic enzyme can turn cytosolic citrate into pyruvate, to feed back into the TCA cycle to power further lipid synthesis (FIG. 4). Many organisms, including *Y. lipolytica* however, do not express a cytosolic malic enzyme.

The inventors further hypothesized that expression of a heterologous $NADP^+$ dependent cytosolic malic enzyme may increase fatty acid production if the primary rate limitation is cofactor supply.

In many organisms, including *Y. lipolytica*, the pentose phosphate pathway (PPP) is the primary source of NADPH reducing equivalents for fatty acid synthesis. The inventors hypothesized that the recombinant microorganisms lipid production and selectivity could further be increased by overexpressing the genes of the upper (oxidative) pentose phosphate pathway (ZWF1, SOL3, and GND1), potentially offering another route to increase biomass and/or fatty acid synthesis.

Experimental Design

Nucleic acids encoding for heterologous malic enzymes, and overexpressing endogenous PPP enzymes, ZWF1, GND1, and SOL3, were introduced into a *Y. lipolytica* microorganism. Three or four clonal isolates of each construct were characterized in a 24-well bioconversion assay, feeding co-substrates glucose/glycerol and methyl palmitate. Fatty acid profiles for all constructs were quantified using GC analysis. Measurements for initial biomass in YPD and final biomass in nitrogen-limited media were taken. Growth of each microorganism was tracked and analyzed for fatty acid profiles in nitrogen-limited media with Solulys95 to confirm that access to methyl palmitate as a co-substrate is necessary to realize improvements in Z11-16Acid selectivity, total fatty acid production, and/or biomass generation. Table 8 provides a summary of the recombinant microorganisms tested. Note that the L. starkeyi construct was excluded from the bioconversion results due to technical issues during the experiment resulting in no growth of the microorganism.

TABLE 8

Enzyme expression constructs in microorganisms: All constructs were integrated at the AXP locus.

| Source organism | Gene | Promoter | Cofactor | Cellular location | Modification | Codon optimization | Plasmid ID |
|---|---|---|---|---|---|---|---|
| *L. starkeyi* | ME | TEF | NAD | Mitochondria | Truncation* Unmodified enzyme-(SEQ ID NO: 24) | human | pPV1279 |
| *R. toruloides* | ME | TEF | NAD | Mitochondria | Truncation* (SEQ ID NO: 25) | human | pPV1280 |
| *M. musculus* | ME | TEF | NADP | Cytosol | (SEQ ID NO: 28) | human | pPV1281 |
| *R. norveg icus* | ME | TEF | NADP | Cytosol | (SEQ ID NO: 27) | human | pPV1282 |
| *H. sapiens* | ME | TEF | NAD | Mitochondria | Truncation* (SEQ ID NO: 26) | human | pPV1283 |
| *E. coli* | ME | TEF | NAD | Cytosol | (SEQ ID NO: 29) | human | pPV1284 |
| *Y. lipolytica* | ZWF1 | TEF | NADP | Cytosol | YALI0E22649g DNA- (SEQ ID NO 39) Prot- (SEQ ID NO 40) | NA | pPV1285 |
| *Y. lipolytica* | GND1 | TEF | NADP | Cytosol | YALI0B15598g DNA-(SEQ ID NO: 41) Prot- (SEQ ID NO: 42) | NA | pPV1286 |
| *Y. lipolytica* | SOL3 | TEF | None | Cytosol | YALI0_E11671g DNA- (SEQ ID NO: 43) Prot- (SEQ ID NO: 44) | NA | pPV1287 |

*Truncation of the mitochondrial targeting sequence. Malic enzyme sequences were analyzed using the TargetP 1.1 server. (Predicting subcellular localization of proteins based on their N-terminal amino acid sequence. Olof Emanuelsson, Henrik Nielsen, Søren Brunak and Gunnar von Heijne. J. Mol. Biol., 300: 1005-1016, 2000.) The predicted mitochondrial targeting sequence of the respective enzymes was removed to direct the enzyme to the cytosol.

Three or four clonal isolates of each construct were selected for screening in a 24-deepwell plate assay (See Materials and Methods for full description of protocol). Initial seeds were grown in YPD medium before transfer to a nitrogen limited medium supplemented with methyl palmitate as a saturated FAME substrate. To evaluate the impact of malic enzyme and PPP overexpression, fatty acid content and biomass generation were quantified (See Materials and Methods).

Experimental Results

Figure 5:
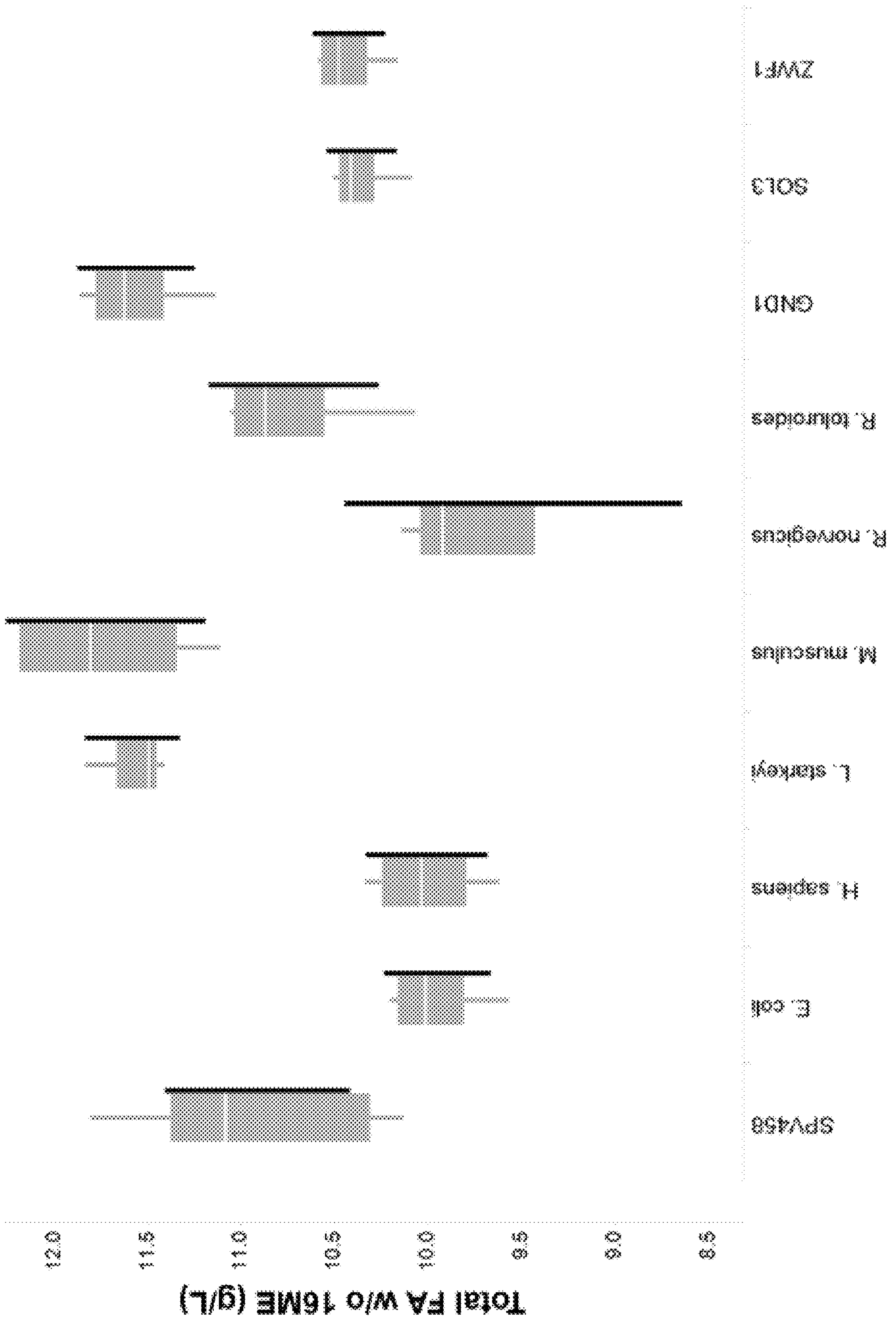
FIG. 5—Total fatty acid content of malic enzyme and PPP recombinant microorganisms. Methyl palmitate was fed to recombinant microrganisms comprising heterologous malic enzyme or upregulated PPP enzymes. The results show a spike in fatty acid production for the GND1, *L. starkeyi*, and *M. musculus* recombinant microorganisms. A Box plot with 95% confidence interval denoted by vertical bar on the right side of each result.

Overexpression of the $NADP^+$ dependent L. starkeyi and *M. musculus* cytosolic malic enzyme, as well as the PPP gene GND1, led to increased titers of total fatty acid compared to the reference strain SPV458 when feeding glucose/glycerol and methyl palmitate co-substrates after 42 hours of bioconversion (FIG. 5). All samples were analyzed for the following fatty acids which were derivatized as fatty acid methyl esters: Z9-16Acid, Z11-16Acid, 18Acid, Z9-18Acid, Z11-18Acid, Z13-18Acid, Z9Z12-18Acid.

Figure 6:
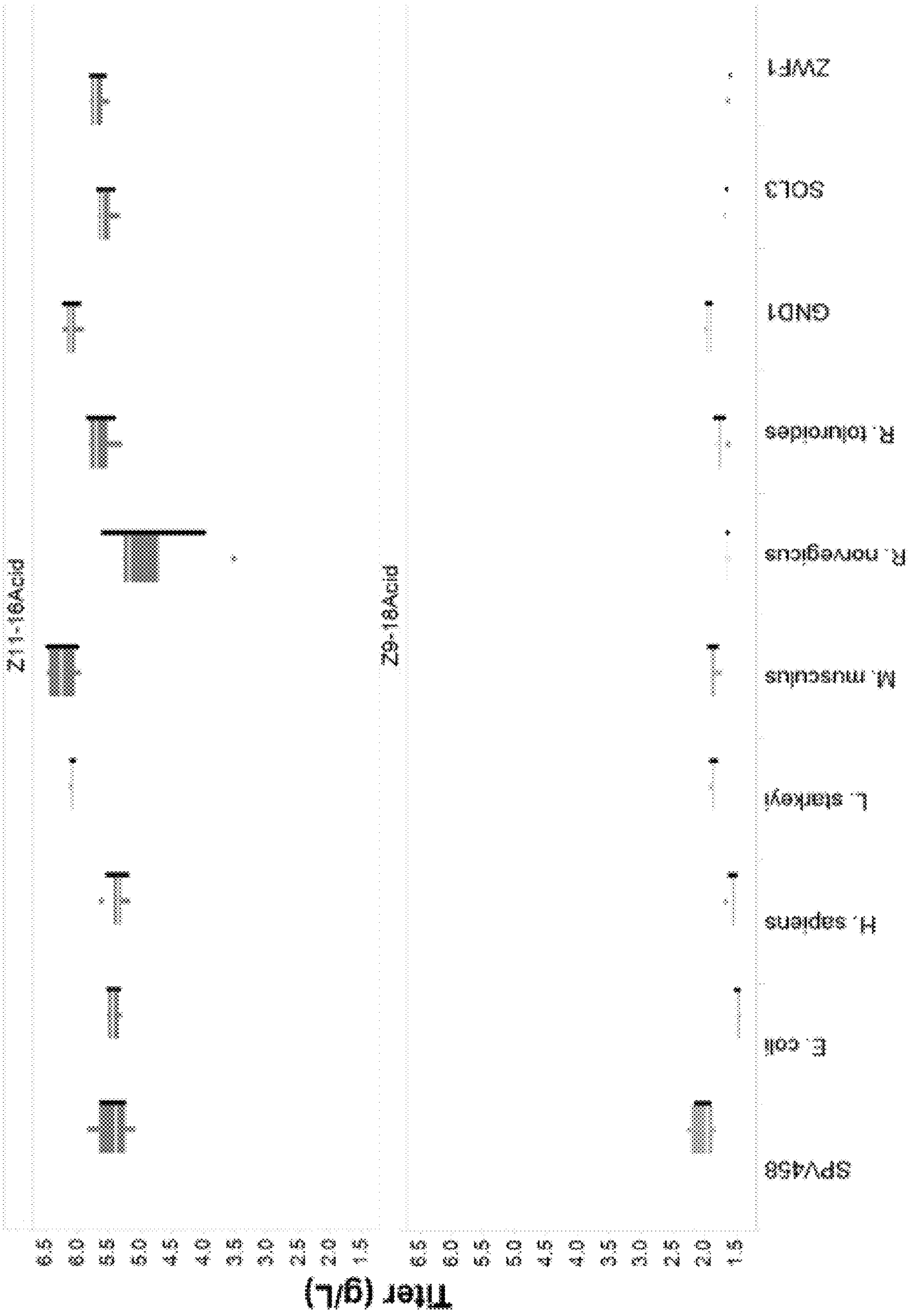
FIG. 6—Z11-16 acid and Z9-18 acid titer of malic enzyme and PPP recombinant microorganisms. The increase in Z11-16 acid in GND1, *L. starkeyi*, and *M. musculus* expressing strains compared to the SPV458 control reveals that most of the increase in total fatty acid production is from increased Z11-16Acid. These three strains do not produce additional Z9-18Acid compared to the control. Box plot with 95% confidence interval denoted by vertical bar on the side of each result.

FIG. 6 shows the specific results for Z11-16 Acid and Z9-18 Acid. These results show that the boost in total fatty acid accumulated in the three improved strains is mostly accounted for by the increase in Z11-16Acid.

Figure 7:
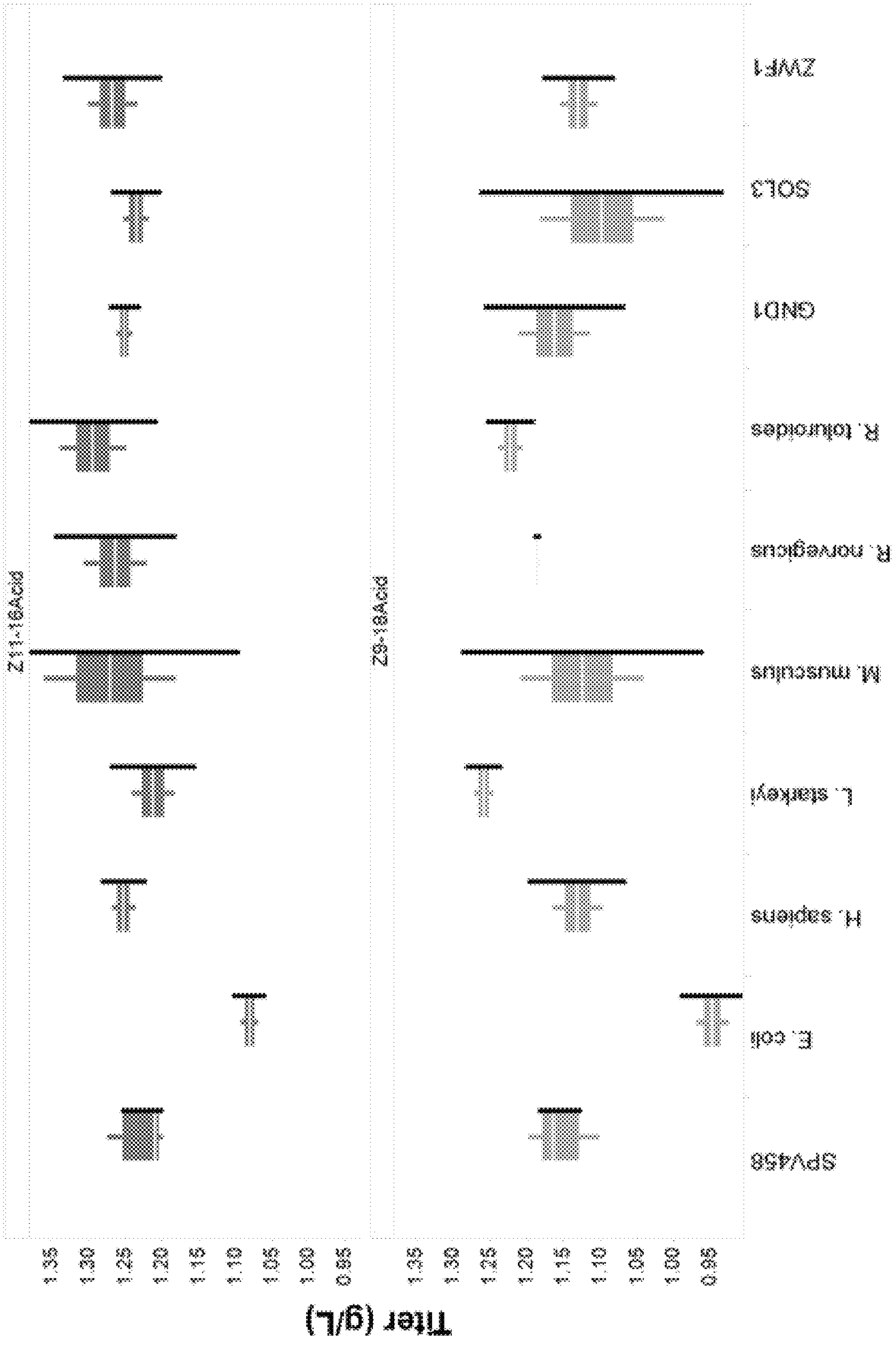
FIG. 7—De novo fatty acid production of malic enzyme and PPP recombinant microorganisms. Recombinant microorganisms cultured in bioprocess media without methyl palmitate substrate do not demonstrate a significant improvement in Z11-16 acid productivity over the control strain. Box plot with 95% confidence interval denoted by vertical bar on the right side of each result.

While three strains produced higher Z11-16Acid titer when fed methyl palmitate, the strains did not exhibit significant improvements in de novo lipid production (FIG. 7). When the strains were tested in lipid-accumulating media without adding substrate, all strains produced Z11-16Acid titers within the margin of error of our SPV458 control. This indicates the dual-substrate approach led to the benefits observed with overexpression of L. starkeyi and *M. musculus* malic enzymes and GND1.

Figure 8:
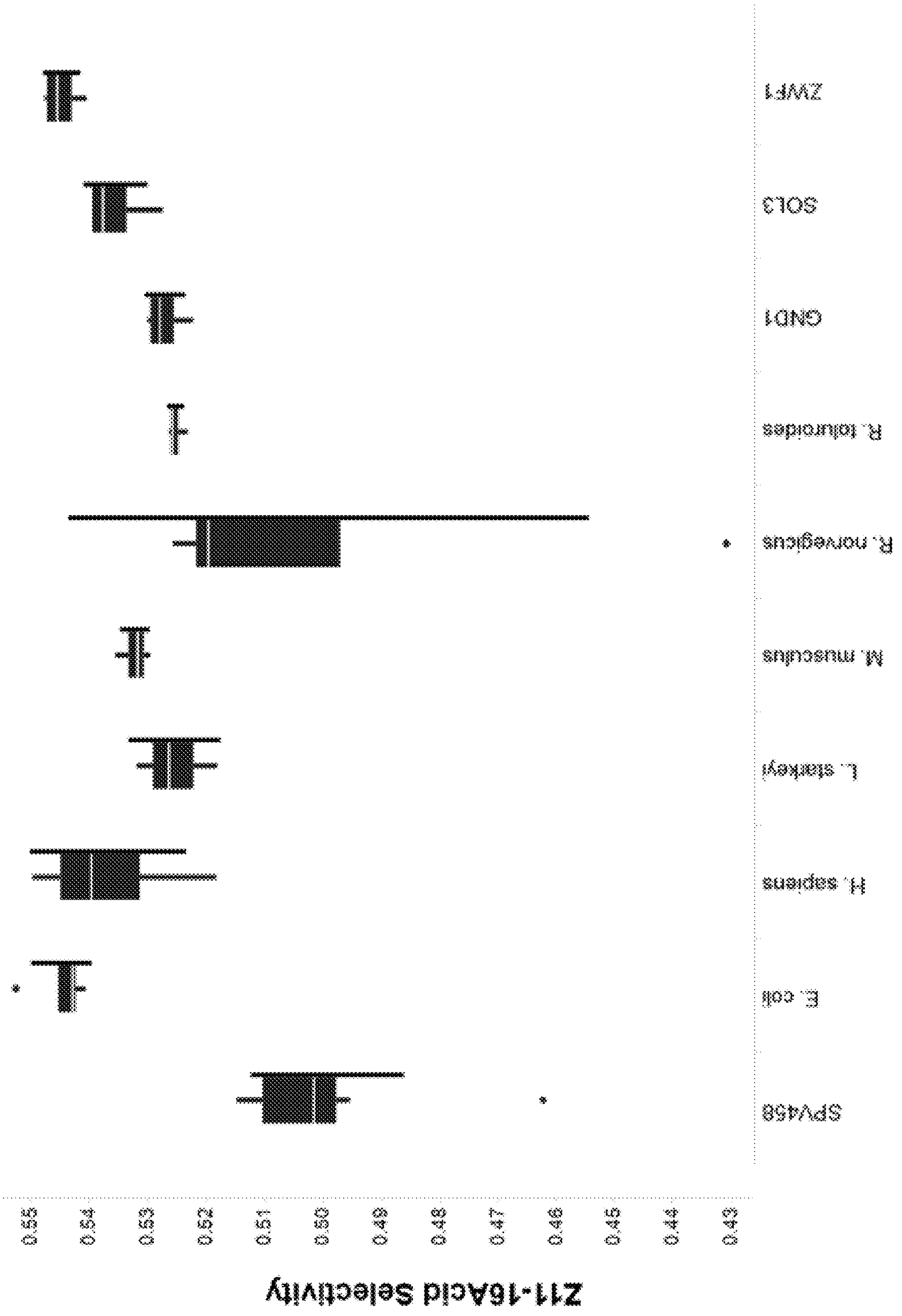
FIG. 8—Z11-16 acid selectivity of malic enzyme and PPP recombinant microorganisms. All modifications demonstrated improvements in Z11-16 acid selectivity over the SPV458 control when fed methyl palmitate in standard bioconversion assays. Box plot with 95% confidence interval denoted by vertical bar on the side of each result.

Surprisingly, all tested strains exhibited an improvement in Z11-16Acid selectivity (FIG. 8). All tested malic enzyme and PPP enzyme-containing microorganisms yielded average Z11-16Acid selectivities greater than the 50% found in SPV458, the highest being overexpression of ZWF1 yielding 55% Z11-16Acid. Of the 3 strains that yielded the highest Z11-16Acid titers, *M. musculus* had the highest selectivity, while GND1 was second, both rounding to 53%.

Figure 9:
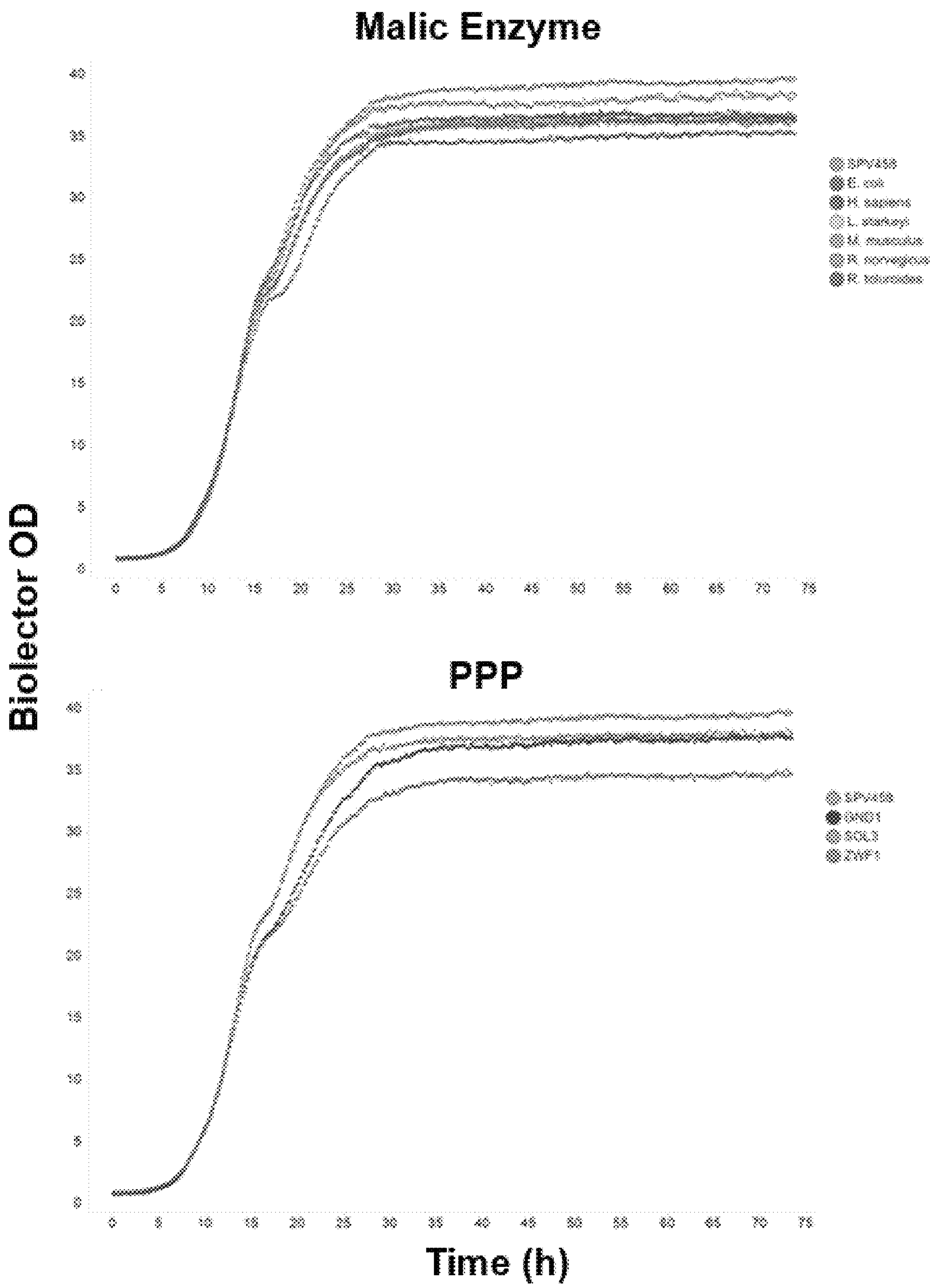
FIG. 9—Biomass of malic enzyme and PPP recombinant microorganisms. In bioprocess media with excess ammonium sulfate and using glucose as the carbon source, the malic enzyme and PPP recombinant microorganisms of Example 2 grow to a stationary phase between 33 and 38 hours.
Figure 10:
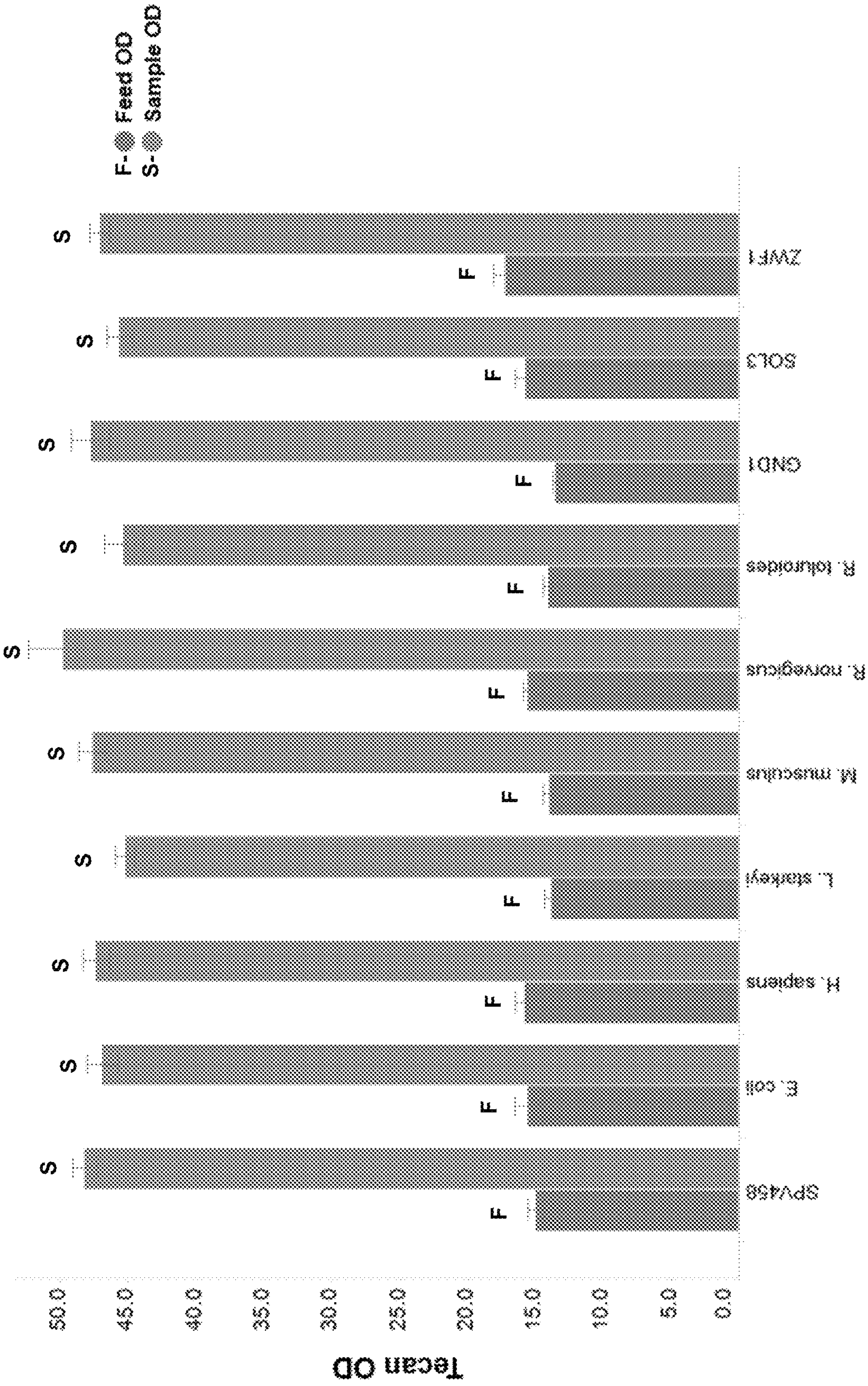
FIG. 10—OD600 readings from Tecan reader in standard bioconversion assay of malic enzyme and PPP recombinant microorganisms. Feed OD is after 24 h growth in YPD and 6 h growth in FERMI media, prior to methyl palmitate feed. Sample OD after an additional 42 h bioconversion in FERMI media, after methyl palmitate feed.

We tested the strains in bioprocess media with glucose and excess nitrogen to assess differences in growth and lean biomass accumulation. As seen in FIG. 9, all strains grow very similarly between 0 and 15 hours during the exponential phase, followed by a change in growth rate in the linear phase. All constructs did accumulate slightly less lean biomass than the SPV458 control.

The bioconversion assay did not uncover a significant increase in biomass production for any of our strains either, further corroborating the hypothesis that improved Z11-16Acid production and selectivity is not a related to increased biomass generation, but primarily to increased bioconversion rate and/or efficiency.

Materials & Methods

24-Deepwell Assay

For each construct three or four clonal isolates were inoculated in 1 ml of YPD seed culture in 17 mm glass vials in 24-deepwell plates for 24 hours at 28° C. and 1000 rpm (Infors plate incubator). Seed cultures were pelleted and supernatant removed before resuspension in 1 mL FERMI media. Cultures were incubated at 28° C. and 1000 rpm (Infors plate shaker) for an additional 6 hours in FERMI media. Then, methyl palmitate was added at 20 g/L with a P200 multi-channel. After an additional 42 hours of bioconversion (72 hours total), 250 μl sample was transferred to a crimp-top GC vial for analysis. Vials were frozen at −80° C. before further processing. Cell density was measured with a Tecan M200 Pro plate reader at feeding and at sampling.

Biolector Growth Assay

For each construct three or four clonal isolates were inoculated in 2 ml of YPD seed culture in 24-deepwell plates for 24 hours at 28° C. and 1000 rpm (Infors plate incubator). 7-8 uL of each seed culture were used to inoculate 750 uL of Bioprocess media in each Biolector plate well. Cultures were incubated at 32° C. and 1500 rpm (Biolector) for an additional 72 hours in Bioprocess media, either with excess nitrogen (10 g/L) or limited nitrogen (2 g/L). After 72 hours of growth, 250 μl sample for the nitrogen-limited condition was transferred to a crimp-top GC vial for analysis. Vials were frozen at −80° C. before further processing. Cell density was measured with a Tecan M200 Pro plate reader at feeding and at sampling. Growth curves for the excess nitrogen condition were assessed to compare lean biomass generation for each strain.

GC Sample Work-Up 250 uL of culture were lyophilized in open glass crimp top vials for at least 3 hours. 500 uL of methanol was added to the vials followed by addition of 35 ul 10M potassium hydroxide. Vials were then sealed with a crimp cap, arrayed in 54-well racks, mixed for 10 minutes at 2000 RPM using a Mixmate plate shaker, and heated at 60C for 40 minutes in a convection oven. Vials were cooled to room temperature and decapped. 29 ul 24N sulfuric acid was added to vials. Vials were then sealed with a crimp cap, arrayed in 54-well racks, mixed for 2 minutes at 2000 RPM using a Mixmate plate shaker, and heated at 60C for 40 minutes in a convection oven. Vials were cooled to room temperature and decapped. 1 ml hexanes was added to vials. Vials were then sealed with a crimp cap, arrayed in 54-well racks, and mixed for 10 minutes at 2000 RPM using a Mixmate plate shaker. Vials then spun down for 5 minutes at 1000 RPM using an Avanti centrifuge. Vials were run on GC-FID.

Example 3. Improving Lipid Production Through Expression of Acetyl-CoA Carboxylase (ACC) Enzymes that are Modified to Prevent Regulatory Inhibition Via Phosphorylation. (Prophetic)

Background and Rationale

ACC catalyzes the irreversible conversion of acetyl-CoA to malonyl-CoA, one of the key substrates in lipid biosynthesis. To regulate lipid biosynthesis, kinases inhibit ACC via post-translational modifications. Kinases phosphorylate ACC serine residues, which, when phosphorylated, interact with two downstream arginine residues to inhibit the activity. In order to counteract the microorganism's native regulation of lipid biosynthesis, a few engineering approaches can be taken to increase lipid accumulation in the microorganism, aided by the fact that neither of the residues involved in ACC inhibition are also involved in the conversion of acetyl-CoA to malonyl-CoA. The first approach is to overexpress heterologous ACC variants which may not be phosphorylated by host kinases and are thus not inhibited by a phosphorylated serine. To further improve lipid production, the heterologous ACC variants are further engineered by eliminating key serine residues through replacement with alternative amino acids. The serine residue is replaced by either a point mutation or through replacement of a loop region of the amino acid sequence which contains the key serine residue. In another strategy to further improve lipid synthesis, the heterologous ACC is mutated by replacing the arginine residues involved in inhibiting ACC with a residue, like alanine, that does not interact with phosphorylated serine to deactivate the enzyme. In addition to overexpression of heterologous feedback-resistant ACC variants, the host's native ACC can be deleted or down-regulated. The overexpression of modified ACC variants relieved of post-translational phosphorylation is expected to lead to enhanced flux towards malonyl-CoA and enhanced fatty acid production.

Experimental Design

An expression cassette containing the nucleic acid encoding select heterologous acetyl-CoA carboxylase (see sequences below) will be introduced into the chromosome of the *Y. lipolytica* host that has been previously engineered to produce insect fatty acid pheromone precursors. Expression of the ACC gene variant will be mediated by a strong promoter such as the yeast transcription elongation factor promoter sequence. In the alternative, ACC variants will be expressed by the microorganism's native ACC promoter sequence. Each transformed gene will contain at least one of the three modifications:

(a) Replacement of the portion of the gene that encodes for an amino acid sequence containing a serine residue targeted for phosphorylation with a glycine linker of 4 to 34 amino acids. (Replaced region from position 1,219 to 1,262 in the alignment of FIG. 11)

(b) Replacement the key serine residue (position that is targeted for phosphorylation with a residue that cannot be phosphorylated. (Position 1249 of the alignment of FIG. 11, residue 1157 of *S. cerevisiae* Acc1p)

(c) Replacement the arginine residues at positions 1,266 and 1,369 in the alignment of FIG. 11 with a residue that will not interact with phosphorylated serine to inactivate ACC.

Genome integration of the cassette will utilize homologous recombination methods used in Examples 1 and 2. Inclusion of an amino acid biosynthetic or antibiotic resistance gene in the cassette allows selection of colonies harboring the cassette by plating on selective agar media. Successful integration of the cassette is verified via PCR and sequencing. Three or four positive clonal isolates harboring each heterologous ACC construct will be characterized in a 24-well bioconversion assay, feeding co-substrates glucose/glycerol and methyl palmitate. Fatty acid profiles for all constructs will be quantified using GC analysis. Measurements for initial biomass in YPD and final biomass in nitrogen-limited media will be taken. Growth of each microorganism will be tracked and analyzed for fatty acid profiles in nitrogen-limited media with Solulys95 to confirm that access to methyl palmitate as a co-substrate is necessary to realize improvements in Z11-16Acid selectivity, total fatty acid production, and/or biomass generation.

Experimental Results

Expression of the heterologous ACC genes including the mutations described above are expected to increase accumulation of total fatty acids. All samples will be analyzed for the following fatty acids: Z9-16Acid, Z11-16Acid, 18Acid, Z9-18Acid, Z11-18Acid, Z13-18Acid, Z9Z12-18Acid.

Numbered Embodiments of the Disclosure

Particular subject matter contemplated by the present disclosure is set out in the below numbered embodiments.

1. A recombinant microorganism having improved production of biomass or improved production of one or more lipids from one or more fatty acid and one or more simple carbon co-substrates, wherein the recombinant microorganism comprises one or more modifications in one or more fields comprising:

tricarboxylic acid cycle;

lipid synthesis;

reducing equivalent availability;

one or more metabolic intermediates availability; and/or increased product purity, wherein the recombinant microorganism has improved production of biomass or improved production of one or more lipids compared to a microorganism without the same modifications.

2. The recombinant microorganism of embodiment 1, wherein the one or more modifications in one or more fields comprising tricarboxylic acid cycle comprises the overexpression of at least one endogenous and/or exogenous nucleic acid molecule encoding an AMP-insensitive isocitrate dehydrogenase (IDH) variant in the recombinant microorganism.

3. The recombinant microorganism of embodiment 2, wherein the at least one nucleic acid molecule encodes for a protein that has at least 70% sequence identity, at least 80% sequence identity, or at least 90% sequence identity to IDH from *Escherichia coli, Mycobacterium smegmatis, Acidithiobacillus thiooxidans*, or *Yarrowia lipolytica.*

4. The recombinant microorganism of embodiment 2, wherein the at least one nucleic acid molecule is from *Yarrowia lipolytica* and comprises isoleucine to alanine substitutions at amino acid positions 279 and 280 of XP_503571.2.

5. The recombinant microorganism of embodiment 1, wherein the one or more modifications in one or more fields comprising tricarboxylic acid cycle and one or more metabolic intermediates availability comprises the overexpression of at least one endogenous and/or exogenous nucleic acid molecule encoding a pyruvate transporter in the recombinant microorganism.

6. The recombinant microorganism of embodiment 5, wherein the one or more metabolic intermediates availability comprises mitochondrial pyruvate availability.

7. The recombinant microorganism of embodiment 5, wherein the at least one nucleic acid molecule encodes for a protein that has at least 70% sequence identity, at least 80% sequence identity, or at least 90% sequence identity to pyruvate transporter from *Saccharomyces cerevisiae, Hanseniaspora osmophila, Yarrowia lipolytica*, or *Talaromyces marneffei* PM1.

8. The recombinant microorganism of embodiment 5, wherein the pyruvate transporter is selected from *Saccharomyces cerevisiae* mpc1*, Saccharomyces cerevisiae* mpc3 (NP_011759.1), *Hanseniaspora osmophila* mpc3 (0EJ86292.1), *Yarrowia lipolytica* mpc, and *Talaromyces marneffei* PM1 mpc3 (KFX48982.1), or homolog thereof.

9. The recombinant microorganism of embodiment 5, wherein the recombinant microorganism is *Saccharomyces cerevisiae* comprising a deletion, disruption, or loss of function mutation in a gene encoding an mpc2 pyruvate transporter.

10. The recombinant microorganism of embodiment 5, wherein the recombinant microorganism is *Yarrowia lipolytica.*

11. The recombinant microorganism of embodiment 1, wherein the one or more modifications in one or more fields comprising lipid synthesis comprises alleviation of acetyl-CoA carboxylase (ACC) inhibition.

12. The recombinant microorganism of embodiment 11, wherein alleviation of ACC inhibition comprises the replacement of endogenous ACC or overexpression of at least one exogenous nucleic acid molecule encoding a feedback-insensitive ACC variant in the recombinant microorganism.

13. The recombinant microorganism of embodiment 11, wherein the at least one nucleic acid molecule encodes for a protein that has at least 70% sequence identity, at least 80% sequence identity, or at least 90% sequence identity to ACC from *Mus musculus, Rattus norvegicus*, or *Homo sapiens.*

14. The recombinant microorganism of embodiment 1, wherein the one or more modifications in one or more fields comprising reducing equivalent availability comprises the overexpression of at least one endogenous and/or exogenous nucleic acid molecule encoding an NADP/NAD-dependent isocitrate dehydrogenase (IDH) in the cytosol of the recombinant microorganism to increase the availability of reducing equivalents.

15. The recombinant microorganism of embodiment 14, wherein the at least one nucleic acid molecule encodes for a protein that has at least 70% sequence identity, at least 80% sequence identity, or at least 90% sequence identity to IDH from *Escherichia coli, Mycobacterium smegmatis, Acidithiobacillus thiooxidans*, or *Yarrowia lipolytica.*

16. The recombinant microorganism of embodiment 14, wherein the IDH is selected from *Escherichia coli* Idh (WP_000444484.1), *Mycobacterium smegmatis* Icd2 (WP_011727802.1), *Acidithiobacillus thiooxidans* Idh (PDB: 2D4V_A), and *Yarrowia lipolytica* Idh1 (XP_503571.2), or homolog thereof.

17. The recombinant microorganism of embodiment 14, wherein the one or more modifications in one or more fields comprising reducing equivalent availability further comprises the overexpression of at least one endogenous and/or exogenous nucleic acid encoding an aconitase in the cytosol of the recombinant microorganism.

18. The recombinant microorganism of embodiment 17, wherein the at least one endogenous and/or exogenous nucleic acid molecule encoding the IDH and the at least one endogenous and/or exogenous nucleic acid molecule encoding the aconitase lack a sequence encoding a mitochondrial-targeting peptide.

19. The recombinant microorganism of embodiment 1, wherein the one or more modifications in one or more fields comprising reducing equivalent availability or one or more metabolic intermediates availability comprise the overexpression of at least one endogenous and/or exogenous nucleic acid encoding a citrate transporter in the recombinant microorganism.

20. The recombinant microorganism of embodiment 19, wherein the one or more metabolic intermediates availability comprises cytosolic citrate/isocitrate availability.

21. The recombinant microorganism of embodiment 19, wherein the at least one nucleic acid molecule encodes for a protein that has at least 70% sequence identity, at least 80% sequence identity, or at least 90% sequence identity to a citrate transporter from *Yarrowia lipolytica, Saccharomyces cerevisiae, Rattus norvegicus, Caenorhabditis elegans*, or *Caliqus* clemensi.

22. The recombinant microorganism of embodiment 19, wherein the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

23. The recombinant microorganism of embodiment 1, wherein the one or more modifications in one or more fields comprising reducing equivalent availability comprises the overexpression of at least one exogenous nucleic acid molecule encoding a decarboxylating malic enzyme in the recombinant microorganism.

24. The recombinant microorganism of embodiment 23, wherein the at least one nucleic acid molecule encodes for a protein that has at least 70% sequence identity, at least 80% sequence identity, or at least 90% sequence identity to a decarboxylating malic enzyme from *Arabidopsis thaliana, Amaranthus hypochondriacus, Rhizobium meliloti, Solanum tuberosum, Homo sapiens*, or *Escherichia coli.*

25. The recombinant microorganism of embodiment 23, wherein the decarboxylating malic enzyme is selected from *Arabidopsis thaliana* Q9SIU0, *Amaranthus hypochondriacus* P37224, *Rhizobium meliloti* 030807, *Solanum tuberosum* P37221, *Homo sapiens* Q16798, and *Escherichia coli* P26616, or homolog thereof.

26. The recombinant microorganism of embodiment 23, wherein the decarboxylating malic enzyme lacks a sequence encoding a mitochondrial-targeting peptide.

27. The recombinant microorganism of embodiment 1, wherein the one or more modifications in one or more fields comprising one or more metabolic intermediates availability comprises the overexpression of at least one endogenous and/or exogenous nucleic acid encoding an ATP-citrate lyase in the recombinant microorganism.

28. The recombinant microorganism of embodiment 27, wherein the one or more metabolic intermediate availability comprises cytosolic oxaloacetate availability.

29. The recombinant microorganism of embodiment 27, wherein the at least one nucleic acid molecule encodes for a protein that has at least 70% sequence identity, at least 80% sequence identity, or at least 90% sequence identity to an ATP-citrate lyase from *Saccharomyces cerevisiae, Yarrowia* lipolytica, *Mus musculus*, and *Aspergillus niger.*

30. The recombinant microorganism of embodiment 27, wherein the ATP-citrate lyase is selected from *Mus musculus* NP_001186225.1, *Mus musculus* NP_598798.1, *Aspergillus niger* XP_001394055.1, and *Aspergillus niger* XP_001394057.1, or homolog thereof.

31. The recombinant microorganism of embodiment 1, wherein the one or more modifications in one or more fields comprising reducing equivalent availability comprises one or more modifications in the pentose phosphate pathway (PPP) in the recombinant microorganism.

32. The recombinant microorganism of embodiment 31, wherein the one or more modifications in the PPP comprises one or more of:

downregulation of hexose kinase activity;

upregulation of one or more oxidative PPP enzyme activity;

downregulation of fructose-6-phosphate kinase activity; and/or expression of one or more oxidative PPP enzyme variant.

33. The recombinant microorganism of embodiment 32, wherein the upregulation of one or more oxidative PPP enzyme activity comprises the overexpression of one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1).

34. The recombinant microorganism of embodiment 32, wherein the downregulation of hexose kinase activity and/or fructose-6-phosphate kinase activity comprises deletion, disruption, and/or mutation of one or more endogenous gene encoding one or more hexose kinase enzyme and/or fructose-6-phosphate kinase enzyme.

35. The recombinant microorganism of embodiment 32, wherein the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1).

36. The recombinant microorganism of embodiment 35, wherein the one or more nucleic acid molecule encodes for a protein that has at least 70% sequence identity, at least 80% sequence identity, or at least 90% sequence identity to an NAD-dependent glucose-6-phosphate dehydrogenase (ZWF1) from *Leuconostoc.*

37. The recombinant microorganism of embodiment 35, wherein the one or more nucleic acid molecule encodes for a protein that has at least 70% sequence identity, at least 80% sequence identity, or at least 90% sequence identity to an NAD-dependent 6-phosphogluconate dehydrogenase (GND1) from *Bradyrhizobium* or *Methylobacillus.*

38. The recombinant microorganism of embodiment 35, wherein the NAD-dependent glucose-6-phosphate dehydrogenase (ZWF1) is selected from *Leuconostoc* AAA25265.1 and *Leuconostoc* P11411, or homolog thereof.

39. The recombinant microorganism of embodiment 35, wherein the NAD-dependent 6-phosphogluconate dehydrogenase (GND1) is selected from *Bradyrhizobium* WP_012029377.1, *Bradyrhizobium* A4YZZ8, *Methylobacillus* AAF34407.1, and *Methylobacillus* Q9L9P8, or homolog thereof.

40. The recombinant microorganism of embodiment 1, wherein the one or more modifications in one or more fields comprising reducing equivalent availability comprises downregulation of mannitol synthesis pathway in the recombinant microorganism.

41. The recombinant microorganism of embodiment 40, wherein downregulation of mannitol synthesis pathway comprises deletion, disruption, and/or mutation of one or more gene encoding an NADPH-dependent mannitol dehydrogenase and/or an aldo-keto reductase.

42. The recombinant microorganism of embodiment 41, wherein the one or more gene encoding an NADPH-dependent mannitol dehydrogenase is selected from YALI0B16192g, YALI0D18964g, and YALI0E12463g, or homolog thereof.

43. The recombinant microorganism of embodiment 41, wherein the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0009119g, YALI0D04092g, YALI0B15268g, YALI0000319g, and YALI0A19910g, or homolog thereof.

44. The recombinant microorganism of embodiment 1, wherein the one or more modifications in one or more fields comprising reducing equivalent availability comprises decoupling and increasing glucose uptake in the recombinant microorganism.

45. The recombinant microorganism of embodiment 44, wherein decoupling and increasing glucose uptake comprises:

upregulation of hexose transporter activity; and/or downregulation of hexose kinase activity.

46. The recombinant microorganism of embodiment 45, wherein the upregulation of one or more hexose transporter activity comprises the overexpression of one or more endogenous and/or exogenous nucleic acid molecule encoding a hexose transporter operably linked to one or more heterologous promoters.

47. The recombinant microorganism of embodiment 46, wherein the one or more endogenous and/or exogenous nucleic acid molecule encodes for a protein that encodes for a protein that has at least 70% sequence identity, at least 80% sequence identity, or at least 90% sequence identity to a hexose transporter from *Yarrowia lipolytica.*

48. The recombinant microorganism of embodiment 46, wherein the one or more endogenous and/or exogenous nucleic acid molecule encoding a hexose transporter is selected from YALI0A14212g, YALI0D01111g, YALI0D00363g, YALI0C16522g, and YALI0F25553g, or homolog thereof.

49. The recombinant microorganism of embodiment 45, wherein the downregulation of hexose kinase activity comprises deletion, disruption, and/or mutation of one or more endogenous gene encoding one or more hexose kinase enzyme.

50. The recombinant microorganism of embodiment 1, wherein the one or more modifications in one or more fields comprising reducing equivalent availability, one or more metabolic intermediates availability, or increased product purity comprises downregulation or inhibition of acetyl-CoA carboxylase (ACC) activity in the recombinant microorganism.

51. The recombinant microorganism of embodiment 50, wherein the downregulation or inhibition of ACC activity comprises deletion, disruption, and/or mutation of one or more endogenous gene encoding one or more ACC enzyme.

52. The recombinant microorganism of embodiment 1, wherein the one or more fatty acid co-substrate is a saturated fatty acid.

53. The recombinant microorganism of embodiment 1, wherein the one or more simple carbon co-substrate is selected from glucose, fructose, and glycerol.

54. The recombinant microorganism of embodiment 1, wherein the improved production of one or more lipid comprises improved production of one or more mono- or poly-unsaturated $C_6$-$C_{24}$ fatty acid, fatty alcohol, aldehyde, or acetate.

55. The recombinant microorganism of embodiment 54, wherein the one or more mono- or poly-unsaturated $C_6$-$C_{24}$ fatty acid, fatty alcohol, aldehyde, or acetate is an insect pheromone.

56. The recombinant microorganism of embodiment 55, wherein the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

57. The recombinant microorganism of any of the preceding embodiments, wherein the recombinant microorganism is a eukaryotic microorganism.

58. The recombinant microorganism of embodiment 57, wherein the eukaryotic microorganism is a yeast.

59. The recombinant microorganism of embodiment 58, wherein the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma.*

60. The recombinant microorganism of embodiment 58, wherein the yeast is an oleaginous yeast.

61. The recombinant microorganism of embodiment 60, wherein the oleaginous yeast is a member of a genus selected from the group consisting of *Yarrowia, Candida, Rhodotorula, Rhodosporidium, Cryptococcus, Trichosporon*, and *Lipomyces.*

62. The recombinant microorganism of embodiment 61, wherein the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T. cutaneum, Cryptococcus curvatus, R. glutinis*, and *R. graminis.*

63. A method of producing one or more lipid using a recombinant microorganism of any of the preceding embodiments, wherein the method comprises cultivating the recombinant microorganism in a culture medium containing a feedstock providing one or more simple carbon and one or more fatty acid until the one or more lipid is produced.

64. A method of producing a recombinant microorganism having improved production of biomass or improved production of one or more lipid from one or more fatty acid and one or more simple carbon co-substrates, comprising modifying a microorganism in one or more fields comprising:

tricarboxylic acid cycle;

lipid synthesis;

reducing equivalent availability;

one or more metabolic intermediates availability; and/or increased product purity, wherein the modifying yields a recombinant microorganism having improved production of biomass or improved production of one or more lipid compared to a microorganism not comprising the same modifications.

65. The method of embodiment 64, wherein the modifying in one or more fields comprising tricarboxylic acid cycle comprises introducing into and/or overexpressing in the recombinant microorganism at least one endogenous and/or exogenous nucleic acid molecule encoding an AMP-insensitive isocitrate dehydrogenase (IDH) variant.

66. The method of embodiment 65, wherein the at least one nucleic acid molecule encodes for a protein that has at least 70% sequence identity, at least 80% sequence identity, or at least 90% sequence identity to IDH from *Escherichia coli, Mycobacterium smegmatis, Acidithiobacillus thiooxidans*, or *Yarrowia lipolytica.*

67. The method of embodiment 65, wherein the at least one nucleic acid molecule is from *Yarrowia lipolytica* and comprises isoleucine to alanine substitutions at amino acid positions 279 and 280 of XP_503571.2, or homolog thereof.

68. The method of embodiment 64, wherein the modifying in one or more fields comprising tricarboxylic acid cycle or one or more metabolic intermediates availability comprises introducing into or overexpressing in the recombinant microorganism at least one endogenous and/or exogenous nucleic acid molecule encoding a pyruvate transporter.

69. The method of embodiment 68, wherein the one or more metabolic intermediates availability comprises mitochondrial pyruvate availability.

70. The method of embodiment 68, wherein the at least one nucleic acid molecule encodes for a protein that has at least 70% sequence identity, at least 80% sequence identity, or at least 90% sequence identity to pyruvate transporter from *Saccharomyces cerevisiae, Hanseniaspora osmophila, Yarrowia lipolytica*, or *Talaromyces marneffei* PM1.

71. The method of embodiment 68, wherein the pyruvate transporter is selected from *Saccharomyces cerevisiae* mpc1, *Saccharomyces cerevisiae* mpc3 (NP_011759.1), *Hanseniaspora osmophila* mpc3 (0EJ86292.1), *Yarrowia lipolytica* mpc, and *Talaromyces marneffei* PM1 mpc3 (KFX48982.1), or homolog thereof.

72. The method of embodiment 68, wherein the recombinant microorganism is *Saccharomyces cerevisiae* comprising a deletion, disruption, or loss of function mutation in a gene encoding an mpc2 pyruvate transporter.

73. The method of embodiment 68, wherein the recombinant microorganism is *Yarrowia* lipolytica.

74. The method of embodiment 64, wherein the modifying in one or more fields comprising lipid synthesis comprises alleviation of acetyl-CoA carboxylase (ACC) inhibition.

75. The method of embodiment 74, wherein alleviation of ACC inhibition comprises introducing into and/or overexpressing in the recombinant microorganism at least one endogenous and/or exogenous nucleic acid molecule encoding a feedback-insensitive ACC variant.

76. The method of embodiment 74, wherein the at least one nucleic acid molecule encodes for a protein that has at least 70% sequence identity, at least 80% sequence identity, or at least 90% sequence identity to ACC from *Mus musculus, Rattus norvegicus*, or *Homo sapiens.*

77. The method of embodiment 64, wherein the modifying in one or more fields comprising reducing equivalent availability comprises introducing into and/or overexpressing in the recombinant microorganism at least one endogenous and/or exogenous nucleic acid molecule encoding an NADP/NAD-dependent isocitrate dehydrogenase (IDH) targeted to the cytosol.

78. The method of embodiment 77, wherein the at least one nucleic acid molecule encodes for a protein that has at least 70% sequence identity, at least 80% sequence identity, or at least 90% sequence identity to IDH from *Escherichia coli, Mycobacterium smegmatis, Acidithiobacillus thiooxidans*, or *Yarrowia lipolytica.*

79. The method of embodiment 77, wherein the IDH is selected from *Escherichia coli* Idh (WP_000444484.1), *Mycobacterium smegmatis* Icd2 (WP_011727802.1), *Acidithiobacillus thiooxidans* Idh (PDB: 2D4V_A), and *Yarrowia lipolytica* Idh1 (XP_503571.2), or homolog thereof.

80. The method of embodiment 77, wherein the method further comprises introducing into or overexpressing in the recombinant microorganism at least one endogenous and/or exogenous nucleic acid encoding an aconitase targeted to the cytosol.

81. The method of embodiment 80, wherein the at least one endogenous and/or exogenous nucleic acid molecule encoding the IDH and the at least one endogenous and/or exogenous nucleic acid molecule encoding the aconitase lack a sequence encoding a mitochondrial-targeting peptide.

82. The method of embodiment 64, wherein the modifying in one or more fields comprising reducing equivalent availability or one or more metabolic intermediates availability comprises introducing into and/or overexpressing in the recombinant microorganism at least one endogenous and/or exogenous nucleic acid encoding a citrate transporter.

83. The method of embodiment 82, wherein the one or more metabolic intermediates comprises cytosolic citrate/isocitrate availability.

84. The method of embodiment 82, wherein the at least one nucleic acid molecule encodes for a protein that has at least 70% sequence identity, at least 80% sequence identity, or at least 90% sequence identity to a citrate transporter from *Yarrowia lipolytica, Saccharomyces cerevisiae, Rattus norvegicus, Caenorhabditis elegans*, or *Caliqus clemensi.*

85. The method of embodiment 82, wherein the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

86. The method of embodiment 64, wherein the modifying in one or more fields comprising reducing equivalent availability comprises introducing into and/or overexpressing in the recombinant microorganism at least one exogenous nucleic acid molecule encoding a decarboxylating malic enzyme.

87. The method of embodiment 86, wherein the at least one nucleic acid molecule encodes for a protein that has at least 70% sequence identity, at least 80% sequence identity, or at least 90% sequence identity to a decarboxylating malic enzyme from *Arabidopsis thaliana, Amaranthus hypochondriacus, Rhizobium meliloti, Solanum tuberosum, Homo sapiens*, or *Escherichia coli.*

88. The method of embodiment 86, wherein the decarboxylating malic enzyme is selected from *Arabidopsis thaliana* Q9SIU0, *Amaranthus hypochondriacus* P37224, *Rhizobium meliloti* 030807, *Solanum tuberosum* P37221, *Homo sapiens* Q16798, and *Escherichia coli* P26616, or homolog thereof.

89. The method of embodiment 86, wherein the decarboxylating malic enzyme lacks a sequence encoding a mitochondrial-targeting peptide.

90. The method of embodiment 64, wherein the modifying in one or more fields comprising one or more metabolic intermediates availability comprises introducing into and/or overexpressing in the recombinant microorganism at least one endogenous and/or exogenous nucleic acid encoding an ATP-citrate lyase.

91. The method of embodiment 90, wherein the one or more metabolic intermediates availability comprises cytosolic oxaloacetate availability.

92. The method of embodiment 90, wherein the at least one nucleic acid molecule encodes for a protein that has at least 70% sequence identity, at least 80% sequence identity, or at least 90% sequence identity to an ATP-citrate lyase from *Saccharomyces cerevisiae, Yarrowia lipolytica, Mus musculus*, and *Aspergillus niger.*

93. The method of embodiment 90, wherein the ATP-citrate lyase is selected from *Mus musculus* NP_001186225.1, *Mus musculus* NP_598798.1, *Aspergillus niger* XP_001394055.1, and *Aspergillus niger* XP_001394057.1, or homolog thereof.

94. The method of embodiment 64, wherein of the modifying in one or more fields comprising reducing equivalent availability comprises modifications in the pentose phosphate pathway (PPP) in the recombinant microorganism.

95. The method of embodiment 94, wherein modifications in the PPP comprises one or more of:

downregulation of hexose kinase activity;

upregulation of one or more oxidative PPP enzyme activity;

downregulation of fructose-6-phosphate kinase activity; and/or expression of one or more oxidative PPP enzyme variant.

96. The method of embodiment 95, wherein the upregulation of one or more oxidative PPP enzyme activity comprises introducing into and/or overexpressing in the recombinant microorganism one or more endogenous and/or exogenous nucleic acid molecule encoding a glucose-6-phosphate dehydrogenase (ZWF1), a 6-phosphogluconolactonase (SOL3), or a 6-phosphogluconate dehydrogenase (GND1).

97. The method of embodiment 95, wherein the downregulation of hexose kinase activity and/or fructose-6-phosphate kinase activity comprises introducing into the recombinant microorganism a deletion, disruption, and/or mutation of one or more endogenous gene encoding one or more hexose kinase enzyme and/or fructose-6-phosphate kinase enzyme.

98. The method of embodiment 95, wherein the one or more oxidative PPP enzyme variant comprises one or more endogenous and/or exogenous nucleic acid molecule encoding an NAD-dependent glucose-6-phosphate dehydrogenase (ZWF1) and/or an NAD-dependent 6-phosphogluconate dehydrogenase (GND1).

99. The method of embodiment 98, wherein the one or more nucleic acid molecule encodes for a protein that has at least 70% sequence identity, at least 80% sequence identity, or at least 90% sequence identity to an NAD-dependent glucose-6-phosphate dehydrogenase (ZWF1) from *Leuconostoc.*

100. The method of embodiment 98, wherein the one or more nucleic acid molecule encodes for a protein that has at least 70% sequence identity, at least 80% sequence identity, or at least 90% sequence identity to an NAD-dependent 6-phosphogluconate dehydrogenase (GND1) from *Bradyrhizobium* or *Methylobacillus.*

101. The method of embodiment 98, wherein the NAD-dependent glucose-6-phosphate dehydrogenase (ZWF1) is selected from *Leuconostoc* AAA25265.1 and *Leuconostoc* P11411, or homolog thereof.

102. The method of embodiment 98, wherein the NAD-dependent 6-phosphogluconate dehydrogenase (GND1) is selected from *Bradyrhizobium* WP_012029377.1, *Bradyrhizobium* A4YZZ8, *Methylobacillus* AAF34407.1, and *Methylobacillus* Q9L9P8, or homolog thereof.

103. The method of embodiment 64, wherein the modifying in one or more fields comprising reducing equivalent availability comprises downregulation of mannitol synthesis pathway in the recombinant microorganism.

104. The method of embodiment 103, wherein downregulation of mannitol synthesis pathway comprises introducing into the recombinant microorganism a deletion, disruption, and/or mutation of one or more gene encoding an NADPH-dependent mannitol dehydrogenase and/or an aldo-keto reductase.

105. The method of embodiment 104, wherein the one or more gene encoding an NADPH-dependent mannitol dehydrogenase is selected from YALI0B16192g, YALI0D18964g, and YALI0E12463g, or homolog thereof.

106. The method of embodiment 104, wherein the one or more gene encoding an aldo-keto reductase is selected from YALI0D07634g, YALI0F18590g, YALI0C13508g, YALI0F06974g, YALI0A15906g, YALI0B21780g, YALI0E18348g, YALI0B07117g, YALI0C09119g, YALI0D04092g, YALI0B15268g, YALI0000319g, and YALI0A19910g, or homolog thereof.

107. The method of embodiment 64, wherein the modifying in one or more fields comprising reducing equivalent availability comprises decoupling and increasing glucose uptake in the recombinant microorganism.

108. The method of embodiment 107, wherein decoupling and increasing glucose uptake comprises:

upregulation of hexose transporter activity; and/or downregulation of hexose kinase activity.

109. The method of embodiment 108, wherein the upregulation of one or more hexose transporter activity comprises introducing into and/or overexpressing in the recombinant microorganism one or more endogenous and/or exogenous nucleic acid molecule encoding a hexose transporter operably linked to one or more heterologous promoters.

110. The method of embodiment 109, wherein the one or more endogenous and/or exogenous nucleic acid molecule encodes for a protein that has at least 70% sequence identity, at least 80% sequence identity, or at least 90% sequence identity to a hexose transporter from *Yarrowia lipolytica.*

111. The method of embodiment 109, wherein the one or more endogenous and/or exogenous nucleic acid molecule encoding a hexose transporter is selected from YALI0A14212g, YALI0D01111g, YALI0D00363g, YALI0C$_{16522}$g, and YALI0F25553g, or homolog thereof.

112. The method of embodiment 108, wherein the downregulation of hexose kinase activity comprises introducing into the recombinant microorganism a deletion, disruption, and/or mutation of one or more endogenous gene encoding one or more hexose kinase enzyme.

113. The method of embodiment 64, wherein the modifying in one or more fields comprising reducing equivalent availability, one or more metabolic intermediates availability, and/or increased product purity comprises downregulation or inhibition of acetyl-CoA carboxylase (ACC) activity in the recombinant microorganism.

114. The method of embodiment 113, wherein the downregulation or inhibition of ACC activity comprises introducing into the recombinant microorganism a deletion, disruption, and/or mutation of one or more endogenous gene encoding one or more ACC enzyme.

115. The method of embodiment 64, wherein the one or more fatty acid co-substrate is a saturated fatty acid.

116. The method of embodiment 64, wherein the one or more simple carbon co-substrate is selected from glucose, fructose, and glycerol.

117. The method of embodiment 64, wherein the improved production of one or more lipid comprises improved production of one or more mono- or poly-unsaturated $C_6$-$C_{24}$ fatty acid, alcohol, aldehyde, or acetate.

118. The method of embodiment 117, wherein the one or more mono- or poly-unsaturated $C_6$-$C_{24}$ fatty acid, alcohol, aldehyde, or acetate is an insect pheromone or fatty acid precursor of an insect pheromone.

119. The method of embodiment 118, wherein the insect pheromone is selected from the group consisting of (Z)-11-hexadecenal, (Z)-11-hexadecenyl acetate, (Z)-9-tetradecenyl acetate, (Z,Z)-11,13-hexadecadienal, (9Z,11E)-hexadeca-9,1-dienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (9Z,12E)-tetradecadienyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

120. The method of any one of embodiments 64-119, wherein the recombinant microorganism is a eukaryotic microorganism.

121. The method of embodiment 120, wherein the eukaryotic microorganism is a yeast.

122. The method of embodiment 121, wherein the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma.*

123. The method of embodiment 121, wherein the yeast is an oleaginous yeast.

124. The method of embodiment 123, wherein the oleaginous yeast is a member of a genus selected from the group consisting of *Yarrowia, Candida, Rhodotorula, Rhodosporidium, Cryptococcus, Trichosporon*, and *Lipomyces*.

125. The method of embodiment 124, wherein the oleaginous yeast is a member of a species selected from *Yarrowia lipolytica, Candida tropicalis, Candida viswanathii, Rhodosporidium toruloides, Lipomyces starkey, L. lipoferus, C. revkaufi, C. pulcherrima, C. utilis, Rhodotorula minuta, Trichosporon pullans, T. cutaneum, Cryptococcus curvatus, R. glutinis*, and *R. graminis*.

Further Embodiments of the Invention

Other subject matter contemplated by the present disclosure is set out in the following numbered embodiments:

1. A recombinant microorganism with improved lipid production from one or more fatty acid, and one or more simple carbon co-substrates, wherein the recombinant microorganism comprises:
   a) a nucleic acid encoding a heterologous AMP-insensitive isocitrate dehydrogenase (IDH) enzyme;

wherein the recombinant microorganism has improved production of one or more lipids compared to a control microorganism without a).

2. The recombinant microorganism of embodiment 1, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

2.1 The recombinant microorganism of embodiment 1, wherein the recombinant microorganism is further engineered to comprise deletions of one or more of the endogenous acyl-CoA oxidases selected from the group consisting of: POX1, POX2, POX3, POX4, POX5, and POX6.

3. The recombinant microorganism of any one of embodiments 1-2.1, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

3.1 The recombinant microorganism of any one of embodiments 1-2.1, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

4. The recombinant microorganism of any one of embodiments 1-3.1, wherein the recombinant microorganism comprises a heterologous nucleic acid molecule encoding a fatty acyl desaturase that catalyzes the conversion of a saturated $C_6$-$C_{24}$ fatty acyl-CoA to a corresponding mono- or poly-unsaturated $C_6$-$C_{24}$ fatty acyl-CoA, wherein the mono- or poly-unsaturated $C_6$-$C_{24}$ fatty acyl-CoA is converted to the corresponding mono- or poly-unsaturated $C_6$-$C_{24}$ fatty alcohol.

4.1 The recombinant microorganism of embodiment 4, wherein the fatty acyl desaturase is a Z11 desaturase.

4.2 The recombinant microorganism of embodiment 4.1, wherein the fatty acyl desaturase is has at least 70% sequence identity, at least 80% sequence identity, or at least 90% sequence identity to an amino acid sequence encoded by SEQ ID NO. 32 or 33.

5. The recombinant microorganism of any one of embodiments 1-4.2, wherein the recombinant microorganism is engineered to reduce or eliminate the expression or activity of endogenous fatty alcohol oxidase (FAO1).

5.1. The recombinant microorganism of any one of embodiments 1-4.2, wherein the recombinant microorganism is engineered to comprise a deletion of endogenous fatty alcohol oxidase (FAO1).

6. The recombinant microorganism of any one of embodiments 1-5.1, wherein the IDH enzyme has at least 70% sequence identity, at least 80% sequence identity, or at least 90% sequence identity to an IDH from *Escherichia coli, Mycobacterium smegmatis, Acidithiobacillus thiooxidans*, and/or *Yarrowia lipolytica*.

7. The recombinant microorganism of any one of embodiments 1-5.1, wherein the IDH enzyme has at least 70% sequence identity, at least 80% sequence identity, or at least 90% sequence identity with a sequence selected from the group consisting of SEQ ID 20, 21, 22, and 23.

8. The recombinant microorganism of any one of embodiments 1-7, wherein the recombinant microorganism is *Yarrowia lipolytica*.

9. The recombinant microorganism of any one of embodiments 1-8, wherein the recombinant microorganism comprises an nucleic acid molecule encoding a heterologous decarboxylating malic enzyme.

10. The recombinant microorganism of embodiment 9, wherein the decarboxylating malic enzyme has at least 70% sequence identity, at least 80% sequence identity, or at least 90% sequence identity to a decarboxylating malic enzyme from *Escherichia coli, Hominidae sapiens*, Lypomyces starkeyi, *Mus musculus*, and *Rattus* novegicus, and/or *Rhodosporidium* toruloides.

11. The recombinant microorganism of embodiment 9, wherein the decarboxylating malic enzyme has at least 70% sequence identity, at least 80% sequence identity, or at least 90% sequence identity with a sequence selected from the group consisting of SEQ ID NO. 24, 25, 26, 27, 28, and 29.

12. The recombinant microorganism of any one of embodiments 1-11, wherein the recombinant microorganism comprises one or more modification(s) to the pentose phosphate pathway (PPP).

13. The recombinant microorganism of embodiment 12, wherein the one or more modification(s) to the PPP pathway is the upregulation of one or more enzymes exhibiting oxidative PPP activity.

14. The recombinant microorganism of embodiment 12, wherein the recombinant microorganism is engineered to overexpress one or more endogenous and/or exogenous enzymes selected from the group consisting of: a glucose-6-phosphate dehydrogenase (ZWF1), a 6-phosphogluconolactonase (SOL3), or a 6-phosphogluconate dehydrogenase (GND1).

15. The recombinant microorganism of embodiment 12, wherein the recombinant microorganism is engineered to overexpress one or more endogenous and/or exogenous enzyme(s) exhibiting at least 70% sequence identity, at least 80% sequence identity, or at least 90% sequence identity with a sequence selected from the group consisting of SEQ ID NO. 40, 42, and 44.

16. A recombinant microorganism with improved Z11-16 acid selectivity, said recombinant microorganism comprising:
   a) a nucleic acid encoding a heterologous decarboxylating malic enzyme; and/or
   b) a genetic modification overexpressing an enzyme exhibiting oxidative PPP activity;

wherein the recombinant microorganism has improved Z11-16 acid selectivity compared to a control microorganism without a) and/or b).

17. A recombinant microorganism with improved lipid production from one or more fatty acid, and one or more simple carbon co-substrates, said recombinant microorganism comprising:

a) a nucleic acid encoding a heterologous decarboxylating malic enzyme from Lypomyces starkeyi and/or *Mus musculus*; and/or b) a genetic modification overexpressing a 6-phosphogluconate dehydrogenase (GND1) enzyme;

wherein the recombinant microorganism has improved lipid production compared to a control microorganism without a) and/or b).

18. The recombinant microorganism of embodiment 17, wherein the decarboxylating malic enzyme has at least 70% sequence identity, at least 80% sequence identity, or at least 90% sequence identity with a sequence selected from the group consisting of SEQ ID NO. 24, 25, 26, 27, 28, and 29.

19. The recombinant microorganism of embodiment 17, wherein the GND1 enzyme has at least 70% sequence identity, at least 80% sequence identity, or at least 90% sequence identity with SEQ ID NO. 42.

20. The recombinant microorganism of any one of embodiments 16-19, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

20.1 The recombinant microorganism of any one of embodiments 16-19, wherein the recombinant microorganism is further engineered to comprise deletions of one or more of the endogenous acyl-CoA oxidases selected from the group consisting of: POX1, POX2, POX3, POX4, POX5, and POX6.

21. The recombinant microorganism of any one of embodiments 16-20, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

21.1 The recombinant microorganism of any one of embodiments 16-20, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

22. The recombinant microorganism of any one of embodiments 16-21, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

22.1 The recombinant microorganism of embodiment 22, wherein the fatty acyl desaturase is a Z11 desaturase.

22.2 The recombinant microorganism of embodiment 22.1, wherein the fatty acyl desaturase comprises an amino acid sequence encoded by SEQ ID NO. 32 or 33.

23. The recombinant microorganism of any one of embodiments 16-22.2, wherein the recombinant microorganism is engineered to reduce or eliminate the expression or activity of endogenous fatty alcohol oxidase (FAO1).

23.1 The recombinant microorganism of any one of embodiments 16-22.2, wherein the recombinant microorganism is engineered to comprise a deletion of endogenous fatty alcohol oxidase (FAO1).

24. The recombinant microorganism of any one of embodiments 16 or 20-23.1, wherein the decarboxylating malic enzyme has at least 70% sequence identity, at least 80% sequence identity, or at least 90% sequence identity to a decarboxylating malic enzyme from *Escherichia coli, Hominidae sapiens*, Lypomyces starkeyi, *Mus musculus*, and *Rattus* novegicus, and/or *Rhodosporidium* toruloides.

25. The recombinant microorganism of any one of embodiments 16 or 20-23.1, wherein the decarboxylating malic enzyme has at least 70% sequence identity, at least 80% sequence identity, or at least 90% sequence identity with a sequence selected from the group consisting of SEQ ID NO. 24, 25, 26, 27, 28, and 29.

26. The recombinant microorganism of any one of embodiments 16 or 20-25, wherein the enzyme exhibiting oxidative PPP activity is selected from the group consisting of glucose-6-phosphate dehydrogenase (ZWF1), a 6-phosphogluconolactonase (SOL3), and a 6-phosphogluconate dehydrogenase (GND1).

27. The recombinant microorganism of embodiments 16 or 20-25, wherein the enzyme exhibiting oxidative PPP activity exhibits at least 70% sequence identity, at least 80% sequence identity, or at least 90% sequence identity with a sequence selected from the group consisting of SEQ ID NO. 40, 42, and 44.

28. The recombinant microorganism of any one of embodiments 16-27, wherein the recombinant microorganism comprises a nucleic acid encoding a heterologous AMP-insensitive isocitrate dehydrogenase (IDH) enzyme.

29. The recombinant microorganism of embodiment 28, wherein the IDH enzyme has at least 70% sequence identity, at least 80% sequence identity, or at least 90% sequence identity to an IDH from *Escherichia coli, Mycobacterium smegmatis, Acidithiobacillus thiooxidans*, and/or *Yarrowia lipolytica.*

30. The recombinant microorganism of embodiment 28, wherein the IDH enzyme has at least 70% sequence identity, at least 80% sequence identity, or at least 90% sequence identity with a sequence selected from the group consisting of SEQ ID 20, 21, 22, and 23.

31. The recombinant microorganism of any one of embodiments 16-30, wherein the recombinant microorganism is *Yarrowia lipolytica.*

32. The recombinant microorganism of any one of embodiments 1-31, wherein the recombinant microorganism comprises a nucleic acid encoding a feedback-insensitive acetyl-CoA carboxylase (ACC) enzyme.

33. The recombinant microorganism of embodiment 32, wherein the ACC enzyme has at least 70% sequence identity, at least 80% sequence identity, or at least 90% sequence identity to ACC from *Mus musculus, Rattus norvegicus*, or *Homo sapiens.*

34. The recombinant microorganism of any one of embodiments 1-33, wherein the recombinant microorganism is modified to overexpress an endogenous aconitase gene and/or comprises an exogenous nucleic acid encoding an aconitase enzyme.

35. The recombinant microorganism of any one of embodiments 1-34, wherein the recombinant microorganism is modified to overexpress an endogenous citrate transporter gene and/or comprises an exogenous nucleic acid encoding a citrate transporter.

36. The recombinant microorganism of embodiment 35, wherein the citrate transporter has at least 70% sequence identity, at least 80% sequence identity, or at least 90% sequence identity to a citrate transporter from *Yarrowia lipolytica, Saccharomyces cerevisiae, Rattus norvegicus, Caenorhabditis elegans*, or *Caliqus clemensi.*

37. The recombinant microorganism of embodiment 35, wherein the citrate transporter is selected from *Yarrowia lipolytica* YALI0F26323p, *Saccharomyces cerevisiae* AAC48984.1, *Rattus norvegicus* AAA18899.1, *Caenorhabditis elegans* P34519.1, and *Caliqus clemensi* ACO14982.1, or homolog thereof.

38. The recombinant microorganism of any one of embodiments 1-37, wherein the recombinant microorganism is modified to overexpress an endogenous hexose transporter gene and/or comprises an exogenous nucleic acid encoding a hexose transporter.

39. The recombinant microorganism of embodiment 38, wherein the hexose transporter has at least 70% sequence identity, at least 80% sequence identity, or at least 90% sequence identity to a hexose transporter from *Yarrowia lipolytica.*

40. The recombinant microorganism of embodiment 38, wherein the hexose transporter is selected from the group consisting of: YALI0A14212g, YALI0D01111g, YALI0D00363g, YALI0C16522g, and YALI0F25553g, or homolog thereof.

41. The recombinant microorganism of any one of embodiments 1-40, wherein the one or more fatty acid co-substrate is a saturated fatty acid.

42. The recombinant microorganism of any one of embodiments 1-41, wherein the one or more simple carbon co-substrate is selected from glucose, fructose, and glycerol.

43. The recombinant microorganism of any one of embodiments 1-42, wherein the oleaginous yeast is a member of a genus selected from the group consisting of *Yarrowia, Candida, Rhodotorula, Rhodosporidium, Cryptococcus, Trichosporon*, and *Lipomyces.*

44. The recombinant microorganism of any one of embodiments 1-43, wherein the oleaginous yeast is a member of a species selected from *Yarrowia lipolytica, Candida tropicalis, Candida* viswanathii, *Rhodosporidium* toruloides, *Lipomyces* starkey, L. lipoferus, C. revkaufi, *C. pulcherrima, C. utilis, Rhodotorula minuta, Trichosporon pullans, T cutaneum, Cryptococcus curvatus, R. glutinis*, and *R. graminis.*

44.1 A composition comprising:
- a) the recombinant microorganism of any one of embodiments 1-44; and
- b) a dual-substrate culture medium comprising:
  - i) a fatty acid precursor substrate; and
  - ii) a simple carbon co-substrate.

44.2 The composition of embodiment 44.1, wherein the fatty acid precursor substrate is a C6-C24 saturated fatty acid.

44.3. The composition of embodiment 44.2, wherein the fatty acid precursor substrate is derived from a plant.

44.4. The composition of embodiment 44.1, wherein the fatty acid precursor substrate is methyl palmitate.

44.5. The composition of any one of embodiments 44.1-44.4, wherein the simple carbon co-substrate is glycerol and/or glucose.

45. A method of producing one or more lipid using a recombinant microorganism of any of the preceding embodiments, wherein the method comprises cultivating the recombinant microorganism in a culture medium containing a feedstock providing one or more simple carbon and one or more fatty acid until the one or more lipid is produced.

45.1 A method for increasing the production of non-native unsaturated fatty acids from a recombinant microorganism in a bypass pathway culture, said method comprising the steps of:
- a) providing a recombinant microorganism comprising a modification to the:
  - i) Tricarboxylic acid cycle;
  - ii) Lipid synthesis;
  - iii) One or more metabolic intermediates; and/or
  - iv) Reducing equivalents; and
- b) contacting said recombinant microorganism with a dual-substrate culture medium comprising:
  - i) a fatty acid precursor substrate; and
  - ii) a simple carbon co-substrate;

wherein the recombinant microorganism exhibits improved production of non-native unsaturated fatty acids compared to a control microorganism without the modification(s) of a).

The inventors intend that embodiments 46-117 can be presented as dependent embodiments from embodiment 45.1.

46. A method for increasing the production of fatty acids from a recombinant microorganism in a bypass pathway culture, said method comprising the steps of:
- a) providing a recombinant microorganism comprising a nucleic acid encoding a heterologous AMP-insensitive isocitrate dehydrogenase (IDH) enzyme capable of catalyzing the oxidation of isocitrate to oxalosuccinate; and
- b) contacting said recombinant microorganism with a dual-substrate culture medium comprising:
  - i) a fatty acid precursor substrate; and
  - ii) a simple carbon co-substrate;

wherein the recombinant microorganism exhibits improved fatty acid production compared to a control microorganism without the nucleic acid encoding the IDH enzyme.

46.1 The method of embodiment 46, wherein the microorganism exhibits improved production of non-native unsaturated fatty acids.

47. The method of embodiment 46 or 46.1, wherein the fatty acid precursor substrate is a C6-C24 saturated fatty acid.

48. The method of embodiment 47, wherein the fatty acid precursor substrate is derived from a plant.

49. The method of embodiment 46 or 46.1, wherein the fatty acid precursor substrate is methyl palmitate.

50. The method of any one of embodiments 46-49, wherein the simple carbon co-substrate is glycerol and/or glucose.

51. The method of any one of embodiments 46-50, wherein the IDH enzyme has at least 70% sequence identity, at least 80% sequence identity, or at least 90% sequence identity to an IDH from *Escherichia coli, Mycobacterium smegmatis, Acidithiobacillus thiooxidans*, or *Yarrowia* lipolytica 52. The method of any one of embodiments 46-50, wherein the IDH enzyme has at least 70% sequence identity, at least 80% sequence identity, or at least 90% sequence identity with a sequence selected from the group consisting of SEQ ID 20, 21, 22, and 23.

53. The method of any one of embodiments 46-52, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

54. The method of any one of embodiments 46-52, wherein the recombinant microorganism is further engineered to comprise deletions of one or more of the endogenous acyl-CoA oxidases selected from the group consisting of: POX1, POX2, POX3, POX4, POX5, and POX6.

55. The method of any one of embodiments 46-54, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

56. The method of any one of embodiments 46-54, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

57. The method of any one of embodiments 46-55, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

58. The method of embodiment 57, wherein the fatty acyl desaturase is a Z11 desaturase.

59. The method of any one of embodiments 46-58, wherein the recombinant microorganism is *Yarrowia lipolytica.*

60. A method for improving the Z11-16 acid selectivity of a recombinant microorganism in a bypass pathway culture, said method comprising the steps of:

a) providing a recombinant microorganism comprising a nucleic acid encoding a heterologous decarboxylating malic enzyme capable of catalyzing the oxidation of malate to pyruvate; and b) contacting said recombinant microorganism with a dual-substrate culture medium comprising:

i) a fatty acid precursor substrate; and ii) a simple carbon co-substrate;

wherein the recombinant microorganism exhibits improved Z11-16 acid selectivity compared to a control microorganism without the nucleic acid encoding the heterologous decarboxylating malic enzyme.

61. The method of embodiment 60, wherein the fatty acid precursor substrate is a C6-C24 saturated fatty acid.

62. The method of embodiment 61, wherein the fatty acid precursor substrate is derived from a plant.

63. The method of embodiment 60, wherein the fatty acid precursor substrate is methyl palmitate.

64. The method of any one of embodiments 60-63, wherein the simple carbon co-substrate is glycerol and/or glucose.

65. The method of any one of embodiments 60-64, wherein the decarboxylating malic enzyme has at least 70% sequence identity, at least 80% sequence identity, or at least 90% sequence identity with a decarboxylating malic enzyme from *Escherichia coli, Hominidae sapiens*, Lypomyces starkeyi, *Mus musculus, Rattus* novegicus, or *Rhodosporidium* toruloides.

66. The method of any one of embodiments 60-64, wherein the heterologous decarboxylating malic enzyme has at least 70% sequence identity, at least 80% sequence identity, or at least 90% sequence identity with SEQ ID NO. 24, 25, 26, 27, 28, and 29.

67. The method of any one of embodiments 60-66, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

68. The method of any one of embodiments 60-66, wherein the recombinant microorganism is further engineered to comprise deletions of one or more of the endogenous acyl-CoA oxidases selected from the group consisting of: POX1, POX2, POX3, POX4, POX5, and POX6.

69. The method of any one of embodiments 60-68, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

70. The method of any one of embodiments 60-68, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

71. The method of any one of embodiments 60-70, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

72. The method of embodiment 71, wherein the fatty acyl desaturase is a Z11 desaturase.

72. The method of any one of embodiments 60-72, wherein the recombinant microorganism is *Yarrowia lipolytica.*

73. A method for improving the Z11-16 acid selectivity of a recombinant microorganism in a bypass pathway culture, said method comprising the steps of:

a) providing a recombinant microorganism comprising a genetic modification overexpressing an enzyme exhibiting oxidative pentose phosphate pathway (PPP) activity; and b) contacting said recombinant microorganism with a dual-substrate culture medium comprising:

i) a fatty acid precursor substrate; and ii) a simple carbon co-substrate;

wherein the recombinant microorganism exhibits improved Z11-16 acid selectivity compared to a control microorganism without the genetic modification overexpressing the enzyme exhibiting oxidative PPP activity.

74. The method of embodiment 73, wherein the fatty acid precursor substrate is a C6-C24 saturated fatty acid.

75. The method of embodiment 74, wherein the fatty acid precursor substrate is derived from a plant.

76. The method of embodiment 73, wherein the fatty acid precursor substrate is methyl palmitate.

77. The method of any one of embodiments 73-76, wherein the simple carbon co-substrate is glycerol and/or glucose.

78. The method of any one of embodiments 73-77, wherein the enzyme exhibiting oxidative PPP activity is selected from the group consisting of: a glucose-6-phosphate dehydrogenase (ZWF1), a 6-phosphogluconolactonase (SOL3), or a 6-phosphogluconate dehydrogenase (GND1).

79. The method of any one of embodiments 73-77, wherein the enzyme exhibiting oxidative PPP activity has at least 70% sequence identity, at least 80% sequence identity, or at least 90% sequence identity with SEQ ID NOs. 40, 42, or 44.

80. The method of any one of embodiments 73-79, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

81. The method of any one of embodiments 73-79, wherein the recombinant microorganism is further engineered to comprise deletions of one or more of the endogenous acyl-CoA oxidases selected from the group consisting of: POX1, POX2, POX3, POX4, POX5, and POX6.

82. The method of any one of embodiments 73-81, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

83. The method of any one of embodiments 73-81, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

84. The method of any one of embodiments 73-83, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

85. The method of embodiment 84, wherein the fatty acyl desaturase is a Z11 desaturase.

86. The method of any one of embodiments 73-85, wherein the recombinant microorganism is *Yarrowia lipolytica.*

87. A method for improving the fatty acid production of a recombinant microorganism in a bypass pathway culture, said method comprising the steps of:

- a) providing a recombinant microorganism comprising:
  - i) a genetic modification overexpressing an enzyme exhibiting oxidative pentose phosphate pathway (PPP) activity; and/or
  - ii) a nucleic acid encoding a heterologous decarboxylating malic enzyme; and
- b) contacting said recombinant microorganism with a dual-substrate culture medium comprising:
  - i) a fatty acid precursor substrate; and
  - ii) a simple carbon co-substrate;

wherein the recombinant microorganism exhibits improved fatty acid production compared to a control microorganism without the genetic modification or nucleic acid of a).

87.1 The method claim 87, wherein the microorganism exhibits improved production of non-native unsaturated fatty acids.

88. The method of embodiment 87 or 87.1, wherein the fatty acid precursor substrate is a C6-C24 saturated fatty acid.

89. The method of embodiment 88, wherein the fatty acid precursor substrate is derived from a plant.

90. The method of embodiment 87 or 87.1, wherein the fatty acid precursor substrate is methyl palmitate.

91. The method of any one of embodiments 87-89, wherein the simple carbon co-substrate is glycerol and/or glucose.

92. The method of any one of embodiments 87-91, wherein the enzyme exhibiting oxidative PPP activity is a 6-phosphogluconate dehydrogenase (GND) enzyme.

93. The method of any one of embodiments 87-91, wherein the enzyme exhibiting oxidative PPP activity has at least 70% sequence identity, at least 80% sequence identity, or at least 90% sequence identity with SEQ ID NO. 42.

94. The method of any one of embodiments 87-93, wherein the decarboxylating malic enzyme has at least 70% sequence identity, at least 80% sequence identity, or at least 90% sequence identity with a decarboxylating malic enzyme from Lypomyces starkeyi or *Mus musculus.*

95. The method of any one of embodiments 87-93, wherein the heterologous decarboxylating malic enzyme has at least 70% sequence identity, at least 80% sequence identity, or at least 90% sequence identity with SEQ ID NO. 24 or 28.

96. The method of any one of embodiments 87-95, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

97. The method of any one of embodiments 87-95, wherein the recombinant microorganism is further engineered to comprise deletions of one or more of the endogenous acyl-CoA oxidases selected from the group consisting of: POX1, POX2, POX3, POX4, POX5, and POX6.

98. The method of any one of embodiments 87-97, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

99. The method of any one of embodiments 87-97, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

100. The method of any one of embodiments 87-99, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

101. The method of embodiment 100, wherein the fatty acyl desaturase is a Z11 desaturase.

102. The method of any one of embodiments 87-101, wherein the recombinant microorganism is *Yarrowia lipolytica.*

103. A method for improving the fatty acid production of a recombinant microorganism in a bypass pathway culture, said method comprising the steps of:

- a) providing a recombinant microorganism comprising:
  - i) a genetic modification overexpressing an endogenous feedback insensitive acetyl-CoA carboxylase (ACC) enzyme; or
  - ii) a nucleic acid encoding a heterologous feedback-insensitive ACC enzyme; and
- b) contacting said recombinant microorganism with a dual-substrate culture medium comprising:
  - i) a fatty acid precursor substrate; and
  - ii) a simple carbon co-substrate;

wherein the recombinant microorganism exhibits improved fatty acid production compared to a control microorganism without the genetic modification or nucleic acid of a).

104. The method of embodiment 103, wherein the heterologous feedback-insensitive ACC has at least 70% sequence identity, at least 80% sequence identity, or at least 90% sequence identity to ACC from *Mus musculus, Rattus norvegicus*, or *Homo sapiens.*

105. The method of embodiment 103 or 104, wherein the fatty acid precursor substrate is a C6-C24 saturated fatty acid.

106. The method of embodiment 105, wherein the fatty acid precursor substrate is derived from a plant.

107. The method of embodiment 103 or 104, wherein the fatty acid precursor substrate is methyl palmitate.

108. The method of any one of embodiments 103-107, wherein the simple carbon co-substrate is glycerol and/or glucose.

109. The method of any one of embodiments 103-108, wherein the ACC enzyme has at least 70% sequence identity, at least 80% sequence identity, or at least 90% sequence identity with a decarboxylating malic enzyme from *Rattus norvegicus, Mus musculus, Saccharomyces cerevisiae, Homo sapiens, Lipomyces* starkeyi, *Komagataella* phaffii, or *Yarrowia lipolytica.*

110. The method of any one of embodiments 103-108, wherein the ACC enzyme has at least 70% sequence identity, at least 80% sequence identity, or at least 90% sequence identity with SEQ ID NO. 50, 51, 52, 53, 54, 55, 56, or 57.

110.1 The method of embodiments of any one of embodiments 103-110, wherein the ACC enzyme:

a) comprises a replacement of a serine residue targeted for phosphorylation with a glycine linker of 4 to 34 amino acids; and/or b) comprises a replacement of the serine residue targeted for phosphorylation with a residue that cannot be phosphorylated; and/or c) comprises a replacement of argenine residues at positions 1266 and 1369 of the alignment of FIG. 11 with a residue that will not interact with the serine residue after phosphorylation to inactivate ACC.

111. The method of any one of embodiments 103-110.1, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

112. The method of any one of embodiments 103-110.1, wherein the recombinant microorganism is further engineered to comprise deletions of one or more of the endogenous acyl-CoA oxidases selected from the group consisting of: POX1, POX2, POX3, POX4, POX5, and POX6.

113. The method of any one of embodiments 103-112, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

114. The method of any one of embodiments 110-112, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

115. The method of any one of embodiments 110-114, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

116. The method of embodiment 115, wherein the fatty acyl desaturase is a Z11 desaturase.

117. The method of any one of embodiments 110-116, wherein the recombinant microorganism is *Yarrowia lipolytica.*

118. A a recombinant microorganism having improved production of non-native unsaturated fatty acids from one or more fatty acids and one or more simple carbon co-substrates wherein said recombinant microorganism comprises:

a) a genetic modification overexpressing an endogenous feedback insensitive acetyl-CoA carboxylase (ACC) enzyme; and/or b) a nucleic acid encoding a heterologous feedback-insensitive ACC enzyme;

wherein the recombinant microorganism exhibits improved fatty acid production compared to a control microorganism without the genetic modification or nucleic acid of a).

119. The recombinant microorganism of embodiment 118, wherein the ACC enzyme has at least 70% sequence identity, at least 80% sequence identity, or at least 90% sequence identity with a decarboxylating malic enzyme from *Rattus norvegicus, Mus musculus, Saccharomyces cerevisiae, Homo sapiens, Lipomyces* starkeyi, *Komagataella* phaffii, or *Yarrowia lipolytica.*

120. The recombinant microorganism of any one of embodiments 118-119, wherein the ACC enzyme has at least 70% sequence identity, at least 80% sequence identity, or at least 90% sequence identity with SEQ ID NO. 50, 51, 52, 53, 54, 55, 56, or 57.

121 The recombinant microorganism of any one of embodiments 118-120, wherein the ACC enzyme:

a) comprises a replacement of an serine residue targeted for phosphorylation with a glycine linker of 4 to 34 amino acids; and/or b) comprises a replacement of the serine residue targeted for phosphorylation with a residue that cannot be phosphorylated; and/or c) comprises a replacement of the argenine residues at positions 1266 and 1369 of the alignment of FIG. 11 with a residue that will not interact with the serine residue after phosphorylation to inactivate ACC.

122. The recombinant microorganism of any one of embodiments 118-121, wherein the recombinant microorganism is further engineered to reduce or eliminate the expression or activity of one or more of the endogenous acyl-CoA oxidases selected from the group consisting of: POX1, POX2, POX3, POX4, POX5, and POX6.

123. The recombinant microorganism of any one of embodiments 118-121, wherein the recombinant microorganism is further engineered to comprise deletions of one or more of the endogenous acyl-CoA oxidases selected from the group consisting of: POX1, POX2, POX3, POX4, POX5, and POX6.

124. The recombinant microorganism of any one of embodiments 118-123, wherein the recombinant microorganism is further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

125. The recombinant microorganism of any one of embodiments 118-123, wherein the recombinant microorganism is further engineered to comprise deletions of one or more endogenous fatty alcohol dehydrogenases selected from the group consisting of FADH, ADH1, ADH2, ADH3, ADH4, ADH5, ADH6, and ADH7.

126. The recombinant microorganism of any one of embodiments 118-125, wherein the recombinant microorganism comprises a heterologous nucleic acid molecule encoding a fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to the corresponding mono- or poly-unsaturated C6-C24 fatty alcohol.

127. The recombinant microorganism of embodiment 126, wherein the fatty acyl desaturase is a Z11 desaturase.

128. The recombinant microorganism of any one of embodiments 118-126, wherein the recombinant microorganism is *Yarrowia lipolytica.*

The foregoing detailed description has been given for clearness of understanding only and no unnecessary limitations should be understood there from as modifications will be obvious to those skilled in the art.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

REFERENCES

1. Zhang, H. et. al. Enhanced lipid accumulation in the yeast *Yarrowia lipolytica* by over-expression of ATP:citrate lyase from *Mus musculus*. J Biotechnol. 2014 Dec. 20; 192.
2. Halperin, M. L. et. al. Effects of Palmitoyl CoA on Citrate and Malate Transport by Rat Liver Mitochondria. Proc Natl Acad Sci USA. 1972 April; 69(4): 1003-1007.
3. Dulermo, T. et. al. Analysis of ATP-citrate lyase and malic enzyme mutants of *Yarrowia lipolytica* points out the importance of mannitol metabolism in fatty acid synthesis. Biochim Biophys Acta. 2015 September; 1851(9): 1107-17. doi: 10.1016/j.bbalip.2015.04.007. Epub 2015 May 8.
4. Morin, N. et. al. Transcriptomic analyses during the transition from biomass production to lipid accumulation in the oleaginous yeast *Yarrowia lipolytica*. PLoS One. 2011; 6(11):e27966. doi: 10.1371/journal.pone.0027966. Epub 2011 Nov. 22.
5. Kavŝĉek, M., Bhutada, G., Madl, T. & Natter, K. Optimization of lipid production with a genome-scale model of *Yarrowia lipolytica. BMC Syst. Biol.* 9, 72 (2015).

LISTING OF SEQUENCES

| SEQ ID | Description of Sequence |
|---|---|
| SEQ ID NO: 1 | Full IDH001 plasmid sequence |
| SEQ ID NO: 2 | IDH002 insert sequence |
| SEQ ID NO: 3 | IDH003 insert sequence |
| SEQ ID NO: 4 | IDH004 insert sequence |
| SEQ ID NO: 5 | IDH005 insert sequence |
| SEQ ID NO: 6 | IDH006 insert sequence |
| SEQ ID NO: 7 | IDH007 plasmid sequence |
| SEQ ID NO: 8 | IDH008 insert sequence |
| SEQ ID NO: 9 | IDH009 insert sequence |
| SEQ ID NO: 10 | IDH010 insert sequence |
| SEQ ID NO: 11 | IDH011 insert sequence |
| SEQ ID NO: 12 | IDH012 insert sequence |
| SEQ ID NO: 13 | IDH013 insert sequence |
| SEQ ID NO: 14 | IDH014 insert sequence |
| SEQ ID NO: 15 | IDH015 insert sequence |
| SEQ ID NO: 16 | IDH016 insert sequence |
| SEQ ID NO: 17 | IDH017 insert sequence |
| SEQ ID NO: 18 | IDH018 insert sequence |
| SEQ ID NO: 19 | IDH019 insert sequence |
| SEQ ID NO: 20 | *Y. lipolytica* IDH1 D279A, I280A amino acid sequence |
| SEQ ID NO: 21 | *E. coli* IDH amino acid sequence WP_000444484.1 |
| SEQ ID NO: 22 | *A. thiooxidans* IDH amino acid sequence PDB: 2D4V_A |
| SEQ ID NO: 23 | *M. smegmatis* IDH amino acid sequence WP_011727802.1 |
| SEQ ID NO: 24 | *L. starkeyi* malic enzyme amino acid sequence (mitochondrial, NAD+, unmodified) |
| SEQ ID NO: 25 | *R. toruloides* malic enzyme amino acid sequence (mitochondrial, NAD+, mitochondrial targeting sequence truncated) |
| SEQ ID NO: 26 | *H. sapiens* malic enzyme amino acid sequence (mitochondrial, NAD+, mitochondrial targeting sequence truncated) |
| SEQ ID NO: 27 | *R. norvegicus* malic enzyme amino acid sequence (cytoplasm, NADP+, unmodified) |
| SEQ ID NO: 28 | *M. musculus* malic enzyme amino acid sequence (cytoplasm, NADP+, unmodified) |
| SEQ ID NO: 29 | *E. coli* malic enzyme amino acid sequence (NAD+, unmodified) P26616 |
| SEQ ID NO: 30 | IDH from *Y. lipolytica* XP_503571.2 |
| SEQ ID NO: 31 | mpc3 Pyruvate Transporter from *Saccharomyces cerevisiae* NP_011759.1 |
| SEQ ID NO: 32 | *Helicoverpa zea* Z11 desaturase |
| SEQ ID NO: 33 | *Helicoverpa zea* Z11 desaturase |
| SEQ ID NO: 34 | Malic Enzyme from *Arabidopsis* Q9SIU0 |
| SEQ ID NO: 35 | Malic Enzyme from *Amaranthus hypochondriacus* P37224 |
| SEQ ID NO: 36 | Malic Enzyme from *Rhizobium meliloti* O30807 |
| SEQ ID NO: 37 | Malic Enzyme from *Solanum tuberosum* P37221 |
| SEQ ID NO: 38 | Malic Enzyme from *Homo sapiens* Q16798 |
| SEQ ID NO: 39 | ZWF1 from *Y. Lipolytica* YALI0E22649g |
| SEQ ID NO: 40 | ZWF1 from *Y. Lipolytica* YALI0E22649g protein |
| SEQ ID NO: 41 | GND1 from *Y. Lipolytica* YALI0B15598g |
| SEQ ID NO: 42 | GND1 from *Y. Lipolytica* YALI0B15598g protein |
| SEQ ID NO: 43 | SOL3 from *Y. Lipolytica* YALI0_E11671g |

-continued

LISTING OF SEQUENCES

| SEQ ID | Description of Sequence |
|---|---|
| SEQ ID NO: 44 | SOL3 from *Y. Lipolytica* YALI0_E11671g |
| SEQ ID NO: 45 | KFX48982.1 Mitochondrial pyruvate carrier 3 [*Talaromyces marneffei* PM1] |
| SEQ ID NO: 46 | OEJ86292.1 Mitochondrial pyruvate carrier 3 [*Hanseniaspora osmophila*] |
| SEQ ID NO: 47 | NP_721100.1 isocitrate dehydrogenase [*Streptococcus mutans* UA159] |
| SEQ ID NO: 48 | WP_003229433.1 MULTISPECIES: NADP-dep endent isocitrate dehydrogenase [*Bacillales*] AMP-insensitive |
| SEQ ID NO: 49 | *Bacillus subtilis* IDH S104A mutant, AMP-insensitive |
| SEQ ID NO: 50 | sp\|P11497\|ACACA_RAT Acetyl-CoA carboxylase 1 OS = *Rattus norvegicus* OX = 10116 GN = Acaca PE = 1 SV = 1 |
| SEQ ID NO: 51 | sp\|Q5SWU9\|ACACA_MOUSE Acetyl-CoA carboxylase 1 OS = *Mus musculus* OX = 10090 GN = Acaca PE = 1 SV = 1 |
| SEQ ID NO: 52 | sp\|Q00955\|ACAC_YEAST Acetyl-CoA carboxylase OS = *Saccharomyces cerevisiae* (strain ATCC 204508/S288c) OX = 559292 GN = ACC1 PE = 1 SV = 2 |
| SEQ ID NO: 53 | sp\|Q13085-3\|ACACA_HUMAN Isoform 3 of Acetyl-CoA carboxylase 1 OS = *Homo sapiens* OX = 9606 GN = ACACA |
| SEQ ID NO: 54 | sp\|Q13085\|ACACA_HUMAN Acetyl-CoA carboxylase 1 OS = *Homo sapiens* OX = 9606 GN = ACACA PE = 1 SV = 2 |
| SEQ ID NO: 55 | tr\|A0A0H3VB41\|A0A0H3VB41_LIPST Acetyl-CoA carboxylase OS = *Lipomyces starkeyi* OX = 29829 GN = ACC1 PE = 4 SV = 1 |
| SEQ ID NO: 56 | tr\|F2QLC7\|F2QLC7_KOMPC Acetyl-CoA carboxylase OS = *Komagataella phaffii* (strain ATCC 76273/CBS 7435/CECT 11047/NRRL Y-11430/Wegner 21-1) OX = 981350 GN = ACC1 PE = 4 SV = 1 |
| SEQ ID NO: 57 | tr\|Q6CC91\|Q6CC91_YARLI YALI0C11407p OS = *Yarrowia lipolytica* (strain CLIB 122/E 150) OX = 284591 GN = YALI0_C11407g PE = 4 SV = 1 |

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:

1. A method for increasing the production of a C6-C24 non-native unsaturated fatty acids in a recombinant *Yarrowia lipolytica* microorganism, said method comprising the steps of:

a) providing a recombinant *Yarrowia lipolytica* microorganism comprising a nucleic acid sequence encoding (i) an isocitrate dehydrogenase (IDH) enzyme comprising an amino acid sequence having at least 95% sequence identity to SEQ ID NO: 20 and having the D298A and I299A mutations comprised therein, or iii) an IDH enzyme comprising an amino acid sequence having at least 95% sequence identity to SEQ ID NO: 22; and b) culturing said recombinant *Yarrowia lipolytica* microorganism in medium comprising a simple carbon substrate;

wherein the recombinant *Yarrowia lipolytica* microorganism exhibits increased production of the C6-C24 non-native unsaturated fatty acid compared to a control *Yarrowia lipolytica* microorganism without the nucleic acid sequence of (a).

2. The method of claim 1, wherein the culture medium comprises a fatty acid precursor substrate.

3. The method of claim 2, wherein the fatty acid precursor substrate is methyl palmitate.

4. The method of claim 1, wherein the simple carbon substrate is glycerol and/or glucose.

5. The method of claim 1, wherein the amino acid sequence comprises SEQ ID NO: 20 or 22.

6. The method of claim 1, wherein the recombinant *Yarrowia lipolytica* microorganism has been further engineered to reduce or eliminate the expression or activity of one or more of the endogenous acyl-CoA oxidases selected from the group consisting of: POX1, POX2, POX3, POX4, POX5, and POX6.

7. The method of claim 1, wherein the recombinant *Yarrowia lipolytica* microorganism has been further engineered to reduce or eliminate the expression or activity of one or more endogenous fatty alcohol dehydrogenases selected from the group consisting of FADH, ADH1, ADH2, ADH3, ADH4, ADH5, ADH6, and ADH7.

8. The method of claim 1, wherein the recombinant *Yarrowia lipolytica* microorganism comprises a nucleic acid molecule encoding a heterologous fatty acyl desaturase that catalyzes the conversion of a saturated C6-C24 fatty acyl-CoA to a corresponding mono- or poly-unsaturated C6-C24 fatty acyl-CoA, wherein the mono- or poly-unsaturated C6-C24 fatty acyl-CoA is converted to a corresponding mono- or poly-unsaturated C6-C24 fatty alcohol.

9. The method of claim 8, wherein the fatty acyl desaturase is a Z11 desaturase.

10. The method of claim 2, wherein the fatty acid precursor substrate is derived from a plant.

11. The method of claim 1, wherein the non-native unsaturated fatty acid is Z11-16Acid.

* * * * *

SEQUENCE LISTING

<160> NUMBER OF SEQ ID NOS: 57

<210> SEQ ID NO 1
<211> LENGTH: 5860
<212> TYPE: DNA
<213> ORGANISM: Artificial Sequence
<220> FEATURE:
<223> OTHER INFORMATION: Full IDH001 plasmid sequence

<400> SEQUENCE: 1
tcgcgcgttt cggtgatgac ggtgaaaacc tctgacacat gcagctcccg gagcccagag 60
agccattgac gttctttcta atttggaccg atagccgtat agtccagtct atctataagt 120
tcaactaact cgtaactatt accataacat atacttcact gccccagata aggttccgat 180
aaaaagttct gcagactaaa tttatttcag tctcctcttc accaccaaaa tgccctccta 240
cgaagctcga gctaacgtcc acaagtccgc ctttgccgct cgagtgctca agctcgtggc 300
agccaagaaa accaacctgt gtgcttctct ggatgttacc accaccaagg agctcattga 360
gcttgccgat aaggtcggac cttatgtgtg catgatcaag acccatatcg acatcattga 420
cgacttcacc tacgccggca ctgtgctccc cctcaaggaa cttgctctta agcacggttt 480
cttcctgttc gaggacagaa agttcgcaga tattggcaac actgtcaagc accagtacaa 540
gaacggtgtc taccgaatcg ccgagtggtc cgatatcacc aacgcccacg gtgtacccgg 600

-continued

```
aaccggaatc attgctggcc tgcgagctgg tgccgaggaa actgtctctg aacagaagaa    660
ggaggacgtc tctgactacg agaactccca gtacaaggag ttcctggtcc cctctcccaa    720
cgagaagctg gccagaggtc tgctcatgct ggccgagctg tcttgcaagg gctctctggc    780
cactggcgag tactccaagc agaccattga gcttgcccga tccgaccccg agtttgtggt    840
tggcttcatt gcccagaacc gacctaaggg cgactctgag gactggctta ttctgacccc    900
cggggtgggt cttgacgaca agggagacgc tctcggacag cagtaccgaa ctgttgagga    960
tgtcatgtct accggaacgg atatcataat tgtcggccga ggtctgtacg gccagaaccg   1020
agatcctatt gaggaggcca agcgatacca gaaggctggc tgggaggctt accagaagat   1080
taactgttag aggttagact atggatatgt aatttaactg tgtatataga gagcgtgcaa   1140
gtatggagcg cttgttcagc ttgtatgatg gtcagacgac ctgtctgatc gagtatgtat   1200
gatactgcac aacctgtgta tccgcatatc ttccaatggg gcatgttgtt gtgttcataa   1260
cttcgtatag catacattat acgaagttat ggccagacgg ccagacaggc caaacctgca   1320
gggtaataat gtgccatgct gtataacaat cgcctttccg cagctgtatc tatgggtatg   1380
attaactctg atgatccgga gataaactaa tcttaaccac tgtacgatac atatactgta   1440
agatggcacc ctgtggttta acccttgtag caatgtgttt aagcaaggga atattgtgat   1500
agagaagtgt atttgaagta tgtggctggt acggtacttg tacgagtgtg tttgtgtatt   1560
ctaaagatgg acattccaca tattcgctgg tcaaggtgtt ttgtttgagg attcagtgag   1620
gcatatttct tcactgggtg tgatggagtt gggtaaggtt ataggttttt accagaactt   1680
gtacttgtag aaatactgaa caactatatc accgtgataa agagtgcata agaaggtgcg   1740
ttgaacatga tgtttcggcg cgcaaaatcg agaatttcaa gttttttggt cggtacttgc   1800
gataagatga gtccaactaa aatgttagat tttcaatacc gctcaaattg cgtgtttatg   1860
agacttcttg aagccgtgat tctcccagct tctccgaact ctacaaggtt cataccgaga   1920
tttggtgatg agtggcaata ggagtgcagc ggttcattga gggcgaaata tcagaagaat   1980
gagaagatgt agttatttca acagtgcaca atgatattat atgctcacgg gactctgaaa   2040
agcctttgaa cgccatattt cagcccaatc acgtttaaac ctcgccgtcc ttaatttcgt   2100
aaaagctttt tttgcatcct cccacataaa actctctctc tctctcttct ttaactagga   2160
caccttttgg caacatcttg tcgtctaatc gaaaacatat ccacatccac aatgcttcga   2220
accgcctacc tggctaaggt gagtactccg ggcgagtcaa tggaggtgac tcaaggtgca   2280
atggaagcac cgctccatgg cacagcgatg cgcgctacat gaccgacgac atctgtgtac   2340
aacccataac attttctcgg aaacaacaac agcatcacag acagagactc ggggcagggg   2400
aagacgccat tgagaccaat ggctagtgta tgtcgcaact ccggcgccga ttgctccaca   2460
gtctcctact ttggtcctgt ccacgtcacc accacccccg gaacatctat gcgtgtattt   2520
attttccctc cactattttt tttcctgcat gtgctacgga gaaaaatagt agcgggcagt   2580
agcacactgt gtggggacag gggaatggag aacaattgag gcgatgcgga tacgaagaca   2640
cctgtttacg ttgttgtcgc acgccgctgc tgttgctggt gtgttttgtg ttaattgccg   2700
cacaccacaa taactatcat cgacaccaaa acattaggat aacatactaa cccaggccgc   2760
ctcggctctc cccaagcgaa ccctcgctac caacgctcga accatgttcc agcccaagga   2820
gtacggatcc aagtacaccg tcaccctcat ccccggtgat ggtatcggta acgagattac   2880
tgacgctgtc aagaccatct tcaagactat ctccgtcccc attgactggg aggttgtcaa   2940
tgtcaccggt gttggcgaga accatctcga cggctacgag gaggccattc gatccatcaa   3000
```

```
ccgaaacaag gttgccatca agggtatcct ccacaccccc gttgagaagc acggtcacac   3060
ttctttcaac gttgccctgc gacgagagct cgacattttt gcttctctcg ttctcatcaa   3120
gaacatcccc ggtgtccaga cccgactcga cggcattgac atggctctga tccgagagaa   3180
cactgagggt gagtactccg gtctggagca ctcccctgtc cccggtgttg ttgagtccat   3240
caaggtcatc accaagcgaa agtccgagcg aattgcccga tttgcctttg actttgctct   3300
caagaacaac cgacacaagg tcactgccat ccacaaggcc aacattatga agcttgccga   3360
tggtctgttc cgaaacacct gtaaggaggt ctccgccgag taccccgaga tccagtacgg   3420
cgacatgatt gtcgacaacg cctccatgca ggccgtctct tggccccagc agtttgacgt   3480
tctcgtcacc cctaaccttt acggaaccat tctgtctaac attggtgccg gtcttgttgg   3540
aggccccggt ctcgtccctg gtgtcaacct gggtaccgag cacgccgttt tcgagcccgg   3600
ttgccgacac gtcggtcttg ccgctaaggg ccgaggtacc gctaacccca ccgccatgat   3660
tctgtcttcc gccatgcttc tgcgacacct caacctcgat gacttcgctg acgtcatctc   3720
caaggctacc tacgacgttc ttgctgaggg ccaggtccga acccccgatc ttggcggcaa   3780
ctccactact gacgagttca ccatggctgt tatcaacaag ctccagtaag cggccgctta   3840
tgtatgattt agatgatatt atgacattga acgaattatt gatgagtagt gggtgtgatg   3900
gatttagtgt ggatgtacac ggttcttggc catataggcc aggccataac ttcgtatagc   3960
atacattata cgaagttata catgtgagca aaaggccagc aaaaggccag gaaccgtaaa   4020
aaggccgcgt tgctggcgtt tttccatagg ctccgccccc ctgacgagca tcacaaaaat   4080
cgacgctcaa gtcagaggtg gcgaaacccg acaggactat aaagatacca ggcgtttccc   4140
cctggaagct ccctcgtgcg ctctcctgtt ccgaccctgc cgcttaccgg atacctgtcc   4200
gcctttctcc cttcgggaag cgtggcgctt tctcatagct cacgctgtag gtatctcagt   4260
tcggtgtagg tcgttcgctc caagctgggc tgtgtgcacg aaccccccgt tcagcccgac   4320
cgctgcgcct tatccggtaa ctatcgtctt gagtccaacc cggtaagaca cgacttatcg   4380
ccactggcag cagccactgg taacaggatt agcagagcga ggtatgtagg cggtgctaca   4440
gagttcttga agtggtggcc taactacggc tacactagaa gaacagtatt tggtatctgc   4500
gctctgctga agccagttac cttcggaaaa agagttggta gctcttgatc cggcaaacaa   4560
accaccgctg gtagcggtgg tttttttgtt tgcaagcagc agattacgcg cagaaaaaaa   4620
ggatctcaag aagatccttt gatcttttct acggggtctg acgctcagtg gaacgaaaac   4680
tcacgttaag ggattttggt catgagatta tcaaaaagga tcttcaccta gatcctttta   4740
aattaaaaat gaagttttaa atcaatctaa agtatatatg agtaaacttg gtctgacagt   4800
taccaatgct taatcagtga ggcacctatc tcagcgatct gtctatttcg ttcatccata   4860
gttgcctgac tccccgtcgt gtagataact acgatacggg agggcttacc atctggcccc   4920
agtgctgcaa tgataccgcg agacccacgc tcaccggctc cagatttatc agcaataaac   4980
cagccagccg gaagggccga gcgcagaagt ggtcctgcaa ctttatccgc ctccatccag   5040
tctattaatt gttgccggga agctagagta agtagttcgc cagttaatag tttgcgcaac   5100
gttgttgcca ttgctacagg catcgtggtg tcacgctcgt cgtttggtat ggcttcattc   5160
agctccggtt cccaacgatc aaggcgagtt acatgatccc ccatgttgtg caaaaaagcg   5220
gttagctcct tcggtcctcc gatcgttgtc agaagtaagt tggccgcagt gttatcactc   5280
atggttatgg cagcactgca taattctctt actgtcatgc catccgtaag atgcttttct   5340
```

-continued

```
gtgactggtg agtactcaac caagtcattc tgagaatagt gtatgcggcg accgagttgc   5400

tcttgcccgg cgtcaatacg ggataatacc gcgccacata gcagaacttt aaaagtgctc   5460

atcattggaa aacgttcttc ggggcgaaaa ctctcaagga tcttaccgct gttgagatcc   5520

agttcgatgt aacccactcg tgcacccaac tgatcttcag catcttttac tttcaccagc   5580

gtttctgggt gagcaaaaac aggaaggcaa aatgccgcaa aaaagggaat aagggcgaca   5640

cggaaatgtt gaatactcat actcttcctt tttcaatatt attgaagcat ttatcagggt   5700

tattgtctca tgagcggata catatttgaa tgtatttaga aaaataaaca aataggggtt   5760

ccgcgcacat ttccccgaaa agtgccacct gacgtctaag aaaccattat tatcatgaca   5820

ttaacctata aaaataggcg tatcacgagg ccctttcgtc                         5860
```

<210> SEQ ID NO 2
<211> LENGTH: 1228
<212> TYPE: DNA
<213> ORGANISM: Artificial Sequence
<220> FEATURE:
<223> OTHER INFORMATION: IDH002 insert sequence

<400> SEQUENCE: 2

```
caattgaggc gatgcggata cgaagacacc tgtttacgtt gttgtcgcac gccgctgctg     60

ttgctggtgt gttttgtgtt aattgccgca caccacaata actatcatcg acaccaaaac    120

attaggataa catactaacc caggccgcct cggctctccc caagcgaacc ctcatggcca    180

ccaacgccag gacaatgttt cagcccaagg agtacggcag caagtatacc gtgacactga    240

tccctggcga cggcatcggc aatgagatca ccgatgccgt gaagaccatc ttcaagacaa    300

tcagcgtgcc catcgactgg gaggtggtga acgtgacagg cgtgggcgag aatcacctgg    360

atggctacga ggaggccatc cggtccatca acagaaataa ggtggccatc aagggcatcc    420

tgcacacccc tgtggagaag cacggccaca catcttttaa cgtggccctg cggagagagc    480

tggacatctt cgccagcctg gtgctgatca agaatatccc aggcgtgcag acccggctgg    540

acggaatcga tatggccctg atcagagaga acacagaggg cgagtattct ggcctggagc    600

acagccccgt gcctggcgtg gtggagagca tcaaagtgat caccaagagg aagtccgaga    660

ggatcgcccg cttcgccttt gacttcgccc tgaagaacaa tcgccacaag gtgaccgcca    720

tccacaaggc caacatcatg aagctggccg atggcctgtt tcggaataca tgcaaggagg    780

tgtctgccga gtaccccgag atccagtatg gcgacatgat cgtggataac gcctccatgc    840

aggccgtgtc ttggcctcag cagttcgatg tgctggtgac cccaaacctg tacggcacaa    900

tcctgtccaa tatcggagca ggactggtgg gaggcccagg cctggtgccc ggcgtgaatc    960

tgggcaccga gcacgccgtg tttgagccag gctgtaggca cgtgggactg gcagcaaagg   1020

gaaggggcac cgccaacccc acagccatga tcctgagcag cgccatgctg ctgcggcacc   1080

tgaatctgga cgattttgcc gacgtgatct ccaaggccac ctatgatgtg ctggccgagg   1140

gccaggtgag aacacctgac ctgggcggca actctaccac agatgagttc acaatggccg   1200

tgatcaacaa gctgcagtga gcggccgc                                      1228
```

<210> SEQ ID NO 3
<211> LENGTH: 1432
<212> TYPE: DNA
<213> ORGANISM: Artificial Sequence
<220> FEATURE:
<223> OTHER INFORMATION: IDH003 insert sequence

<400> SEQUENCE: 3

```
caattgaggc gatgcggata cgaagacacc tgtttacgtt gttgtcgcac gccgctgctg      60

ttgctggtgt gttttgtgtt aattgccgca caccacaata actatcatcg acaccaaaac     120

attaggataa catactaacc caggccgcct cggctctccc caagcgaacc ctcatggaga     180

gcaaggtggt ggtgccagcc cagggcaaga agatcaccct gcagaacggc aagctgaatg     240

tgccagagaa ccccatcatc ccttacatcg agggcgacgg catcggcgtg gatgtgacac     300

cagcaatgct gaaggtggtg gacgcagcag tggagaaggc ctataagggc gagaggaaga     360

tctcttggat ggagatctac accggcgaga agagcacaca ggtgtatgga caggacgtgt     420

ggctgcctgc agagaccctg gatctgatcc gggagtacag agtggccatc aagggaccac     480

tgaccacacc agtgggagga ggcatcaggt ctctgaatgt ggccctgcgc caggagctgg     540

atctgtatat ctgcctgagg cctgtgcgct actatcaggg cacccccagc cctgtgaagc     600

acccagagct gacagacatg gtcatcttcc gggagaactc cgaggacatc tacgccggca     660

tcgagtggaa ggccgactct gccgatgccg agaaagtgat caagttcctg cgggaggaga     720

tgggcgtgaa gaagatcaga tttcccgagc actgcggcat cggcatcaag ccttgtagcg     780

aggagggcac caagcggctg gtgagagcag ccatcgagta cgccatcgcc aatgacaggg     840

attccgtgac cctggtgcac aagggcaaca tcatgaagtt cacagagggc gcctttaagg     900

actggggcta tcagctggcc cgcgaggagt tcggaggaga gctgatcgat ggaggacctt     960

ggctgaaggt gaagaaccca aatacaggca aggagatcgt gatcaaggac gtgatcgccg    1020

atgcctttct gcagcagatc ctgctgaggc cagcagagta cgacgtgatc gcatgcatga    1080

acctgaatgg cgactatatc tccgatgcac tggcagcaca agtgggagga atcggaatcg    1140

cccctggcgc caatatcggc gacgagtgtg ccctgtttga ggccacccac ggcacagcac    1200

caaagtacgc aggacaggat aaggtgaacc ccggcagcat catcctgtcc gccgagatga    1260

tgctgaggca catgggatgg accgaggcag cagacctgat cgtgaagggc atggagggcg    1320

ccatcaatgc caagaccgtg acctacgact tcgagagact gatggatggc gccaagctgc    1380

tgaagtgttc tgagtttggc gatgccatca tcgagaacat gtgagcggcc gc            1432
```

<210> SEQ ID NO 4
<211> LENGTH: 1471
<212> TYPE: DNA
<213> ORGANISM: Artificial Sequence
<220> FEATURE:
<223> OTHER INFORMATION: IDH004 insert sequence

<400> SEQUENCE: 4

```
caattgaggc gatgcggata cgaagacacc tgtttacgtt gttgtcgcac gccgctgctg      60

ttgctggtgt gttttgtgtt aattgccgca caccacaata actatcatcg acaccaaaac     120

attaggataa catactaacc caggccgcct cggctctccc caagcgaacc ctcatgacca     180

cacacatcca gaagccagca accggctccc ctctgacact gctgaacggc gtgctgcagg     240

tgccagacca gcccatcatc cctttcatcg agggcgacgg aatcggatgc gatgtgaccc     300

ctgccatgcg ctctgtggtg gatgcagcag tggcaaaggt gtacggagga cagaggcaga     360

tcgcatggat ggagctgttt gcaggacaga aggcagtgca gctgtacgga gagggccagt     420

atctgccaga cgagacaatg gccgccatcc gggagtataa ggtggccatc aagggaccac     480

tggagacacc agtgggagga ggcatccgca gcctgaacgt ggccatgcgg caggacctgg     540

atctgtacgt gtgcctgcgg cccgtgagat atttcgaggg cacccccctcc cctatgagac    600
```

-continued

```
accctgagaa ggtggacatg gtcatcttcc gggagaacag cgaggacatc tacgcaggaa    660
tcgagtggcc tgcaggcagc ccagaggccg agaagatcat caggttcctg cgcgaggaga    720
tgggcgtgac aaagatcaga tttccagaca gctccgccat cggcatcaag cccgtgagca    780
ccgagggctc cgagaggctg atccggagaa caatccagta cgccctggag cacggcaagc    840
catccgtgtc tctggtgcac aagggcaaca tcatgaagtt caccgagggc ggctttcgcg    900
attggggata tgcactggca gagagggagt tcgcaggaag agtgtttaca tggaggcaga    960
aggccgccat cagcaaggca gagggcaagg cagcaggaca gaaggcagag cagcaggcca   1020
tcgccgacgg caagctgatc atcaaggacg tgatcgccga taatttcctg cagcagatcc   1080
tgctgcggcc agaggattac tccgtggtgg ccaccctgaa cctgaatggc gactacgtga   1140
gcgatgcact ggcagcagaa gtgggaggaa tcggaatggc cctggcgcc aacctgtctg   1200
acacacacgc catctttgag gccacccacg gcacagcacc tgacatcgca ggacagggca   1260
aggcaaatcc atctagcctg atcctgagcg ccgtgatgat gctggagcac ctgggatggg   1320
gagaggcagc acaggccatc gtggcagcaa tgaatgcaac catcgccgca ggagaggtga   1380
caggcgacct ggccgccctg agaggcgatg tgcctgccct gtccaccaca gagttcaccg   1440
ccgccctgat caggcgcttt tgagcggccg c                                  1471
```

<210> SEQ ID NO 5
<211> LENGTH: 2413
<212> TYPE: DNA
<213> ORGANISM: Artificial Sequence
<220> FEATURE:
<223> OTHER INFORMATION: IDH005 insert sequence

<400> SEQUENCE: 5

```
caattgaggc gatgcggata cgaagacacc tgtttacgtt gttgtcgcac gccgctgctg     60
ttgctggtgt gttttgtgtt aattgccgca caccacaata actatcatcg acaccaaaac    120
attaggataa catactaacc caggccgcct cggctctccc caagcgaacc ctcatgagcg    180
cccagcagcc caccatcatc tataccctga cagatgaggc cccactgctg gccacatacg    240
ccttcctgcc cgtggtgagg aagtttgccg aggccgccgg catcgatgtg aagaccagcg    300
acatctccgt ggccgccaga atcctggccg agttcggcga tcacctgacc gaggagcaga    360
gagtgcctga caacctggga gagctgggcg ccctgacaca ggacccatcc gccaacatca    420
tcaagctgcc taatatcagc gcctccgtgc cacagctgct ggcagccatc aaggagctgc    480
agggcaaggg ctataacgtg ccagattacc ccgccaatcc taagaccgac gatgagaaga    540
agatcaagga cagatacgcc aagatcctgg gctctgccgt gaaccctgtg ctgcgcgagg    600
gcaatagcga tcggagagcc ccaaaggccg tgaaggagta tgcaaggaag cacccacaca    660
gcatgggcga gtggtctcag gccagcagaa cccacgtggc caccatgaag acaggcgact    720
tctaccacgg cgagaagtct atgaccctgg accgcgatag gcgcgtgaag atggtgctga    780
agacaaagag cggcgaggag atcgtgctga agcccgaggt gaagctggac gccggcgaca    840
tcatcgacag catgtacatg tccaagaagg ccctgatcgc cttctatgag gagcagatcg    900
aggacgccta caagaccggc gtgatgtttt ccctgcacgt gaaggccaca atgatgaagg    960
tgtctcaccc tatcgtgttc ggccacgccg tgaaggtgtt ctacaaggat gcctttgcca   1020
agcacgagaa gctgtttgac gagctgggcg tgaacgtgaa caatggcctg agcgatctgt   1080
atgacaagat cgaggccctg ccagcatccc agagggagga gatcatcgag gatctgcaca   1140
agtgccacga gcacaggcca gagctggcta tggtggactc cgccaagggc atctctaatt   1200
```

tccactctcc tagcgatgtg atcgtggacg cctccatgcc agccatgatc aggctgggcg 1260
gcaagatgta tggcgccgat ggccgcacca aggacacaaa ggccgtgaac ccagagtcca 1320
ccttttctag gatgtaccag gagatgatca atttctgtaa gacccacggc cagtttgatc 1380
ccaccacaat gggcacagtg cctaacgtgg gcctgatggc ccagaaggcc gaggagtacg 1440
gctcccacga caagacattc gagatccccg aggatggcgt ggccgacatc gtggacatcg 1500
ataccggcga ggtgctgctg acacagaatg tggaggaggg cgacatctgg cggatgccaa 1560
tcgtgaagga tgcccccatc agagactggg tgaagctggc agtgaccagg gcccgcctgt 1620
ctggcatgcc cgtggtgttt tggctggaca cagagaggcc tcacgaggtg gagctgcgca 1680
agaaggtgaa ggagtatctg aaggaccacg ataccgaggg cctgaagatc cagatcatgc 1740
ctcaagtgtg ggccatgcgg tacacactgg agcgggtggt gagaggcaag gataccatcg 1800
ccgccacagg caacatcctg agagattatc tgaccgacct gttccccatc ctggagctgg 1860
gcacaagcgc caagatgctg tccatcgtgc ctctgatggc aggaggagga ctgtatgaga 1920
ccggagcagg aggcagcgcc ccaaagcacg tgcaccagct ggtggaggag aatcacctgc 1980
ggtgggatag cctgggagag tttctggccc tgggagcctc cctggaggac atgggcaaca 2040
agacaggcaa tgagaaggcc aaggtgctgg ccaaggccct ggataccgcc acaggcaagc 2100
tgctggagga gaacaagtcc ccttctcgga gaaccggcga gctggacaat aggggctctc 2160
agttctacct gagcctgttt tgggcacagg ccctggcaga gcagacagag gacgcagagc 2220
tggcagagcg gttcaagcca ctggcaaagg ccctggcaga gcaggaggag gccatcgtgt 2280
ctgagctgaa cagcgtgcag ggcaagaccg tggacatcgg cggctactat taccccgacc 2340
ctgagaagac ctccgaagtg atgagaccct ctaagacctt caacaccaca ctggagtccg 2400
tgtgagcggc cgc 2413

<210> SEQ ID NO 6
<211> LENGTH: 901
<212> TYPE: DNA
<213> ORGANISM: Artificial Sequence
<220> FEATURE:
<223> OTHER INFORMATION: IDH006 insert sequence

<400> SEQUENCE: 6
caattgaggc gatgcggata cgaagacacc tgtttacgtt gttgtcgcac gccgctgctg 60
ttgctggtgt gttttgtgtt aattgccgca caccacaata actatcatcg acaccaaaac 120
attaggataa catactaacc caggccgcct cggctctccc caagcgaacc ctcatggtga 180
gcaagcagat cctgaagaac accggcctgc aggagatcat gagcttcaag gtgaacctgg 240
agggcgtggt gaacaaccac gtgttcacca tggagggctg cggcaagggc aacatcctgt 300
tcggcaacca gctggtgcag atccgcgtga ccaagggcgc ccccctgccc ttcgccttcg 360
acatcctgag ccccgccttc cagtacggca accgcacctt caccaagtac cccgaggaca 420
tcagcgactt cttcatccag agcttccccg ccggcttcgt gtacgagcgc accctgcgct 480
acgaggacgg cggcctggtg gagatccgca gcgacatcaa cctgatcgag gagatgttcg 540
tgtaccgcgt ggagtacaag ggccgcaact tccccaacga cggccccgtg atgaagaaga 600
ccatcaccgg cctgcagccc agcttcgagg tggtgtacat gaacgacggc gtgctggtgg 660
gccaggtgat cctggtgtac cgcctgaaca gcggcaagtt ctacagctgc cacatgcgca 720
ccctgatgaa gagcaagggc gtggtgaagg acttccccga gtaccacttc atccagcacc 780

-continued gcctggagaa gacctacgtg gaggacggcg gcttcgtgga gcagcacgag accgccatcg 840
cccagctgac cagcctgggc aagcccctgg gcagcctgca cgagtgggtg taagcggccg 900
c 901

<210> SEQ ID NO 7
<211> LENGTH: 6774
<212> TYPE: DNA
<213> ORGANISM: Artificial Sequence
<220> FEATURE:
<223> OTHER INFORMATION: IDH007 plasmid sequence

<400> SEQUENCE: 7
tcgcgcgttt cggtgatgac ggtgaaaacc tctgacacat gcagctcccg gagcccagag 60
agccattgac gttctttcta atttggaccg atagccgtat agtccagtct atctataagt 120
tcaactaact cgtaactatt accataacat atacttcact gccccagata aggttccgat 180
aaaaagttct gcagactaaa tttatttcag tctcctcttc accaccaaaa tgccctccta 240
cgaagctcga gctaacgtcc acaagtccgc ctttgccgct cgagtgctca agctcgtggc 300
agccaagaaa accaacctgt gtgcttctct ggatgttacc accaccaagg agctcattga 360
gcttgccgat aaggtcggac cttatgtgtg catgatcaag acccatatcg acatcattga 420
cgacttcacc tacgccggca ctgtgctccc cctcaaggaa cttgctctta agcacggttt 480
cttcctgttc gaggacagaa agttcgcaga tattggcaac actgtcaagc accagtacaa 540
gaacggtgtc taccgaatcg ccgagtggtc cgatatcacc aacgcccacg gtgtacccgg 600
aaccggaatc attgctggcc tgcgagctgg tgccgaggaa actgtctctg aacagaagaa 660
ggaggacgtc tctgactacg agaactccca gtacaaggag ttcctggtcc cctctcccaa 720
cgagaagctg gccagaggtc tgctcatgct ggccgagctg tcttgcaagg gctctctggc 780
cactggcgag tactccaagc agaccattga gcttgcccga tccgaccccg agtttgtggt 840
tggcttcatt gcccagaacc gacctaaggg cgactctgag gactggctta ttctgacccc 900
cggggtgggt cttgacgaca agggagacgc tctcggacag cagtaccgaa ctgttgagga 960
tgtcatgtct accggaacgg atatcataat tgtcggccga ggtctgtacg gccagaaccg 1020
agatcctatt gaggaggcca agcgatacca gaaggctggc tgggaggctt accagaagat 1080
taactgttag aggttagact atggatatgt aatttaactg tgtatataga gagcgtgcaa 1140
gtatggagcg cttgttcagc ttgtatgatg gtcagacgac ctgtctgatc gagtatgtat 1200
gatactgcac aacctgtgta tccgcatatc ttccaatggg gcatgttgtt gtgttcataa 1260
cttcgtatag catacattat acgaagttat ggccagacag gccaaacctg cagggctgag 1320
cacgcgagta cacccccctca agtacagtag ctatatattg ggtatgtac tgtacatact 1380 gtacagacat acagatagat agatacaagt acaaacccaa gtacaagtac cggtactcta 1440
cacgcctcgt actcgaatgc tcatcacgga gtggttaaac tcatgctcac taatcagagg 1500
ccgatctcga tgccccttca tacaccacca ataactcaat gagctaaaaa atgcggcatt 1560
ttttcatttc ttcaaattac ttgccacaag cacttacatt ttttctttcc ccgattctct 1620
gatgtgcaca tcgctactgt tttttcttat tggctcgtat ttcgatcagt cgatttatgg 1680
gttgcctaaa cgaagctaat acccgtaaca cactacaagg aactaacaca agattgttat 1740
aattatatat atactccagt agaaagccac gatatgataa gatagcgcag aagccactgg 1800
atgttaaagg tgctgccgta tacatgattc tctgcctcgc ttaagcggtc agtccagtat 1860
tacgtatgtg cagcacttcc gcgctgtagg gtaattaaca cacgaccatc gtcacctcgc 1920

-continued

```
tcataataat ggtttgtcca caagagcaat atatcgccta tacacccaac gagaaaacgg   1980
ttcaacacgc acactaattg tattaacgcg ccccagacct gtcagtgttc cctagacacc   2040
acacaaaacc aaaccgccga cgaaaactac cgctcttatc atgaatatca taacttataa   2100
tatgtaaggt cagaatgagt tgttgtgtgc catacatttc tctgaccgaa ttaatggatg   2160
ccagactcac gtcgtccttc cacgggtaaa aacgtcatgc caaaaccatg cccttcattt   2220
cagttcctcc ttggtcaatc tccttagttg tacgacagat cgtttaaact cgccacctgt   2280
ccacgtctcg gaacacgccc ctacaaactt gtagggtttg tgcggctcgg gatctcgtgc   2340
tctagtctcg gtggcggatc aagtgcagat catcttatga agcggaggaa gtgggtgaga   2400
ataaaggatg taaatagttt catattgaga gatatttgat atttcaccgg gagaagttgt   2460
agaaataatt ctagtctaaa tttgagtata ttgatccatt gatagtcctc aaaacacact   2520
atcaatcatc caggtatgct gatgacttat cctcccgacg atcttagttt ctgtttttca   2580
cgtttcaccc caacaacctt agacaccaac ggctgcatgt gtgacgctag gtgggtttgc   2640
aacgtgtgga gaaatgtggt acgattcagc gggtttatca ggcgattaat gctatcatat   2700
gtaggatggg tggcaaaagt atgtggcatt tcattcacat gtttgcacgt gacgtttcca   2760
gctctgtcgc gagctgcagg tacaacatta gcgtctgctg ttctgacgtc tgtcttatta   2820
attagtgggg tggtaaccac atgctacata ttggtctatt agtagcacga tcacgtgtct   2880
accgttgcca ccggtttcag tgtaatatat accctcttac aagtactcta caattgctct   2940
ctaacatctg tcgtatttct gttattattc tcggaaatgc aacggcatta ttatcaactc   3000
ccccccagat tgcatacaga gccaagaagt gcatgatagg cgttggggga ggattgcgat   3060
ggggcggaga gcgtgataat aggcctgaca aaataaattt ctttgtctca tctactgtac   3120
ttcagaaaaa atagactgta tgcatgggct catcctcttg acgtgtcctt ctcaccacac   3180
gtcgcttcgc ttaattaaga gaccgggttg gcggcgcatt tgtgtcccaa aaaacagccc   3240
caattgcccc aattgacccc aaattgaccc agtagcgggc ccaaccccgg cgagagcccc   3300
cttctcccca catatcaaac ctcccccggt tcccacactt gccgttaagg gcgtagggta   3360
ctgcagtctg gaatctacgc ttgttcagac tttgtactag tttctttgtc tggccatccg   3420
ggtaacccat gccggacgca aaatagacta ctgaaaattt ttttgctttg tggttgggac   3480
tttagccaag ggtataaaag accaccgtcc ccgaattacc tttcctcttc ttttctctct   3540
ctccttgtca actcacaccc gaaatcgtta agcatttcct tctgagtata agaatcattc   3600
aaaatgcttc gaaccgccta cctggctaag gccgcctcgg ctctccccaa gcgaaccctc   3660
gctaccaacg ctcgaaccat gttccagccc aaggagtacg gatccaagta caccgtcacc   3720
ctcatccccg gtgatggtat cggtaacgag attactgacg ctgtcaagac catcttcaag   3780
actatctccg tccccattga ctgggaggtt gtcaatgtca ccggtgttgg cgagaaccat   3840
ctcgacggct acgaggaggc cattcgatcc atcaaccgaa acaaggttgc catcaagggt   3900
atcctccaca cccccgttga gaagcacggt cacacttctt tcaacgttgc cctgcgacga   3960
gagctcgaca tttttgcttc tctcgttctc atcaagaaca tccccggtgt ccagacccga   4020
ctcgacggca ttgacatggc tctgatccga gagaacactg agggtgagta ctccggtctg   4080
gagcactccc ctgtccccgg tgttgttgag tccatcaagg tcatcaccaa gcgaaagtcc   4140
gagcgaattg cccgatttgc ctttgacttt gctctcaaga acaaccgaca caaggtcact   4200
gccatccaca aggccaacat tatgaagctt gccgatggtc tgttccgaaa cacctgtaag   4260
```

-continued

```
gaggtctccg ccgagtaccc cgagatccag tacggcgaca tgattgtcga caacgcctcc   4320
atgcaggccg tctcttggcc ccagcagttt gacgttctcg tcacccctaa cctttacgga   4380
accattctgt ctaacattgg tgccggtctt gttggaggcc ccggtctcgt ccctggtgtc   4440
aacctgggta ccgagcacgc cgttttcgag cccggttgcc gacacgtcgg tcttgccgct   4500
aagggccgag gtaccgctaa ccccaccgcc atgattctgt cttccgccat gcttctgcga   4560
cacctcaacc tcgatgactt cgctgacgtc atctccaagg ctacctacga cgttcttgct   4620
gagggccagg tccgaacccc cgatcttggc ggcaactcca ctactgacga gttcaccatg   4680
gctgttatca acaagctcca gtaagcggcc gcaaattaac agatagtttg ccggtgataa   4740
ttctcttaac ctcccacact cctttgacat aacgatttat gtaacgaaac tgaaatttga   4800
ccagatattg ttgtaaatag aaaatctggc ttgtaggtgg caaaatcccg tctttgttca   4860
taacttcgta tagcatacat tatacgaagt tatacatgtg agcaaaaggc cagcaaaagg   4920
ccaggaaccg taaaaaggcc gcgttgctgg cgtttttcca taggctccgc ccccctgacg   4980
agcatcacaa aaatcgacgc tcaagtcaga ggtggcgaaa cccgacagga ctataaagat   5040
accaggcgtt tccccctgga agctccctcg tgcgctctcc tgttccgacc ctgccgctta   5100
ccggatacct gtccgccttt ctcccttcgg gaagcgtggc gctttctcat agctcacgct   5160
gtaggtatct cagttcggtg taggtcgttc gctccaagct gggctgtgtg cacgaacccc   5220
ccgttcagcc cgaccgctgc gccttatccg gtaactatcg tcttgagtcc aacccggtaa   5280
gacacgactt atcgccactg gcagcagcca ctggtaacag gattagcaga gcgaggtatg   5340
taggcggtgc tacagagttc ttgaagtggt ggcctaacta cggctacact agaagaacag   5400
tatttggtat ctgcgctctg ctgaagccag ttaccttcgg aaaaagagtt ggtagctctt   5460
gatccggcaa acaaaccacc gctggtagcg gtggtttttt tgtttgcaag cagcagatta   5520
cgcgcagaaa aaaaggatct caagaagatc ctttgatctt ttctacgggg tctgacgctc   5580
agtggaacga aaactcacgt taagggattt tggtcatgag attatcaaaa aggatcttca   5640
cctagatcct tttaaattaa aaatgaagtt ttaaatcaat ctaaagtata tatgagtaaa   5700
cttggtctga cagttaccaa tgcttaatca gtgaggcacc tatctcagcg atctgtctat   5760
ttcgttcatc catagttgcc tgactccccg tcgtgtagat aactacgata cgggagggct   5820
taccatctgg ccccagtgct gcaatgatac cgcgagaccc acgctcaccg gctccagatt   5880
tatcagcaat aaaccagcca gccggaaggg ccgagcgcag aagtggtcct gcaactttat   5940
ccgcctccat ccagtctatt aattgttgcc gggaagctag agtaagtagt tcgccagtta   6000
atagtttgcg caacgttgtt gccattgcta caggcatcgt ggtgtcacgc tcgtcgtttg   6060
gtatggcttc attcagctcc ggttcccaac gatcaaggcg agttacatga tcccccatgt   6120
tgtgcaaaaa agcggttagc tccttcggtc ctccgatcgt tgtcagaagt aagttggccg   6180
cagtgttatc actcatggtt atggcagcac tgcataattc tcttactgtc atgccatccg   6240
taagatgctt ttctgtgact ggtgagtact caaccaagtc attctgagaa tagtgtatgc   6300
ggcgaccgag ttgctcttgc ccggcgtcaa tacgggataa taccgcgcca catagcagaa   6360
ctttaaaagt gctcatcatt ggaaaacgtt cttcggggcg aaaactctca aggatcttac   6420
cgctgttgag atccagttcg atgtaaccca ctcgtgcacc caactgatct tcagcatctt   6480
ttactttcac cagcgtttct gggtgagcaa aaacaggaag gcaaaatgcc gcaaaaaagg   6540
gaataagggc gacacggaaa tgttgaatac tcatactctt cctttttcaa tattattgaa   6600
gcatttatca gggttattgt ctcatgagcg gatacatatt tgaatgtatt tagaaaaata   6660
```

-continued aacaaatagg ggttccgcgc acatttcccc gaaaagtgcc acctgacgtc taagaaacca 6720
ttattatcat gacattaacc tataaaaata ggcgtatcac gaggcccttt cgtc 6774

<210> SEQ ID NO 8
<211> LENGTH: 1467
<212> TYPE: DNA
<213> ORGANISM: Artificial Sequence
<220> FEATURE:
<223> OTHER INFORMATION: IDH008 insert sequence

<400> SEQUENCE: 8
actagtttct ttgtctggcc atccgggtaa cccatgccgg acgcaaaata gactactgaa 60 aattttttg ctttgtggtt gggactttag ccaagggtat aaaagaccac cgtccccgaa 120
ttacctttcc tcttcttttc tctctctcct tgtcaactca cacccgaaat cgttaagcat 180
ttccttctga gtataagaat cattcaaaat ggagagcaag gtggtggtgc cagcccaggg 240
caagaagatc accctgcaga acggcaagct gaatgtgcca gagaacccca tcatccctta 300
catcgagggc gacggcatcg gcgtggatgt gacaccagca atgctgaagg tggtggacgc 360
agcagtggag aaggcctata agggcgagag gaagatctct tggatggaga tctacaccgg 420
cgagaagagc acacaggtgt atggacagga cgtgtggctg cctgcagaga ccctggatct 480
gatccgggag tacagagtgg ccatcaaggg accactgacc acaccagtgg gaggaggcat 540
caggtctctg aatgtggccc tgcgccagga gctggatctg tatatctgcc tgaggcctgt 600
gcgctactat cagggcaccc ccagccctgt gaagcaccca gagctgacag acatggtcat 660
cttccgggag aactccgagg acatctacgc cggcatcgag tggaaggccg actctgccga 720
tgccgagaaa gtgatcaagt tcctgcggga ggagatgggc gtgaagaaga tcagatttcc 780
cgagcactgc ggcatcggca tcaagccttg tagcgaggag ggcaccaagc ggctggtgag 840
agcagccatc gagtacgcca tcgccaatga cagggattcc gtgaccctgg tgcacaaggg 900
caacatcatg aagttcacag agggcgcctt taaggactgg ggctatcagc tggcccgcga 960
ggagttcgga ggagagctga tcgatggagg accttggctg aaggtgaaga acccaaatac 1020
aggcaaggag atcgtgatca aggacgtgat cgccgatgcc tttctgcagc agatcctgct 1080
gaggccagca gagtacgacg tgatcgcatg catgaacctg aatggcgact atatctccga 1140
tgcactggca gcacaagtgg gaggaatcgg aatcgcccct ggcgccaata tcggcgacga 1200
gtgtgccctg tttgaggcca cccacggcac agcaccaaag tacgcaggac aggataaggt 1260
gaaccccggc agcatcatcc tgtccgccga gatgatgctg aggcacatgg gatggaccga 1320
ggcagcagac ctgatcgtga agggcatgga gggcgccatc aatgccaaga ccgtgaccta 1380
cgacttcgag agactgatgg atggcgccaa gctgctgaag tgttctgagt ttggcgatgc 1440
catcatcgag aacatgtgag cggccgc 1467

<210> SEQ ID NO 9
<211> LENGTH: 1521
<212> TYPE: DNA
<213> ORGANISM: Artificial Sequence
<220> FEATURE:
<223> OTHER INFORMATION: IDH009 insert sequence

<400> SEQUENCE: 9
actagtttct ttgtctggcc atccgggtaa cccatgccgg acgcaaaata gactactgaa 60 aattttttg ctttgtggtt gggactttag ccaagggtat aaaagaccac cgtccccgaa 120

```
ttacctttcc tcttcttttc tctctctcct tgtcaactca cacccgaaat cgttaagcat    180

ttccttctga gtataagaat cattcaaaat gctgaggacc gcatacctgg caaaggcagc    240

atctgccctg cctaagcgca cactggagag caaggtggtg gtgccagccc agggcaagaa    300

gatcaccctg cagaacggca agctgaatgt gccagagaac cccatcatcc cttacatcga    360

gggcgacggc atcggcgtgg atgtgacacc tgccatgctg aaggtggtgg acgccgccgt    420

ggagaaggcc tataagggcg agcggaagat ctcctggatg gagatctaca ccggcgagaa    480

gtctacacag gtgtatggac aggacgtgtg gctgccagca gagaccctgg atctgatccg    540

ggagtacaga gtggccatca agggaccact gaccacacca gtgggaggag gcatcaggtc    600

cctgaatgtg gccctgcgcc aggagctgga tctgtatatc tgcctgaggc ccgtgcgcta    660

ctatcagggc accccctctc ctgtgaagca ccctgagctg acagacatgg tcatcttccg    720

ggagaacagc gaggacatct acgcaggaat cgagtggaag gcagactccg ccgatgccga    780

gaaagtgatc aagttcctgc gggaggagat gggcgtgaag aagatcagat ttcccgagca    840

ctgcggcatc ggcatcaagc cttgttctga ggagggcacc aagcggctgg tgagagcagc    900

catcgagtac gccatcgcca atgaccggga tagcgtgacc ctggtgcaca agggcaacat    960

catgaagttc acagagggcg cctttaagga ctggggctat cagctggcca gagaggagtt   1020

cggaggagag ctgatcgatg gaggaccttg gctgaaggtg aagaacccaa atacaggcaa   1080

ggagatcgtg atcaaggacg tgatcgccga tgcctttctg cagcagatcc tgctgcggcc   1140

agccgagtac gacgtgatcg cctgcatgaa cctgaatggc gactatatca gcgatgcact   1200

ggcagcacaa gtgggaggaa tcggaatcgc ccctggcgcc aatatcggcg acgagtgtgc   1260

cctgtttgag gccacccacg gcacagcacc aaagtacgca ggacaggata aggtgaaccc   1320

cggcagcatc atcctgtccg ccgagatgat gctgaggcac atgggatgga ccgaggcagc   1380

agacctgatc gtgaagggca tggagggcgc catcaatgcc aagaccgtga cctacgactt   1440

cgagcgcctg atggatggcg ccaagctgct gaagtgttcc gagtttggcg atgccatcat   1500

cgagaacatg tgagcggccg c                                             1521
```

<210> SEQ ID NO 10
<211> LENGTH: 1506
<212> TYPE: DNA
<213> ORGANISM: Artificial Sequence
<220> FEATURE:
<223> OTHER INFORMATION: IDH010 insert sequence

<400> SEQUENCE: 10

```
actagtttct ttgtctggcc atccgggtaa cccatgccgg acgcaaaata gactactgaa     60

aatttttttg ctttgtggtt gggactttag ccaagggtat aaaagaccac cgtccccgaa    120

ttacctttcc tcttcttttc tctctctcct tgtcaactca cacccgaaat cgttaagcat    180

ttccttctga gtataagaat cattcaaaat gaccacacac atccagaagc cagcaaccgg    240

ctcccctctg acactgctga acggcgtgct gcaggtgcca gaccagccca tcatcccttt    300

catcgagggc gacggaatcg gatgcgatgt gacccctgcc atgcgctctg tggtggatgc    360

agcagtggca aaggtgtacg gaggacagag gcagatcgca tggatggagc tgtttgcagg    420

acagaaggca gtgcagctgt acggagaggg ccagtatctg ccagacgaga caatggccgc    480

catccgggag tataaggtgg ccatcaaggg accactggag acaccagtgg gaggaggcat    540

ccgcagcctg aacgtggcca tgcggcagga cctggatctg tacgtgtgcc tgcggcccgt    600

gagatatttc gagggcaccc cctcccctat gagacaccct gagaaggtgg acatggtcat    660
```

cttccgggag aacagcgagg acatctacgc aggaatcgag tggcctgcag gcagcccaga 720
ggccgagaag atcatcaggt tcctgcgcga ggagatgggc gtgacaaaga tcagatttcc 780
agacagctcc gccatcggca tcaagcccgt gagcaccgag ggctccgaga ggctgatccg 840
gagaacaatc cagtacgccc tggagcacgg caagccatcc gtgtctctgg tgcacaaggg 900
caacatcatg aagttcaccg agggcggctt tcgcgattgg ggatatgcac tggcagagag 960
ggagttcgca ggaagagtgt ttacatggag gcagaaggcc gccatcagca aggcagaggg 1020
caaggcagca ggacagaagg cagagcagca ggcaatcgca gacggcaagc tgatcatcaa 1080
ggacgtgatc gccgataatt tcctgcagca gatcctgctg cggccagagg attactccgt 1140
ggtggccacc ctgaacctga atggcgacta cgtgagcgat gcactggcag cagaagtggg 1200
aggaatcgga atggcccctg gcgccaacct gtctgacaca cacgccatct ttgaggccac 1260
ccacggcaca gcacctgaca tcgcaggaca gggcaaggca aatccatcta gcctgatcct 1320
gagcgccgtg atgatgctgg agcacctggg atggggagag gcagcacagg ccatcgtggc 1380
agcaatgaat gcaaccatcg cagcaggaga ggtgacaggc gacctggccg ccctgagagg 1440
cgatgtgcct gccctgtcca ccacagagtt caccgccgcc ctgatcaggc gcttttgagc 1500
ggccgc 1506

<210> SEQ ID NO 11
<211> LENGTH: 1560
<212> TYPE: DNA
<213> ORGANISM: Artificial Sequence
<220> FEATURE:
<223> OTHER INFORMATION: IDH011 insert sequence

<400> SEQUENCE: 11
actagtttct ttgtctggcc atccgggtaa cccatgccgg acgcaaaata gactactgaa 60 aattttttg ctttgtggtt gggactttag ccaagggtat aaaagaccac cgtccccgaa 120
ttacctttcc tcttcttttc tctctctcct tgtcaactca cacccgaaat cgttaagcat 180
ttccttctga gtataagaat cattcaaaat gctgcgcacc gcatacctgg caaaggcagc 240
aagcgccctg cccaagcgga cactgaccac acacatccag aagccagcaa ccggctcccc 300
tctgacactg ctgaacggcg tgctgcaggt gccagaccag cccatcatcc ctttcatcga 360
gggcgacgga atcggatgcg atgtgacccc tgccatgaga agcgtggtgg atgcagcagt 420
ggcaaaggtg tacggaggac agaggcagat cgcctggatg gagctgtttg caggacagaa 480
ggcagtgcag ctgtacggag agggccagta tctgccagac gagacaatgg ccgccatccg 540
cgagtataag gtggccatca agggaccact ggagacacca gtgggaggag gcatccgctc 600
tctgaacgtg gccatgcggc aggacctgga tctgtacgtg tgcctgcggc ccgtgagata 660
tttcgagggc acccccagcc ctatgagaca ccctgagaag gtggacatgg tcatcttccg 720
ggagaacagc gaggacatct acgcaggaat cgagtggcct gcaggcagcc cagaggccga 780
gaagatcatc aggttcctgc gcgaggagat gggcgtgaca aagatccgct ttccagacag 840
ctccgccatc ggcatcaagc ccgtgagcac cgagggctcc gagcggctga tccggagaac 900
aatccagtac gccctggagc acggcaagcc atccgtgtct ctggtgcaca agggcaacat 960
catgaagttc accgagggcg gctttagaga ttggggctat gcactggcag agagggagtt 1020
cgcaggaaga gtgtttacat ggaggcagaa ggccgccatc agcaaggcag agggcaaggc 1080
agcaggacag aaggcagagc agcaggcaat cgcagacggc aagctgatca tcaaggacgt 1140

-continued

```
gatcgccgat aatttcctgc agcagatcct gctgaggcca gaggattact ccgtggtggc   1200

caccctgaac ctgaatggcg actacgtgag cgatgcactg gcagcagaag tgggaggaat   1260

cggaatggcc cctggcgcaa acctgtccga cacacacgcc atctttgagg ccacccacgg   1320

cacagcacct gacatcgcag gacagggcaa ggcaaatcca tctagcctga tcctgtctgc   1380

cgtgatgatg ctggagcacc tgggatgggg agaggcagca caggccatcg tggcagcaat   1440

gaatgcaacc atcgcagcag gagaggtgac aggcgacctg gccgccctga ggggcgatgt   1500

gcctgccctg tccaccacag agttcaccgc cgccctgatc aggcgctttt gagcggccgc   1560
```

<210> SEQ ID NO 12
<211> LENGTH: 2448
<212> TYPE: DNA
<213> ORGANISM: Artificial Sequence
<220> FEATURE:
<223> OTHER INFORMATION: IDH012 insert sequence

<400> SEQUENCE: 12

```
actagtttct ttgtctggcc atccgggtaa cccatgccgg acgcaaaata gactactgaa     60

aattttttg ctttgtggtt gggactttag ccaagggtat aaaagaccac cgtccccgaa    120

ttacctttcc tcttcttttc tctctctcct tgtcaactca cacccgaaat cgttaagcat    180

ttccttctga gtataagaat cattcaaaat gagcgcccag cagcccacca tcatctatac    240

cctgacagat gaggccccac tgctggccac atacgccttc ctgcccgtgg tgaggaagtt    300

tgccgaggcc gccggcatcg atgtgaagac cagcgacatc tccgtggccg ccagaatcct    360

ggccgagttc ggcgatcacc tgaccgagga gcagagagtg cctgacaacc tgggagagct    420

gggcgccctg acacaggacc catccgccaa catcatcaag ctgcctaata tcagcgcctc    480

cgtgccacag ctgctggcag ccatcaagga gctgcagggc aagggctata acgtgccaga    540

ttaccccgcc aatcctaaga ccgacgatga gaagaagatc aaggacagat acgccaagat    600

cctgggctct gccgtgaacc ctgtgctgcg cgagggcaat agcgatcgga gagccccaaa    660

ggccgtgaag gagtatgcaa ggaagcaccc acacagcatg ggcgagtggt ctcaggccag    720

cagaacccac gtggccacca tgaagacagg cgacttctac cacggcgaga agtctatgac    780

cctggaccgc gataggcgcg tgaagatggt gctgaagaca aagagcggcg aggagatcgt    840

gctgaagccc gaggtgaagc tggacgccgg cgacatcatc gacagcatgt acatgtccaa    900

gaaggccctg atcgccttct atgaggagca gatcgaggac gcctacaaga ccggcgtgat    960

gttttccctg cacgtgaagg ccacaatgat gaaggtgtct caccctatcg tgttcggcca   1020

cgccgtgaag gtgttctaca aggatgcctt tgccaagcac gagaagctgt ttgacgagct   1080

gggcgtgaac gtgaacaatg gcctgagcga tctgtatgac aagatcgagg ccctgccagc   1140

atcccagagg gaggagatca tcgaggatct gcacaagtgc cacgagcaca ggccagagct   1200

ggctatggtg gactccgcca agggcatctc taatttccac tctcctagcg atgtgatcgt   1260

ggacgcctcc atgccagcca tgatcaggct gggcggcaag atgtatggcg ccgatggccg   1320

caccaaggac acaaaggccg tgaacccaga gtccaccttt tctaggatgt accaggagat   1380

gatcaatttc tgtaagaccc acggccagtt tgatcccacc acaatgggca cagtgcctaa   1440

cgtgggcctg atggcccaga aggccgagga gtacggctcc cacgacaaga cattcgagat   1500

ccccgaggat ggcgtggccg acatcgtgga catcgatacc ggcgaggtgc tgctgacaca   1560

gaatgtggag gagggcgaca tctggcggat gccaatcgtg aaggatgccc ccatcagaga   1620

ctgggtgaag ctggcagtga ccagggcccg cctgtctggc atgcccgtgg tgttttggct   1680
```

```
ggacacagag aggcctcacg aggtggagct gcgcaagaag gtgaaggagt atctgaagga   1740
ccacgatacc gagggcctga agatccagat catgcctcaa gtgtgggcca tgcggtacac   1800
actggagcgg gtggtgagag gcaaggatac catcgccgcc acaggcaaca tcctgagaga   1860
ttatctgacc gacctgttcc ccatcctgga gctgggcaca agcgccaaga tgctgtccat   1920
cgtgcctctg atggcaggag gaggactgta tgagaccgga gcaggaggca gcgccccaaa   1980
gcacgtgcac cagctggtgg aggagaatca cctgcggtgg gatagcctgg gagagtttct   2040
ggccctggga gcctccctgg aggacatggg caacaagaca ggcaatgaga aggccaaggt   2100
gctggccaag gccctggata ccgccacagg caagctgctg gaggagaaca agtccccttc   2160
tcggagaacc ggcgagctgg acaatagggg ctctcagttc tacctgagcc tgttttgggc   2220
acaggccctg gcagagcaga cagaggacgc agagctggca gagcggttca agccactggc   2280
aaaggccctg gcagagcagg aggaggcaat cgtgtctgag ctgaacagcg tgcagggcaa   2340
gaccgtggac atcggcggct actattaccc cgaccctgag aagacctccg aagtgatgag   2400
accctctaag accttcaaca ccacactgga gtccgtgtga gcggccgc                2448
```

<210> SEQ ID NO 13
<211> LENGTH: 2502
<212> TYPE: DNA
<213> ORGANISM: Artificial Sequence
<220> FEATURE:
<223> OTHER INFORMATION: IDH013 insert sequence

<400> SEQUENCE: 13

```
actagtttct ttgtctggcc atccgggtaa cccatgccgg acgcaaaata gactactgaa     60
aatttttttg ctttgtggtt gggactttag ccaagggtat aaaagaccac cgtccccgaa    120
ttacctttcc tcttcttttc tctctctcct tgtcaactca cacccgaaat cgttaagcat    180
ttccttctga gtataagaat cattcaaaat gctgcggacc gcatacctgg caaaggcagc    240
aagcgccctg ccaaagagaa ccctgtccgc ccagcagccc acaatcatct ataccctgac    300
agatgaggcc cctctgctgg ccacctacgc cttcctgcca gtggtgcgga agtttgcaga    360
ggcagcagga atcgatgtga agacaagcga catctccgtg gccgccagaa tcctggccga    420
gttcggcgat cacctgaccg aggagcagcg cgtgcccgac aacctgggag agctgggcgc    480
cctgacacag gacccttctg ccaacatcat caagctgcct aatatcagcg cctccgtgcc    540
acagctgctg gcagccatca aggagctgca gggcaagggc tataacgtgc cagattaccc    600
cgccaatcct aagaccgacg atgagaagaa gatcaaggac cggtacgcca agatcctggg    660
ctccgccgtg aaccccgtgc tgagagaggg caattctgat cggagagccc ctaaggccgt    720
gaaggagtat gccaggaagc acccacacag catgggcgag tggtctcagg ccagccgcac    780
ccacgtggca accatgaaga caggcgactt ctaccacggc gagaagtcca tgaccctgga    840
cagagatagg cgcgtgaaga tggtgctgaa gacaaagtct ggcgaggaga tcgtgctgaa    900
gccagaggtg aagctggacg ccggcgacat catcgacagc atgtatatgt ccaagaaggc    960
cctgatcgcc ttctatgagg agcagatcga ggacgcctac aagaccggcg tgatgtttag   1020
cctgcacgtg aaggccacaa tgatgaaggt gtcccacccc atcgtgttcg gccacgccgt   1080
gaaggtgttc tacaaggatg cctttgccaa gcacgagaag ctgtttgacg agctgggcgt   1140
gaacgtgaac aatggcctgt ctgatctgta tgacaagatc gaggccctgc ctgcaagcca   1200
gagggaggag atcatcgagg atctgcacaa gtgccacgag cacagaccag agctggctat   1260
```

-continued

```
ggtggactcc gccaagggca tctctaattt ccactctccc agcgatgtga tcgtggacgc   1320
cagcatgcct gccatgatca ggctgggcgg caagatgtat ggcgccgatg gccgcaccaa   1380
ggacacaaag gccgtgaacc ctgagtccac cttttctcgg atgtaccagg agatgatcaa   1440
tttctgtaag acccacggcc agtttgatcc caccacaatg ggcacagtgc ctaacgtggg   1500
cctgatggcc cagaaggccg aggagtacgg cagccacgac aagacattcg agatcccaga   1560
ggatggcgtg gccgacatcg tggacatcga taccggcgag gtgctgctga cacagaatgt   1620
ggaggagggc gacatctggc ggatgccaat cgtgaaggat gcccccatca gagactgggt   1680
gaagctggca gtgaccaggg cccgcctgtc cggcatgcca gtggtgtttt ggctggacac   1740
agagaggccc cacgaggtgg agctgcgcaa gaaggtgaag gagtatctga aggaccacga   1800
taccgagggc ctgaagatcc agatcatgcc ccaagtgtgg gccatgaggt acacactgga   1860
gcgggtggtg agaggcaagg ataccatcgc cgccacaggc aacatcctgc gcgattatct   1920
gaccgacctg ttcccaatcc tggagctggg cacaagcgcc aagatgctgt ccatcgtgcc   1980
actgatggca ggaggaggac tgtatgagac cggagcagga ggcagcgccc ctaagcacgt   2040
gcaccagctg gtggaggaga atcacctgag atgggattct ctgggagagt ttctggccct   2100
gggagccagc ctggaggaca tggcaacaa gacaggcaat gagaaggcca aggtgctggc   2160
caaggccctg gataccgcca caggcaagct gctggaggag aacaagtccc cctctcggag   2220
aaccggcgag ctggacaatc ggggctctca gttctacctg agcctgtttt gggcacaggc   2280
cctggcagag cagacagagg acgcagagct ggccgagaga ttcaagcctc tggcaaaggc   2340
cctggcagag caggaggagg caatcgtgtc tgagctgaac agcgtgcagg gcaagaccgt   2400
ggacatcggc ggctactatt accccgaccc tgagaagacc tccgaagtga tgcgcccctc   2460
taagaccttc aacaccacac tggagtccgt gtgagcggcc gc                      2502
```

<210> SEQ ID NO 14
<211> LENGTH: 1467
<212> TYPE: DNA
<213> ORGANISM: Artificial Sequence
<220> FEATURE:
<223> OTHER INFORMATION: IDH014 insert sequence

<400> SEQUENCE: 14

```
actagtttct ttgtctggcc atccgggtaa cccatgccgg acgcaaaata gactactgaa     60
aattttttg ctttgtggtt gggactttag ccaagggtat aaaagaccac cgtccccgaa     120
ttacctttcc tcttcttttc tctctctcct tgtcaactca cacccgaaat cgttaagcat    180
ttccttctga gtataagaat cattcaaaat ggaaagtaaa gtagttgttc cggcacaagg    240
caagaagatc accctgcaaa acggcaaact caacgttcct gaaaatccga ttatccctta    300
cattgaaggt gatggaatcg gtgtagatgt aaccccagcc atgctgaaag tggtcgacgc    360
tgcagtcgag aaagcctata aaggcgagcg taaaatctcc tggatggaaa tttacaccgg    420
tgaaaaatcc acacaggttt atggtcagga cgtctggctg cctgctgaaa ctcttgatct    480
gattcgtgaa tatcgcgttg ccattaaagg tccgctgacc actccggttg gtggcggtat    540
tcgctctctg aacgttgccc tgcgccagga actggatctc tacatctgcc tgcgtccggt    600
acgttactat cagggcactc caagcccggt taaacaccct gaactgaccg atatggttat    660
cttccgtgaa aactcggaag acatttatgc gggtatcgaa tggaaagcag actctgccga    720
cgccgagaaa gtgattaaat tcctgcgtga agagatgggg gtgaagaaaa ttcgcttccc    780
ggaacattgt ggtatcggta ttaagccgtg ttcggaagaa ggcaccaaac gtctggttcg    840
```

tgcagcgatc gaatacgcaa ttgctaacga tcgtgactct gtgactctgg tgcacaaagg 900
caacatcatg aagttcaccg aaggagcgtt taaagactgg ggctaccagc tggcgcgtga 960
agagtttggc ggtgaactga tcgacggtgg cccgtggctg aaagttaaaa acccgaacac 1020
tggcaaagag atcgtcatta aagacgtgat tgctgatgca ttcctgcaac agatcctgct 1080
gcgtccggct gaatatgatg ttatcgcctg tatgaacctg aacggtgact acatttctga 1140
cgccctggca gcgcaggttg gcggtatcgg tatcgcccct ggtgcaaaca tcggtgacga 1200
atgcgccctg tttgaagcca cccacggtac tgcgccgaaa tatgccggtc aggacaaagt 1260
aaatcctggc tctattattc tctccgctga gatgatgctg cgccacatgg gttggaccga 1320
agcggctgac ttaattgtta aaggtatgga aggcgcaatc aacgcgaaaa ccgtaaccta 1380
tgacttcgag cgtctgatgg atggcgctaa actgctgaaa tgttcagagt ttggtgacgc 1440
gatcatcgaa aacatgtaag cggccgc 1467

<210> SEQ ID NO 15
<211> LENGTH: 1521
<212> TYPE: DNA
<213> ORGANISM: Artificial Sequence
<220> FEATURE:
<223> OTHER INFORMATION: IDH015 insert sequence

<400> SEQUENCE: 15
actagtttct ttgtctggcc atccgggtaa cccatgccgg acgcaaaata gactactgaa 60
aatttttttg ctttgtggtt gggactttag ccaagggtat aaaagaccac cgtccccgaa 120
ttacctttcc tcttcttttc tctctctcct tgtcaactca cacccgaaat cgttaagcat 180
ttccttctga gtataagaat cattcaaaat gcttcgaacc gcctacctgg ctaaggccgc 240
ctcggctctc cccaagcgaa ccctcgaaag taaagtagtt gttccggcac aaggcaagaa 300
gatcaccctg caaaacggca aactcaacgt tcctgaaaat ccgattatcc cttacattga 360
aggtgatgga atcggtgtag atgtaacccc agccatgctg aaagtggtcg acgctgcagt 420
cgagaaagcc tataaaggcg agcgtaaaat ctcctggatg gaaatttaca ccggtgaaaa 480
atccacacag gtttatggtc aggacgtctg gctgcctgct gaaactcttg atctgattcg 540
tgaatatcgc gttgccatta aaggtccgct gaccactccg gttggtggcg gtattcgctc 600
tctgaacgtt gccctgcgcc aggaactgga tctctacatc tgcctgcgtc cggtacgtta 660
ctatcagggc actccaagcc cggttaaaca ccctgaactg accgatatgg ttatcttccg 720
tgaaaactcg gaagacattt atgcgggtat cgaatggaaa gcagactctg ccgacgccga 780
gaaagtgatt aaattcctgc gtgaagagat gggggtgaag aaaattcgct tcccggaaca 840
ttgtggtatc ggtattaagc cgtgttcgga agaaggcacc aaacgtctgg ttcgtgcagc 900
gatcgaatac gcaattgcta acgatcgtga ctctgtgact ctggtgcaca aaggcaacat 960
catgaagttc accgaaggag cgtttaaaga ctggggctac cagctggcgc gtgaagagtt 1020
tggcggtgaa ctgatcgacg gtggcccgtg gctgaaagtt aaaaacccga acactggcaa 1080
agagatcgtc attaaagacg tgattgctga tgcattcctg caacagatcc tgctgcgtcc 1140
ggctgaatat gatgttatcg cctgtatgaa cctgaacggt gactacattt ctgacgccct 1200
ggcagcgcag gttggcggta tcggtatcgc ccctggtgca aacatcggtg acgaatgcgc 1260
cctgtttgaa gccacccacg gtactgcgcc gaaatatgcc ggtcaggaca aagtaaatcc 1320
tggctctatt attctctccg ctgagatgat gctgcgccac atgggttgga ccgaagcggc 1380

-continued

```
tgacttaatt gttaaaggta tggaaggcgc aatcaacgcg aaaaccgtaa cctatgactt   1440

cgagcgtctg atggatggcg ctaaactgct gaaatgttca gagtttggtg acgcgatcat   1500

cgaaaacatg taagcggccg c                                             1521
```

<210> SEQ ID NO 16
<211> LENGTH: 1506
<212> TYPE: DNA
<213> ORGANISM: Artificial Sequence
<220> FEATURE:
<223> OTHER INFORMATION: IDH016 insert sequence

<400> SEQUENCE: 16

```
actagtttct ttgtctggcc atccgggtaa cccatgccgg acgcaaaata gactactgaa     60

aattttttttg ctttgtggtt gggactttag ccaagggtat aaaagaccac cgtccccgaa   120

ttacctttcc tcttcttttc tctctctcct tgtcaactca cacccgaaat cgttaagcat   180

ttccttctga gtataagaat cattcaaaat gacgacccat attcagaaac ccgcaacagg   240

cagtccctta acactgctga atggggtgtt gcaggtgcct gatcaaccca ttattccctt   300

cattgaaggc gacggaattg gttgtgatgt aaccccggcc atgcgcagtg tggtggatgc   360

ggcagtggcc aaagtctatg gaggacagcg gcagattgcc tggatggagt tgtttgcagg   420

tcagaaggcc gtgcaactgt atggtgaagg gcagtatttg cccgatgaga ccatggccgc   480

cattcgggaa tataaagtcg ccatcaaagg tcctctggaa actccggtgg gcggggggat   540

tcgtagcctg aatgtggcca tgcgtcagga tcttgatttg tatgtctgcc tccggccggt   600

gcgttatttt gaggggacgc ccagccccat gcggcatccg gaaaaagtgg atatggtcat   660

ttttcgcgaa aactccgagg acatttacgc cggtattgaa tggcctgcgg gtagtcccga   720

agcagaaaaa atcatccgtt ttctgcggga agaaatgggc gtcacaaaaa tccgctttcc   780

cgacagctct gccattggca tcaaacccgt atcgacggaa ggttcggaac gtctgatccg   840

gcgtaccatt caatacgctc tggaacatgg caagccctct gtgagtctgg tgcacaaggg   900

taatatcatg aaattcaccg aaggcggttt ccgtgactgg ggttatgccc tggcggagcg   960

ggagttcgcc ggtcgggtgt ttacctggag gcaaaaggcc gccatcagca aggcagaggg  1020

taaggcggca gggcagaaag ccgagcagca ggccattgcc gacgggaagc tgatcatcaa  1080

ggacgtgatt gccgataatt ttctgcagca gattttgctg cgcccggaag attactctgt  1140

ggttgccacg ctgaacttga atggtgacta tgtttctgat gccctggccg cagaagtagg  1200

gggtattggt atggcacccg gtgccaacct ttctgatacc cacgcgattt ttgaagctac  1260

ccatggtacg gcaccggata ttgccgggca gggcaaagcc aaccccagct cgctgatttt  1320

gtcggctgtc atgatgctgg agcatctggg ctggggagaa gctgctcagg cgattgtggc  1380

ggccatgaat gccaccattg cggctggtga agtcaccggt gatctggcgg ccttgcgggg  1440

tgatgtgccg gcactgagca ccacagagtt tacggcagca ctgatccggc gtttttaagc  1500

ggccgc                                                              1506
```

<210> SEQ ID NO 17
<211> LENGTH: 1560
<212> TYPE: DNA
<213> ORGANISM: Artificial Sequence
<220> FEATURE:
<223> OTHER INFORMATION: IDH017 insert sequence

<400> SEQUENCE: 17

```
actagtttct ttgtctggcc atccgggtaa cccatgccgg acgcaaaata gactactgaa     60
```

```
aatttttttg ctttgtggtt gggactttag ccaagggtat aaaagaccac cgtccccgaa    120

ttacctttcc tcttcttttc tctctctcct tgtcaactca cacccgaaat cgttaagcat    180

ttccttctga gtataagaat cattcaaaat gcttcgaacc gcctacctgg ctaaggccgc    240

ctcggctctc cccaagcgaa ccctcacgac ccatattcag aaacccgcaa caggcagtcc    300

cttaacactg ctgaatgggg tgttgcaggt gcctgatcaa cccattattc ccttcattga    360

aggcgacgga attggttgtg atgtaacccc ggccatgcgc agtgtggtgg atgcggcagt    420

ggccaaagtc tatggaggac agcggcagat tgcctggatg gagttgtttg caggtcagaa    480

ggccgtgcaa ctgtatggtg aagggcagta tttgcccgat gagaccatgg ccgccattcg    540

ggaatataaa gtcgccatca aaggtcctct ggaaactccg gtgggcgggg ggattcgtag    600

cctgaatgtg gccatgcgtc aggatcttga tttgtatgtc tgcctccggc cggtgcgtta    660

ttttgagggg acgcccagcc ccatgcggca tccggaaaaa gtggatatgg tcatttttcg    720

cgaaaactcc gaggacattt acgccggtat tgaatggcct gcgggtagtc ccgaagcaga    780

aaaaatcatc cgttttctgc gggaagaaat gggcgtcaca aaaatccgct ttcccgacag    840

ctctgccatt ggcatcaaac ccgtatcgac ggaaggttcg gaacgtctga tccggcgtac    900

cattcaatac gctctggaac atggcaagcc ctctgtgagt ctggtgcaca agggtaatat    960

catgaaattc accgaaggcg gtttccgtga ctggggttat gccctggcgg agcgggagtt   1020

cgccggtcgg gtgtttacct ggaggcaaaa ggccgccatc agcaaggcag agggtaaggc   1080

ggcagggcag aaagccgagc agcaggccat tgccgacggg aagctgatca tcaaggacgt   1140

gattgccgat aatttttctgc agcagatttt gctgcgcccg gaagattact ctgtggttgc   1200

cacgctgaac ttgaatggtg actatgtttc tgatgccctg gccgcagaag taggggggtat   1260

tggtatggca cccggtgcca acctttctga tacccacgcg atttttgaag ctacccatgg   1320

tacggcaccg gatattgccg ggcagggcaa agccaacccc agctcgctga ttttgtcggc   1380

tgtcatgatg ctggagcatc tgggctgggg agaagctgct caggcgattg tggcggccat   1440

gaatgccacc attgcggctg gtgaagtcac cggtgatctg gcggccttgc ggggtgatgt   1500

gccggcactg agcaccacag agtttacggc agcactgatc cggcgttttt aagcggccgc   1560
```

<210> SEQ ID NO 18
<211> LENGTH: 2448
<212> TYPE: DNA
<213> ORGANISM: Artificial Sequence
<220> FEATURE:
<223> OTHER INFORMATION: IDH018 insert sequence

<400> SEQUENCE: 18

```
actagtttct ttgtctggcc atccgggtaa cccatgccgg acgcaaaata gactactgaa     60

aatttttttg ctttgtggtt gggactttag ccaagggtat aaaagaccac cgtccccgaa    120

ttacctttcc tcttcttttc tctctctcct tgtcaactca cacccgaaat cgttaagcat    180

ttccttctga gtataagaat cattcaaaat gagcgcccag cagccgacca tcatctacac    240

gctgaccgac gaggcgccgc tgcttgcgac ctatgccttc ttgccggtgg tacggaaatt    300

cgccgaagcg gcaggcatcg acgtcaaaac cagcgacatc tcggttgcgg cccgcatcct    360

ggccgagttc ggggatcacc tgaccgagga gcagcgggtc ccggacaacc tgggtgagct    420

gggcgcgctg acgcaggacc ccagcgccaa catcatcaag ctgccgaaca tcagcgcttc    480

ggtgccgcag ctgctcgcgg cgatcaagga gctgcagggc aaggggtaca acgtgccgga    540
```

```
ttacccggcc aacccgaaga ccgacgacga gaagaagatc aaggaccgct acgccaagat    600

cctcggcagc gcggtgaacc ccgttctgcg cgaaggcaac tcggaccgcc gcgcacccaa    660

ggcggtcaag gagtacgcgc gcaagcaccc gcacagcatg ggtgagtgga gccaggcgtc    720

gcgcacccac gtcgcgacca tgaagaccgg cgacttctac cacggcgaga agtcgatgac    780

gctggaccgc gaccgccgcg tcaagatggt gctcaagacc aagagcggcg aggagatcgt    840

cctcaagccc gaggtcaagc tcgacgcggg cgacatcatc gactcgatgt acatgagcaa    900

gaaggcgctc atcgcgttct acgaggagca gatcgaggac gcctacaaga ccggcgtcat    960

gttcagcctt cacgtcaagg cgaccatgat gaaggtgtcg caccccatcg tgttcggcca   1020

cgcggtcaag gtcttctaca aggacgcgtt cgccaagcac gagaagctgt tcgacgagct   1080

cggtgtcaac gtcaacaacg gtctgtccga tctgtacgac aagatcgagg cgctgcccgc   1140

gtcgcagcgc gaggagatca tcgaggatct gcacaagtgc cacgagcacc ggccggagct   1200

cgcgatggtc gactcggcca agggcatctc gaacttccac tcgccgtccg acgtcatcgt   1260

cgacgcctcg atgcccgcga tgatccgcct cggcggcaag atgtacggcg cagacggccg   1320

caccaaggac accaaggccg tcaacccgga gtcgaccttc tcccgcatgt accaggagat   1380

gatcaacttc tgcaagacgc acggccagtt cgatcccacc accatgggca cggtgccgaa   1440

cgtcggactg atggcgcaga aggccgagga gtacggcagc cacgacaaga ccttcgagat   1500

ccccgaggac ggcgtcgccg acatcgtcga catcgacacc ggtgaggtgc tgctcaccca   1560

gaacgtcgaa gagggcgata tctggcgcat gccgatcgtc aaggacgcgc cgatccgcga   1620

ctgggtcaag ctggccgtca cgcgcgctcg gctgtccggc atgcccgtgg tgttctggct   1680

cgacaccgag cgtccgcacg aggtcgagct gcgcaagaag gtcaaggagt acctcaagga   1740

ccacgacacc gaaggcctga aaatccagat catgccgcag gtgtgggcca tgcggtacac   1800

gctggagcgg gtcgtccgcg gcaaggacac catcgccgcg accggcaaca tcctgcgcga   1860

ctacctcacc gacctgttcc cgatcctgga gctgggcacc agcgccaaga tgctgtcgat   1920

cgtgccgctg atggccggcg gcggtctgta cgagaccggg gcgggcggct cggcgcccaa   1980

gcatgtgcac cagctcgtcg aggagaacca cctgcggtgg gattcgctgg gtgagttcct   2040

cgcactcggc gccagccttg aggacatggg caacaagacc ggcaacgaga aggccaaggt   2100

gctggccaag gcgctcgaca ccgcgaccgg aaagttgttg gaggagaaca agagcccgtc   2160

gcgtcgtacc ggtgagctgg acaaccgcgg cagccagttc tacctgtcgc tgttctgggc   2220

ccaggccctg gccgagcaga ccgaggacgc cgaactcgcc gagcgcttca agccgctggc   2280

caaggcgctc gccgagcagg aggaggccat cgtctccgag ctgaactcgg tgcagggcaa   2340

gacggtcgac atcggcggtt actactaccc ggatccggag aagacctccg aggtgatgcg   2400

tccgagcaag acgttcaaca ccacgctcga atcggtgtaa gcggccgc                2448
```

<210> SEQ ID NO 19
<211> LENGTH: 2502
<212> TYPE: DNA
<213> ORGANISM: Artificial Sequence
<220> FEATURE:
<223> OTHER INFORMATION: IDH019 insert sequence

<400> SEQUENCE: 19

```
actagtttct ttgtctggcc atccgggtaa cccatgccgg acgcaaaata gactactgaa     60

aatttttttg ctttgtggtt gggactttag ccaagggtat aaaagaccac cgtccccgaa    120

ttacctttcc tcttcttttc tctctctcct tgtcaactca cacccgaaat cgttaagcat    180
```

-continued

```
ttccttctga gtataagaat cattcaaaat gcttcgaacc gcctacctgg ctaaggccgc    240
ctcggctctc cccaagcgaa ccctcagcgc ccagcagccg accatcatct acacgctgac    300
cgacgaggcg ccgctgcttg cgacctatgc cttcttgccg gtggtacgga aattcgccga    360
agcggcaggc atcgacgtca aaaccagcga catctcggtt gcggcccgca tcctggccga    420
gttcggggat cacctgaccg aggagcagcg ggtcccggac aacctgggtg agctgggcgc    480
gctgacgcag gaccccagcg ccaacatcat caagctgccg aacatcagcg cttcggtgcc    540
gcagctgctc gcggcgatca aggagctgca gggcaagggg tacaacgtgc cggattaccc    600
ggccaacccg aagaccgacg acgagaagaa gatcaaggac cgctacgcca agatcctcgg    660
cagcgcggtg aaccccgttc tgcgcgaagg caactcggac cgccgcgcac ccaaggcggt    720
caaggagtac gcgcgcaagc acccgcacag catgggtgag tggagccagg cgtcgcgcac    780
ccacgtcgcg accatgaaga ccggcgactt ctaccacggc gagaagtcga tgacgctgga    840
ccgcgaccgc cgcgtcaaga tggtgctcaa gaccaagagc ggcgaggaga tcgtcctcaa    900
gcccgaggtc aagctcgacg cgggcgacat catcgactcg atgtacatga gcaagaaggc    960
gctcatcgcg ttctacgagg agcagatcga ggacgcctac aagaccggcg tcatgttcag   1020
ccttcacgtc aaggcgacca tgatgaaggt gtcgcacccc atcgtgttcg gccacgcggt   1080
caaggtcttc tacaaggacg cgttcgccaa gcacgagaag ctgttcgacg agctcggtgt   1140
caacgtcaac aacggtctgt ccgatctgta cgacaagatc gaggcgctgc ccgcgtcgca   1200
gcgcgaggag atcatcgagg atctgcacaa gtgccacgag caccggccgg agctcgcgat   1260
ggtcgactcg gccaagggca tctcgaactt ccactcgccg tccgacgtca tcgtcgacgc   1320
ctcgatgccc gcgatgatcc gcctcggcgg caagatgtac ggcgcagacg gccgcaccaa   1380
ggacaccaag gccgtcaacc cggagtcgac cttctcccgc atgtaccagg agatgatcaa   1440
cttctgcaag acgcacggcc agttcgatcc caccaccatg ggcacggtgc cgaacgtcgg   1500
actgatggcg cagaaggccg aggagtacgg cagccacgac aagaccttcg agatccccga   1560
ggacggcgtc gccgacatcg tcgacatcga caccggtgag gtgctgctca cccagaacgt   1620
cgaagagggc gatatctggc gcatgccgat cgtcaaggac gcgccgatcc gcgactgggt   1680
caagctggcc gtcacgcgcg ctcggctgtc cggcatgccc gtggtgttct ggctcgacac   1740
cgagcgtccg cacgaggtcg agctgcgcaa gaaggtcaag gagtacctca aggaccacga   1800
caccgaaggc ctgaaaatcc agatcatgcc gcaggtgtgg gccatgcggt acacgctgga   1860
gcgggtcgtc cgcggcaagg acaccatcgc cgcgaccggc aacatcctgc gcgactacct   1920
caccgacctg ttcccgatcc tggagctggg caccagcgcc aagatgctgt cgatcgtgcc   1980
gctgatggcc ggcggcggtc tgtacgagac cggggcgggc ggctcggcgc ccaagcatgt   2040
gcaccagctc gtcgaggaga accacctgcg gtgggattcg ctgggtgagt tcctcgcact   2100
cggcgccagc cttgaggaca tggcaacaa gaccggcaac gagaaggcca aggtgctggc    2160
caaggcgctc gacaccgcga ccggaaagtt gttggaggag aacaagagcc cgtcgcgtcg   2220
taccggtgag ctggacaacc gcggcagcca gttctacctg tcgctgttct gggcccaggc   2280
cctggccgag cagaccgagg acgccgaact cgccgagcgc ttcaagccgc tggccaaggc   2340
gctcgccgag caggaggagg ccatcgtctc cgagctgaac tcggtgcagg gcaagacggt   2400
cgacatcggc ggttactact acccggatcc ggagaagacc tccgaggtga tgcgtccgag   2460
caagacgttc aacaccacgc tcgaatcggt gtaagcggcc gc                      2502
```

<210> SEQ ID NO 20
<211> LENGTH: 366
<212> TYPE: PRT
<213> ORGANISM: Yarrowia lipolytica

<400> SEQUENCE: 20

```
Met Leu Arg Thr Ala Tyr Leu Ala Lys Ala Ala Ser Ala Leu Pro Lys
1               5                   10                  15

Arg Thr Leu Ala Thr Asn Ala Arg Thr Met Phe Gln Pro Lys Glu Tyr
            20                  25                  30

Gly Ser Lys Tyr Thr Val Thr Leu Ile Pro Gly Asp Gly Ile Gly Asn
        35                  40                  45

Glu Ile Thr Asp Ala Val Lys Thr Ile Phe Lys Thr Ile Ser Val Pro
    50                  55                  60

Ile Asp Trp Glu Val Val Asn Val Thr Gly Val Gly Glu Asn His Leu
65                  70                  75                  80

Asp Gly Tyr Glu Glu Ala Ile Arg Ser Ile Asn Arg Asn Lys Val Ala
                85                  90                  95

Ile Lys Gly Ile Leu His Thr Pro Val Glu Lys His Gly His Thr Ser
            100                 105                 110

Phe Asn Val Ala Leu Arg Arg Glu Leu Asp Ile Phe Ala Ser Leu Val
        115                 120                 125

Leu Ile Lys Asn Ile Pro Gly Val Gln Thr Arg Leu Asp Gly Ile Asp
    130                 135                 140

Met Ala Leu Ile Arg Glu Asn Thr Glu Gly Glu Tyr Ser Gly Leu Glu
145                 150                 155                 160

His Ser Pro Val Pro Gly Val Val Glu Ser Ile Lys Val Ile Thr Lys
                165                 170                 175

Arg Lys Ser Glu Arg Ile Ala Arg Phe Ala Phe Asp Phe Ala Leu Lys
            180                 185                 190

Asn Asn Arg His Lys Val Thr Ala Ile His Lys Ala Asn Ile Met Lys
        195                 200                 205

Leu Ala Asp Gly Leu Phe Arg Asn Thr Cys Lys Glu Val Ser Ala Glu
    210                 215                 220

Tyr Pro Glu Ile Gln Tyr Gly Asp Met Ile Val Asp Asn Ala Ser Met
225                 230                 235                 240

Gln Ala Val Ser Trp Pro Gln Gln Phe Asp Val Leu Val Thr Pro Asn
                245                 250                 255

Leu Tyr Gly Thr Ile Leu Ser Asn Ile Gly Ala Gly Leu Val Gly Gly
            260                 265                 270

Pro Gly Leu Val Pro Gly Val Asn Leu Gly Thr Glu His Ala Val Phe
        275                 280                 285

Glu Pro Gly Cys Arg His Val Gly Leu Ala Ala Lys Gly Arg Gly Thr
    290                 295                 300

Ala Asn Pro Thr Ala Met Ile Leu Ser Ser Ala Met Leu Leu Arg His
305                 310                 315                 320

Leu Asn Leu Asp Asp Phe Ala Asp Val Ile Ser Lys Ala Thr Tyr Asp
                325                 330                 335

Val Leu Ala Glu Gly Gln Val Arg Thr Pro Asp Leu Gly Gly Asn Ser
            340                 345                 350

Thr Thr Asp Glu Phe Thr Met Ala Val Ile Asn Lys Leu Gln
        355                 360                 365
```

<210> SEQ ID NO 21

```
<211> LENGTH: 416
<212> TYPE: PRT
<213> ORGANISM: Escherichia coli

<400> SEQUENCE: 21

Met Glu Ser Lys Val Val Val Pro Ala Gln Gly Lys Lys Ile Thr Leu
1               5                   10                  15

Gln Asn Gly Lys Leu Asn Val Pro Glu Asn Pro Ile Ile Pro Tyr Ile
            20                  25                  30

Glu Gly Asp Gly Ile Gly Val Asp Val Thr Pro Ala Met Leu Lys Val
        35                  40                  45

Val Asp Ala Ala Val Glu Lys Ala Tyr Lys Gly Glu Arg Lys Ile Ser
    50                  55                  60

Trp Met Glu Ile Tyr Thr Gly Glu Lys Ser Thr Gln Val Tyr Gly Gln
65                  70                  75                  80

Asp Val Trp Leu Pro Ala Glu Thr Leu Asp Leu Ile Arg Glu Tyr Arg
                85                  90                  95

Val Ala Ile Lys Gly Pro Leu Thr Thr Pro Val Gly Gly Gly Ile Arg
            100                 105                 110

Ser Leu Asn Val Ala Leu Arg Gln Glu Leu Asp Leu Tyr Ile Cys Leu
        115                 120                 125

Arg Pro Val Arg Tyr Tyr Gln Gly Thr Pro Ser Pro Val Lys His Pro
    130                 135                 140

Glu Leu Thr Asp Met Val Ile Phe Arg Glu Asn Ser Glu Asp Ile Tyr
145                 150                 155                 160

Ala Gly Ile Glu Trp Lys Ala Asp Ser Ala Asp Ala Glu Lys Val Ile
                165                 170                 175

Lys Phe Leu Arg Glu Glu Met Gly Val Lys Lys Ile Arg Phe Pro Glu
            180                 185                 190

His Cys Gly Ile Gly Ile Lys Pro Cys Ser Glu Glu Gly Thr Lys Arg
        195                 200                 205

Leu Val Arg Ala Ala Ile Glu Tyr Ala Ile Ala Asn Asp Arg Asp Ser
    210                 215                 220

Val Thr Leu Val His Lys Gly Asn Ile Met Lys Phe Thr Glu Gly Ala
225                 230                 235                 240

Phe Lys Asp Trp Gly Tyr Gln Leu Ala Arg Glu Glu Phe Gly Gly Glu
                245                 250                 255

Leu Ile Asp Gly Gly Pro Trp Leu Lys Val Lys Asn Pro Asn Thr Gly
            260                 265                 270

Lys Glu Ile Val Ile Lys Asp Val Ile Ala Asp Ala Phe Leu Gln Gln
        275                 280                 285

Ile Leu Leu Arg Pro Ala Glu Tyr Asp Val Ile Ala Cys Met Asn Leu
    290                 295                 300

Asn Gly Asp Tyr Ile Ser Asp Ala Leu Ala Ala Gln Val Gly Gly Ile
305                 310                 315                 320

Gly Ile Ala Pro Gly Ala Asn Ile Gly Asp Glu Cys Ala Leu Phe Glu
                325                 330                 335

Ala Thr His Gly Thr Ala Pro Lys Tyr Ala Gly Gln Asp Lys Val Asn
            340                 345                 350

Pro Gly Ser Ile Ile Leu Ser Ala Glu Met Met Leu Arg His Met Gly
        355                 360                 365

Trp Thr Glu Ala Ala Asp Leu Ile Val Lys Gly Met Glu Gly Ala Ile
    370                 375                 380

Asn Ala Lys Thr Val Thr Tyr Asp Phe Glu Arg Leu Met Asp Gly Ala
```

385 390 395 400

Lys Leu Leu Lys Cys Ser Glu Phe Gly Asp Ala Ile Ile Glu Asn Met
405 410 415

<210> SEQ ID NO 22
<211> LENGTH: 429
<212> TYPE: PRT
<213> ORGANISM: Acidithiobacillus thiooxidans

<400> SEQUENCE: 22

Met Thr Thr His Ile Gln Lys Pro Ala Thr Gly Ser Pro Leu Thr Leu
1 5 10 15

Leu Asn Gly Val Leu Gln Val Pro Asp Gln Pro Ile Ile Pro Phe Ile
20 25 30

Glu Gly Asp Gly Ile Gly Cys Asp Val Thr Pro Ala Met Arg Ser Val
35 40 45

Val Asp Ala Ala Val Ala Lys Val Tyr Gly Gly Gln Arg Gln Ile Ala
50 55 60

Trp Met Glu Leu Phe Ala Gly Gln Lys Ala Val Gln Leu Tyr Gly Glu
65 70 75 80

Gly Gln Tyr Leu Pro Asp Glu Thr Met Ala Ala Ile Arg Glu Tyr Lys
85 90 95

Val Ala Ile Lys Gly Pro Leu Glu Thr Pro Val Gly Gly Gly Ile Arg
100 105 110

Ser Leu Asn Val Ala Met Arg Gln Asp Leu Asp Leu Tyr Val Cys Leu
115 120 125

Arg Pro Val Arg Tyr Phe Glu Gly Thr Pro Ser Pro Met Arg His Pro
130 135 140

Glu Lys Val Asp Met Val Ile Phe Arg Glu Asn Ser Glu Asp Ile Tyr
145 150 155 160

Ala Gly Ile Glu Trp Pro Ala Gly Ser Pro Glu Ala Glu Lys Ile Ile
165 170 175

Arg Phe Leu Arg Glu Glu Met Gly Val Thr Lys Ile Arg Phe Pro Asp
180 185 190

Ser Ser Ala Ile Gly Ile Lys Pro Val Ser Thr Glu Gly Ser Glu Arg
195 200 205

Leu Ile Arg Arg Thr Ile Gln Tyr Ala Leu Glu His Gly Lys Pro Ser
210 215 220

Val Ser Leu Val His Lys Gly Asn Ile Met Lys Phe Thr Glu Gly Gly
225 230 235 240

Phe Arg Asp Trp Gly Tyr Ala Leu Ala Glu Arg Glu Phe Ala Gly Arg
245 250 255

Val Phe Thr Trp Arg Gln Lys Ala Ala Ile Ser Lys Ala Glu Gly Lys
260 265 270

Ala Ala Gly Gln Lys Ala Glu Gln Gln Ala Ile Ala Asp Gly Lys Leu
275 280 285

Ile Ile Lys Asp Val Ile Ala Asp Asn Phe Leu Gln Gln Ile Leu Leu
290 295 300

Arg Pro Glu Asp Tyr Ser Val Val Ala Thr Leu Asn Leu Asn Gly Asp
305 310 315 320

Tyr Val Ser Asp Ala Leu Ala Ala Glu Val Gly Gly Ile Gly Met Ala
325 330 335

Pro Gly Ala Asn Leu Ser Asp Thr His Ala Ile Phe Glu Ala Thr His
340 345 350

```
Gly Thr Ala Pro Asp Ile Ala Gly Gln Gly Lys Ala Asn Pro Ser Ser
        355                 360                 365

Leu Ile Leu Ser Ala Val Met Met Leu Glu His Leu Gly Trp Gly Glu
    370                 375                 380

Ala Ala Gln Ala Ile Val Ala Ala Met Asn Ala Thr Ile Ala Ala Gly
385                 390                 395                 400

Glu Val Thr Gly Asp Leu Ala Ala Leu Arg Gly Asp Val Pro Ala Leu
                405                 410                 415

Ser Thr Thr Glu Phe Thr Ala Ala Leu Ile Arg Arg Phe
            420                 425


<210> SEQ ID NO 23
<211> LENGTH: 743
<212> TYPE: PRT
<213> ORGANISM: Mycobacterium smegmatis

<400> SEQUENCE: 23

Met Ser Ala Gln Gln Pro Thr Ile Ile Tyr Thr Leu Thr Asp Glu Ala
1               5                   10                  15

Pro Leu Leu Ala Thr Tyr Ala Phe Leu Pro Val Val Arg Lys Phe Ala
            20                  25                  30

Glu Ala Ala Gly Ile Asp Val Lys Thr Ser Asp Ile Ser Val Ala Ala
        35                  40                  45

Arg Ile Leu Ala Glu Phe Gly Asp His Leu Thr Glu Glu Gln Arg Val
    50                  55                  60

Pro Asp Asn Leu Gly Glu Leu Gly Ala Leu Thr Gln Asp Pro Ser Ala
65                  70                  75                  80

Asn Ile Ile Lys Leu Pro Asn Ile Ser Ala Ser Val Pro Gln Leu Leu
                85                  90                  95

Ala Ala Ile Lys Glu Leu Gln Gly Lys Gly Tyr Asn Val Pro Asp Tyr
            100                 105                 110

Pro Ala Asn Pro Lys Thr Asp Asp Glu Lys Lys Ile Lys Asp Arg Tyr
        115                 120                 125

Ala Lys Ile Leu Gly Ser Ala Val Asn Pro Val Leu Arg Glu Gly Asn
    130                 135                 140

Ser Asp Arg Arg Ala Pro Lys Ala Val Lys Glu Tyr Ala Arg Lys His
145                 150                 155                 160

Pro His Ser Met Gly Glu Trp Ser Gln Ala Ser Arg Thr His Val Ala
                165                 170                 175

Thr Met Lys Thr Gly Asp Phe Tyr His Gly Glu Lys Ser Met Thr Leu
            180                 185                 190

Asp Arg Asp Arg Arg Val Lys Met Val Leu Lys Thr Lys Ser Gly Glu
        195                 200                 205

Glu Ile Val Leu Lys Pro Glu Val Lys Leu Asp Ala Gly Asp Ile Ile
    210                 215                 220

Asp Ser Met Tyr Met Ser Lys Lys Ala Leu Ile Ala Phe Tyr Glu Glu
225                 230                 235                 240

Gln Ile Glu Asp Ala Tyr Lys Thr Gly Val Met Phe Ser Leu His Val
                245                 250                 255

Lys Ala Thr Met Met Lys Val Ser His Pro Ile Val Phe Gly His Ala
            260                 265                 270

Val Lys Val Phe Tyr Lys Asp Ala Phe Ala Lys His Glu Lys Leu Phe
        275                 280                 285

Asp Glu Leu Gly Val Asn Val Asn Asn Gly Leu Ser Asp Leu Tyr Asp
    290                 295                 300
```

```
Lys Ile Glu Ala Leu Pro Ala Ser Gln Arg Glu Glu Ile Ile Glu Asp
305                 310                 315                 320

Leu His Lys Cys His Glu His Arg Pro Glu Leu Ala Met Val Asp Ser
                325                 330                 335

Ala Lys Gly Ile Ser Asn Phe His Ser Pro Ser Asp Val Ile Val Asp
            340                 345                 350

Ala Ser Met Pro Ala Met Ile Arg Leu Gly Gly Lys Met Tyr Gly Ala
        355                 360                 365

Asp Gly Arg Thr Lys Asp Thr Lys Ala Val Asn Pro Glu Ser Thr Phe
    370                 375                 380

Ser Arg Met Tyr Gln Glu Met Ile Asn Phe Cys Lys Thr His Gly Gln
385                 390                 395                 400

Phe Asp Pro Thr Thr Met Gly Thr Val Pro Asn Val Gly Leu Met Ala
                405                 410                 415

Gln Lys Ala Glu Glu Tyr Gly Ser His Asp Lys Thr Phe Glu Ile Pro
            420                 425                 430

Glu Asp Gly Val Ala Asp Ile Val Asp Ile Asp Thr Gly Glu Val Leu
        435                 440                 445

Leu Thr Gln Asn Val Glu Glu Gly Asp Ile Trp Arg Met Pro Ile Val
    450                 455                 460

Lys Asp Ala Pro Ile Arg Asp Trp Val Lys Leu Ala Val Thr Arg Ala
465                 470                 475                 480

Arg Leu Ser Gly Met Pro Val Val Phe Trp Leu Asp Thr Glu Arg Pro
                485                 490                 495

His Glu Val Glu Leu Arg Lys Lys Val Lys Glu Tyr Leu Lys Asp His
            500                 505                 510

Asp Thr Glu Gly Leu Lys Ile Gln Ile Met Pro Gln Val Trp Ala Met
        515                 520                 525

Arg Tyr Thr Leu Glu Arg Val Val Arg Gly Lys Asp Thr Ile Ala Ala
    530                 535                 540

Thr Gly Asn Ile Leu Arg Asp Tyr Leu Thr Asp Leu Phe Pro Ile Leu
545                 550                 555                 560

Glu Leu Gly Thr Ser Ala Lys Met Leu Ser Ile Val Pro Leu Met Ala
                565                 570                 575

Gly Gly Gly Leu Tyr Glu Thr Gly Ala Gly Gly Ser Ala Pro Lys His
            580                 585                 590

Val His Gln Leu Val Glu Glu Asn His Leu Arg Trp Asp Ser Leu Gly
        595                 600                 605

Glu Phe Leu Ala Leu Gly Ala Ser Leu Glu Asp Met Gly Asn Lys Thr
    610                 615                 620

Gly Asn Glu Lys Ala Lys Val Leu Ala Lys Ala Leu Asp Thr Ala Thr
625                 630                 635                 640

Gly Lys Leu Leu Glu Glu Asn Lys Ser Pro Ser Arg Arg Thr Gly Glu
                645                 650                 655

Leu Asp Asn Arg Gly Ser Gln Phe Tyr Leu Ser Leu Phe Trp Ala Gln
            660                 665                 670

Ala Leu Ala Glu Gln Thr Glu Asp Ala Glu Leu Ala Glu Arg Phe Lys
        675                 680                 685

Pro Leu Ala Lys Ala Leu Ala Glu Gln Glu Glu Ala Ile Val Ser Glu
    690                 695                 700

Leu Asn Ser Val Gln Gly Lys Thr Val Asp Ile Gly Gly Tyr Tyr Tyr
705                 710                 715                 720
```

-continued

Pro Asp Pro Glu Lys Thr Ser Glu Val Met Arg Pro Ser Lys Thr Phe
725 730 735

Asn Thr Thr Leu Glu Ser Val
740

<210> SEQ ID NO 24
<211> LENGTH: 572
<212> TYPE: PRT
<213> ORGANISM: Lipomyces starkeyi

<400> SEQUENCE: 24

Met Ala Pro Lys Ser Ser Thr Arg Val Pro Leu Ser Val Lys Gly Pro
1 5 10 15

Ile Asp Cys Pro Tyr Glu Gly Lys Glu Met Leu Asn Leu Pro Gln Phe
20 25 30

Asn Arg Gly Thr Ala Phe Thr Ala Glu Glu Arg Asp Leu Phe Asn Leu
35 40 45

Val Gly Asn Leu Pro Ala Ala Leu Gln Thr Leu Gln Asn Gln Val Asp
50 55 60

Arg Ala Tyr Asp Gln Tyr Ser Ser Ile Ser Thr Ala Leu Gly Lys Asn
65 70 75 80

Thr Phe Leu Met Ser Leu Lys Val Gln Asn Glu Val Leu Tyr Phe Lys
85 90 95

Leu Leu Gln Asp His Leu Lys Glu Met Phe Ser Ile Ile Tyr Thr Pro
100 105 110

Thr Glu Ser Glu Ala Ile Glu His Tyr Ser Arg Leu Phe Arg Arg Pro
115 120 125

Glu Gly Cys Phe Leu Asn Ile Asn His Pro Glu Tyr Ile Glu Arg Ser
130 135 140

Leu Ala Ala Trp Gly Thr Glu Glu Asp Ile Asp Tyr Ile Ile Val Ser
145 150 155 160

Asp Gly Glu Glu Ile Leu Gly Ile Gly Asp Gln Gly Val Gly Ala Ile
165 170 175

Gly Ile Ser Ser Ala Lys Ala Val Leu Met Thr Leu Cys Ala Gly Val
180 185 190

His Pro Ser Arg Cys Ile Pro Val Ala Leu Asp Val Gly Thr Asp Asn
195 200 205

Glu Gln Leu Leu Glu Asp Glu Leu Tyr Leu Gly Asn Arg His Asn Arg
210 215 220

Val Arg Gly Gly Arg Tyr Asp Lys Phe Val Asp Asp Phe Val Gln Cys
225 230 235 240

Val Lys Lys Leu Tyr Pro Arg Ala Val Leu His Phe Glu Asp Phe Gly
245 250 255

Leu Pro Asn Ala Arg Arg Leu Leu Asp Thr Tyr Arg Pro Arg Leu Ala
260 265 270

Cys Phe Asn Asp Asp Val Gln Gly Thr Gly Ala Val Thr Leu Ala Ala
275 280 285

Leu Ser Ser Ala Val Arg Val Ala Gly Ile Asp Phe Arg Asp Leu Arg
290 295 300

Thr Val Ile Phe Gly Ala Gly Thr Ala Gly Thr Gly Ile Ala Asp Gln
305 310 315 320

Leu Arg Asp Phe Leu Asn Thr Gln Gly Ile Ser Lys Gln Gln Val Ile
325 330 335

Asp His Ile Trp Leu Val Asp Lys Pro Gly Leu Leu Leu Lys Ser Met
340 345 350

His Asp Lys Leu Thr Ser Ala Gln Arg Pro Tyr Ala Ala Ser Asp Asp
355 360 365

Arg Trp Lys Glu Ile Asp Thr Lys Ser Leu Ser Glu Ile Val Lys Lys
370 375 380

Val Lys Pro His Val Leu Ile Gly Cys Ser Thr Lys Pro Lys Ala Phe
385 390 395 400

Asn Glu Ala Val Leu Arg Glu Met Ala Lys His Val Glu Arg Pro Ile
405 410 415

Val Phe Pro Leu Ser Asn Pro Thr Arg Leu His Glu Ala Thr Pro Ala
420 425 430

Glu Ile Phe Lys Tyr Thr Asp Gly Lys Ala Leu Val Ala Thr Gly Ser
435 440 445

Pro Phe Asp Pro Val Asp Gly Lys Glu Ile Ala Glu Asn Asn Asn Cys
450 455 460

Phe Val Tyr Pro Gly Ile Gly Met Gly Ser Ile Leu Ser Arg Ala Asp
465 470 475 480

Arg Val Thr Glu Thr Met Ile Ala Ala Val Val Lys Glu Leu Ala Ser
485 490 495

Leu Ala Pro Ser Glu Lys Asp Pro Thr Gly Ala Leu Leu Pro Asp Val
500 505 510

Ala Asp Ile Arg Asp Ile Ser Ala Lys Ile Ala Thr Ala Val Val Leu
515 520 525

Gln Ala Leu Glu Glu Gly Thr Ala Arg Val Glu Glu Ile Glu Gly Ile
530 535 540

Lys Val Pro Arg Asp Arg Asp His Cys Leu Glu Trp Val Lys Glu Gln
545 550 555 560

Met Trp Lys Pro Glu Tyr Arg Pro Leu Arg Lys Val
565 570

<210> SEQ ID NO 25
<211> LENGTH: 599
<212> TYPE: PRT
<213> ORGANISM: Rhodosporidium toruloides

<400> SEQUENCE: 25

Met Asn Lys Leu Arg Leu Gln Ala Lys Asp Ala Asp Glu Glu Gly Ala
1 5 10 15

Ala Leu His Asp Ser Thr Ile Ser Asn Lys Glu Tyr Leu Gln His Ser
20 25 30

Lys Asn Glu Arg Pro Ile Trp Thr Ala Leu Arg Gly Arg Ala Leu Leu
35 40 45

Asn Glu Pro Ala Leu Asn Lys Gly Ala Gly Phe Thr Pro Glu Glu Arg
50 55 60

Asp Thr Phe Gly Leu Thr Gly Leu Leu Pro His Glu Val His Ser Leu
65 70 75 80

Asp Gln Gln Cys Lys Arg Ala Tyr Ser Gln Leu Gln Glu Arg Pro Ser
85 90 95

Ala Leu Ala Lys Tyr Thr Phe Leu Ser Ser Leu Arg Asp Gln Asn Ile
100 105 110

Ile Leu Phe Tyr Ala Leu Cys Leu Arg His Leu Asn Glu Leu Leu Pro
115 120 125

Val Ile Tyr Thr Pro Thr Val Gly Glu Ala Ile Gln Lys Tyr Ser Thr
130 135 140

Ile Trp Arg Arg Pro Asp Gly Leu Phe Leu Ser Tyr Ala His Arg His

-continued

```
145                 150                 155                 160

Lys Met Arg Glu Met Met Met Gln Ala Lys Arg Pro Lys Asp Val Asp
                165                 170                 175

Leu Val Ile Val Thr Asp Ser Glu Gly Ile Leu Gly Ile Gly Asp Gln
            180                 185                 190

Gly Val Gly Gly Ile Leu Ile Ala Gln Gly Lys Ala Asn Leu Tyr Thr
        195                 200                 205

Leu Gly Ala Gly Ile Asp Pro Ser Arg Ile Leu Ser Val Val Leu Asp
    210                 215                 220

Val Gly Thr Asp Asn Ser Ala Leu Leu Asn Asp Pro Leu Tyr Leu Gly
225                 230                 235                 240

Leu Arg Arg Lys Arg Val Arg Gly Ala Glu Tyr Asp Lys Phe Val Asp
                245                 250                 255

Arg Phe Cys Glu Leu Val Arg Glu Glu Tyr Pro Gln Ala Leu Leu His
            260                 265                 270

Phe Glu Asp Phe Gly Val Ser Asn Ala Ser Lys Ile Leu Thr Thr Tyr
        275                 280                 285

Arg Asn Lys Gln Ser Val Phe Asn Asp Asp Met Gln Gly Thr Ala Ala
    290                 295                 300

Val Val Leu Ala Ala Leu Leu Ser Ala Val Lys Val Thr Lys Ser Glu
305                 310                 315                 320

Leu Lys Asp Gln Arg Ile Val Val Phe Gly Phe Gly Thr Ala Gly Tyr
                325                 330                 335

Gly Ile Ala Asp Gly Ile Arg Asn Ala Leu Met Leu Glu Ala Gly Leu
            340                 345                 350

Ser Ser Glu Glu Val Arg Lys Ile Phe Trp Cys Val Asp Arg Pro Gly
        355                 360                 365

Leu Leu Thr Thr Glu His Ser Pro Thr Leu Arg Pro Gly Gln Glu His
    370                 375                 380

Phe Ile Arg Asp Ala Ser Glu Val Ser Ser Trp Glu Arg Asp Ala Glu
385                 390                 395                 400

Gly Arg Ile Ser Leu Leu Glu Val Val Lys Gln Ala Lys Pro Thr Ile
                405                 410                 415

Leu Val Gly Cys Ser Thr Met Ser Gly Ala Phe Asp Glu Glu Val Val
            420                 425                 430

Arg Glu Met Ala Lys His Val Glu Arg Pro Ile Val Phe Pro Leu Ser
        435                 440                 445

Asn Pro Thr Lys Leu Ala Glu Ala Asp Pro Ala Asp Ile Asn Glu Trp
    450                 455                 460

Thr Asn Gly Leu Ala Leu Met Ala Thr Gly Ser Pro Phe Pro Pro Val
465                 470                 475                 480

Lys Thr Pro Arg Gly Lys Glu His Lys Ile Ala Glu Ala Asn Asn Gly
                485                 490                 495

Leu Leu Tyr Pro Gly Leu Gly Leu Gly Val Val Val Ser Arg Ala Ser
            500                 505                 510

Phe Leu Thr Glu Lys Met Ile Thr Ala Gly Val Ala Ala Leu Ala Arg
        515                 520                 525

Met Ala Pro Ala Leu Asp Asp Pro Asp Glu Ser Leu Leu Pro Pro Leu
    530                 535                 540

Ser Asp Leu Arg His Val Ser Val Lys Val Ala Thr Ala Val Ala Asn
545                 550                 555                 560

Ala Ala Lys Glu Glu Gly Val Ser Gln Ile Lys Arg Asp Asp Pro Phe
                565                 570                 575
```

Ser Glu Asp Glu Val Arg Ala Ala Gln Trp Asp Pro Val Tyr Arg Pro
580 585 590

Leu Glu Leu Val Asp Arg His
595

<210> SEQ ID NO 26
<211> LENGTH: 567
<212> TYPE: PRT
<213> ORGANISM: Homo sapiens

<400> SEQUENCE: 26

Met Leu His Ile Lys Glu Lys Gly Lys Pro Leu Met Leu Asn Pro Arg
1 5 10 15

Thr Asn Lys Gly Met Ala Phe Thr Leu Gln Glu Arg Gln Met Leu Gly
20 25 30

Leu Gln Gly Leu Leu Pro Pro Lys Ile Glu Thr Gln Asp Ile Gln Ala
35 40 45

Leu Arg Phe His Arg Asn Leu Lys Lys Met Thr Ser Pro Leu Glu Lys
50 55 60

Tyr Ile Tyr Ile Met Gly Ile Gln Glu Arg Asn Glu Lys Leu Phe Tyr
65 70 75 80

Arg Ile Leu Gln Asp Asp Ile Glu Ser Leu Met Pro Ile Val Tyr Thr
85 90 95

Pro Thr Val Gly Leu Ala Cys Ser Gln Tyr Gly His Ile Phe Arg Arg
100 105 110

Pro Lys Gly Leu Phe Ile Ser Ile Ser Asp Arg Gly His Val Arg Ser
115 120 125

Ile Val Asp Asn Trp Pro Glu Asn His Val Lys Ala Val Val Val Thr
130 135 140

Asp Gly Glu Arg Ile Leu Gly Leu Gly Asp Leu Gly Val Tyr Gly Met
145 150 155 160

Gly Ile Pro Val Gly Lys Leu Cys Leu Tyr Thr Ala Cys Ala Gly Ile
165 170 175

Arg Pro Asp Arg Cys Leu Pro Val Cys Ile Asp Val Gly Thr Asp Asn
180 185 190

Ile Ala Leu Leu Lys Asp Pro Phe Tyr Met Gly Leu Tyr Gln Lys Arg
195 200 205

Asp Arg Thr Gln Gln Tyr Asp Asp Leu Ile Asp Glu Phe Met Lys Ala
210 215 220

Ile Thr Asp Arg Tyr Gly Arg Asn Thr Leu Ile Gln Phe Glu Asp Phe
225 230 235 240

Gly Asn His Asn Ala Phe Arg Phe Leu Arg Lys Tyr Arg Glu Lys Tyr
245 250 255

Cys Thr Phe Asn Asp Asp Ile Gln Gly Thr Ala Ala Val Ala Leu Ala
260 265 270

Gly Leu Leu Ala Ala Gln Lys Val Ile Ser Lys Pro Ile Ser Glu His
275 280 285

Lys Ile Leu Phe Leu Gly Ala Gly Glu Ala Ala Leu Gly Ile Ala Asn
290 295 300

Leu Ile Val Met Ser Met Val Glu Asn Gly Leu Ser Glu Gln Glu Ala
305 310 315 320

Gln Lys Lys Ile Trp Met Phe Asp Lys Tyr Gly Leu Leu Val Lys Gly
325 330 335

Arg Lys Ala Lys Ile Asp Ser Tyr Gln Glu Pro Phe Thr His Ser Ala

```
            340                 345                 350

Pro Glu Ser Ile Pro Asp Thr Phe Glu Asp Ala Val Asn Ile Leu Lys
        355                 360                 365

Pro Ser Thr Ile Ile Gly Val Ala Gly Ala Gly Arg Leu Phe Thr Pro
    370                 375                 380

Asp Val Ile Arg Ala Met Ala Ser Ile Asn Glu Arg Pro Val Ile Phe
385                 390                 395                 400

Ala Leu Ser Asn Pro Thr Ala Gln Ala Glu Cys Thr Ala Glu Glu Ala
                405                 410                 415

Tyr Thr Leu Thr Glu Gly Arg Cys Leu Phe Ala Ser Gly Ser Pro Phe
            420                 425                 430

Gly Pro Val Lys Leu Thr Asp Gly Arg Val Phe Thr Pro Gly Gln Gly
        435                 440                 445

Asn Asn Val Tyr Ile Phe Pro Gly Val Ala Leu Ala Val Ile Leu Cys
    450                 455                 460

Asn Thr Arg His Ile Ser Asp Ser Val Phe Leu Glu Ala Ala Lys Ala
465                 470                 475                 480

Leu Thr Ser Gln Leu Thr Asp Glu Glu Leu Ala Gln Gly Arg Leu Tyr
                485                 490                 495

Pro Pro Leu Ala Asn Ile Gln Glu Val Ser Ile Asn Ile Ala Ile Lys
            500                 505                 510

Val Thr Glu Tyr Leu Tyr Ala Asn Lys Met Ala Phe Arg Tyr Pro Glu
        515                 520                 525

Pro Glu Asp Lys Ala Lys Tyr Val Lys Glu Arg Thr Trp Arg Ser Glu
    530                 535                 540

Tyr Asp Ser Leu Leu Pro Asp Val Tyr Glu Trp Pro Glu Ser Ala Ser
545                 550                 555                 560

Ser Pro Pro Val Ile Thr Glu
                565


<210> SEQ ID NO 27
<211> LENGTH: 572
<212> TYPE: PRT
<213> ORGANISM: Rattus norvegicus

<400> SEQUENCE: 27

Met Asp Pro Arg Ala Pro Arg Arg Arg His Thr His Gln Arg Gly Tyr
1               5                   10                  15

Leu Leu Thr Arg Asp Pro His Leu Asn Lys Asp Leu Ala Phe Thr Leu
            20                  25                  30

Glu Glu Arg Gln Gln Leu Lys Ile His Gly Leu Leu Pro Pro Cys Ile
        35                  40                  45

Val Asn Gln Glu Ile Gln Val Leu Arg Val Ile Lys Asn Phe Glu Arg
    50                  55                  60

Leu Asn Ser Asp Phe Asp Arg Tyr Leu Leu Leu Met Asp Leu Gln Asp
65                  70                  75                  80

Arg Asn Glu Lys Leu Phe Tyr Ser Val Leu Met Ser Asn Val Glu Lys
                85                  90                  95

Phe Met Pro Ile Val Tyr Thr Pro Thr Val Gly Leu Ala Cys Gln Gln
            100                 105                 110

Tyr Ser Leu Ala Phe Arg Lys Pro Arg Gly Leu Phe Ile Ser Ile His
        115                 120                 125

Asp Lys Gly His Ile Ala Ser Val Leu Asn Ala Trp Pro Glu Asp Val
    130                 135                 140
```

-continued

```
Val Lys Ala Ile Val Val Thr Asp Gly Glu Arg Ile Leu Gly Leu Gly
145                 150                 155                 160

Asp Leu Gly Cys Asn Gly Met Gly Ile Pro Val Gly Lys Leu Ala Leu
                165                 170                 175

Tyr Thr Ala Cys Gly Gly Val Asn Pro Gln Gln Cys Leu Pro Ile Thr
            180                 185                 190

Leu Asp Val Gly Thr Glu Asn Glu Glu Leu Leu Lys Asp Pro Leu Tyr
        195                 200                 205

Ile Gly Leu Arg His Arg Arg Val Arg Gly Pro Glu Tyr Asp Ala Phe
    210                 215                 220

Leu Asp Glu Phe Met Glu Ala Ala Ser Ser Lys Tyr Gly Met Asn Cys
225                 230                 235                 240

Leu Ile Gln Phe Glu Asp Phe Ala Asn Leu Asn Ala Phe Arg Leu Leu
                245                 250                 255

Asn Lys Tyr Arg Asn Lys Tyr Cys Thr Phe Asn Asp Asp Ile Gln Gly
            260                 265                 270

Thr Ala Ser Val Ala Val Ala Gly Leu Leu Ala Ala Leu Arg Ile Thr
        275                 280                 285

Lys Asn Lys Leu Ser Asp Gln Thr Val Leu Phe Gln Gly Ala Gly Glu
    290                 295                 300

Ala Ala Leu Gly Ile Ala His Leu Ile Val Met Ala Met Glu Lys Glu
305                 310                 315                 320

Gly Leu Ser Lys Glu Lys Ala Arg Gln Lys Ile Trp Leu Val Asp Ser
                325                 330                 335

Lys Gly Leu Ile Val Lys Gly Arg Ala Ser Leu Thr Glu Glu Lys Glu
            340                 345                 350

Val Phe Ala His Glu His Glu Glu Met Lys Asn Leu Glu Ala Ile Val
        355                 360                 365

Gln Lys Ile Lys Pro Thr Ala Leu Ile Gly Val Ala Ala Ile Gly Gly
    370                 375                 380

Ala Phe Thr Glu Gln Ile Leu Lys Asp Met Ala Ala Phe Asn Glu Arg
385                 390                 395                 400

Pro Ile Ile Phe Ala Leu Ser Asn Pro Thr Ser Lys Ala Glu Cys Ser
                405                 410                 415

Ala Glu Glu Cys Tyr Lys Val Thr Lys Gly Arg Ala Ile Phe Ala Ser
            420                 425                 430

Gly Ser Pro Phe Asp Pro Val Thr Leu Pro Asp Gly Arg Thr Leu Phe
        435                 440                 445

Pro Gly Gln Gly Asn Asn Ser Tyr Val Phe Pro Gly Val Ala Leu Gly
    450                 455                 460

Val Val Ala Cys Gly Leu Arg His Ile Asn Asp Ser Val Phe Leu Thr
465                 470                 475                 480

Thr Ala Glu Val Ile Ser Gln Gln Val Ser Asp Lys His Leu Glu Glu
                485                 490                 495

Gly Arg Leu Tyr Pro Pro Leu Asn Thr Ile Arg Asp Val Ser Leu Lys
            500                 505                 510

Ile Ala Val Lys Ile Val Gln Asp Ala Tyr Lys Glu Lys Met Ala Thr
        515                 520                 525

Val Tyr Pro Glu Pro Gln Asn Lys Glu Glu Phe Val Ser Ser Gln Met
    530                 535                 540

Tyr Ser Thr Asn Tyr Asp Gln Ile Leu Pro Asp Cys Tyr Ser Trp Pro
545                 550                 555                 560

Glu Glu Val Gln Lys Ile Gln Thr Lys Val Asn Gln
```

565 570

<210> SEQ ID NO 28
<211> LENGTH: 572
<212> TYPE: PRT
<213> ORGANISM: Mus musculus

<400> SEQUENCE: 28

Met Glu Pro Arg Ala Pro Arg Arg Arg His Thr His Gln Arg Gly Tyr
1 5 10 15

Leu Leu Thr Arg Asp Pro His Leu Asn Lys Asp Leu Ala Phe Thr Leu
20 25 30

Glu Glu Arg Gln Gln Leu Asn Ile His Gly Leu Leu Pro Pro Cys Ile
35 40 45

Ile Ser Gln Glu Leu Gln Val Leu Arg Ile Ile Lys Asn Phe Glu Arg
50 55 60

Leu Asn Ser Asp Phe Asp Arg Tyr Leu Leu Leu Met Asp Leu Gln Asp
65 70 75 80

Arg Asn Glu Lys Leu Phe Tyr Ser Val Leu Met Ser Asp Val Glu Lys
85 90 95

Phe Met Pro Ile Val Tyr Thr Pro Thr Val Gly Leu Ala Cys Gln Gln
100 105 110

Tyr Ser Leu Ala Phe Arg Lys Pro Arg Gly Leu Phe Ile Ser Ile His
115 120 125

Asp Lys Gly His Ile Ala Ser Val Leu Asn Ala Trp Pro Glu Asp Val
130 135 140

Val Lys Ala Ile Val Val Thr Asp Gly Glu Arg Ile Leu Gly Leu Gly
145 150 155 160

Asp Leu Gly Cys Asn Gly Met Gly Ile Pro Val Gly Lys Leu Ala Leu
165 170 175

Tyr Thr Ala Cys Gly Gly Val Asn Pro Gln Gln Cys Leu Pro Ile Thr
180 185 190

Leu Asp Val Gly Thr Glu Asn Glu Glu Leu Leu Lys Asp Pro Leu Tyr
195 200 205

Ile Gly Leu Arg His Arg Arg Val Arg Gly Pro Glu Tyr Asp Ala Phe
210 215 220

Leu Asp Glu Phe Met Glu Ala Ala Ser Ser Lys Tyr Gly Met Asn Cys
225 230 235 240

Leu Ile Gln Phe Glu Asp Phe Ala Asn Arg Asn Ala Phe Arg Leu Leu
245 250 255

Asn Lys Tyr Arg Asn Lys Tyr Cys Thr Phe Asn Asp Asp Ile Gln Gly
260 265 270

Thr Ala Ser Val Ala Val Ala Gly Leu Leu Ala Ala Leu Arg Ile Thr
275 280 285

Lys Asn Lys Leu Ser Asp Gln Thr Val Leu Phe Gln Gly Ala Gly Glu
290 295 300

Ala Ala Leu Gly Ile Ala His Leu Val Val Met Ala Met Glu Lys Glu
305 310 315 320

Gly Leu Ser Lys Glu Asn Ala Arg Lys Lys Ile Trp Leu Val Asp Ser
325 330 335

Lys Gly Leu Ile Val Lys Gly Arg Ala Ser Leu Thr Glu Glu Lys Glu
340 345 350

Val Phe Ala His Glu His Glu Glu Met Lys Asn Leu Glu Ala Ile Val
355 360 365

```
Gln Lys Ile Lys Pro Thr Ala Leu Ile Gly Val Ala Ala Ile Gly Gly
    370                 375                 380

Ala Phe Thr Glu Gln Ile Leu Lys Asp Met Ala Ala Phe Asn Glu Arg
385                 390                 395                 400

Pro Ile Ile Phe Ala Leu Ser Asn Pro Thr Ser Lys Ala Glu Cys Ser
                405                 410                 415

Ala Glu Gln Cys Tyr Lys Val Thr Lys Gly Arg Ala Ile Phe Ala Ser
            420                 425                 430

Gly Ser Pro Phe Asp Pro Val Thr Leu Pro Asp Gly Arg Thr Leu Phe
        435                 440                 445

Pro Gly Gln Gly Asn Asn Ser Tyr Val Phe Pro Gly Val Ala Leu Gly
    450                 455                 460

Val Val Ala Cys Gly Leu Arg His Ile Asp Asp Lys Val Phe Leu Thr
465                 470                 475                 480

Thr Ala Glu Val Ile Ser Gln Gln Val Ser Asp Lys His Leu Gln Glu
                485                 490                 495

Gly Arg Leu Tyr Pro Pro Leu Asn Thr Ile Arg Gly Val Ser Leu Lys
            500                 505                 510

Ile Ala Val Lys Ile Val Gln Asp Ala Tyr Lys Glu Lys Met Ala Thr
        515                 520                 525

Val Tyr Pro Glu Pro Gln Asn Lys Glu Glu Phe Val Ser Ser Gln Met
    530                 535                 540

Tyr Ser Thr Asn Tyr Asp Gln Ile Leu Pro Asp Cys Tyr Pro Trp Pro
545                 550                 555                 560

Ala Glu Val Gln Lys Ile Gln Thr Lys Val Asn Gln
                565                 570


<210> SEQ ID NO 29
<211> LENGTH: 565
<212> TYPE: PRT
<213> ORGANISM: Escherichia coli

<400> SEQUENCE: 29

Met Glu Pro Lys Thr Lys Lys Gln Arg Ser Leu Tyr Ile Pro Tyr Ala
1               5                   10                  15

Gly Pro Val Leu Leu Glu Phe Pro Leu Leu Asn Lys Gly Ser Ala Phe
            20                  25                  30

Ser Met Glu Glu Arg Arg Asn Phe Asn Leu Leu Gly Leu Leu Pro Glu
        35                  40                  45

Val Val Glu Thr Ile Glu Glu Gln Ala Glu Arg Ala Trp Ile Gln Tyr
    50                  55                  60

Gln Gly Phe Lys Thr Glu Ile Asp Lys His Ile Tyr Leu Arg Asn Ile
65                  70                  75                  80

Gln Asp Thr Asn Glu Thr Leu Phe Tyr Arg Leu Val Asn Asn His Leu
                85                  90                  95

Asp Glu Met Met Pro Val Ile Tyr Thr Pro Thr Val Gly Ala Ala Cys
            100                 105                 110

Glu Arg Phe Ser Glu Ile Tyr Arg Arg Ser Arg Gly Val Phe Ile Ser
        115                 120                 125

Tyr Gln Asn Arg His Asn Met Asp Asp Ile Leu Gln Asn Val Pro Asn
    130                 135                 140

His Asn Ile Lys Val Ile Val Val Thr Asp Gly Glu Arg Ile Leu Gly
145                 150                 155                 160

Leu Gly Asp Gln Gly Ile Gly Gly Met Gly Ile Pro Ile Gly Lys Leu
                165                 170                 175
```

```
Ser Leu Tyr Thr Ala Cys Gly Gly Ile Ser Pro Ala Tyr Thr Leu Pro
            180                 185                 190

Val Val Leu Asp Val Gly Thr Asn Asn Gln Gln Leu Leu Asn Asp Pro
        195                 200                 205

Leu Tyr Met Gly Trp Arg Asn Pro Arg Ile Thr Asp Asp Glu Tyr Tyr
    210                 215                 220

Glu Phe Val Asp Glu Phe Ile Gln Ala Val Lys Gln Arg Trp Pro Asp
225                 230                 235                 240

Val Leu Leu Gln Phe Glu Asp Phe Ala Gln Lys Asn Ala Met Pro Leu
                245                 250                 255

Leu Asn Arg Tyr Arg Asn Glu Ile Cys Ser Phe Asn Asp Asp Ile Gln
            260                 265                 270

Gly Thr Ala Ala Val Thr Val Gly Thr Leu Ile Ala Ala Ser Arg Ala
        275                 280                 285

Ala Gly Gly Gln Leu Ser Glu Lys Lys Ile Val Phe Leu Gly Ala Gly
    290                 295                 300

Ser Ala Gly Cys Gly Ile Ala Glu Met Ile Ile Ser Gln Thr Gln Arg
305                 310                 315                 320

Glu Gly Leu Ser Glu Glu Ala Ala Arg Gln Lys Val Phe Met Val Asp
                325                 330                 335

Arg Phe Gly Leu Leu Thr Asp Lys Met Pro Asn Leu Leu Pro Phe Gln
            340                 345                 350

Thr Lys Leu Val Gln Lys Arg Glu Asn Leu Ser Asp Trp Asp Thr Asp
        355                 360                 365

Ser Asp Val Leu Ser Leu Leu Asp Val Val Arg Asn Val Lys Pro Asp
    370                 375                 380

Ile Leu Ile Gly Val Ser Gly Gln Thr Gly Leu Phe Thr Glu Glu Ile
385                 390                 395                 400

Ile Arg Glu Met His Lys His Cys Pro Arg Pro Ile Val Met Pro Leu
                405                 410                 415

Ser Asn Pro Thr Ser Arg Val Glu Ala Thr Pro Gln Asp Ile Ile Ala
            420                 425                 430

Trp Thr Glu Gly Asn Ala Leu Val Ala Thr Gly Ser Pro Phe Asn Pro
        435                 440                 445

Val Val Trp Lys Asp Lys Ile Tyr Pro Ile Ala Gln Cys Asn Asn Ala
    450                 455                 460

Phe Ile Phe Pro Gly Ile Gly Leu Gly Val Ile Ala Ser Gly Ala Ser
465                 470                 475                 480

Arg Ile Thr Asp Glu Met Leu Met Ser Ala Ser Glu Thr Leu Ala Gln
                485                 490                 495

Tyr Ser Pro Leu Val Leu Asn Gly Glu Gly Met Val Leu Pro Glu Leu
            500                 505                 510

Lys Asp Ile Gln Lys Val Ser Arg Ala Ile Ala Phe Ala Val Gly Lys
        515                 520                 525

Met Ala Gln Gln Gln Gly Val Ala Val Lys Thr Ser Ala Glu Ala Leu
    530                 535                 540

Gln Gln Ala Ile Asp Asp Asn Phe Trp Gln Ala Glu Tyr Arg Asp Tyr
545                 550                 555                 560

Arg Arg Thr Ser Ile
                565
```

<210> SEQ ID NO 30
<211> LENGTH: 366

<212> TYPE: PRT
<213> ORGANISM: Yarrowia lipolytica

<400> SEQUENCE: 30

```
Met Leu Arg Thr Ala Tyr Leu Ala Lys Ala Ala Ser Ala Leu Pro Lys
1               5                   10                  15

Arg Thr Leu Ala Thr Asn Ala Arg Thr Met Phe Gln Pro Lys Glu Tyr
            20                  25                  30

Gly Ser Lys Tyr Thr Val Thr Leu Ile Pro Gly Asp Gly Ile Gly Asn
        35                  40                  45

Glu Ile Thr Asp Ala Val Lys Thr Ile Phe Lys Thr Ile Ser Val Pro
    50                  55                  60

Ile Asp Trp Glu Val Val Asn Val Thr Gly Val Gly Glu Asn His Leu
65                  70                  75                  80

Asp Gly Tyr Glu Glu Ala Ile Arg Ser Ile Asn Arg Asn Lys Val Ala
                85                  90                  95

Ile Lys Gly Ile Leu His Thr Pro Val Glu Lys His Gly His Thr Ser
            100                 105                 110

Phe Asn Val Ala Leu Arg Arg Glu Leu Asp Ile Phe Ala Ser Leu Val
        115                 120                 125

Leu Ile Lys Asn Ile Pro Gly Val Gln Thr Arg Leu Asp Gly Ile Asp
    130                 135                 140

Met Ala Leu Ile Arg Glu Asn Thr Glu Gly Glu Tyr Ser Gly Leu Glu
145                 150                 155                 160

His Ser Pro Val Pro Gly Val Val Glu Ser Ile Lys Val Ile Thr Lys
                165                 170                 175

Arg Lys Ser Glu Arg Ile Ala Arg Phe Ala Phe Asp Phe Ala Leu Lys
            180                 185                 190

Asn Asn Arg His Lys Val Thr Ala Ile His Lys Ala Asn Ile Met Lys
        195                 200                 205

Leu Ala Asp Gly Leu Phe Arg Asn Thr Cys Lys Glu Val Ser Ala Glu
    210                 215                 220

Tyr Pro Glu Ile Gln Tyr Gly Asp Met Ile Val Asp Asn Ala Ser Met
225                 230                 235                 240

Gln Ala Val Ser Trp Pro Gln Gln Phe Asp Val Leu Val Thr Pro Asn
                245                 250                 255

Leu Tyr Gly Thr Ile Leu Ser Asn Ile Gly Ala Gly Leu Val Gly Gly
            260                 265                 270

Pro Gly Leu Val Pro Gly Val Asn Leu Gly Thr Glu His Ala Val Phe
        275                 280                 285

Glu Pro Gly Cys Arg His Val Gly Leu Asp Ile Lys Gly Arg Gly Thr
    290                 295                 300

Ala Asn Pro Thr Ala Met Ile Leu Ser Ser Ala Met Leu Leu Arg His
305                 310                 315                 320

Leu Asn Leu Asp Asp Phe Ala Asp Val Ile Ser Lys Ala Thr Tyr Asp
                325                 330                 335

Val Leu Ala Glu Gly Gln Val Arg Thr Pro Asp Leu Gly Gly Asn Ser
            340                 345                 350

Thr Thr Asp Glu Phe Thr Met Ala Val Ile Asn Lys Leu Gln
        355                 360                 365
```

<210> SEQ ID NO 31
<211> LENGTH: 146
<212> TYPE: PRT
<213> ORGANISM: Saccharomyces cerevisiae

<400> SEQUENCE: 31

Met Ser Ala Ser Ala Phe Asn Phe Ala Phe Arg Arg Phe Trp Asn Ser
1 5 10 15

Glu Thr Gly Pro Lys Thr Val His Phe Trp Ala Pro Thr Leu Lys Trp
20 25 30

Gly Leu Val Phe Ala Gly Leu Asn Asp Ile Lys Arg Pro Val Glu Lys
35 40 45

Val Ser Gly Ala Gln Asn Leu Ser Leu Leu Ala Thr Ala Leu Ile Trp
50 55 60

Thr Arg Trp Ser Phe Val Ile Lys Pro Lys Asn Tyr Leu Leu Ala Ser
65 70 75 80

Val Asn Phe Phe Leu Gly Cys Thr Ala Gly Tyr His Leu Thr Arg Ile
85 90 95

Ala Asn Phe Arg Ile Arg Asn Gly Asp Ser Phe Lys Gln Val Ile His
100 105 110

Tyr Ile Ile Lys Gly Glu Thr Pro Ala Ala Val Ala Ala Lys Gln Thr
115 120 125

Ala Ser Thr Ser Met Asn Lys Gly Val Ile Gly Thr Asn Pro Pro Ile
130 135 140

Thr His
145

<210> SEQ ID NO 32
<211> LENGTH: 338
<212> TYPE: PRT
<213> ORGANISM: Helicoverpa zea

<400> SEQUENCE: 32

Met Ala Gln Ser Tyr Gln Ser Thr Thr Val Leu Ser Glu Glu Lys Glu
1 5 10 15

Leu Thr Leu Gln His Leu Val Pro Gln Ala Ser Pro Arg Lys Tyr Gln
20 25 30

Ile Val Tyr Pro Asn Leu Ile Thr Phe Gly Tyr Trp His Ile Ala Gly
35 40 45

Leu Tyr Gly Leu Tyr Leu Cys Phe Thr Ser Ala Lys Trp Ala Thr Ile
50 55 60

Leu Phe Ser Tyr Ile Leu Phe Val Leu Ala Glu Ile Gly Ile Thr Ala
65 70 75 80

Gly Ala His Arg Leu Trp Ala His Lys Thr Tyr Lys Ala Lys Leu Pro
85 90 95

Leu Glu Ile Leu Leu Met Val Phe Asn Ser Ile Ala Phe Gln Asn Ser
100 105 110

Ala Ile Asp Trp Val Arg Asp His Arg Leu His His Lys Tyr Ser Asp
115 120 125

Thr Asp Ala Asp Pro His Asn Ala Ser Arg Gly Phe Phe Tyr Ser His
130 135 140

Val Gly Trp Leu Leu Val Arg Lys His Pro Glu Val Lys Lys Arg Gly
145 150 155 160

Lys Glu Leu Asn Met Ser Asp Ile Tyr Asn Asn Pro Val Leu Arg Phe
165 170 175

Gln Lys Lys Tyr Ala Ile Pro Phe Ile Gly Ala Val Cys Phe Ala Leu
180 185 190

Pro Thr Met Ile Pro Val Tyr Phe Trp Gly Glu Thr Trp Ser Asn Ala
195 200 205

```
Trp His Ile Thr Met Leu Arg Tyr Ile Met Asn Leu Asn Val Thr Phe
    210                 215                 220

Leu Val Asn Ser Ala Ala His Ile Trp Gly Asn Lys Pro Tyr Asp Ala
225                 230                 235                 240

Lys Ile Leu Pro Ala Gln Asn Val Ala Val Ser Val Ala Thr Gly Gly
                245                 250                 255

Glu Gly Phe His Asn Tyr His His Val Phe Pro Trp Asp Tyr Arg Ala
            260                 265                 270

Ala Glu Leu Gly Asn Asn Ser Leu Asn Leu Thr Thr Lys Phe Ile Asp
        275                 280                 285

Leu Phe Ala Ala Ile Gly Trp Ala Tyr Asp Leu Lys Thr Val Ser Glu
    290                 295                 300

Asp Met Ile Lys Gln Arg Ile Lys Arg Thr Gly Asp Gly Thr Asp Leu
305                 310                 315                 320

Trp Gly His Glu Gln Asn Cys Asp Glu Val Trp Asp Val Lys Asp Lys
                325                 330                 335

Ser Ser


<210> SEQ ID NO 33
<211> LENGTH: 353
<212> TYPE: PRT
<213> ORGANISM: Helicoverpa zea

<400> SEQUENCE: 33

Met Ala Pro Asn Ile Ser Glu Asp Val Asn Gly Val Leu Phe Glu Ser
1               5                   10                  15

Asp Ala Ala Thr Pro Asp Leu Ala Leu Ser Thr Pro Pro Val Gln Lys
            20                  25                  30

Ala Asp Asn Arg Pro Lys Gln Leu Val Trp Arg Asn Ile Leu Leu Phe
        35                  40                  45

Ala Tyr Leu His Leu Ala Ala Leu Tyr Gly Gly Tyr Leu Phe Leu Phe
    50                  55                  60

Ser Ala Lys Trp Gln Thr Asp Ile Phe Ala Tyr Ile Leu Tyr Val Ile
65                  70                  75                  80

Ser Gly Leu Gly Ile Thr Ala Gly Ala His Arg Leu Trp Ala His Lys
                85                  90                  95

Ser Tyr Lys Ala Lys Trp Pro Leu Arg Val Ile Leu Val Ile Phe Asn
            100                 105                 110

Thr Val Ala Phe Gln Asp Ala Ala Met Asp Trp Ala Arg Asp His Arg
        115                 120                 125

Met His His Lys Tyr Ser Glu Thr Asp Ala Asp Pro His Asn Ala Thr
    130                 135                 140

Arg Gly Phe Phe Phe Ser His Ile Gly Trp Leu Leu Val Arg Lys His
145                 150                 155                 160

Pro Asp Leu Lys Glu Lys Gly Lys Gly Leu Asp Met Ser Asp Leu Leu
                165                 170                 175

Ala Asp Pro Ile Leu Arg Phe Gln Lys Lys Tyr Tyr Leu Ile Leu Met
            180                 185                 190

Pro Leu Ala Cys Phe Val Met Pro Thr Val Ile Pro Val Tyr Phe Trp
        195                 200                 205

Gly Glu Thr Trp Thr Asn Ala Phe Phe Val Ala Ala Met Phe Arg Tyr
    210                 215                 220

Ala Phe Ile Leu Asn Val Thr Trp Leu Val Asn Ser Ala Ala His Lys
225                 230                 235                 240
```

Trp Gly Asp Lys Pro Tyr Asp Lys Ser Ile Lys Pro Ser Glu Asn Leu
245 250 255

Ser Val Ala Met Phe Ala Leu Gly Glu Gly Phe His Asn Tyr His His
260 265 270

Thr Phe Pro Trp Asp Tyr Lys Thr Ala Glu Leu Gly Asn Asn Lys Leu
275 280 285

Asn Phe Thr Thr Thr Phe Ile Asn Phe Phe Ala Lys Ile Gly Trp Ala
290 295 300

Tyr Asp Leu Lys Thr Val Ser Asp Asp Ile Val Lys Asn Arg Val Lys
305 310 315 320

Arg Thr Gly Asp Gly Ser His His Leu Trp Gly Trp Gly Asp Glu Asn
325 330 335

Gln Ser Lys Glu Glu Ile Asp Ala Ala Ile Arg Ile Asn Pro Lys Asp
340 345 350

Asp

<210> SEQ ID NO 34
<211> LENGTH: 623
<212> TYPE: PRT
<213> ORGANISM: Arabidopsis thaliana

<400> SEQUENCE: 34

Met Gly Ile Ala Asn Lys Leu Arg Leu Ser Ser Ser Ser Leu Ser Arg
1 5 10 15

Ile Leu His Arg Arg Ile Leu Tyr Ser Ser Ala Val Arg Ser Phe Thr
20 25 30

Thr Ser Glu Gly His Arg Pro Thr Ile Val His Lys Gln Gly Leu Asp
35 40 45

Ile Leu His Asp Pro Trp Phe Asn Lys Gly Thr Ala Phe Thr Met Thr
50 55 60

Glu Arg Asn Arg Leu Asp Leu Arg Gly Leu Leu Pro Pro Asn Val Met
65 70 75 80

Asp Ser Glu Gln Gln Ile Phe Arg Phe Met Thr Asp Leu Lys Arg Leu
85 90 95

Glu Glu Gln Ala Arg Asp Gly Pro Ser Asp Pro Asn Ala Leu Ala Lys
100 105 110

Trp Arg Ile Leu Asn Arg Leu His Asp Arg Asn Glu Thr Met Tyr Tyr
115 120 125

Lys Val Leu Ile Asn Asn Ile Glu Glu Tyr Ala Pro Ile Val Tyr Thr
130 135 140

Pro Thr Val Gly Leu Val Cys Gln Asn Tyr Ser Gly Leu Phe Arg Arg
145 150 155 160

Pro Arg Gly Met Tyr Phe Ser Ala Glu Asp Arg Gly Glu Met Met Ser
165 170 175

Met Val Tyr Asn Trp Pro Ala Glu Gln Val Asp Met Ile Val Val Thr
180 185 190

Asp Gly Ser Arg Ile Leu Gly Leu Gly Asp Leu Gly Val His Gly Ile
195 200 205

Gly Ile Ala Val Gly Lys Leu Asp Leu Tyr Val Ala Ala Ala Gly Ile
210 215 220

Asn Pro Gln Arg Val Leu Pro Val Met Ile Asp Val Gly Thr Asn Asn
225 230 235 240

Glu Lys Leu Arg Asn Asp Pro Met Tyr Leu Gly Leu Gln Gln Arg Arg
245 250 255

```
Leu Glu Asp Asp Asp Tyr Ile Asp Val Ile Asp Glu Phe Met Glu Ala
            260                 265                 270

Val Tyr Thr Arg Trp Pro His Val Ile Val Gln Phe Glu Asp Phe Gln
        275                 280                 285

Ser Lys Trp Ala Phe Lys Leu Leu Gln Arg Tyr Arg Cys Thr Tyr Arg
    290                 295                 300

Met Phe Asn Asp Asp Val Gln Gly Thr Ala Gly Val Ala Ile Ala Gly
305                 310                 315                 320

Leu Leu Gly Ala Val Arg Ala Gln Gly Arg Pro Met Ile Asp Phe Pro
                325                 330                 335

Lys Met Lys Ile Val Val Ala Gly Ala Gly Ser Ala Gly Ile Gly Val
            340                 345                 350

Leu Asn Ala Ala Arg Lys Thr Met Ala Arg Met Leu Gly Asn Thr Glu
        355                 360                 365

Thr Ala Phe Asp Ser Ala Gln Ser Gln Phe Trp Val Val Asp Ala Gln
    370                 375                 380

Gly Leu Ile Thr Glu Gly Arg Glu Asn Ile Asp Pro Glu Ala Gln Pro
385                 390                 395                 400

Phe Ala Arg Lys Thr Lys Glu Met Glu Arg Gln Gly Leu Lys Glu Gly
                405                 410                 415

Ala Thr Leu Val Glu Val Val Arg Glu Val Lys Pro Asp Val Leu Leu
            420                 425                 430

Gly Leu Ser Ala Val Gly Gly Leu Phe Ser Lys Glu Val Leu Glu Ala
        435                 440                 445

Met Lys Gly Ser Thr Ser Thr Arg Pro Ala Ile Phe Ala Met Ser Asn
    450                 455                 460

Pro Thr Lys Asn Ala Glu Cys Thr Pro Gln Asp Ala Phe Ser Ile Leu
465                 470                 475                 480

Gly Glu Asn Met Ile Phe Ala Ser Gly Ser Pro Phe Lys Asn Val Glu
                485                 490                 495

Phe Gly Asn Gly His Val Gly His Cys Asn Gln Gly Asn Asn Met Tyr
            500                 505                 510

Leu Phe Pro Gly Ile Gly Leu Gly Thr Leu Leu Ser Gly Ala Pro Ile
        515                 520                 525

Val Ser Asp Gly Met Leu Gln Ala Ala Ser Glu Cys Leu Ala Ala Tyr
    530                 535                 540

Met Ser Glu Glu Glu Val Leu Glu Gly Ile Ile Tyr Pro Pro Ile Ser
545                 550                 555                 560

Arg Ile Arg Asp Ile Thr Lys Arg Ile Ala Ala Ala Val Ile Lys Glu
                565                 570                 575

Ala Ile Glu Glu Asp Leu Val Glu Gly Tyr Arg Glu Met Asp Ala Arg
            580                 585                 590

Glu Ile Gln Lys Leu Asp Glu Glu Gly Leu Met Glu Tyr Val Glu Asn
        595                 600                 605

Asn Met Trp Asn Pro Glu Tyr Pro Thr Leu Val Tyr Lys Asp Asp
    610                 615                 620


<210> SEQ ID NO 35
<211> LENGTH: 623
<212> TYPE: PRT
<213> ORGANISM: Amaranthus hypochondriacus

<400> SEQUENCE: 35

Met Leu Val Leu Cys Ser Arg Ser Arg Leu Thr Ser Ser Leu Ile Arg
```

-continued

```
1               5                   10                  15

Arg Leu Lys Asp Gln Ile Ala Asn Val Ser Asn His Arg Ser Phe Ala
            20                  25                  30

Thr Ser Glu Gly His Arg Leu Ala Ile Val Asn Lys Arg Ser Leu Asp
        35                  40                  45

Ile Leu Gln Asp Pro Trp Phe Asn Lys Gly Thr Ala Phe Ser Met Thr
    50                  55                  60

Glu Arg Asp Arg Leu Asp Leu Arg Gly Leu Leu Pro Pro Asn Val Met
65                  70                  75                  80

Thr Thr Glu Gln Gln Ile Glu Arg Phe Thr Ala Asp Leu Arg Val Leu
                85                  90                  95

Glu Leu Thr Thr Lys Asp Gly Pro Ser Asp Thr Tyr Asp Leu Ala Lys
            100                 105                 110

Trp Arg Ile Leu Asn Arg Leu His Asp Arg Asn Glu Thr Met Phe Phe
        115                 120                 125

Lys Val Leu Ile Glu Asn Ile Glu Glu Tyr Ala Pro Ile Val Ser Thr
    130                 135                 140

Pro Thr Val Gly Leu Val Cys Gln Lys Phe Ser Gly Leu Tyr Arg Arg
145                 150                 155                 160

Pro Arg Gly Met Tyr Phe Ser Ser Asp Asp Arg Gly Glu Met Met Ser
                165                 170                 175

Met Val Tyr Asn Trp Pro Ala Glu Gln Val Asp Met Ile Val Val Thr
            180                 185                 190

Asp Gly Ser Arg Ile Leu Gly Leu Gly Asp Leu Gly Val His Gly Ile
        195                 200                 205

Gly Val Ala Ile Gly Lys Leu Asp Leu Tyr Val Ala Ala Ala Gly Ile
    210                 215                 220

Asn Pro Gln Arg Val Leu Pro Val Met Ile Asp Val Gly Thr Asn Asn
225                 230                 235                 240

Glu Asp Leu Leu Lys Asn Pro Leu Tyr Leu Gly Leu Gln Lys Lys Arg
                245                 250                 255

Leu Asp Gly Glu Glu Tyr Leu Ala Val Met Asp Glu Phe Met Glu Ala
            260                 265                 270

Val Phe Thr Arg Trp Pro Asn Val Ile Val Gln Phe Glu Asp Ile Gln
        275                 280                 285

Asn Lys Trp Ala Leu Thr Leu Leu Gln Arg Tyr Arg His Lys Tyr Arg
    290                 295                 300

Thr Phe Asn Val Asp Val Gln Gly Thr Ser Gly Val Ala Ile Ala Gly
305                 310                 315                 320

Leu Leu Gly Ala Val Arg Ala Gln Gly Arg Pro Met Ile Asp Phe Pro
                325                 330                 335

Lys Gln Lys Ile Val Val Ala Gly Ala Gly Ser Ser Gly Val Gly Val
            340                 345                 350

Leu Asn Ala Ala Arg Lys Thr Met Ala Arg Met Leu Gly Asn Asp Glu
        355                 360                 365

Ser Ala Phe Asp Arg Ala Arg Ser Gln Phe Trp Val Val Asp Asp Lys
    370                 375                 380

Gly Leu Ile Thr Glu Lys Arg Ala Asn Leu Asp Pro Glu Val Gln Pro
385                 390                 395                 400

Phe Ala Trp Lys Glu Asn Glu Ile Ser Leu Gln Gly Leu Asn Glu Gly
                405                 410                 415

Ala Lys Leu Val Glu Val Val Arg Gln Val Lys Pro Asp Val Leu Leu
            420                 425                 430
```

```
Gly Leu Ser Ala Tyr Gly Gly Leu Phe Ser Lys Glu Val Leu Glu Ala
        435                 440                 445

Leu Lys Asp Ser Thr Ser Thr Arg Pro Ala Ile Phe Ala Met Ser Asn
    450                 455                 460

Pro Thr Lys Asn Ala Glu Cys Thr Pro Glu Glu Ala Phe Ser Ile Val
465                 470                 475                 480

Gly Asp His Val Val Tyr Ala Ser Gly Ser Pro Phe Lys Asp Val Asp
                485                 490                 495

Leu Gly Asn Gly Lys Ile Gly His Val Asn Gln Gly Asn Asn Met Tyr
            500                 505                 510

Leu Phe Pro Gly Ile Gly Leu Gly Val Leu Leu Ser Gly Ser Arg Ile
        515                 520                 525

Ile Ser Asp Ser Met Phe Gln Ala Ala Ala Glu Arg Leu Ala Gly Tyr
    530                 535                 540

Met Thr Asp Glu Glu Val Ile Asn Gly Val Ile Tyr Pro Ser Ile Ser
545                 550                 555                 560

Arg Ile Arg Asp Ile Thr Lys Glu Val Ala Ala Ala Val Ile Lys Glu
                565                 570                 575

Ala Val Glu Glu Asp Leu Ala Glu Gly Tyr Arg Asp Met Asp Ala Arg
            580                 585                 590

Glu Leu Gln Lys Leu Asn Glu Glu Gln Ile Leu Glu Tyr Ile Glu Lys
        595                 600                 605

Asn Met Trp Asn Pro Glu Tyr Pro Thr Leu Val Tyr Lys Lys Arg
    610                 615                 620
```

<210> SEQ ID NO 36
<211> LENGTH: 770
<212> TYPE: PRT
<213> ORGANISM: Rhizobium meliloti

<400> SEQUENCE: 36

```
Met Asn Thr Gly Asp Lys Ala Lys Ser Gln Ala Val Pro Ala Ser Gly
1               5                   10                  15

Asp Ile Asp Gln Gln Ala Leu Phe Phe His Arg Tyr Pro Arg Pro Gly
            20                  25                  30

Lys Leu Glu Ile Gln Pro Thr Lys Pro Leu Gly Asn Gln Arg Asp Leu
        35                  40                  45

Ala Leu Ala Tyr Ser Pro Gly Val Ala Ala Pro Cys Leu Ala Ile Lys
    50                  55                  60

Asp Asn Pro Glu Thr Ala Ala Asp Phe Thr Ala Arg Ala Asn Leu Val
65                  70                  75                  80

Ala Val Val Ser Asn Gly Thr Ala Val Leu Gly Leu Gly Asn Ile Gly
                85                  90                  95

Pro Leu Ala Ser Lys Pro Val Met Glu Gly Lys Ala Val Leu Phe Lys
            100                 105                 110

Lys Phe Ala Gly Ile Asp Val Phe Asp Ile Glu Ile Asp Ala Pro Thr
        115                 120                 125

Val Asp Arg Met Val Asp Val Ile Ser Ala Leu Glu Pro Thr Phe Gly
    130                 135                 140

Gly Ile Asn Leu Glu Asp Ile Lys Ala Pro Glu Cys Phe Glu Val Glu
145                 150                 155                 160

Arg Arg Leu Arg Glu Lys Met Glu Ile Pro Val Phe His Asp Asp Gln
                165                 170                 175

His Gly Thr Ala Ile Ile Val Ala Ala Ala Val Leu Asn Gly Leu Glu
```

-continued

```
            180                 185                 190

Leu Ala Gly Lys Asp Ile Ala Glu Ala Lys Ile Val Ala Ser Gly Ala
        195                 200                 205

Gly Ala Ala Ala Leu Ala Cys Leu Asn Leu Leu Val Thr Leu Gly Ala
    210                 215                 220

Arg Arg Glu Asn Ile Trp Val His Asp Ile Glu Gly Leu Val Tyr Lys
225                 230                 235                 240

Gly Arg Glu Ala Leu Met Asp Glu Trp Lys Ala Val Tyr Ala Gln Glu
                245                 250                 255

Ser Asp Asn Arg Val Leu Ala Asp Ser Ile Gly Gly Ala Asp Val Phe
            260                 265                 270

Leu Gly Leu Ser Ala Ala Gly Val Leu Lys Pro Glu Leu Leu Ala Arg
        275                 280                 285

Met Ala Glu Lys Pro Leu Ile Met Ala Leu Ala Asn Pro Thr Pro Glu
    290                 295                 300

Ile Met Pro Glu Val Ala Arg Ala Ala Arg Pro Asp Ala Met Ile Cys
305                 310                 315                 320

Thr Gly Arg Ser Asp Phe Pro Asn Gln Val Asn Asn Val Leu Cys Phe
                325                 330                 335

Pro His Ile Phe Arg Gly Ala Leu Asp Cys Gly Ala Arg Thr Ile Asn
            340                 345                 350

Glu Glu Met Lys Met Ala Ala Val Arg Ala Ile Ala Gly Leu Ala Arg
        355                 360                 365

Glu Glu Pro Ser Asp Val Ala Ala Arg Ala Tyr Ser Gly Glu Thr Pro
    370                 375                 380

Val Phe Gly Pro Asp Tyr Leu Ile Pro Ser Pro Phe Asp Gln Arg Leu
385                 390                 395                 400

Ile Leu Arg Ile Ala Pro Ala Val Ala Lys Ala Ala Ala Glu Ser Gly
                405                 410                 415

Val Ala Thr Arg Pro Ile Gln Asp Phe Asp Ala Tyr Leu Asp Lys Leu
            420                 425                 430

Asn Arg Phe Val Phe Arg Ser Gly Phe Ile Met Lys Pro Val Phe Ala
        435                 440                 445

Ala Ala Lys Asn Ala Ala Lys Asn Arg Val Ile Phe Ala Glu Gly Glu
    450                 455                 460

Asp Glu Arg Val Leu Arg Ala Ala Gln Val Leu Leu Glu Glu Gly Thr
465                 470                 475                 480

Ala Lys Pro Ile Leu Ile Gly Arg Pro Gln Ile Ile Glu Thr Arg Leu
                485                 490                 495

Arg Arg Tyr Gly Leu Arg Ile Arg Pro Asp Val Asp Phe Glu Val Val
            500                 505                 510

Asn Pro Glu Gly Asp Pro Arg Tyr Arg Asp Tyr Val Asp Asp Tyr Phe
        515                 520                 525

Ala Leu Val Gly Arg Leu Gly Val Ile Pro Glu Ala Ala Arg Thr Ile
    530                 535                 540

Val Arg Thr Asn Thr Thr Val Ile Gly Ala Leu Ala Val Lys Arg Gly
545                 550                 555                 560

Glu Ala Asp Ala Leu Ile Cys Gly Val Glu Gly Arg Tyr Ser Arg His
                565                 570                 575

Leu Arg Asp Val Ser Gln Ile Ile Gly Lys Arg Ser Gly Val Leu Asp
            580                 585                 590

Phe Ser Ala Leu Ser Leu Leu Ile Ser Gln Arg Gly Ala Thr Phe Phe
        595                 600                 605
```

```
Thr Asp Thr Tyr Val Ser Phe Ser Pro Ser Ala Glu Glu Ile Ala Gln
    610                 615                 620

Thr Thr Val Met Ala Ala Asn Glu Ile Arg Arg Phe Gly Ile Thr Pro
625                 630                 635                 640

Arg Ala Ala Leu Val Ser His Ser Asn Phe Gly Ser Arg Asp Ser Glu
                645                 650                 655

Ser Ala Phe Lys Met Arg Thr Ala Leu Gln Leu Val Arg Glu Leu Ala
            660                 665                 670

Pro Asp Leu Glu Val Asp Gly Glu Met His Gly Asp Ser Ala Ile Ser
        675                 680                 685

Glu Val Leu Arg Gln Arg Val Met Pro Asp Ser Thr Leu Asn Gly Glu
    690                 695                 700

Ala Asn Leu Leu Val Phe Pro Asn Leu Asp Ala Ala Asn Ile Thr Leu
705                 710                 715                 720

Gly Val Val Lys Thr Met Thr Asp Ser Leu His Val Gly Pro Ile Leu
                725                 730                 735

Leu Gly Ser Ala Leu Pro Ala His Ile Leu Ser Pro Ser Val Thr Ser
            740                 745                 750

Arg Gly Val Val Asn Met Ala Ala Leu Ala Val Val Glu Ser Ser His
        755                 760                 765

Pro Val
    770


<210> SEQ ID NO 37
<211> LENGTH: 626
<212> TYPE: PRT
<213> ORGANISM: Solanum tuberosum

<400> SEQUENCE: 37

Met Ala Ile Phe Ser Asn Gln Met Arg Leu Ser Ser Thr Leu Leu Lys
1               5                   10                  15

Arg Leu His Gln Arg Val Ala Ala Ala Val Asn Ser Ser Ser Ser Arg
            20                  25                  30

Asn Phe Thr Thr Thr Glu Gly His Arg Pro Thr Ile Val His Lys Arg
        35                  40                  45

Ser Leu Asp Ile Leu His Asp Pro Trp Phe Asn Lys Gly Thr Ala Phe
    50                  55                  60

Ser Phe Thr Glu Arg Asp Arg Leu His Ile Arg Gly Leu Leu Pro Pro
65                  70                  75                  80

Asn Val Met Ser Phe Glu Gln Gln Ile Ala Arg Phe Met Ala Asp Leu
                85                  90                  95

Lys Arg Leu Glu Val Gln Ala Arg Asp Gly Pro Ser Asp Pro Tyr Val
            100                 105                 110

Leu Ala Lys Trp Arg Ile Leu Asn Arg Leu His Asp Arg Asn Glu Thr
        115                 120                 125

Leu Tyr Tyr Lys Val Leu Met Glu Asn Ile Glu Glu Tyr Ala Pro Ile
    130                 135                 140

Val Tyr Thr Pro Thr Val Gly Leu Val Cys Gln Lys Tyr Ser Gly Leu
145                 150                 155                 160

Phe Arg Arg Pro Arg Gly Met Tyr Phe Ser Ala Glu Asp Arg Gly Glu
                165                 170                 175

Met Met Ser Met Val Tyr Asn Trp Pro Ala Asp Gln Val Asp Met Ile
            180                 185                 190

Val Val Thr Asp Gly Ser Arg Ile Leu Gly Leu Gly Asp Leu Gly Ile
```

-continued

```
        195                 200                 205

Gln Gly Ile Gly Ile Ala Ile Gly Lys Leu Asp Leu Tyr Val Ala Ala
    210                 215                 220

Ala Gly Ile Asn Pro Gln Arg Val Leu Pro Val Met Ile Asp Val Gly
225                 230                 235                 240

Thr Asp Asn Glu Asn Leu Leu Lys Asp Pro Leu Tyr Leu Gly Leu Gln
                245                 250                 255

Asp His Arg Leu Asp Gly Glu Glu Tyr Ile Glu Val Ile Asp Glu Phe
            260                 265                 270

Met Glu Ala Val Phe Thr Arg Trp Pro His Val Ile Val Gln Phe Glu
        275                 280                 285

Asp Phe Gln Ser Lys Trp Ala Phe Lys Leu Leu Gln Arg Tyr Arg Asn
    290                 295                 300

Asn Tyr Arg Met Phe Asn Asp Asp Ile Gln Gly Thr Ala Gly Val Ala
305                 310                 315                 320

Ile Ala Gly Leu Leu Gly Ala Val Arg Ala Gln Gly Arg Pro Met Ile
                325                 330                 335

Asp Phe Pro Lys Met Lys Ile Val Val Ala Gly Ala Gly Ser Ala Gly
            340                 345                 350

Ile Gly Val Leu Asn Ala Ala Arg Lys Thr Met Ala Arg Met Leu Gly
        355                 360                 365

Asn Thr Glu Ile Ala Phe Glu Ser Ala Arg Ser Gln Phe Trp Val Val
    370                 375                 380

Asp Ala Lys Gly Leu Ile Thr Glu Ala Arg Glu Asn Val Asp Pro Asp
385                 390                 395                 400

Ala Arg Pro Phe Ala Arg Lys Ile Lys Glu Ile Glu Arg Gln Gly Leu
                405                 410                 415

Ser Glu Gly Ala Thr Leu Ala Glu Val Val Arg Glu Val Lys Pro Asp
            420                 425                 430

Val Leu Leu Gly Leu Ser Ala Cys Gly Gly Leu Phe Ser Lys Glu Val
        435                 440                 445

Leu Glu Ala Leu Lys His Ser Thr Ser Thr Arg Pro Ala Ile Phe Pro
    450                 455                 460

Met Ser Asn Pro Thr Arg Asn Ala Glu Cys Thr Pro Glu Glu Ala Phe
465                 470                 475                 480

Ser Ile Leu Gly Glu Asn Ile Ile Phe Ala Ser Gly Ser Pro Phe Lys
                485                 490                 495

Asp Val Asp Leu Gly Asn Gly His Val Gly His Cys Asn Gln Ala Asn
            500                 505                 510

Asn Met Phe Leu Phe Pro Gly Ile Gly Leu Gly Thr Leu Leu Ser Gly
        515                 520                 525

Ser Arg Ile Val Ser Asp Gly Met Leu Gln Ala Ala Ala Glu Cys Leu
    530                 535                 540

Ala Ala Tyr Ile Thr Glu Glu Glu Val Leu Lys Gly Ile Ile Tyr Pro
545                 550                 555                 560

Ser Ile Ser Arg Ile Arg Asp Ile Thr Lys Glu Val Ala Ala Ala Val
                565                 570                 575

Val Lys Glu Ala Ile Glu Glu Asp Leu Ala Glu Gly Tyr Arg Glu Met
            580                 585                 590

Asp Ser Arg Glu Leu Arg Lys Leu Asp Glu Ala Gln Ile Ser Glu Phe
        595                 600                 605

Val Glu Asn Asn Met Trp Ser Pro Asp Tyr Pro Thr Leu Val Tyr Lys
    610                 615                 620
```

-continued

```
Lys Asp
625


<210> SEQ ID NO 38
<211> LENGTH: 604
<212> TYPE: PRT
<213> ORGANISM: Homo sapiens

<400> SEQUENCE: 38

Met Gly Ala Ala Leu Gly Thr Gly Thr Arg Leu Ala Pro Trp Pro Gly
1               5                   10                  15

Arg Ala Cys Gly Ala Leu Pro Arg Trp Thr Pro Thr Ala Pro Ala Gln
            20                  25                  30

Gly Cys His Ser Lys Pro Gly Pro Ala Arg Pro Val Pro Leu Lys Lys
        35                  40                  45

Arg Gly Tyr Asp Val Thr Arg Asn Pro His Leu Asn Lys Gly Met Ala
    50                  55                  60

Phe Thr Leu Glu Glu Arg Leu Gln Leu Gly Ile His Gly Leu Ile Pro
65                  70                  75                  80

Pro Cys Phe Leu Ser Gln Asp Val Gln Leu Leu Arg Ile Met Arg Tyr
                85                  90                  95

Tyr Glu Arg Gln Gln Ser Asp Leu Asp Lys Tyr Ile Ile Leu Met Thr
            100                 105                 110

Leu Gln Asp Arg Asn Glu Lys Leu Phe Tyr Arg Val Leu Thr Ser Asp
        115                 120                 125

Val Glu Lys Phe Met Pro Ile Val Tyr Thr Pro Thr Val Gly Leu Ala
    130                 135                 140

Cys Gln His Tyr Gly Leu Thr Phe Arg Arg Pro Arg Gly Leu Phe Ile
145                 150                 155                 160

Thr Ile His Asp Lys Gly His Leu Ala Thr Met Leu Asn Ser Trp Pro
                165                 170                 175

Glu Asp Asn Ile Lys Ala Val Val Val Thr Asp Gly Glu Arg Ile Leu
            180                 185                 190

Gly Leu Gly Asp Leu Gly Cys Tyr Gly Met Gly Ile Pro Val Gly Lys
        195                 200                 205

Leu Ala Leu Tyr Thr Ala Cys Gly Gly Val Asn Pro Gln Gln Cys Leu
    210                 215                 220

Pro Val Leu Leu Asp Val Gly Thr Asn Asn Glu Glu Leu Leu Arg Asp
225                 230                 235                 240

Pro Leu Tyr Ile Gly Leu Lys His Gln Arg Val His Gly Lys Ala Tyr
                245                 250                 255

Asp Asp Leu Leu Asp Glu Phe Met Gln Ala Val Thr Asp Lys Phe Gly
            260                 265                 270

Ile Asn Cys Leu Ile Gln Phe Glu Asp Phe Ala Asn Ala Asn Ala Phe
        275                 280                 285

Arg Leu Leu Asn Lys Tyr Arg Asn Lys Tyr Cys Met Phe Asn Asp Asp
    290                 295                 300

Ile Gln Gly Thr Ala Ser Val Ala Val Ala Gly Ile Leu Ala Ala Leu
305                 310                 315                 320

Arg Ile Thr Lys Asn Lys Leu Ser Asn His Val Phe Val Phe Gln Gly
                325                 330                 335

Ala Gly Glu Ala Ala Met Gly Ile Ala His Leu Leu Val Met Ala Leu
            340                 345                 350

Glu Lys Glu Gly Val Pro Lys Ala Glu Ala Thr Arg Lys Ile Trp Met
```

```
        355                 360                 365

Val Asp Ser Lys Gly Leu Ile Val Lys Gly Arg Ser His Leu Asn His
    370                 375                 380

Glu Lys Glu Met Phe Ala Gln Asp His Pro Glu Val Asn Ser Leu Glu
385                 390                 395                 400

Glu Val Val Arg Leu Val Lys Pro Thr Ala Ile Ile Gly Val Ala Ala
                405                 410                 415

Ile Ala Gly Ala Phe Thr Glu Gln Ile Leu Arg Asp Met Ala Ser Phe
            420                 425                 430

His Glu Arg Pro Ile Ile Phe Ala Leu Ser Asn Pro Thr Ser Lys Ala
        435                 440                 445

Glu Cys Thr Ala Glu Lys Cys Tyr Arg Val Thr Glu Gly Arg Gly Ile
    450                 455                 460

Phe Ala Ser Gly Ser Pro Phe Lys Ser Val Thr Leu Glu Asp Gly Lys
465                 470                 475                 480

Thr Phe Ile Pro Gly Gln Gly Asn Asn Ala Tyr Val Phe Pro Gly Val
                485                 490                 495

Ala Leu Gly Val Ile Ala Gly Gly Ile Arg His Ile Pro Asp Glu Ile
            500                 505                 510

Phe Leu Leu Thr Ala Glu Gln Ile Ala Gln Glu Val Ser Glu Gln His
        515                 520                 525

Leu Ser Gln Gly Arg Leu Tyr Pro Pro Leu Ser Thr Ile Arg Asp Val
    530                 535                 540

Ser Leu Arg Ile Ala Ile Lys Val Leu Asp Tyr Ala Tyr Lys His Asn
545                 550                 555                 560

Leu Ala Ser Tyr Tyr Pro Glu Pro Lys Asp Lys Glu Ala Phe Val Arg
                565                 570                 575

Ser Leu Val Tyr Thr Pro Asp Tyr Asp Ser Phe Thr Leu Asp Ser Tyr
            580                 585                 590

Thr Trp Pro Lys Glu Ala Met Asn Val Gln Thr Val
        595                 600


<210> SEQ ID NO 39
<211> LENGTH: 1497
<212> TYPE: DNA
<213> ORGANISM: Yarrowia lipolytica

<400> SEQUENCE: 39

atgactggca ccttacccaa gttcggcgac ggaaccacca ttgtggttct tggagcctcc      60

ggcgacctcg ctaagaagaa gaccttcccc gccctcttcg gcctttaccg aaacggcctg     120

ctgcccaaaa atgttgaaat catcggctac gcacggtcga aaatgactca ggaggagtac     180

cacgagcgaa tcagccacta cttcaagacc cccgacgacc agtccaagga gcaggccaag     240

aagttccttg agaacacctg ctacgtccag ggcccttacg acggtgccga gggctaccag     300

cgactgaatg aaaagattga ggagtttgag aagaagaagc ccgagcccca ctaccgtctt     360

ttctacctgg ctctgccccc cagcgtcttc cttgaggctg ccaacggtct gaagaagtat     420

gtctaccccg gcgagggcaa ggcccgaatc atcatcgaga agccctttgg ccacgacctg     480

gcctcgtcac gagagctcca ggacggcctt gctcctctct ggaaggagtc tgagatcttc     540

cgaatcgacc actacctcgg aaaggagatg gtcaagaacc tcaacattct gcgatttggc     600

aaccagttcc tgtccgccgt gtgggacaag aacaccattt ccaacgtcca gatctccttc     660

aaggagccct ttggcactga gggccgaggt ggatacttca acgacattgg aatcatccga     720
```

-continued

```
gacgttattc agaaccatct gttgcaggtt ctgtccattc tagccatgga gcgacccgtc    780

actttcggcg ccgaggacat tcgagatgag aaggtcaagg tgctccgatg tgtcgacatt    840

ctcaacattg acgacgtcat tctcggccag tacggcccct ctgaagacgg aaagaagccc    900

ggatacaccg atgacgatgg cgttcccgat gactcccgag ctgtgacctt tgctgctctc    960

catctccaga tccacaacga cagatgggag ggtgttcctt tcatcctccg agccggtaag   1020

gctctggacg agggcaaggt cgagatccga gtgcagttcc gagacgtgac caagggcgtt   1080

gtggaccatc tgcctcgaaa tgagctcgtc atccgaatcc agccctccga gtccatctac   1140

atgaagatga actccaagct gcctggcctt actgccaaga acattgtcac cgacctggat   1200

ctgacctaca accgacgata ctcggacgtg cgaatccctg aggcttacga gtctctcatt   1260

ctggactgcc tcaagggtga ccacaccaac tttgtgcgaa acgacgagct ggacatttcc   1320

tggaagattt tcaccgatct gctgcacaag attgacgagg acaagagcat tgtgcccgag   1380

aagtacgcct acggctctcg tggccccgag cgactcaagc agtggctccg agaccgaggc   1440

tacgtgcgaa acggcaccga gctgtaccaa tggcctgtca ccaagggctc ctcgtga      1497
```

```
<210> SEQ ID NO 40
<211> LENGTH: 498
<212> TYPE: PRT
<213> ORGANISM: Yarrowia lipolytica

<400> SEQUENCE: 40

Met Thr Gly Thr Leu Pro Lys Phe Gly Asp Gly Thr Thr Ile Val Val
1               5                   10                  15

Leu Gly Ala Ser Gly Asp Leu Ala Lys Lys Lys Thr Phe Pro Ala Leu
            20                  25                  30

Phe Gly Leu Tyr Arg Asn Gly Leu Leu Pro Lys Asn Val Glu Ile Ile
        35                  40                  45

Gly Tyr Ala Arg Ser Lys Met Thr Gln Glu Glu Tyr His Glu Arg Ile
    50                  55                  60

Ser His Tyr Phe Lys Thr Pro Asp Asp Gln Ser Lys Glu Gln Ala Lys
65                  70                  75                  80

Lys Phe Leu Glu Asn Thr Cys Tyr Val Gln Gly Pro Tyr Asp Gly Ala
                85                  90                  95

Glu Gly Tyr Gln Arg Leu Asn Glu Lys Ile Glu Glu Phe Glu Lys Lys
            100                 105                 110

Lys Pro Glu Pro His Tyr Arg Leu Phe Tyr Leu Ala Leu Pro Pro Ser
        115                 120                 125

Val Phe Leu Glu Ala Ala Asn Gly Leu Lys Lys Tyr Val Tyr Pro Gly
    130                 135                 140

Glu Gly Lys Ala Arg Ile Ile Ile Glu Lys Pro Phe Gly His Asp Leu
145                 150                 155                 160

Ala Ser Ser Arg Glu Leu Gln Asp Gly Leu Ala Pro Leu Trp Lys Glu
                165                 170                 175

Ser Glu Ile Phe Arg Ile Asp His Tyr Leu Gly Lys Glu Met Val Lys
            180                 185                 190

Asn Leu Asn Ile Leu Arg Phe Gly Asn Gln Phe Leu Ser Ala Val Trp
        195                 200                 205

Asp Lys Asn Thr Ile Ser Asn Val Gln Ile Ser Phe Lys Glu Pro Phe
    210                 215                 220

Gly Thr Glu Gly Arg Gly Gly Tyr Phe Asn Asp Ile Gly Ile Ile Arg
225                 230                 235                 240
```

-continued

```
Asp Val Ile Gln Asn His Leu Leu Gln Val Leu Ser Ile Leu Ala Met
                245                 250                 255

Glu Arg Pro Val Thr Phe Gly Ala Glu Asp Ile Arg Asp Glu Lys Val
            260                 265                 270

Lys Val Leu Arg Cys Val Asp Ile Leu Asn Ile Asp Asp Val Ile Leu
        275                 280                 285

Gly Gln Tyr Gly Pro Ser Glu Asp Gly Lys Lys Pro Gly Tyr Thr Asp
    290                 295                 300

Asp Asp Gly Val Pro Asp Asp Ser Arg Ala Val Thr Phe Ala Ala Leu
305                 310                 315                 320

His Leu Gln Ile His Asn Asp Arg Trp Glu Gly Val Pro Phe Ile Leu
                325                 330                 335

Arg Ala Gly Lys Ala Leu Asp Glu Gly Lys Val Glu Ile Arg Val Gln
            340                 345                 350

Phe Arg Asp Val Thr Lys Gly Val Val Asp His Leu Pro Arg Asn Glu
        355                 360                 365

Leu Val Ile Arg Ile Gln Pro Ser Glu Ser Ile Tyr Met Lys Met Asn
    370                 375                 380

Ser Lys Leu Pro Gly Leu Thr Ala Lys Asn Ile Val Thr Asp Leu Asp
385                 390                 395                 400

Leu Thr Tyr Asn Arg Arg Tyr Ser Asp Val Arg Ile Pro Glu Ala Tyr
                405                 410                 415

Glu Ser Leu Ile Leu Asp Cys Leu Lys Gly Asp His Thr Asn Phe Val
            420                 425                 430

Arg Asn Asp Glu Leu Asp Ile Ser Trp Lys Ile Phe Thr Asp Leu Leu
        435                 440                 445

His Lys Ile Asp Glu Asp Lys Ser Ile Val Pro Glu Lys Tyr Ala Tyr
    450                 455                 460

Gly Ser Arg Gly Pro Glu Arg Leu Lys Gln Trp Leu Arg Asp Arg Gly
465                 470                 475                 480

Tyr Val Arg Asn Gly Thr Glu Leu Tyr Gln Trp Pro Val Thr Lys Gly
                485                 490                 495

Ser Ser
```

<210> SEQ ID NO 41
<211> LENGTH: 1470
<212> TYPE: DNA
<213> ORGANISM: Yarrowia lipolytica

<400> SEQUENCE: 41

```
atgactgaca cttcaaacat caagcctgtc gctgacattg ccctcatcgg tctcgccgtc      60

atgggccaga acctgatcct caacatggcc gaccacggct acgaggttgt tgcctacaac     120

cgaaccacct ccaaggtcga ccacttcctc gagaacgagg ccaagggaaa gtccattatt     180

ggtgctcact ctatcaagga gctgtgtgct ctgctgaagc gaccccgacg aatcattctg     240

ctcgttaagg ccggtgctgc tgtcgattct ttcatcgaac agctcctgcc ctatctcgat     300

aagggtgata tcatcattga cggtggtaac tcccacttcc ccgactccaa ccgacgatac     360

gaggagctta acgagaaggg aatcctcttt gttggttccg gtgtttccgg cggtgaggag     420

ggtgcccgat acggtccctc catcatgccc ggtggaaaca aggaggcctg gccccacatt     480

aagaagattt tccaggacat ctctgctaag gctgatggtg agccctgctg tgactgggtc     540

ggtgacgctg gtgccggcca ctttgtcaag atggttcaca acggtattga gtatggtgac     600

atgcagctta tctgcgaggc ttacgacctc atgaagcgag gtgctggttt caccaatgag     660
```

-continued

```
gagattggag acgttttcgc caagtggaac aacggtatcc tcgactcctt cctcattgag    720

atcacccgag acatcttcaa gtacgacgac ggctctggaa ctcctctcgt tgagaagatc    780

tccgacactg ctggccagaa gggtactgga aagtggaccg ctatcaacgc tcttgacctt    840

ggtatgcccg tcaccctgat cggtgaggcc gtcttcgctc gatgcctttc tgccctcaag    900

caggagcgtg tccgagcttc caaggttctt gatggccccg agcccgtcaa gttcactggt    960

gacaagaagg agtttgtcga ccagctcgag caggcccttt acgcctccaa gatcatctct   1020

tacgcccagg gtttcatgct tatccgagag gccgccaaga cctacggctg ggagctcaac   1080

aacgccggta ttgccctcat gtggcgaggt ggttgcatca tccgatccgt cttccttgct   1140

gacatcacca aggcttaccg acaggacccc aacctcgaga acctgctgtt caacgacttc   1200

ttcaagaacg ccatctccaa ggccaacccc tcttggcgag ctaccgtggc caaggctgtc   1260

acctggggtg ttcccactcc cgcctttgcc tcggctctgg ctttctacga cggttaccga   1320

tctgccaagc tccccgctaa cctgctccag gcccagcgag actacttcgg cgcccacacc   1380

taccagctcc tcgatggtga tggaaagtgg atccacacca actggaccgg ccgaggtggt   1440

gaggtttctt cttccactta cgatgcttaa                                    1470
```

```
<210> SEQ ID NO 42
<211> LENGTH: 489
<212> TYPE: PRT
<213> ORGANISM: Yarrowia lipolytica

<400> SEQUENCE: 42

Met Thr Asp Thr Ser Asn Ile Lys Pro Val Ala Asp Ile Ala Leu Ile
1               5                   10                  15

Gly Leu Ala Val Met Gly Gln Asn Leu Ile Leu Asn Met Ala Asp His
            20                  25                  30

Gly Tyr Glu Val Val Ala Tyr Asn Arg Thr Thr Ser Lys Val Asp His
        35                  40                  45

Phe Leu Glu Asn Glu Ala Lys Gly Lys Ser Ile Ile Gly Ala His Ser
    50                  55                  60

Ile Lys Glu Leu Cys Ala Leu Leu Lys Arg Pro Arg Arg Ile Ile Leu
65                  70                  75                  80

Leu Val Lys Ala Gly Ala Ala Val Asp Ser Phe Ile Glu Gln Leu Leu
                85                  90                  95

Pro Tyr Leu Asp Lys Gly Asp Ile Ile Ile Asp Gly Gly Asn Ser His
            100                 105                 110

Phe Pro Asp Ser Asn Arg Arg Tyr Glu Glu Leu Asn Glu Lys Gly Ile
        115                 120                 125

Leu Phe Val Gly Ser Gly Val Ser Gly Gly Glu Glu Gly Ala Arg Tyr
    130                 135                 140

Gly Pro Ser Ile Met Pro Gly Gly Asn Lys Glu Ala Trp Pro His Ile
145                 150                 155                 160

Lys Lys Ile Phe Gln Asp Ile Ser Ala Lys Ala Asp Gly Glu Pro Cys
                165                 170                 175

Cys Asp Trp Val Gly Asp Ala Gly Ala Gly His Phe Val Lys Met Val
            180                 185                 190

His Asn Gly Ile Glu Tyr Gly Asp Met Gln Leu Ile Cys Glu Ala Tyr
        195                 200                 205

Asp Leu Met Lys Arg Gly Ala Gly Phe Thr Asn Glu Glu Ile Gly Asp
    210                 215                 220
```

-continued

```
Val Phe Ala Lys Trp Asn Asn Gly Ile Leu Asp Ser Phe Leu Ile Glu
225                 230                 235                 240

Ile Thr Arg Asp Ile Phe Lys Tyr Asp Asp Gly Ser Gly Thr Pro Leu
                245                 250                 255

Val Glu Lys Ile Ser Asp Thr Ala Gly Gln Lys Gly Thr Gly Lys Trp
            260                 265                 270

Thr Ala Ile Asn Ala Leu Asp Leu Gly Met Pro Val Thr Leu Ile Gly
        275                 280                 285

Glu Ala Val Phe Ala Arg Cys Leu Ser Ala Leu Lys Gln Glu Arg Val
    290                 295                 300

Arg Ala Ser Lys Val Leu Asp Gly Pro Glu Pro Val Lys Phe Thr Gly
305                 310                 315                 320

Asp Lys Lys Glu Phe Val Asp Gln Leu Glu Gln Ala Leu Tyr Ala Ser
                325                 330                 335

Lys Ile Ile Ser Tyr Ala Gln Gly Phe Met Leu Ile Arg Glu Ala Ala
            340                 345                 350

Lys Thr Tyr Gly Trp Glu Leu Asn Asn Ala Gly Ile Ala Leu Met Trp
        355                 360                 365

Arg Gly Gly Cys Ile Ile Arg Ser Val Phe Leu Ala Asp Ile Thr Lys
    370                 375                 380

Ala Tyr Arg Gln Asp Pro Asn Leu Glu Asn Leu Leu Phe Asn Asp Phe
385                 390                 395                 400

Phe Lys Asn Ala Ile Ser Lys Ala Asn Pro Ser Trp Arg Ala Thr Val
                405                 410                 415

Ala Lys Ala Val Thr Trp Gly Val Pro Thr Pro Ala Phe Ala Ser Ala
            420                 425                 430

Leu Ala Phe Tyr Asp Gly Tyr Arg Ser Ala Lys Leu Pro Ala Asn Leu
        435                 440                 445

Leu Gln Ala Gln Arg Asp Tyr Phe Gly Ala His Thr Tyr Gln Leu Leu
    450                 455                 460

Asp Gly Asp Gly Lys Trp Ile His Thr Asn Trp Thr Gly Arg Gly Gly
465                 470                 475                 480

Glu Val Ser Ser Ser Thr Tyr Asp Ala
                485
```

<210> SEQ ID NO 43
<211> LENGTH: 747
<212> TYPE: DNA
<213> ORGANISM: Yarrowia lipolytica

<400> SEQUENCE: 43

```
atgcccaagg tcatctctaa gaacgaatcg caactggtcg ctgaggctgc tgccgctgag      60

atcattcgac tccagaacga gtcaattgct gccactggag ctttccatgt tgccgtatct     120

ggaggctctc tggtgtctgc tctccgaaag ggtctggtca acaactcgga gaccaagttc     180

cccaagtgga agattttctt ctccgacgaa cggctggtca agctggacga tgccgactcc     240

aactacggtc tcctcaagaa ggatctgctc gatcacatcc ccaaggatca gcaaccacag     300

gtcttcaccg tcaaggagtc tcttctgaac gactctgatg ccgtctccaa ggactaccag     360

gagcagattg tcaagaatgt gcctctcaac ggccagggag tgcctgtttt cgatctcatt     420

ctgctcggat gcggtcctga tggccacact tgctcgctgt tccctggaca cgctctgctc     480

aaggaggaga ccaagtttgt cgccaccatt gaggactctc ccaagcctcc tcctcgacga     540

atcaccatca ctttccccgt tctcaaggct gccaaggcca tcgctttcgt cgccgaggga     600
```

gccggaaagg cccctgtcct caagcagatc ttcgaggagc ccgagcccac tcttccctct 660
gccattgtca acaaggtcgc taccggaccc gttttctggt ttgtttccga ctctgccgtt 720
gagggcgtca acctctccaa gatctag 747

<210> SEQ ID NO 44
<211> LENGTH: 248
<212> TYPE: PRT
<213> ORGANISM: Yarrowia lipolytica

<400> SEQUENCE: 44

Met Pro Lys Val Ile Ser Lys Asn Glu Ser Gln Leu Val Ala Glu Ala
1 5 10 15

Ala Ala Ala Glu Ile Ile Arg Leu Gln Asn Glu Ser Ile Ala Ala Thr
20 25 30

Gly Ala Phe His Val Ala Val Ser Gly Gly Ser Leu Val Ser Ala Leu
35 40 45

Arg Lys Gly Leu Val Asn Asn Ser Glu Thr Lys Phe Pro Lys Trp Lys
50 55 60

Ile Phe Phe Ser Asp Glu Arg Leu Val Lys Leu Asp Asp Ala Asp Ser
65 70 75 80

Asn Tyr Gly Leu Leu Lys Lys Asp Leu Leu Asp His Ile Pro Lys Asp
85 90 95

Gln Gln Pro Gln Val Phe Thr Val Lys Glu Ser Leu Leu Asn Asp Ser
100 105 110

Asp Ala Val Ser Lys Asp Tyr Gln Glu Gln Ile Val Lys Asn Val Pro
115 120 125

Leu Asn Gly Gln Gly Val Pro Val Phe Asp Leu Ile Leu Leu Gly Cys
130 135 140

Gly Pro Asp Gly His Thr Cys Ser Leu Phe Pro Gly His Ala Leu Leu
145 150 155 160

Lys Glu Glu Thr Lys Phe Val Ala Thr Ile Glu Asp Ser Pro Lys Pro
165 170 175

Pro Pro Arg Arg Ile Thr Ile Thr Phe Pro Val Leu Lys Ala Ala Lys
180 185 190

Ala Ile Ala Phe Val Ala Glu Gly Ala Gly Lys Ala Pro Val Leu Lys
195 200 205

Gln Ile Phe Glu Glu Pro Glu Pro Thr Leu Pro Ser Ala Ile Val Asn
210 215 220

Lys Val Ala Thr Gly Pro Val Phe Trp Phe Val Ser Asp Ser Ala Val
225 230 235 240

Glu Gly Val Asn Leu Ser Lys Ile
245

<210> SEQ ID NO 45
<211> LENGTH: 182
<212> TYPE: PRT
<213> ORGANISM: Talaromyces marneffei

<400> SEQUENCE: 45

Met Ser Ser Arg Val Gly Leu Arg Phe Leu Ala Asn Ser Arg Ala Ala
1 5 10 15

Phe Arg Asn Leu Arg Gln Asn Val Ser Asn Asn Lys Gly Phe Arg Phe
20 25 30

Ser Ser Thr Glu Ala Ser Ala Ala Gly Ala Glu Gln Ser Gln Asn Ala
35 40 45

```
Phe Gln Arg Met Trp Asn Ser Pro Val Gly Phe Lys Thr Val His Phe
    50                  55                  60

Trp Ala Pro Val Met Lys Trp Ser Leu Val Ile Ala Gly Ile Ser Asp
65                  70                  75                  80

Leu Ala Arg Pro Ala Glu Lys Leu Ser Leu Thr Gln Asn Leu Ala Leu
                85                  90                  95

Val Ala Thr Gly Thr Ile Trp Thr Arg Trp Cys Phe Val Ile Thr Pro
            100                 105                 110

Lys Asn Met Leu Leu Ala Ala Val Asn Phe Phe Leu Ala Cys Thr Gly
        115                 120                 125

Ala Ala Gln Leu Thr Arg Ile Phe Leu Trp Arg Arg Ser Gln Asp Gly
    130                 135                 140

Ser Ala Lys Glu Ala Val Lys Asp Met Ala Val Asp Thr Val Glu Ser
145                 150                 155                 160

Ala Lys Leu Val Thr Asp Gly Ala Lys Gly Ala Val Lys Ala Ala Glu
                165                 170                 175

Glu Lys Phe Lys Ser Ser
            180


<210> SEQ ID NO 46
<211> LENGTH: 165
<212> TYPE: PRT
<213> ORGANISM: Hanseniaspora osmophila
<220> FEATURE:
<221> NAME/KEY: misc_feature
<222> LOCATION: (58)..(58)
<223> OTHER INFORMATION: Xaa can be any naturally occurring amino acid

<400> SEQUENCE: 46

Met Ser Phe Thr Arg Ala Thr Ile Asn Ala Gly Lys Lys Thr Gln Trp
1               5                   10                  15

Ser Ser Lys Phe Asn Ser Phe Ile Asn Ser Glu Ala Gly Pro Lys Thr
            20                  25                  30

Ile His Phe Trp Ala Pro Thr Leu Lys Trp Gly Leu Val Phe Ala Gly
        35                  40                  45

Ile Ser Asp Leu Gln Arg Pro Val Asp Xaa Ile Ser Gly Ala Gln Asn
    50                  55                  60

Leu Ser Leu Leu Ala Thr Ala Met Ile Trp Thr Arg Trp Ser Phe Val
65                  70                  75                  80

Ile Lys Pro Lys Asn Met Leu Leu Ala Ser Val Asn Phe Phe Leu Gly
                85                  90                  95

Cys Thr Ala Gly Tyr Gln Leu Gly Arg Ile Val Asp Tyr Arg Leu Lys
            100                 105                 110

Glu Gly Asp Ser Lys Ser Gln Val Leu Asp Tyr Ile Ile Asn Gly Gly
        115                 120                 125

Lys Glu Thr Gly Val Lys Ala Pro Glu Gln Glu Ala Asn Val Asn Lys
    130                 135                 140

Pro Leu Ile His His Pro Leu Asn Asp Asn Asn Asp Val Val Ile Gly
145                 150                 155                 160

Asp Ala Arg Thr Asn
                165


<210> SEQ ID NO 47
<211> LENGTH: 393
<212> TYPE: PRT
<213> ORGANISM: Streptococcus mutans UA159

<400> SEQUENCE: 47
```

-continued

```
Met Ala Glu Lys Val Ser Phe Glu Glu Gly Lys Leu Gln Val Pro Asp
1               5                   10                  15

Lys Pro Val Ile Pro Tyr Ile Glu Gly Asp Gly Val Gly Gln Asp Ile
            20                  25                  30

Trp Lys Asn Ala Gln Ile Val Phe Asp Lys Ala Ile Ala Lys Val Tyr
        35                  40                  45

Gly Gly His Lys Gln Val Ile Trp Arg Glu Val Leu Ala Gly Lys Lys
    50                  55                  60

Ala Tyr Asn Glu Thr Gly Asn Trp Leu Pro Asn Glu Thr Leu Glu Ile
65                  70                  75                  80

Ile Lys Thr His Leu Leu Ala Ile Lys Gly Pro Leu Glu Thr Pro Val
                85                  90                  95

Gly Gly Gly Ile Arg Ser Leu Asn Val Ala Leu Arg Gln Glu Leu Asp
            100                 105                 110

Leu Phe Ala Cys Val Arg Pro Val Arg Tyr Phe Lys Gly Val Pro Ser
        115                 120                 125

Pro Leu Lys His Pro Glu Lys Thr Ala Ile Thr Ile Phe Arg Glu Asn
    130                 135                 140

Thr Glu Asp Ile Tyr Ala Gly Ile Glu Trp Asn Ala Gly Thr Ala Glu
145                 150                 155                 160

Val Gln Lys Val Ile Asn Phe Leu Gln Asp Asp Met Gln Val Lys Lys
                165                 170                 175

Ile Arg Phe Pro Lys Ser Ser Ser Ile Gly Ile Lys Pro Ile Ser Ile
            180                 185                 190

Glu Gly Ser Gln Arg Leu Ile Arg Ala Ala Ile Glu Tyr Ala Leu Ala
        195                 200                 205

Asn Asn Leu Thr Lys Val Thr Leu Val His Lys Gly Asn Ile Gln Lys
    210                 215                 220

Phe Thr Glu Gly Gly Phe Arg Lys Trp Gly Tyr Glu Leu Ala Lys Arg
225                 230                 235                 240

Glu Tyr Ala Ala Glu Leu Ala Ser Gly Gln Leu Val Val Asp Asp Ile
                245                 250                 255

Ile Ala Asp Asn Phe Leu Gln Gln Ile Leu Leu Lys Pro Glu Arg Phe
            260                 265                 270

Asp Val Val Ala Leu Thr Asn Leu Asn Gly Asp Tyr Ala Ser Asp Ala
        275                 280                 285

Leu Ala Ala Gln Val Gly Gly Ile Gly Ile Ser Pro Gly Ala Asn Ile
    290                 295                 300

Asn Tyr Gln Thr Gly His Ala Ile Phe Glu Ala Thr His Gly Thr Ala
305                 310                 315                 320

Pro Asp Ile Ala Gly Gln Asp Leu Ala Asn Pro Ser Ser Val Leu Leu
                325                 330                 335

Ser Gly Cys Met Leu Phe Asp Tyr Ile Gly Trp Ser Lys Val Ser Asp
            340                 345                 350

Leu Ile Met Lys Ala Val Glu Lys Ala Ile Ala Asn Gly Gln Val Thr
        355                 360                 365

Ile Asp Phe Ala Lys Glu Leu Gly Val Glu Ala Leu Thr Thr Arg Gln
    370                 375                 380

Phe Ser Glu Val Leu Leu Thr Tyr Leu
385                 390
```

<210> SEQ ID NO 48
<211> LENGTH: 423

<212> TYPE: PRT
<213> ORGANISM: Unknown
<220> FEATURE:
<223> OTHER INFORMATION: Bacillales sp.

<400> SEQUENCE: 48

Met Ala Gln Gly Glu Lys Ile Thr Val Ser Asn Gly Val Leu Asn Val
1 5 10 15

Pro Asn Asn Pro Ile Ile Pro Phe Ile Glu Gly Asp Gly Thr Gly Pro
20 25 30

Asp Ile Trp Asn Ala Ala Ser Lys Val Leu Glu Ala Ala Val Glu Lys
35 40 45

Ala Tyr Lys Gly Glu Lys Lys Ile Thr Trp Lys Glu Val Tyr Ala Gly
50 55 60

Glu Lys Ala Tyr Asn Lys Thr Gly Glu Trp Leu Pro Ala Glu Thr Leu
65 70 75 80

Asp Val Ile Arg Glu Tyr Phe Ile Ala Ile Lys Gly Pro Leu Thr Thr
85 90 95

Pro Val Gly Gly Gly Ile Arg Ser Leu Asn Val Ala Leu Arg Gln Glu
100 105 110

Leu Asp Leu Phe Val Cys Leu Arg Pro Val Arg Tyr Phe Thr Gly Val
115 120 125

Pro Ser Pro Val Lys Arg Pro Glu Asp Thr Asp Met Val Ile Phe Arg
130 135 140

Glu Asn Thr Glu Asp Ile Tyr Ala Gly Ile Glu Tyr Ala Lys Gly Ser
145 150 155 160

Glu Glu Val Gln Lys Leu Ile Ser Phe Leu Gln Asn Glu Leu Asn Val
165 170 175

Asn Lys Ile Arg Phe Pro Glu Thr Ser Gly Ile Gly Ile Lys Pro Val
180 185 190

Ser Glu Glu Gly Thr Ser Arg Leu Val Arg Ala Ala Ile Asp Tyr Ala
195 200 205

Ile Glu His Gly Arg Lys Ser Val Thr Leu Val His Lys Gly Asn Ile
210 215 220

Met Lys Phe Thr Glu Gly Ala Phe Lys Asn Trp Gly Tyr Glu Leu Ala
225 230 235 240

Glu Lys Glu Tyr Gly Asp Lys Val Phe Thr Trp Ala Gln Tyr Asp Arg
245 250 255

Ile Ala Glu Glu Gln Gly Lys Asp Ala Ala Asn Lys Ala Gln Ser Glu
260 265 270

Ala Glu Ala Ala Gly Lys Ile Ile Ile Lys Asp Ser Ile Ala Asp Ile
275 280 285

Phe Leu Gln Gln Ile Leu Thr Arg Pro Asn Glu Phe Asp Val Val Ala
290 295 300

Thr Met Asn Leu Asn Gly Asp Tyr Ile Ser Asp Ala Leu Ala Ala Gln
305 310 315 320

Val Gly Gly Ile Gly Ile Ala Pro Gly Ala Asn Ile Asn Tyr Glu Thr
325 330 335

Gly His Ala Ile Phe Glu Ala Thr His Gly Thr Ala Pro Lys Tyr Ala
340 345 350

Gly Leu Asp Lys Val Asn Pro Ser Ser Val Ile Leu Ser Gly Val Leu
355 360 365

Leu Leu Glu His Leu Gly Trp Asn Glu Ala Ala Asp Leu Val Ile Lys
370 375 380

Ser Met Glu Lys Thr Ile Ala Ser Lys Val Val Thr Tyr Asp Phe Ala
385 390 395 400

Arg Leu Met Asp Gly Ala Thr Glu Val Lys Cys Ser Glu Phe Gly Glu
405 410 415

Glu Leu Ile Lys Asn Met Asp
420

<210> SEQ ID NO 49
<211> LENGTH: 423
<212> TYPE: PRT
<213> ORGANISM: Bacillus subtilis

<400> SEQUENCE: 49

Met Ala Gln Gly Glu Lys Ile Thr Val Ser Asn Gly Val Leu Asn Val
1 5 10 15

Pro Asn Asn Pro Ile Ile Pro Phe Ile Glu Gly Asp Gly Thr Gly Pro
20 25 30

Asp Ile Trp Asn Ala Ala Ser Lys Val Leu Glu Ala Ala Val Glu Lys
35 40 45

Ala Tyr Lys Gly Glu Lys Lys Ile Thr Trp Lys Glu Val Tyr Ala Gly
50 55 60

Glu Lys Ala Tyr Asn Lys Thr Gly Glu Trp Leu Pro Ala Glu Thr Leu
65 70 75 80

Asp Val Ile Arg Glu Tyr Phe Ile Ala Ile Lys Gly Pro Leu Thr Thr
85 90 95

Pro Val Gly Gly Gly Ile Arg Ala Leu Asn Val Ala Leu Arg Gln Glu
100 105 110

Leu Asp Leu Phe Val Cys Leu Arg Pro Val Arg Tyr Phe Thr Gly Val
115 120 125

Pro Ser Pro Val Lys Arg Pro Glu Asp Thr Asp Met Val Ile Phe Arg
130 135 140

Glu Asn Thr Glu Asp Ile Tyr Ala Gly Ile Glu Tyr Ala Lys Gly Ser
145 150 155 160

Glu Glu Val Gln Lys Leu Ile Ser Phe Leu Gln Asn Glu Leu Asn Val
165 170 175

Asn Lys Ile Arg Phe Pro Glu Thr Ser Gly Ile Gly Ile Lys Pro Val
180 185 190

Ser Glu Glu Gly Thr Ser Arg Leu Val Arg Ala Ala Ile Asp Tyr Ala
195 200 205

Ile Glu His Gly Arg Lys Ser Val Thr Leu Val His Lys Gly Asn Ile
210 215 220

Met Lys Phe Thr Glu Gly Ala Phe Lys Asn Trp Gly Tyr Glu Leu Ala
225 230 235 240

Glu Lys Glu Tyr Gly Asp Lys Val Phe Thr Trp Ala Gln Tyr Asp Arg
245 250 255

Ile Ala Glu Glu Gln Gly Lys Asp Ala Ala Asn Lys Ala Gln Ser Glu
260 265 270

Ala Glu Ala Ala Gly Lys Ile Ile Ile Lys Asp Ser Ile Ala Asp Ile
275 280 285

Phe Leu Gln Gln Ile Leu Thr Arg Pro Asn Glu Phe Asp Val Val Ala
290 295 300

Thr Met Asn Leu Asn Gly Asp Tyr Ile Ser Asp Ala Leu Ala Ala Gln
305 310 315 320

Val Gly Gly Ile Gly Ile Ala Pro Gly Ala Asn Ile Asn Tyr Glu Thr
325 330 335

Gly His Ala Ile Phe Glu Ala Thr His Gly Thr Ala Pro Lys Tyr Ala
340 345 350

Gly Leu Asp Lys Val Asn Pro Ser Ser Val Ile Leu Ser Gly Val Leu
355 360 365

Leu Leu Glu His Leu Gly Trp Asn Glu Ala Ala Asp Leu Val Ile Lys
370 375 380

Ser Met Glu Lys Thr Ile Ala Ser Lys Val Val Thr Tyr Asp Phe Ala
385 390 395 400

Arg Leu Met Asp Gly Ala Thr Glu Val Lys Cys Ser Glu Phe Gly Glu
405 410 415

Glu Leu Ile Lys Asn Met Asp
420

<210> SEQ ID NO 50
<211> LENGTH: 2345
<212> TYPE: PRT
<213> ORGANISM: Rattus norvegicus

<400> SEQUENCE: 50

Met Asp Glu Pro Ser Pro Leu Ala Lys Thr Leu Glu Leu Asn Gln His
1 5 10 15

Ser Arg Phe Ile Ile Gly Ser Val Ser Glu Asp Asn Ser Glu Asp Glu
20 25 30

Ile Ser Asn Leu Val Lys Leu Asp Leu Glu Glu Lys Glu Gly Ser Leu
35 40 45

Ser Pro Ala Ser Val Ser Ser Asp Thr Leu Ser Asp Leu Gly Ile Ser
50 55 60

Ala Leu Gln Asp Gly Leu Ala Phe His Met Arg Ser Ser Met Ser Gly
65 70 75 80

Leu His Leu Val Lys Gln Gly Arg Asp Arg Lys Lys Ile Asp Ser Gln
85 90 95

Arg Asp Phe Thr Val Ala Ser Pro Ala Glu Phe Val Thr Arg Phe Gly
100 105 110

Gly Asn Lys Val Ile Glu Lys Val Leu Ile Ala Asn Asn Gly Ile Ala
115 120 125

Ala Val Lys Cys Met Arg Ser Ile Arg Arg Trp Ser Tyr Glu Met Phe
130 135 140

Arg Asn Glu Arg Ala Ile Arg Phe Val Val Met Val Thr Pro Glu Asp
145 150 155 160

Leu Lys Ala Asn Ala Glu Tyr Ile Lys Met Ala Asp His Tyr Val Pro
165 170 175

Val Pro Gly Gly Ala Asn Asn Asn Asn Tyr Ala Asn Val Glu Leu Ile
180 185 190

Leu Asp Ile Ala Lys Arg Ile Pro Val Gln Ala Val Trp Ala Gly Trp
195 200 205

Gly His Ala Ser Glu Asn Pro Lys Leu Pro Glu Leu Leu Leu Lys Asn
210 215 220

Gly Ile Ala Phe Met Gly Pro Pro Ser Gln Ala Met Trp Ala Leu Gly
225 230 235 240

Asp Lys Ile Ala Ser Ser Ile Val Ala Gln Thr Ala Gly Ile Pro Thr
245 250 255

Leu Pro Trp Ser Gly Ser Gly Leu Arg Val Asp Trp Gln Glu Asn Asp
260 265 270

Phe Ser Lys Arg Ile Leu Asn Val Pro Gln Asp Leu Tyr Glu Lys Gly

-continued

```
        275                 280                 285

Tyr Val Lys Asp Val Asp Asp Gly Leu Lys Ala Ala Glu Glu Val Gly
    290                 295                 300

Tyr Pro Val Met Ile Lys Ala Ser Glu Gly Gly Gly Gly Lys Gly Ile
305                 310                 315                 320

Arg Lys Val Asn Asn Ala Asp Asp Phe Pro Asn Leu Phe Arg Gln Val
                325                 330                 335

Gln Ala Glu Val Pro Gly Ser Pro Ile Phe Val Met Arg Leu Ala Lys
            340                 345                 350

Gln Ser Arg His Leu Glu Val Gln Ile Leu Ala Asp Gln Tyr Gly Asn
        355                 360                 365

Ala Ile Ser Leu Phe Gly Arg Asp Cys Ser Val Gln Arg Arg His Gln
    370                 375                 380

Lys Ile Ile Glu Glu Ala Pro Ala Ala Ile Ala Thr Pro Ala Val Phe
385                 390                 395                 400

Glu His Met Glu Gln Cys Ala Val Lys Leu Ala Lys Met Val Gly Tyr
                405                 410                 415

Val Ser Ala Gly Thr Val Glu Tyr Leu Tyr Ser Gln Asp Gly Ser Phe
            420                 425                 430

Tyr Phe Leu Glu Leu Asn Pro Arg Leu Gln Val Glu His Pro Cys Thr
        435                 440                 445

Glu Met Val Ala Asp Val Asn Leu Pro Ala Ala Gln Leu Gln Ile Ala
    450                 455                 460

Met Gly Ile Pro Leu Phe Arg Ile Lys Asp Ile Arg Met Met Tyr Gly
465                 470                 475                 480

Val Ser Pro Trp Gly Asp Ala Pro Ile Asp Phe Glu Asn Ser Ala His
                485                 490                 495

Val Pro Cys Pro Arg Gly His Val Ile Ala Ala Arg Ile Thr Ser Glu
            500                 505                 510

Asn Pro Asp Glu Gly Phe Lys Pro Ser Ser Gly Thr Val Gln Glu Leu
        515                 520                 525

Asn Phe Arg Ser Asn Lys Asn Val Trp Gly Tyr Phe Ser Val Ala Ala
    530                 535                 540

Ala Gly Gly Leu His Glu Phe Ala Asp Ser Gln Phe Gly His Cys Phe
545                 550                 555                 560

Ser Trp Gly Glu Asn Arg Glu Glu Ala Ile Ser Asn Met Val Val Ala
                565                 570                 575

Leu Lys Glu Leu Ser Ile Arg Gly Asp Phe Arg Thr Thr Val Glu Tyr
            580                 585                 590

Leu Ile Lys Leu Leu Glu Thr Glu Ser Phe Gln Leu Asn Arg Ile Asp
        595                 600                 605

Thr Gly Trp Leu Asp Arg Leu Ile Ala Glu Lys Val Gln Ala Glu Arg
    610                 615                 620

Pro Asp Thr Met Leu Gly Val Val Cys Gly Ala Leu His Val Ala Asp
625                 630                 635                 640

Val Asn Leu Arg Asn Ser Ile Ser Asn Phe Leu His Ser Leu Glu Arg
                645                 650                 655

Gly Gln Val Leu Pro Ala His Thr Leu Leu Asn Thr Val Asp Val Glu
            660                 665                 670

Leu Ile Tyr Glu Gly Ile Lys Tyr Val Leu Lys Val Thr Arg Gln Ser
        675                 680                 685

Pro Asn Ser Tyr Val Val Ile Met Asn Gly Ser Cys Val Glu Val Asp
    690                 695                 700
```

```
Val His Arg Leu Ser Asp Gly Gly Leu Leu Leu Ser Tyr Asp Gly Ser
705                 710                 715                 720

Ser Tyr Thr Thr Tyr Met Lys Glu Glu Val Asp Arg Tyr Arg Ile Thr
                725                 730                 735

Ile Gly Asn Lys Thr Cys Val Phe Glu Lys Glu Asn Asp Pro Ser Val
            740                 745                 750

Met Arg Ser Pro Ser Ala Gly Lys Leu Ile Gln Tyr Ile Val Glu Asp
        755                 760                 765

Gly Gly His Val Phe Ala Gly Gln Cys Tyr Ala Glu Ile Glu Val Met
    770                 775                 780

Lys Met Val Met Thr Leu Thr Ala Val Glu Ser Gly Cys Ile His Tyr
785                 790                 795                 800

Val Lys Arg Pro Gly Ala Ala Leu Asp Pro Gly Cys Val Ile Ala Lys
                805                 810                 815

Met Gln Leu Asp Asn Pro Ser Lys Val Gln Gln Ala Glu Leu His Thr
            820                 825                 830

Gly Ser Leu Pro Gln Ile Gln Ser Thr Ala Leu Arg Gly Glu Lys Leu
        835                 840                 845

His Arg Val Phe His Tyr Val Leu Asp Asn Leu Val Asn Val Met Asn
    850                 855                 860

Gly Tyr Cys Leu Pro Asp Pro Phe Phe Ser Ser Lys Val Lys Asp Trp
865                 870                 875                 880

Val Glu Arg Leu Met Lys Thr Leu Arg Asp Pro Ser Leu Pro Leu Leu
                885                 890                 895

Glu Leu Gln Asp Ile Met Thr Ser Val Ser Gly Arg Ile Pro Leu Asn
            900                 905                 910

Val Glu Lys Ser Ile Lys Lys Glu Met Ala Gln Tyr Ala Ser Asn Ile
        915                 920                 925

Thr Ser Val Leu Cys Gln Phe Pro Ser Gln Gln Ile Ala Asn Ile Leu
    930                 935                 940

Asp Ser His Ala Ala Thr Leu Asn Arg Lys Ser Glu Arg Glu Val Phe
945                 950                 955                 960

Phe Met Asn Thr Gln Ser Ile Val Gln Leu Val Gln Arg Tyr Arg Ser
                965                 970                 975

Gly Ile Arg Gly His Met Lys Ala Val Val Met Asp Leu Leu Arg Gln
            980                 985                 990

Tyr Leu Arg Val Glu Thr Gln Phe  Gln Asn Gly His Tyr  Asp Lys Cys
        995                 1000                1005

Val Phe  Ala Leu Arg Glu Glu  Asn Lys Ser Asp Met  Asn Thr Val
    1010                1015                1020

Leu Asn  Tyr Ile Phe Ser His  Ala Gln Val Thr Lys  Lys Asn Leu
    1025                1030                1035

Leu Val  Thr Met Leu Ile Asp  Gln Leu Cys Gly Arg  Asp Pro Thr
    1040                1045                1050

Leu Thr  Asp Glu Leu Leu Asn  Ile Leu Thr Glu Leu  Thr Gln Leu
    1055                1060                1065

Ser Lys  Thr Thr Asn Ala Lys  Val Ala Leu Arg Ala  Arg Gln Val
    1070                1075                1080

Leu Ile  Ala Ser His Leu Pro  Ser Tyr Asp Val Arg  His Asn Gln
    1085                1090                1095

Val Glu  Ser Ile Phe Leu Ser  Ala Ile Asp Met Tyr  Gly His Gln
    1100                1105                1110
```

-continued

```
Phe Cys  Ile Glu Asn Leu Gln  Lys Leu Ile Leu Ser  Glu Thr Ser
    1115                 1120                 1125

Ile Phe  Asp Val Leu Pro Asn  Phe Phe Tyr His Ser  Asn Gln Val
    1130                 1135                 1140

Val Arg  Met Ala Ala Leu Glu  Val Tyr Val Arg Arg  Ala Tyr Ile
    1145                 1150                 1155

Ala Tyr  Glu Leu Asn Ser Val  Gln His Arg Gln Leu  Lys Asp Asn
    1160                 1165                 1170

Thr Cys  Val Val Glu Phe Gln  Phe Met Leu Pro Thr  Ser His Pro
    1175                 1180                 1185

Asn Arg  Gly Asn Ile Pro Thr  Leu Asn Arg Met Ser  Phe Ala Ser
    1190                 1195                 1200

Asn Leu  Asn His Tyr Gly Met  Thr His Val Ala Ser  Val Ser Asp
    1205                 1210                 1215

Val Leu  Leu Asp Asn Ala Phe  Thr Pro Pro Cys Gln  Arg Met Gly
    1220                 1225                 1230

Gly Met  Val Ser Phe Arg Thr  Phe Glu Asp Phe Val  Arg Ile Phe
    1235                 1240                 1245

Asp Glu  Val Met Gly Cys Phe  Cys Asp Ser Pro Pro  Gln Ser Pro
    1250                 1255                 1260

Thr Phe  Pro Glu Ser Gly His  Thr Ser Leu Tyr Asp  Glu Asp Lys
    1265                 1270                 1275

Val Pro  Arg Asp Glu Pro Ile  His Ile Leu Asn Val  Ala Ile Lys
    1280                 1285                 1290

Thr Asp  Gly Asp Ile Glu Asp  Asp Arg Leu Ala Ala  Met Phe Arg
    1295                 1300                 1305

Glu Phe  Thr Gln Gln Asn Lys  Ala Thr Leu Val Glu  His Gly Ile
    1310                 1315                 1320

Arg Arg  Leu Thr Phe Leu Val  Ala Gln Lys Asp Phe  Arg Lys Gln
    1325                 1330                 1335

Val Asn  Cys Glu Val Asp Gln  Arg Phe His Arg Glu  Phe Pro Lys
    1340                 1345                 1350

Phe Phe  Thr Phe Arg Ala Arg  Asp Lys Phe Glu Glu  Asp Arg Ile
    1355                 1360                 1365

Tyr Arg  His Leu Glu Pro Ala  Leu Ala Phe Gln Leu  Glu Leu Asn
    1370                 1375                 1380

Arg Met  Arg Asn Phe Asp Leu  Thr Ala Ile Pro Cys  Ala Asn His
    1385                 1390                 1395

Lys Met  His Leu Tyr Leu Gly  Ala Ala Lys Val Glu  Val Gly Thr
    1400                 1405                 1410

Glu Val  Thr Asp Tyr Arg Phe  Phe Val Arg Ala Ile  Ile Arg His
    1415                 1420                 1425

Ser Asp  Leu Val Thr Lys Glu  Ala Ser Phe Glu Tyr  Leu Gln Asn
    1430                 1435                 1440

Glu Gly  Glu Arg Leu Leu Leu  Glu Ala Met Asp Glu  Leu Glu Val
    1445                 1450                 1455

Ala Phe  Asn Asn Thr Asn Val  Arg Thr Asp Cys Asn  His Ile Phe
    1460                 1465                 1470

Leu Asn  Phe Val Pro Thr Val  Ile Met Asp Pro Ser  Lys Ile Glu
    1475                 1480                 1485

Glu Ser  Val Arg Ser Met Val  Met Arg Tyr Gly Ser  Arg Leu Trp
    1490                 1495                 1500

Lys Leu  Arg Val Leu Gln Ala  Glu Leu Lys Ile Asn  Ile Arg Leu
```

-continued

```
    1505                1510                1515

Thr Thr  Thr Gly Lys Ala Ile  Pro Ile Arg Leu Phe  Leu Thr Asn
    1520                1525                1530

Glu Ser  Gly Tyr Tyr Leu Asp  Ile Ser Leu Tyr Lys  Glu Val Thr
    1535                1540                1545

Asp Ser  Arg Thr Ala Gln Ile  Met Phe Gln Ala Tyr  Gly Asp Lys
    1550                1555                1560

Gln Gly  Pro Leu His Gly Met  Leu Ile Asn Thr Pro  Tyr Val Thr
    1565                1570                1575

Lys Asp  Leu Leu Gln Ser Lys  Arg Phe Gln Ala Gln  Ser Leu Gly
    1580                1585                1590

Thr Thr  Tyr Ile Tyr Asp Ile  Pro Glu Met Phe Arg  Gln Ser Leu
    1595                1600                1605

Ile Lys  Leu Trp Glu Ser Met  Ser Thr Gln Ala Phe  Leu Pro Ser
    1610                1615                1620

Pro Pro  Leu Pro Ser Asp Ile  Leu Thr Tyr Thr Glu  Leu Val Leu
    1625                1630                1635

Asp Asp  Gln Gly Gln Leu Val  His Met Asn Arg Leu  Pro Gly Gly
    1640                1645                1650

Asn Glu  Ile Gly Met Val Ala  Trp Lys Met Ser Leu  Lys Ser Pro
    1655                1660                1665

Glu Tyr  Pro Asp Gly Arg Asp  Val Ile Val Ile Gly  Asn Asp Ile
    1670                1675                1680

Thr Tyr  Arg Ile Gly Ser Phe  Gly Pro Gln Glu Asp  Leu Leu Phe
    1685                1690                1695

Leu Arg  Ala Ser Glu Leu Ala  Arg Ala Glu Gly Ile  Pro Arg Ile
    1700                1705                1710

Tyr Val  Ala Ala Asn Ser Gly  Ala Arg Ile Gly Leu  Ala Glu Glu
    1715                1720                1725

Ile Arg  His Met Phe His Val  Ala Trp Val Asp Ser  Glu Asp Pro
    1730                1735                1740

Tyr Lys  Gly Tyr Lys Tyr Leu  Tyr Leu Thr Pro Gln  Asp Tyr Lys
    1745                1750                1755

Arg Val  Ser Ala Leu Asn Ser  Val His Cys Glu His  Val Glu Asp
    1760                1765                1770

Glu Gly  Glu Ser Arg Tyr Lys  Ile Thr Asp Ile Ile  Gly Lys Glu
    1775                1780                1785

Glu Gly  Leu Gly Ala Glu Asn  Leu Arg Gly Ser Gly  Met Ile Ala
    1790                1795                1800

Gly Glu  Ser Ser Leu Ala Tyr  Asp Glu Ile Ile Thr  Ile Ser Leu
    1805                1810                1815

Val Thr  Cys Arg Ala Ile Gly  Ile Gly Ala Tyr Leu  Val Arg Leu
    1820                1825                1830

Gly Gln  Arg Thr Ile Gln Val  Glu Asn Ser His Leu  Ile Leu Thr
    1835                1840                1845

Gly Ala  Gly Ala Leu Asn Lys  Val Leu Gly Arg Glu  Val Tyr Thr
    1850                1855                1860

Ser Asn  Asn Gln Leu Gly Gly  Ile Gln Ile Met His  Asn Asn Gly
    1865                1870                1875

Val Thr  His Cys Thr Val Cys  Asp Asp Phe Glu Gly  Val Phe Thr
    1880                1885                1890

Val Leu  His Trp Leu Ser Tyr  Met Pro Lys Asn Val  His Ser Ser
    1895                1900                1905
```

```
Val Pro  Leu Leu Asn Ser Lys  Asp Pro Ile Asp Arg  Ile Ile Glu
    1910                 1915                 1920

Phe Val  Pro Thr Lys Ala Pro  Tyr Asp Pro Arg Trp  Met Leu Ala
    1925                 1930                 1935

Gly Arg  Pro His Pro Thr Gln  Lys Gly Gln Trp Leu  Ser Gly Phe
    1940                 1945                 1950

Phe Asp  Tyr Gly Ser Phe Ser  Glu Ile Met Gln Pro  Trp Ala Gln
    1955                 1960                 1965

Thr Val  Val Val Gly Arg Ala  Arg Leu Gly Gly Ile  Pro Val Gly
    1970                 1975                 1980

Val Val  Ala Val Glu Thr Arg  Thr Val Glu Leu Ser  Val Pro Ala
    1985                 1990                 1995

Asp Pro  Ala Asn Leu Asp Ser  Glu Ala Lys Ile Ile  Gln Gln Ala
    2000                 2005                 2010

Gly Gln  Val Trp Phe Pro Asp  Ser Ala Phe Lys Thr  Tyr Gln Ala
    2015                 2020                 2025

Ile Lys  Asp Phe Asn Arg Glu  Gly Leu Pro Leu Met  Val Phe Ala
    2030                 2035                 2040

Asn Trp  Arg Gly Phe Ser Gly  Gly Met Lys Asp Met  Tyr Asp Gln
    2045                 2050                 2055

Val Leu  Lys Phe Gly Ala Tyr  Ile Val Asp Gly Leu  Arg Glu Cys
    2060                 2065                 2070

Ser Gln  Pro Val Met Val Tyr  Ile Pro Pro Gln Ala  Glu Leu Arg
    2075                 2080                 2085

Gly Gly  Ser Trp Val Val Ile  Asp Pro Thr Ile Asn  Pro Arg His
    2090                 2095                 2100

Met Glu  Met Tyr Ala Asp Arg  Glu Ser Arg Gly Ser  Val Leu Glu
    2105                 2110                 2115

Pro Glu  Gly Thr Val Glu Ile  Lys Phe Arg Lys Lys  Asp Leu Val
    2120                 2125                 2130

Lys Thr  Met Arg Arg Val Asp  Pro Val Tyr Ile Arg  Leu Ala Glu
    2135                 2140                 2145

Arg Leu  Gly Thr Pro Glu Leu  Ser Pro Thr Glu Arg  Lys Glu Leu
    2150                 2155                 2160

Glu Ser  Lys Leu Lys Glu Arg  Glu Glu Phe Leu Ile  Pro Ile Tyr
    2165                 2170                 2175

His Gln  Val Ala Val Gln Phe  Ala Asp Leu His Asp  Thr Pro Gly
    2180                 2185                 2190

Arg Met  Gln Glu Lys Gly Val  Ile Asn Asp Ile Leu  Asp Trp Lys
    2195                 2200                 2205

Thr Ser  Arg Thr Phe Phe Tyr  Trp Arg Leu Arg Arg  Leu Leu Leu
    2210                 2215                 2220

Glu Asp  Leu Val Lys Lys Lys  Ile His Ser Ala Asn  Pro Glu Leu
    2225                 2230                 2235

Thr Asp  Gly Gln Ile Gln Ala  Met Leu Arg Arg Trp  Phe Val Glu
    2240                 2245                 2250

Val Glu  Gly Thr Val Lys Ala  Tyr Val Trp Asp Asn  Asn Lys Asp
    2255                 2260                 2265

Leu Val  Glu Trp Leu Glu Lys  Gln Leu Thr Glu Glu  Asp Gly Val
    2270                 2275                 2280

Arg Ser  Val Ile Glu Glu Asn  Ile Lys Tyr Ile Ser  Arg Asp Tyr
    2285                 2290                 2295
```

```
Val Leu  Lys Gln Ile Arg Ser  Leu Val Gln Ala Asn  Pro Glu Val
    2300                 2305                 2310

Ala Met  Asp Ser Ile Val His  Met Thr Gln His Ile  Ser Pro Thr
    2315                 2320                 2325

Gln Arg  Ala Glu Val Val Arg  Ile Leu Ser Thr Met  Asp Ser Pro
    2330                 2335                 2340

Ser Thr
    2345
```

<210> SEQ ID NO 51
<211> LENGTH: 2345
<212> TYPE: PRT
<213> ORGANISM: Mus musculus

<400> SEQUENCE: 51

```
Met Asp Glu Pro Ser Pro Leu Ala Lys Thr Leu Glu Leu Asn Gln His
1               5                   10                  15

Ser Arg Phe Ile Ile Gly Ser Val Ser Glu Asp Asn Ser Glu Asp Glu
            20                  25                  30

Ile Ser Asn Leu Val Lys Leu Asp Leu Glu Glu Lys Glu Gly Ser Leu
        35                  40                  45

Ser Pro Ala Ser Val Ser Ser Asp Thr Leu Ser Asp Leu Gly Ile Ser
    50                  55                  60

Gly Leu Gln Asp Gly Leu Ala Phe His Met Arg Ser Ser Met Ser Gly
65                  70                  75                  80

Leu His Leu Val Lys Gln Gly Arg Asp Arg Lys Lys Ile Asp Ser Gln
                85                  90                  95

Arg Asp Phe Thr Val Ala Ser Pro Ala Glu Phe Val Thr Arg Phe Gly
            100                 105                 110

Gly Asn Lys Val Ile Glu Lys Val Leu Ile Ala Asn Asn Gly Ile Ala
        115                 120                 125

Ala Val Lys Cys Met Arg Ser Ile Arg Arg Trp Ser Tyr Glu Met Phe
    130                 135                 140

Arg Asn Glu Arg Ala Ile Arg Phe Val Val Met Val Thr Pro Glu Asp
145                 150                 155                 160

Leu Lys Ala Asn Ala Glu Tyr Ile Lys Met Ala Asp His Tyr Val Pro
                165                 170                 175

Val Pro Gly Gly Pro Asn Asn Asn Asn Tyr Ala Asn Val Glu Leu Ile
            180                 185                 190

Leu Asp Ile Ala Lys Arg Ile Pro Val Gln Ala Val Trp Ala Gly Trp
        195                 200                 205

Gly His Ala Ser Glu Asn Pro Lys Leu Pro Glu Leu Leu Leu Lys Asn
    210                 215                 220

Gly Ile Ala Phe Met Gly Pro Pro Ser Gln Ala Met Trp Ala Leu Gly
225                 230                 235                 240

Asp Lys Ile Ala Ser Ser Ile Val Ala Gln Thr Ala Gly Ile Pro Thr
                245                 250                 255

Leu Pro Trp Ser Gly Ser Gly Leu Arg Val Asp Trp Gln Glu Asn Asp
            260                 265                 270

Phe Ser Lys Arg Ile Leu Asn Val Pro Gln Asp Leu Tyr Glu Lys Gly
        275                 280                 285

Tyr Val Lys Asp Val Asp Asp Gly Leu Lys Ala Ala Glu Glu Val Gly
    290                 295                 300

Tyr Pro Val Met Ile Lys Ala Ser Glu Gly Gly Gly Gly Lys Gly Ile
305                 310                 315                 320
```

-continued

```
Arg Lys Val Asn Asn Ala Asp Asp Phe Pro Asn Leu Phe Arg Gln Val
                325                 330                 335

Gln Ala Glu Val Pro Gly Ser Pro Ile Phe Val Met Arg Leu Ala Lys
            340                 345                 350

Gln Ser Arg His Leu Glu Val Gln Ile Leu Ala Asp Gln Tyr Gly Asn
        355                 360                 365

Ala Ile Ser Leu Phe Gly Arg Asp Cys Ser Val Gln Arg Arg His Gln
    370                 375                 380

Lys Ile Ile Glu Glu Ala Pro Ala Ala Ile Ala Thr Pro Ala Val Phe
385                 390                 395                 400

Glu His Met Glu Gln Cys Ala Val Lys Leu Ala Lys Met Val Gly Tyr
                405                 410                 415

Val Ser Ala Gly Thr Val Glu Tyr Leu Tyr Ser Gln Asp Gly Ser Phe
            420                 425                 430

Tyr Phe Leu Glu Leu Asn Pro Arg Leu Gln Val Glu His Pro Cys Thr
        435                 440                 445

Glu Met Val Ala Asp Val Asn Leu Pro Ala Ala Gln Leu Gln Ile Ala
    450                 455                 460

Met Gly Ile Pro Leu Phe Arg Ile Lys Asp Ile Arg Met Met Tyr Gly
465                 470                 475                 480

Val Ser Pro Trp Gly Asp Ala Pro Ile Asp Phe Glu Asn Ser Ala His
                485                 490                 495

Val Pro Cys Pro Arg Gly His Val Ile Ala Ala Arg Ile Thr Ser Glu
            500                 505                 510

Asn Pro Asp Glu Gly Phe Lys Pro Ser Ser Gly Thr Val Gln Glu Leu
        515                 520                 525

Asn Phe Arg Ser Asn Lys Asn Val Trp Gly Tyr Phe Ser Val Ala Ala
    530                 535                 540

Ala Gly Gly Leu His Glu Phe Ala Asp Ser Gln Phe Gly His Cys Phe
545                 550                 555                 560

Ser Trp Gly Glu Asn Arg Glu Glu Ala Ile Ser Asn Met Val Val Ala
                565                 570                 575

Leu Lys Glu Leu Ser Ile Arg Gly Asp Phe Arg Thr Thr Val Glu Tyr
            580                 585                 590

Leu Ile Lys Leu Leu Glu Thr Glu Ser Phe Gln Leu Asn Arg Ile Asp
        595                 600                 605

Thr Gly Trp Leu Asp Arg Leu Ile Ala Glu Lys Val Gln Ala Glu Arg
    610                 615                 620

Pro Asp Thr Met Leu Gly Val Val Cys Gly Ala Leu His Val Ala Asp
625                 630                 635                 640

Val Ser Leu Arg Asn Ser Ile Ser Asn Phe Leu His Ser Leu Glu Arg
                645                 650                 655

Gly Gln Val Leu Pro Ala His Thr Leu Leu Asn Thr Val Asp Val Glu
            660                 665                 670

Leu Ile Tyr Glu Gly Ile Lys Tyr Val Leu Lys Val Thr Arg Gln Ser
        675                 680                 685

Pro Asn Ser Tyr Val Val Ile Met Asn Gly Ser Cys Val Glu Val Asp
    690                 695                 700

Val His Arg Leu Ser Asp Gly Gly Leu Leu Leu Ser Tyr Asp Gly Ser
705                 710                 715                 720

Ser Tyr Thr Thr Tyr Met Lys Glu Glu Val Asp Arg Tyr Arg Ile Thr
                725                 730                 735
```

```
Ile Gly Asn Lys Thr Cys Val Phe Glu Lys Glu Asn Asp Pro Ser Val
            740                 745                 750

Met Arg Ser Pro Ser Ala Gly Lys Leu Ile Gln Tyr Ile Val Glu Asp
        755                 760                 765

Gly Gly His Val Phe Ala Gly Gln Cys Tyr Ala Glu Ile Glu Val Met
    770                 775                 780

Lys Met Val Met Thr Leu Thr Ala Val Glu Ser Gly Cys Ile His Tyr
785                 790                 795                 800

Val Lys Arg Pro Gly Ala Ala Leu Asp Pro Gly Cys Val Ile Ala Lys
                805                 810                 815

Met Gln Leu Asp Asn Pro Ser Lys Val Gln Gln Ala Glu Leu His Thr
            820                 825                 830

Gly Ser Leu Pro Gln Ile Gln Ser Thr Ala Leu Arg Gly Glu Lys Leu
        835                 840                 845

His Arg Val Phe His Tyr Val Leu Asp Asn Leu Val Asn Val Met Asn
    850                 855                 860

Gly Tyr Cys Leu Pro Asp Pro Phe Phe Ser Ser Arg Val Lys Asp Trp
865                 870                 875                 880

Val Glu Arg Leu Met Lys Thr Leu Arg Asp Pro Ser Leu Pro Leu Leu
                885                 890                 895

Glu Leu Gln Asp Ile Met Thr Ser Val Ser Gly Arg Ile Pro Leu Asn
            900                 905                 910

Val Glu Lys Ser Ile Lys Lys Glu Met Ala Gln Tyr Ala Ser Asn Ile
        915                 920                 925

Thr Ser Val Leu Cys Gln Phe Pro Ser Gln Gln Ile Ala Asn Ile Leu
    930                 935                 940

Asp Ser His Ala Ala Thr Leu Asn Arg Lys Ser Glu Arg Glu Val Phe
945                 950                 955                 960

Phe Met Asn Thr Gln Ser Ile Val Gln Leu Val Gln Arg Tyr Arg Ser
                965                 970                 975

Gly Ile Arg Gly His Met Lys Ala Val Val Met Asp Leu Leu Arg Gln
            980                 985                 990

Tyr Leu Arg Val Glu Thr Gln Phe  Gln Asn Gly His Tyr  Asp Lys Cys
        995                 1000                1005

Val Phe  Ala Leu Arg Glu Glu  Asn Lys Ser Asp Met  Asn Thr Val
    1010                1015                1020

Leu Asn  Tyr Ile Phe Ser His  Ala Gln Val Thr Lys  Lys Asn Leu
    1025                1030                1035

Leu Val  Thr Met Leu Ile Asp  Gln Leu Cys Gly Arg  Asp Pro Thr
    1040                1045                1050

Leu Thr  Asp Glu Leu Leu Asn  Ile Leu Thr Glu Leu  Thr Gln Leu
    1055                1060                1065

Ser Lys  Thr Thr Asn Ala Lys  Val Ala Leu Arg Ala  Arg Gln Val
    1070                1075                1080

Leu Ile  Ala Ser His Leu Pro  Ser Tyr Glu Leu Arg  His Asn Gln
    1085                1090                1095

Val Glu  Ser Ile Phe Leu Ser  Ala Ile Asp Met Tyr  Gly His Gln
    1100                1105                1110

Phe Cys  Ile Glu Asn Leu Gln  Lys Leu Ile Leu Ser  Glu Thr Ser
    1115                1120                1125

Ile Phe  Asp Val Leu Pro Asn  Phe Phe Tyr His Ser  Asn Gln Val
    1130                1135                1140

Val Arg  Met Ala Ala Leu Glu  Val Tyr Val Arg Arg  Ala Tyr Ile
```

-continued

```
    1145                1150                1155

Ala Tyr  Glu Leu Asn Ser Val  Gln His Arg Gln Leu  Lys Asp Asn
    1160                1165                1170

Thr Cys  Val Val Glu Phe Gln  Phe Met Leu Pro Thr  Ser His Pro
    1175                1180                1185

Asn Arg  Gly Asn Ile Pro Thr  Leu Asn Arg Met Ser  Phe Ala Ser
    1190                1195                1200

Asn Leu  Asn His Tyr Gly Met  Thr His Val Ala Ser  Val Ser Asp
    1205                1210                1215

Val Leu  Leu Asp Asn Ala Phe  Thr Pro Pro Cys Gln  Arg Met Gly
    1220                1225                1230

Gly Met  Val Ser Phe Arg Thr  Phe Glu Asp Phe Val  Arg Ile Phe
    1235                1240                1245

Asp Glu  Ile Met Gly Cys Phe  Cys Asp Ser Pro Pro  Gln Ser Pro
    1250                1255                1260

Thr Phe  Pro Glu Ser Gly His  Thr Ser Leu Tyr Asp  Glu Asp Lys
    1265                1270                1275

Val Pro  Arg Asp Glu Pro Ile  His Ile Leu Asn Val  Ala Ile Lys
    1280                1285                1290

Thr Asp  Gly Asp Ile Glu Asp  Asp Arg Leu Ala Ala  Met Phe Arg
    1295                1300                1305

Glu Phe  Thr Gln Gln Asn Lys  Ala Thr Leu Val Glu  His Gly Ile
    1310                1315                1320

Arg Arg  Leu Thr Phe Leu Val  Ala Gln Lys Asp Phe  Arg Lys Gln
    1325                1330                1335

Val Asn  Cys Glu Val Asp Gln  Arg Phe His Arg Glu  Phe Pro Lys
    1340                1345                1350

Phe Phe  Thr Phe Arg Ala Arg  Asp Lys Phe Glu Glu  Asp Arg Ile
    1355                1360                1365

Tyr Arg  His Leu Glu Pro Ala  Leu Ala Phe Gln Leu  Glu Leu Asn
    1370                1375                1380

Arg Met  Arg Asn Phe Asp Leu  Thr Ala Ile Pro Cys  Ala Asn His
    1385                1390                1395

Lys Met  His Leu Tyr Leu Gly  Ala Ala Lys Val Glu  Val Gly Thr
    1400                1405                1410

Glu Val  Thr Asp Tyr Arg Phe  Phe Val Arg Ala Ile  Ile Arg His
    1415                1420                1425

Ser Asp  Leu Val Thr Lys Glu  Ala Ser Phe Glu Tyr  Leu Gln Asn
    1430                1435                1440

Glu Gly  Glu Arg Leu Leu Leu  Glu Ala Met Asp Glu  Leu Glu Val
    1445                1450                1455

Ala Phe  Asn Asn Thr Asn Val  Arg Thr Asp Cys Asn  His Ile Phe
    1460                1465                1470

Leu Asn  Phe Val Pro Thr Val  Ile Met Asp Pro Ser  Lys Ile Glu
    1475                1480                1485

Glu Ser  Val Arg Ser Met Val  Met Arg Tyr Gly Ser  Arg Leu Trp
    1490                1495                1500

Lys Leu  Arg Val Leu Gln Ala  Glu Leu Lys Ile Asn  Ile Arg Leu
    1505                1510                1515

Thr Thr  Thr Gly Lys Ala Ile  Pro Ile Arg Leu Phe  Leu Thr Asn
    1520                1525                1530

Glu Ser  Gly Tyr Tyr Leu Asp  Ile Ser Leu Tyr Lys  Glu Val Thr
    1535                1540                1545
```

-continued

```
Asp Ser  Arg Thr Ala Gln Ile  Met Phe Gln Ala Tyr  Gly Asp Lys
    1550                 1555                 1560

Gln Gly  Pro Leu His Gly Met  Leu Ile Asn Thr Pro  Tyr Val Thr
    1565                 1570                 1575

Lys Asp  Leu Leu Gln Ser Lys  Arg Phe Gln Ala Gln  Ser Leu Gly
    1580                 1585                 1590

Thr Thr  Tyr Ile Tyr Asp Ile  Pro Glu Met Phe Arg  Gln Ser Leu
    1595                 1600                 1605

Ile Lys  Leu Trp Glu Ser Met  Ser Thr Gln Ala Phe  Leu Pro Ser
    1610                 1615                 1620

Pro Pro  Leu Pro Ser Asp Ile  Leu Thr Tyr Thr Glu  Leu Val Leu
    1625                 1630                 1635

Asp Asp  Gln Gly Gln Leu Val  His Met Asn Arg Leu  Pro Gly Gly
    1640                 1645                 1650

Asn Glu  Ile Gly Met Val Ala  Trp Lys Met Ser Leu  Lys Ser Pro
    1655                 1660                 1665

Glu Tyr  Pro Asp Gly Arg Asp  Ile Ile Val Ile Gly  Asn Asp Ile
    1670                 1675                 1680

Thr Tyr  Arg Ile Gly Ser Phe  Gly Pro Gln Glu Asp  Leu Leu Phe
    1685                 1690                 1695

Leu Arg  Ala Ser Glu Leu Ala  Arg Ala Glu Gly Ile  Pro Arg Ile
    1700                 1705                 1710

Tyr Val  Ala Ala Asn Ser Gly  Ala Arg Ile Gly Leu  Ala Glu Glu
    1715                 1720                 1725

Ile Arg  His Met Phe His Val  Ala Trp Val Asp Pro  Glu Asp Pro
    1730                 1735                 1740

Tyr Lys  Gly Tyr Lys Tyr Leu  Tyr Leu Thr Pro Gln  Asp Tyr Lys
    1745                 1750                 1755

Arg Val  Ser Ala Leu Asn Ser  Val His Cys Glu His  Val Glu Asp
    1760                 1765                 1770

Glu Gly  Glu Ser Arg Tyr Lys  Ile Thr Asp Ile Ile  Gly Lys Glu
    1775                 1780                 1785

Glu Gly  Leu Gly Ala Glu Asn  Leu Arg Gly Ser Gly  Met Ile Ala
    1790                 1795                 1800

Gly Glu  Ser Ser Leu Ala Tyr  Asp Glu Val Ile Thr  Ile Ser Leu
    1805                 1810                 1815

Val Thr  Cys Arg Ala Ile Gly  Ile Gly Ala Tyr Leu  Val Arg Leu
    1820                 1825                 1830

Gly Gln  Arg Thr Ile Gln Val  Glu Asn Ser His Leu  Ile Leu Thr
    1835                 1840                 1845

Gly Ala  Gly Ala Leu Asn Lys  Val Leu Gly Arg Glu  Val Tyr Thr
    1850                 1855                 1860

Ser Asn  Asn Gln Leu Gly Gly  Ile Gln Ile Met His  Asn Asn Gly
    1865                 1870                 1875

Val Thr  His Ser Thr Val Cys  Asp Asp Phe Glu Gly  Val Phe Thr
    1880                 1885                 1890

Val Leu  His Trp Leu Ser Tyr  Met Pro Lys Ser Val  His Ser Ser
    1895                 1900                 1905

Val Pro  Leu Leu Asn Ser Lys  Asp Pro Ile Asp Arg  Ile Ile Glu
    1910                 1915                 1920

Phe Val  Pro Thr Lys Ala Pro  Tyr Asp Pro Arg Trp  Met Leu Ala
    1925                 1930                 1935
```

-continued

```
Gly Arg  Pro His Pro Thr Gln  Lys Gly Gln Trp Leu  Ser Gly Phe
    1940                1945                1950

Phe Asp  Tyr Gly Ser Phe Ser  Glu Ile Met Gln Pro  Trp Ala Gln
    1955                1960                1965

Thr Val  Val Val Gly Arg Ala  Arg Leu Gly Gly Ile  Pro Val Gly
    1970                1975                1980

Val Val  Ala Val Glu Thr Arg  Thr Val Glu Leu Ser  Ile Pro Ala
    1985                1990                1995

Asp Pro  Ala Asn Leu Asp Ser  Glu Ala Lys Ile Ile  Gln Gln Ala
    2000                2005                2010

Gly Gln  Val Trp Phe Pro Asp  Ser Ala Phe Lys Thr  Tyr Gln Ala
    2015                2020                2025

Ile Lys  Asp Phe Asn Arg Glu  Gly Leu Pro Leu Met  Val Phe Ala
    2030                2035                2040

Asn Trp  Arg Gly Phe Ser Gly  Gly Met Lys Asp Met  Tyr Asp Gln
    2045                2050                2055

Val Leu  Lys Phe Gly Ala Tyr  Ile Val Asp Gly Leu  Arg Glu Cys
    2060                2065                2070

Ser Gln  Pro Val Met Val Tyr  Ile Pro Pro Gln Ala  Glu Leu Arg
    2075                2080                2085

Gly Gly  Ser Trp Val Val Ile  Asp Pro Thr Ile Asn  Pro Arg His
    2090                2095                2100

Met Glu  Met Tyr Ala Asp Arg  Glu Ser Arg Gly Ser  Val Leu Glu
    2105                2110                2115

Pro Glu  Gly Thr Val Glu Ile  Lys Phe Arg Lys Lys  Asp Leu Val
    2120                2125                2130

Lys Thr  Met Arg Arg Val Asp  Pro Val Tyr Ile Arg  Leu Ala Glu
    2135                2140                2145

Arg Leu  Gly Thr Pro Glu Leu  Ser Pro Thr Glu Arg  Lys Glu Leu
    2150                2155                2160

Glu Ser  Lys Leu Lys Glu Arg  Glu Glu Phe Leu Ile  Pro Ile Tyr
    2165                2170                2175

His Gln  Val Ala Val Gln Phe  Ala Asp Leu His Asp  Thr Pro Gly
    2180                2185                2190

Arg Met  Gln Glu Lys Gly Val  Ile Asn Asp Ile Leu  Asp Trp Lys
    2195                2200                2205

Thr Ser  Arg Thr Phe Phe Tyr  Trp Arg Leu Arg Arg  Leu Leu Leu
    2210                2215                2220

Glu Asp  Leu Val Lys Lys Lys  Ile His Asn Ala Asn  Pro Glu Leu
    2225                2230                2235

Thr Asp  Gly Gln Ile Gln Ala  Met Leu Arg Arg Trp  Phe Val Glu
    2240                2245                2250

Val Glu  Gly Thr Val Lys Ala  Tyr Val Trp Asp Asn  Asn Lys Asp
    2255                2260                2265

Leu Val  Glu Trp Leu Glu Lys  Gln Leu Thr Glu Glu  Asp Gly Val
    2270                2275                2280

Arg Ser  Val Ile Glu Glu Asn  Ile Lys Tyr Ile Ser  Arg Asp Tyr
    2285                2290                2295

Val Leu  Lys Gln Ile Arg Ser  Leu Val Gln Ala Asn  Pro Glu Val
    2300                2305                2310

Ala Met  Asp Ser Ile Val His  Met Thr Gln His Ile  Ser Pro Thr
    2315                2320                2325

Gln Arg  Ala Glu Val Val Arg  Ile Leu Ser Thr Met  Asp Ser Pro
```

```
    2330                2335                2340

Ser Thr
    2345


<210> SEQ ID NO 52
<211> LENGTH: 2233
<212> TYPE: PRT
<213> ORGANISM: Saccharomyces cerevisiae

<400> SEQUENCE: 52

Met Ser Glu Glu Ser Leu Phe Glu Ser Ser Pro Gln Lys Met Glu Tyr
1               5                   10                  15

Glu Ile Thr Asn Tyr Ser Glu Arg His Thr Glu Leu Pro Gly His Phe
            20                  25                  30

Ile Gly Leu Asn Thr Val Asp Lys Leu Glu Glu Ser Pro Leu Arg Asp
        35                  40                  45

Phe Val Lys Ser His Gly Gly His Thr Val Ile Ser Lys Ile Leu Ile
    50                  55                  60

Ala Asn Asn Gly Ile Ala Ala Val Lys Glu Ile Arg Ser Val Arg Lys
65                  70                  75                  80

Trp Ala Tyr Glu Thr Phe Gly Asp Asp Arg Thr Val Gln Phe Val Ala
                85                  90                  95

Met Ala Thr Pro Glu Asp Leu Glu Ala Asn Ala Glu Tyr Ile Arg Met
            100                 105                 110

Ala Asp Gln Tyr Ile Glu Val Pro Gly Gly Thr Asn Asn Asn Asn Tyr
        115                 120                 125

Ala Asn Val Asp Leu Ile Val Asp Ile Ala Glu Arg Ala Asp Val Asp
    130                 135                 140

Ala Val Trp Ala Gly Trp Gly His Ala Ser Glu Asn Pro Leu Leu Pro
145                 150                 155                 160

Glu Lys Leu Ser Gln Ser Lys Arg Lys Val Ile Phe Ile Gly Pro Pro
                165                 170                 175

Gly Asn Ala Met Arg Ser Leu Gly Asp Lys Ile Ser Ser Thr Ile Val
            180                 185                 190

Ala Gln Ser Ala Lys Val Pro Cys Ile Pro Trp Ser Gly Thr Gly Val
        195                 200                 205

Asp Thr Val His Val Asp Glu Lys Thr Gly Leu Val Ser Val Asp Asp
    210                 215                 220

Asp Ile Tyr Gln Lys Gly Cys Cys Thr Ser Pro Glu Asp Gly Leu Gln
225                 230                 235                 240

Lys Ala Lys Arg Ile Gly Phe Pro Val Met Ile Lys Ala Ser Glu Gly
                245                 250                 255

Gly Gly Gly Lys Gly Ile Arg Gln Val Glu Arg Glu Glu Asp Phe Ile
            260                 265                 270

Ala Leu Tyr His Gln Ala Ala Asn Glu Ile Pro Gly Ser Pro Ile Phe
        275                 280                 285

Ile Met Lys Leu Ala Gly Arg Ala Arg His Leu Glu Val Gln Leu Leu
    290                 295                 300

Ala Asp Gln Tyr Gly Thr Asn Ile Ser Leu Phe Gly Arg Asp Cys Ser
305                 310                 315                 320

Val Gln Arg Arg His Gln Lys Ile Ile Glu Glu Ala Pro Val Thr Ile
                325                 330                 335

Ala Lys Ala Glu Thr Phe His Glu Met Glu Lys Ala Ala Val Arg Leu
            340                 345                 350
```

-continued

```
Gly Lys Leu Val Gly Tyr Val Ser Ala Gly Thr Val Glu Tyr Leu Tyr
        355                 360                 365

Ser His Asp Asp Gly Lys Phe Tyr Phe Leu Glu Leu Asn Pro Arg Leu
    370                 375                 380

Gln Val Glu His Pro Thr Thr Glu Met Val Ser Gly Val Asn Leu Pro
385                 390                 395                 400

Ala Ala Gln Leu Gln Ile Ala Met Gly Ile Pro Met His Arg Ile Ser
                405                 410                 415

Asp Ile Arg Thr Leu Tyr Gly Met Asn Pro His Ser Ala Ser Glu Ile
            420                 425                 430

Asp Phe Glu Phe Lys Thr Gln Asp Ala Thr Lys Lys Gln Arg Arg Pro
        435                 440                 445

Ile Pro Lys Gly His Cys Thr Ala Cys Arg Ile Thr Ser Glu Asp Pro
    450                 455                 460

Asn Asp Gly Phe Lys Pro Ser Gly Gly Thr Leu His Glu Leu Asn Phe
465                 470                 475                 480

Arg Ser Ser Ser Asn Val Trp Gly Tyr Phe Ser Val Gly Asn Asn Gly
                485                 490                 495

Asn Ile His Ser Phe Ser Asp Ser Gln Phe Gly His Ile Phe Ala Phe
            500                 505                 510

Gly Glu Asn Arg Gln Ala Ser Arg Lys His Met Val Val Ala Leu Lys
        515                 520                 525

Glu Leu Ser Ile Arg Gly Asp Phe Arg Thr Thr Val Glu Tyr Leu Ile
    530                 535                 540

Lys Leu Leu Glu Thr Glu Asp Phe Glu Asp Asn Thr Ile Thr Thr Gly
545                 550                 555                 560

Trp Leu Asp Asp Leu Ile Thr His Lys Met Thr Ala Glu Lys Pro Asp
                565                 570                 575

Pro Thr Leu Ala Val Ile Cys Gly Ala Ala Thr Lys Ala Phe Leu Ala
            580                 585                 590

Ser Glu Glu Ala Arg His Lys Tyr Ile Glu Ser Leu Gln Lys Gly Gln
        595                 600                 605

Val Leu Ser Lys Asp Leu Leu Gln Thr Met Phe Pro Val Asp Phe Ile
    610                 615                 620

His Glu Gly Lys Arg Tyr Lys Phe Thr Val Ala Lys Ser Gly Asn Asp
625                 630                 635                 640

Arg Tyr Thr Leu Phe Ile Asn Gly Ser Lys Cys Asp Ile Ile Leu Arg
                645                 650                 655

Gln Leu Ser Asp Gly Gly Leu Leu Ile Ala Ile Gly Gly Lys Ser His
            660                 665                 670

Thr Ile Tyr Trp Lys Glu Glu Val Ala Ala Thr Arg Leu Ser Val Asp
        675                 680                 685

Ser Met Thr Thr Leu Leu Glu Val Glu Asn Asp Pro Thr Gln Leu Arg
    690                 695                 700

Thr Pro Ser Pro Gly Lys Leu Val Lys Phe Leu Val Glu Asn Gly Glu
705                 710                 715                 720

His Ile Ile Lys Gly Gln Pro Tyr Ala Glu Ile Glu Val Met Lys Met
                725                 730                 735

Gln Met Pro Leu Val Ser Gln Glu Asn Gly Ile Val Gln Leu Leu Lys
            740                 745                 750

Gln Pro Gly Ser Thr Ile Val Ala Gly Asp Ile Met Ala Ile Met Thr
        755                 760                 765

Leu Asp Asp Pro Ser Lys Val Lys His Ala Leu Pro Phe Glu Gly Met
```

```
    770                 775                 780

Leu Pro Asp Phe Gly Ser Pro Val Ile Glu Gly Thr Lys Pro Ala Tyr
785                 790                 795                 800

Lys Phe Lys Ser Leu Val Ser Thr Leu Glu Asn Ile Leu Lys Gly Tyr
                805                 810                 815

Asp Asn Gln Val Ile Met Asn Ala Ser Leu Gln Gln Leu Ile Glu Val
            820                 825                 830

Leu Arg Asn Pro Lys Leu Pro Tyr Ser Glu Trp Lys Leu His Ile Ser
        835                 840                 845

Ala Leu His Ser Arg Leu Pro Ala Lys Leu Asp Glu Gln Met Glu Glu
    850                 855                 860

Leu Val Ala Arg Ser Leu Arg Arg Gly Ala Val Phe Pro Ala Arg Gln
865                 870                 875                 880

Leu Ser Lys Leu Ile Asp Met Ala Val Lys Asn Pro Glu Tyr Asn Pro
                885                 890                 895

Asp Lys Leu Leu Gly Ala Val Val Glu Pro Leu Ala Asp Ile Ala His
            900                 905                 910

Lys Tyr Ser Asn Gly Leu Glu Ala His Glu His Ser Ile Phe Val His
        915                 920                 925

Phe Leu Glu Glu Tyr Tyr Glu Val Glu Lys Leu Phe Asn Gly Pro Asn
    930                 935                 940

Val Arg Glu Glu Asn Ile Ile Leu Lys Leu Arg Asp Glu Asn Pro Lys
945                 950                 955                 960

Asp Leu Asp Lys Val Ala Leu Thr Val Leu Ser His Ser Lys Val Ser
                965                 970                 975

Ala Lys Asn Asn Leu Ile Leu Ala Ile Leu Lys His Tyr Gln Pro Leu
            980                 985                 990

Cys Lys Leu Ser Ser Lys Val Ser  Ala Ile Phe Ser Thr  Pro Leu Gln
        995                 1000                1005

His Ile  Val Glu Leu Glu Ser  Lys Ala Thr Ala Lys  Val Ala Leu
    1010                1015                1020

Gln Ala  Arg Glu Ile Leu Ile  Gln Gly Ala Leu Pro  Ser Val Lys
    1025                1030                1035

Glu Arg  Thr Glu Gln Ile Glu  His Ile Leu Lys Ser  Ser Val Val
    1040                1045                1050

Lys Val  Ala Tyr Gly Ser Ser  Asn Pro Lys Arg Ser  Glu Pro Asp
    1055                1060                1065

Leu Asn  Ile Leu Lys Asp Leu  Ile Asp Ser Asn Tyr  Val Val Phe
    1070                1075                1080

Asp Val  Leu Leu Gln Phe Leu  Thr His Gln Asp Pro  Val Val Thr
    1085                1090                1095

Ala Ala  Ala Ala Gln Val Tyr  Ile Arg Arg Ala Tyr  Arg Ala Tyr
    1100                1105                1110

Thr Ile  Gly Asp Ile Arg Val  His Glu Gly Val Thr  Val Pro Ile
    1115                1120                1125

Val Glu  Trp Lys Phe Gln Leu  Pro Ser Ala Ala Phe  Ser Thr Phe
    1130                1135                1140

Pro Thr  Val Lys Ser Lys Met  Gly Met Asn Arg Ala  Val Ser Val
    1145                1150                1155

Ser Asp  Leu Ser Tyr Val Ala  Asn Ser Gln Ser Ser  Pro Leu Arg
    1160                1165                1170

Glu Gly  Ile Leu Met Ala Val  Asp His Leu Asp Asp  Val Asp Glu
    1175                1180                1185
```

-continued

```
Ile Leu  Ser Gln Ser Leu Glu  Val Ile Pro Arg His  Gln Ser Ser
    1190                 1195                 1200

Ser Asn  Gly Pro Ala Pro Asp  Arg Ser Gly Ser Ser  Ala Ser Leu
    1205                 1210                 1215

Ser Asn  Val Ala Asn Val Cys  Val Ala Ser Thr Glu  Gly Phe Glu
    1220                 1225                 1230

Ser Glu  Glu Glu Ile Leu Val  Arg Leu Arg Glu Ile  Leu Asp Leu
    1235                 1240                 1245

Asn Lys  Gln Glu Leu Ile Asn  Ala Ser Ile Arg Arg  Ile Thr Phe
    1250                 1255                 1260

Met Phe  Gly Phe Lys Asp Gly  Ser Tyr Pro Lys Tyr  Tyr Thr Phe
    1265                 1270                 1275

Asn Gly  Pro Asn Tyr Asn Glu  Asn Glu Thr Ile Arg  His Ile Glu
    1280                 1285                 1290

Pro Ala  Leu Ala Phe Gln Leu  Glu Leu Gly Arg Leu  Ser Asn Phe
    1295                 1300                 1305

Asn Ile  Lys Pro Ile Phe Thr  Asp Asn Arg Asn Ile  His Val Tyr
    1310                 1315                 1320

Glu Ala  Val Ser Lys Thr Ser  Pro Leu Asp Lys Arg  Phe Phe Thr
    1325                 1330                 1335

Arg Gly  Ile Ile Arg Thr Gly  His Ile Arg Asp Asp  Ile Ser Ile
    1340                 1345                 1350

Gln Glu  Tyr Leu Thr Ser Glu  Ala Asn Arg Leu Met  Ser Asp Ile
    1355                 1360                 1365

Leu Asp  Asn Leu Glu Val Thr  Asp Thr Ser Asn Ser  Asp Leu Asn
    1370                 1375                 1380

His Ile  Phe Ile Asn Phe Ile  Ala Val Phe Asp Ile  Ser Pro Glu
    1385                 1390                 1395

Asp Val  Glu Ala Ala Phe Gly  Gly Phe Leu Glu Arg  Phe Gly Lys
    1400                 1405                 1410

Arg Leu  Leu Arg Leu Arg Val  Ser Ser Ala Glu Ile  Arg Ile Ile
    1415                 1420                 1425

Ile Lys  Asp Pro Gln Thr Gly  Ala Pro Val Pro Leu  Arg Ala Leu
    1430                 1435                 1440

Ile Asn  Asn Val Ser Gly Tyr  Val Ile Lys Thr Glu  Met Tyr Thr
    1445                 1450                 1455

Glu Val  Lys Asn Ala Lys Gly  Glu Trp Val Phe Lys  Ser Leu Gly
    1460                 1465                 1470

Lys Pro  Gly Ser Met His Leu  Arg Pro Ile Ala Thr  Pro Tyr Pro
    1475                 1480                 1485

Val Lys  Glu Trp Leu Gln Pro  Lys Arg Tyr Lys Ala  His Leu Met
    1490                 1495                 1500

Gly Thr  Thr Tyr Val Tyr Asp  Phe Pro Glu Leu Phe  Arg Gln Ala
    1505                 1510                 1515

Ser Ser  Ser Gln Trp Lys Asn  Phe Ser Ala Asp Val  Lys Leu Thr
    1520                 1525                 1530

Asp Asp  Phe Phe Ile Ser Asn  Glu Leu Ile Glu Asp  Glu Asn Gly
    1535                 1540                 1545

Glu Leu  Thr Glu Val Glu Arg  Glu Pro Gly Ala Asn  Ala Ile Gly
    1550                 1555                 1560

Met Val  Ala Phe Lys Ile Thr  Val Lys Thr Pro Glu  Tyr Pro Arg
    1565                 1570                 1575
```

```
Gly Arg  Gln Phe Val Val Val  Ala Asn Asp Ile Thr  Phe Lys Ile
    1580                 1585                 1590

Gly Ser  Phe Gly Pro Gln Glu  Asp Glu Phe Phe Asn  Lys Val Thr
    1595                 1600                 1605

Glu Tyr  Ala Arg Lys Arg Gly  Ile Pro Arg Ile Tyr  Leu Ala Ala
    1610                 1615                 1620

Asn Ser  Gly Ala Arg Ile Gly  Met Ala Glu Glu Ile  Val Pro Leu
    1625                 1630                 1635

Phe Gln  Val Ala Trp Asn Asp  Ala Ala Asn Pro Asp  Lys Gly Phe
    1640                 1645                 1650

Gln Tyr  Leu Tyr Leu Thr Ser  Glu Gly Met Glu Thr  Leu Lys Lys
    1655                 1660                 1665

Phe Asp  Lys Glu Asn Ser Val  Leu Thr Glu Arg Thr  Val Ile Asn
    1670                 1675                 1680

Gly Glu  Glu Arg Phe Val Ile  Lys Thr Ile Ile Gly  Ser Glu Asp
    1685                 1690                 1695

Gly Leu  Gly Val Glu Cys Leu  Arg Gly Ser Gly Leu  Ile Ala Gly
    1700                 1705                 1710

Ala Thr  Ser Arg Ala Tyr His  Asp Ile Phe Thr Ile  Thr Leu Val
    1715                 1720                 1725

Thr Cys  Arg Ser Val Gly Ile  Gly Ala Tyr Leu Val  Arg Leu Gly
    1730                 1735                 1740

Gln Arg  Ala Ile Gln Val Glu  Gly Gln Pro Ile Ile  Leu Thr Gly
    1745                 1750                 1755

Ala Pro  Ala Ile Asn Lys Met  Leu Gly Arg Glu Val  Tyr Thr Ser
    1760                 1765                 1770

Asn Leu  Gln Leu Gly Gly Thr  Gln Ile Met Tyr Asn  Asn Gly Val
    1775                 1780                 1785

Ser His  Leu Thr Ala Val Asp  Asp Leu Ala Gly Val  Glu Lys Ile
    1790                 1795                 1800

Val Glu  Trp Met Ser Tyr Val  Pro Ala Lys Arg Asn  Met Pro Val
    1805                 1810                 1815

Pro Ile  Leu Glu Thr Lys Asp  Thr Trp Asp Arg Pro  Val Asp Phe
    1820                 1825                 1830

Thr Pro  Thr Asn Asp Glu Thr  Tyr Asp Val Arg Trp  Met Ile Glu
    1835                 1840                 1845

Gly Arg  Glu Thr Glu Ser Gly  Phe Glu Tyr Gly Leu  Phe Asp Lys
    1850                 1855                 1860

Gly Ser  Phe Phe Glu Thr Leu  Ser Gly Trp Ala Lys  Gly Val Val
    1865                 1870                 1875

Val Gly  Arg Ala Arg Leu Gly  Gly Ile Pro Leu Gly  Val Ile Gly
    1880                 1885                 1890

Val Glu  Thr Arg Thr Val Glu  Asn Leu Ile Pro Ala  Asp Pro Ala
    1895                 1900                 1905

Asn Pro  Asn Ser Ala Glu Thr  Leu Ile Gln Glu Pro  Gly Gln Val
    1910                 1915                 1920

Trp His  Pro Asn Ser Ala Phe  Lys Thr Ala Gln Ala  Ile Asn Asp
    1925                 1930                 1935

Phe Asn  Asn Gly Glu Gln Leu  Pro Met Met Ile Leu  Ala Asn Trp
    1940                 1945                 1950

Arg Gly  Phe Ser Gly Gly Gln  Arg Asp Met Phe Asn  Glu Val Leu
    1955                 1960                 1965

Lys Tyr  Gly Ser Phe Ile Val  Asp Ala Leu Val Asp  Tyr Lys Gln
```

```
    1970                1975                1980

Pro Ile  Ile Ile Tyr Ile Pro  Pro Thr Gly Glu Leu  Arg Gly Gly
    1985                1990                1995

Ser Trp  Val Val Val Asp Pro  Thr Ile Asn Ala Asp  Gln Met Glu
    2000                2005                2010

Met Tyr  Ala Asp Val Asn Ala  Arg Ala Gly Val Leu  Glu Pro Gln
    2015                2020                2025

Gly Met  Val Gly Ile Lys Phe  Arg Arg Glu Lys Leu  Leu Asp Thr
    2030                2035                2040

Met Asn  Arg Leu Asp Asp Lys  Tyr Arg Glu Leu Arg  Ser Gln Leu
    2045                2050                2055

Ser Asn  Lys Ser Leu Ala Pro  Glu Val His Gln Gln  Ile Ser Lys
    2060                2065                2070

Gln Leu  Ala Asp Arg Glu Arg  Glu Leu Leu Pro Ile  Tyr Gly Gln
    2075                2080                2085

Ile Ser  Leu Gln Phe Ala Asp  Leu His Asp Arg Ser  Ser Arg Met
    2090                2095                2100

Val Ala  Lys Gly Val Ile Ser  Lys Glu Leu Glu Trp  Thr Glu Ala
    2105                2110                2115

Arg Arg  Phe Phe Phe Trp Arg  Leu Arg Arg Arg Leu  Asn Glu Glu
    2120                2125                2130

Tyr Leu  Ile Lys Arg Leu Ser  His Gln Val Gly Glu  Ala Ser Arg
    2135                2140                2145

Leu Glu  Lys Ile Ala Arg Ile  Arg Ser Trp Tyr Pro  Ala Ser Val
    2150                2155                2160

Asp His  Glu Asp Asp Arg Gln  Val Ala Thr Trp Ile  Glu Glu Asn
    2165                2170                2175

Tyr Lys  Thr Leu Asp Asp Lys  Leu Lys Gly Leu Lys  Leu Glu Ser
    2180                2185                2190

Phe Ala  Gln Asp Leu Ala Lys  Lys Ile Arg Ser Asp  His Asp Asn
    2195                2200                2205

Ala Ile  Asp Gly Leu Ser Glu  Val Ile Lys Met Leu  Ser Thr Asp
    2210                2215                2220

Asp Lys  Glu Lys Leu Leu Lys  Thr Leu Lys
    2225                2230
```

<210> SEQ ID NO 53
<211> LENGTH: 2268
<212> TYPE: PRT
<213> ORGANISM: Homo sapiens

<400> SEQUENCE: 53

```
Met Ser Gly Leu His Leu Val Lys Gln Gly Arg Asp Arg Lys Lys Ile
1               5                   10                  15

Asp Ser Gln Arg Asp Phe Thr Val Ala Ser Pro Ala Glu Phe Val Thr
            20                  25                  30

Arg Phe Gly Gly Asn Lys Val Ile Glu Lys Val Leu Ile Ala Asn Asn
        35                  40                  45

Gly Ile Ala Ala Val Lys Cys Met Arg Ser Ile Arg Arg Trp Ser Tyr
    50                  55                  60

Glu Met Phe Arg Asn Glu Arg Ala Ile Arg Phe Val Val Met Val Thr
65                  70                  75                  80

Pro Glu Asp Leu Lys Ala Asn Ala Glu Tyr Ile Lys Met Ala Asp His
                85                  90                  95
```

-continued

```
Tyr Val Pro Val Pro Gly Gly Pro Asn Asn Asn Asn Tyr Ala Asn Val
            100                 105                 110

Glu Leu Ile Leu Asp Ile Ala Lys Arg Ile Pro Val Gln Ala Val Trp
        115                 120                 125

Ala Gly Trp Gly His Ala Ser Glu Asn Pro Lys Leu Pro Glu Leu Leu
    130                 135                 140

Leu Lys Asn Gly Ile Ala Phe Met Gly Pro Pro Ser Gln Ala Met Trp
145                 150                 155                 160

Ala Leu Gly Asp Lys Ile Ala Ser Ser Ile Val Ala Gln Thr Ala Gly
                165                 170                 175

Ile Pro Thr Leu Pro Trp Ser Gly Ser Gly Leu Arg Val Asp Trp Gln
            180                 185                 190

Glu Asn Asp Phe Ser Lys Arg Ile Leu Asn Val Pro Gln Glu Leu Tyr
        195                 200                 205

Glu Lys Gly Tyr Val Lys Asp Val Asp Asp Gly Leu Gln Ala Ala Glu
    210                 215                 220

Glu Val Gly Tyr Pro Val Met Ile Lys Ala Ser Glu Gly Gly Gly Gly
225                 230                 235                 240

Lys Gly Ile Arg Lys Val Asn Asn Ala Asp Asp Phe Pro Asn Leu Phe
                245                 250                 255

Arg Gln Val Gln Ala Glu Val Pro Gly Ser Pro Ile Phe Val Met Arg
            260                 265                 270

Leu Ala Lys Gln Ser Arg His Leu Glu Val Gln Ile Leu Ala Asp Gln
        275                 280                 285

Tyr Gly Asn Ala Ile Ser Leu Phe Gly Arg Asp Cys Ser Val Gln Arg
    290                 295                 300

Arg His Gln Lys Ile Ile Glu Glu Ala Pro Ala Thr Ile Ala Thr Pro
305                 310                 315                 320

Ala Val Phe Glu His Met Glu Gln Cys Ala Val Lys Leu Ala Lys Met
                325                 330                 335

Val Gly Tyr Val Ser Ala Gly Thr Val Glu Tyr Leu Tyr Ser Gln Asp
            340                 345                 350

Gly Ser Phe Tyr Phe Leu Glu Leu Asn Pro Arg Leu Gln Val Glu His
        355                 360                 365

Pro Cys Thr Glu Met Val Ala Asp Val Asn Leu Pro Ala Ala Gln Leu
    370                 375                 380

Gln Ile Ala Met Gly Ile Pro Leu Tyr Arg Ile Lys Asp Ile Arg Met
385                 390                 395                 400

Met Tyr Gly Val Ser Pro Trp Gly Asp Ser Pro Ile Asp Phe Glu Asp
                405                 410                 415

Ser Ala His Val Pro Cys Pro Arg Gly His Val Ile Ala Ala Arg Ile
            420                 425                 430

Thr Ser Glu Asn Pro Asp Glu Gly Phe Lys Pro Ser Ser Gly Thr Val
        435                 440                 445

Gln Glu Leu Asn Phe Arg Ser Asn Lys Asn Val Trp Gly Tyr Phe Ser
    450                 455                 460

Val Ala Ala Ala Gly Gly Leu His Glu Phe Ala Asp Ser Gln Phe Gly
465                 470                 475                 480

His Cys Phe Ser Trp Gly Glu Asn Arg Glu Glu Ala Ile Ser Asn Met
                485                 490                 495

Val Val Ala Leu Lys Glu Leu Ser Ile Arg Gly Asp Phe Arg Thr Thr
            500                 505                 510

Val Glu Tyr Leu Ile Lys Leu Leu Glu Thr Glu Ser Phe Gln Met Asn
```

```
        515                 520                 525

Arg Ile Asp Thr Gly Trp Leu Asp Arg Leu Ile Ala Glu Lys Val Gln
    530                 535                 540

Ala Glu Arg Pro Asp Thr Met Leu Gly Val Val Cys Gly Ala Leu His
545                 550                 555                 560

Val Ala Asp Val Ser Leu Arg Asn Ser Val Ser Asn Phe Leu His Ser
                565                 570                 575

Leu Glu Arg Gly Gln Val Leu Pro Ala His Thr Leu Leu Asn Thr Val
            580                 585                 590

Asp Val Glu Leu Ile Tyr Glu Gly Val Lys Tyr Val Leu Lys Val Thr
        595                 600                 605

Arg Gln Ser Pro Asn Ser Tyr Val Val Ile Met Asn Gly Ser Cys Val
    610                 615                 620

Glu Val Asp Val His Arg Leu Ser Asp Gly Gly Leu Leu Leu Ser Tyr
625                 630                 635                 640

Asp Gly Ser Ser Tyr Thr Thr Tyr Met Lys Glu Glu Val Asp Arg Tyr
                645                 650                 655

Arg Ile Thr Ile Gly Asn Lys Thr Cys Val Phe Glu Lys Glu Asn Asp
            660                 665                 670

Pro Ser Val Met Arg Ser Pro Ser Ala Gly Lys Leu Ile Gln Tyr Ile
        675                 680                 685

Val Glu Asp Gly Gly His Val Phe Ala Gly Gln Cys Tyr Ala Glu Ile
    690                 695                 700

Glu Val Met Lys Met Val Met Thr Leu Thr Ala Val Glu Ser Gly Cys
705                 710                 715                 720

Ile His Tyr Val Lys Arg Pro Gly Ala Ala Leu Asp Pro Gly Cys Val
                725                 730                 735

Leu Ala Lys Met Gln Leu Asp Asn Pro Ser Lys Val Gln Gln Ala Glu
            740                 745                 750

Leu His Thr Gly Ser Leu Pro Arg Ile Gln Ser Thr Ala Leu Arg Gly
        755                 760                 765

Glu Lys Leu His Arg Val Phe His Tyr Val Leu Asp Asn Leu Val Asn
    770                 775                 780

Val Met Asn Gly Tyr Cys Leu Pro Asp Pro Phe Phe Ser Ser Lys Val
785                 790                 795                 800

Lys Asp Trp Val Glu Arg Leu Met Lys Thr Leu Arg Asp Pro Ser Leu
                805                 810                 815

Pro Leu Leu Glu Leu Gln Asp Ile Met Thr Ser Val Ser Gly Arg Ile
            820                 825                 830

Pro Pro Asn Val Glu Lys Ser Ile Lys Lys Glu Met Ala Gln Tyr Ala
        835                 840                 845

Ser Asn Ile Thr Ser Val Leu Cys Gln Phe Pro Ser Gln Gln Ile Ala
    850                 855                 860

Asn Ile Leu Asp Ser His Ala Ala Thr Leu Asn Arg Lys Ser Glu Arg
865                 870                 875                 880

Glu Val Phe Phe Met Asn Thr Gln Ser Ile Val Gln Leu Val Gln Arg
                885                 890                 895

Tyr Arg Ser Gly Ile Arg Gly His Met Lys Ala Val Val Met Asp Leu
            900                 905                 910

Leu Arg Gln Tyr Leu Arg Val Glu Thr Gln Phe Gln Asn Gly His Tyr
        915                 920                 925

Asp Lys Cys Val Phe Ala Leu Arg Glu Glu Asn Lys Ser Asp Met Asn
    930                 935                 940
```

```
Thr Val Leu Asn Tyr Ile Phe Ser His Ala Gln Val Thr Lys Lys Asn
945                 950                 955                 960

Leu Leu Val Thr Met Leu Ile Asp Gln Leu Cys Gly Arg Asp Pro Thr
                965                 970                 975

Leu Thr Asp Glu Leu Leu Asn Ile Leu Thr Glu Leu Thr Gln Leu Ser
            980                 985                 990

Lys Thr Thr Asn Ala Lys Val Ala  Leu Arg Ala Arg Gln  Val Leu Ile
        995                 1000                 1005

Ala Ser  His Leu Pro Ser Tyr  Glu Leu Arg His Asn  Gln Val Glu
    1010                 1015                 1020

Ser Ile  Phe Leu Ser Ala Ile  Asp Met Tyr Gly His  Gln Phe Cys
    1025                 1030                 1035

Ile Glu  Asn Leu Gln Lys Leu  Ile Leu Ser Glu Thr  Ser Ile Phe
    1040                 1045                 1050

Asp Val  Leu Pro Asn Phe Phe  Tyr His Ser Asn Gln  Val Val Arg
    1055                 1060                 1065

Met Ala  Ala Leu Glu Val Tyr  Val Arg Arg Ala Tyr  Ile Ala Tyr
    1070                 1075                 1080

Glu Leu  Asn Ser Val Gln His  Arg Gln Leu Lys Asp  Asn Thr Cys
    1085                 1090                 1095

Val Val  Glu Phe Gln Phe Met  Leu Pro Thr Ser His  Pro Asn Arg
    1100                 1105                 1110

Gly Asn  Ile Pro Thr Leu Asn  Arg Met Ser Phe Ser  Ser Asn Leu
    1115                 1120                 1125

Asn His  Tyr Gly Met Thr His  Val Ala Ser Val Ser  Asp Val Leu
    1130                 1135                 1140

Leu Asp  Asn Ser Phe Thr Pro  Pro Cys Gln Arg Met  Gly Gly Met
    1145                 1150                 1155

Val Ser  Phe Arg Thr Phe Glu  Asp Phe Val Arg Ile  Phe Asp Glu
    1160                 1165                 1170

Val Met  Gly Cys Phe Ser Asp  Ser Pro Pro Gln Ser  Pro Thr Phe
    1175                 1180                 1185

Pro Glu  Ala Gly His Thr Ser  Leu Tyr Asp Glu Asp  Lys Val Pro
    1190                 1195                 1200

Arg Asp  Glu Pro Ile His Ile  Leu Asn Val Ala Ile  Lys Thr Asp
    1205                 1210                 1215

Cys Asp  Ile Glu Asp Asp Arg  Leu Ala Ala Met Phe  Arg Glu Phe
    1220                 1225                 1230

Thr Gln  Gln Asn Lys Ala Thr  Leu Val Asp His Gly  Ile Arg Arg
    1235                 1240                 1245

Leu Thr  Phe Leu Val Ala Gln  Lys Asp Phe Arg Lys  Gln Val Asn
    1250                 1255                 1260

Tyr Glu  Val Asp Arg Arg Phe  His Arg Glu Phe Pro  Lys Phe Phe
    1265                 1270                 1275

Thr Phe  Arg Ala Arg Asp Lys  Phe Glu Glu Asp Arg  Ile Tyr Arg
    1280                 1285                 1290

His Leu  Glu Pro Ala Leu Ala  Phe Gln Leu Glu Leu  Asn Arg Met
    1295                 1300                 1305

Arg Asn  Phe Asp Leu Thr Ala  Ile Pro Cys Ala Asn  His Lys Met
    1310                 1315                 1320

His Leu  Tyr Leu Gly Ala Ala  Lys Val Glu Val Gly  Thr Glu Val
    1325                 1330                 1335
```

```
Thr Asp  Tyr Arg Phe Phe Val  Arg Ala Ile Ile Arg  His Ser Asp
    1340                 1345                 1350

Leu Val  Thr Lys Glu Ala Ser  Phe Glu Tyr Leu Gln  Asn Glu Gly
    1355                 1360                 1365

Glu Arg  Leu Leu Leu Glu Ala  Met Asp Glu Leu Glu  Val Ala Phe
    1370                 1375                 1380

Asn Asn  Thr Asn Val Arg Thr  Asp Cys Asn His Ile  Phe Leu Asn
    1385                 1390                 1395

Phe Val  Pro Thr Val Ile Met  Asp Pro Ser Lys Ile  Glu Glu Ser
    1400                 1405                 1410

Val Arg  Ser Met Val Met Arg  Tyr Gly Ser Arg Leu  Trp Lys Leu
    1415                 1420                 1425

Arg Val  Leu Gln Ala Glu Leu  Lys Ile Asn Ile Arg  Leu Thr Pro
    1430                 1435                 1440

Thr Gly  Lys Ala Ile Pro Ile  Arg Leu Phe Leu Thr  Asn Glu Ser
    1445                 1450                 1455

Gly Tyr  Tyr Leu Asp Ile Ser  Leu Tyr Lys Glu Val  Thr Asp Ser
    1460                 1465                 1470

Arg Thr  Ala Gln Ile Met Phe  Gln Ala Tyr Gly Asp  Lys Gln Gly
    1475                 1480                 1485

Pro Leu  His Gly Met Leu Ile  Asn Thr Pro Tyr Val  Thr Lys Asp
    1490                 1495                 1500

Leu Leu  Gln Ser Lys Arg Phe  Gln Ala Gln Ser Leu  Gly Thr Thr
    1505                 1510                 1515

Tyr Ile  Tyr Asp Ile Pro Glu  Met Phe Arg Gln Ser  Leu Ile Lys
    1520                 1525                 1530

Leu Trp  Glu Ser Met Ser Thr  Gln Ala Phe Leu Pro  Ser Pro Pro
    1535                 1540                 1545

Leu Pro  Ser Asp Met Leu Thr  Tyr Thr Glu Leu Val  Leu Asp Asp
    1550                 1555                 1560

Gln Gly  Gln Leu Val His Met  Asn Arg Leu Pro Gly  Gly Asn Glu
    1565                 1570                 1575

Ile Gly  Met Val Ala Trp Lys  Met Thr Phe Lys Ser  Pro Glu Tyr
    1580                 1585                 1590

Pro Glu  Gly Arg Asp Ile Ile  Val Ile Gly Asn Asp  Ile Thr Tyr
    1595                 1600                 1605

Arg Ile  Gly Ser Phe Gly Pro  Gln Glu Asp Leu Leu  Phe Leu Arg
    1610                 1615                 1620

Ala Ser  Glu Leu Ala Arg Ala  Glu Gly Ile Pro Arg  Ile Tyr Val
    1625                 1630                 1635

Ser Ala  Asn Ser Gly Ala Arg  Ile Gly Leu Ala Glu  Glu Ile Arg
    1640                 1645                 1650

His Met  Phe His Val Ala Trp  Val Asp Pro Glu Asp  Pro Tyr Lys
    1655                 1660                 1665

Gly Tyr  Arg Tyr Leu Tyr Leu  Thr Pro Gln Asp Tyr  Lys Arg Val
    1670                 1675                 1680

Ser Ala  Leu Asn Ser Val His  Cys Glu His Val Glu  Asp Glu Gly
    1685                 1690                 1695

Glu Ser  Arg Tyr Lys Ile Thr  Asp Ile Ile Gly Lys  Glu Glu Gly
    1700                 1705                 1710

Ile Gly  Pro Glu Asn Leu Arg  Gly Ser Gly Met Ile  Ala Gly Glu
    1715                 1720                 1725

Ser Ser  Leu Ala Tyr Asn Glu  Ile Ile Thr Ile Ser  Leu Val Thr
```

```
    1730                1735                1740

Cys Arg  Ala Ile Gly Ile Gly  Ala Tyr Leu Val Arg  Leu Gly Gln
    1745                1750                1755

Arg Thr  Ile Gln Val Glu Asn  Ser His Leu Ile Leu  Thr Gly Ala
    1760                1765                1770

Gly Ala  Leu Asn Lys Val Leu  Gly Arg Glu Val Tyr  Thr Ser Asn
    1775                1780                1785

Asn Gln  Leu Gly Gly Ile Gln  Ile Met His Asn Asn  Gly Val Thr
    1790                1795                1800

His Cys  Thr Val Cys Asp Asp  Phe Glu Gly Val Phe  Thr Val Leu
    1805                1810                1815

His Trp  Leu Ser Tyr Met Pro  Lys Ser Val His Ser  Ser Val Pro
    1820                1825                1830

Leu Leu  Asn Ser Lys Asp Pro  Ile Asp Arg Ile Ile  Glu Phe Val
    1835                1840                1845

Pro Thr  Lys Thr Pro Tyr Asp  Pro Arg Trp Met Leu  Ala Gly Arg
    1850                1855                1860

Pro His  Pro Thr Gln Lys Gly  Gln Trp Leu Ser Gly  Phe Phe Asp
    1865                1870                1875

Tyr Gly  Ser Phe Ser Glu Ile  Met Gln Pro Trp Ala  Gln Thr Val
    1880                1885                1890

Val Val  Gly Arg Ala Arg Leu  Gly Gly Ile Pro Val  Gly Val Val
    1895                1900                1905

Ala Val  Glu Thr Arg Thr Val  Glu Leu Ser Ile Pro  Ala Asp Pro
    1910                1915                1920

Ala Asn  Leu Asp Ser Glu Ala  Lys Ile Ile Gln Gln  Ala Gly Gln
    1925                1930                1935

Val Trp  Phe Pro Asp Ser Ala  Phe Lys Thr Tyr Gln  Ala Ile Lys
    1940                1945                1950

Asp Phe  Asn Arg Glu Gly Leu  Pro Leu Met Val Phe  Ala Asn Trp
    1955                1960                1965

Arg Gly  Phe Ser Gly Gly Met  Lys Asp Met Tyr Asp  Gln Val Leu
    1970                1975                1980

Lys Phe  Gly Ala Tyr Ile Val  Asp Gly Leu Arg Glu  Cys Cys Gln
    1985                1990                1995

Pro Val  Leu Val Tyr Ile Pro  Pro Gln Ala Glu Leu  Arg Gly Gly
    2000                2005                2010

Ser Trp  Val Val Ile Asp Ser  Ser Ile Asn Pro Arg  His Met Glu
    2015                2020                2025

Met Tyr  Ala Asp Arg Glu Ser  Arg Gly Ser Val Leu  Glu Pro Glu
    2030                2035                2040

Gly Thr  Val Glu Ile Lys Phe  Arg Arg Lys Asp Leu  Val Lys Thr
    2045                2050                2055

Met Arg  Arg Val Asp Pro Val  Tyr Ile His Leu Ala  Glu Arg Leu
    2060                2065                2070

Gly Thr  Pro Glu Leu Ser Thr  Ala Glu Arg Lys Glu  Leu Glu Asn
    2075                2080                2085

Lys Leu  Lys Glu Arg Glu Glu  Phe Leu Ile Pro Ile  Tyr His Gln
    2090                2095                2100

Val Ala  Val Gln Phe Ala Asp  Leu His Asp Thr Pro  Gly Arg Met
    2105                2110                2115

Gln Glu  Lys Gly Val Ile Ser  Asp Ile Leu Asp Trp  Lys Thr Ser
    2120                2125                2130
```

Arg Thr Phe Phe Tyr Trp Arg Leu Arg Arg Leu Leu Leu Glu Asp
    2135                2140                2145

Leu Val Lys Lys Lys Ile His Asn Ala Asn Pro Glu Leu Thr Asp
    2150                2155                2160

Gly Gln Ile Gln Ala Met Leu Arg Arg Trp Phe Val Glu Val Glu
    2165                2170                2175

Gly Thr Val Lys Ala Tyr Val Trp Asp Asn Asn Lys Asp Leu Ala
    2180                2185                2190

Glu Trp Leu Glu Lys Gln Leu Thr Glu Glu Asp Gly Val His Ser
    2195                2200                2205

Val Ile Glu Glu Asn Ile Lys Cys Ile Ser Arg Asp Tyr Val Leu
    2210                2215                2220

Lys Gln Ile Arg Ser Leu Val Gln Ala Asn Pro Glu Val Ala Met
    2225                2230                2235

Asp Ser Ile Ile His Met Thr Gln His Ile Ser Pro Thr Gln Arg
    2240                2245                2250

Ala Glu Val Ile Arg Ile Leu Ser Thr Met Asp Ser Pro Ser Thr
    2255                2260                2265

<210> SEQ ID NO 54
<211> LENGTH: 2346
<212> TYPE: PRT
<213> ORGANISM: Homo sapiens

<400> SEQUENCE: 54

Met Asp Glu Pro Ser Pro Leu Ala Gln Pro Leu Glu Leu Asn Gln His
1               5                   10                  15

Ser Arg Phe Ile Ile Gly Ser Val Ser Glu Asp Asn Ser Glu Asp Glu
            20                  25                  30

Ile Ser Asn Leu Val Lys Leu Asp Leu Leu Glu Glu Lys Glu Gly Ser
        35                  40                  45

Leu Ser Pro Ala Ser Val Gly Ser Asp Thr Leu Ser Asp Leu Gly Ile
    50                  55                  60

Ser Ser Leu Gln Asp Gly Leu Ala Leu His Ile Arg Ser Ser Met Ser
65                  70                  75                  80

Gly Leu His Leu Val Lys Gln Gly Arg Asp Arg Lys Lys Ile Asp Ser
                85                  90                  95

Gln Arg Asp Phe Thr Val Ala Ser Pro Ala Glu Phe Val Thr Arg Phe
            100                 105                 110

Gly Gly Asn Lys Val Ile Glu Lys Val Leu Ile Ala Asn Asn Gly Ile
        115                 120                 125

Ala Ala Val Lys Cys Met Arg Ser Ile Arg Arg Trp Ser Tyr Glu Met
    130                 135                 140

Phe Arg Asn Glu Arg Ala Ile Arg Phe Val Val Met Val Thr Pro Glu
145                 150                 155                 160

Asp Leu Lys Ala Asn Ala Glu Tyr Ile Lys Met Ala Asp His Tyr Val
                165                 170                 175

Pro Val Pro Gly Gly Pro Asn Asn Asn Asn Tyr Ala Asn Val Glu Leu
            180                 185                 190

Ile Leu Asp Ile Ala Lys Arg Ile Pro Val Gln Ala Val Trp Ala Gly
        195                 200                 205

Trp Gly His Ala Ser Glu Asn Pro Lys Leu Pro Glu Leu Leu Leu Lys
    210                 215                 220

Asn Gly Ile Ala Phe Met Gly Pro Pro Ser Gln Ala Met Trp Ala Leu

-continued

```
225                 230                 235                 240

Gly Asp Lys Ile Ala Ser Ser Ile Val Ala Gln Thr Ala Gly Ile Pro
                245                 250                 255

Thr Leu Pro Trp Ser Gly Ser Gly Leu Arg Val Asp Trp Gln Glu Asn
            260                 265                 270

Asp Phe Ser Lys Arg Ile Leu Asn Val Pro Gln Glu Leu Tyr Glu Lys
        275                 280                 285

Gly Tyr Val Lys Asp Val Asp Asp Gly Leu Gln Ala Ala Glu Glu Val
    290                 295                 300

Gly Tyr Pro Val Met Ile Lys Ala Ser Glu Gly Gly Gly Gly Lys Gly
305                 310                 315                 320

Ile Arg Lys Val Asn Asn Ala Asp Asp Phe Pro Asn Leu Phe Arg Gln
                325                 330                 335

Val Gln Ala Glu Val Pro Gly Ser Pro Ile Phe Val Met Arg Leu Ala
            340                 345                 350

Lys Gln Ser Arg His Leu Glu Val Gln Ile Leu Ala Asp Gln Tyr Gly
        355                 360                 365

Asn Ala Ile Ser Leu Phe Gly Arg Asp Cys Ser Val Gln Arg Arg His
    370                 375                 380

Gln Lys Ile Ile Glu Glu Ala Pro Ala Thr Ile Ala Thr Pro Ala Val
385                 390                 395                 400

Phe Glu His Met Glu Gln Cys Ala Val Lys Leu Ala Lys Met Val Gly
                405                 410                 415

Tyr Val Ser Ala Gly Thr Val Glu Tyr Leu Tyr Ser Gln Asp Gly Ser
            420                 425                 430

Phe Tyr Phe Leu Glu Leu Asn Pro Arg Leu Gln Val Glu His Pro Cys
        435                 440                 445

Thr Glu Met Val Ala Asp Val Asn Leu Pro Ala Ala Gln Leu Gln Ile
    450                 455                 460

Ala Met Gly Ile Pro Leu Tyr Arg Ile Lys Asp Ile Arg Met Met Tyr
465                 470                 475                 480

Gly Val Ser Pro Trp Gly Asp Ser Pro Ile Asp Phe Glu Asp Ser Ala
                485                 490                 495

His Val Pro Cys Pro Arg Gly His Val Ile Ala Ala Arg Ile Thr Ser
            500                 505                 510

Glu Asn Pro Asp Glu Gly Phe Lys Pro Ser Ser Gly Thr Val Gln Glu
        515                 520                 525

Leu Asn Phe Arg Ser Asn Lys Asn Val Trp Gly Tyr Phe Ser Val Ala
    530                 535                 540

Ala Ala Gly Gly Leu His Glu Phe Ala Asp Ser Gln Phe Gly His Cys
545                 550                 555                 560

Phe Ser Trp Gly Glu Asn Arg Glu Glu Ala Ile Ser Asn Met Val Val
                565                 570                 575

Ala Leu Lys Glu Leu Ser Ile Arg Gly Asp Phe Arg Thr Thr Val Glu
            580                 585                 590

Tyr Leu Ile Lys Leu Leu Glu Thr Glu Ser Phe Gln Met Asn Arg Ile
        595                 600                 605

Asp Thr Gly Trp Leu Asp Arg Leu Ile Ala Glu Lys Val Gln Ala Glu
    610                 615                 620

Arg Pro Asp Thr Met Leu Gly Val Val Cys Gly Ala Leu His Val Ala
625                 630                 635                 640

Asp Val Ser Leu Arg Asn Ser Val Ser Asn Phe Leu His Ser Leu Glu
                645                 650                 655
```

-continued

```
Arg Gly Gln Val Leu Pro Ala His Thr Leu Leu Asn Thr Val Asp Val
            660                 665                 670

Glu Leu Ile Tyr Glu Gly Val Lys Tyr Val Leu Lys Val Thr Arg Gln
        675                 680                 685

Ser Pro Asn Ser Tyr Val Val Ile Met Asn Gly Ser Cys Val Glu Val
    690                 695                 700

Asp Val His Arg Leu Ser Asp Gly Gly Leu Leu Leu Ser Tyr Asp Gly
705                 710                 715                 720

Ser Ser Tyr Thr Thr Tyr Met Lys Glu Glu Val Asp Arg Tyr Arg Ile
                725                 730                 735

Thr Ile Gly Asn Lys Thr Cys Val Phe Glu Lys Glu Asn Asp Pro Ser
            740                 745                 750

Val Met Arg Ser Pro Ser Ala Gly Lys Leu Ile Gln Tyr Ile Val Glu
        755                 760                 765

Asp Gly Gly His Val Phe Ala Gly Gln Cys Tyr Ala Glu Ile Glu Val
    770                 775                 780

Met Lys Met Val Met Thr Leu Thr Ala Val Glu Ser Gly Cys Ile His
785                 790                 795                 800

Tyr Val Lys Arg Pro Gly Ala Ala Leu Asp Pro Gly Cys Val Leu Ala
                805                 810                 815

Lys Met Gln Leu Asp Asn Pro Ser Lys Val Gln Gln Ala Glu Leu His
            820                 825                 830

Thr Gly Ser Leu Pro Arg Ile Gln Ser Thr Ala Leu Arg Gly Glu Lys
        835                 840                 845

Leu His Arg Val Phe His Tyr Val Leu Asp Asn Leu Val Asn Val Met
    850                 855                 860

Asn Gly Tyr Cys Leu Pro Asp Pro Phe Phe Ser Ser Lys Val Lys Asp
865                 870                 875                 880

Trp Val Glu Arg Leu Met Lys Thr Leu Arg Asp Pro Ser Leu Pro Leu
                885                 890                 895

Leu Glu Leu Gln Asp Ile Met Thr Ser Val Ser Gly Arg Ile Pro Pro
            900                 905                 910

Asn Val Glu Lys Ser Ile Lys Lys Glu Met Ala Gln Tyr Ala Ser Asn
        915                 920                 925

Ile Thr Ser Val Leu Cys Gln Phe Pro Ser Gln Gln Ile Ala Asn Ile
    930                 935                 940

Leu Asp Ser His Ala Ala Thr Leu Asn Arg Lys Ser Glu Arg Glu Val
945                 950                 955                 960

Phe Phe Met Asn Thr Gln Ser Ile Val Gln Leu Val Gln Arg Tyr Arg
                965                 970                 975

Ser Gly Ile Arg Gly His Met Lys Ala Val Val Met Asp Leu Leu Arg
            980                 985                 990

Gln Tyr Leu Arg Val Glu Thr Gln  Phe Gln Asn Gly His  Tyr Asp Lys
        995                 1000                 1005

Cys Val  Phe Ala Leu Arg Glu  Glu Asn Lys Ser Asp  Met Asn Thr
    1010                 1015                 1020

Val Leu  Asn Tyr Ile Phe Ser  His Ala Gln Val Thr  Lys Lys Asn
    1025                 1030                 1035

Leu Leu  Val Thr Met Leu Ile  Asp Gln Leu Cys Gly  Arg Asp Pro
    1040                 1045                 1050

Thr Leu  Thr Asp Glu Leu Leu  Asn Ile Leu Thr Glu  Leu Thr Gln
    1055                 1060                 1065
```

```
Leu Ser  Lys Thr Thr Asn Ala  Lys Val Ala Leu Arg  Ala Arg Gln
    1070                 1075                 1080

Val Leu  Ile Ala Ser His Leu  Pro Ser Tyr Glu Leu  Arg His Asn
    1085                 1090                 1095

Gln Val  Glu Ser Ile Phe Leu  Ser Ala Ile Asp Met  Tyr Gly His
    1100                 1105                 1110

Gln Phe  Cys Ile Glu Asn Leu  Gln Lys Leu Ile Leu  Ser Glu Thr
    1115                 1120                 1125

Ser Ile  Phe Asp Val Leu Pro  Asn Phe Phe Tyr His  Ser Asn Gln
    1130                 1135                 1140

Val Val  Arg Met Ala Ala Leu  Glu Val Tyr Val Arg  Arg Ala Tyr
    1145                 1150                 1155

Ile Ala  Tyr Glu Leu Asn Ser  Val Gln His Arg Gln  Leu Lys Asp
    1160                 1165                 1170

Asn Thr  Cys Val Val Glu Phe  Gln Phe Met Leu Pro  Thr Ser His
    1175                 1180                 1185

Pro Asn  Arg Gly Asn Ile Pro  Thr Leu Asn Arg Met  Ser Phe Ser
    1190                 1195                 1200

Ser Asn  Leu Asn His Tyr Gly  Met Thr His Val Ala  Ser Val Ser
    1205                 1210                 1215

Asp Val  Leu Leu Asp Asn Ser  Phe Thr Pro Pro Cys  Gln Arg Met
    1220                 1225                 1230

Gly Gly  Met Val Ser Phe Arg  Thr Phe Glu Asp Phe  Val Arg Ile
    1235                 1240                 1245

Phe Asp  Glu Val Met Gly Cys  Phe Ser Asp Ser Pro  Pro Gln Ser
    1250                 1255                 1260

Pro Thr  Phe Pro Glu Ala Gly  His Thr Ser Leu Tyr  Asp Glu Asp
    1265                 1270                 1275

Lys Val  Pro Arg Asp Glu Pro  Ile His Ile Leu Asn  Val Ala Ile
    1280                 1285                 1290

Lys Thr  Asp Cys Asp Ile Glu  Asp Asp Arg Leu Ala  Ala Met Phe
    1295                 1300                 1305

Arg Glu  Phe Thr Gln Gln Asn  Lys Ala Thr Leu Val  Asp His Gly
    1310                 1315                 1320

Ile Arg  Arg Leu Thr Phe Leu  Val Ala Gln Lys Asp  Phe Arg Lys
    1325                 1330                 1335

Gln Val  Asn Tyr Glu Val Asp  Arg Arg Phe His Arg  Glu Phe Pro
    1340                 1345                 1350

Lys Phe  Phe Thr Phe Arg Ala  Arg Asp Lys Phe Glu  Glu Asp Arg
    1355                 1360                 1365

Ile Tyr  Arg His Leu Glu Pro  Ala Leu Ala Phe Gln  Leu Glu Leu
    1370                 1375                 1380

Asn Arg  Met Arg Asn Phe Asp  Leu Thr Ala Ile Pro  Cys Ala Asn
    1385                 1390                 1395

His Lys  Met His Leu Tyr Leu  Gly Ala Ala Lys Val  Glu Val Gly
    1400                 1405                 1410

Thr Glu  Val Thr Asp Tyr Arg  Phe Phe Val Arg Ala  Ile Ile Arg
    1415                 1420                 1425

His Ser  Asp Leu Val Thr Lys  Glu Ala Ser Phe Glu  Tyr Leu Gln
    1430                 1435                 1440

Asn Glu  Gly Glu Arg Leu Leu  Leu Glu Ala Met Asp  Glu Leu Glu
    1445                 1450                 1455

Val Ala  Phe Asn Asn Thr Asn  Val Arg Thr Asp Cys  Asn His Ile
```

```
    1460                1465                1470

Phe Leu  Asn Phe Val Pro Thr  Val Ile Met Asp Pro  Ser Lys Ile
    1475                1480                1485

Glu Glu  Ser Val Arg Ser Met  Val Met Arg Tyr Gly  Ser Arg Leu
    1490                1495                1500

Trp Lys  Leu Arg Val Leu Gln  Ala Glu Leu Lys Ile  Asn Ile Arg
    1505                1510                1515

Leu Thr  Pro Thr Gly Lys Ala  Ile Pro Ile Arg Leu  Phe Leu Thr
    1520                1525                1530

Asn Glu  Ser Gly Tyr Tyr Leu  Asp Ile Ser Leu Tyr  Lys Glu Val
    1535                1540                1545

Thr Asp  Ser Arg Thr Ala Gln  Ile Met Phe Gln Ala  Tyr Gly Asp
    1550                1555                1560

Lys Gln  Gly Pro Leu His Gly  Met Leu Ile Asn Thr  Pro Tyr Val
    1565                1570                1575

Thr Lys  Asp Leu Leu Gln Ser  Lys Arg Phe Gln Ala  Gln Ser Leu
    1580                1585                1590

Gly Thr  Thr Tyr Ile Tyr Asp  Ile Pro Glu Met Phe  Arg Gln Ser
    1595                1600                1605

Leu Ile  Lys Leu Trp Glu Ser  Met Ser Thr Gln Ala  Phe Leu Pro
    1610                1615                1620

Ser Pro  Pro Leu Pro Ser Asp  Met Leu Thr Tyr Thr  Glu Leu Val
    1625                1630                1635

Leu Asp  Asp Gln Gly Gln Leu  Val His Met Asn Arg  Leu Pro Gly
    1640                1645                1650

Gly Asn  Glu Ile Gly Met Val  Ala Trp Lys Met Thr  Phe Lys Ser
    1655                1660                1665

Pro Glu  Tyr Pro Glu Gly Arg  Asp Ile Ile Val Ile  Gly Asn Asp
    1670                1675                1680

Ile Thr  Tyr Arg Ile Gly Ser  Phe Gly Pro Gln Glu  Asp Leu Leu
    1685                1690                1695

Phe Leu  Arg Ala Ser Glu Leu  Ala Arg Ala Glu Gly  Ile Pro Arg
    1700                1705                1710

Ile Tyr  Val Ser Ala Asn Ser  Gly Ala Arg Ile Gly  Leu Ala Glu
    1715                1720                1725

Glu Ile  Arg His Met Phe His  Val Ala Trp Val Asp  Pro Glu Asp
    1730                1735                1740

Pro Tyr  Lys Gly Tyr Arg Tyr  Leu Tyr Leu Thr Pro  Gln Asp Tyr
    1745                1750                1755

Lys Arg  Val Ser Ala Leu Asn  Ser Val His Cys Glu  His Val Glu
    1760                1765                1770

Asp Glu  Gly Glu Ser Arg Tyr  Lys Ile Thr Asp Ile  Ile Gly Lys
    1775                1780                1785

Glu Glu  Gly Ile Gly Pro Glu  Asn Leu Arg Gly Ser  Gly Met Ile
    1790                1795                1800

Ala Gly  Glu Ser Ser Leu Ala  Tyr Asn Glu Ile Ile  Thr Ile Ser
    1805                1810                1815

Leu Val  Thr Cys Arg Ala Ile  Gly Ile Gly Ala Tyr  Leu Val Arg
    1820                1825                1830

Leu Gly  Gln Arg Thr Ile Gln  Val Glu Asn Ser His  Leu Ile Leu
    1835                1840                1845

Thr Gly  Ala Gly Ala Leu Asn  Lys Val Leu Gly Arg  Glu Val Tyr
    1850                1855                1860
```

-continued

```
Thr Ser  Asn Asn Gln Leu Gly  Gly Ile Gln Ile Met  His Asn Asn
    1865                 1870                 1875

Gly Val  Thr His Cys Thr Val  Cys Asp Asp Phe Glu  Gly Val Phe
    1880                 1885                 1890

Thr Val  Leu His Trp Leu Ser  Tyr Met Pro Lys Ser  Val His Ser
    1895                 1900                 1905

Ser Val  Pro Leu Leu Asn Ser  Lys Asp Pro Ile Asp  Arg Ile Ile
    1910                 1915                 1920

Glu Phe  Val Pro Thr Lys Thr  Pro Tyr Asp Pro Arg  Trp Met Leu
    1925                 1930                 1935

Ala Gly  Arg Pro His Pro Thr  Gln Lys Gly Gln Trp  Leu Ser Gly
    1940                 1945                 1950

Phe Phe  Asp Tyr Gly Ser Phe  Ser Glu Ile Met Gln  Pro Trp Ala
    1955                 1960                 1965

Gln Thr  Val Val Val Gly Arg  Ala Arg Leu Gly Gly  Ile Pro Val
    1970                 1975                 1980

Gly Val  Val Ala Val Glu Thr  Arg Thr Val Glu Leu  Ser Ile Pro
    1985                 1990                 1995

Ala Asp  Pro Ala Asn Leu Asp  Ser Glu Ala Lys Ile  Ile Gln Gln
    2000                 2005                 2010

Ala Gly  Gln Val Trp Phe Pro  Asp Ser Ala Phe Lys  Thr Tyr Gln
    2015                 2020                 2025

Ala Ile  Lys Asp Phe Asn Arg  Glu Gly Leu Pro Leu  Met Val Phe
    2030                 2035                 2040

Ala Asn  Trp Arg Gly Phe Ser  Gly Gly Met Lys Asp  Met Tyr Asp
    2045                 2050                 2055

Gln Val  Leu Lys Phe Gly Ala  Tyr Ile Val Asp Gly  Leu Arg Glu
    2060                 2065                 2070

Cys Cys  Gln Pro Val Leu Val  Tyr Ile Pro Pro Gln  Ala Glu Leu
    2075                 2080                 2085

Arg Gly  Gly Ser Trp Val Val  Ile Asp Ser Ser Ile  Asn Pro Arg
    2090                 2095                 2100

His Met  Glu Met Tyr Ala Asp  Arg Glu Ser Arg Gly  Ser Val Leu
    2105                 2110                 2115

Glu Pro  Glu Gly Thr Val Glu  Ile Lys Phe Arg Arg  Lys Asp Leu
    2120                 2125                 2130

Val Lys  Thr Met Arg Arg Val  Asp Pro Val Tyr Ile  His Leu Ala
    2135                 2140                 2145

Glu Arg  Leu Gly Thr Pro Glu  Leu Ser Thr Ala Glu  Arg Lys Glu
    2150                 2155                 2160

Leu Glu  Asn Lys Leu Lys Glu  Arg Glu Glu Phe Leu  Ile Pro Ile
    2165                 2170                 2175

Tyr His  Gln Val Ala Val Gln  Phe Ala Asp Leu His  Asp Thr Pro
    2180                 2185                 2190

Gly Arg  Met Gln Glu Lys Gly  Val Ile Ser Asp Ile  Leu Asp Trp
    2195                 2200                 2205

Lys Thr  Ser Arg Thr Phe Phe  Tyr Trp Arg Leu Arg  Arg Leu Leu
    2210                 2215                 2220

Leu Glu  Asp Leu Val Lys Lys  Lys Ile His Asn Ala  Asn Pro Glu
    2225                 2230                 2235

Leu Thr  Asp Gly Gln Ile Gln  Ala Met Leu Arg Arg  Trp Phe Val
    2240                 2245                 2250
```

Glu Val Glu Gly Thr Val Lys Ala Tyr Val Trp Asp Asn Asn Lys
2255 2260 2265

Asp Leu Ala Glu Trp Leu Glu Lys Gln Leu Thr Glu Glu Asp Gly
2270 2275 2280

Val His Ser Val Ile Glu Glu Asn Ile Lys Cys Ile Ser Arg Asp
2285 2290 2295

Tyr Val Leu Lys Gln Ile Arg Ser Leu Val Gln Ala Asn Pro Glu
2300 2305 2310

Val Ala Met Asp Ser Ile Ile His Met Thr Gln His Ile Ser Pro
2315 2320 2325

Thr Gln Arg Ala Glu Val Ile Arg Ile Leu Ser Thr Met Asp Ser
2330 2335 2340

Pro Ser Thr
2345

<210> SEQ ID NO 55
<211> LENGTH: 2234
<212> TYPE: PRT
<213> ORGANISM: Lipomyces starkeyi

<400> SEQUENCE: 55

Met Ser Ala Ala Ala Ser Ser Leu Pro Ser His Phe Ile Gly Leu Asn
1 5 10 15

Thr Val Asp Val Ala Ala Asn Ser Pro Val Lys Asp Phe Val Gln Asn
20 25 30

His Gly Gly His Thr Val Ile Thr Ser Val Leu Ile Ala Asn Asn Gly
35 40 45

Ile Ala Ala Val Lys Glu Ile Arg Ser Val Arg Lys Trp Ala Tyr Glu
50 55 60

Thr Phe Gly Asp Glu Arg Ala Ile Ser Phe Thr Val Met Ala Thr Pro
65 70 75 80

Glu Asp Leu Lys Ala Asn Ala Asp Tyr Ile Arg Met Ala Asp Gln Tyr
85 90 95

Val Glu Val Pro Gly Gly Thr Asn Asn Asn Asn Phe Ala Asn Val Glu
100 105 110

Leu Ile Val Asp Ile Ala Glu Arg Met Asn Val His Ala Val Trp Ala
115 120 125

Gly Trp Gly His Ala Ser Glu Asn Pro Lys Leu Pro Glu Ser Leu Ala
130 135 140

Gln Ser Pro Lys Lys Ile Val Phe Ile Gly Pro Pro Gly Ser Ala Met
145 150 155 160

Arg Ser Leu Gly Asp Lys Ile Ser Ser Thr Ile Val Ala Gln His Ala
165 170 175

Lys Val Pro Cys Ile Pro Trp Ser Gly Thr Gly Val Asp Glu Val Gln
180 185 190

Ile Asp Ser Val Ser Gly Leu Val Thr Val Ser Asp Glu Ile Tyr Ala
195 200 205

Lys Gly Cys Thr Ser Thr Ala Glu Glu Ala Leu Glu Lys Ala Arg Ile
210 215 220

Ile Gly Phe Pro Val Met Ile Lys Ala Ser Glu Gly Gly Gly Gly Lys
225 230 235 240

Gly Ile Arg Lys Val Glu Ser Glu Asp Asn Phe His Ser Leu Tyr Ser
245 250 255

Gln Val Ala Asn Glu Val Pro Gly Ser Pro Ile Phe Val Met Lys Leu
260 265 270

```
Ala Gly Asn Ala Arg His Leu Glu Val Gln Leu Leu Ala Asp Gln Tyr
        275                 280                 285

Gly Asn Asn Ile Ser Leu Phe Gly Arg Asp Cys Ser Val Gln Arg Arg
    290                 295                 300

His Gln Lys Ile Ile Glu Glu Ala Pro Val Thr Val Ala Asn Pro Ala
305                 310                 315                 320

Thr Phe Ser Ala Met Glu His Ala Ala Val Arg Leu Gly Gln Leu Val
                325                 330                 335

Gly Tyr Val Ser Ala Gly Thr Val Glu Tyr Leu Tyr Ser His Asp Asp
            340                 345                 350

Asp Lys Phe Tyr Phe Leu Glu Leu Asn Pro Arg Leu Gln Val Glu His
        355                 360                 365

Pro Thr Thr Glu Met Val Thr Gly Val Asn Leu Pro Ala Ala Gln Leu
    370                 375                 380

Gln Ile Ala Met Gly Val Ser Leu His Arg Ile Arg Asp Ile Arg Leu
385                 390                 395                 400

Phe Tyr Gly Val Asp Pro His Thr Ser Thr Glu Ile Asp Phe Asp Phe
                405                 410                 415

Ser Lys Glu Gly Ser Leu Gln Thr Gln Arg Arg Pro Val Pro Lys Gly
            420                 425                 430

His Thr Thr Ala Cys Arg Ile Thr Ser Glu Asp Pro Gly Glu Gly Phe
        435                 440                 445

Lys Pro Ser Ser Gly Val Met His Glu Leu Asn Phe Arg Ser Ser Ser
    450                 455                 460

Asn Val Trp Gly Tyr Phe Ser Val Gly Asn Gln Gly Gly Ile His Ser
465                 470                 475                 480

Phe Ser Asp Ser Gln Phe Gly His Ile Phe Ala Phe Gly Glu Asn Arg
                485                 490                 495

Ser Ala Ser Arg Lys His Met Val Val Ala Leu Lys Glu Leu Ser Ile
            500                 505                 510

Arg Gly Asp Phe Arg Thr Thr Val Glu Tyr Leu Ile Lys Leu Leu Glu
        515                 520                 525

Thr Pro Asp Phe Glu Ser Asn Lys Ile Thr Thr Gly Trp Leu Asp Glu
    530                 535                 540

Leu Ile Ser Lys Lys Leu Thr Ala Glu Arg Pro Asp Pro Val Val Ala
545                 550                 555                 560

Val Val Cys Gly Ala Val Thr Lys Ala His Leu Ala Ser Glu Ala Cys
                565                 570                 575

Phe Gln Glu Tyr Lys Asn Ser Leu Glu Lys Gly Gln Val Pro Ser Lys
            580                 585                 590

Asp Ile Leu Lys Thr Leu Phe Pro Val Asp Phe Ile Tyr Glu Gly Ser
        595                 600                 605

Arg Tyr Lys Phe Thr Val Thr Arg Ser Ser Met Asp Leu Tyr Gln Ile
    610                 615                 620

Phe Ile Asn Gly Ser Lys Cys Leu Val Gly Val Lys Ser Leu Ser Asp
625                 630                 635                 640

Gly Gly Leu Leu Val Leu Leu Gly Gly Lys Ser His Asn Val Tyr Trp
                645                 650                 655

Lys Asp Glu Val Gly Thr Thr Arg Leu Ser Val Asp Ser Lys Thr Cys
            660                 665                 670

Leu Leu Glu Gln Glu Asn Asp Pro Thr Gln Leu Arg Thr Pro Ser Pro
        675                 680                 685
```

```
Gly Lys Leu Val Lys Phe Leu Val Glu Asn Gly Glu His Val Lys Thr
    690                 695                 700

Gly Gln Pro Phe Ala Glu Val Glu Val Met Lys Met Tyr Met Pro Leu
705                 710                 715                 720

Ile Ala Gln Glu Asp Gly Ile Val Gln Leu Ile Lys Gln Pro Gly Ala
                725                 730                 735

Thr Leu Glu Ala Gly Asp Ile Leu Gly Ile Leu Ala Leu Asp Asp Pro
            740                 745                 750

Ser Arg Val Lys His Ala Lys Pro Phe Glu Gly Gln Leu Pro Asp Phe
        755                 760                 765

Gly Ser Pro Leu Val Leu Gly Ser Lys Pro Ser Gln Arg Phe Asn Leu
    770                 775                 780

Leu Leu Ser Thr Leu Arg Asn Ile Leu Ala Gly Phe Asp Asn Gln Val
785                 790                 795                 800

Leu Leu Ala Ser Thr Leu Lys Asp Leu Ser Gln Val Leu Lys Asp Asp
                805                 810                 815

Ala Leu Pro Tyr Ser Glu Trp Asn Ala Gln Phe Ser Ala Leu His Ser
            820                 825                 830

Arg Ile Pro Gln Lys Leu Asp Ala Thr Leu Ser Ser Leu Ile Glu Arg
        835                 840                 845

Ser Lys Ser Lys Asp Ala Glu Phe Pro Ala Lys Leu Leu Leu Arg Ala
    850                 855                 860

Ile Glu Arg Phe Ala Glu Glu Phe Ile Gln Pro Gln Asp Leu Phe Val
865                 870                 875                 880

Phe Lys Gln Gln Val Glu Pro Leu Val Thr Ile Ala Thr Arg Tyr Gln
                885                 890                 895

Ala Gly Leu Lys Ala His Glu Tyr Gly Val Ile Ala Glu Leu Leu Glu
            900                 905                 910

Gln Tyr Leu Ala Val Glu Lys Leu Phe Ser Gly Ala Asn Ile Arg Asp
        915                 920                 925

Glu Asp Val Phe Leu Arg Leu Arg Asp Glu Asn Lys Asp Asp Ile Phe
    930                 935                 940

Lys Val Val Met Thr Val Phe Ser His Gly Arg Val Gly Ala Lys Asn
945                 950                 955                 960

Asn Leu Ile Leu Ala Ile Leu Ala Ala Leu Arg Ser Asp Arg Ser Glu
                965                 970                 975

Val Ser Glu Val Ala Lys Tyr Leu Arg Pro Ala Leu Lys Thr Leu Thr
            980                 985                 990

Glu Leu Asp Ser Gly Val Thr Ala  Pro Val Ala Leu Lys  Ala Arg Glu
        995                 1000                 1005

Leu Leu  Ile Gln Cys Ala Leu  Pro Ser Leu Glu Glu  Arg Thr Ala
    1010                 1015                 1020

Gln Leu  Glu His Ile Leu Arg  Ser Ser Val Val Glu  Ser Arg Tyr
    1025                 1030                 1035

Gly Glu  Val Gly Phe Glu His  Ser Ala Pro Arg Ile  Asp Val Leu
    1040                 1045                 1050

Lys Glu  Val Ile Asp Ser Gln  Tyr Ile Val Phe Asp  Val Leu Pro
    1055                 1060                 1065

Lys Phe  Phe Ala His Ser Asp  Arg Tyr Val Thr Leu  Ala Ala Leu
    1070                 1075                 1080

Glu Leu  Tyr Val Arg Arg Ala  Tyr Arg Ala Tyr Asn  Val Met Ser
    1085                 1090                 1095

Met Glu  Tyr His Asn Glu Gly  Asp Leu Val Pro Val  Val Thr Phe
```

1100 1105 1110

Lys Phe Leu Leu Ala Ala Ile Gly Asn Pro Ala Tyr Asn Ile Val
1115 1120 1125

Gly Gln Gly Ala Pro Ser Gly Asp Ser Arg Ile Asp Phe Gln Arg
1130 1135 1140

Ala Ala Ser Val Ser Asp Leu Thr Phe Met Met Ser Lys Ser Asp
1145 1150 1155

Ser Glu Ser Leu Arg Ser Gly Val Ile Val Pro Val Ala Asp Ile
1160 1165 1170

Ala Asp Ile Asp Glu Val Leu Pro Arg Ala Leu Asp Tyr Leu Pro
1175 1180 1185

Gln Arg Ala Gly Ala Gly Ser Gly Gly Phe Ser Phe Ser Ala Lys
1190 1195 1200

Ser Asp Leu Asp Ser Lys Arg Arg Pro Ala Pro Pro Lys Pro Glu
1205 1210 1215

Ser Leu Ser Asn Ile Cys Asn Val Leu Ile Arg Lys Thr Ala Lys
1220 1225 1230

Thr Asp Asp Ala Ala Leu Val Ser Asp Ile Lys Phe Ile Val Asp
1235 1240 1245

Glu Tyr Lys Glu Glu Phe Leu Leu Arg Ser Ile Arg Arg Val Thr
1250 1255 1260

Phe Val Cys Gly Arg Glu Asp Gly Ser Tyr Pro Gly Tyr Phe Thr
1265 1270 1275

Phe Arg Gly Pro Asp Tyr Val Glu Asp Glu Ser Ile Arg His Ile
1280 1285 1290

Glu Pro Ala Leu Ala Tyr Gln Leu Glu Leu Gly Arg Leu Ser Asn
1295 1300 1305

Phe Asn Tyr Lys Pro Ile Phe Thr Asp Asn Arg Asn Ile His Val
1310 1315 1320

Tyr Gln Ala Ile Gly Lys Asp Val Pro Ser Asp Lys Arg Phe Phe
1325 1330 1335

Val Arg Gly Ile Val Arg Pro Gly Arg Leu Arg Asp Glu Ile Pro
1340 1345 1350

Thr Ser Glu Tyr Leu Ile Ser Glu Thr Asp Arg Leu Met Ser Asp
1355 1360 1365

Ile Leu Asp Ala Leu Glu Val Ile Gly Pro Asn Asn Thr Asp Met
1370 1375 1380

Asn His Ile Phe Ile Asn Phe Ser Pro Ile Phe His Leu Val Pro
1385 1390 1395

Glu Glu Val Glu Ala Ala Phe Gly Gln Phe Leu Glu Arg Phe Gly
1400 1405 1410

Arg Arg Leu Trp Arg Leu Arg Val Thr Gly Ala Glu Ile Arg Ile
1415 1420 1425

Met Cys Thr Asp Pro Glu Thr Asn Val Pro Tyr Pro Leu Arg Ala
1430 1435 1440

Ile Ile Thr Asn Val Ser Gly Tyr Val Val Gln Ser Glu Leu Tyr
1445 1450 1455

Thr Glu Val Lys Asn Asp Lys Gly Gln Trp Val Phe Lys Ser Leu
1460 1465 1470

Gly Lys Pro Gly Asn Met His Leu Arg Ser Ile Thr Thr Pro Tyr
1475 1480 1485

Ala Thr Lys Glu Trp Leu Gln Pro Lys Arg Tyr Lys Ala His Leu
1490 1495 1500

-continued

Met Gly Thr Thr Phe Val Tyr Asp Phe Pro Glu Leu Phe Asn Gln
1505 1510 1515

Ala Ile Arg Ala Ser Trp Arg Ala Ala Gln Gln Gln Ser Pro Glu
1520 1525 1530

Asn Val Leu Thr Tyr Lys Glu Leu Ile Met Asp Asp Ser Gly Glu
1535 1540 1545

Leu Ser Glu Val Ser Arg Glu Pro Gly Ala Asn Thr Cys Gly Met
1550 1555 1560

Val Ala Trp Leu Phe Thr Ala Leu Thr Pro Glu Tyr Pro Thr Gly
1565 1570 1575

Arg Gln Phe Ile Val Val Ala Asn Asp Ile Thr Tyr Lys Ile Gly
1580 1585 1590

Ser Phe Gly Pro Gln Glu Asp Lys Tyr Phe His Thr Val Thr Gln
1595 1600 1605

Leu Ala Val Lys Leu Gly Ile Pro Arg Ile Tyr Leu Ser Ala Asn
1610 1615 1620

Ser Gly Ala Arg Ile Gly Val Ala Asp Glu Phe Val Ser Leu Phe
1625 1630 1635

Ser Val Ala Trp Asn Asp Ser Ser Asn Pro Glu Lys Gly Phe Lys
1640 1645 1650

Tyr Leu Tyr Leu Thr Pro Ala Ile Tyr Asn Gly Leu Ser Asp Ala
1655 1660 1665

Ala Lys Lys Thr Val Leu Thr Glu Arg Ile Val Glu Glu Gly Glu
1670 1675 1680

Glu Arg Tyr Val Ile Thr Thr Ile Ile Gly Ala Glu Asp Gly Leu
1685 1690 1695

Gly Val Glu Cys Leu Arg Gly Ser Gly Leu Ile Ala Gly Ala Thr
1700 1705 1710

Ser Lys Ala Tyr Lys Asp Ile Phe Thr Ile Thr Leu Val Thr Cys
1715 1720 1725

Arg Ser Val Gly Ile Gly Ala Tyr Leu Val Arg Leu Gly Gln Arg
1730 1735 1740

Ala Ile Gln Ile Glu Gly Gln Pro Ile Ile Leu Thr Gly Ala Pro
1745 1750 1755

Ala Ile Asn Lys Leu Leu Gly Arg Glu Val Tyr Ser Ser Asn Leu
1760 1765 1770

Gln Leu Gly Gly Thr Gln Ile Met Tyr Lys Asn Gly Val Ser His
1775 1780 1785

Leu Thr Ala Asn Asp Asp Leu Ala Gly Val Met Lys Ile Ile Glu
1790 1795 1800

Trp Met Ser Tyr Val Pro Tyr Lys Lys Gly Gly Gln Leu Pro Ile
1805 1810 1815

Tyr Pro Ser Ser Asp Thr Trp Asp Arg Asp Val Thr Tyr Thr Pro
1820 1825 1830

Pro Lys Gln Val Pro Tyr Asp Val Arg Trp Leu Ile Ala Gly Arg
1835 1840 1845

Glu Asp Glu Glu Gly Gly Phe Glu Tyr Gly Leu Phe Asp Lys Asp
1850 1855 1860

Ser Phe Gln Glu Thr Leu Ser Gly Trp Ala Arg Thr Val Val Val
1865 1870 1875

Gly Arg Ala Arg Leu Gly Gly Ile Pro Val Gly Val Ile Gly Val
1880 1885 1890

Glu Val Arg Ser Val Glu Asn Ile Phe Pro Ala Asp Pro Ala Asn
1895 1900 1905

Pro Asp Ser Thr Glu Met Val Val Gln Glu Ala Gly Gln Val Trp
1910 1915 1920

Tyr Pro Asn Ser Ala Phe Lys Thr Ala Gln Ala Ile Asn Asp Phe
1925 1930 1935

Asn His Gly Glu Glu Leu Pro Leu Val Ile Leu Ala Asn Trp Arg
1940 1945 1950

Gly Phe Ser Gly Gly Gln Arg Asp Met Tyr Asn Glu Val Leu Lys
1955 1960 1965

Tyr Gly Ser Phe Ile Val Asp Ala Leu Val Gly Tyr Lys Gln Pro
1970 1975 1980

Ile Phe Val Tyr Ile Pro Pro His Ala Glu Leu Arg Gly Gly Ser
1985 1990 1995

Trp Val Val Ile Asp Pro Thr Ile Asn Ser Asp Gln Met Glu Met
2000 2005 2010

Tyr Ala Asp Asp Glu Ala Arg Ala Gly Val Leu Glu Pro Glu Gly
2015 2020 2025

Met Val Gly Ile Lys Tyr Arg Arg Asp Arg Leu Leu Glu Thr Met
2030 2035 2040

Thr Arg Leu Asp Pro Val Tyr Ala Ser Leu Lys Arg Gln Ala Asp
2045 2050 2055

Lys Lys Asp Leu Ala Pro Ala Ile Ala Gln Asp Leu Lys Val Lys
2060 2065 2070

Leu Ser Glu Arg Glu Ser Thr Leu Met Pro Ile Tyr Arg Gln Ile
2075 2080 2085

Ser Leu Gln Phe Ala Asp Leu His Asp Arg Ala Gly Arg Met Lys
2090 2095 2100

Ala Lys Gly Thr Ile Arg Glu Val Leu His Trp Arg Glu Ala Arg
2105 2110 2115

Arg Phe Phe Tyr Trp Arg Val Arg Arg Arg Val Gly Glu Ser Tyr
2120 2125 2130

Ile Leu Arg Asp Leu Glu Ala Ala Asn Pro Lys Ser Thr Arg Leu
2135 2140 2145

Glu Arg Val Ala Arg Leu Lys Ser Trp Tyr Ala Glu Ala Gly Ile
2150 2155 2160

Asn Glu Ser Ser Asp Ala Asp Val Ala Ser Trp Ile Glu Lys Ser
2165 2170 2175

Gly Ala Ala Ile Thr Ser Lys Val Lys Gln Val Arg Lys Asp Ala
2180 2185 2190

Lys Ile Gln Asp Leu Leu Ala Leu Val Arg Ala Asp Lys Asp Val
2195 2200 2205

Ala Leu Gln Gly Leu Val Glu Ser Leu Lys Ala Leu Ser Thr Glu
2210 2215 2220

Glu Arg Asp Ala Ile Phe Lys Gln Ala Ser Asn
2225 2230

<210> SEQ ID NO 56
<211> LENGTH: 2234
<212> TYPE: PRT
<213> ORGANISM: Komagataella phaffii

<400> SEQUENCE: 56

Met Ser Ser Val Asn His Ser Leu Arg His Ser Lys Leu Pro Pro His
1 5 10 15

```
Phe Leu Gly Leu Asn Ser Val Glu Val Ala Ala Pro Ser Lys Val Arg
            20                  25                  30

Asp Phe Val Arg Asp His Gly Gly His Ser Val Ile Thr Arg Val Leu
        35                  40                  45

Ile Ala Asn Asn Gly Ile Ala Ala Val Lys Glu Ile Arg Ser Val Arg
    50                  55                  60

Lys Trp Ala Tyr Glu Thr Phe Gly Asn Asp Arg Ala Ile Gln Phe Ile
65                  70                  75                  80

Val Met Ala Thr Pro Glu Asp Leu Glu Ala Asn Ala Glu Tyr Ile Arg
                85                  90                  95

Met Ala Asp Gln Tyr Val Met Val Pro Gly Gly Thr Ala Asn Asn Asn
            100                 105                 110

Tyr Ala Asn Val Asp Leu Ile Val Glu Ile Ala Glu Ser Thr Asp Ala
        115                 120                 125

His Ala Val Trp Ala Gly Trp Gly Phe Ala Ser Glu Asn Pro His Leu
    130                 135                 140

Pro Glu Gln Leu Ala Ala Ser Pro Lys Lys Ile Ile Phe Ile Gly Pro
145                 150                 155                 160

Pro Gly Ser Ala Met Arg Ser Leu Gly Asp Lys Ile Ser Ser Thr Ile
                165                 170                 175

Val Ala Gln His Ala Lys Val Pro Cys Ile Pro Trp Ser Gly Thr Gly
            180                 185                 190

Val Asp Gln Val Ile Ile Asp Pro Val Ser Asn Leu Val Ser Val Asp
        195                 200                 205

Glu Glu Thr Tyr Ala Lys Gly Cys Cys Ser Asp Pro Gln Asp Gly Leu
    210                 215                 220

Ala Lys Ala Lys Ala Ile Gly Phe Pro Val Met Ile Lys Ala Ser Glu
225                 230                 235                 240

Gly Gly Gly Gly Lys Gly Ile Arg Lys Val Asp Arg Glu Glu Asp Phe
                245                 250                 255

Leu Ser Leu Tyr Asp Gln Ala Ala Asn Glu Ile Pro Gly Ser Pro Ile
            260                 265                 270

Phe Ile Met Lys Leu Ala Gly Asp Ala Arg His Leu Glu Val Gln Leu
        275                 280                 285

Leu Ala Asp Gln Tyr Gly Thr Asn Ile Ser Leu Phe Gly Arg Asp Cys
    290                 295                 300

Ser Val Gln Arg Arg His Gln Lys Ile Ile Glu Glu Ala Pro Val Thr
305                 310                 315                 320

Ile Ala Lys Gln Asp Thr Phe Arg Gln Met Glu Gln Ala Ala Val Arg
                325                 330                 335

Leu Gly Gln Leu Val Gly Tyr Val Ser Ala Gly Thr Val Glu Tyr Leu
            340                 345                 350

Tyr Ser His Ala Glu Asp Lys Phe Tyr Phe Leu Glu Leu Asn Pro Arg
        355                 360                 365

Leu Gln Val Glu His Pro Thr Thr Glu Met Ala Thr Gly Val Asn Leu
    370                 375                 380

Pro Val Ala Gln Leu Leu Ile Ala Met Gly Ile Pro Leu Asn Arg Ile
385                 390                 395                 400

Arg Asp Ile Arg Val Leu Tyr Gly Leu Glu Pro Asn Gly Ala Thr Glu
                405                 410                 415

Ile Asp Phe Glu Phe Lys Thr Glu Glu Ser Leu Lys Ser Gln Arg Lys
            420                 425                 430
```

Pro Ile Pro Lys Gly His Thr Ile Ala Cys Arg Ile Thr Ser Glu Asp
435 440 445

Pro Gly Glu Gly Phe Lys Pro Ser Gly Gly Ala Leu Tyr Glu Leu Asn
450 455 460

Phe Arg Ser Ser Ser Ser Val Trp Gly Tyr Phe Ser Val Gly Asn Lys
465 470 475 480

Ser Ser Ile His Ser Phe Ser Asp Ser Gln Phe Gly His Ile Phe Ser
485 490 495

Phe Gly Glu Asn Arg Gln Ile Ala Arg Lys Asn Met Val Val Ala Leu
500 505 510

Lys Glu Leu Ser Ile Arg Gly Asp Phe Arg Thr Thr Ile Glu Tyr Leu
515 520 525

Ile Lys Leu Leu Glu Thr Ala Asp Phe Glu Asn Asn Thr Ile Thr Thr
530 535 540

Gly Trp Leu Asp Glu Leu Ile Ser Lys Lys Leu Thr Ala Glu Arg Pro
545 550 555 560

Asp Glu Thr Thr Ala Ile Leu Cys Gly Ala Val Thr Lys Ala Tyr Ile
565 570 575

Gln Trp Asp Leu Cys Arg Lys Glu Tyr Val Ala Ser Leu Glu Lys Gly
580 585 590

Gln Ile Pro Gly Lys Glu Leu Leu Arg Thr Ile Phe Pro Ile Glu Phe
595 600 605

Ile Tyr Glu Gly Lys Lys Tyr Lys Phe Thr Val Val Gln Ala Ala Phe
610 615 620

Asp Lys Tyr Asn Val Phe Val Asn Gly Cys Met Ile Thr Val Ser Val
625 630 635 640

Thr His Leu Lys Asp Gly Ser Leu Leu Val Ala Leu Asp Gly Lys Ser
645 650 655

His Ser Val Tyr Tyr Leu Gln Glu Glu Val Gly Asn Thr Arg Leu Ser
660 665 670

Val Asp Gly Lys Ser Cys Ile Leu Glu Val Glu His Glu Pro Thr Glu
675 680 685

Leu Arg Thr Pro Ser Pro Gly Lys Leu Ile Lys Tyr Leu Val Glu His
690 695 700

Gly Asp His Val Lys Ile Gly Gln Pro Tyr Ala Glu Val Glu Val Met
705 710 715 720

Lys Met Cys Met Pro Leu Val Ser Gln Glu Asn Gly Thr Ile Arg Leu
725 730 735

Leu Lys Gln Pro Gly Ser Ser Val Ala Ala Gly Asp Ile Leu Ala Ile
740 745 750

Leu Ala Leu Asp Asp Pro Ser Lys Val Lys His Ala Leu Pro Phe Asp
755 760 765

Gly Thr Ile Pro Asp Met Lys Gln Pro Phe Ile His Ser Asn Lys Pro
770 775 780

Val Tyr Lys Phe Ile Ser Leu Leu Ser Val Leu Lys Asn Ile Leu Ala
785 790 795 800

Gly Tyr Asp Asn Gln Val Val Met Asn Asp Thr Leu Gln Ser Leu Leu
805 810 815

Asp Val Leu Lys Asn Pro Glu Leu Pro Tyr Ser Glu Trp Asn His Ser
820 825 830

Ile Ser Ala Leu His Ser Arg Leu Pro Ile His Leu Asp Glu Gln Leu
835 840 845

Thr Ser Leu Ile Glu Arg Ser His Gln Arg Gly Ala Asp Phe Pro Ala

```
    850                 855                 860

Lys His Leu Leu Lys Leu Leu Asp Lys Glu Gln Ala Val Asn Pro Asp
865                 870                 875                 880

Pro Leu Phe Ser Gln Val Ile Ala Pro Leu Thr Ala Val Ala Lys Ser
                885                 890                 895

Tyr Glu His Gly Leu Glu Val His Glu His Asn Val Phe Ala Asp Leu
            900                 905                 910

Ile Thr Gln Tyr Tyr Asp Ile Glu Ser Leu Phe Ala Asp Lys Arg Glu
        915                 920                 925

Glu Asp Val Ile Leu Gln Leu Arg Asp Glu Asn Lys Ser Ser Leu Asp
    930                 935                 940

Lys Val Ile Asp Val Val Leu Ser His Ser Arg Val Gly Ala Lys Asn
945                 950                 955                 960

His Leu Ile Arg Ala Ile Leu Glu Ile Tyr Gln Thr Ile Cys Gln Asn
                965                 970                 975

Asp Leu Gln Ala Ala Thr Ile Leu Lys Lys Pro Leu Lys Lys Ile Val
            980                 985                 990

Glu Leu Asp Ser Arg Phe Thr Ala  Lys Val Ser Leu Lys  Ala Arg Glu
        995                 1000                1005

Ile Leu  Ile Gln Cys Ser Leu  Pro Ser Ile Lys Glu  Arg Ser Asp
    1010                 1015                 1020

Gln Leu  Glu His Ile Leu Arg  Ser Ser Val Val Gln  Thr Gln Tyr
    1025                 1030                 1035

Gly Glu  Ser Phe Asn Gly Asn  Tyr Lys Leu Pro Asn  Leu Asp Val
    1040                 1045                 1050

Ile Gln  Asp Val Ile Asp Ser  Lys Tyr Ile Val Phe  Asp Val Leu
    1055                 1060                 1065

Thr Gln  Phe Val Val Ser Pro  Asn Lys Tyr Ile Phe  Ala Ala Ala
    1070                 1075                 1080

Ala Glu  Val Tyr Leu Arg Arg  Ala Tyr Arg Ala Tyr  Ser Val Arg
    1085                 1090                 1095

Glu Val  Lys His His Phe Val  Gly Asp Ser Ala Leu  Pro Ile Val
    1100                 1105                 1110

Glu Trp  Lys Phe Gln Leu Pro  Leu Leu Ser Thr Ala  Ala Tyr Asn
    1115                 1120                 1125

Ser Val  Pro Glu Ala Met Arg  Asn Ser Ser Ser Asn  Arg Ser Ser
    1130                 1135                 1140

Ile Ser  Met Asp Arg Ala Val  Ser Val Ser Asp Leu  Thr Phe Met
    1145                 1150                 1155

Ile Asn  Lys Asn Asp Ser Gln  Pro Leu Arg Thr Gly  Ile Ile Ile
    1160                 1165                 1170

Pro Thr  Asn His Leu Asp Asp  Ile Glu Glu Ser Leu  Ser Ser Ala
    1175                 1180                 1185

Ile Asp  Val Phe Pro Lys Arg  Pro Arg Asn Asn Gly  Pro Ala Pro
    1190                 1195                 1200

Asp Arg  Thr Asn Val Ala Pro  Glu Gln Pro Thr Asn  Val Cys Asn
    1205                 1210                 1215

Val Phe  Ile Ala Asn Val Ser  Gly Tyr Asn Ser Glu  Ala Glu Ile
    1220                 1225                 1230

Val Asp  Lys Ile Ser Ser Val  Leu Ser Glu Leu Lys  Asp Asp Leu
    1235                 1240                 1245

Arg Ala  Ser Gly Val Arg Arg  Val Thr Phe Val Leu  Gly Asp Lys
    1250                 1255                 1260
```

```
Val Gly  Thr Tyr Pro Lys Tyr  Tyr Thr Phe Lys Phe  Pro Asp Tyr
    1265                 1270                 1275

Phe Glu  Asp Glu Thr Ile Arg  His Ile Glu Pro Ala  Leu Ala Phe
    1280                 1285                 1290

Gln Leu  Glu Leu Arg Arg Leu  Ser Asn Phe Asn Ile  Lys Pro Val
    1295                 1300                 1305

Pro Thr  Glu Asn Arg Asn Ile  His Val Tyr Glu Ala  Val Ala Lys
    1310                 1315                 1320

Asn Thr  Ser Cys Ile Asp Arg  Arg Phe Phe Thr Arg  Gly Ile Ile
    1325                 1330                 1335

Arg Thr  Ser Arg Ile Arg Glu  Asp Val Thr Ile Ser  Glu Tyr Leu
    1340                 1345                 1350

Ile Ser  Glu Ala Asn Arg Leu  Met Ser Asp Ile Leu  Asp Ala Leu
    1355                 1360                 1365

Glu Ile  Ile Asp Thr Ser Asn  Thr Asp Leu Asn His  Ile Phe Ile
    1370                 1375                 1380

Asn Phe  Ser Ala Val Phe Asn  Val Thr Pro Asp Asp  Val Glu Ala
    1385                 1390                 1395

Ala Phe  Gly Gly Phe Leu Glu  Arg Phe Gly Arg Arg  Leu Trp Arg
    1400                 1405                 1410

Leu Arg  Val Ser Ala Ala Glu  Ile Arg Ile Met Cys  Thr Asp Pro
    1415                 1420                 1425

Glu Thr  Gly Ile Pro Phe Pro  Leu Arg Ala Leu Ile  Asn Asn Val
    1430                 1435                 1440

Ser Gly  Tyr Val Val Lys Ser  Glu Met Tyr Gln Glu  Val Lys Asn
    1445                 1450                 1455

Asp His  Gly Glu Trp Val Phe  Lys Ser Leu Gly Pro  Thr Pro Gly
    1460                 1465                 1470

Ser Met  His Leu Arg Pro Ile  Ser Thr Pro Tyr Pro  Thr Lys Glu
    1475                 1480                 1485

Trp Leu  Gln Pro Lys Arg Tyr  Lys Ala His Leu Met  Gly Thr Thr
    1490                 1495                 1500

Tyr Val  Tyr Asp Phe Pro Glu  Leu Phe Arg Gln Ala  Thr Leu Ser
    1505                 1510                 1515

Gln Trp  Lys Lys Tyr Ser Pro  Thr Ala Arg Val Pro  Ser Asp Val
    1520                 1525                 1530

Phe Val  Ala Asn Glu Leu Ile  Val Asp Asp Ser Gly  Glu Leu Thr
    1535                 1540                 1545

Glu Val  Ser Arg Glu Pro Gly  Ala Asn Val Val Gly  Met Val Ala
    1550                 1555                 1560

Phe Lys  Val Thr Ala Lys Thr  Pro Glu Tyr Pro Arg  Gly Arg His
    1565                 1570                 1575

Phe Ile  Ile Ile Ala Asn Asp  Ile Thr Phe Lys Ile  Gly Ser Phe
    1580                 1585                 1590

Gly Pro  Gln Glu Asp Glu Tyr  Phe Asn Lys Ala Thr  Gln Leu Ala
    1595                 1600                 1605

Arg Lys  Leu Gly Ile Pro Arg  Ile Tyr Leu Ser Ala  Asn Ser Gly
    1610                 1615                 1620

Ala Arg  Ile Gly Val Ala Glu  Glu Leu Leu Pro Leu  Phe Lys Val
    1625                 1630                 1635

Ala Trp  Lys Glu Glu Gly Lys  Pro Ser Lys Gly Phe  Glu Tyr Leu
    1640                 1645                 1650
```

-continued

```
Tyr Leu  Thr Ser Glu Asp Leu  Thr Leu Leu Glu Lys  Ser Gly Lys
    1655                 1660                 1665

Ser Asn  Ser Val Thr Thr Gln  Arg Ile Val Glu Glu  Gly Glu Glu
    1670                 1675                 1680

Arg His  Val Ile Thr Ala Ile  Ile Gly Ala Ser Asp  Gly Leu Gly
    1685                 1690                 1695

Val Glu  Cys Leu Arg Gly Ser  Gly Leu Ile Ala Gly  Ala Thr Ser
    1700                 1705                 1710

Arg Ala  Tyr Lys Asp Ile Phe  Thr Ile Thr Leu Val  Thr Cys Arg
    1715                 1720                 1725

Ser Val  Gly Ile Gly Ala Tyr  Leu Val Arg Leu Gly  Gln Arg Ala
    1730                 1735                 1740

Ile Gln  Ile Glu Gly Gln Pro  Ile Ile Leu Thr Gly  Ala Pro Ala
    1745                 1750                 1755

Ile Asn  Lys Leu Leu Gly Arg  Glu Val Tyr Ser Ser  Asn Leu Gln
    1760                 1765                 1770

Leu Gly  Gly Thr Gln Ile Met  Tyr Lys Asn Gly Val  Ser His Leu
    1775                 1780                 1785

Thr Ala  Asn Asp Asp Leu Ala  Gly Val Glu Lys Ile  Met Asp Trp
    1790                 1795                 1800

Leu Ala  Tyr Val Pro Ala Lys  Arg Asn Met Pro Val  Pro Ile Leu
    1805                 1810                 1815

Glu Ser  Leu His Asp Lys Trp  Asp Arg Asp Val Asp  Tyr Lys Pro
    1820                 1825                 1830

Thr Arg  Asn Glu Pro Tyr Asp  Val Arg Trp Met Ile  Ser Gly Arg
    1835                 1840                 1845

Glu Thr  Pro Asp Gly Glu Phe  Glu Ser Gly Leu Phe  Asp Ser Gly
    1850                 1855                 1860

Ser Phe  Thr Glu Thr Leu Ser  Gly Trp Ala Lys Gly  Val Val Val
    1865                 1870                 1875

Gly Arg  Ala Arg Leu Gly Gly  Ile Pro Met Gly Val  Ile Gly Val
    1880                 1885                 1890

Glu Thr  Arg Val Thr Glu Asn  Leu Ile Pro Ala Asp  Pro Ala Asn
    1895                 1900                 1905

Pro Asp  Ser Thr Glu Met Met  Ile Gln Glu Ala Gly  Gln Val Trp
    1910                 1915                 1920

Tyr Pro  Asn Ser Ala Phe Lys  Thr Ala Gln Ala Ile  Asn Asp Phe
    1925                 1930                 1935

Asn Asn  Gly Glu Gln Leu Pro  Leu Met Ile Leu Ala  Asn Trp Arg
    1940                 1945                 1950

Gly Phe  Ser Gly Gly Gln Arg  Asp Met Tyr Asn Glu  Val Leu Lys
    1955                 1960                 1965

Tyr Gly  Ser Phe Ile Val Asp  Ala Leu Val Asp Phe  Lys Gln Pro
    1970                 1975                 1980

Ile Phe  Thr Tyr Ile Pro Pro  Thr Ala Glu Leu Arg  Gly Gly Ser
    1985                 1990                 1995

Trp Val  Val Val Asp Pro Thr  Ile Asn Glu Asp Met  Met Glu Met
    2000                 2005                 2010

Tyr Ala  Asp Val Glu Ser Arg  Ala Gly Val Leu Glu  Pro Glu Gly
    2015                 2020                 2025

Met Val  Gly Ile Lys Tyr Arg  Lys Asp Lys Leu Leu  Ala Thr Met
    2030                 2035                 2040

Glu Arg  Leu Asp Ala Lys Tyr  Ala Glu Leu Lys Ser  Lys Val Ser
```

```
    2045                2050                2055

Asp Thr  Ser Leu Ser Glu Lys  Asp Val Ser Glu Ile  Lys Lys Gln
    2060                2065                2070

Ile Glu  Gln Arg Glu Lys Gln  Leu Leu Pro Ile Tyr  Ala Gln Ile
    2075                2080                2085

Ser Ile  Gln Phe Ala Asp Leu  His Asp Arg Ser Gly  Arg Met Leu
    2090                2095                2100

Ala Lys  Gly Val Ile Lys Lys  Glu Leu Glu Trp Val  Asn Ser Arg
    2105                2110                2115

Arg Phe  Phe Phe Trp Arg Val  Arg Arg Arg Leu Asn  Glu Glu Tyr
    2120                2125                2130

Leu Ile  Lys Arg Ile Thr Glu  Phe Leu Ser Ala Ser  Ala Thr Arg
    2135                2140                2145

Leu Asp  Lys Ile Ser Arg Ile  Asn Ser Trp Leu Pro  Thr Ser Ile
    2150                2155                2160

Asp Leu  Glu Asp Asp Gln Lys  Val Ala Ile Trp Leu  Glu Glu Asn
    2165                2170                2175

Arg Lys  Ala Leu Asp Ala Asn  Ile Lys Glu Leu Arg  Ala Glu His
    2180                2185                2190

Val Arg  Arg Thr Leu Ala Thr  Leu Val Arg Thr Asp  Met Asp Thr
    2195                2200                2205

Thr Ser  Lys Ser Leu Ala Glu  Leu Ile Asn Leu Leu  Pro Glu Thr
    2210                2215                2220

Glu Lys  Glu Ser Ile Leu Ser  Lys Ile Lys Ser
    2225                2230


<210> SEQ ID NO 57
<211> LENGTH: 2266
<212> TYPE: PRT
<213> ORGANISM: Yarrowia lipolytica

<400> SEQUENCE: 57

Met Arg Leu Gln Leu Arg Thr Leu Thr Arg Arg Phe Phe Ser Met Ala
1               5                   10                  15

Ser Gly Ser Ser Thr Pro Asp Val Ala Pro Leu Val Asp Pro Asn Ile
            20                  25                  30

His Lys Gly Leu Ala Ser His Phe Phe Gly Leu Asn Ser Val His Thr
        35                  40                  45

Ala Lys Pro Ser Lys Val Lys Glu Phe Val Ala Ser His Gly Gly His
    50                  55                  60

Thr Val Ile Asn Lys Val Leu Ile Ala Asn Asn Gly Ile Ala Ala Val
65                  70                  75                  80

Lys Glu Ile Arg Ser Val Arg Lys Trp Ala Tyr Glu Thr Phe Gly Asp
                85                  90                  95

Glu Arg Ala Ile Ser Phe Thr Val Met Ala Thr Pro Glu Asp Leu Ala
            100                 105                 110

Ala Asn Ala Asp Tyr Ile Arg Met Ala Asp Gln Tyr Val Glu Val Pro
        115                 120                 125

Gly Gly Thr Asn Asn Asn Asn Tyr Ala Asn Val Glu Leu Ile Val Asp
    130                 135                 140

Val Ala Glu Arg Phe Gly Val Asp Ala Val Trp Ala Gly Trp Gly His
145                 150                 155                 160

Ala Ser Glu Asn Pro Leu Leu Pro Glu Ser Leu Ala Ala Ser Pro Arg
                165                 170                 175
```

-continued

```
Lys Ile Val Phe Ile Gly Pro Pro Gly Ala Ala Met Arg Ser Leu Gly
            180                 185                 190

Asp Lys Ile Ser Ser Thr Ile Val Ala Gln His Ala Lys Val Pro Cys
        195                 200                 205

Ile Pro Trp Ser Gly Thr Gly Val Asp Glu Val Val Val Asp Lys Ser
    210                 215                 220

Thr Asn Leu Val Ser Val Ser Glu Glu Val Tyr Thr Lys Gly Cys Thr
225                 230                 235                 240

Thr Gly Pro Lys Gln Gly Leu Glu Lys Ala Lys Gln Ile Gly Phe Pro
                245                 250                 255

Val Met Ile Lys Ala Ser Glu Gly Gly Gly Gly Lys Gly Ile Arg Lys
            260                 265                 270

Val Glu Arg Glu Glu Asp Phe Glu Ala Ala Tyr His Gln Val Glu Gly
        275                 280                 285

Glu Ile Pro Gly Ser Pro Ile Phe Ile Met Gln Leu Ala Gly Asn Ala
    290                 295                 300

Arg His Leu Glu Val Gln Leu Leu Ala Asp Gln Tyr Gly Asn Asn Ile
305                 310                 315                 320

Ser Leu Phe Gly Arg Asp Cys Ser Val Gln Arg Arg His Gln Lys Ile
                325                 330                 335

Ile Glu Glu Ala Pro Val Thr Val Ala Gly Gln Gln Thr Phe Thr Ala
            340                 345                 350

Met Glu Lys Ala Ala Val Arg Leu Gly Lys Leu Val Gly Tyr Val Ser
        355                 360                 365

Ala Gly Thr Val Glu Tyr Leu Tyr Ser His Glu Asp Asp Lys Phe Tyr
    370                 375                 380

Phe Leu Glu Leu Asn Pro Arg Leu Gln Val Glu His Pro Thr Thr Glu
385                 390                 395                 400

Met Val Thr Gly Val Asn Leu Pro Ala Ala Gln Leu Gln Ile Ala Met
                405                 410                 415

Gly Ile Pro Leu Asp Arg Ile Lys Asp Ile Arg Leu Phe Tyr Gly Val
            420                 425                 430

Asn Pro His Thr Thr Thr Pro Ile Asp Phe Asp Phe Ser Gly Glu Asp
        435                 440                 445

Ala Asp Lys Thr Gln Arg Arg Pro Val Pro Arg Gly His Thr Thr Ala
    450                 455                 460

Cys Arg Ile Thr Ser Glu Asp Pro Gly Glu Gly Phe Lys Pro Ser Gly
465                 470                 475                 480

Gly Thr Met His Glu Leu Asn Phe Arg Ser Ser Ser Asn Val Trp Gly
                485                 490                 495

Tyr Phe Ser Val Gly Asn Gln Gly Gly Ile His Ser Phe Ser Asp Ser
            500                 505                 510

Gln Phe Gly His Ile Phe Ala Phe Gly Glu Asn Arg Ser Ala Ser Arg
        515                 520                 525

Lys His Met Val Val Ala Leu Lys Glu Leu Ser Ile Arg Gly Asp Phe
    530                 535                 540

Arg Thr Thr Val Glu Tyr Leu Ile Lys Leu Leu Glu Thr Pro Asp Phe
545                 550                 555                 560

Glu Asp Asn Thr Ile Thr Thr Gly Trp Leu Asp Glu Leu Ile Ser Asn
                565                 570                 575

Lys Leu Thr Ala Glu Arg Pro Asp Ser Phe Leu Ala Val Val Cys Gly
            580                 585                 590

Ala Ala Thr Lys Ala His Arg Ala Ser Glu Asp Ser Ile Ala Thr Tyr
```

```
        595                 600                 605

Met Ala Ser Leu Glu Lys Gly Gln Val Pro Ala Arg Asp Ile Leu Lys
    610                 615                 620

Thr Leu Phe Pro Val Asp Phe Ile Tyr Glu Gly Gln Arg Tyr Lys Phe
625                 630                 635                 640

Thr Ala Thr Arg Ser Ser Glu Asp Ser Tyr Thr Leu Phe Ile Asn Gly
                645                 650                 655

Ser Arg Cys Asp Ile Gly Val Arg Pro Leu Ser Asp Gly Gly Ile Leu
            660                 665                 670

Cys Leu Val Gly Gly Arg Ser His Asn Val Tyr Trp Lys Glu Glu Val
        675                 680                 685

Gly Ala Thr Arg Leu Ser Val Asp Ser Lys Thr Cys Leu Leu Glu Val
    690                 695                 700

Glu Asn Asp Pro Thr Gln Leu Arg Ser Pro Ser Pro Gly Lys Leu Val
705                 710                 715                 720

Lys Phe Leu Val Glu Asn Gly Asp His Val Arg Ala Asn Gln Pro Tyr
                725                 730                 735

Ala Glu Ile Glu Val Met Lys Met Tyr Met Thr Leu Thr Ala Gln Glu
            740                 745                 750

Asp Gly Ile Val Gln Leu Met Lys Gln Pro Gly Ser Thr Ile Glu Ala
        755                 760                 765

Gly Asp Ile Leu Gly Ile Leu Ala Leu Asp Asp Pro Ser Lys Val Lys
    770                 775                 780

His Ala Lys Pro Phe Glu Gly Gln Leu Pro Glu Leu Gly Pro Pro Thr
785                 790                 795                 800

Leu Ser Gly Asn Lys Pro His Gln Arg Tyr Glu His Cys Gln Asn Val
                805                 810                 815

Leu His Asn Ile Leu Leu Gly Phe Asp Asn Gln Val Val Met Lys Ser
            820                 825                 830

Thr Leu Gln Glu Met Val Gly Leu Leu Arg Asn Pro Glu Leu Pro Tyr
        835                 840                 845

Leu Gln Trp Ala His Gln Val Ser Ser Leu His Thr Arg Met Ser Ala
    850                 855                 860

Lys Leu Asp Ala Thr Leu Ala Gly Leu Ile Asp Lys Ala Lys Gln Arg
865                 870                 875                 880

Gly Gly Glu Phe Pro Ala Lys Gln Leu Leu Arg Ala Leu Glu Lys Glu
                885                 890                 895

Ala Ser Ser Gly Glu Val Asp Ala Leu Phe Gln Gln Thr Leu Ala Pro
            900                 905                 910

Leu Phe Asp Leu Ala Arg Glu Tyr Gln Asp Gly Leu Ala Ile His Glu
        915                 920                 925

Leu Gln Val Ala Ala Gly Leu Leu Gln Ala Tyr Tyr Asp Ser Glu Ala
    930                 935                 940

Arg Phe Cys Gly Pro Asn Val Arg Asp Glu Asp Val Ile Leu Lys Leu
945                 950                 955                 960

Arg Glu Glu Asn Arg Asp Ser Leu Arg Lys Val Val Met Ala Gln Leu
                965                 970                 975

Ser His Ser Arg Val Gly Ala Lys Asn Asn Leu Val Leu Ala Leu Leu
            980                 985                 990

Asp Glu Tyr Lys Val Ala Asp Gln  Ala Gly Thr Asp Ser  Pro Ala Ser
        995                 1000                1005

Asn Val  His Val Ala Lys Tyr  Leu Arg Pro Val Leu  Arg Lys Ile
    1010                1015                1020
```

-continued

```
Val Glu  Leu Glu Ser Arg Ala  Ser Ala Lys Val Ser  Leu Lys Ala
    1025                 1030                 1035

Arg Glu  Ile Leu Ile Gln Cys  Ala Leu Pro Ser Leu  Lys Glu Arg
    1040                 1045                 1050

Thr Asp  Gln Leu Glu His Ile  Leu Arg Ser Ser Val  Val Glu Ser
    1055                 1060                 1065

Arg Tyr  Gly Glu Val Gly Leu  Glu His Arg Thr Pro  Arg Ala Asp
    1070                 1075                 1080

Ile Leu  Lys Glu Val Val Asp  Ser Lys Tyr Ile Val  Phe Asp Val
    1085                 1090                 1095

Leu Ala  Gln Phe Phe Ala His  Asp Asp Pro Trp Ile  Val Leu Ala
    1100                 1105                 1110

Ala Leu  Glu Leu Tyr Ile Arg  Arg Ala Cys Lys Ala  Tyr Ser Ile
    1115                 1120                 1125

Leu Asp  Ile Asn Tyr His Gln  Asp Ser Asp Leu Pro  Pro Val Ile
    1130                 1135                 1140

Ser Trp  Arg Phe Arg Leu Pro  Thr Met Ser Ser Ala  Leu Tyr Asn
    1145                 1150                 1155

Ser Val  Val Ser Ser Gly Ser  Lys Thr Pro Thr Ser  Pro Ser Val
    1160                 1165                 1170

Ser Arg  Ala Asp Ser Val Ser  Asp Phe Ser Tyr Thr  Val Glu Arg
    1175                 1180                 1185

Asp Ser  Ala Pro Ala Arg Thr  Gly Ala Ile Val Ala  Val Pro His
    1190                 1195                 1200

Leu Asp  Asp Leu Glu Asp Ala  Leu Thr Arg Val Leu  Glu Asn Leu
    1205                 1210                 1215

Pro Lys  Arg Gly Ala Gly Leu  Ala Ile Ser Val Gly  Ala Ser Asn
    1220                 1225                 1230

Lys Ser  Ala Ala Ala Ser Ala  Arg Asp Ala Ala Ala  Ala Ala Ala
    1235                 1240                 1245

Ser Ser  Val Asp Thr Gly Leu  Ser Asn Ile Cys Asn  Val Met Ile
    1250                 1255                 1260

Gly Arg  Val Asp Glu Ser Asp  Asp Asp Asp Thr Leu  Ile Ala Arg
    1265                 1270                 1275

Ile Ser  Gln Val Ile Glu Asp  Phe Lys Glu Asp Phe  Glu Ala Cys
    1280                 1285                 1290

Ser Leu  Arg Arg Ile Thr Phe  Ser Phe Gly Asn Ser  Arg Gly Thr
    1295                 1300                 1305

Tyr Pro  Lys Tyr Phe Thr Phe  Arg Gly Pro Ala Tyr  Glu Glu Asp
    1310                 1315                 1320

Pro Thr  Ile Arg His Ile Glu  Pro Ala Leu Ala Phe  Gln Leu Glu
    1325                 1330                 1335

Leu Ala  Arg Leu Ser Asn Phe  Asp Ile Lys Pro Val  His Thr Asp
    1340                 1345                 1350

Asn Arg  Asn Ile His Val Tyr  Glu Ala Thr Gly Lys  Asn Ala Ala
    1355                 1360                 1365

Ser Asp  Lys Arg Phe Phe Thr  Arg Gly Ile Val Arg  Pro Gly Arg
    1370                 1375                 1380

Leu Arg  Glu Asn Ile Pro Thr  Ser Glu Tyr Leu Ile  Ser Glu Ala
    1385                 1390                 1395

Asp Arg  Leu Met Ser Asp Ile  Leu Asp Ala Leu Glu  Val Ile Gly
    1400                 1405                 1410
```

Thr Thr Asn Ser Asp Leu Asn His Ile Phe Ile Asn Phe Ser Ala
1415 1420 1425

Val Phe Ala Leu Lys Pro Glu Glu Val Glu Ala Ala Phe Gly Gly
1430 1435 1440

Phe Leu Glu Arg Phe Gly Arg Arg Leu Trp Arg Leu Arg Val Thr
1445 1450 1455

Gly Ala Glu Ile Arg Met Met Val Ser Asp Pro Glu Thr Gly Ser
1460 1465 1470

Ala Phe Pro Leu Arg Ala Met Ile Asn Asn Val Ser Gly Tyr Val
1475 1480 1485

Val Gln Ser Glu Leu Tyr Ala Glu Ala Lys Asn Asp Lys Gly Gln
1490 1495 1500

Trp Ile Phe Lys Ser Leu Gly Lys Pro Gly Ser Met His Met Arg
1505 1510 1515

Ser Ile Asn Thr Pro Tyr Pro Thr Lys Glu Trp Leu Gln Pro Lys
1520 1525 1530

Arg Tyr Lys Ala His Leu Met Gly Thr Thr Tyr Cys Tyr Asp Phe
1535 1540 1545

Pro Glu Leu Phe Arg Gln Ser Ile Glu Ser Asp Trp Lys Lys Tyr
1550 1555 1560

Asp Gly Lys Ala Pro Asp Asp Leu Met Thr Cys Asn Glu Leu Ile
1565 1570 1575

Leu Asp Glu Asp Ser Gly Glu Leu Gln Glu Val Asn Arg Glu Pro
1580 1585 1590

Gly Ala Asn Asn Val Gly Met Val Ala Trp Lys Phe Glu Ala Lys
1595 1600 1605

Thr Pro Glu Tyr Pro Arg Gly Arg Ser Phe Ile Val Val Ala Asn
1610 1615 1620

Asp Ile Thr Phe Gln Ile Gly Ser Phe Gly Pro Ala Glu Asp Gln
1625 1630 1635

Phe Phe Phe Lys Val Thr Glu Leu Ala Arg Lys Leu Gly Ile Pro
1640 1645 1650

Arg Ile Tyr Leu Ser Ala Asn Ser Gly Ala Arg Ile Gly Ile Ala
1655 1660 1665

Asp Glu Leu Val Gly Lys Tyr Lys Val Ala Trp Asn Asp Glu Thr
1670 1675 1680

Asp Pro Ser Lys Gly Phe Lys Tyr Leu Tyr Phe Thr Pro Glu Ser
1685 1690 1695

Leu Ala Thr Leu Lys Pro Asp Thr Val Val Thr Thr Glu Ile Glu
1700 1705 1710

Glu Glu Gly Pro Asn Gly Val Glu Lys Arg His Val Ile Asp Tyr
1715 1720 1725

Ile Val Gly Glu Lys Asp Gly Leu Gly Val Glu Cys Leu Arg Gly
1730 1735 1740

Ser Gly Leu Ile Ala Gly Ala Thr Ser Arg Ala Tyr Lys Asp Ile
1745 1750 1755

Phe Thr Leu Thr Leu Val Thr Cys Arg Ser Val Gly Ile Gly Ala
1760 1765 1770

Tyr Leu Val Arg Leu Gly Gln Arg Ala Ile Gln Ile Glu Gly Gln
1775 1780 1785

Pro Ile Ile Leu Thr Gly Ala Pro Ala Ile Asn Lys Leu Leu Gly
1790 1795 1800

Arg Glu Val Tyr Ser Ser Asn Leu Gln Leu Gly Gly Thr Gln Ile

-continued

```
    1805                1810                1815

Met Tyr  Asn Asn Gly Val Ser  His Leu Thr Ala Arg  Asp Asp Leu
    1820                1825                1830

Asn Gly  Val His Lys Ile Met  Gln Trp Leu Ser Tyr  Ile Pro Ala
    1835                1840                1845

Ser Arg  Gly Leu Pro Val Pro  Val Leu Pro His Lys  Thr Asp Val
    1850                1855                1860

Trp Asp  Arg Asp Val Thr Phe  Gln Pro Val Arg Gly  Glu Gln Tyr
    1865                1870                1875

Asp Val  Arg Trp Leu Ile Ser  Gly Arg Thr Leu Glu  Asp Gly Ala
    1880                1885                1890

Phe Glu  Ser Gly Leu Phe Asp  Lys Asp Ser Phe Gln  Glu Thr Leu
    1895                1900                1905

Ser Gly  Trp Ala Lys Gly Val  Val Val Gly Arg Ala  Arg Leu Gly
    1910                1915                1920

Gly Ile  Pro Phe Gly Val Ile  Gly Val Glu Thr Ala  Thr Val Asp
    1925                1930                1935

Asn Thr  Thr Pro Ala Asp Pro  Ala Asn Pro Asp Ser  Ile Glu Met
    1940                1945                1950

Ser Thr  Ser Glu Ala Gly Gln  Val Trp Tyr Pro Asn  Ser Ala Phe
    1955                1960                1965

Lys Thr  Ser Gln Ala Ile Asn  Asp Phe Asn His Gly  Glu Ala Leu
    1970                1975                1980

Pro Leu  Met Ile Leu Ala Asn  Trp Arg Gly Phe Ser  Gly Gly Gln
    1985                1990                1995

Arg Asp  Met Tyr Asn Glu Val  Leu Lys Tyr Gly Ser  Phe Ile Val
    2000                2005                2010

Asp Ala  Leu Val Asp Tyr Lys  Gln Pro Ile Met Val  Tyr Ile Pro
    2015                2020                2025

Pro Thr  Gly Glu Leu Arg Gly  Gly Ser Trp Val Val  Val Asp Pro
    2030                2035                2040

Thr Ile  Asn Ser Asp Met Met  Glu Met Tyr Ala Asp  Val Glu Ser
    2045                2050                2055

Arg Gly  Gly Val Leu Glu Pro  Glu Gly Met Val Gly  Ile Lys Tyr
    2060                2065                2070

Arg Arg  Asp Lys Leu Leu Asp  Thr Met Ala Arg Leu  Asp Pro Glu
    2075                2080                2085

Tyr Ser  Ser Leu Lys Lys Gln  Leu Glu Glu Ser Pro  Asp Ser Glu
    2090                2095                2100

Glu Leu  Lys Val Lys Leu Ser  Val Arg Glu Lys Ser  Leu Met Pro
    2105                2110                2115

Ile Tyr  Gln Gln Ile Ser Val  Gln Phe Ala Asp Leu  His Asp Arg
    2120                2125                2130

Ala Gly  Arg Met Glu Ala Lys  Gly Val Ile Arg Glu  Ala Leu Val
    2135                2140                2145

Trp Lys  Asp Ala Arg Arg Phe  Phe Phe Trp Arg Ile  Arg Arg Arg
    2150                2155                2160

Leu Val  Glu Glu Tyr Leu Ile  Thr Lys Ile Asn Ser  Ile Leu Pro
    2165                2170                2175

Ser Cys  Thr Arg Leu Glu Cys  Leu Ala Arg Ile Lys  Ser Trp Lys
    2180                2185                2190

Pro Ala  Thr Leu Asp Gln Gly  Ser Asp Arg Gly Val  Ala Glu Trp
    2195                2200                2205
```

-continued

| | | | | | | | | | | | | | | |
|---|---|---|---|---|---|---|---|---|---|---|---|---|---|---|
| Phe | Asp | Glu | Asn | Ser | Asp | Ala | Val | Ser | Ala | Arg | Leu | Ser | Glu | Leu |
| | 2210 | | | | | 2215 | | | | | 2220 | | | |
| Lys | Lys | Asp | Ala | Ser | Ala | Gln | Ser | Phe | Ala | Ser | Gln | Leu | Arg | Lys |
| | 2225 | | | | | 2230 | | | | | 2235 | | | |
| Asp | Arg | Gln | Gly | Thr | Leu | Gln | Gly | Met | Lys | Gln | Ala | Leu | Ala | Ser |
| | 2240 | | | | | 2245 | | | | | 2250 | | | |
| Leu | Ser | Glu | Ala | Glu | Arg | Ala | Glu | Leu | Leu | Lys | Gly | Leu | | |
| | 2255 | | | | | 2260 | | | | | 2265 | | | |

UNITED STATES PATENT AND TRADEMARK OFFICE
CERTIFICATE OF CORRECTION

PATENT NO. : 11,220,675 B2
APPLICATION NO. : 16/401690
DATED : January 11, 2022
INVENTOR(S) : Leonard et al.

It is certified that error appears in the above-identified patent and that said Letters Patent is hereby corrected as shown below:

In the Claims

At Column 329, Claim number 1, Line number 17:
"acids in"
Should read:
-- acid in --

At Column 329, Claim number 1, Line number 25:
"or iii)"
Should read:
-- or (ii) --

Signed and Sealed this
Seventeenth Day of May, 2022

Katherine Kelly Vidal
*Director of the United States Patent and Trademark Office*